US011041214B2

(12) United States Patent
Faruki et al.

(10) Patent No.: US 11,041,214 B2
(45) Date of Patent: Jun. 22, 2021

(54) METHODS FOR SUBTYPING OF LUNG SQUAMOUS CELL CARCINOMA

(71) Applicants: GeneCentric Therapeutics, Inc., Research Triangle Park, NC (US); The University of North Carolina at Chapel Hill, Chapel Hill, NC (US)

(72) Inventors: Hawazin Faruki, Durham, NC (US); Myla Lai-Goldman, Durham, NC (US); Greg Mayhew, Durham, NC (US); Jonathan Serody, Duham, NC (US); Charles Perou, Carrboro, NC (US); David Neil Hayes, Chapel Hill, NC (US)

(73) Assignees: GeneCentric Therapeutics, Inc., Research Triangle Park, NC (US); The University of North Carolina at Chapel Hill, Chapel Hill, NC (US)

( * ) Notice: Subject to any disclaimer, the term of this patent is extended or adjusted under 35 U.S.C. 154(b) by 233 days.

(21) Appl. No.: 16/302,170

(22) PCT Filed: May 17, 2017

(86) PCT No.: PCT/US2017/033107
§ 371 (c)(1),
(2) Date: Nov. 16, 2018

(87) PCT Pub. No.: WO2017/201164
PCT Pub. Date: Nov. 23, 2017

(65) Prior Publication Data

US 2019/0338366 A1 Nov. 7, 2019

Related U.S. Application Data

(60) Provisional application No. 62/337,645, filed on May 17, 2016, provisional application No. 62/379,402, filed on Aug. 25, 2016, provisional application No. 62/396,587, filed on Sep. 19, 2016, provisional application No. 62/420,836, filed on Nov. 11, 2016, provisional application No. 62/425,717, filed on Nov. 23, 2016.

(51) Int. Cl.
*C12Q 1/6886* (2018.01)
*G16H 50/30* (2018.01)
*G16B 40/10* (2019.01)

(52) U.S. Cl.
CPC .......... *C12Q 1/6886* (2013.01); *G16B 40/10* (2019.02); *G16H 50/30* (2018.01); *C12Q 2600/106* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,202 | A | 7/1987 | Mullis |
| 4,843,155 | A | 6/1989 | Chomczynski |
| 5,384,261 | A | 1/1995 | Winkler et al. |
| 5,445,934 | A | 8/1995 | Fodor et al. |
| 5,677,195 | A | 10/1997 | Winkler et al. |
| 5,708,153 | A | 1/1998 | Dower et al. |
| 5,744,305 | A | 4/1998 | Fodor et al. |
| 5,770,358 | A | 6/1998 | Dower et al. |
| 5,770,722 | A | 6/1998 | Lockhart et al. |
| 5,789,162 | A | 8/1998 | Dower et al. |
| 5,800,992 | A | 9/1998 | Fodor et al. |
| 5,854,033 | A | 12/1998 | Lizardi |
| 5,856,174 | A | 1/1999 | Lipshutz et al. |
| 5,874,219 | A | 2/1999 | Rava et al. |
| 5,922,591 | A | 7/1999 | Anderson et al. |
| 6,020,135 | A | 2/2000 | Levine et al. |
| 6,033,860 | A | 3/2000 | Lockhart et al. |
| 6,040,138 | A | 3/2000 | Lockhart et al. |
| 6,040,193 | A | 3/2000 | Winkler et al. |
| 6,344,316 | B1 | 2/2002 | Lockhart et al. |
| 6,524,581 | B1 | 2/2003 | Adamis |
| 7,473,767 | B2 | 1/2009 | Dimitrov |
| 8,492,094 | B2 | 7/2013 | Dimitrov et al. |
| 10,829,819 | B2 | 11/2020 | Faruki et al. |
| 10,934,595 | B2 | 3/2021 | Faruki et al. |
| 2003/0092009 | A1 | 5/2003 | Palm |
| 2004/0009489 | A1 | 1/2004 | Golub et al. |

(Continued)

FOREIGN PATENT DOCUMENTS

| | | | |
|---|---|---|---|
| CN | 101509035 | A | 8/2009 |
| WO | WO 2003/029273 | A2 | 4/2003 |

(Continued)

OTHER PUBLICATIONS

Alimta® (Pemetrexed disodium) Eli Lilly & Co., Indianapolis, IN prescribing information. http://pi.lilly.com/us/alimta-pi.pdf, 31 pages (2018).
American Cancer Society. Cancer Facts and Figures, retrieved Sep. 25, 2018 from https://www.cancer.org/research/cancer-facts-statistics/all-cancer-facts-figures/cancer-facts-figures-2014.html, 6 pages.
Avastin® (Bevacizumab) Genetech Inc, San Francisco, CA prescribing information (2018). Retrieved online Oct. 10, 2018 at https://www.gene.com/download/pdf/avastin_prescribing.pdf, 41 pages.
Barany, "Cloning, overexpression and nucleotide sequence of a thermostable DNA ligase-encoding gene," Proc. Natl. Acad. Sci. USA 88:189-193 (1991).

(Continued)

*Primary Examiner* — Carla J Myers
(74) *Attorney, Agent, or Firm* — Cooley LLP

(57) ABSTRACT

Methods and compositions are provided for determining a subtype of lung squamous cell carcinoma (SQ) of an individual by detecting the expression level of at least one classifier biomarker selected from a group of gene signatures for lung squamous cell carcinoma. Also provided herein are methods and compositions for determining the response of an individual with a squamous cell carcinoma subtype to a therapy such as immunotherapy.

14 Claims, 36 Drawing Sheets

Specification includes a Sequence Listing.

(56) References Cited

U.S. PATENT DOCUMENTS

2006/0024692 A1 2/2006 Nakamura et al.
2010/0233695 A1 9/2010 Hayes et al.
2015/0140017 A1 5/2015 Dhodapkar et al.
2017/0114416 A1 4/2017 Faruki et al.
2019/0203296 A1 7/2019 Faruki et al.
2019/0338365 A1 11/2019 Faruki et al.

FOREIGN PATENT DOCUMENTS

WO WO 2004/031413 A2 4/2004
WO WO 2008/151110 A2 12/2008
WO WO 2015/184461 6/2015
WO WO 2016/168446 A1 10/2016
WO WO 2017/201164 A1 11/2017
WO WO 2017/201165 A1 11/2017

OTHER PUBLICATIONS

Bibikova et al., "Quantitative gene expression profiling in formalin-fixed, paraffin-embedded tissues using universal bead arrays," Am J. Pathol 165:1799-1807 (2004).
Bild AH, Yao G, Chang JT, et al. Oncogenic pathway signatures in human cancers as a guide to targeted therapies. Nature 439(7074): 353-357 (2006).
Bindea et al., "Spatiotemporal dynamics of intratumoral immune cells reveal the immune landscape in human cancer," Immunity 39(4); 782-795 (2013).
Bolstad et al., "A comparison of normalization methods for high density oligonucleotide array data based on variance and bias," Bioinformatics Bioinformatics 19(2):185-193 (2003).
Brenner et al., "Gene expression analysis by massively parallel signature sequencing (MPSS) on microbead arrays," Nat. Biotech. 18:630-34, 2000.
Broomhead DS, Jones R, King GP., "Comment on Singular-value decomposition and embedding dimension," Phys Rev A Gen Phys. Jun. 15;37(12):5004-5005 (1988).
Calabrese et al., "Serpin B4 lsoform Overexpression is Associated with Aberrant Epithelial Proliferation and Lung Cancer in Idiopathic Pulmonary Fibrosis," Pathology 44(3):192-198 (2012).
Cancer Genome Atlas Research Network. "Comprehensive genomic characterization of squamous cell lung cancers." Nature 489.7417 (2012): 519-525.
Cao et al., "Role of LKB1-CRTC1 on glycosylated COX-2 and response to COX-2 inhibition in lung cancer," JNatl Cancer Inst. 2015;107(1):1-11.
Clark et al., "Suppression of nonspecific binding of avidin-biotin complex (ABC) to proteins electroblotted to nitrocellulose paper," J Histochem Cytochem 34:1509-1512 (1986).
Collisson E., et al., "Comprehensive Molecular Profiling of Lung Adenocarcinoma," Nature 511(7511):543-550 (2014).
Cronin et al., "Measurement of gene expression in archival paraffin-embedded tissues: development and performance of a 92-gene reverse transcriptase-polymerase chain reaction assay," Am. J Pathol. 164(1):35-42 (2004).
Dabney AR ClaNC: Point-and-click software for classifying microarrays to nearest centroids. Bioinformatics. 2006;22: 122-123.
Dabney, "Classification of microarrays to nearest centroids," Bioinformatics 21(22):4148-4154 (2005).
Ettinger et al., "Non-small cell lung cancer, version 2.2013." J Natl Compr Canc Netw. Jun. 1, 2013;11(6):645-53; quiz 653.
Extended European Search Report issued by the European Patent Office for Application No. 16780736.1, dated Nov. 9, 2018, 13 pages.
Fan et al., "A Versatile Assay for High-Throughput Gene Expression Profiling on Universal Array Matrices," Genome Res. 14:878-885 (2004).
Faruki et al., "Lung Adenocarcinoma and Squamous Cell Carcinoma Gene Expression Subtypes Demonstrate Significant Differences in Tumor Immune Landscape," Journal of Thoracic Oncology 12(6):943-953 (2017).
Faruki H, et al., "Validation of the Lung Subtyping Panel in Multiple Fresh-Frozen and Formalin-Fixed, Paraffin-Embedded Lung Tumor Gene Expression Data Sets," Archives Path & Lab Med. Oct. 2015.
Fennell et al., "Association between Gene Expression Profile and Clinical Outcome of Pemetrexed-Based Treatment in Patients ,with Advanced Non-Small Cell Lung Cancer: Exploratory Results from a Phase II study," PLOS one 2014; Sep. 14 9(9): e107455, 8 pages.
Fishel and Kaufman et al., "Meta-analysis of gene expression data: a predictor-based approach ," Bioinformatics 23(13): 1599-606 ( 2007).
Forero et al., "Expression of the MHC class II pathway in triple negative breast cancer tumor cells is associated with a good prognosis and infiltrating lymphocytes," Cancer Immunol Res 4(5):390-399 2016.
Foundation Medicine Solid Tumor Mutation Panel accessed Oct. 2014, 2 pages.
Fox et al., "Formaldehyde Fixation," J Histochem Cytochem 33:845-853 (1985).
Friedman et al., "Regularization Paths for Generalized Linear Models via Coordinate Descent," Journal of statistical software 33(1): 1-22 (2010).
Geiss et al., "Direct multiplexed measurement of gene expression with color-coded probe pairs," Nat. Biotechnol. 26:317-325 (2008).
Grilley-Olson et al. Validation of interobserver agreement in lung cancer assessment: hematoxylin-eosin diagnostic reproducibility for non small cell lung cancer. Arch Pathol Lab Med 2013; 137: 32-40.
Guatelli et al., "Isothermal, in vitro amplification of nucleic acids by a multienzyme reaction modeled after retroviral replication," Proc Natl Acad Sci U S A. 87(5):1874-1878 (1990).
Hast et al., Cancer-derived mutations in KEAP1 impair NRF2 degradation but not ubiquitination. Cancer Res 2014; 74(3): 808-817.
Hayes DN, Monti S, Parmigiani G, et al. Gene expression profiling reveals reproducible human lung adenocarcinoma subtypes in multiple independent patient cohorts. J Clin Oncol 24(31): 5079-5090 (2006).
Hubbell, "Robust estimators for expression analysis," Bioinformatics (2002) 18(12):1585-1592.
International Search Report and Written Opinion issued by the International Searching Authority for Application No. PCT/US2015/033611, dated Sep. 14, 2015, 10 pages.
International Search Report and Written Opinion issued by the International Searching Authority for Application No. PCT/US2016/027503, dated Jul. 14, 2016, 10 pages.
International Search Report and Written Opinion issued by the International Searching Authority for Application No. PCT/US2017/033107, dated Oct. 23, 2017, 21 pages.
International Search Report and Written Opinion issued by the International Searching Authority for Application No. PCT/US2017/033110, dated Oct. 20, 2017, 21 pages.
Irizarry et al., "Exploration, normalization, and summaries of high density oligonucleotide array probe level data," Biostatistics Apr. 4(2): 249-64 (2003).
Koyama et al., STK11/LKB1 deficiency promotes neutrophil recruitment and proinflammatory cytokine production to suppress T-cell activity in the lung tumor microenvironment. Cancer Res 76(5): 999-1008 (2016).
Kratz JR, et al., "A practical molecular assay to predict survival in resected non-squamous, non-small-cell lung cancer: development and international validation studies," Lancet 379(9818):823-832 (2012).
Kwoh et al., "Transcription-based amplification system and detection of amplified human immunodeficiency virus type 1 with a bead-based sandwich hybridization format (TI RNA polymerase/in vitro nucleic acid amplification)," Proc. Natl. Acad. Sci. USA, 86:1173-1177 (1989).
Landegren et al., "A ligase-mediated gene detection technique," Science, 241(4869):1077-1080 (1988), retrieved from http://science.sciencemag.org/ on Oct. 29, 2018+A71.
Lee ES, et al., "Prediction of recurrence-free survival in postoperative non-small cell lung cancer patients by using an integrated model of clinical information and gene expression." Clinical Cancer Research 14(22):7397-7404 (2008).

(56) References Cited

OTHER PUBLICATIONS

Li and Dewey, "RSEM: accurate transcript quantification from RNA-Seq data with or without a reference genome," BMC Bioinformatics 2011 12:323, 16 pages.
McGhee and von Hippel, "Formaldehyde as a probe of DNA structure. II. Reaction with endocyclic imino groups of DNA bases," Biochemistry 14:1281-1296 (1975).
Mukhopadhyay S., "Utility of Small Biopsies for Diagnosis of Lung Nodules: Doing More with Less," Modern Pathology, 25(1):S43-S57 (2012).
Mullins et al., "Agreement in breast cancer classification between microarray and quantitative reverse transcription PCR from fresh-frozen and formalin-fixed, paraffin-embedded tissues," Clin Chem. 53(7):1273-1279 (2007).
Nielsen, "A comparison of PAM50 intrinsic subtyping with immunohistochemistry and clinical prognostic factors in tamoxifen-treated estrogen receptor-positive breast cancer," Clin Cancer Res. Nov. 1, 2010;16(21):5222-32. doi: 10.1158/1078-0432.CCR-10-1282. Epub Sep. 13, 2010, Downloaded from clincancerres. aacrjournals.org on Oct. 10, 2018.
Niki, T., et al., "Expression of Vascular Endothelial Growth Factors A, B. C, and D and Their Relationships to Lymph Node Status in Lung Adenocarcinoma," Clinical Cancer Research 6(6):2431-2439 (2000).
Paolillo et al., "Small molecule integrin antagonists in cancer therapy," Mini Rev Med Chem 12:1439-1446 (2009).
Parzen, "On Estimation of a Probability Density Function and Mode," Stanford University, 1065-1076 (1962).
Prasad et al., "Differential Expression of Degradome Components in Cutaneous Squamous Cell Carcinomas," Modern Pathology 27:495-957 (2014).
Quinlan, "Induction of Decision Trees," Machine Learning 1(1):81-106 (1986).
Raponi et al. "Gene expression signatures for predicting prognosis of squamous cell and adenocarcinomas of the lung," Cancer Res 66(7): 466-472 (2006).
Rekhtman et al., "Distinct profile of driver mutations and clinical features in immunomarker-defined subsets of pulmonary large-cell carcinoma," Mod Pathol 26(4): 511-22 (2013).
Rekhtman et al., "Immunnohistochemical algorithm for differentiation of lung adenocarcinoma and squamous cell carcinoma based on large series of whole-tissue sections with validation in small specimens," Modern Path. 24:1348-1359 (2011).
Ringnér, M., et al., "Prognostic and Chemotherapy Predictive Value of Gene-Expression Phenotypes in Primary Lung Adenocarcinoma," Clinical Cancer Research 22(1):218-229 (2015).
Robin et al., "pROC: an open source package for R and S+ to analyze and compare ROC curves," BMC bioinformatic 12:77 (2011), 8 pages.
Roepman P, et al. An immune response enriched 72-gene prognostic profile for early stage non-small-cell lung cancer. Clinical Cancer Research 15.1:284-290 (2009).
Rossi G, Mengoli MC, Cavazza A, et al. Large cell carcinoma of the lung: clinically oriented classification integrating immunohistochemistry and molecular biology. Virchows Arch. 2014; 464: 61-68. DOI 10.1007/s00428-013-1501-6.
Rouskin et al., "Genome-wide probing of RNA structure reveals active unfolding of mRNA structures in vivo," Nature 505, pp. 701-705 (2014).
Rousseaux S, et al. Ectopic activation of germline and placental genes identifies aggressive metastasis-prone lung cancers. Sci Transl Med. 5(186):186ra66 (2013).
Rupp G and Locker J., University of Pittsburgh School of Medicine, "Purification and analysis of RNA from paraffin embedded tissues," BioTechniques 6(1):56-60 (1988).
Schabath et al., "Differential association of STK11 and TP53 with KRAS mutation-associated gene expression, proliferation, and immune surveillance in lung adenocarcinoma," Oncogene 35(24):3209-3216, Author manuscript, 13 pages (2016).
Schafer, G., et al., *Homo sapiens* Vascular Endothelial Growth Factor D (FIGF) Gene, Promoter Region and 5' UTR. National Center fnr Biotechnology Information. Genbank Entry. Jan. 3, 2005 [retrieved on Sep. 27, 2017] Retrieved from the Internet: <URL: https://www.ncbi.nlm.nih.gov/nucleotide/58223364?report=genbank&log$=nuclalign&blast_rank=5&RID=WWYAJBVM015>; pp. 1-2.
Shedden K, Taylor JMG, Enkemann SA, et al. Gene expression-based survival prediction in lung adenocarcinoma: a multi-site, blinded validation study: director's challenge consortium for the molecular classification of lung adenocarcinoma. Nat Med 14(8): 822-827 (2008). doi: 10.1038/nm. 1790.
Skoulidis et al., "Co occuring genomic alterations define major subsets of KRAS-mutant lung adenocarcinoma with distinct biology, immune profiles, and therapeutic vulnerabilities," Cancer Discov 5(8): 860-77 (2015).
Smyth, G. K., Limma: linear models for microarray data. In: Bioinformatics and Computational Biology Solutions using Rand Bioconductor, R. Gentleman, V. Carey, S. Dudoit, R.Irizarry, W. Huber (eds.), Springer, New York, pp. 397-420 (2005).
Smyth, G. K., "Linear Models and Empirical Bayes Methods for Assessing Differential Expression in Microarray Experiments," Stat. Appi. Genet. Mol. Biol. 3: Article 3, 28 pages (2004).
Statistical analyses R 3.2.0 software (http://www.R-project.org) retrieved online Jan. 7, 2019 at http://www.R-project.org, 3 pages.
Suykens JAK, Vandewalle J., "Least Squares Support Vector Machine Classifiers," Neural Processing Letters 9(3): 293-300 (1999).
Szumilas, "Explaining odds ratios," J. Can. Acad. Child Adolesc. Psychiatry 19(3): 227-229 (2010).
Tang et al., "Advances in lung adenocarcinoma classification: a summary of the new international multidisciplinary classification system (IASLC/ATS/ERS) ," J Thorac Dis 2014; 6(S5):S489-S501.
The Clinical Lung Cancer Genome Project (CLCGP) and Network Genomic Medicine (NGM). A genomics-based classification of human lung tumors. Sci Transl Med 5, 209ra153, 28 pages (2013).
Thunnissen et al., "Reproducibility of histopathological subtypes and invasion in pulmonary adenocarcinoma. An international interobserver study," Mod Pathol 2012; 25(12):1574-1583. Doi: 10.1038/modpathol.2012.106 Epub Jul. 20, 2012.
Thunnissen et al., "Correlation of immunohistochemical staining p63 and TTF-1 with EGFR and K-ras mutational spectrum and diagnostic reproducibility in non small cell lung carcinoma," Virchows Arch 2012; 46(6)1:629-38.
Thunnissen et al., "Reproducibility of histopathological diagnosis in poorly differentiated NSCLC: an international multiobserver study," J Thorac Oncol 2014; 9(9): 1354-1362.
Tibshirani et al., "Diagnosis of multiple cancer types by shrunken centroids of gene expression," Proc. Natl. Acad. Sci. USA 99(10):6576-6572) (2002).
Tomida S., et al., "Relapse-related molecular signature in lung adenocarcinomas identifies patients with dismal prognosis," J Clin Oncol 27(17): 2793-99 (2009).
Trapnell et al., "Transcript assembly and quantification by RNA-Seq reveals unannotated transcripts and isoform switching during cell differentiation," Nature biotechnology 28(5):511-515 (2010).
Trapnell et al., "TopHat: discovering splice junctions with RNA-Seq.," Bioinformatics 25(9):1105-11 (2009).
Travis et al., "Diagnosis of lung cancer in small biopsies and cytology: implications of the 2011 International Association for the Study of Lung Cancer/American Thoracic Society/European Respiratory Society classification," Arch Pathol Lab Med 2013; 137(5):668-84.
Travis and Rekhtman, "Pathological diagnosis and classification of lung cancer in small biopsies and cytology: strategic management of tissue for molecular testing," Sem Resp and Crit Care Med 32(1): 22-31 (2011).
Travis et al., "International Association for the study of lung cancer/American Thoracic Society/European Respiratory Society International multidisciplinary classification of lung adenocarcinoma," J Thorac Oncol, 6:244-285 (2011).
Travis et al., "New pathologic classification of lung cancer: relevance for clinical practice and clinical trials," J Clin Oncol 31:992-1001 (2013).

(56) References Cited

OTHER PUBLICATIONS

Velculescu et al., "Characterization of the yeast transcriptome," Cell 88(2):243-251 (1997).
Velculescu et al., "Serial analysis of gene expression," Science 270(5235):484-487 (1995), retrieved from http://science.sciencemag.org/ on Oct. 29, 2018.
Vermeulen, Pediatric Primitive Neuroectodermal Tumors of the Central Nervous System Differentially Express Granzyme Inhibitors. PLoS One. 11(3):1-8 (2016).
Wilkerson et al., Lung Squamous Cell Carcinoma mRNA Expression Subtypes are Reproducible, Clinically Important and Correspond to Different Normal Cell Types. Clinical Clin Cancer Res 16(19):4864-4875 (2010).
Wilkerson et al., "Differential pathogenesis of lung adenocarcinoma subtypes involving sequence mutations, copy number, chromosomal instability, and methylation," PLoS ONE. 2012; 7(5) e36530. Doi:10.1371/joumal.pone.0036530, 13 pages.
Wilkerson et al., "Prediction of lung cancer histological types by RT-qPCR gene expression in FFPE specimens," J Molec Diagn 15(4):485-497 (2013).
Wilkerson, M.D. et al. Supplemental Figure S2, Journal of Molecular Diagnostics 15(4):485 (Jul. 2013; online May 22, 2013), 1 page.
Wistuba et al., "Validation of a proliferation-based expression signature as prognostic marker in early stage lung adenocarcinoma," Clin Cancer Res 19(22):6261-6271 (2013), Downloaded from clincancerres.aacrjournals.org on Oct. 10, 2018.
Wold, et al., "Genome expression and mRNA maturation at late stages of productive adenovirus type 2 infection," J Virol. Nov. 1976;20(2):465-77.
Wu and Wallace, "The ligation amplification reaction (LAR)—amplification of specific DNA sequences using sequential rounds of template dependent ligation.," Genomics, 4(4):560-569 (1989).
Yang et al, "Normalization for cDNA microarray data: a robust composite method addressing single and multiple slide systematic variation," Feb. 15, 2002;30(4):e15, 10 pages.
Zhang et al., "Assessment of VEGF-D Expression Measured by Immunohistochemical Staining and F-18 FDG Uptake on PET as Biological Prognostic Factors for Recurrence in Patients with Surgically Resected Lung Adenocarcinoma," Annals of Nuclear Medicine. 24(7):533-540 (2010).
Zhu CQ, et al., "Prognostic and predictive gene signature for adjuvant chemotherapy in resected non-small-cell lung cancer," J Clin Oncol 28(29); 4417-4424 (2010).
"Rare lung cancers," Breathe (Sheffield, England), 11(4):323-330 (2015).
Bhattacharjee et al., Classification of Human Lung Carcinomas by mRNA Expression Profiling Reveals Distinct Adenocarcinoma Subclasses, PNAS 98(24):13790-13795 (2001).
Charych et al., Intra-tumoral immune 1 cell mobilization and anti-tumor activity after treatment with the engineered cytokine NKTR-214 in multiple preclinical mouse tumor models, European Journal of Cancer vol. 69, Jan. 1, 2016, Poster (Board P132), No. 306, 1 page.
Extended European Search Report issued by the European Patent Office for Application No. 17800090.7, dated Jan. 27, 2020, 6pages.
Extended European Search Report issued by the European Patent Office for Application No. 17800091.5, dated Jan. 28, 2020, 7 pages.
Filosso et al., "Adenosquamous lung carcinomas: A histologic subtype with poor prognosis," Lung Cancer, 74(1):25-29 (2011).
Han et al., "RNA sequencing identifies novel markers of non-small cell lung cancer," Lung Cancer 84:229-23 (2014).
Hou et al., "Gene Expression-Based Classification of Non-Small Cell Lung Carcinomas and Survival Prediction," PLoS ONE. 2010. 6(4): e10312, p. 1-12 (2010).
Kuang et al., "The prognostic value of platelet endothelial cell adhesion molecule-I in non-small-cell lung cancer patients," Med. Oneal. 30:536 (2013).
Lee et al, "Multiregion gene expression profiling reveals heterogeneity in molecular subtypes and immunotherapy response signatures in lung cancer," Modern Pathology, Nature Publishing Group, GB, 31(6):947-955 (2018).

Lung Cancer Subtyping

FIG. 2

| Characteristic | TCGA[4] | Lee[8] | Raponi[9] | UNC[3] |
|---|---|---|---|---|
| Total # of samples | 501 | 75 | 129 | 56 |
| Tissue preservation | Fresh Frozen | Fresh Frozen | Fresh Frozen | Fresh Frozen |
| Subtype | | | | |
| basal | 137 | 13 | 35 | 12 |
| classical | 170 | 31 | 42 | 21 |
| primitive | 73 | 12 | 23 | 9 |
| secretory | 121 | 19 | 29 | 14 |
| Gender | | | | |
| Female/Male/NA | 125/363/13 | 5/70/0 | 47/82/0 | 24/32/0 |
| Age of diagnosis | | | | |
| Median/(Range) | 68/(39-90) | 65/(41-82) | 68/(42-91) | 67/(41-85) |
| Age not available | 22 | 0 | 0 | 0 |
| Stage | | | | |
| I | 241 | 0 | 73 | 34 |
| II | 152 | 0 | 33 | 19 |
| III | 85 | 0 | 23 | 3 |
| IV | 7 | 0 | 0 | 0 |
| Stage not available | 16 | 75 | 0 | 0 |
| Smoking ever | | | | |
| yes | 416 | 0 | 119 | 56 |
| no | 0 | 0 | 4 | 0 |
| Smoking status not available | 85 | 75 | 6 | 0 |

TCGA SQ n=501

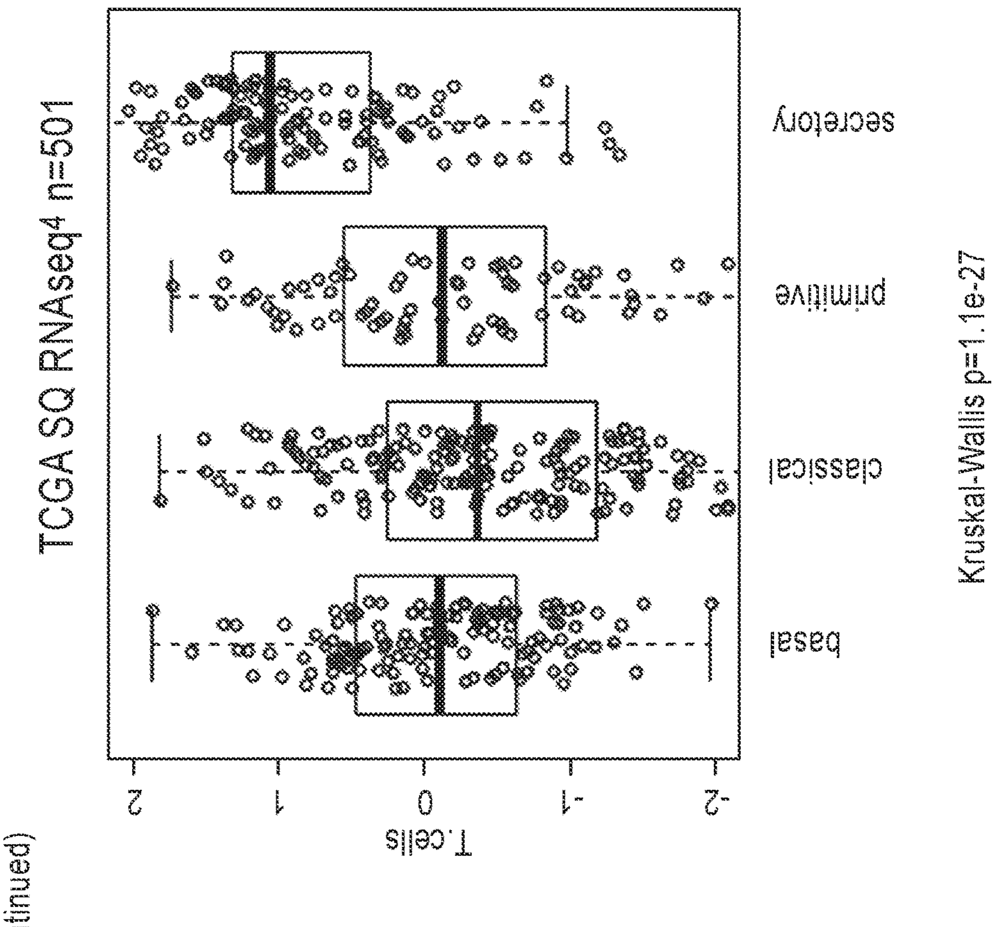
FIG. 5
(continued)
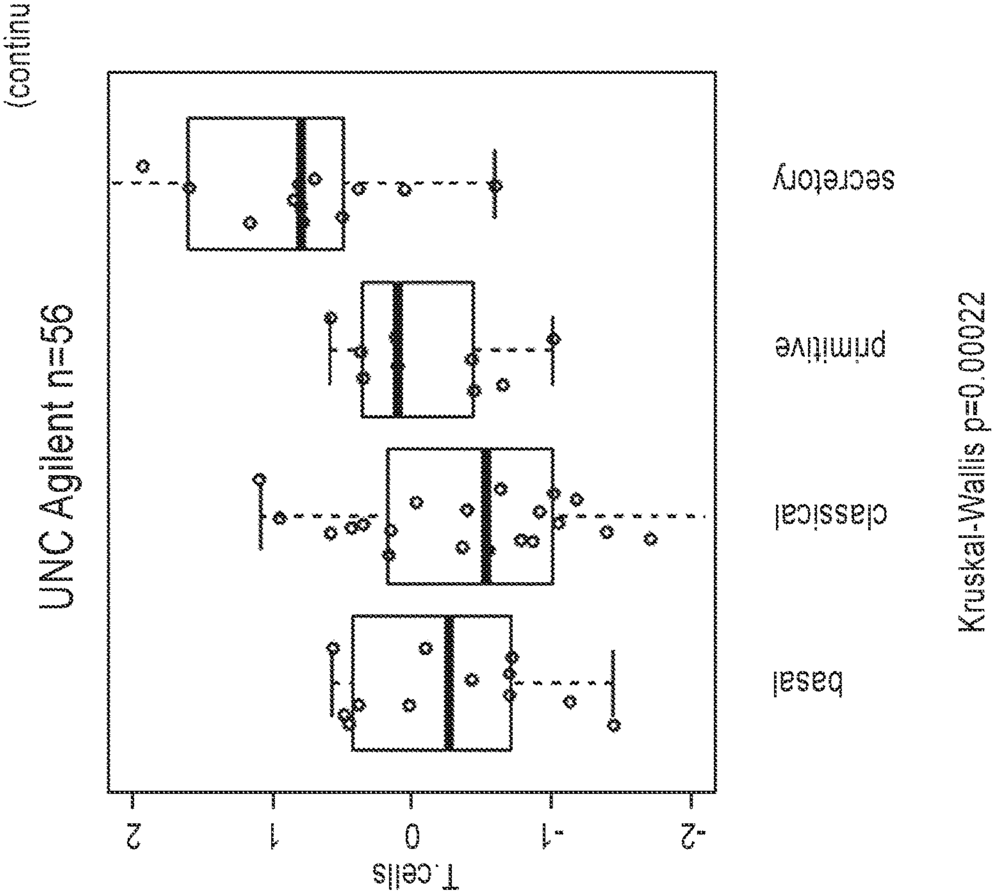

FIG. 16

Gold standard (rows) vs clanc80 (columns)

| | | basal | classical | primitive | secretory |
|---|---|---|---|---|---|
| Lee | basal | 13 | 0 | 0 | 0 |
| | classical | 2 | 29 | 0 | 0 |
| | primitive | 1 | 3 | 8 | 0 |
| | secretory | 5 | 1 | 0 | 13 |
| Raponi | basal | 35 | 0 | 0 | 0 |
| | classical | 0 | 42 | 0 | 0 |
| | primitive | 0 | 2 | 18 | 3 |
| | secretory | 4 | 0 | 3 | 23 |
| GeneCentric FFPE | basal | 8 | 0 | 0 | 0 |
| | classical | 1 | 15 | 2 | 0 |
| | primitive | 0 | 0 | 5 | 0 |
| | secretory | 1 | 0 | 2 | 12 |
| TCGA | basal | 130 | 3 | 1 | 3 |
| | classical | 4 | 165 | 1 | 0 |
| | primitive | 2 | 6 | 56 | 9 |
| | secretory | 13 | 4 | 12 | 92 |
| UNC | basal | 12 | 0 | 0 | 0 |
| | classical | 1 | 20 | 0 | 0 |
| | primitive | 0 | 2 | 7 | 0 |
| | secretory | 3 | 0 | 0 | 11 |

Agreement

| | Lee | Raponi | GeneCentric FFPE | TCGA | UNC |
|---|---|---|---|---|---|
| Agree | 0.84 | 0.91 | 0.87 | 0.88 | 0.89 |

TCGA SQ n=501

SEQUENCE LISTING

```
<160> NUMBER OF SEQ ID NOS: 80

<210> SEQ ID NO 1
<211> LENGTH: 1787
<212> TYPE: DNA
<213> ORGANISM: Homo sapiens

<400> SEQUENCE: 1

aaccacagag ggaaaggcag caagaggaga ggcataaatt taggatctca cccttcattc      60

cacagacaca cacagcctct ctgcccacct ctgcttcctc taggaacaca ggagttccag     120

atcacatcga gttcaccatg aattcactca gtgaagccaa caccaagttc atgttcgatc     180

tgttccaaca gttcagaaaa tcaaaagaga acaacatctt ctattcccct atcagcatca     240

catcagcatt agggatggtc ctcttaggag ccaaagacaa cactgcacaa caaattagca     300

aggttcttca ctttgatcaa gtcacagaga acaccacaga aaaagctgca acatatcatg     360

ttgataggtc aggaaatgtt catcaccagt ttcaaaagct tctgactgaa ttcaacaaat     420
```

ccactgatgc atatgagctg aagatcgcca acaagctctt cggagaaaag acgtatcaat 480
ttttacagga atatttagat gccatcaaga aattttacca gaccagtgtg gaatctactg 540
attttgcaaa tgctccagaa gaaagtcgaa agaagattaa ctcctgggtg gaaagtcaaa 600
cgaatgaaaa aattaaaaac ctatttcctg atgggactat tggcaatgat acgacactgg 660
ttcttgtgaa cgcaatctat ttcaaagggc agtgggagaa taaatttaaa aaagaaaaca 720
ctaaagagga aaaattttgg ccaaacaaga atacatacaa atctgtacag atgatgaggc 780
aatacaattc ctttaatttt gccttgctgg aggatgtaca ggccaaggtc ctggaaatac 840
catacaaagg caaagatcta agcatgattg tgctgctgcc aaatgaaatc gatggtctgc 900
agaagcttga agagaaactc actgctgaga aattgatgga atggacaagt ttgcagaata 960
tgagagagac atgtgtcgat ttacacttac ctcggttcaa aatggaagag agctatgacc 1020
tcaaggacac gttgagaacc atgggaatgg tgaatatctt caatggggat gcagacctct 1080
caggcatgac ctggagccac ggtctctcag tatctaaagt cctacacaag gcctttgtgg 1140
aggtcactga ggagggagtg gaagctgcag ctgccaccgc tgtagtagta gtcgaattat 1200
catctccttc aactaatgaa gagttctgtt gtaatcaccc tttcctattc ttcataaggc 1260
aaaataagac caacagcatc ctcttctatg gcagattctc atccccatag atgcaattag 1320
tctgtcactc catttagaaa atgttcacct agaggtgttc tggtaaactg attgctggca 1380
acaacagatt ctcttggctc atatttcttt tctatctcat cttgatgatg atagtcatca 1440
tcaagaattt aatgattaaa atagcatgcc tttctctctt tctcttaata agcccacata 1500
taaatgtact tttccttcca gaaaaatttc ccttgaggaa aaatgtccaa gataagatga 1560
atcatttaat accgtgtctt ctaaatttga aatataattc tgtttctgac ctgttttaaa 1620
tgaaccaaac caaatcatac tttctcttca aatttagcaa cctagaaaca cacatttctt 1680
tgaatttagg tgatacctaa atccttctta tgtttctaaa ttttgtgatt ctataaaaca 1740
catcatcaat aaaataatga cataaaatca aaaaaaaaaa aaaaaaa 1787

<210> SEQ ID NO 2
<211> LENGTH: 1184
<212> TYPE: DNA
<213> ORGANISM: Homo sapiens

<400> SEQUENCE: 2
cacagagccc gggccgcagg cacctcctcg ccagctcttc cgctcctctc acagccgcca 60
gacccgcctg ctgagcccca tggcccgcgc tgctctctcc gccgccccca gcaatccccg 120
gctcctgcga gtggcactgc tgctcctgct cctggtagcc gctggccggc gcgcagcagg 180
agcgtccgtg gccactgaac tgcgctgcca gtgcttgcag accctgcagg gaattcaccc 240
caagaacatc caaagtgtga acgtgaagtc ccccggaccc cactgcgccc aaaccgaagt 300
catagccaca ctcaagaatg ggcggaaagc ttgcctcaat cctgcatccc ccatagttaa 360
gaaaatcatc gaaaagatgc tgaacagtga caaatccaac tgaccagaag ggaggaggaa 420
gctcactggt ggctgttcct gaaggaggcc ctgcccttat aggaacagaa gaggaaagag 480
agacacagct gcagaggcca cctggattgt gcctaatgtg tttgagcatc gcttaggaga 540
agtcttctat ttatttattt attcattagt tttgaagatt ctatgttaat attttaggtg 600
taaaataatt aagggtatga ttaactctac ctgcacactg tcctattata ttcattcttt 660
ttgaaatgtc aaccccaagt tagttcaatc tggattcata tttaatttga aggtagaatg 720

-continued

```
ttttcaaatg ttctccagtc attatgttaa tatttctgag gagcctgcaa catgccagcc    780

actgtgatag aggctggcgg atccaagcaa atggccaatg agatcattgt gaaggcaggg    840

gaatgtatgt gcacatctgt tttgtaactg tttagatgaa tgtcagttgt tatttattga    900

aatgatttca cagtgtgtgg tcaacatttc tcatgttgaa actttaagaa ctaaaatgtt    960

ctaaatatcc cttggacatt ttatgtcttt cttgtaaggc atactgcctt gtttaatggt   1020

agttttacag tgtttctggc ttagaacaaa ggggcttaat tattgatgtt ttcatagaga   1080

atataaaaat aaagcactta tagaaaaaac tcgtttgatt tttgggggga aacaagggct   1140

acctttactg gaaaatctgg tgatttataa aaaaaaaaaa aaaa                    1184
```

<210> SEQ ID NO 3
<211> LENGTH: 586
<212> TYPE: DNA
<213> ORGANISM: Homo sapiens

<400> SEQUENCE: 3

```
aaacactctg tgtggctcct cggctttgac agagtgcaag acgatgactt gcaaaatgtc     60

gcagctggaa cgcaacatag agaccatcat caacaccttc caccaatact ctgtgaagct    120

ggggcaccca gacaccctga accaggggga attcaaagag ctggtgcgaa aagatctgca    180

aaattttctc aagaaggaga ataagaatga aaaggtcata gaacacatca tggaggacct    240

ggacacaaat gcagacaagc agctgagctt cgaggagttc atcatgctga tggcgaggct    300

aacctgggcc tcccacgaga agatgcacga gggtgacgag ggccctggcc accaccataa    360

gccaggcctc ggggagggca ccccctaaga ccacagtggc caagatcaca gtggccacgg    420

ccacggccac agtcatggtg gccacggcca cagccactaa tcaggaggcc aggccaccct    480

gcctctaccc aaccagggcc ccggggcctg ttatgtcaaa ctgtcttggc tgtggggcta    540

ggggctgggg ccaaataaag tctcttcctc caagtcaaaa aaaaaa                    586
```

<210> SEQ ID NO 4
<211> LENGTH: 549
<212> TYPE: DNA
<213> ORGANISM: Homo sapiens

<400> SEQUENCE: 4

```
gagaaaccag agactgtagc aactctggca gggagaagct gtctctgatg gcctgaagct     60

gtgggcagct ggccaagcct aaccgctata aaaaggagct gcctctcagc cctgcatgtc    120

tcttgtcagc tgtctttcag aagacctgaa ggttctgttt ttcaggtggg gcaagtccgt    180

gggcatcatg ttgaccgagc tggagaaagc cttgaactct atcatcgacg tctaccacaa    240

gtactccctg ataaagggga atttccatgc cgtctacagg gatgacctga agaaattgct    300

agagaccgag tgtcctcagt atatcaggaa aaagggtgca gacgtctggt tcaaagagtt    360

ggatatcaac actgatggtg cagttaactt ccaggagttc ctcattctgg tgataaagat    420

gggcgtggca gcccacaaaa aaagccatga agaaagccac aaagagtagc tgagttactg    480

ggcccagagg ctgggcccct ggacatgtac ctgcagaata ataaagtcat caatacctca    540

aaaaaaaaa                                                            549
```

<210> SEQ ID NO 5
<211> LENGTH: 1793
<212> TYPE: DNA
<213> ORGANISM: Homo sapiens

<400> SEQUENCE: 5

```
aaatactaac cacagaggga gaggcagcaa gaggagaggc ataaattcag gatctcaccc     60
ttcattccac agacacacat agcctctctg cccacctctg cttcctctag gaacacagga    120
gttccagatc acatcgagtt caccatgaat tcactcagtg aagccaacac caagttcatg    180
ttcgacctgt tccaacagtt cagaaaatca aaagagaaca acatcttcta ttcccctatc    240
agcatcacat cagcattagg gatggtcctc ttaggagcca aagacaacac tgcacaacag    300
attaagaagg ttcttcactt tgatcaagtc acagagaaca ccacaggaaa agctgcaaca    360
tatcatgttg ataggtcagg aaatgttcat caccagtttc aaaagcttct gactgaattc    420
aacaaatcca ctgatgcata tgagctgaag atcgccaaca agctcttcgg agaaaaaacg    480
tatctatttt tacaggaata tttagatgcc atcaagaaat tttaccagac cagtgtggaa    540
tctgttgatt ttgcaaatgc tccagaagaa agtcgaaaga agattaactc ctgggtggaa    600
agtcaaacga atgaaaaaat taaaaaccta attcctgaag gtaatattgg cagcaatacc    660
acattggttc ttgtgaacgc aatctatttc aaagggcagt gggagaagaa atttaataaa    720
gaagatacta aagaggaaaa attttggcca aacaagaata catacaagtc catacagatg    780
atgaggcaat acacatcttt tcattttgcc tcgctggagg atgtacaggc caaggtcctg    840
gaaataccat acaaaggcaa agatctaagc atgattgtgt tgctgccaaa tgaaatcgat    900
ggtctccaga agcttgaaga gaaactcact gctgagaaat tgatggaatg gacaagtttg    960
cagaatatga gagagacacg tgtcgattta cacttacctc ggttcaaagt ggaagagagc   1020
tatgacctca aggacacgtt gagaaccatg ggaatggtgg atatcttcaa tggggatgca   1080
gacctctcag gcatgaccgg gagccgcggt ctcgtgctat ctggagtcct acacaaggcc   1140
tttgtggagg ttacagagga gggagcagaa gctgcagctg ccaccgctgt agtaggattc   1200
ggatcatcac ctacttcaac taatgaagag ttccattgta atcacccttt cctattcttc   1260
ataaggcaaa ataagaccaa cagcatcctc ttctatggca gattctcatc cccgtagatg   1320
caattagtct gtcactccat ttggaaaatg ttcacctgca gatgttctgg taaactgatt   1380
gctggcaaca acagattctc ttggctcata tttctttttct ttctcatctt gatgatgatc   1440
gtcatcatca agaatttaat gattaaaata gcatgccttt ctctctttct cttaataagc   1500
ccacatataa atgtactttt tcttccagaa aaattctcct tgaggaaaaa tgtccaaaat   1560
aagatgaatc acttaatacc gtatcttcta aatttgaaat ataattctgt ttgtgacctg   1620
ttttaaatga accaaaccaa atcatacttt ttctttgaat ttagcaacct agaaacacac   1680
atttctttga atttaggtga tacctaaatc cttcttatgt ttctaaattt tgtgattcta   1740
taaaacacat catcaataaa atagtgacat aaaatcaaaa aaaaaaaaaa aaa          1793
```

<210> SEQ ID NO 6
<211> LENGTH: 3992
<212> TYPE: DNA
<213> ORGANISM: Homo sapiens

<400> SEQUENCE: 6

```
agggcatgaa tgaacaggag tcggttctca cccaacttcc attaaggact cggggcagga     60
ggggcagaag ttgcgcgcag gccggcgggc gggagcggac accgaggccg gcgtgcaggc    120
gtgcgggtgt gcgggagccg ggctcggggg gatcggaccg agagcgagaa gcgcggcatg    180
gagctccagg cagcccgcgc ctgcttcgcc ctgctgtggg gctgtgcgct ggccgcggcc    240
gcggcggcgc agggcaagga agtggtactg ctggactttg ctgcagctgg aggggagctc    300
```

-continued

```
ggctggctca cacacccgta tggcaaaggg tgggacctga tgcagaacat catgaatgac    360
atgccgatct acatgtactc cgtgtgcaac gtgatgtctg gcgaccagga caactggctc    420
cgcaccaact gggtgtaccg aggagaggct gagcgtatct tcattgagct caagtttact    480
gtacgtgact gcaacagctt ccctggtggc gccagctcct gcaaggagac tttcaacctc    540
tactatgccg agtcggacct ggactacggc accaacttcc agaagcgcct gttcaccaag    600
attgacacca ttgcgcccga tgagatcacc gtcagcagcg acttcgaggc acgccacgtg    660
aagctgaacg tggaggagcg ctccgtgggg ccgctcaccc gcaaaggctt ctacctggcc    720
ttccaggata tcggtgcctg tgtggcgctg ctctccgtcc gtgtctacta caagaagtgc    780
cccgagctgc tgcagggcct ggcccacttc cctgagacca tcgccggctc tgatgcacct    840
tccctggcca ctgtggccgg cacctgtgtg gaccatgccg tggtgccacc gggggtgaa     900
gagccccgta tgcactgtgc agtggatggc gagtggctgg tgcccattgg gcagtgcctg    960
tgccaggcag gctacgagaa ggtggaggat gcctgccagg cctgctcgcc tggatttttt   1020
aagtttgagg catctgagag cccctgcttg gagtgccctg agcacacgct gccatcccct   1080
gagggtgcca cctcctgcga gtgtgaggaa ggcttcttcc gggcacctca ggacccagcg   1140
tcgatgcctt gcacacgacc cccctccgcc ccacactacc tcacagccgt gggcatgggt   1200
gccaaggtgg agctgcgctg gacgcccccct caggacagcg gggccgcgga ggacattgtc  1260
tacagcgtca cctgcgaaca gtgctggccc gagtctgggg aatgcgggcc gtgtgaggcc   1320
agtgtgcgct actcggagcc tcctcacgga ctgacccgca ccagtgtgac agtgagcgac   1380
ctggagcccc acatgaacta caccttcacc gtggaggccc gcaatggcgt ctcaggcctg   1440
gtaaccagcc gcagcttccg tactgccagt gtcagcatca accagacaga gcccccccaag  1500
gtgaggctgg agggccgcag caccacctcg cttagcgtct cctggagcat cccccccgccg  1560
cagcagagcc gagtgtggaa gtacgaggtc acttaccgca agaagggaga ctccaacagc   1620
tacaatgtgc gccgcaccga gggtttctcc gtgaccctgg acgacctggc cccagacacc   1680
acctacctgg tccaggtgca ggcactgacg caggagggcc agggggccgg cagcaaggtg   1740
cacgaattcc agacgctgtc cccggaggga tctggcaact tggcggtgat tggcggcgtg   1800
gctgtcggtg tggtcctgct tctggtgctg gcaggagttg gcttctttat ccaccgcagg   1860
aggaagaacc agcgtgcccg ccagtccccg gaggacgttt acttctccaa gtcagaacaa   1920
ctgaagcccc tgaagacata cgtggacccc cacacatatg aggaccccaa ccaggctgtg   1980
ttgaagttca ctaccgagat ccatccatcc tgtgtcactc ggcagaaggt gatcggagca   2040
ggagagtttg gggaggtgta caagggcatg ctgaagacat cctcggggaa gaaggaggtg   2100
ccggtggcca tcaagacgct gaaagccggc tacacagaga agcagcgagt ggacttcctc   2160
ggcgaggccg gcatcatggg ccagttcagc caccacaaca tcatccgcct agagggcgtc   2220
atctccaaat acaagcccat gatgatcatc actgagtaca tggagaatgg ggccctggac   2280
aagttccttc gggagaagga tggcgagttc agcgtgctgc agctggtggg catgctgcgg   2340
ggcatcgcag ctggcatgaa gtacctggcc aacatgaact atgtgcaccg tgacctggct   2400
gcccgcaaca tcctcgtcaa cagcaacctg gtctgcaagg tgtctgactt tggcctgtcc   2460
cgcgtgctgg aggacgaccc cgaggccacc tacaccacca gtggcggcaa gatccccatc   2520
cgctggaccg ccccggaggc catttcctac cggaagttca cctctgccag cgacgtgtgg   2580
agctttggca ttgtcatgtg ggaggtgatg acctatggcg agcggcccta ctgggagttg   2640
tccaaccacg aggtgatgaa agccatcaat gatggcttcc ggctccccac acccatggac   2700
```

tgcccctccg ccatctacca gctcatgatg cagtgctggc agcaggagcg tgcccgccgc 2760
cccaagttcg ctgacatcgt cagcatcctg gacaagctca ttcgtgcccc tgactccctc 2820
aagaccctgg ctgactttga cccccgcgtg tctatccggc tccccagcac gagcggctcg 2880
gagggggtgc ccttccgcac ggtgtccgag tggctggagt ccatcaagat gcagcagtat 2940
acggagcact tcatggcggc cggctacact gccatcgaga aggtggtgca gatgaccaac 3000
gacgacatca agaggattgg ggtgcggctg cccggccacc agaagcgcat cgcctacagc 3060
ctgctgggac tcaaggacca ggtgaacact gtggggatcc ccatctgagc ctcgacaggg 3120
cctggagccc catcggccaa gaatacttga agaaacagag tggcctccct gctgtgccat 3180
gctgggccac tggggacttt atttatttct agttctttcc tccccctgca acttccgctg 3240
aggggtctcg gatgacaccc tggcctgaac tgaggagatg accagggatg ctgggctggg 3300
ccctctttcc ctgcgagacg cacacagctg agcacttagc aggcaccgcc acgtcccagc 3360
atccctggag caggagcccc gccacagcct tcggacagac atatgggata ttcccaagcc 3420
gaccttccct ccgccttctc ccacatgagg ccatctcagg agatggaggg cttggcccag 3480
cgccaagtaa acagggtacc tcaagcccca tttcctcaca ctaagagggc agactgtgaa 3540
cttgactggg tgagacccaa agcggtccct gtccctctag tgccttcttt agaccctcgg 3600
gccccatcct catccctgac tggccaaacc cttgctttcc tgggcctttg caagatgctt 3660
ggttgtgttg aggtttttaa atatatattt tgtactttgt ggagagaatg tgtgtgtgtg 3720
gcagggggcc ccgccagggc tggggacaga gggtgtcaaa cattcgtgag ctggggactc 3780
agggaccggt gctgcaggag tgtcctgccc atgccccagt cggccccatc tctcatcctt 3840
ttggataagt ttctattctg tcagtgttaa agattttgtt ttgttggaca ttttttttcga 3900 atcttaattt attatttttt ttatatttat tgttagaaaa tgacttattt ctgctctgga 3960
ataaagttgc agatgattca aaccgaaaaa aa 3992

<210> SEQ ID NO 7
<211> LENGTH: 970
<212> TYPE: DNA
<213> ORGANISM: Homo sapiens

<400> SEQUENCE: 7
ctcccctcac cccggtccag gatgcccagt ccccacgaca cctcccactt cccactgtgg 60
cctgggtggg ctcaggggct gcccttgacc tggcctagag ccctccccca gctggtggtg 120
gagctggcac tctctgggag ggaggggct gggagggaat gagtgggaat ggcaagaggc 180
cagggtttgg tgggatcagg ttgaggcagg tttggtttcc ttaaaatgcc aagttggggg 240
ccagtggggc ccacatataa atcctcaccc tgggagcctg gctgccttgc tctccttcct 300
gggtctgtct ctgccacctg gtctgccaca gatccatgat gtgcagttct ctggagcagg 360
cgctggctgt gctggtcact accttccaca agtactcctg ccaagagggc gacaagttca 420
agctgagtaa gggggaaatg aaggaacttc tgcacaagga gctgcccagc tttgtggggg 480
agaaagtgga tgaggagggg ctgaagaagc tgatgggcag cctggatgag aacagtgacc 540
agcaggtgga cttccaggag tatgctgttt tcctggcact catcactgtc atgtgcaatg 600
acttcttcca gggctgccca gaccgaccct gaagcagaac tcttgacttc ctgccatgga 660
tctcttgggc ccaggactgt tgatgccttt gagttttgta ttcaataaac ttttttttgtc 720 tgttgataat attttaattg ctcagtgatg ttccataacc cggctggctc agctggagtg 780
ctgggagatg agggcctcct ggatcctgct cccttctggg ctctgactct cctggaaatc 840
tctccaaggc cagagctatg ctttaggtct caattttgga atttcaaaca ccagcaaaaa 900
attggaaatc gagataggtt gctgactttt attttgtcaa ataaagatat taaaaaaggc 960
aaaaaaaaaa 970

<210> SEQ ID NO 8
<211> LENGTH: 1777
<212> TYPE: DNA
<213> ORGANISM: Homo sapiens

<400> SEQUENCE: 8
agaagcccag tagacaaaga aggtaagggc agtgagaatg atgcatcttg cattccttgt 60
gctgttgtgt ctgccagtct gctctgccta tcctctgagt ggggcagcaa aagaggagga 120
ctccaacaag gatcttgccc agcaatacct agaaaagtac tacaacctcg aaaaggatgt 180
gaaacagttt agaagaaagg acagtaatct cattgttaaa aaaatccaag gaatgcagaa 240
gttccttggg ttggaggtga cagggaagct agacactgac actctggagg tgatgcgcaa 300
gcccaggtgt ggagttcctg acgttggtca cttcagctcc tttcctggca tgccgaagtg 360
gaggaaaacc caccttacat acaggattgt gaattataca ccagatttgc caagagatgc 420
tgttgattct gccattgaga aagctctgaa agtctgggaa gaggtgactc cactcacatt 480
ctccaggctg tatgaaggag aggctgatat aatgatctct tttgcagtta aagaacatgg 540
agacttttac tcttttgatg gcccaggaca cagtttggct catgcctacc cacctggacc 600
tgggctttat ggagatattc actttgatga tgatgaaaaa tggacagaag atgcatcagg 660
caccaattta ttcctcgttg ctgctcatga acttggccac tccctggggc tctttcactc 720
agccaacact gaagctttga tgtacccact ctacaactca ttcacagagc tcgcccagtt 780
ccgcctttcg caagatgatg tgaatggcat tcagtctctc tacggacctc cccctgcctc 840
tactgaggaa cccctggtgc ccacaaaatc tgttccttcg ggatctgaga tgccagccaa 900
gtgtgatcct gctttgtcct tcgatgccat cagcactctg aggggagaat atctgttctt 960
taaagacaga tatttttggc gaagatccca ctggaaccct gaacctgaat ttcatttgat 1020
ttctgcattt tggccctctc ttccatcata tttggatgct gcatatgaag ttaacagcag 1080
ggacaccgtt tttattttta aaggaaatga gttctgggcc atcagaggaa atgaggtaca 1140
agcaggttat ccaagaggca tccataccct gggttttcct ccaaccataa ggaaaattga 1200
tgcagctgtt tctgacaagg aaaagaagaa aacatacttc tttgcagcgg acaaatactg 1260
gagatttgat gaaaatagcc agtccatgga gcaaggcttc cctagactaa tagctgatga 1320
ctttccagga gttgagccta aggttgatgc tgtattacag gcatttggat ttttctactt 1380
cttcagtgga tcatcacagt ttgagtttga ccccaatgcc aggatggtga cacacatatt 1440
aaagagtaac agctggttac attgctaggc gagatagggg gaagacagat atgggtgttt 1500
ttaataaatc taataattat tcatctaatg tattatgagc caaaatggtt aatttttcct 1560
gcatgttctg tgactgaaga agatgagcct tgcagatatc tgcatgtgtc atgaagaatg 1620
tttctggaat tcttcacttg cttttgaatt gcactgaaca gaattaagaa atactcatgt 1680
gcaataggtg agagaatgta ttttcataga tgtgttatta cttcctcaat aaaaagtttt 1740
attttgggcc tgttccttaa aaaaaaaaaa aaaaaaa 1777

<210> SEQ ID NO 9
<211> LENGTH: 3710

-continued

<212> TYPE: DNA
<213> ORGANISM: Homo sapiens

<400> SEQUENCE: 9
gggtctccgc gcccaggaaa gccccgcgcg gcgcgggcca gggaagggcc acccaggggt 60
cccccacttc ccgcttgggc gcccggacgg cgaatggagc aggggcgcgc agataattaa 120
agatttacac acagctggaa gaaatcatag agaagccggg cgtggtggct catgcctata 180
atcccagcac ttttggaggc tgaggcgggc agatcacttg agatcaggag ttcgagacca 240
gcctggtgcc ttggcatctc ccaatggggt ggctttgctc tgggctcctg ttccctgtga 300
gctgcctggt cctgctgcag gtggcaagct ctgggaacat gaaggtcttg caggagccca 360
cctgcgtctc cgactacatg agcatctcta cttgcgagtg gaagatgaat ggtcccacca 420
attgcagcac cgagctccgc ctgttgtacc agctggtttt tctgctctcc gaagcccaca 480
cgtgtatccc tgagaacaac ggaggcgcgg ggtgcgtgtg ccacctgctc atggatgacg 540
tggtcagtgc ggataactat acactggacc tgtgggctgg gcagcagctg ctgtggaagg 600
gctccttcaa gcccagcgag catgtgaaac ccagggcccc aggaaacctg acagttcaca 660
ccaatgtctc cgacactctg ctgctgacct ggagcaaccc gtatcccct gacaattacc 720 tgtataatca tctcacctat gcagtcaaca tttggagtga aaacgacccg gcagatttca 780
gaatctataa cgtgacctac ctagaaccct ccctccgcat cgcagccagc accctgaagt 840
ctgggatttc ctacagggca cgggtgaggg cctgggctca gtgctataac accacctgga 900
gtgagtggag ccccagcacc aagtggcaca actcctacag ggagcccttc gagcagcacc 960
tcctgctggg cgtcagcgtt tcctgcattg tcatcctggc cgtctgcctg ttgtgctatg 1020
tcagcatcac caagattaag aaagaatggt gggatcagat tcccaaccca gcccgcagcc 1080
gcctcgtggc tataataatc caggatgctc aggggtcaca gtgggagaag cggtcccgag 1140
gccaggaacc agccaagtgc ccacactgga agaattgtct taccaagctc ttgccctgtt 1200
ttctggagca caacatgaaa agggatgaag atcctcacaa ggctgccaaa gagatgcctt 1260
tccagggctc tggaaaatca gcatggtgcc cagtggagat cagcaagaca gtcctctggc 1320
cagagagcat cagcgtggtg cgatgtgtgg agttgtttga ggccccggtg gagtgtgagg 1380
aggaggagga ggtagaggaa gaaaaaggga gcttctgtgc atcgcctgag agcagcaggg 1440
atgacttcca ggagggaagg gagggcattg tggcccggct aacagagagc ctgttcctgg 1500
acctgctcgg agaggagaat gggggctttt gccagcagga catgggggag tcatgccttc 1560
ttccaccttc gggaagtacg agtgctcaca tgccctggga tgagttccca agtgcagggc 1620
ccaaggaggc acctccctgg ggcaaggagc agcctctcca cctggagcca agtcctcctg 1680
ccagcccgac ccagagtcca gacaacctga cttgcacaga gacgcccctc gtcatcgcag 1740
gcaaccctgc ttaccgcagc ttcagcaact ccctgagcca gtcaccgtgt cccagagagc 1800
tgggtccaga cccactgctg gccagacacc tggaggaagt agaacccgag atgccctgtg 1860
tcccccagct ctctgagcca accactgtgc cccaacctga gccagaaacc tgggagcaga 1920
tcctccgccg aaatgtcctc cagcatgggg cagctgcagc cccccgtctcg gcccccacca 1980 gtggctatca ggagtttgta catgcggtgg agcagggtgg cacccaggcc agtgcggtgg 2040
tgggcttggg tcccccagga gaggctggtt acaaggcctt ctcaagcctg cttgccagca 2100
gtgctgtgtc cccagagaaa tgtgggtttg gggctagcag tggggaagag gggtataagc 2160
ctttccaaga cctcattcct ggctgccctg ggggaccctgc cccagtccct gtccccttgt 2220

-continued tcacctttgg actggacagg gagccacctc gcagtccgca gagctcacat ctcccaagca 2280
gctccccaga gcacctgggt ctggagccgg gggaaaaggt agaggacatg ccaaagcccc 2340
cacttcccca ggagcaggcc acagaccccc ttgtggacag cctgggcagt ggcattgtct 2400
actcagccct tacctgccac ctgtgcggcc acctgaaaca gtgtcatggc caggaggatg 2460
gtggccagac ccctgtcatg gccagtcctt gctgtggctg ctgctgtgga gacaggtcct 2520
cgccccctac aaccccccctg agggccccag acccctctcc aggtggggtt ccactggagg 2580
ccagtctgtg tccggcctcc ctggcaccct cgggcatctc agagaagagt aaatcctcat 2640
catccttcca tcctgcccct ggcaatgctc agagctcaag ccagaccccc aaaatcgtga 2700
actttgtctc cgtgggaccc acatacatga gggtctctta ggtgcatgtc ctcttgttgc 2760
tgagtctgca gatgaggact agggcttatc catgcctggg aaatgccacc tcctggaagg 2820
cagccaggct ggcagatttc caaaagactt gaagaaccat ggtatgaagg tgattggccc 2880
cactgacgtt ggcctaacac tgggctgcag agactggacc ccgcccagca ttgggctggg 2940
ctcgccacat cccatgagag tagagggcac tgggtcgccg tgccccacgg caggcccctg 3000
caggaaaact gaggcccttg ggcacctcga cttgtgaacg agttgttggc tgctccctcc 3060
acagcttctg cagcagactg tccctgttgt aactgcccaa ggcatgtttt gcccaccaga 3120
tcatggccca cgtggaggcc cacctgcctc tgtctcactg aactagaagc cgagcctaga 3180
aactaacaca gccatcaagg gaatgacttg ggcggccttg ggaaatcgat gagaaattga 3240
acttcaggga gggtggtcat tgcctagagg tgctcattca tttaacagag cttccttagg 3300
ttgatgctgg aggcagaatc ccggctgtca aggggtgttc agttaagggg agcaacagag 3360
gacatgaaaa attgctatga ctaaagcagg gacaatttgc tgccaaacac ccatgcccag 3420
ctgtatggct gggggctcct cgtatgcatg gaacccccag aataaatatg ctcagccacc 3480
ctgtgggccg ggcaatccag acagcaggca taaggcacca gttaccctgc atgttggccc 3540
agacctcagg tgctagggaa ggcgggaacc ttgggttgag taatgctcgt ctgtgtgttt 3600
tagtttcatc acctgttatc tgtgtttgct gaggagagtg gaacagaagg ggtggagttt 3660
tgtataaata aagtttcttt gtctctttaa aaaaaaaaaa aaaaaaaaaa 3710

<210> SEQ ID NO 10
<211> LENGTH: 894
<212> TYPE: DNA
<213> ORGANISM: Homo sapiens

<400> SEQUENCE: 10
gcccgtcttc gtgtctcctc cctccctcgc cttcctcctt cctagctcct ctcctccagg 60
gccagactga gcccaggttg atttcaggcg gacaccaata gactccacag cagctccagg 120
agcccagaca ccggcggcca gaagcaaggc taggagctgc tgcagccatg tcggccctca 180
gcctcctcat tctgggcctg ctcacggcag tgccacctgc cagctgtcag caaggcctgg 240
ggaaccttca gccctggatg cagggcctta tcgcggtggc cgtgttcctg gtcctcgttg 300
caatcgcctt tgcagtcaac cacttctggt gccaggagga gccggagcct gcacacatga 360
tcctgaccgt cggaaacaag gcagatggag tcctggtggg aacagatgga aggtactctt 420
cgatggcggc cagtttcagg tccagtgagc atgagaatgc ctatgagaat gtgcccgagg 480
aggaaggcaa ggtccgcagc accccgatgt aaccttctct gtggctccaa ccccaagact 540
cccaggcaca tgggatggat gtccagtgct accacccaag ccccctcctt ctttgtgtgg 600
aatctgcaat agtgggctga ctccctccag ccccatgccg gccctacccg cccttgaagt 660
atagccagcc aaggttggag ctcagaccgt gtctaggttg gggctcggct gtggccctgg 720
ggtctcctgc tcagctcaga agagccttct ggagaggaca gtcagctgag cacctcccat 780
cctgctcaca cgtccttccc cataactatg gaaatggccc taatttctgt gaaataaaga 840
ctttttgtat ttctggggct gaggctcagc aacagcccct caggcttcca gtga 894

<210> SEQ ID NO 11
<211> LENGTH: 6242
<212> TYPE: DNA
<213> ORGANISM: Homo sapiens

<400> SEQUENCE: 11
ctcgtttccg taggaagaag cgccgggaaa gatggcggcg tctgtggttt gaattccagc 60
ggcgccgcca gagtctgaac aagagctggg gtggaggggg cggggacctg ggagcccgg 120 cgggtcgcta tcgcgggggg tactagtggc gccgccgcca cagacaccaa cgctgtcgcc 180
acctctgtag ccatgatgga cttggtgttg gaagaggacg tcaccgtccc tgggacgctc 240
agcggctgca gtggccttgt tcccagtgta ccagatgacc tggatggcat caaccccaat 300
gctgggttgg gaaatggtct gctcccaaat gtgtcagaag aaacagtgtc tcccaccaga 360
gcacggaaca tgaaggactt tgaaaatcaa atcactgaat tgaagaaaga aaactttaac 420
ctaaagctcc gcatctattt ccttgaggaa agaatgcaac aggaatttca tggccccact 480
gaacatatct acaaaactaa cattgagctc aaggtggaag tagaaagtct gaagcgggaa 540
ctccaggaga gagagcagct gctcatcaaa gcctccaaag cagttgagag cttagctgaa 600
gcaggtggct ctgaaatcca gcgggtgaaa gaagatgctc gaaagaaggt gcagcaggtg 660
gaagatctcc taactaaaag aatactcctt ttggaaaagg atgtgacagc cgcccaggca 720
gaactggaaa aggcctttgc agggacagag acggagaagg ctcttcggtt gcgtttggaa 780
agcaagcttt cagagatgaa gaagatgcac gagggggact tggcgatggc tctggtcctg 840
gatgagaaag acagactgat tgaggagttg aagctgtctt tgaagagcaa agaagcttta 900
attcagtgcc ttaaagagga gaaatctcag atggcatgtc ctgatgagaa tgtgtcatct 960
ggagagctcc gaggactttg tgctgctcca agggaagaaa aggagagaga aactgaggct 1020
gcacaaatgg agcatcagaa ggagagaaac agctttgaag agaggatcca ggcacttgaa 1080
gaggacctga gagagaagga aagagaaatt gctacagaga agaaaaatag tctaaagagg 1140
gataaagcca ttcagggttt aaccatggca ttaaaatcaa aggaaaaaaa ggttgaagaa 1200
cttaactctg aaattgaaaa gctcagtgct gcctttgcta aagccagaga ggccctacag 1260
aaagcacaga cccaggaatt tcaggggtct gaagactatg agactgctct atcaggaaag 1320
gaagcccttt cggctgcgct gcgctcacaa aacctcacca agagtacaga gaaccacaga 1380
ctgcgtagaa gcattaagaa gatcacccag gagctgagtg acttgcagca ggagagggag 1440
agactggaga aggacctgga ggaagcccat cgagagaaga gcaaaggaga ctgcaccatc 1500
cgtgatctta gaaatgaagt tgaaaaatta cgcaatgaag tgaatgaaag agagaaagca 1560
atggaaaatc gttacaagag tcttctgagt gaaagcaata aaaaattgca caatcaagag 1620
caagtgatca aacatctaac agaaagtacc aatcagaagg acgtgttgct tcagaaattc 1680
aatgaaaaag atttggaagt aatacagcag aactgctatt taatggctgc agaggatctt 1740
gagctcagga gtgaaggctt aataacagaa aagtgctctt ctcaacagcc accaggcagc 1800
aaaaccatct tctctaagga aaagaaacaa tcatcagact atgaagagct gattcaggtc 1860

-continued

```
ttaaagaaag agcaggacat ctatacccat ctggtcaaat ctctgcagga atcagacagt   1920
atcaacaacc tgcaggctga gttaaacaag atttttgccc tgcggaagca actggagcag   1980
gatgtgcttt catatcagaa tttgcggaag accttggagg agcagatcag cgaaattcgg   2040
aggcgggaag aagaatcatt ttcactttat agtgatcaaa catcttatct aagtatttgc   2100
cttgaagaaa acaatcggtt tcaagtggaa catttttctc aagaagaact taagaaaaag   2160
gtcagtgacc ttatacagct agtgaaggag ctgtatacag acaaccagca cctgaagaaa   2220
accatttttg atctctcctg catgggtttc cagggaaatg ggtttccaga tagacttgcg   2280
tctacagaac aaacagagct tctggctagc aaggaggacg aggacacgat caaaattggg   2340
gaggatgacg agattaattt cctgagtgac cagcatttgc agcagagtaa tgagattatg   2400
aaagaccttt ccaaaggagg ctgcaaaaat ggatacttaa ggcacacgga gtctaagatt   2460
tcagattgtg atggggccca cgcacctggc tgcctagaag aaggtgcatt cataaacctg   2520
cttgcccctt tgttcaatga gaaggccaca ttattactgg aatccaggcc agaccttctg   2580
aaagtggtac gggaactgct tctgggacaa ctattcttga cagagcagga agtttctgga   2640
gaacaccttg atggtaaaac tgagaagaca cctaagcaaa aaggtgaact tgtacatttt   2700
gtccaaacca actcattttc caagccacat gatgaactga agttgtcttg tgaggcccag   2760
ctagtaaagg caggcgaagt gcccaaggta ggactgaaag atgcctcagt gcagactgtg   2820
gccacggagg gcgacctgct gagattcaag catgaagcaa caagagaggc ttgggaagag   2880
aaaccgatca acactgcact cagcgcagag catcggccag agaacctgca cggggtgcct   2940
gggtggcagg ctgccctcct ttccctccct ggtattacca acagagaggc taagaagtcc   3000
cgcttgccaa tcctaataaa accatcccgg tcattaggaa atatgtatcg tctccctgcc   3060
acccaggagg tggtgacgca gctgcagagc cagatcttgg agctgcaggg ggagctgaag   3120
gagtttaaaa cttgtaataa gcaacttcac caaaagttaa ttctggctga agcagtgatg   3180
gaggggaggc caacgcccga caaaacgttg ctgaatgctc agccccctgt gggagcagcc   3240
taccaggaca gcccaggaga gcagaaagga attaaaacca catcttctgt ctggagagac   3300
aaggaaatgg acagtgatca gcaaagaagc tacgagattg actctgagat ttgcccacct   3360
gatgaccttg ccagcttgcc atcatgcaaa gaaaatcctg aagatgttct gagcccaact   3420
tcagtagcta cttacctgag ttccaagagt cagccttctg ctaaagtcag tgtgatgggg   3480
actgatcagt cagagagcat taatacctca aatgagacag aatacttaaa acagaaaatc   3540
catgacttgg aaactgagct ggaaggctac cagaatttca tatttcagct tcaaaagcac   3600
tcccagtgca gtgaggccat aattacagtt ttgtgtggga cagaaggggc ccaggatggc   3660
ttgagcaagc ccaagaatgg ttctgatggg gaagaaatga ccttttcaag tttgcaccaa   3720
gtgcgatacg tgaaacacgt gaaaatcctc ggtccgctgg ccccagagat gattgacagc   3780
agggtgctgg agaacctcaa acagcagctg gaggaacagg aatacaagct gcagaaggag   3840
cagaatttga acatgcaact tttcagtgag atccataatc tgcagaataa gttcagagat   3900
ctctcacctc ccagatacga ttcattagtt cagtcccaag ccagggagct ctcccttcaa   3960
cggcagcaga ttaaggatgg ccatggcatc tgtgtcatct cccgtcaaca catgaacacc   4020
atgattaagg catttgagga gttgctgcag gccagtgatg tggattactg tgtggccgag   4080
ggtttccagg aacagctgaa tcaatgtgct gagctgctgg agaaattgga aaagctattt   4140
ctcaacggaa aatcagttgg agtggaaatg aacacccaga atgaactgat ggagaggatt   4200
gaggaagaca acttaaccta ccaacatctt ctgcctgaat ctcctgagcc ttcagcctct   4260
```

catgcgctct ctgattatga aacatctgaa aagtccttct tctcacgaga ccagaagcaa 4320
gataatgaga cagagaagac ttcagttatg gtgaacagtt tttctcaaga cttactaatg 4380
gaacacatac aggaaattcg aactttgaga aagcgtttag aagaatctat taaaacaaat 4440
gagaagctac ggaaacagtt ggaacggcaa ggatctgaat ttgttcaagg ttctacaagc 4500
atttttgctt ctggttcaga gcttcatagt tctctaacat cagaaattca tttcttgagg 4560
aagcagaacc aggccctcaa tgcaatgctc attaaaggat ccagagataa acagaaggag 4620
aatgacaaat tacgagagtc cctctccagg aagaccgtga gcctggagca ccttcagcgg 4680
gagtatgcca gcgtgaagga agaaaatgaa aggctgcaga aagaaggcag cgagaaggag 4740
agacacaacc agcagctgat ccaggaggtc cgctgcagcg gccaggagct gagcagggtg 4800
caggaggagg tgaagttgag gcagcagctg ctctcacaga atgacaagct attgcagtct 4860
ctccgagtgg agctgaaggc gtatgagaag ctggatgaag agcacaggag actgagagag 4920
gcgtcgggag aaggctggaa ggggcaggat cctttcaggg acctgcacag cctcctgatg 4980
gagatccagg ctctgcgctt gcaactagaa aggagcatcg aaaccagcag cactctgcag 5040
agcaggctca aggaacagct ggcaaggggg gcagagaagg cacaggaagg agccctcact 5100
ctggctgtcc aagccgtgtc catccctgag gtgccccttc agcctgacaa acacgatggt 5160
gacaaatatc ccatggaaag tgataattca tttgatctgt ttgattcctc ccaggcagtg 5220
acaccaaaat cagtttcaga gactcctcca ctctctggga atgacacgga ctccctctcc 5280
tgcgacagtg gcagttcggc aactagcact ccgtgtgtgt cccgcctggt cactggccac 5340
cacctgtggg ccagcaagaa tggccgccat gtcctgggcc tgattgagga ctatgaggcc 5400
ctgctcaaac agatcagcca gggacagagg ctccttgctg aaatggacat tcaaacccaa 5460
gaggctccca gctccacaag tcaagagctg ggaacaaagg gtccacaccc agcaccactg 5520
agcaagtttg tgagcagtgt gagcacggcc aagctgaccc tggaagaggc ctacaggcgg 5580
ctgaagcttc tctggagagt ctcactcccc gaggatggcc agtgccccct tcactgtgag 5640
cagattggag aaatgaaggc agaggtcacc aaactacata aaaaattgtt tgaacaagaa 5700
aagaagttgc aaaacaccat gaagcttttg cagctgagca agcgccagga aaaagtcatc 5760
tttgatcaat tggtcgtaac ccacaaaatc cttcggaagg ccagaggaaa cctggagctt 5820
aggcctgggg gagcccatcc aggaacatgc agtcccagca gaccaggctc ctgagaagaa 5880
ctttcagcca ataaagcttg tgcttccccc accgagctca cgctgtctct ttgttccaag 5940
tgtggttcct atttattgag gaagaaagag ctgtctggcc aaaggaaatc tatttttttcc 6000 cttcatgttt tctctctgaa agttggcttg agagttgttg tcagaaaggt gcaggtgctc 6060
cacaaacggg tggtaaaaag gcctcgagct cttggatgtt gtatttcaga tcaggggcag 6120
gcaccggagt tgaggctgtg cgccttggtg ggcttcacgt cttcccctgg atttgcttag 6180
tactcagcca gtgccacagt ttgaagattc tcattaaatg attcatttca tttcaccttg 6240
aa 6242

<210> SEQ ID NO 12
<211> LENGTH: 2701
<212> TYPE: DNA
<213> ORGANISM: Homo sapiens

<400> SEQUENCE: 12
gggggctcga gctgcggcgc cggctcctgc cgcctgggcc ccgggcccgg cccctcccgc 60

-continued

```
gccgcccggg cgatgagaag ctgcttctgc gtgagacgga gccgggaccc gccgccgccg    120
cagccaccgc cgccgccgcc ccagcgggga acagaccagt ccaccatgcc tgaagtcaaa    180
gacctctcag aagccttgcc agaaacatca atggatccca tcacgggagt cggggtggtg    240
gcttctcgga accgagcccc gacaggctat gacgtagttg cacagacagc agatggtgtg    300
gatgctgacc tctggaaaga cggcttattt aaatccaagg ttaccagata cctgtgtttc    360
acaagatcat tttccaaaga aaatagtcat ctggggaacg tgttagtaga tatgaagctc    420
attgacatca aggacacact gcctgtgggc ttcatcccaa ttcaggagac ggtggacaca    480
caggaagtgg cttttaggaa gaagaggctg tgcattaaat ttattccacg ggattcaacg    540
gaagctgcga tttgtgacat tcggatcatg ggccggacca agcaggcccc gcctcagtac    600
acgtttattg ggaactgaa cagcatgggg atctggtatc gaatgggcag agtaccaaga    660
aatcatgact catctcaacc cacaacgcct tcccagtcat cagctgcctc caccccagcc    720
cccaaccttc ccaggtgagg ccttgtcggg gtgtcttgca ttgtcctgtg gtcttaggtc    780
cctgcacaac attttagaac accaccactt agtgtctgct gaaatactgc aaagtacagc    840
tgaataattg tagaagcaat atatctttag aggagatttt taaaaatcca cttggaaatc    900
tttgcattac atgaatgcaa aggccattct atagtctatt ttgtgcgtgt tctgcaggct    960
tctaaaattg cagattatgc aacttaaaat tggctcccta ttcaaaagag ctgctagcta   1020
cacacagaca cgtgctgtat agccatgggg ttgggatcac tggccttaag gtcaaattcc   1080
ttctctgtct tggccagcaa ctcatttgaa acccaggagg gtaggtgagt tcttatattc   1140
ttcattttca tataatttct ttttccaatg agctataaag taagaaatgg gtagtttggg   1200
tatgagagaa tagtgaggag tttttcagga aatgctagtt ttaacaattg tctccgcaaa   1260
gaaacttggg tgagccaact gtttgctctg caactgattt cagtcataac agaggtagta   1320
acagtctcta cactttctgc aaaaagaatc ctgtcaaata aaaatcctgt gcatcactag   1380
gagtaaacta agggcaagga acaaacagca ctgatggatt aagcttgaga aagggattgc   1440
aaaagtaaat aaaacaagaa cggtgaggca gcaacactta gggattgaca taacgtaaat   1500
gagaatggat ctccaagctt ccacgtgggt gaatagagat gaacaaaatc tgtcaggaac   1560
cggacagaag agtcaccagt aggtcttcct gggccatcca caatacagcc tgccctccgg   1620
gacataccac cagctctctg tactctgttc ctctgtgcca agcctccgtc tcacttggaa   1680
gaatgtgctg taatgaggct ccaaagccct gaggactctg tcctctggga catcccccta   1740
taaagacaat ctggtccttc tcatgacagt ttcacaaacc aagagtggta tttaaactta   1800
actacccctg gaattgcctg aaactttaga agtagttttc agtttcattt ggcataaaaa   1860
gataggaatc tctaataagc ctcccagagt tgcagggtga acagttgagt ctctgttggg   1920
ttcaagagtg tgaggttcgc actgcccatc agcacttgtt cctcacttct gagccagagc   1980
gctgtcagct ccgccctgga gggcactgct gagggtcact gtctcctgtg ctcaaggcta   2040
tatcaggtgt gtcacctgtg ctggggagtc agctaagtcc atcacctgtg tgtcggggtc   2100
ctccatcacc tgtgctgagg cccatcactt gtacttggag cagctcaagt gtgggctcct   2160
tgcagaggct ggaaagcccc cacaggagca gttgccctga agttgttaca gctgctccct   2220
gctgacatca tgtggtctag aagggcccag aaatgggcac cacctcaggc aggttttgac   2280
tttctgtggt taaagaaaga acaccagttc tctcatataa agcagagaga gctctcagaa   2340
gcctgctggt gactgtgaga gcaaagtcac ttgcacctga agcaagacag ccgagaacac   2400
cgagccaccg gcagcctggt gggtttggag ggtagtgcgt cagaaccaga tgtttataag   2460
```

-continued gcttatgtat tttatcacct ctgctgtaca gtttatggtt tacaatggct gcaaggaaat 2520
cggatcagtt ttgttttact tgccaaataa aacaaatgtc aaaatagtca atataaaatg 2580
tattctaatt tggctgagtt aagtcagcca atatgcaaca ggataattga atgttcatta 2640
atgcttccaa gtaaaagcca tttgtctgtc agaaaaaaaa aaaaaaaaaa aaaaaaaaaa 2700
a 2701

<210> SEQ ID NO 13
<211> LENGTH: 2870
<212> TYPE: DNA
<213> ORGANISM: Homo sapiens

<400> SEQUENCE: 13
gcgggcgtca gcgcggtggc cagcgcgcag aggcgggcgc ggaggcggct agaaggtgac 60
cgcggatccc agcttcctgc agccagccct gaaggatggc tgccatattg ggagacacca 120
tcatggtggc taaaggcctt gtcaagctga cccaggcggc cgtggaaacc cacctgcagc 180
acttgggcat cggaggggag ctgatcatgg cggccagggc cctgcagtcc acggctgtgg 240
agcagattgg catgttcttg ggaaggtgc agggtcagga taaacatgaa gaatattttg 300
ctgagaactt cggcggccca gaaggggagt tccacttctc agtcccgcat gcagccggag 360
cctccacaga cttctcttca gcctccgctc ccgaccagtc agcgcccccca tccctgggtc 420 atgcccacag cgagggccca gctcctgcct acgtggccag tggacccttt agagaagccg 480
ggttccccgg ccaggcctcc tcccctctgg gcagggccaa cgggaggctc tttgcaaacc 540
ccagagactc attctctgcc atgggctttc agcgaaggtt cttccaccag gaccaatccc 600
ctgttggggg cctcacagcc gaggacattg agaaggcccg gcaggctaag gctcgccccg 660
agaacaagca gcacaaacag acgctcagcg agcatgcccg ggagcggaag gtgcctgtga 720
cgaggattgg ccggctggcc aacttcggag gtctggccgt gggcctgggc ttcggggcac 780
tggcagaggt cgccaagaag agcctgcgct ccgaggaccc ctcagggaag aaggccgtgc 840
tgggttccag tcctttcctg tccgaggcca atgcagagcg gatcgtgcgc acgctctgca 900
aggtgcgtgg tgcggcactc aagctgggcc agatgctgag catccaggat gatgccttta 960
tcaaccccca cctggctaag atcttcgagc gggtgcggca gagcgcggac ttcatgccac 1020
tgaagcagat gatgaaaact ctcaacaacg acctgggccc caactggcgg gacaagttgg 1080
aatacttcga ggagcggccc ttcgccgccg catccattgg gcaggtgcac ttggcccgaa 1140
tgaagggcgg ccgcgaggtg gccatgaaga tccagtaccc tggcgtggcc cagagcatca 1200
acagtgatgt caacaacctc atggccgtgt tgaacatgag caacatgctt ccagaaggcc 1260
tgttccccga gcacctgatc gacgtgctga ggcgggagct ggccctggag tgtgactacc 1320
agcgagaggc cgcctgtgcc cgcaagttca gggacctgct gaagggccac cccttcttct 1380
atgtgcctga gattgtggat gagctctgca gcccacatgt gctgaccaca gagctggtgt 1440
ctggcttccc cctggaccag gccgaagggc tcagccagga gattcggaac gagatctgct 1500
acaacatcct ggttctgtgc ctgagggagc tgtttgagtt ccacttcatg caaacagacc 1560
ccaactggtc caacttcttc tatgaccccc agcagcacaa ggtggctctt ttggattttg 1620
gggcaacgcg ggaatatgac agatccttca ccgacctcta cattcagatc atcagggctg 1680
ctgccgacag ggacagggag actgtgcggg cgaaatccat agagatgaag ttcctcaccg 1740
gctacgaggt caaggtcatg gaagacgccc acttggatgc catcctcatc ctgggggagg 1800

-continued

```
ccttcgcctc cgatgagcct tttgattttg gcactcagag caccaccgag aagatccaca   1860
acctgattcc cgtcatgctg aggcaccgtc tcgtcccccc acccgaggaa acctactccc   1920
tgcacaggaa gatgggggc tccttcctca tctgctccaa gctgaaggcc cgcttcccct   1980
gcaaggccat gttcgaggag gcctacagca actactgcaa gaggcaggcc cagcagtagg   2040
gctgcgggcc acgcccaggc cggctccgcg ggaactctct ccctcagaca ggccaaaaac   2100
cagtagcgag gtcgtggtga tgctcttttt aactcctttg cccaataagg ggggtggctg   2160
cctggagccc cgtagccagc gctttccacg gtttctgttg ctaaatggtt gtagggtgag   2220
aagtgcaaga atgaagatga agccccactg ctcggtcagt ctgcctccgt gtgtcctctg   2280
aaataagcag atgaagatga aagggcaact ttgttttctt ctttttcctg atgtgaatgt   2340
taagcagaag ggagagagtc cttactccct tccaatctct gttcagtgca aaacccagaa   2400
acatgaacag atacgattgt gggattttta tcatctgtgt agtaggtgtg tgtatgtgtt   2460
tctagagtga gatttgtgtt ttctgccctt ttcctctcca gccgatgggc tggagctggg   2520
agaggtgctg agctaacagt gccaacaagt gctccttaag cctgcgaggc ccaggcctgt   2580
ggggctggtt ctcacctttg acagctgaat gttcctaaag aactgctgcc ccacagtgag   2640
ggtgggagca gcggaacagg gaatgccaga cacaggctcg ctgctgctgg aaggcggggt   2700
gggacttcct tcctctgtcc ggaaaggcac aggtgtcacc agttccagcc aaaggctcct   2760
cacaggcgct gtgaattttt gtacaagtct tgtaattatc gaatcaacaa cttgttttca   2820
atttaataaa aatgctcatg ggaagtgaaa aaaaaaaaaa aaaaaaaaaa              2870
```

<210> SEQ ID NO 14
<211> LENGTH: 2307
<212> TYPE: DNA
<213> ORGANISM: Homo sapiens

<400> SEQUENCE: 14

```
gaagccgggg gcgggggcca cgcgtggggc aggcggtgct cggctcggct gacgtcggcc     60
cgccggcgcc ccaccagctc cgcgcgggcc cgggttggcc accgccgggc ccccgcccct    120
cccccggcgg tgtcccggcc ggaaccgatc gtggctggtt tgagctggtg cgtctccatg    180
gcgacccgcc ggtgctataa gtagggagcg gcgtgccgtg gggctttgtc agtccctcct    240
gtagccgccg ccgccgccgc ccgccgcccc tctgccagca gctccggcgc cacctcgggc    300
cggcgtctcc ggcgggcggg agccaggcgc tgacgggcgc ggcgggggcg gccgagcgct    360
cctgcggctg cgactcaggc tccggcgtct gcgcttcccc atggggctgg cctgcggcgc    420
ctgggcgctc tgagattgtc actgctgttc caagggcaca cgcagaggga tttggaattc    480
ctggagagtt gcctttgtga gaagctggaa atatttcttt caattccatc tcttagtttt    540
ccataggaac atcaagaaat catgaacaac tttggtaatg aagagtttga ctgccacttc    600
ctcgatgaag gttttactgc caaggacatt ctggaccaga aaattaatga agtttcttct    660
tctgatgata aggatgcctt ctatgtggca gacctgggag acattctaaa gaaacatctg    720
aggtggttaa aagctctccc tcgtgtcacc cccttttatg cagtcaaatg taatgatagc    780
aaagccatcg tgaagaccct tgctgctacc gggacaggat ttgactgtgc tagcaagact    840
gaaatacagt tggtgcagag tctgggggtg cctccagaga ggattatcta tgcaaatcct    900
tgtaaacaag tatctcaaat taagtatgct gctaataatg gagtccagat gatgactttt    960
gatagtgaag ttgagttgat gaaagttgcc agagcacatc ccaaagcaaa gttggttttg   1020
cggattgcca ctgatgattc caaagcagtc tgtcgtctca gtgtgaaatt cggtgccacg   1080
```

ctcagaacca gcaggctcct tttggaacgg gcgaaagagc taaatatcga tgttgttggt 1140
gtcagcttcc atgtaggaag cggctgtacc gatcctgaga ccttcgtgca ggcaatctct 1200
gatgcccgct gtgtttttga catgggggct gaggttggtt tcagcatgta tctgcttgat 1260
attggcggtg gctttcctgg atctgaggat gtgaaactta aatttgaaga gatcaccggc 1320
gtaatcaacc cagcgttgga caaatacttt ccgtcagact ctggagtgag aatcatagct 1380
gagcccggca gatactatgt tgcatcagct ttcacgcttg cagttaatat cattgccaag 1440
aaaattgtat taaaggaaca gacgggctct gatgacgaag atgagtcgag tgagcagacc 1500
tttatgtatt atgtgaatga tggcgtctat ggatcattta attgcatact ctatgaccac 1560
gcacatgtaa agccccttct gcaaaagaga cctaaaccag atgagaagta ttattcatcc 1620
agcatatggg gaccaacatg tgatggcctc gatcggattg ttgagcgctg tgacctgcct 1680
gaaatgcatg tgggtgattg gatgctcttt gaaaacatgg gcgcttacac tgttgctgct 1740
gcctctacgt tcaatggctt ccagaggccg acgatctact atgtgatgtc agggcctgcg 1800
tggcaactca tgcagcaatt ccagaacccc gacttcccac ccgaagtaga ggaacaggat 1860
gccagcaccc tgcctgtgtc ttgtgcctgg gagagtggga tgaaacgcca cagagcagcc 1920
tgtgcttcgg ctagtattaa tgtgtagata gcactctggt agctgttaac tgcaagttta 1980
gcttgaatta agggatttgg ggggaccatg taacttaatt actgctagtt ttgaaatgtc 2040
tttgtaagag tagggtcgcc atgatgcagc catatggaag actaggatat gggtcacact 2100
tatctgtgtt cctatggaaa ctatttgaat atttgtttta tatggatttt tattcactct 2160
tcagacacgc tactcaagag tgcccctcag ctgctgaaca agcatttgta gcttgtacaa 2220
tggcagaatg ggccaaaagc ttagtgttgt gacctgtttt taaaataaag tatcttgaaa 2280
taattaggca ttgggacgtt aaaaaaa 2307

<210> SEQ ID NO 15
<211> LENGTH: 5392
<212> TYPE: DNA
<213> ORGANISM: Homo sapiens

<400> SEQUENCE: 15
gccccgcccc cgaaggcgag ctgcgctgac agccggcggc gggctgggtg tttgcaatac 60
aaaggcggcc acgcgcggcg ccgctcggtg cagaccatga attacgtggg gcagttagcc 120
ggccaggtgt ttgtcaccgt gaaggagctc tacaaggggc tgaatcccgc cacactctca 180
gggtgcattg acatcattgt catccgccag cccaatggaa acctccaatg ctcccctttc 240
cacgtccgct ttgggaagat gggggtcctg cgctcccgag agaaagtggt tgacatagaa 300
atcaatgggg aatctgtgga tttgcatatg aaattgggag ataatggaga agcatttttt 360
gttcaagaaa cagataatga tcaggaagtt atccctatgc acctggccac ctcccccatc 420
ctgtcagaag gagcttcgag aatggaatgc cagctgaaaa ggggctctgt ggacaggatg 480
agaggcctgg accccagcac gccagcccaa gtgatcgctc ccagcgagac gccgtcaagc 540
agctctgtag taaagaagag aagaaaaagg aggagaaagt cacagctgga cagcctgaag 600
agagatgaca acatgaacac atctgaggat gaggacatgt tccccatcga gatgagctcg 660
gatgaggcca tggagctgct ggagagcagc agaactcttc ctaatgatat acctccattc 720
caagatgata ttcctgagga aaacctctcc ctggctgtga tttaccctca gtcagcctca 780
taccctaatt cggatagaga gtggtcaccc actcccagtc cttccggttc ccgaccttca 840

-continued

```
acacctaaaa gtgattcaga attggtcagc aagtccacgg aaaggacagg gcagaagaac    900
ccagaaatgc tttggctgtg gggagagctg ccgcaggctg ctaagtcttc ttctccacac    960
aagatgaaag agtccagccc attgagcagt agaaaaattt gtgataaaag tcactttcag   1020
gccattcaca gcgaatcttc agacactttt agtgaccaat cgccaactct ggtcggtggg   1080
gcacttttgg accagaacaa gcctcagaca gaaatgcagt ttgtgaatga agaagacctg   1140
gagaccttag gagcagcagc gccactcttg cccatgatcg aggagctcaa acccccctct   1200
gccagtgtag tccagacagc aaacaagacg gattctcctt ccaggaaaag agataaacga   1260
agccgacatc ttggtgctga cggcgtctac ttggatgacc tcacagacat ggatcctgaa   1320
gtggcggccc tgtattttcc caaaaacgga gatccttccg gactcgcaaa acatgcaagc   1380
gacaacggag cccggtcagc caaccagtcc ccgcagtcgg tgggcagctc gggcgtggac   1440
agtggcgtgg agagcacctc ggacgggctg agggacctcc cttccatcgc catctccctc   1500
tgcgggggcc tcagcgacca ccgggagatc acgaaagatg cattcctgga gcaagctgtg   1560
tcatatcaac agtttgtgga caaccccgct attatcgatg accccaatct cgtggtaaag   1620
attgggagta aatattataa ctggacaaca gcagcacccc tcctcctggc aatgcaggcc   1680
ttccagaaac ctttgccaaa ggccactgtg gaatctatca tgagggataa aatgcccaaa   1740
aagggaggaa gatggtggtt ttcatggagg ggaagaaaca ccacaatcaa ggaggaaagt   1800
aagccagagc agtgcttggc tggcaaggcc catagcaccg gagagcaacc gccgcagctc   1860
agcttggcca ccagggtaaa gcatgaatca tcctccagtg atgaggagcg cgcagctgcc   1920
aagccatcaa acgcaggcca cctccctctt ctgcctaatg tcagctacaa gaagactctc   1980
cggctgactt ccgagcagct taaaagcttg aagttgaaga atggccccaa cgacgtggtt   2040
ttcagtgtca ccacgcagta ccaaggcacg tgccgctgtg agggcaccat ctatctgtgg   2100
aactgggatg ataaagtcat catttctgat attgatggga caattaccag atcagatact   2160
cttggccaca ttttgcccac ccttgggaag gattggaccc atcagggcat cgctaagctg   2220
taccataaag tgagccagaa tggatataaa tttctctact gttctgcccg tgccatcggg   2280
atggcggaca tgacgcgggg ctacctgcac tgggtcaacg agaggggcac ggtgctgccc   2340
caggggcccc tgctgctgag tcccagcagc ctcttctctg ccctgcacag agaagtgatt   2400
gaaaagaagc cagaaaagtt taaagtccag tgtttgacag acatcaaaaa cctgtttttc   2460
cccaacacag aacccttta tgctgctttt ggaaaccgac cagctgatgt gtattcatac   2520
aagcaagtag gagtgtcttt gaatagaata tttaccgtca accctaaagg agagctggta   2580
caggaacatg caaagaccaa catctcttcg tatgtgagac tctgtgaagt agtcgaccac   2640
gttttcccgt tgctgaaaag aagccattct tcagactttc cctgttcgga taccttcagt   2700
aacttcacct tttggagaga gccactgcca cctttgaaa accaggacat tcattctgcc   2760
tcagcgtaaa atgtcccaag cagcctcttg ccagcagtgc agagcctggt tgtcacccat   2820
taaaggatag gtctccccgg agtgcacagc tccacctggg agcctggcgc gtcatcattg   2880
gcctgacagc agagagaatt gagaagcatt tctcccctgc cccaccccgg ggctgacatt   2940
tctaagcaag ataggaaggg agcactttct aggctaggag ttgggtgcat ttgtaccgtg   3000
aaaagcattc ctcagttgtg gcttaatgcc agttacgacg ctgcctttcc ggcctgctcc   3060
agcaagtagc tactggttca cgtgcagttt ggggctgtga aacctaggca gaaggcggct   3120
gtctgagggc tgtccccgcc taggacaggg tcaatcgagg aatgccagat gtgcacggtt   3180
tttggcaaag tagggggcac atttccatta tagcaatgtt agtgccacca ccttctgaac   3240
```

-continued

```
acagtgggga gggctgtgaa ggctcatgtg acctggatct gaggtctctg atagaaatct   3300
ggacgccacc gggtccaggc ctggcctcag acttggcctt gtggatgggc cccttacagt   3360
atttgctgac tagtctcatt tttaggtgat aaatttttct ttaattcctt tggttaaaga   3420
tagtctattt cattggcata tctcccccca gtttttgtgg ctcaaggctg gaatatttat   3480
gccttaatat atctatggca gacatttaag aatgcgcttt atctagctca tggtaacttt   3540
gcaacgcctt agattaaaat gacagtaaat attactaagg cagtattttg aatgagtttg   3600
acactgccgg cttccttcca tccagcgagg tggtgctgac agtgtggact tgagcacact   3660
tatgccaaat gataatgata ctgacttctg ttgggagctc tccaaagaaa ctggttggtt   3720
ttaagaaaat agtttcaaga agttcaacta tattctttta gatattatgt attgttttac   3780
tctgattagg ttactgtgat aggcatttat tcatattctt tctataccac tgtcattaat   3840
atattaaaaa gatgtatgtg ttagactatc gaaagggcct tattctctct ttctcataga   3900
ctgaccttct tttggaattt ctgagtcatt tattttcctt agctttttcc actcaaatta   3960
agggcaagcg aaaaagtaat aatttggcat tctttaagcc tacagaatgt gattctttca   4020
cttgtttatt acactggctc gtggacagaa caatttgaaa agtgaaagaa ttattttggt   4080
aaaagatttt gctttacttt tcgaagcatt attttttaa agagtgtttt actccaacga   4140
ttgaaacatt ttcctattta aatttcattg ttagaatcac aggaggcaaa aaatggaacg   4200
gttgaatgaa attttactct ttctgtgaaa gaaaatccac agagttgttg cctccgttgt   4260
agttggtggg ccccgttagc attggatgcc tttgccaaat ggttcatgtg gacacacaaa   4320
ggcaaacaga tctgccatcg atcgcagatt tctgtagaaa cacggatgtg catgtgcaga   4380
ttccctttg caggtattaa aaataattaa aaatagtcct gcctgaggtt gcagtgagcc   4440
gagcttgcac tactgcactc cagcctgggt gacagagtaa gactccatgt caaaaaaaaa   4500
aaaaaaaaaa aaaaagtcct gccttaacta actcctctgc gcttgttcac tagtaaccta   4560
aagaggctat attcattctt tatgcaatga gggtattttt gagtgaattt taactgctct   4620
gaactaagta taagctcatg ggcctgcaaa ggttcagacg gtttctcctt tgcacccagg   4680
aggaactttg gctgcgagaa tggggggatg tatccctcat gcagttggca tccaggcagc   4740
cctctgcagc agcacaccct gcaggcggag ttttcagagg atgcaatttt ggatcccgaa   4800
ttttgatgta ccttaaactt ccacatcact gcaccctgaa acagagcatg ctttccagaa   4860
agtcacactc tcagatctgt gtcaagttca atgtgagccc tggcaaggct ggcatattaa   4920
cacctgcctt ctggcttctg aaagtgagat ttgtatatgg gctgcactca cgcatatacg   4980
agttggttta tctttgtgta catgactata acccagtgat gctgaggtca tgtgctggaa   5040
tgctgtattt ggaccacaca tttcaaagtt gccctatgga aatgaatcct acttagtgac   5100
aagtcatcaa atgtttgtca catgtgatga agacaaatat gtatacctgg catagagaaa   5160
aatatatacc tggtacattg gagaaaaata attacacttt caaagagaat tccctttgca   5220
attttatgtt tggatcacca ctgtaagcac actttatttg catttgatct gtatttgtat   5280
atgctgatgc aatgataaaa atcactgtaa tacttcattg tgttgtactg gatgcaaagc   5340
tagaaaatat tgcaataaat gagaccgatg aaagacttct ctgaaaaaaa aa           5392
```

<210> SEQ ID NO 16
<211> LENGTH: 3230
<212> TYPE: DNA
<213> ORGANISM: Homo sapiens

<400> SEQUENCE: 16
agcagtgttc tcttcgtccc cctcccccaa actgaggatt gggcaatacc acagaacctc 60
aggaaagggg ggaagagcga gcttcggccc cactaatggg ggagtgggcg gaggctggat 120
ttcccacctc ggctgcacct gggcactgga ggctgaagag gaaagtgaga atctgaagtt 180
ttgagacctc tgactggcca ggaatagctc ctggggcggg gggcaaggat gggaccatag 240
gcggaaagag tctcgcggtc ccccctgctt ctggcgcggg tccctgcgcc cggttgtgga 300
gcgtctcgcg cggggagggg gcggggggaa cggcagctcg cggtgttgtt cactcgcgcg 360
tcgagcacac ggtgggtccg gcggcgggtt ggcgccccag gcggcgttcc ctgtggcctg 420
gcgcctgggc cgctgccctg agcgggttcc gccccagagc ccgaccctcc tgggggctct 480
aggcggagtc ccgcgagccg agggggaccg gcgaccgctg ccgaagcatg aagaaggggt 540
aaggcgtgag cccccaagat ttcacgcatg cccccctagct tcggtactct gacaccttct 600
cttgcacttg cggatgatga actggaataa cgatgaaaga aagcacatcc gatctcaaca 660
ttcacgtcct gccctataac cgattaatta attgatcccc agctagacta gtgttggaga 720
aatcagcatg ttaaaacaac tgttgatgat agctgttgga gtaaagttgc agtggaagct 780
atggctgcaa aatcgttaaa atcttcaagg tgaactggca caaaggttaa tctcaagatg 840
ccgctagtga aaagaaacat cgatcctagg cacttgtgcc acacagcact gcctagaggc 900
attaagaatg aactggaatg tgtaaccaat atttccttgg caaatataat tagacaacta 960
agtagcctaa gtaaatatgc tgaagatata tttggagaat tattcaatga agcacatagt 1020
ttttccttca gagtcaactc attgcaagaa cgtgtggacc gtttatctgt tagtgttaca 1080
cagcttgatc caaaggaaga agaattgtct ttgcaagata taacaatgag gaaagctttc 1140
cgaagttcta caattcaaga ccagcagctt ttcgatcgca agactttgcc tattccatta 1200
caggagacgt acgatgtttg tgaacagcct ccacctctca atatactcac tccttataga 1260
gatgatggta aagaaggtct gaagttttat accaatcctt cgtatttctt tgatctatgg 1320
aaagaaaaaa tgttgcaaga tacagaggat aagaggaagg aaaagaggaa gcagaagcag 1380
aaaaatctag atcgtcctca tgaaccagaa aaagtgccaa gagcacctca tgacaggcgg 1440
cgagaatggc agaagctggc ccaaggtcca gagctggctg aagatgatgc taatctctta 1500
cataagcata ttgaagttgc taatggccca gcctctcatt ttgaaacaag acctcagaca 1560
tacgtggatc atatggatgg atcttactca ctttctgcct tgccatttag tcagatgagt 1620
gagcttctga ctagagctga ggaaagggta ttagtcagac cacatgaacc acctccacct 1680
ccaccaatgc atggagcagg agatgcaaaa ccgataccca cctgtatcag ttctgctaca 1740
ggtttgatag aaaatcgccc tcagtcacca gctacaggca gaacacctgt gtttgtgagc 1800
cccactcccc cacctcctcc accacctctt ccatctgcct tgtcaacttc ctcattaaga 1860
gcttcaatga cttcaactcc tccccctcca gtacctcccc cacctccacc tccagccact 1920
gctttgcaag ctccagcagt accaccacct ccagctcctc ttcagattgc cccctggagtt 1980
cttcacccag ctcctcctcc aattgcacct cctctagtac agccctctcc accagtagct 2040
agagctgccc cagtatgtga gactgtacca gttcatccac tcccacaagg tgaagttcag 2100
gggctgcctc cacccccacc accgcctcct ctgcctccac ctggcattcg accatcatca 2160
cctgtcacag ttacagctct tgctcatcct ccctctgggc tacatccaac tccatctact 2220
gccccaggtc cccatgttcc attaatgcct ccatctcctc catcacaagt tatacctgct 2280
tctgagccaa agcgccatcc atcaacccta cctgtaatca gtgatgccag gagtgtgcta 2340

```
ctggaagcaa tacgaaaagg tattcagcta cgcaaagtag aagagcagcg tgaacaggaa   2400

gctaagcatg aacgcattga aaacgatgtt gccaccatcc tgtctcgccg tattgctgtt   2460

gaatatagtg attcggaaga tgattcagaa tttgatgaag tagattggtt ggagtaagaa   2520

aaatgcattg ataaatatta caaaactgaa tgcaaatgtc ctttgtggtg cttgttcctt   2580

gaaaatgttt ggtcattcta gtgttttgct ttcttttcct tataataaat gacccttttc   2640

ctccataact tttgatttct aaggaaaata ttagcataca tttcaaacta aatgttttac   2700

agtggcttat cttttttttc cccctgaaaa gactaatttg gtcaaataaa ccactaagta   2760

ttaagcatgg acagctgttg ttagagtagc agattcagtt ttttgatata tcttaattgt   2820

gtactttgtg aattttaatt taaagaaagc aactgaaatt gaaatcttga gggcagctgt   2880

gtctactaat gagccttatt ccatttcctg atgttttaaa agaagaaaca ctgccttgat   2940

tatacgaata cactcagaaa gtacatttag cttgtagtgt tgaattctct taaaggaatg   3000

cttgaatttt ttcattattg ttttattgtt tttatatact tgccttattt gaatgtttag   3060

cagtatcccc ttcccactta tatattgtgt gatatgattt tgcttgccta taggagttaa   3120

aaacttttcc atgtgaaata ctctgactta aacatacatg taacttacat aactgttaag   3180

aataacagtc tgatttaata aatggttcat tttaaaagtt aaaaaaaaaa             3230
```

<210> SEQ ID NO 17
<211> LENGTH: 7933
<212> TYPE: DNA
<213> ORGANISM: Homo sapiens

<400> SEQUENCE: 17

```
gctcgctggc gccgccgccg ccggcagacc ccgcgctccg gctccggctc ggctcgctcg     60

gctccggtgc gcgccgaggc catgcagcgc cggggcgccc tgttcggcat gccgggcggc    120

agcggaggca ggaagatggc tgcaggagac atcggcgagc tgctagtgcc ccacatgccc    180

acgatccgcg tgcccaggtc cggcgacagg gtctacaaga acgagtgcgc cttctcctac    240

gactctccca attctgaagg tggactctat gtatgcatga atacattttt ggcctttgga    300

agggaacatg ttgaaagaca ttttcgaaaa actggacaga gtgtatacat gcacctgaaa    360

agacatgtgc gagagaaggt aagaggggcg tctggtggag cgttaccaaa aaggaggaat    420

tccaagattt ttttagatct agatactgat gacgatttaa atagcgacga ttatgaatat    480

gaagatgaag ccaaacttgt tatattccca gatcactatg aaatagcact accaaatatt    540

gaggagttac cagccctggt aacaattgct tgtgatgcag ttctcagctc aaaatctcca    600

tacagaaagc aggacccaga cacgtgggaa aatgaattgc cagtatctaa atatgccaac    660

aacctcaccc agctggacaa tggagtcagg attcctccaa gtggttggaa gtgtgccaga    720

tgcgacctgc gagaaaacct ctggttgaat ctgactgacg gctctgtcct gtgtggaaag    780

tggttctttg acagctctgg gggcaacggg catgcgctgg agcattacag agacatgggc    840

tacccactag ccgtgaaact gggaaccatc actcctgacg gggcagatgt ttattctttt    900

caagaagaag aacctgtttt ggatcctcat ttggccaagc acttagcgca ttttggaatt    960

gatatgcttc atatgcatgg gacagagaat gggctccagg acaatgacat caagctgagg   1020

gtcagtgagt gggaagtgat ccaggagtcg ggcacgaaac tgaagccaat gtatggtcct   1080

ggctacacgg gtctgaagaa cctgggcaac agctgctatc tcagctctgt catgcaggcc   1140

atcttcagca tcccagaatt ccagagagcg tatgtaggaa accttcccag aatatttgac   1200
```

-continued

```
tactcgcctt tagatccaac acaagatttc aacacacaga tgactaagtt aggacatggc   1260
cttctctcag gccagtattc aaagcctccg gtgaaatctg aactcattga acaggtgatg   1320
aaggaggagc acaagccaca gcagaacggg atctctccgc gcatgtttaa ggcctttgta   1380
agcaagagcc acccggaatt ctcctctaac aggcagcaag atgcccagga attcttcttg   1440
cacctggtga atctagtaga gaggaaccgc atcggctcag aaaacccaag cgatgttttt   1500
cgtttttgg tggaagaacg cattcagtgc tgtcagaccc ggaaagtccg ctacacggag    1560
agggtggatt acctgatgca gttacctgtg gccatggagg cggcaaccaa caaggatgaa   1620
ctgatcgctt atgaactaac gagaagggaa gcagaagcaa acagaagacc ccttcctgag   1680
ttggtacgtg ccaagatacc atttagtgcc tgccttcagg ccttctctga accagaaaat   1740
gttgatgatt tctggagcag tgccctacaa gcaaagtctg cgggtgtgaa aacatctcgc   1800
tttgcttcat tccctgaata cttggtagtg cagataaaga agttcacttt tggtcttgac   1860
tgggttccca aaaaatttga tgtttctatt gatatgccag acctacttga tatcaaccat   1920
ctccgagcca gggggttaca gccaggagag gaagaacttc cagacatcag cccccccata   1980
gtcattcctg atgactcaaa agatcgcctg atgaaccaat tgatagaccc atcagacatc   2040
gatgagtcat cagtgatgca gctggccgag atgggtttcc cgctggaagc atgtcgcaag   2100
gctgtgtact tcactggaaa tatgggcgcc gaggtggcct tcaactggat cattgttcac   2160
atggaagagc cagattttgc tgagccgctg accatgcctg gttatggagg ggcagcttct   2220
gctggagcct ctgtttttgg tgcttctgga ctggataacc aacctccaga ggaaatcgta   2280
gctatcatca cctccatggg atttcagcga aatcaggcta ttcaggcact acgagcaacg   2340
aataataacc tggaaagagc actggattgg atctttagcc accctgagtt tgaagaagac   2400
agtgattttg tgattgagat ggagaataat gccaatgcaa acattatttc tgaggccaag   2460
cccgaaggac ctagagtcaa ggatggatct ggaacatatg agctatttgc attcatcagt   2520
cacatgggaa catccacaat gagtggtcat tacatttgcc atatcaaaaa ggaaggaaga   2580
tgggtgattt acaatgacca caaagtttgt gcctcagaaa ggcccccctaa agacctgggc  2640
tacatgtact tttaccgcag gataccaagc taaacctcaa atataaaaat tggcgaaaag   2700
aagccatacg cctttttaat ttgccaaaaa aaaaaagaag aagaagaagt tgaaacaact   2760
agacatgaag gaatatatgg ggtatttatc gtttatttaa agagcacgat cagttgacac   2820
cttctgaaat agaactgaga agaaatttct attagtgatg atacactatt atattgtaga   2880
tagtttttat aaatgttcaa aaagatgatg atatttaaaa acaaaaaaag tattcatatt   2940
gctggtggag gatctgccat cagcacatca aaaatgggga tgtgccccca gccctctatt   3000
ttgctttggg ggtcagtgat agtggcctct ggagaaacca aataatgtgg ccagtggtgt   3060
ggccttaccc acaacaaatg aaaagcccac ttgtgtttca tatagaaaat cagcagttgg   3120
gtggggcttt atttgtgaca taattttttt catgacatac aataatttct gatgtatcca   3180
tgtagatatt atgctctgtc cataatagag cctctgcaat gaaagatatt tttaatttgt   3240
cacattaaaa ttcataatac gattgtgtga atgtgtgtga gactgactga gagtgtgaga   3300
cttttactag aaaagtgagt ccactagaaa atctgtgaca agttggtttt taaagtctga   3360
acagttgata ttaagcatat ctgaaaaaag caagtaaata ttttaacaaa actatgactc   3420
aggaaccttc gagaagatta gttccccact tagattttta aggagtaaaa agggctgagt   3480
tatgccttta agtgctgtca agaattcact tgggtttggg acatttgctg gtgtaatgct   3540
agatgcccac agcagcataa tattgtactt tgtcaaaggt aggtaaattc tctgtttctc   3600
```

-continued

```
agcagccctt tccccaaaag gtatggtgtt tatttttagt aaaaatagct aatctctttt   3660
taccatctca catgataact ctttggagtc atgtcaagtg ccccaaattt gtctgtgatt   3720
ttcccatctc tgagctcttt atctgcctcc gtttccttgt ttttctgggg ccagagtctc   3780
atctctgcct ttttttggtg tatcaccttc tgacttgcct tcattgcttg tctgatgtga   3840
ccaacagtgt gatcttggac acactaagga ttttagatgc aaagaaactt tatacaacat   3900
tatgaaagac tatcctttcc attttggtta tttcagcatt ttagttgcaa cctgggatta   3960
gattagagtt tccaacgtga tgaaaagtgg aatgatagca ttctataatt tccataattt   4020
tcctactggt ccgtaccaaa ttctagagtc tctggagttg ctatttcaga gtatttggtc   4080
aaacgaaaaa gaatttattg ctgtctgttt aacatgtatt tgtttggttg aaaggatctt   4140
tttagaaact gtaggaaaat aaacagaacc aaccaggtga aacaaagcac agacattggg   4200
ttaggatgta gtgagttgtg aacaatcagg attctgggtg tgatgggggt ccctgtctca   4260
taggtgatcc tttggtgcca tgtgaccgag agacatggtg tctaaggccc atggcctgga   4320
gacctgggtg ctgctcctag ctgactgtgg accttgggca agtccttcat ccgtcctgtg   4380
cctcactgtc ctcatctgaa caatggtatg atgacacctg ccctctcttt caatcatgct   4440
ttgaggatac agtgagattg gttacagtga accttcaatg agtagaatgt ggtatgccat   4500
ggtgggttgt agtagatggt gctccctgcc ttttctcctc tgttttcctc aatttgggaa   4560
caaatgagat tggcagaagg agggagctca cggtgcagta cttttctacc aaagtgtgcc   4620
cactggtgtc acctcctaat gttaacttgg atttcctaaa gcagtcccac tctgttatga   4680
gagtcactga ctcccgtgga catccccaca gtaagcagcc ttacaaaatc cagtcccctt   4740
agggcagagt gagtgtcata gaataatgac tccaaaccca cgtcaaaaat ggcttgtttt   4800
cagcgatgtt ataaaacaaa ggcctgtttt ttggaattgg gggtgactgg gtggtttgga   4860
ttgaaatgtg gacaaagata gcatgtgtat tttgaataaa ataaaaattt tgtaataaaa   4920
cttttaaaaa tcagtgatgt aaaatcaata tttaagacta taggctataa attgtttgat   4980
ttcattaact agccctttg atgcctagac atgttgtaaa aaaattgtgc tatggctgcc   5040
ttttcttctg ccccacaaca caaagggcta tttctacaag gcaaagtttt gtatatgtgc   5100
tattctttac ttcagattga gagttgggaa aaactggagt aaataatggg tttcttactt   5160
gcttaaaagc atatttatat gtgtatctca atatatacaa ggcaggttcc cctataaaag   5220
tctggaatgt actgcttaat tttacacttg tgtagacacg attatttgtg actgaaaagt   5280
ggaataacgt gtggatttg tcaactcatt atcagtctgt tagcagtcct ctatgtgagg   5340
catggtggtc taattgtgaa attctccctg tatatgggtg tctgtgtgaa agacagcact   5400
ttcttcctgt aaatatcttt tgatatccat ttatgtagaa ttccaatgaa tatgtctttg   5460
gaaaaggtaa tgtatcaaag tttttatttt gccaattgat ctaaatgccc atataactaa   5520
tcagaaatcc agtttggttc agattgggat tttcttttaa agaaaaaaaa agtatgcaga   5580
aaagactatt ggaagaatca tgtgttagtg acactttaca tcaacgttgc ttcaatattt   5640
tggaattgac caggctgctt tctcctacct gcaagagaat gtgcctgaca tttcccagtg   5700
cttactttgg gctataggaa gtccagcggg gatagctcga gcctcttgct ccctgagtca   5760
tttattccct ttacctgaac agagccttac ctgcaattca tagtgagagc acctgggtct   5820
gtatcctgac tccactctaa gtgaggtggg actgaatcac tgtacctctc tgggcctttt   5880
catttgaaac aagtgggtta gactagatta gctccaaagt cctctcttgc cctaacattt   5940
```

-continued tatttttatt ttcctgtggt taccactagg gtctgacacg taaaatgtga gggatcactt 6000
agaggtttgg atgttatatt tttgcattgt tacagcttat actccccagt tgaggacctg 6060
tgtcattctt agtggcccca cgacccctct gtttgtattc ctgctccact tatctatact 6120
tttttgggta atcatcccac ttttttttt tcttgagatg gagtctcgct gtgttgccaa 6180
ggctggagta cagtggtgca atctcagctc actgcagcct cctcccgggt tcaagtgatt 6240
ctcctgcctc agcttcccaa gtagctggga ttactggcgc acgccactac gcccagctaa 6300
tttttgtatt tttagtagag acagggtttt gccatgttgg ccaggctggt cttgaactct 6360
tgacctcaac ctgcctcagc ctcccaaagt gctgggatta cacgcatgag ctaccgcgtc 6420
cagccccact ttttttctac tcttgaaaaa aacaactttc tagtccatga ggtactttgg 6480
ctccatcccc ctcaaaaaca aaacaaaaaa tccatttaaa gtgtcctcct agaaaagcct 6540
cagaactgcc ttcaactaca tctgtcacct ttatagaata ttttgaaatt ctggaagagg 6600
atgggaaaca aaattctaat ttagctagag ctgtgatccc caaataagtg ctgacaaaat 6660
tgtctaccac agaaaggccg tccttgtcat cttgtaggca tcactgctgc taaatcacat 6720
cagtacatgc cttctgtggg gagatggcag gggcagggg caggaccagg ggatgggatt 6780
agataaagtg tgataatgtc ctttagataa aagaaatcct acgctataga acaaggttct 6840
gtactcttga gttggtgtct gagatcacct gcacagtgtt acagagattt tccactccat 6900
aaatcactct aaaagagttt gcataagact cggtagacct gtgctattca atgtggcagt 6960
caacagccat atgtggcgat gactactcaa agtttggctt gttcaaatcg agactgtgtt 7020
gtacacatac aatacacacc agattttgaa ggcttggtac caaaaaggaa tttaaaatat 7080
ttcaccaata tttcatattg ataacatgct gaaatgacac tattttggat gtactaagta 7140
aaatattaac aatttaatat atttatataa ttgaaattaa aattcttttc acccattttt 7200 attttttaa aaatgtggcc cctaaagaac ttcaaattag acatgtggat aacgttatac 7260
ttctattgga cagccccact ctagacttac atggtgtggg gtaggcagtg aaatccgtaa 7320
ataggaaacg caattctgca aagtatctaa atagacagaa acaacacaaa tatttttgct 7380
ggagtcagga gcactgtgag gcacagaaca tctcccagaa agcagatttt tttttctgc 7440 cgaaaaacca atatatatat gtatgatccc aattaaaaga caaaagcaaa tgagccccaa 7500
actgcctgtc ttcagctttg cctgggagct gctacctttg ctcttctagc atcttctagg 7560
taccaaggat attagccact tgagggtgtt gggcatattt gtttcattgt aggcaaaatc 7620
ctcttgtggt ttcccctccc caggtattgt tgagtctgtt caaagctggg tgtgttgaaa 7680
cactgcacaa atcctgccac tcttgatgtg ccgcttgtct cagccttggc agaggctgag 7740
tctgttcctg tgcccacctg tccagcaggt tttgatgttg gctcctgaaa gagtttgtat 7800
ttattttatt ttgcactagt cacagttgtt gttaaactgt atcaaatgtt ttgggagatt 7860
atttgcctga gatggaaaga gagatggatg atttattgct tcaattgttt taaattaaaa 7920
gctattctca caa 7933

<210> SEQ ID NO 18
<211> LENGTH: 7218
<212> TYPE: DNA
<213> ORGANISM: Homo sapiens

<400> SEQUENCE: 18
tgctggcctg gcgcgcgcgc gggcgggagc ggagggcaac ggggcggcgc gggcggccgg 60
gcgcagggtc gcgggaggtg acgcgcggcg aggatggcgg cgcggggccg ggggctgctg 120

-continued

```
ctgctgacgc tgtcggtgct gttggcggcg ggcccctccg ccgctgcggc caagctcaac    180
atccccaaag tgctgctgcc cttcacgcgg gccacgcgcg ttaacttcac gctggaggcc    240
tcggagggct gctaccgctg gttgtccacc cggccggagg tggccagcat cgagccgctg    300
ggcctggacg agcagcagtg ctcccagaag gcagtggtgc aggcccgcct gacccagcct    360
gcccgcctca ccagcatcat cttcgcagag gacatcacca caggccaggt cctgcgctgt    420
gatgccattg tggacctcat ccatgacatc cagatcgtct ccaccacccg cgagctctac    480
ctggaggact ccccccctgga gctgaagatc caggccctgg actccgaagg gaacaccttc    540
agcactctgg ctggactggt cttcgagtgg acgattgtga aggactccga ggcggacagg    600
ttctcagact cccacaatgc gctgcgaatc ctcactttct tggagtctac gtacatccct    660
ccttcttaca tctcagagat ggagaaggct gccaagcaag ggacaccat cctggtgtct    720
gggatgaaga ccgggagctc caagctcaag gctcgcatcc aggaggctgt ctacaagaat    780
gtacgccctg cagaagtcag gctgctgatt ttggaaaaca tccttctgaa cccggcctat    840
gacgtctacc tgatggtggg aacctccatt cactacaagg tgcagaagat caggcaaggg    900
aaaattacag aactctccat gccttccgat cagtacgagt tgcagcttca gaacagcatc    960
ccgggccccg aaggagaccc agcccggccg gtggctgtct tggcccagga cacgtcgatg   1020
gtcactgcac tgcagctggg acagagcagc ctcgtccttg gccacaggag tattcgcatg   1080
caaggtgctt ctaggttacc caacagcact atctacgtgg tcgaacctgg atacctaggg   1140
ttcactgttc accctggtga caggtgggtg ctggagaccg gccgcctgta tgaaatcacc   1200
atcgaagttt ttgacaagtt cagcaacaag gtctatgtat ctgacaacat ccgaattgaa   1260
actgtgcttc ctgctgagtt cttcgaggtg ctctcgtcct cccagaatgg gtcataccat   1320
cgcatcaggg cactaaagag gggacagacg gccattgacg cggccctcac ctctgtggtg   1380
gaccaggatg gaggggtcca catactacag gtgcctgtgt ggaaccagca ggaggtggaa   1440
attcacatcc cgatcaccct gtatcccagc atcttgacat ttccgtggca accaaagacg   1500
ggcgcctatc agtacacaat aagggcccac ggtggcagtg ggaacttcag ctggtcttcg   1560
tcaagccacc tggttgccac agttactgtc aagggcgtga tgaccacagg cagtgacatc   1620
gggttcagtg tgatccaggc acatgatgtg cagaacccac tccatttcgg tgagatgaag   1680
gtgtatgtga tcgagcccca cagcatggag tttgccccgt gccaggtgga ggcacgtgtg   1740
ggccaggccc tggagctgcc cctgaggatc agtggcctca tgcccggcgg ggccagtgag   1800
gtggtcacct tgagcgactg ctcccacttt gacttggctg tcgaggtgga gaaccagggt   1860
gtgttccagc cactcccagg gaggctgccg ccaggctctg agcactgcag cggcatccgg   1920
gtaaaggccg aggcccaggg ctctaccacg cttcttgtga gctacagaca cggccacgtc   1980
cacctgagtg ccaagatcac cattgctgcc tacctgcccc tcaaggctgt ggatccctcc   2040
tctgttgcct tggtaaccct gggctcctca aaggagatgc tgtttgaagg aggtcccaga   2100
ccttggatcc tcgagccgtc caaattcttc cagaacgtca ccgctgagga cactgacagc   2160
atcggcctgg ctctctttgc cccccattcc tcccggaatt atcagcaaca ctggatcctt   2220
gtgacctgtc aggccttggg tgagcaggtc atcgccctgt cggtggggaa caagcccagc   2280
ctcaccaacc cctttcctgc ggtggagcct gccgtggtga agttcgtctg cgccccaccg   2340
tccaggctca ccctcgcgcc tgtctacacc agcccccagc tggacatgtc ctgtccgctg   2400
ctgcagcaga acaagcaggt ggtcccagtg tccagccacc gcaacccccg gctggacctg   2460
```

-continued

```
gctgcttacg accaggaggg ccgccggttc gacaacttca gctctctgag catccagtgg   2520
gagtccacca ggccagtgtt ggccagcatc gagcctgagc tgcccatgca gctggtgtcc   2580
caggacgatg agagtggcca aaagaagctg cacggtttgc aggccatttt ggttcacgag   2640
gcatcaggaa ccacagccat cactgccact gccactggct accaggagtc ccacctcagc   2700
tctgccagaa caaagcagcc gcatgaccct ctggtgcctc tgtcggcctc catagagctc   2760
atcctggtgg aggacgtgag ggtgagccca gaagaggtga ccatctacaa ccaccctggc   2820
atccaggcag agctccgcat cagggaaggc tcaggttact tcttcctcaa caccagcacc   2880
gcagatgttg tcaaggtggc ctaccaggag gccaggggtg tcgccatggt gcaccctttg   2940
ctcccgggct catccaccat catgatccat gacttgtgcc tcgtcttccc ggccccagcc   3000
aaggctgtcg tttacgtgtc ggacattcag gagctgtaca tccgtgtggt tgacaaggtg   3060
gagattggga agacagtgaa ggcatacgtc cgcgtgctgg acttgcacaa gaagcccttc   3120
cttgccaaat acttcccctt tatggacctg aagctccgag cagcctcccc gatcattaca   3180
ttggtggccc ttgatgaagc ccttgacaac tacaccatca cattcctcat ccgcggtgtg   3240
gccatcggcc agaccagtct aactgcaagt gtgaccaata aagctggaca gagaatcaac   3300
tcagccccac aacagattga agtctttccc ccgttcaggc tgatgcccag gaaggtgaca   3360
ctgcttatcg ggggccacgat gcaggtcacc tccgagggcg gcccccagcc tcagtccaac   3420
atccttttct ccatcagcaa tgagagcgtt gcgctggtga gcgctgctgg gctggtacag   3480
ggcctcgcca tcgggaacgg cactgtgtct gggctcgtgc aggcagtgga tgcagagacc   3540
ggcaaggtgg tcatcatctc tcaggacctc gtgcaggtgg aggtgctgct gctaagggcc   3600
gtgaggatcc gcgcccccat catgcggatg aggacgggca cccagatgcc catctatgtc   3660
accggcatca ccaaccacca gaaccctttc tcctttggca atgccgtgcc aggcctgacc   3720
ttccactggt ctgtcaccaa gcgggacgtc ctggacctcc gagggcggca ccacgaggcg   3780
tcgatccgac tcccgtcaca gtacaacttt gccatgaacg tgctcggccg ggtaaaaggc   3840
cggaccgggc tgagggtggt ggtcaaggct gtggacccca catcggggca gctgtatggc   3900
ctggccagag aactctcgga tgagatccaa gtccaggtgt ttgagaagct gcagctgctc   3960
aaccctgaaa tagaagcaga acaaatatta atgtcgccca actcatatat aaagctgcag   4020
acaaacaggg atggtgcagc ctctctgagc taccgcgtcc tggatggacc cgaaaaggtt   4080
ccagttgtgc atgttgatga gaaaggcttt ctagcatcag ggtctatgat cgggacatcc   4140
accatcgaag tgattgcaca agagcccttt ggggccaacc aaaccatcat tgttgctgta   4200
aaggtatccc ctgtttccta cctgagggtt tccatgagcc ctgtcctgca cacccagaac   4260
aaggaggccc tggtggccgt gcctttggga atgaccgtga ccttcactgt ccacttccac   4320
gacaactctg gagatgtctt ccatgctcac agttcggtcc tcaactttgc cactaacaga   4380
gacgactttg tgcagatcgg gaagggcccc accaacaaca cctgcgttgt ccgcacagtc   4440
agcgtgggcc tgacactgct ccgtgtgtgg gacgcagagc acccgggcct ctcggacttc   4500
atgcccctgc ctgtcctaca ggccatctcc ccagagctgt ctggggccat ggtggtgggg   4560
gacgtgctct gtctggccac tgttctgacc agcctggaag gcctctcagg aacctggagc   4620
tcctcggcca acagcatcct ccacatcgac cccaagacgg gtgtggctgt ggcccgggcc   4680
gtgggatccg tgacggttta ctatgaggtc gctgggcacc tgaggaccta caaggaggtg   4740
gtggtcagcg tccctcagag gatcatggcc cgtcacctcc accccatcca gaccagcttc   4800
caggaggcta cagcctccaa agtgattgtt gccgtgggag acagaagctc taacctgaga   4860
```

-continued

```
ggcgagtgca cccccaccca gagggaagtc atccaggcct tgcacccaga gaccctcatc   4920
agctgccagt cccagttcaa gccggccgtc tttgatttcc catctcaaga tgtgttcacc   4980
gtggagccac agtttgacac tgctctcggc cagtacttct gctcaatcac aatgcacagg   5040
ctgacggaca agcagcggaa gcacctgagc atgaagaaga cagctctggt ggtcagtgcc   5100
tccctctcca gcagccactt ctccacagag caggtggggg ccgaggtgcc cttcagccca   5160
ggtctcttcg ccgaccaggc tgaaatcctt ttgagcaacc actacaccag ttccgagatc   5220
agggtctttg gtgccccgga ggttctggag aacttggagg tgaaatccgg gtccccggcc   5280
gtgctggcat tcgcaaagga gaagtctttt gggtggccca gcttcatcac atacacggtc   5340
ggcgtcttgg accccgcggc tggcagccaa gggcctctgt ccactaccct gaccttctcc   5400
agccccgtga ccaaccaagc cattgccatc ccagtgacag tggcttttgt ggtggatcgc   5460
cgtgggcccg gtccttatgg agccagcctc ttccagcact tcctggattc ctaccaggtc   5520
atgttcttca cgctcttcgc cctgttggct gggacagcgg tcatgatcat agcctaccac   5580
actgtctgca cgccccggga tcttgctgtg cctgcagccc tcacgcctcg agccagccct   5640
ggacacagcc cccactattt cgctgcctca tcacccacat ctcccaatgc attgcctcct   5700
gctcgcaaag ccagccctcc ctcagggctg tggagcccag cctatgcctc ccactaggcc   5760
gcgtgaaggt tcccggagga tgggtctcag ccgagcctcg tgcaccccca agatggaaca   5820
tccctgctgc attcacactg gaacaagccc ctccagatga gtgccccggc cccaggccag   5880
cttcactgcc gtctcttcac acagagctgt agtttcggct ctgcccatta gctcatttta   5940
tgtaggagtt ttaaatgtgt gtttttttcc tttcaagtct tacaaagcta agactttttg   6000
gctcattcct ttttgcatgg ttgtctaggg tttctggaca atgtgctgtt gcatttttat   6060
tttcctagcc ttgctaaaat ctttcccttc tcaagacttt gagcagttag aagtgctctt   6120
tagaagttgt ctgtgggtga tgttactgta gtggtctcag ggaaaggatt gtccagttac   6180
tttagggggt ttttggtggg gtttttcccc ctgtgaaaac ttactttgcc cctagtctgg   6240
ctgctgctag gacttctgag gagcaatggg acatgagtgt ccctgtatct gcgccactgc   6300
cgcaagggaa gcctcaggaa ccagcacctg gaggccagga tagccaagcc ctgggtgagc   6360
gagaggctgg agaacacagg agctcaccca gggctgctgc ccaaccatgg gccactgtga   6420
acagacttca gtcctctgtt tttgtttcat aagccgttga gacatctgat ggacttggct   6480
taggccctgc tgggacatcc cacgtgtgat ccctttcact ccatcaggac accaggactg   6540
tccttaggaa aatgtccttg agatggcagc aggagtcata ttttctgtgt gtgtgtttcg   6600
gaaagccgct gtgtcctgcc tcagcacaaa gacccagtgt catttgctcc tcctgttcct   6660
gtgccactcc agaacctcag cagatctgag ccaccgcctg ccagtgtgag aggcggccac   6720
tttcatggca gctcatcagg cgcagggccc cagacagctt cccagcaggc cctagagccc   6780
ggcctgggcc aatgatggag ggcggccgcc agcccagggc ctgcccatcc agaagggact   6840
ccccagggcc tgggggagga gacccttgga aaagtcctct cttcccagct cctgattctg   6900
gatctgagat tctcagatca caggccccctg tgctccaggc cgaggctggg ctaccctcag   6960
ggagatccag agactcatgc ccatggccat ccatgcgtgg acgctgtgtg gagagtccag   7020
gatgacggga tcccgcacaa gctcccttca gtccttcagg gctgggccat gtggttgatt   7080
tttctaaagc tggagaaagg aagaattgtg ccttgcatat tacttgagct taaactgaca   7140
acctggatgt aaataggagc ctttctactg gtttatttaa taaagttcta tgtgattttt   7200
```

```
taagagggaa aaaaaaaa                                                 7218


<210> SEQ ID NO 19
<211> LENGTH: 6780
<212> TYPE: DNA
<213> ORGANISM: Homo sapiens

<400> SEQUENCE: 19

gattgccacc caggacgatg agcggctgag atggagacgt ctgcctcagc cactgcctcc     60

gagaagcaag aagccaaaag tgggatcctg gaggccgctg gcttccccga cccgggtaaa    120

aaggcctctc ctttggtggt ggctgcagcg gcagcagcag cggtagctgc ccaaggagtg    180

ccgcagcatc tcttgccacc attccatgcg cccctaccga ttgacatgcg acaccaggaa    240

ggaaggtacc attacgagcc tcattctgtc cacggtgtgc acgggccccc tgccctcagc    300

ggcagccctg tcatctctga catctccttg atccggcttt ccccgcaccc ggctggccct    360

ggggagtccc ccttcaacgc cccccacccg tacgtgaacc cccacatgga gcactacctc    420

cgttctgtgc acagcagccc cacgctctcc atgatctctg cagccagggg cctcagcccc    480

gctgatgtgg cccaggagca ccttaaggag aggggactgt ttggccttcc tgctccaggc    540

accacccect cagactatta ccaccagatg accctcgtgg caggccaccc cgcgccctac    600

ggggacctgc tgatgcagag cgggggcgct gccagcgcac cccatctcca cgactacctc    660

aaccccgtgg acgtgtcccg tttctccagc ccgcgggtga cgccccgcct gagccgcaag    720

cgggcgctgt ccatctcccc actctcagac gccagcctgg acctgcagcg gatgatccgc    780

acctcaccca actcgctagt ggcctacatc aacaactccc gaagcagctc ggcggccagc    840

ggttcctacg ggcatctgtc agcgggtgcc ctcagcccag ccttcacctt cccccacccc    900

atcaaccccg tggcctacca gcagattctg agccagcaga ggggtctggg gtcagccttt    960

ggacacacac cacccctgat ccagccctca cccaccttcc tggcccagca gcccatggcc   1020

ctcacctcca tcaatgccac gcccacccag ctcagcagca gcagcaactg tctgagtgac   1080

accaaccaga acaagcagag cagtgagtcg gccgtcagca gcaccgtcaa ccctgtcgcc   1140

attcacaagc gcagcaaggt caagaccgag cctgagggcc tgcggccggc ctcccctctg   1200

gcgctgacgc agggccaggt gtctggacac ggctcatgtg ggtgtgccct tcccctctcc   1260

caggagcagc tggctgacct caaggaagat ctggacaggg atgactgtaa gcaggaggct   1320

gaggtggtca tctatgagac caactgccac tgggaagact gcaccaagga gtacgacacc   1380

caggagcagc tggtgcatca catcaacaac gagcacatcc acggggagaa gaaggagttt   1440

gtgtgccgct ggcaggcctg cacgcgggag cagaagccct tcaaggcgca gtacatgctg   1500

gtggtgcaca tgcggcgaca cacgggcgag aagccccaca agtgcacgtt cgagggctgc   1560

tcgaaggcct actcccgcct ggagaacctg aagacacacc tgcggtccca caccggggag   1620

aagccatatg tgtgtgagca cgagggctgc aacaaagcct tctccaacgc ctcggaccgc   1680

gccaagcacc agaatcgcac ccactccaac gagaaaccct acatctgcaa gatcccaggc   1740

tgcaccaaga gatacacaga ccccagctct ctccggaagc atgtgaaaac ggtccacggc   1800

ccagatgccc acgtcaccaa gaagcagcgc aatgacgtgc acctccgcac accgctgctc   1860

aaagagaatg ggacagtgga ggccggcacg gagcctggcg gcccagagag caccgaggcc   1920

agcagcacca gccaggccgt ggaggactgc ctgcacgtca gagccatcaa gaccgagagc   1980

tccgggctgt gtcagtccag ccccggggcc cagtcgtcct gcagcagcga gccctctcct   2040

ctgggcagtg cccccaacaa tgacagtggc gtggagatgc cggggacggg gcccgggagc   2100
```

-continued ctgggagacc tgacggcact ggatgacaca cccccagggg ccgacacctc agccctggct 2160
gccccctccg ctggtggcct ccagctgcgc aaacacatga ccaccatgca ccggttcgag 2220
cagctcaaga aggagaagct caagtcactc aaggattcct gctcatgggc cgggccgact 2280
ccacacacgc ggaacaccaa gctgcctccc ctcccgggaa gtggctccat cctggaaaac 2340
ttcagtggca gtgggggcgg cgggcccgcg gggctgctgc cgaacccgcg gctgtcggag 2400
ctgtccgcga gcgaggtgac catgctgagc cagctgcagg agcgccgcga cagctccacc 2460
agcacggtca gctcggccta caccgtgagc cgccgctcct ccggcatctc cccctacttc 2520
tccagccgcc gctccagcga ggcctcgccc ctgggcgccg gccgcccgca caacgcgagc 2580
tccgctgact cctacgaccc catctccacg gacgcgtcgc ggcgctcgag cgaggccagc 2640
cagtgcagcg gcggctccgg gctgctcaac ctcacgccgg cgcagcagta cagcctgcgg 2700
gccaagtacg cggcagccac tggcggcccc ccgcccactc cgctgccggg cctggagcgc 2760
atgagcctgc ggaccaggct ggcgctgctg gacgcgcccg agcgcacgct gcccgccggc 2820
tgcccacgcc cactggggcc gcggcgtggc agcgacgggc cgacctatgg ccacggccac 2880
gcgggggctg cgcccgcctt cccccacgag gctccaggcg gcggagccag gcgggccagc 2940
gaccctgtgc ggcggcccga tgccctgtcc ctgccgcggg tgcagcgctt ccacagcacc 3000
cacaacgtga accccggccc gctgccgccc tgtgccgaca ggcgaggcct ccgcctgcag 3060
agccacccga gcaccgacgg cggcctggcc cgcggcgcct actcgccccg gccgcctagc 3120
atcagcgaga acgtggcgat ggaggccgtg gcggcaggag tggacggcgc ggggcccgag 3180
gccgacctgg ggctgccgga ggacgacctg gtgcttccag acgacgtggt gcagtacatc 3240
aaggcgcacg ccagtggcgc tctggacgag ggcaccgggc aggtgtatcc cacggaaagc 3300
actggcttct ctgacaaccc cagactaccc agcccggggc tgcacggcca gcgcaggatg 3360
gtggctgcgg actccaacgt gggcccctcc gcccctatgc tgggaggatg ccagttaggc 3420
tttggggcgc cctccagcct gaacaaaaat aacatgcctg tgcagtggaa tgaggtgagc 3480
tccggcaccg tagacgccct ggccagccag gtgaagcctc caccctttcc tcagggcaac 3540
ctggcggtgg tgcagcagaa gcctgccttt ggccagtacc cgggctacag tccgcaaggc 3600
ctacaggcta gccctggggg cctggacagc acgcagccac acctgcagcc ccgcagcgga 3660
gccccctccc agggcatccc cagggtaaac tacatgcagc agctgcgaca gccagtggca 3720
ggcagccagt gtcctggcat gactaccact atgagccccc atgcctgcta tggccaagtc 3780
cacccccagc tgagccccag caccatcagt ggggccctca accagttccc ccaatcctgc 3840
agcaacatgc cagccaagcc agggcatctg gggcaccctc agcagacaga agtggcacct 3900
gaccccacca cgatgggcaa tcgccacagg gaacttgggg tccccgattc agccctggct 3960
ggagtgccac cacctcaccc agtccagagc tacccacagc agagccatca cctggcagcc 4020
tccatgagcc aggagggcta ccaccaggtc cccagccttc tgcctgcccg ccagcctggc 4080
ttcatggagc cccaaacagg cccgatgggg gtggctacag caggctttgg cctagtgcag 4140
ccccggcctc ccctcgagcc cagccccact ggccgccacc gtggggtacg tgctgtgcag 4200
cagcagctgg cctacgccag ggccacaggc catgccatgg ctgccatgcc gtccagtcag 4260
gaaacagcag aggctgtgcc caagggagcg atgggcaaca tggggtcggt gcctccccag 4320
ccgcctccgc aggacgcagg tggggccccg gaccacagca tgctctacta ctacggccag 4380
atccacatgt acgaacagga tggaggcctg gagaacctcg ggagctgcca ggtcatgcgg 4440

-continued tcccagccac cacagccaca ggcctgtcag gacagcatcc agccccagcc cttgccctca 4500
ccaggggtca accaggtgtc cagcactgtg gactcccagc tcctggaggc cccccagatt 4560
gacttcgatg ccatcatgga tgatggcgat cactcgagtt tgttctcggg tgctctgagc 4620
cccagcctcc tccacagcct ctcccagaac tcctcccgcc tcaccacccc ccgaaactcc 4680
ttgaccctgc cctccatccc cgcaggcatc agcaacatgg ctgtcgggga catgagctcc 4740
atgctcacca gcctcgccga ggagagcaag ttcctgaaca tgatgaccta gaggcccgag 4800
cgcctggtgc tgagtgcacc cggaggggtc atcgctgccc agagcctggg gattccagct 4860
gtcttgtctt tttccaaaaa agtgttaaat aggcttgagg ggttgttgcg caatggccgc 4920
ttcagatgac agatgttgta agagaaggtt tatgggcatc ctctctggtc ttttggatta 4980
ttcctcagaa caatgaaaaa agtctccata ggacaggaag gaatgcaaaa ctcatttaca 5040
cagtgctttc cagcctttgg tgcttacagg accgcgctgt tccggcttct tcacggctga 5100
cattcggcta acgagggatt actttggcca aaacctttca aaggatatgc agaaagatgg 5160
tagggagcat ttgggtttga atctgaatgc tatactggat actctgctcc ggaaagatga 5220
gctttttatt ctactacttg gaaggaaaag gaattcctgg tccacctgaa ttcctctatg 5280
aagcctaact cttgaggtct ctaacatacc ttgtcataga ggaaaagcac agattatacc 5340
tggatgattc aggagcacat tctgattcca ggtttggtag agctggctct tctactccgt 5400
aaagccgagt ctgggactgg cagcccatcc aagtgtatat gaatgaataa agcatccaag 5460
tatatatgaa tgaataaagt atgtaagtat caccagaaaa aggaaagaaa aaatgtactc 5520
cttggggcaa gcccagaagc tgccctggcc tctccagacc gtgtttacag tgtttgcatg 5580
tagaatgtag cccttcctga aaagaagact tgtttctaaa tacctcgggg ctgctggagc 5640
cgctgtgggt tagggatgga ctgaggcctc gaggagtgag ggtgcacccg gggcccagcc 5700
tcaggctgcc ctagggatct ctcagtagga agaggaagtt gcgtgtttac ccaatcctgt 5760
ttctccaatg caacgtccac ccactttacc accaaaaact ccagggcctg acggcagccc 5820
ggtcccccag cactcaccag cagcccagtg ttctccacca agccacagtg tgcatgcctg 5880
gtatcctccg gattcccttc cttctgcccg ctgagtcact gggcagagaa tgatgacatg 5940
tgtaggtggt gtggttgggg gtggaaaggg gaaggggttg atcctcagga ctctgaggga 6000
gcatcgttga attttcctgt tcagtgtgac caagacccac ctggaaatgg aatttggaac 6060
tggcttcagg agacatcatt cctgaacaca ctgtagggtg aattggtgca tcttccccac 6120
catacacaca cacacacaca cacacacaca cacacacaca cacacacccc aaaccttttc 6180
atggggaatg tgtggcaacc ttgccaaaca gcaccactca gagtgtgact ctgactgtga 6240
ccttggcctt aatgaggaac ttcttaggag agtttgagga caaggccaac atcgtcatct 6300
gggctcgctg cgtcccagca catcaaactc tgtccagaga caaggccaac tgcaaatgaa 6360
agccagggaa cattgctaag ggtctgtggc tctgtggtgg tgttcatcgc cttcctgaga 6420
taggatttcc cttgccagtc ccaacctgta tatattctgt acagaagaca tccctgaata 6480
tactgtaggt gagtcgtcca gccaaattta tatctccaaa acatttttag ctttttctac 6540
atgctatgaa ttgagatgac atgctcaact tgtaaataag tctttttgta cattaaaaaa 6600
gtaatttttt cataatttat cttgtctatc tgcttccccc ttgacagtag ttaatgagaa 6660
cctgggcagt aaatttggtg cattcgagca gaaattaggc tgtatttttt cttaacagtg 6720
tcaaaattga ctatcccgcc tttgccaaga aatgtttaat gctgaggcaa aaaaaaaaaa 6780

<210> SEQ ID NO 20
<211> LENGTH: 3824
<212> TYPE: DNA
<213> ORGANISM: Homo sapiens

<400> SEQUENCE: 20
ggaagcgcag agcaggttca aacacagacg gcgggtgaac atggcgtcct cgacttggtc 60
tgagacgtga taggcctgcc ttctggttga agatgtggcg agtgaaaaaa ctgagcctca 120
gcctgtcgcc ttcgccccag acgggaaaac catctatgag aactcctctc cgtgaactta 180
ccctgcagcc cggtgccctc accaactctg gaaaaagatc ccccgcttgc tcctcgctga 240
ccccatcact gtgcaagctg gggctgcagg aaggcagcaa caactcatct ccagtggatt 300
ttgtaaataa caagaggaca gacttatctt cagaacattt cagtcattcc tcaaagtggc 360
tagaaacttg tcagcatgaa tcagatgagc agcctctaga tccaattccc caaattagct 420
ctactcctaa aacgtctgag gaagcagtag acccactggg caattatatg gttaaaacca 480
tcgtccttgt accatctcca ctggggcagc aacaagacat gatatttgag gcccgtttag 540
ataccatggc agagacaaac agcatatctt taaatggacc tttgagaaca gacgatctgg 600
tgagagagga ggtggcaccc tgcatgggag acaggttttc agaagttgct gctgtatctg 660
agaaacctat ctttcaggaa tctccgtccc atctcttaga ggagtctcca ccaaatccct 720
gttctgaaca actacattgc tccaaggaaa gcctgagcag tagaactgag gctgtgcgtg 780
aggacttagt accttctgaa agtaacgcct tcttgccttc ctctgttctc tggctttccc 840
cttcaactgc cttggcagca gatttccgtg tcaatcatgt ggacccagag gaggaaattg 900
tagagcatgg agctatggag gaaagagaaa tgaggtttcc cacacatcct aaggagtctg 960
aaacagaaga tcaagcactt gtctcaagtg tggaagatat tctgtccaca tgcctgacac 1020
caaatctagt agaaatggaa tcccaagaag ctccaggccc agcagtagaa gatgttggta 1080
ggattcttgg ctctgataca gagtcttgga tgtccccact ggcctggctg gaaaaaggtg 1140
taaatacctc cgtcatgctg gaaaatctcc gccaaagctt atcccttccc tcgatgcttc 1200
gggatgctgc aattggcact accccttttct ctacttgctc ggtggggact tggtttactc 1260
cttcagcacc acaggaaaag agtacaaaca catcccagac aggcctggtt ggcaccaagc 1320
acagtacttc tgagacagag cagctcctgt gtggccggcc tccagatctg actgccttgt 1380
ctcgacatga cttggaagat aacctgctga gctctcttgt cattctggag gttctctccc 1440
gccagcttcg ggactggaag agccagctgg ctgtccctca cccagaaacc caggacagta 1500
gcacacagac tgacacatct cacagtggga taactaataa acttcagcat cttaaggaga 1560
gccatgagat gggacaggcc ctacagcagg ccagaaatgt catgcaatca tgggtgctta 1620
tctctaaaga gctgatatcc ttgcttcacc tatccctgtt gcatttagaa gaagataaga 1680
ctactgtgag tcaggagtct cggcgtgcag aaacattggt ctgttgctgt tttgatttgc 1740
tgaagaaatt gagggcaaag ctccagagcc tcaaagcaga aagggaggag gcaaggcaca 1800
gagaggaaat ggctctcaga ggcaaggatg cggcagagat agtgttggag gctttctgtg 1860
cacacgccag ccagcgcatc agccagctgg aacaggacct agcatccatg cgggaattca 1920
gaggccttct gaaggatgcc cagacccaac tggtagggct tcatgccaag caagaagagc 1980
tggttcagca gacagtgagt cttacttcta ccttgcaaca agactggagg tccatgcaac 2040
tggattatac aacatggaca gctttgctga gtcggtcccg acaactcaca gagaaactca 2100
cagtcaagag ccagcaagcc ctgcaggaac gtgatgtggc aattgaggaa aagcaggagg 2160

-continued

```
tttctagggt gctggaacaa gtctctgccc agttagagga gtgcaaaggc caaacagaac   2220

aactggagtt ggaaaacagt cgtctagcaa cagatctccg ggctcagttg cagattctgg   2280

ccaacatgga cagccagcta aaagagctac agagtcagca tacccattgt gcccaggacc   2340

tggctatgaa ggatgagtta ctctgccagc ttacccagag caatgaggag caggctgctc   2400

aatggcaaaa ggaagagatg gcactaaaac acatgcaggc agaactgcag cagcaacaag   2460

ctgtcctggc caaagaggtg cgggacctga aagagacctt ggagtttgca gaccaggaga   2520

atcaggttgc tcacctggag ctgggtcagg ttgagtgtca attgaaaacc acactggaag   2580

tgctccggga gcgcagcttg cagtgtgaga acctcaagga cactgtagag aacctaacgg   2640

ctaaactggc cagcaccata gcagataacc aggagcaaga tctggagaaa acacggcagt   2700

actctcaaaa gctagggctg ctgactgagc aactacagag cctgactctc tttctacaga   2760

caaaactaaa ggagaagact gaacaagaga cccttctgct gagtacagcc tgtcctccca   2820

cccaggaaca ccctctgcct aatgacagga ccttcctggg aagcatcttg acagcagtgg   2880

cagatgaaga gccagaatca actcctgtgc ccttgcttgg aagtgacaag agtgctttca   2940

cccgagtagc atcaatggtt tcccttcagc ccgcagagac cccaggcatg gaggagagcc   3000

tggcagaaat gagtattatg actactgagc ttcagagtct ttgttccctg ctacaagagt   3060

ctaaagaaga agccatcagg actctgcagc gaaaaatttg tgagctgcaa gctaggctgc   3120

aggcccagga agaacagcat caggaagtcc agaaggcaaa agaagcagac atagagaagc   3180

tgaaccaggc cttgtgcttg cgctacaaga atgaaaagga gctccaggaa gtgatacagc   3240

agcagaatga gaagatccta gaacagatag acaagagtgg cgagctcata agccttagag   3300

aggaggtgac ccaccttacc cgctcacttc ggcgtgcgga gacagagacc aaagtgctcc   3360

aggaggccct ggcaggccag ctggactcca actgccagcc tatggccacc aattggatcc   3420

aggagaaagt gtggctctct caggaggtgg acaaactgag agtgatgttc ctggagatga   3480

aaaatgagaa ggaaaaactc atgatcaagt tccagagcca tagaaatatc ctagaggaga   3540

accttcggcg ctctgacaag gagttagaaa aactagatga cattgttcag catatttata   3600

agaccctgct ctctattcca gaggtggtga ggggatgcaa agaactacag ggattgctgg   3660

aatttctgag ctaagaaact gaaagccaga atctgcttca cctcttttta cctgcaatac   3720

ccccttaccc caataccaag accaactggc atagagccaa ctgagataaa tgctatttaa   3780

ataaagtgta tttaatgaat ttctccaaaa aaaaaaaaaa aaaa                    3824
```

```
<210> SEQ ID NO 21
<211> LENGTH: 3519
<212> TYPE: DNA
<213> ORGANISM: Homo sapiens

<400> SEQUENCE: 21

ctcacacgcc ggctcggatg atctcctgcc atgactcagc gcttctcgca ggctgccctg     60

ctggggacac cggcttcgct cgggcccctc ccgacgcgtc cacccccctct cgccacccac    120

gcccgccccc agccgctggg cctttcccag tgcggccgcc gccgccacag ctgcagtcag    180

caccgtcacc ccagcagcat ccgccgcctg caccgcgcgt gcggcccgcc ccggcctgac    240

cccgccgccg aacccggcgc cagccatgga gcccgaagcc ccccgtcgcc gccacaccca    300

tcagcgcggc tacctgctga cacggaaccc tcacctcaac aaggacttgg cctttaccct    360

ggaagagaga cagcaattga acattcatgg attgttgcca ccttccttca acagtcagga    420

gatccaggtt cttagagtag taaaaaattt cgagcatctg aactctgact ttgacaggta    480
```

-continued

```
tcttctctta atggatctcc aagatagaaa tgaaaaactc ttttatagag tgctgacatc    540
tgacattgag aaattcatgc ctattgttta tactcccact gtgggtctgg cttgccaaca    600
atatagtttg gtgtttcgga agccaagagg tctctttatt actatccacg atcgagggca    660
tattgcttca gttctcaatg catggccaga agatgtcatc aaggccattg tggtgactga    720
tggagagcgt attcttggct tgggagacct tggctgtaat ggaatgggca tccctgtggg    780
taaattggct ctatatacag cttgcggagg gatgaatcct caagaatgtc tgcctgtcat    840
tctggatgtg ggaaccgaaa atgaggagtt acttaaagat ccactctaca ttggactacg    900
gcagagaaga gtaagaggtt ctgaatatga tgattttttg gacgaattca tggaggcagt    960
ttcttccaag tatggcatga attgccttat tcagtttgaa gattttgcca atgtgaatgc   1020
atttcgtctc ctgaacaagt atcgaaacca gtattgcaca ttcaatgatg atattcaagg   1080
aacagcatct gttgcagttg caggtctcct tgcagctctt cgaataacca agaacaaact   1140
gtctgatcaa acaatactat tccaaggagc tggagaggct gccctaggga ttgcacacct   1200
gattgtgatg gccttggaaa aagaaggttt accaaaagag aaagccatca aaaagatatg   1260
gctggttgat tcaaaaggat taatagttaa gggacgtgct tccttaacac aagagaaaga   1320
gaagtttgcc catgaacatg aagaaatgaa gaacctagaa gccattgttc aagaaataaa   1380
accaactgcc ctcataggag ttgctgcaat tggtggtgca ttctcagaac aaattctcaa   1440
agatatggct gccttcaatg aacggcctat tatttttgct ttgagtaatc caactagcaa   1500
agcagaatgt tctgcagagc agtgctacaa aataaccaag ggacgtgcaa tttttgccag   1560
tggcagtcct tttgatccag tcactcttcc aaatggacag accctatatc ctggccaagg   1620
caacaattcc tatgtgttcc ctggagttgc tcttggtgtt gtggcgtgtg gattgaggca   1680
gatcacagat aatattttcc tcactactgc tgaggttata gctcagcaag tgtcagataa   1740
acacttggaa gagggtcggc tttatcctcc tttgaatacc attagagatg tttctctgaa   1800
aattgcagaa aagattgtga aagatgcata ccaagaaaag acagccacag tttatcctga   1860
accgcaaaac aaagaagcat ttgtccgctc ccagatgtat agtactgatt atgaccagat   1920
tctacctgat tgttattctt ggcctgaaga ggtgcagaaa atacagacca aagttgacca   1980
gtaggataat agcaaacatt tctaactcta ttaatgaggt ctttaaacct ttcataattt   2040
ttaaaggttg gaatctttta taatgattca taagacactt agattaagat tttactttaa   2100
cagtctaaaa attgatagaa gaatatcgat ataaattggg ataaacatca catgagacaa   2160
ttttgcttca ctttgccttc tggttattta tggtttctgt ctgaattatt ctgcctacgt   2220
tctctttaaa agctgttgta cgtactacgg agaaactcat catttttata caggacacta   2280
atgggaagac caaaattact aataaattga cataaccaac attaaaactc ataattattt   2340
tgttgaccat tttgttaaaa tctacttttc aaaaaaaaaa agctagaaat gaatctaggc   2400
gtaggtgaac ttttgctaag cagaaataac actactttgt tgcctagaga aagataactt   2460
ctcaagtatt tttattccag tcctagatca tatatgttct tttgtgcaac ggaattctaa   2520
cagttctaag agaaagatca ctgctgttta cagcgccttg tgcagcctta gattttaata   2580
ttcttttgtc attgttacat ctcatagagt aaagctctta ttaccttgat cctgagtcag   2640
aaatcccacc tgaaatcacc ttttttcccc cttgatcaaa catcccatcc ttcagctacc   2700
atactgttgc tacagggatt ttgtggactg tggcccctgt cccgaggttg gcaccttcag   2760
ttcagcacag cctgagcagt gagaaggtct gaaaggagag tatatagtta agatccttga   2820
```

gaaagggctg cctgaggaac tgacctctta aagatctcag gatctttaag acaacaagtt 2880
aggttcctac tggagttacc tgccagaatg gcctcttaat taactcaggt aatgaagagc 2940
taactgtgtt ataatcatct tgcttttgcc tgaatttgga gaaagtatta taattaagtt 3000
cccagtatca gaaatgtcct tacataagat taaaatatct tgatgactaa taccattcta 3060
tgagaaagag tagttatatg cccagactgt attaatttac tttagaaact aatgtttgaa 3120
gtaatggaaa aaattttaaa ttataaagct aaggtgcaat aacatttgct acttatttat 3180
agaattattt gaagaatttt gtttttgaag taatgcttta aggagtataa gatattcaag 3240
ataaattata ctataaaatg attttattga aagttgaagg ttacacaaat tgttttaggt 3300
atgagcagaa gaggttaagg tatttctaaa ggtaacatat agtcaagagt ttcctcaaaa 3360
tagttatttg gagaagaatc agaatgtctg tgtatttctt gtctgtttct atgttgtctt 3420
atagctctga ctaaatgtgt ttacctatgc aaaagattta ttaaagcata gaaaaggtga 3480
atgaataaaa atataaaata attgtccttt ttcttaaaa 3519

<210> SEQ ID NO 22
<211> LENGTH: 1319
<212> TYPE: DNA
<213> ORGANISM: Homo sapiens

<400> SEQUENCE: 22
cgcgcccgtc ccgtcgccgc cgccgccgcc gcagacccct cggtcttgct atgtcgagct 60
cacccgtgaa gcgtcagagg atggagtccg cgctggacca gctcaagcag ttcaccaccg 120
tggtggccga cacgggcgac ttccacgcca tcgacgagta caagccccag gatgctacca 180
ccaacccgtc cctgatcctg gccgcagcac agatgcccgc ttaccaggag ctggtggagg 240
aggcgattgc ctatggccgg aagctgggcg ggtcacaaga ggaccagatt aaaaatgcta 300
ttgataaact tttgtgttg tttggagcag aaatactaaa gaagattccg ggccgagtat 360
ccacagaagt agacgcaagg ctctcctttg ataaagatgc gatggtggcc agagccaggc 420
ggctcatcga gctctacaag gaagctggga tcagcaagga ccgaattctt ataaagctgt 480
catcaacctg ggaaggaatt caggctggaa aggagctcga ggagcagcac ggcatccact 540
gcaacatgac gttactcttc tccttcgccc aggctgtggc ctgtgccgag gcgggtgtga 600
ccctcatctc ccccatttgtt gggcgcatcc ttgattggca tgtggcaaac accgacaaga 660
aatcctatga gcccctggaa gaccctgggg taaagagtgt cactaaaatc tacaactact 720
acaagaagtt tagctacaaa accattgtca tgggcgcctc cttccgcaac acgggcgaga 780
tcaaagcact ggccggctgt gacttcctca ccatctcacc caagctcctg ggagagctgc 840
tgcaggacaa cgccaagctg gtgcctgtgc tctcagccaa ggcggcccaa gccagtgacc 900
tggaaaaaat ccacctggat gagaagtctt tccgttggtt gcacaacgag gaccagatgg 960
ctgtggagaa gctctctgac gggatccgca agtttgccgc tgatgcagtg aagctggagc 1020
ggatgctgac agaacgaatg ttcaatgcag agaatggaaa gtagcgcatc cctgaggctg 1080
gactccagat ctgcaccgcc ggccagctgg gatctgactg cacgtggctt ctgatgaatc 1140
ttgcgttttt tacaaattgg agcagggaca gatcatagat ttctgatttt atgtaaaatt 1200
ttgcctaata cattaaagca gtcacttttc ctgtgctgtt tcaaaaaaaa aaaaaaaaaa 1260
aaaaaaaaaa aaaaaaaaaa aaaaaaaaaa aaaaaaaaaa aaaaaaaaaa aaaaaaaaa 1319

<210> SEQ ID NO 23
<211> LENGTH: 1251

<212> TYPE: DNA
<213> ORGANISM: Homo sapiens

<400> SEQUENCE: 23

```
gcccattgtt tttgtaatct ctgaggagaa gcagcagcaa acatttgcta gtcagacaag     60
tgacagggaa tggattccaa acaccagtgt gtaaagctaa atgatggcca cttcatgcct    120
gtattgggat ttggcaccta tgcacctcca gaggttccga gaagtaaagc tttggaggtc    180
acaaaattag caatagaagc tgggttccgc catatagatt ctgctcattt atacaataat    240
gaggagcagg ttggactggc catccgaagc aagattgcag atggcagtgt gaagagagaa    300
gacatattct acacttcaaa gctttggtcc acttttcatc gaccagagtt ggtccgacca    360
gccttggaaa actcactgaa gaaagctcaa ttggactatg ttgacctcta tcttattcat    420
tctccaatgt ctctaaagcc aggtgaggaa ctttcaccaa cagatgaaaa tggaaaagta    480
atatttgaca tagtggatct ctgtaccacc tgggaggcca tggagaagtg taaggatgca    540
ggattggcca agtccattgg ggtgtcaaac ttcaaccgca ggcagctgga gatgatcctc    600
aacaagccag gactcaagta caagcctgtc tgcaaccagg tagaatgtca tccgtatttc    660
aaccggagta aattgctaga tttctgcaag tcgaaagata ttgttctggt tgcctatagt    720
gctctgggat ctcaacgaga caaacgatgg gtggacccga actccccggt gctcttggag    780
gacccagtcc tttgtgcctt ggcaaaaaag cacaagcgaa ccccagccct gattgccctg    840
cgctaccagc tgcagcgtgg ggttgtggtc ctggccaaga gctacaatga gcagcgcatc    900
agacagaacg tgcaggtttt tgagttccag ttgactgcag aggacatgaa agccatagat    960
ggcctagaca gaaatctcca ctattttaac agtgatagtt ttgctagcca ccctaattat   1020
ccatattcag atgaatatta acatggaggg ctttgcctga tgtctaccag aagccctgtg   1080
tgtggatggt gacgcagagg acgtctctat gccggtgact ggacatatca cctctactta   1140
aatccgtcct gtttagcgac ttcagtcaac tacagctgag tccataggcc agaaagacaa   1200
taaattttta tcattttgaa ataaaaaaaa aaaaaaaaaa aaaaaaaaaa a            1251
```

<210> SEQ ID NO 24
<211> LENGTH: 886
<212> TYPE: DNA
<213> ORGANISM: Homo sapiens

<400> SEQUENCE: 24

```
ctcgcaggct ccaggggcgg ggcgtggccg gggcgcagcg acgggcgcgg aggtccggcc     60
gggcgcgcgc gcccccgcca cacgcacgcc gggcgtgcca gtttataaag ggagagagca    120
agcagcgagt cttgaagctc tgtttggtgc tttggatcca tttccatcgg tccttacagc    180
cgctcgtcag actccagcag ccaagatggt gaagcagatc gagagcaaga ctgcttttca    240
ggaagccttg gacgctgcag gtgataaact tgtagtagtt gacttctcag ccacgtggtg    300
tgggccttgc aaaatgatca agcctttctt tcattccctc tctgaaaagt attccaacgt    360
gatattcctt gaagtagatg tggatgactg tcaggatgtt gcttcagagt gtgaagtcaa    420
atgcatgcca acattccagt tttttaagaa gggacaaaag gtgggtgaat tttctggagc    480
caataaggaa aagcttgaag ccaccattaa tgaattagtc taatcatgtt ttctgaaaat    540
ataaccagcc attggctatt taaaacttgt aatttttta atttacaaaa atataaaata    600
tgaagacata aacccagttg ccatctgcgt gacaataaaa cattaatgct aacacttttt    660
aaaaccgtct catgtctgaa tagctttcaa aataaatgtg aaatggtcat ttaatgtatt    720
```

-continued ttcctatatt ctcaatcact ttttagtaac cttgtaggcc actgattatt ttaagatttt 780
aaaaattatt attgctacct taatgtattg ctacaaaaat ctcttgttgg gggcaatgca 840
ggtaataaag tagtatgttg ttatttgtaa aaaaaaaaaa aaaaaa 886

<210> SEQ ID NO 25
<211> LENGTH: 1944
<212> TYPE: DNA
<213> ORGANISM: Homo sapiens

<400> SEQUENCE: 25
atcagctttg caagcaagta agggagcgga aaaggccggg aaaggccctg ccgcgagcac 60
gctgccaaga gcccccagca gcagttcggc ttaggactcg ggttgcggcg ggtgtcacct 120
tctcaggggc tagcaaggca gccagggccc aggcgtctga gtgaggggcg ggagaggagg 180
cgaggcagaa agtggacctt ccagcggaaa ggccattttc cccaaggccg agcccaggga 240
agtcccttcc tatagaattc aggcagggtg ggaggcaggg cgcgctcgtg cccctcagcc 300
agctgcaggt gctctctgtc cccaggcgcc atgagcaaga tcagcgaggc cgtgaagcgc 360
gcccgcgccg ccttcagctc gggcaggacc cgtccgctgc agttccggat ccagcagctg 420
gaggcgctgc agcgcctgat ccaggagcag gagcaggagc tggtgggcgc gctggccgca 480
gacctgcaca agaatgaatg gaacgcctac tatgaggagg tggtgtacgt cctagaggag 540
atcgagtaca tgatccagaa gctccctgag tgggccgcgg atgagcccgt ggagaagacg 600
ccccagactc agcaggacga gctctacatc cactcggagc cactgggcgt ggtcctcgtc 660
attggcacct ggaactaccc cttcaacctc accatccagc ccatggtggg cgccatcgct 720
gcagggaact cagtggtcct caagccctcg gagctgagtg agaacatggc gagcctgctg 780
gctaccatca tcccccagta cctggacaag gatctgtacc cagtaatcaa tgggggtgtc 840
cctgagacca cggagctgct caaggagagg ttcgaccata tcctgtacac gggcagcacg 900
ggggtgggga agatcatcat gacggctgct gccaagcacc tgacccctgt cacgctggag 960
ctgggaggga agagtccctg ctacgtggac aagaactgtg acctggacgt ggcctgccga 1020
cgcatcgcct gggggaaatt catgaacagt ggccagacct gcgtggcccc tgactacatc 1080
ctctgtgacc cctcgatcca gaaccaaatt gtggagaagc tcaagaagtc actgaaagag 1140
ttctacgggg aagatgctaa gaaatcccgg gactatggaa gaatcattag tgcccggcac 1200
ttccagaggg tgatgggcct gattgagggc cagaaggtgg cttatggggg caccggggat 1260
gccgccactc gctacatagc ccccaccatc ctcacggacg tggacccccca gtccccggtg 1320 atgcaagagg agatcttcgg gcctgtgctg cccatcgtgt gcgtgcgcag cctggaggag 1380
gccatccagt tcatcaacca gcgtgagaag cccctggccc tctacatgtt ctccagcaac 1440
gacaaggtga ttaagaagat gattgcagag acatccagtg gtggggtggc ggccaacgat 1500
gtcatcgtcc acatcacctt gcactctctg cccttcgggg gcgtggggaa cagcggcatg 1560
ggatcctacc atggcaagaa gagcttcgag actttctctc accgccgctc ttgcctggtg 1620
aggcctctga tgaatgatga aggcctgaag gtcagatacc ccccgagccc ggccaagatg 1680
acccagcact gaggaggggt tgctccgcct ggcctggcca tactgtgtcc catcggagtg 1740
cggaccaccc tcactggctc tcctggccct gggagaatcg ctcctgcagc cccagcccag 1800
ccccactcct ctgctgacct gctgacctgt gcacacccca ctcccacatg ggcccaggcc 1860
tcaccattcc aagtctccac ccctttctag accaataaag agacgaatac aattttctaa 1920
ctcagcaaaa aaaaaaaaaa aaaa 1944

<210> SEQ ID NO 26
<211> LENGTH: 2474
<212> TYPE: DNA
<213> ORGANISM: Homo sapiens

<400> SEQUENCE: 26
aaaggcgggg cgggcggctg ccaagccggc caataggcgg ctctccggct gctaagccga 60
gagggcaggg gcgccgtcag tagcaccacc gccttccaag tttccccttg tggatgcgcg 120
gccccgcggc tctgctcctc ccggcgcaga ggggccggga gaggccacag gagcggacct 180
ggcacgggat ttctgaggaa cgggagaaga ctggcgcccg acccgctctg gagggtcggt 240
gaacgatgaa gggccggcgg cggcgacgcc gagagtactg caagttcgcg ctgctgttgg 300
tgctgtacac gctggtgctg ttgctcgtcc cctccgtatt ggacggcggc cgcgacgggg 360
acaagggcgc cgagcactgc cccggcctgc agcgcagcct gggagtgtgg agcctggagg 420
cggcggcggc cggcgaacgc gagcagggag cggaggcgcg ggccgccgag gaagggggcg 480
cgaaccagtc tcctcggttc ccaagcaacc tcagcggcgc tgtcggggag gcagtgtctc 540
gcgagaagca gcacatctac gtgcatgcca cctggcgcac cggctcgtcc ttcctgggcg 600
aactctttaa ccagcacccg gacgttttct acttgtatga gcccatgtgg catctatggc 660
aggcgctgta tccgggcgac gccgagagct tgcagggcgc gctgcgcgac atgctgcgtt 720
cgctcttccg ctgcgacttc tccgtgctgc ggctgtacgc gccgccgggg gaccccgctg 780
cgcgcgcccc ggacacggcc aatcttacca cggccgccct cttccgctgg cggactaaca 840
aggtcatctg ctcgccgcca ctgtgtcctg gcgcaccccg tgcccgggcc gaggtgggcc 900
tcgtcgagga caccgcctgc gagcgcagct gcccacccgt ggcgatacgc gccctggagg 960
ccgagtgccg aaagtacccg gtggtggtca tcaaggacgt gcgcctgctc gatctgggcg 1020
tgctggtgcc cctgttgcgt gatccaggcc tcaacctgaa ggtggtgcag cttttccgcg 1080
acccgagggc ggtgcacaac tcgcgcctca agtctaggca gggactgctg cgcgagagca 1140
tccaggtgct gcgcacccgc cagaggggcg accgcttcca ccgtgtgctg ctggcgcacg 1200
gcgtgggtgc tcgccccggg ggccagtctc gcgcgctgcc cgccgcgccg cgcgccgatt 1260
tcttcctgac cggtgcgctc gaggtgatct gcgaagcctg gctgcgcgat ctgcttttcg 1320
cgcgcggcgc gcccgcctgg ctgcggcgcc gctacctgag gctgcgctat gaggacctgg 1380
tgcggcagcc acgcgcccag ctgcgccgcc tgctgcgctt ctccgggcta cgcgcgctcg 1440
cagcgctcga tgccttcgcg ctcaacatga ctcgcggcgc ggcctacggc gccgaccggc 1500
ccttccacct gtcagcgcgc gacgcccggg aggcggtgca cgcctggcgc gagcgcctga 1560
gccgagagca ggtgcgccag gtggaggccg cctgcgctcc agccatgcgt ctgctcgcct 1620
accctcgcag cggagaggag ggcgacgcgg agcagcccag ggaaggggag acgccgctgg 1680
agatggatgc cgacggcgcc acgtagcctc ccatccctgt ccccggcacg gatccgggtc 1740
agtcaccacg aacaggggca ctcggcatgc tgccccagca ctggagaagc agcgctgtgg 1800
gggcaatctg tcacactctc agagtctggg acttgacttg ctaccaacaa ctgctgtgca 1860
attctgctga gcaggaatat catgagctgt tcaataatga cggacgcatt ggttgagatg 1920
aagtttccag taaggaagtg acagtgcaat gtggatattt atggctgtaa aataggaaga 1980
gctttagttc ccaggctgaa cctgccactg ctggagccat ttcaacaagg catcctcaca 2040
acaaagaaga gatgtgattt ggtaccattt cacaccagca ggtgtctgga cgaaaacatc 2100

-continued

```
aatgtgaata agggccaagt gcagtcctgt cttgattaaa ttacttaata atattattaa   2160

ataataatag gtctgggcag tattgttttt aacctgactc atccagctgt ccttcaaata   2220

gctccgtctc cctctaccca gaactgattt ttaaaaagaa gtaatttttc tccctgggct   2280

gggaaaaccc taatgaactg aaacacactt ttactttaaa atttttctgt ctggcgtttt   2340

tgtaatcata ctattaaatg actctggagt catgttaatg acaggatttg ttttgtttgg   2400

atgcagttca attgcatggt ttgggtaaaa gctagcctac atacaaagga atatgaagac   2460

tgtggaagaa actg                                                     2474


<210> SEQ ID NO 27
<211> LENGTH: 6236
<212> TYPE: DNA
<213> ORGANISM: Homo sapiens

<400> SEQUENCE: 27

tcctctgcgt cccgccccgg gagtggctgc gaggctaggc gagccgggaa agggggcgcc     60

gcccagcccc gagccccgcg ccccgtgccc cgagcccgga gccccctgcc cgccgcggca    120

ccatgcgcgc cgagccggcg tgaccggctc cgcccgcggc cgccccgcag ctagcccggc    180

gctctcgccg gccacacgga gcggcgcccg ggagctatga gccatgaagc cgcccggcag    240

cagctcgcgg cagccgcccc tggcgggctg cagccttgcc ggcgcttcct gcggccccca    300

acgcggcccc gccggctcgg tgcctgccag cgccccggcc cgcacgccgc cctgccgcct    360

gcttctcgtc cttctcctgc tgcctccgct cgccgcctcg tcccggcccc gcgcctgggg    420

ggctgctgcg cccagcgctc cgcattggaa tgaaactgca gaaaaaaatt tgggagtcct    480

ggcagatgaa gacaatacat tgcaacagaa tagcagcagt aatatcagtt acagcaatgc    540

aatgcagaaa gaaatcacac tgccttcaag actcatatat tacatcaacc aagactcgga    600

aagcccttat cacgttcttg acacaaaggc aagacaccag caaaaacata ataaggctgt    660

ccatctggcc caggcaagct tccagattga agccttcggc tccaaattca ttcttgacct    720

catactgaac aatggtttgt tgtcttctga ttatgtggag attcactacg aaaatgggaa    780

accacagtac tctaagggtg gagagcactg ttactaccat ggaagcatca gaggcgtcaa    840

agactccaag gtggctctgt caacctgcaa tggacttcat ggcatgtttg aagatgatac    900

cttcgtgtat atgatagagc cactagagct ggttcatgat gagaaaagca caggtcgacc    960

acatataatc cagaaaacct tggcaggaca gtattctaag caaatgaaga atctcactat   1020

ggaaagaggt gaccagtggc cctttctctc tgaattacag tggttgaaaa gaaggaagag   1080

agcagtgaat ccatcacgtg gtatatttga agaaatgaaa tatttggaac ttatgattgt   1140

taatgatcac aaaacgtata agaagcatcg ctcttctcat gcacatacca acaactttgc   1200

aaagtccgtg gtcaaccttg tggattctat ttacaaggag cagctcaaca ccagggttgt   1260

cctggtggct gtagagacct ggactgagaa ggatcagatt gacatcacca ccaaccctgt   1320

gcagatgctc catgagttct caaaataccg gcagcgcatt aagcagcatg ctgatgctgt   1380

gcacctcatc tcgcgggtga catttcacta taagagaagc agtctgagtt actttggagg   1440

tgtctgttct cgcacaagag gagttggtgt gaatgagtat ggtcttccaa tggcagtggc   1500

acaagtatta tcgcagagcc tggctcaaaa ccttggaatc caatgggaac cttctagcag   1560

aaagccaaaa tgtgactgca cagaatcctg ggggtggctgc atcatggagg aaacaggggt   1620

gtcccattct cgaaaatttt caaagtgcag cattttggag tatagagact ttttacagag   1680

aggaggtgga gcctgccttt tcaacaggcc aacaaagcta tttgagccca cggaatgtgg   1740
```

aaatggatac gtggaagctg gggaggagtg tgattgtggt tttcatgtgg aatgctatgg 1800
attatgctgt aagaaatgtt ccctctccaa cggggctcac tgcagcgacg ggccctgctg 1860
taacaatacc tcatgtcttt ttcagccacg agggtatgaa tgccgggatg ctgtgaacga 1920
gtgtgatatt actgaatatt gtactggaga ctctggtcag tgcccaccaa atcttcataa 1980
gcaagacgga tatgcatgca atcaaaatca gggccgctgc tacaatggcg agtgcaagac 2040
cagagacaac cagtgtcagt acatctgggg aacaaaggct gcagggtctg acaagttctg 2100
ctatgaaaag ctgaatacag aaggcactga gaagggaaac tgcgggaagg atggagaccg 2160
gtggattcag tgcagcaaac atgatgtgtt ctgtggattc ttactctgta ccaatcttac 2220
tcgagctcca cgtattggtc aacttcaggg tgagatcatt ccaacttcct tctaccatca 2280
aggccgggtg attgactgca gtggtgccca tgtagtttta gatgatgata cggatgtggg 2340
ctatgtagaa gatggaacgc catgtggccc gtctatgatg tgtttagatc ggaagtgcct 2400
acaaattcaa gccctaaata tgagcagctg tccactcgat tccaagggta aagtctgttc 2460
gggccatggg gtgtgtagta atgaagccac ctgcatttgt gatttcacct gggcagggac 2520
agattgcagt atccgggatc cagttaggaa ccttcacccc cccaaggatg aaggacccaa 2580
gggtcctagt gccaccaatc tcataatagg ctccatcgct ggtgccatcc tggtagcagc 2640
tattgtcctt gggggcacag gctggggatt taaaaatgtc aagaagagaa ggttcgatcc 2700
tactcagcaa ggccccatct gaatcagctg cgctggatgg acaccgcctt gcactgttgg 2760
attctgggta tgacatactc gcagcagtgt tactggaact attaagtttg taaacaaaac 2820
ctttgggtgg taatgactac ggagctaaag ttggggtgac aaggatgggg taaaagaaaa 2880
ctgtctcttt tggaaataat gtcaaagaac acctttcacc acctgtcagt aaacggggga 2940
gggggcaaaa gaccatgcta taaaaagaac tgttccagaa tctttttttt ccctaatgga 3000
cgaaggaaca acacacacac aaaaattaaa tgcaataaag gaatcattaa aaaaaatagt 3060
aaatgatttt ttttccctca gcctgctggc acttaatatc ttctaaatga tttggcatga 3120
tttttttttc tttactaccg atgacaaact ccagtggcat gaagatctaa ttttcaaaag 3180
ggtaaaaact gcatggcata tatacaacaa gctagcaagc caattctcag caaaacctgc 3240
aacagaattc ctaaagtgaa gatgacagat gaacacaaag aagctgcctg ggcctcttca 3300
cttaaacatg tccccacacc ccatcctctc ggagccccac ttcttacccc ccacctccca 3360
ccctctataa tccccactcc ccattggaga ccaggccagg gcagaactcc acggaccttg 3420
ctcttgttga ttcactttcc ccattgtgtt ttctcctgga ctgagcatcc tttggaaatg 3480
ggagctggaa tttgaacaat gatgctattg tatagttctt ttataaatgt aaatatggaa 3540
ataagagatt ttgacacatc attttcactt gtctgtattg agatattttc cttgtaaagg 3600
ttctctgtaa acttgagttg atttttttgct ccccatcttt tttgtttctt gtctctcttt 3660
ctctgtctct gtccttctct cttgtaacgt gttatacaat gactcttggg cttgcttaaa 3720
aagacagata tagccacaga tgcagggagt ttgggcacaa aacacgtgca gtttaaagtt 3780
ggtgtgcgtt aaaccaaaaa taaaaggggg gacataaaca acaaaataac ccatatcaaa 3840
gacacaaaat tatgtaaatg gaaatatatg tactaagttt cgaaaatttt ttgatgtcat 3900
tataaaccta tgtaaataat gtaagaaagt agacaccctt tcagattaat cacaaaagtg 3960
ccaagctcat gattttggtt ttcggttttg acaattttct ttccctgtct ttaatgtgaa 4020
aggaggataa acttaaagcc ttaaataaaa aaattttttt aaatgttaaa agcttggaaa 4080
aaattaagct ttccatttta tttgtatttg ttagtgtcaa tatttcatcc atgctcattt 4140
tcctgcctca aaatatatat ggtagaaccc tattggaaaa gtggtaatgg gaatagaagg 4200
agcagttacc tttgtatccg cattgttaaa ataggctttt atgctgtgct gtgctttcaa 4260
gaaaccttgt ttgacctctg gcattttact gatcagtgga ccgttgcact ggattataat 4320
gggattctac tatatacaaa tccacattgt tcttctccct ccagccagat ttgcagatgt 4380
aatctgggct ttccaagtcc ctctgagttt ccttcacttt tactgatttt tttcttctaa 4440
atatggtcaa gatagcttct gtcacatgtt aagtaaataa gctgaagaaa tttggtcccg 4500
gctttgtttt aatgtacaaa ccggtatgtg atcacttcag tgagcatccc tctatagatg 4560
ggctttagta aagactgtcc caaagagccc ctacttctct aatgcccccc cccttttttt 4620
tttaggaaaa gaacatgcag ttttactcat cacttcttca tgacaccaaa tccattgcta 4680
ggtttagctc ctggtccctt ttcagcaaga ttcatgttat ccgtcttaca actttgattt 4740
tggaaagtat tatgtcctaa aaatgcactg cttaacacag tggggttttt ttcccccgag 4800
gtgtctttaa ctggggaagt accacaaaca tagagcagag actttaattt ctatattcta 4860
caatagacca tcaccaaaca tcttatcatg ttgttgcttt ctgagtaata ggtgctacgc 4920
aggtaggcgg gctttctcta ggactaggtg tacgtttatt ttgtaataac agggctatct 4980
acaaggcctc tcagccttac tcctggcttc ataggacaca ggtagcatcc ctctagtcat 5040
tggcaatggc tctttcagct cggaggaagc ttggaggaaa ctcagattac ttggtatctt 5100
ttcctgttgc tgcattgctt agtgtttcct tgttgctggg tcctactctc tagtagatac 5160
taaactgctg tgaagtacac catacacatt tcactaagat tccagagcca ccttggtgac 5220
ataacagaaa caaaatcatg ttggttacaa aacaaattaa atctctattg ttaactttta 5280
agcatttcac aaacaacatt gtaaatgtgc gatgttacgt tttaaatcag accacagtgg 5340
tccccaaata ttatgtacat atggcaaatg tcagtgtaac tttttgttac actggcaatt 5400
tcataggtaa tcgaacctat gctccaatgt taaattattt gtgtatatgt aaaatacaca 5460
agctttaagc tatgtgtgta tgaatatgaa agttaatgca accatatcaa ttgtaaaaat 5520
ggattataat tatttttgat ggtattaggt tatgtagttt caaactcttt gctgtatttt 5580
gttttgcacc tgccattcat ttgctaattt ttgtggcgtg gagattcttt tttattaatt 5640
tgagctcaca gcacaagtgt atcactgttt aatgttaccc aacaagagtt agtgttaagt 5700
gatgatcaag ttcccatttc acctgctcta cttttgctgc attaattaat gacacccgga 5760
tgaggagacg tgcgctaact tcattgctca tctgggatag tgcatgagcc cattgaatta 5820
gagctgctcc tactagataa ctgagcagta cacataagtg catgttatga aacatgaatc 5880
acatagagca gtggagtttt accaagtggt gtgtgtggtt tttgtttttt actatgcaaa 5940
gatgggaaat gcacaaactt ttcaaagact agtgtctgaa gaactttaca aacaatactt 6000
gaaccctttc tttaaagtta tcccatcatg ttttatagtc attgttgctt ccattgttag 6060
tttccatttt caagtgcttt gtaatttttt aagtgcacta cctgaaattt tgtttgaaat 6120
taataaattc attcgtatct tgttggctgc ctatgaatgg agattcagta gtcattgtat 6180
gcatctttaa gtcaaatgtg tattaaaact ttcgttaacg tagaaaaaaa aaaaaa 6236

<210> SEQ ID NO 28
<211> LENGTH: 3127
<212> TYPE: DNA
<213> ORGANISM: Homo sapiens

<400> SEQUENCE: 28

-continued

```
gcccagttgg agccagacag cggggtggac aagtggcgtg tgtgctgcga ccccgaggga     60
agatgaacgg gacgcggaac tggtgtaccc tggtggacgt gcacccagag gaccaggcgg    120
cgggcagcgt ggacattctc aggctgactc tccagggtga actgacagga gatgaacttg    180
aacacatagc ccagaaggcg ggcaggaaga cctatgccat ggtgtccagc cactcagctg    240
gtcattctct ggcttcagaa ctggtggagt cccatgatgg acatgaggag atcattaagg    300
tgtacttgaa ggggaggtct ggagacaaga tgattcacga gaagaatatt aaccagctga    360
agagtgaggt ccagtacatc caggaggcca ggaactgcct acagaagctc cgggaggata    420
taagtagcaa gcttgacagg aacctaggag attctctcca tcgacaggag atacaggtgg    480
tgctagaaaa gccaaatggc tttagtcaga gtcccacagc cctgtacagc agcccacctg    540
aggtggacac ctgtataaat gaggatgttg agagcttgag gaagacggtg caggacttgc    600
tggccaagct tcaggaggcc aagcggcaac accagtcaga ctgtgtggct tttgaggtca    660
cactcagccg gtaccagagg gaagcagaac aaagtaatgt ggcccttcag agagaggagg    720
acagagtgga gcagaaagag gcagaagtcg gagagctgca gaggcgcttg ctagggatgg    780
agacggagca tcaggcctta ctggcgaaag tgagggaagg ggaggtggcc ctagaggaac    840
ttcggagcaa caatgctgac tgccaagcag aacgagaaaa ggctgctacc ctggaaaagg    900
aagtggccgg gttgcgggag aagatccacc acttggatga catgctcaag agccagcagc    960
ggaaagtccg gcaaatgata gagcagctcc agaattcaaa agctgtgatc cagtcaaagg   1020
acgccaccat ccaggagctc aaggagaaaa tcgcctatct ggaggcagag aatttagaga   1080
tgcatgaccg gatggaacac ctgatagaaa aacaaatcag tcatggcaac ttcagcaccc   1140
aggcccgggc caagacagag aacccgggca gtattaggat atccaagccg cctagcccga   1200
agcccatgcc tgtcatccga gtggtggaaa cctgagctgc ctggagatgg ttgctgccat   1260
tgctgctgcc tctgcctcgg agaagcccac tgcccctgtt ggctgttaac actgcctttg   1320
acttcctgac tgtcccctgg ctgcacccag gacttcgggc tcctgtgtct caccattccc   1380
aagcccctgg ccactctaag ctgggcagac ggagcacgag cacctattca aggcactgca   1440
gccctttgga agacattgtc ctgcaagcag gagccagggc aatatctata ttcctacagt   1500
gactattttt ctctgtagag agcctccctt ctgttgtaga ctggactctg gctgtgccat   1560
aagccaggcc ttcatcagat tgggagaggt gacaagattt gcctcagccc taaaagctgg   1620
agacacagat gtccagagtg attggagaat gtcctggggg aatgaagttc cttccacaaa   1680
cacagctcag ttcttagcaa caaactgttt gtttttctac ttgctccatc tgcagcctac   1740
gctgccctgg cctcctgcag acagatagtg gggttacctg gcaaggcctg gtgagagcca   1800
gtgaacctaa gctttgactg ggtggccttg tctttctggg gaggagggaa tgtacattca   1860
gggagtagcc ttttgcggaa aaattctcta gggctacaga cagtcatgtg tgacttctct   1920
ctgctgtgaa aactcccaga gtctctttag ggattttccc taaggtgtac caccaggcac   1980
acctcagtct tcttgaccca gagcctgaaa actgttttca ctgggttcca ccagtcccag   2040
caaaatcctc tttgtattta ttttgctaag ttattggtgg ttttgcttac atctcatgat   2100
tgatataata ccaaagttct atagccttct cttgcagtat ttggatttgc ttgaaaccgg   2160
gaaaactgtt cccattaggc ttgttaatgt cagagtgaca ctattatgaa tctttctctc   2220
cctttcctct gcctgtttct tctctctttc tccttcaaac ttgctctgca gctaaggaag   2280
gtgagtctac tttccctgag gctttggggt cagagtatat gttgtttgga gaaagagggc   2340
```

-continued aatcaggact cttctgggac ccagatgagt tcttcactag cccttctgaa ccccttgctc 2400
cataattggt cttttatcct ggctctgaat gaccctgcag gtcatcatgg ttttcttttt 2460
ttattgtttt tttttttttc tgagacagag tctcactctg tcacccaggc tggagtgcag 2520
tggcgcgatc tcagctcact gcaacctctg cctcccggat ttaagcgatt cttctgcctc 2580
agcctcccga gtagctggga ctacaggtgt gccaccacgc ctggctgatt tttgtatttt 2640
tagtagagat ggggtttcac catactggct aggctggtct cgaattcctg acctcaggtg 2700
atccacccac ctcggcttcc caaagtgcta ggattatagg cttgagctac tgcgcccggc 2760
ccatggtgtt tttctttagg gctcttccta caaccttgag aagtagatag gcatcagagt 2820
atggtactat aggaatcaga aaaattcaaa acaaatgtgg attaagtgtt taggctctat 2880
gtggctcacg cagccagaat ccttaagtct gtgtgtttct gtgtctcaag actgggctca 2940
cattctggct ttgtccataa caatgctctg ggatttcagg gagttccctc atttgtaaaa 3000
tgagggggtc agagcaggtg atatccatgt ttcttccctt tctgatattg ttgtctgtgg 3060
catattcttt gtatggcgaa tttaataaat tatattaatg tgtctctttg aaaaaaaaaa 3120
aaaaaaa 3127

<210> SEQ ID NO 29
<211> LENGTH: 3473
<212> TYPE: DNA
<213> ORGANISM: Homo sapiens

<400> SEQUENCE: 29
ctcgccagcg gtccgcaggg ctggagaccc acgccgtgga gaggaccagc ctcaggtcgc 60
cccgcctggg cccgcgcccc gacctcgctg cccccgcctc gcctctctgc ccgtggcgct 120
tacggccacc ttggcctcgg gggcagggca tgggcggccc ccgccagatc gcccagcgcc 180
agtactaact gccctcgctc tggccttcga gcccgaagcc tcttctgcgc gcacaaccta 240
ggcagtaatc ctaaactagc gggcaccaca gaccagctgc agccacccca acccagggat 300
cacttccgga cccctcgacc gcccggcacc agcgcgcaag ggacccttca gccggagacc 360
agagtccagt cccggtcacg aggccaccgc cgctgcccgc ctcgagaagc accacgcggg 420
ctgagccgtc ggctagcggg tcactcccga gcctctgtct gcaccgcgcc agccccagac 480
cacggacgct gagcctccag cgcgtgccag cctgggccgc tgggctctcg gggccagccc 540
gcgacgatcc cctgagctct ccgcagaagg gccgagcgtc cgttccgggg acgccaggcc 600
cgcccccgcc ccccgacagc cgcgggggatc cagagcccgg gggtgcggga cgcccgcgcc 660
atgactgccg agagcgggcc gccgccgccg cagccggagg tgctggctac cgtgaaggaa 720
gagcgcggcg agacggcagc aggggccggg gtcccagggg aggccacggg ccgcggggcg 780
ggcgggcggc gccgcaagcg ccccctgcag cgcgggaagc cgccctacag ctacatcgcg 840
ctcatcgcca tggccatcgc gcacgcgccc gagcgccgcc tcacgctggg cggcatctac 900
aagttcatca ccgagcgctt cccettctac cgcgacaacc ccaaaaagtg gcagaacagc 960
atccgccaca acctcacact caacgactgc ttcctcaaga tcccgcgcga ggccggccgc 1020
ccgggtaagg gcaactactg ggcgcttgac cccaacgcgg aggacatgtt cgagagcggc 1080
agcttcctgc gccgccgcaa gcgcttcaag cgctcggacc tctccaccta cccggcttac 1140
atgcacgacg cggcggctgc cgcagccgcc gccgccgccg ccgccgccgc cgccgccatc 1200
ttcccaggcg cggtgcccgc cgcgcgcccc ccctacccgg gcgccgtcta tgcaggctac 1260
gcgccgccgt cgctggccgc gccgcctcca gtctactacc ccgcggcgtc gcccggccct 1320

-continued

```
tgccgcgtct tcggcctggt tcctgagcgg ccgctcagcc cagagctggg gcccgcaccg   1380
tcggggcccg gcggctcttg cgcctttgcc tccgccggcg cccccgctac caccaccggc   1440
taccagcccg caggctgcac cggggcccgg ccggccaacc cctccgccta tgcggctgcc   1500
tacgcgggcc ccgacggcgc gtacccgcag ggcgccggca gtgcgatctt tgccgctgct   1560
ggccgcctgg cgggacccgc ttcgccccca gcgggcggca gcagtggcgg cgtggagacc   1620
acggtggact tctacgggcg cacgtcgccc ggccagttcg gagcgctggg agcctgctac   1680
aaccctggcg ggcagctcgg aggggccagt gcaggcgcct accatgctcg ccatgctgcc   1740
gcttatcccg gtgggataga tcggttcgtg tccgccatgt gagccagcgt agggacgaaa   1800
actcatagac acatcggctg ttcacacgtt ccccgcaatc tgagaacgaa caggaatgga   1860
gagaggactc aactgggacc cacgtggaaa agaccgagca ggccacagag gctcggtctc   1920
cccgcgcaca gcgtaggcac ccggtgtact ctgtaaacgg gaggaggtgg ggcgaggcag   1980
ccagagccct tggactggca cagggaccct cgatggagcg aagccctcaa acgggatgct   2040
ttctggtatt ctatcgggga gggtccttgg cggtaaccag agggcagcgt agtgtcaaca   2100
ccagagacca ggatccaaat tgtggggaat cagtttcagc cttccatgtg ctgccggaac   2160
tcgggccttt ttacgcggtt cgtcctctag tgcctttaac tgcgttacta caataaaagg   2220
ctgcggcagc gcctttcttc ttaaagtgag gaggacaaat ttgcaaaaga aataggcttt   2280
tcttcttttt taaattggag aaatctctgc tctggttgac ctgggctggt tttccctgtc   2340
tctgagaact tgagacctag ctccgagttg aactgtgcgt cagcactcca gtcccatcac   2400
ctgaaccttc agtctccccc atctgttaca ctagagggct gcaggactct atccaccgcc   2460
cccgggttat cattcagggc cccatcatct tggatgctgc cctgcgtatt tggcagcaat   2520
ggtgggccac ccagggcctc tgagtagcca cccaaagcct agccgctgtt ctagggaacg   2580
gaaaagagtt catggccaag cgtctaacct aaagtcccag gattggctcc aggcagcaat   2640
tatatcataa cttattgaac ttttgagcag gacgtgctgg taatttcatg gctgttactg   2700
cccagtcata aatctgcttt tccattataa ggcagagaga agtacattcg ttcatttgtc   2760
cactgtttct tgtcatcacg cagccctgga cccaaagggt gaactaaagt ttaaggagat   2820
gagaggattc aaggagcccg ttggtgacgc ctttcagtag ctggggaggg ctcttccatc   2880
cccagcaccc cctgctacac ctcagcagcc tcccccatgc aaaaaggaaa gagaaaaatt   2940
aagttagggc agtcagtaaa gtgagcttta gaaagaaact ggaattttaa cttcattttg   3000
tatcttgctt aagtagcagg ctcactaaaa ttagagaaag tccaataact ctcccccttt   3060
cccttgagaa atctttaagt ttcgattctg gagcaaaaac tttcagcatt aaatatttca   3120
gaggctccat tcacagcttt cagataaact ggagtgttca gatggactgt tttaataaaa   3180
atctttgagc aagtgagtta tggcaagaga aactcagcct ctttctgtat aaacttaaca   3240
gggaagggct ggggtgtgaa aaagaagatt gtatgaaaac cattggtaat ttttattttt   3300
tatttttggg actgcactat cctgttcacg aagacatgtg aacttggttc agtccaaatg   3360
gggatttgta taaaccagtg ctctccatta gaaatatggt gcaagccaca tatgtaattt   3420
taaatattct agtagccaca ttaataaagt aaaaagaaac aaaaaaaaaa aaa          3473
```

<210> SEQ ID NO 30
<211> LENGTH: 3823
<212> TYPE: DNA
<213> ORGANISM: Homo sapiens

<400> SEQUENCE: 30
agtcctcccc cggcgcctcc gactggcagt gggactcagc gggcgtggag gtcgcggctg 60
agcgagcgag ccctgggcga gtgaattgtg gctgtgggtt gacggtggag acacccccg 120
gagggaggcg gagggaaggg aggcgaggcc tgcacctgca tgcttcccgc ctcccactcc 180
ccagcgcccc cggaccgtgc agttctctgc aggaccaggc catggagctc gaagtccggc 240
gggtccgaca ggcgttcctg tccggccggt cgcgacctct gcggtttcgg ctgcagcagc 300
tggaggccct gcggaggatg gtgcaggagc gcgagaagga tatcctgacg gccatcgccg 360
ccgacctgtg caagagtgaa ttcaatgtgt acagtcagga agtcattact gtccttgggg 420
aaattgattt tatgcttgag aatcttcctg aatgggttac tgctaaacca gttaagaaga 480
acgtgctcac catgctggat gaggcctata ttcagccaca gcctctggga gtggtgctga 540
taatcggagc ttggaattac cccttcgttc tcaccattca gccactgata ggagccatcg 600
ctgcaggaaa tgctgtgatt ataaagcctt ctgaactgag tgaaaataca gccaagatct 660
tggcaaagct tctccctcag tatttagacc aggatctcta tattgttatt aatggtggtg 720
ttgaggaaac cacggagctc ctgaagcagc gatttgacca cattttctat acgggaaaca 780
ctgcggttgg caaaattgtc atggaagctg ctgccaagca tctgacccct gtgactcttg 840
aactgggagg gaaaagtcca tgttatattg ataaagattg tgacctggac attgtttgca 900
gacgcataac ctggggaaaa tacatgaatt gtggccaaac ctgcattgca cccgactata 960
ttctctgtga agcatccctc caaaatcaaa ttgtatggaa gattaaggaa acagtgaagg 1020
aattttatgg agaaaatata aaagagtctc ctgattatga aaggatcatc aatcttcgtc 1080
attttaagag gatactaagt ttgcttgaag gacaaaagat agcttttggt ggggagactg 1140
atgaggccac acgctacata gccccaacag tacttaccga tgttgatcct aaaaccaagg 1200
tgatgcaaga agaaattttt ggaccaattc ttccaatagt gcctgtgaaa aatgtagatg 1260
aggccataaa tttcataaat gaacgtgaaa agcctctggc tctttatgta ttttcgcata 1320
accataagct catcaaacgg atgattgatg agacatccag tggaggtgtc acaggcaatg 1380
acgtcattat gcacttcacg ctcaactctt tcccatttgg aggagtgggt tccagtggga 1440
tgggagctta tcacggaaaa catagttttg atactttttc tcatcagcgt ccctgtttat 1500
taaaaagttt aaagagagaa ggtgctaaca aactcagata tcctcccaac agccagtcaa 1560
aggtggattg ggaaaaattt tttctcttga aacggttcaa caaagaaaaa ctcggtctcc 1620
tgttgctcac tttcctgggt attgtagccg ctgtgcttgt caagaaatac caagctgtgc 1680
tgaggagaaa ggccctgttg atttttctgg tagttcacag actgcgttgg tccagtaagc 1740
agagatgaac accagatttc aaaacccagc cctgtctgtt aagagtgagg cagaatatta 1800
ctgaagaatg atcctgttca acctcctagt gcctctactg aattattcct cttttaaatg 1860
gttaatgaac caataatttt taaatcatac caaaaatagt aagaaaatat gcaaacactc 1920
tgtgatcaaa cttaaaagtc attgccattc atcattaata aaagttgcca tttcaactac 1980
gtcccaacat tccctaatag ggtattcagg gaacctgtct taaattgtgc ttatctaaat 2040
cttggaactt tgagctaggg gaggagaatg tattagacta aatacaaact gcggggttgt 2100
aagggagtct cagaacctca ctgaatcctt cactccagtt aatggcactg ctcacttcct 2160
gcctctgctg ccaccatcac tgtgtgaagc tttcaagagc ttggtacttc ccagggctac 2220
cggcagtcct ctgtagtcca gagaggtgag attagatctt cttggttccc tgtgaggttt 2280
caggcactaa aactctatgt ggggaaggga ggggttactc ctcctccaat gggactcaag 2340

-continued gacttgacct ccaggagtag gcccctggtc agaagtgcca tctcaccagt ggtcttcatt 2400
cttcctcatt cattctttat catcctgtgt tctgtttagt tgcaacaatc tcttgtgact 2460
aatgtcactc aaagcatctt gtaaatccta gggcttcctg gaagttagtt gccaaagtca 2520
tgcaagcatc acctgtcatt cttgtgttgg agttatagaa ttctacatct tataaaacct 2580
aactggcatt taaaaaatac tgtggccggg cgtggtggct catgcctgta atcccagcac 2640
tttgggaggc cgaggtggga ggattgcttg agtccaggaa tttgagacca gcctggacaa 2700
cacagtgaga cctcatctct atcaaaaaat aaaaattagc tagatgtggt ggcatgagcc 2760
tgtgttccca gctgcttagg aggctgaagc aggaggattg attgagcctg cgaggccaag 2820
gctgcagcag gctgtgattg caccactgca cttcagcttg ggcaacagag caagaccctg 2880
tctccgaaac aaataaaaaa tactgtaata aaagtactta taaacatact aatcctcttt 2940
caggacccta aagttgcagg ttagtaggtc ttcaaggaca aatctgtaag tttcttattt 3000
ctgtagtgca agtaaaattt cactttttga aactatagag agatcccttt ctgattagcc 3060
tacagaactt aaagtgaggg aaccatttcc tctcacagac aaagaggcct gggatattag 3120
gactttgggg tttgagagca tcatggggca gacagatggt ggatggtctg gacaagaagc 3180
gagtaagcca ctgcggttgg tcatactgaa gggaattgat ggcaagagga tcccctgagc 3240
aagtcagaag ttactctcat cagtcgttca tggtcacaac ctgaggtact ctgctgagtg 3300
ggcaaggctg aagaagaggc ctgtggaatg cagcattacc tgctggacag agcagggcag 3360
gcagttctat gccttggagc tcctgactgc agggactctg tccccacact caaaaagact 3420
cagctcactc aatgagagaa tgtgatttac tttatagaac gtataatcaa ctttgttgaa 3480
taatttgttc tattaaggct gtctaaagta tgtgatgtct tcatcatagt atgaagtgtt 3540
gaaaattaat aacgagccta gtttaggaaa aagctgctta aaactgtggc tctaagagag 3600
taatcataaa ataccttaga taaaattgca ctatggaatt ttcattgagt atgtttaaat 3660
tattggcttg tctactaata cacatctgct tcaaaatgaa catatttcat aaaattggca 3720
tcaattttaa tgacgctcct ggtatggaac ctcagatata ccctattgga gacaatcctt 3780
tgatcataaa ttctccccaa ctataaatca ttttatgtct tta 3823

<210> SEQ ID NO 31
<211> LENGTH: 3873
<212> TYPE: DNA
<213> ORGANISM: Homo sapiens

<400> SEQUENCE: 31
catctgcctg cccttctgcc atccgagcgc cctgactgcg ccacactgca ggccatggag 60
aatgagctgc cagtcccaca tacatctagc agtgcctgtg ccaccagcag taccagcggg 120
gccagtagca gcagtggctg caacaacagc agcagtggtg gaagtggccg ccccaccggg 180
ccccagattt ctgtgtacag tggtattcca gaccggcaga ccgtgcaggt gatccagcag 240
gccctgcaca gacagcccag cacggccgct cagtacctgc agcagatgta cgccgcccag 300
cagcagcacc tcatgctgca gaccgcggcg ctccagcagc agcacctcag cagcgcccag 360
ctccagagcc tggcagccgt acagcaggca agcctggtat ccaatagaca aggaagcact 420
tcaggcagca atgtgtctgc gcaggccccg gcccagtcat cttcgatcaa cctggcagcc 480
tccccagcag cagcccagct cctcaaccgg gcccagagtg tgaactctgc agcagcctca 540
ggcatcgctc agcaggctgt gctcttgggc aacacgtctt ccccagccct gactgcaagc 600

-continued

```
caagcacaga tgtatctgag ggcacagatg ctcatcttca cgcccacggc caccgtcgct    660
actgtgcagc ctgagctcgg cactggctcc cccgcccggc cccccacccc cgcccaggta    720
cagaacttga ccctccgaac acagcagaca ccagcggcag cagcctcggg ccccacccccc   780
actcagcctg tcctgcccag cttggccctg aaacccacgc cgggcggtag ccagcctctg    840
cctaccccag cacagagcag aaatactgct caggcttccc ctgcaggtgc caagcctggc    900
atagctgaca gtgtgatgga gccacacaag aaaggagatg gcaacagcag tgtgccaggg    960
agcatggaag gccgggctgg gctcagccgg acggttcctg ctgtggctgc ccaccccctc   1020
attgcaccag cctatgctca gctgcagcca caccagctcc tcccacagcc atcctcaaag   1080
cacctgcagc cccaatttgt gatccagcag cagccacagc cacaacagca gcagccgccg   1140
ccccagcagt cacggcctgt gctccaagct gagccccacc cccagctcgc ctcagtctct   1200
ccaagcgtgg ccctccagcc cagctcagag gcccatgcca tgccactagg cccggttaca   1260
cccgccctgc cactccagtg tcccactgcc aacctgcaca agcctggcgg cagtcagcag   1320
tgtcaccctc ccacacctga tactgggcct cagaatggac atcccgaggg cgtgccccac   1380
acccctcaac gcaggttcca gcacacttca gctgtcatct tacaactgca gcctgcttca   1440
ccaccccagc agtgtgtccc tgatgactgg aaagaagtgg caccagggga gaaaagtgtg   1500
cctgagacgc ggtctggccc atcaccacat cagcaggcta ttgtcactgc catgcctggt   1560
ggcctgcctg tacccacgag ccctaacatc cagccgtccc cagctcacga gacagggcag   1620
ggcattgttc atgcactgac cgacctcagc agccccggca tgacctcagg gaacggaaac   1680
tctgcctcca gcatcgccgg cactgccccc cagaatggtg agaataaacc accacaggcc   1740
attgtgaaac cccaaatcct gacgcatgtt atcgaagggt ttgtgatcca ggagggggcg   1800
gagcctttcc cggtgggacg ctcgtccctg ctggtgggga atctcaagaa gaagtatgca   1860
caggggttcc tgcctgagaa acttccacag caggatcaca ccaccaccac tgactcggag   1920
atggaggagc cctatctgca agaatccaaa gaggagggtg ctcccctcaa actcaagtgt   1980
gagctctgtg gccgggtgga ctttgcctat aagttcaagc gttccaagcg cttctgttcc   2040
atggcttgtg caaagaggta caacgtggga tgcaccaaac gggtgggact tttccactca   2100
gaccggagca agctgcagaa ggcaggagct gcgacccaca accgccgtcg ggccagcaaa   2160
gccagtctgc caccacttac caaggatacc aagaagcagc caacaggcac tgtgcccctt   2220
tcggttactg ctgctttgca gctaacacac agccaggaag actccagccg ttgctcagat   2280
aactcaagct atgaggaacc cttgtcaccc atctcagcca gctcatctac ttcccgccgg   2340
cgacaaggcc agcgggacct ggagctcccc gacatgcata tgcgggacct ggtgggcatg   2400
ggacaccact tcctgccaag tgagcccacc aagtggaatg tagaagacgt ctacgaattc   2460
atccgctctc tgccaggctg ccaggagata gcagaggaat tccgtgccca ggaaatcgac   2520
gggcaagccc tgctgctgct caaggaggac cacctgatga gcgccatgaa catcaagctg   2580
gggcccgccc tgaagatcta cgcccgcatc agcatgctca aggactccta gggctggtgg   2640
cagccaggat tctggcccag ggcgcctcct cccgactgag cagagccaga cagacattcc   2700
tgaggggccc agaaatgggg ccggttggag ggcaggggct ctccctaggg gcatagctgg   2760
tgaggaggtc tgggcacctc ctccatggct ctcaggggcc tttcatttct gtgggagggg   2820
cagagaggta ggtggcacag aagatggggc tttatgcttg taaatattga tagcactggc   2880
ttcctccaaa gtcccaatac tctagccccg ctctcttccc ctctttctgt cccccatttt   2940
ccagggggta tatggtcagg gctccccaac ctgagttggg ttacttcaag ggcagccagc   3000
```

-continued

```
aggcctggat ggaggcctag aaagcccttg ccttccttcc tcccacttct ttctccaggc   3060
ctggttaact cttccgttgt cagcttctcc cccttcagcc tgtttctgca gcagccaggg   3120
ttctcccccc tacaccctct gcaggtggag agagagaagc tgggcccagc cgggccgtgc   3180
ctgctggcac agacgcctta acgctgtgtg tatgactgtg tgactgtgtg ggagcctgga   3240
ctgacagata ggccaagggc tactctctgg catctccagg tgttttgtag caaacagcca   3300
cttagtgctt tgtcctggac tccactcagc ctcaggatgg ggaatagcca agaatggcag   3360
cctcagcgca gaggcaaggt cagaaagaga cggcgcttca gagtttcctt tccagacacc   3420
cctccccgca ctgtgaagtt cccctgaccg ccctcctggt tcacaaagag cattaagaaa   3480
gctgcggtgg tctgagcaac atagcccaaa gggctgagcc tcctggcctg cctgcccgcc   3540
caccctggga gtcccagtgg tgaggctcag agaactgcta aggggaaaga acagctggag   3600
tttctgttga tgtgaagaag gcagctcttg gcctcccact cccacacttc tttgcctata   3660
aatcttccta gcagcaattt gagctacctg aggaggaggc agggcagaaa gggcgagggc   3720
ctgcctctga cctgccgtgt cctttgcagg aaggaggtag gcacctttct gagcttattc   3780
tattccccac ccacaccccc aggcagggtt ggaaatgaag gactttttta acctttgttt   3840
tgtttttaa aaataaatct gtaaaatctg tct                                  3873
```

<210> SEQ ID NO 32
<211> LENGTH: 2904
<212> TYPE: DNA
<213> ORGANISM: Homo sapiens

<400> SEQUENCE: 32

```
ggagagcccc ggcgcggagc aggcgggtag ggcgaagggt cccctttcgg gcgccatggg     60
gcgccgagcg cggcctggcc cctcgggctc ctctgcgggg agggcaggcc gcaggctgga    120
gcggggtgcg gaggctggcg gggagcggcc cccggaggct ttcctggtag aagttgatgc    180
gaggaagggc ggcggggacc aggggacggt attcagaatt cgagcgcagg agctccgctt    240
ctccacctgc tcccggggag ctattgggat ccagagaatc acccgctgat ggtttttgcc    300
caggcctgaa acaaccagag agctacggga aaggaagggc ttggcttgcc agaggaattt    360
tccaagtgct caaacgccag gcttacggcg cctgtgatcc gtccaggagg acaaagtggg    420
atttgaagat ccactccact tctgctcatg gcgggccagg gcctgcccct gcacgtggcc    480
acactgctga ctgggctgct ggaatgcctg ggctttgctg gcgtcctctt tggctggcct    540
tcactagtgt ttgtcttcaa gaatgaagat tactttaagg atctgtgtgg accagatgct    600
gggccgattg gcaatgccac agggcaggct gactgcaaag cccaggatga gaggttctca    660
ctcatcttca ccctggggtc cttcatgaac aacttcatga cattccccac tggctacatc    720
tttgaccggt tcaagaccac cgtggcacgc ctcatagcca tatttttcta caccaccgcc    780
acactcatca tagccttcac ctctgcaggc tcagccgtgc tgctcttcct ggccatgcca    840
atgctcacca ttgggggaat cctgtttctc atcaccaacc tgcagattgg gaacctattt    900
ggccaacacc gttcgaccat catcactctg tacaatggag catttgactc ttcctcggca    960
gtcttcctta ttattaagct tctttatgaa aaaggcatca gcctcagggc ctccttcatc   1020
ttcatctctg tctgcagtac ctggcatgta gcacgcactt tcctcctgat gccccggggg   1080
cacatcccat acccactgcc ccccaactac agctatggcc tgtgccctgg gaatggcacc   1140
acaaaggaag agaaggaaac agctgagcat gaaaacaggg agctacagtc aaaggagttc   1200
```

-continued

```
ctttcagcga aggaagagac cccaggggca gggcagaagc aggaactccg ctccttctgg   1260
agctacgctt tctctcggcg ctttgcctgg cacctggtgt ggctgtctgt gatacagttg   1320
tggcactacc tcttcattgg cactctcaac tccttgctga ccaacatggc cggtggggac   1380
atggcacgag tcagcaccta cacaaatgcc tttgccttca ctcagttcgg agtgctgtgt   1440
gccccctgga atggcctgct catggaccgg cttaaacaga agtaccagaa ggaagcaaga   1500
aagacaggtt cctccacttt ggcggtggcc ctctgctcga cggtgccttc gctggccctg   1560
acatccctgc tgtgcctggg cttcgccctc tgtgcctcag tccccatcct ccctctccag   1620
tacctcacct tcatcctgca agtgatcagc cgctccttcc tctatgggag caacgcggcc   1680
ttcctcaccc ttgctttccc ttcagagcac tttggcaagc tctttgggct ggtgatggcc   1740
ttgtcggctg tggtgtctct gctccagttc cccatcttca ccctcatcaa aggctccctt   1800
cagaatgacc cattttacgt gaatgtgatg ttcatgcttg ccattcttct gacattcttc   1860
cacccctttc tggtatatcg ggaatgccgt acttggaaag aaagtccctc tgcaattgca   1920
tagttcagaa gccctcactt ttcagccccg aggatggttt tgttcatctt ccaccacctt   1980
tgaggacctc gtgtcccaaa agactttgcc tatcccagca aaacacacac acacacacac   2040
acacacacaa aataaagaca cacaaggacg tctgcgcagc aagaaaagaa tctcagttgc   2100
caagcagatt gatatcacac agactcaaag caaaggcatg tggaacttct ttatttcaaa   2160
acagaagtgt ctccttgcac ttagccttgg cagacccttg actccagggg agatgacctg   2220
ggggaggaag tgtgtcaact atttctttag gcctgtttgg ctccgaagcc tatatgtgcc   2280
tggatcctct gccacgggtt aaattttcag gtgaagagtg aggttgtcat ggcctcagct   2340
atgcttcctg gctctccctc aagagtgcag ccttggctag agaactcaca gctctgggaa   2400
aaagaggagc agacagggtt ccctgggccc agtctcagcc cagccactga tgctggatga   2460
ccttggcctg accctggtct ggtctcagaa tcacttttcc catctgtaaa attgagatga   2520
attttggtgt tgaaagttct tcctggagca gatgtcctag aaggttttag gaatagtgac   2580
agagtcaggc caccccaagg gccatgggag ccagctgacc tgcttgaccg aaggatttct   2640
gacagactat ctttggggat gttttcaaga agggatataa gttatttact ttgggcattt   2700
aaaagaaaat ttctctcggg aataatttta tagaaaaata aagcttctgt gtctaaggca   2760
aaaaaaaaaa aaaaaaaaaa aaaaaaaaaa aaaaaaaaaa aaaaaaaaaa aaaaaaaaaa   2820
aaaaaaaaaa aaaaaaaaaa aaaaaaaaaa aaaaaaaaaa aaaaaaaaaa aaaaaaaaaa   2880
aaaaaaaaaa aaaaaaaaaa aaaa                                          2904
```

<210> SEQ ID NO 33
<211> LENGTH: 1797
<212> TYPE: DNA
<213> ORGANISM: Homo sapiens

<400> SEQUENCE: 33

```
ttggccgcga gctggcggcg tggggggcgg gcccgggccg ggccggggcg gggaaggaag     60
gtggcggcgg cccggcgcgg ggggaggggg gtgctgaccc ggatgttcac tcctgggcac    120
ccggggaagt ggaagcgccg ggccctgctg cggggggag agccactgac gccgggaccg    180
ggaccgccgc cgccgccgcc accatgagtg atcagcagct ggactgtgcc ttggacctaa    240
tgaggcgcct gcctccccag caaatcgaga aaaacctcag cgacctgatc gacctggtcc    300
ccagtctatg tgaggatctc ctgtcttctg ttgaccagcc actgaaaatt gccagagaca    360
aggtggtggg aaaggattac cttttgtgtg actacaacag agatggggac tcctataggt    420
```

caccatggag taacaagtat gaccctccct tggaggatgg ggccatgccg tcagctcggc 480
tgagaaagct ggaggtggaa gccaacaatg cctttgacca gtatcgagac ctgtattttg 540
aaggtggcgt ctcatctgtc tacctctggg atctggatca tggctttgct ggagtgatcc 600
tcataaagaa ggctggagat ggatcaaaga agatcaaagg ctgctgggat tccatccacg 660
tggtagaagt gcaggagaaa tccagcggtc gcaccgccca ttacaagttg acctccacgg 720
tgatgctgtg gctgcagacc aacaaatctg gctctggcac catgaacctc ggaggcagcc 780
ttaccagaca gatggagaag gatgaaactg tgagtgactg ctccccacac atagccaaca 840
tcgggcgcct ggtagaggac atggaaaata aaatcagaag tacgctgaac gagatctact 900
ttggaaaaac aaaggatatc gtcaatgggc tgaggtctgt gcagactttt gcagacaaat 960
caaaacaaga agctctgaag aatgacctgg tggaggcttt gaagagaaag cagcaatgct 1020
aaacctctgt ttcatgctaa ccagacacgc cgtgcactcg ttagattcct ttcttagaaa 1080
actcgttttc tgctcccttc cctcgtccct tccctccccg acaggtcaca taacagctgc 1140
atcattgacc gcacagcgcc atctctccct gagaataaag ccgatagcca ccctcctccg 1200
gctccgagcc tgcttctgcc acacctcgct ctcagttctc tccacatttc catagagacc 1260
gtgtggtttt tgttcacccg ggccccccgt cttcctccct gtccccccat ttataggcat 1320
aaaatccact gtctgccagc ctcccttccc tcccaccttt ttggtacatt ggtgtaaaaa 1380
atgtaaaaca aaaaaatttt atgaactaac tgtggtgtgt gaaagagaga agaaaaactg 1440
gaaatcttat tccgtgtgtg tttgggagtt gcttggggtt gggggtcgtg gggacagggg 1500
acagctctgg gagcagaggt ggccctcggt gccgtcctgc gcagactctc ccgtcccacg 1560
gaggccgcgg ggtgggggct gggggggggtg ccgccgaccg ttccgctctt ccggccaggt 1620
gcttttctgt caatttctat ggaatgcaaa aggaggtttt tgttttattt tgttttttttg 1680 taaagcttaa gaaaaaaatc tacatcttat acttgagcct ccatacttaa aaaaagaaaa 1740
gaaaagaaat caataaaaag aaactggggc gcagttagca aaaaaaaaaa aaaaaaa 1797

<210> SEQ ID NO 34
<211> LENGTH: 5617
<212> TYPE: DNA
<213> ORGANISM: Homo sapiens

<400> SEQUENCE: 34
tataaaaaaa gtactgaaga cattttcccc gcacaactgc taaagctcca gagacacgag 60
cgtgtgtggc agcaagagcc gccagttcgg gaccaccgca gctggggtgg cagcggcgca 120
ggaggggtcg cggggaggga gtggtgagcg caggcggcag gggtctggga aagacgaagt 180
cgctatttgc tgtctgagcg cgctcgcagc tcctggaagt gttgccgcct ctcggtttcg 240
ctctcgctcg ctgcgctcct agaaggggcg gccgcctcca ggactgacca gggccaagtg 300
gcgctcggcg ggcactacat ggcggagggt gaagggtact tcgccatgtc tgaggacgag 360
ctggcctgca gcccctacat ccccctaggc ggcgacttcg gcggcggcga cttcggcggc 420
ggcgacttcg gcggcggcga cttcggcggt ggcggcagct tcggtgggca ttgcttggac 480
tattgcgaaa gccctacggc gcactgcaat gtgctgaact gggagcaagt gcagcggctg 540
gacggcatcc tgagcgagac cattccgatt cacgggcgcg gcaacttccc cacgctcgag 600
ctgcagccga gcctgatcgt gaaggtggtg cggcggcgcc tggccgagaa gcgcattggc 660
gtccgcgacg tgcgcctcaa cggctcggca gccagccatg tcctgcacca ggacagcggc 720

-continued

```
ctgggctaca aggacctgga cctcatcttc tgcgccgacc tgcgcgggga aggggagttt    780
cagactgtga aggacgtcgt gctggactgc ctgttggact tcttacccga gggggtgaac    840
aaagagaaga tcacaccact cacgctcaag gaagcttatg tgcagaaaat ggttaaagtg    900
tgcaatgact ctgaccgatg gagtcttata tccctgtcaa acaacagtgg caaaaaatgtg   960
gaactgaaat ttgtggattc cctccggagg cagtttgaat tcagtgtaga ttcttttcaa   1020
atcaaattag actctcttct gctcttttat gaatgttcag agaacccaat gactgagaca   1080
tttcacccca caataatcgg ggagagcgtc tatggcgatt tccaggaagc ctttgatcac   1140
ctttgtaaca agatcattgc caccaggaac ccagaggaaa tccgaggggg aggcctgctt   1200
aagtactgca acctcttggt gaggggcttt aggcccgcct ctgatgaaat caagaccctt   1260
caaaggtata tgtgttccag gtttttcatc gacttctcag acattggaga gcagcagaga   1320
aaactggagt cctatttgca gaaccacttt gtgggattgg aagaccgcaa gtatgagtat   1380
ctcatgaccc ttcatggagt ggtaaatgag agcacagtgt gcctgatggg acatgaaaga   1440
agacagactt taaaccttat caccatgctg gctatccggg tgttagctga ccaaaatgtc   1500
attcctaatg tggctaatgt cacttgctat taccagccag cccccctatgt agcagatgcc  1560
aactttagca attactacat tgcacaggtt cagccagtat tcacgtgcca gcaacagacc   1620
tactccactt ggctaccctg caattaagaa tcatttaaaa atgtcctgtg gggaagccat   1680
ttcagacaag acaggagaga aaaaaaaaaa aaagaaaaaa aaaagagtga tccagccctt   1740
attagggatg tgttttgtgc aatgatgata tgctcctggt tttaagtttg gcaaagctta   1800
tgtatctttt aatagatgtg ggagcatgat ctcgaaagga tccttttccc ttctcttatt   1860
ctcctaccca attggattct atcctgcaaa aaaagagaga cctgtcatta gaagcaacca   1920
ggttctcctg atacaagaga agaaatgtgt gatgacaata tgggtttgct gtatctgctc   1980
ccatagcttt gccataggaa aaaaaaaagt ggaaagtttc ttttaagatg gaattcataa   2040
aagggaaaat acggaggaaa aaaggtctca ctccaacttg tgaatcagtt taggagttca   2100
gatattaata gtaacaatac aggaaaaagg ggaactccaa cgttgggatt actgtctgag   2160
gcttgtagca agtgctttct gtggaatgat cttgttttgc taacaaacgg cttgctccaa   2220
atgaacagta gtaggttggt gcagttctcg taacaatcag cagaacttat gatgacacaa   2280
tccattaatt ccagctgcgt gcatagatca catttttaaa atgtaaaaat gcaagcaaaa   2340
acagctgtaa caaagaaagt gtgctcaagg accaaagatt taacagataa aaatacccaa   2400
ttagaagaga tatagtagac tatatgaaga gagattatat ttgttacaca ccaatataca   2460
tcaaagtgcc tgttgccttc tgaaaatttg aagtggcaaa attattttat ggtttaatga   2520
ttattttatt ttatcaggga ctgcctcaag aagaaaataa cataagcttg tgaatggtgg   2580
agaaaatgcc ctatttttttc ttgcaaatac ttgtataaag ttaacatttg ttgatctgat  2640
attatcatag gtacatgtgt atgtgtgtat aaattatatg tgtgtgtgta tatatacatt   2700
ttatatatac attttatatg tatatataca cagtagattg actatgatct agaataatgt   2760
ctcaaatagg aaatgtttaa atactgtgtg tttttatgtt ttcaacagga taacatgaga   2820
cgtgggcata ttgcaatgat gaattaaatc cacatctaaa aaaattaaat gaaggaggga   2880
accaagtaat atatttcata ggaagagcag aaattatact gttttagtgg gatttttttt   2940
tcttttttttt tttttctttg gtgagccata aaattccaca aatgggagaa tatttgtttg  3000
gcagagcact ctttttttata ttgaactgcc attttgacag ttggaaccca tttattaaaa  3060
aaaaaattgc attcctctat gatgtttaat ctagtggatc atggatcagt aataggctac   3120
```

-continued ttaaatccct gactgctaaa aaggatttcc ggtgatctaa acactacttg ctaatgttta 3180
aatgaatttt aatgaatgca ttctgcattt ctggaccact agaatttagt aatgtgaaat 3240
gacccttttt acagaatatt tgcacaattg cttaaaattt atatatgaga tatatattat 3300
atataacatt ttataaatca tgtcaatatg aaacatcttt gatctggttg tcacactgca 3360
tttaaatatt tagtactgta ctttaaatcg ctttccatta aatcaaatcc aactttattt 3420
tctttcttac aaaaatacca gttatacctt tgtgaaatga actggcatta ctatttcagt 3480
tcaataacag ctaatcctaa aaccaccctt tctcctagcc agtagttcct ctagatactg 3540
gtctctgaaa atgcatttgt taaaaacaaa acaaaactaa cacataagaa ccttcccttt 3600
gtgttgtgaa acaaccacat aatctccaca accttagtgg atgactgctt gctatgataa 3660
ttcctcgaag acccaattag aagattttca tcatcagtta aagagagacc acgggagaaa 3720
aaaatatcct cctgttggca gtataatttg tttgtttgtt tatctaggga tcctcagatg 3780
cttagtgcta ggttaatcca ggttaatccg tctggactac cttttgtgca tctttctttg 3840
aagccttaat gggaacctga tgggtttgct gtagcagctt ccttgtgaat tctgtcagag 3900
ctgcaacagc cgctgcactg ccactcagtt ttctaaggaa ctcctcctac taccatcttg 3960
gctcagtctc cctcacttaa gccctgggtt tgaaaaatta attgcaactt cccaggaaac 4020
attgttcagt ttgcagatta agcctggcac tcacctatca gaaaccagag ctccgcctgc 4080
ttagttgttt caaagttttc tgaaagaaaa ctaggggagc acttgtgaac acaggagcag 4140
ctggtgatct gctttcttac cctaactctt gacaaatgag tcgtctacta ttttaaagag 4200
tctggaggtc tctgactctg ccataacaat aacctgctgt taatttataa cacagatttt 4260
tgtttggaag agccttattt gaaatacact ttgatttatt ttcttaaata tttatattct 4320
tttcttgctt acttcagggt tggtagctta gttggaagtg ccagcacctg gcacctattc 4380
atatagaaca ggctgtactc aagacaactt ctagcattta ctttaagact tatataattt 4440
atttctattt tgtgtgtact atagtcttgt gcatatgtag ttgaacacac agtgaaatat 4500
atgtctctct ttgtggatgt gcggcctaaa aatttgaatg tctggtgaga gagagccatg 4560
tgtataggtc agagaaaaga acagctcccg actccctatt agcgcctgtg atttgtttcc 4620
ttttgtgttt atctggccta gtgtgctgtt tctttaaacc aggaagaagt tttgtctttt 4680
ggaggctctt ctcacctgtc cagcctggca tgtcagagaa cacatagcct gtgacaatgc 4740
cgtttttaaa ggtttactta atttgcagta aatccagctg cctcaagaac tcctacacca 4800
agatggacat ttcctttcca gaaatgggat caagtatctg ctcactttgg tattggatgg 4860
actaataatg tagctccaaa aatgcaagga tggaagaata tgtgtaatcc aaaccaagga 4920
aggaaatgaa aagtgaacgt actgttttta ccaccccttt ctgtttgctt attgttggtt 4980
gcttcactgt gcataaagtt gttttcaatg caacgcttgt taaataaata ttgtgaacta 5040
ttttgtaaat gaaatgtatt atgttgaaag ctgtcagttc aaaaataagc ttttttgttg 5100
ttgttgaaga tgaagtgtgt taggtgaaac caaaaagcca aaaaaagtaa tttcatatat 5160
agcatctatt tgaatataat ctttctttaa aatttctttt agcatagcat tttcagtgct 5220
aagaaagaat ctctatgtta tattttgtta aaataatggc tttctaacaa agcaaatggt 5280
aaagtacaaa gttggaagat gtcaagttaa cgagacttgc tgcaaagcct tgcagaacgg 5340
aggaggctct gcctgctggc tgtctctccc tccaacctct ctacaatcat gcctgctttg 5400
aggtgttctg ttgcagcaag ctgcaccttg ggtcactctt ttggaatatt ttgactatag 5460

-continued

```
gctgcgtcac aggcagaaaa ggagttgatg gaaaatggac taaaaaactg acatgtttga   5520

atcagtgcta gagggaacag attgtgaatt ttgtttacag catccaatat ttggattttt   5580

ttgtaaataa aaaagttatt tttttctatt gaaaaaa                            5617
```

<210> SEQ ID NO 35
<211> LENGTH: 3939
<212> TYPE: DNA
<213> ORGANISM: Homo sapiens

<400> SEQUENCE: 35

```
gcggcggcgg gagctggttc cggctgcgcg cgcagcggtg gtggtggcgg cgcgatcggc     60

cgggctgtaa ccgtcgtctg tccgggagcg gctggagcgg cagcggcggc cgggcacggc    120

gcgaggtgac gccacagggc agcggcggca gcggaggcag cggcggcagc aggagacgca    180

gcggcggccg cagcagcagc agcaagacgg actcgtggag acgcgccgcc gccgccgccg    240

ccgggccggg ccgggtgtcg cgcgccgagg ctggggggga gtcgtcgccg ccgccgccac    300

cgctaccgcc gccgccgccg ccgccgaggt gactgaggag agaggcgcct cctcgctccc    360

gccaccgccg gacttcaatg cccagtcccc agctcgccag cgtttttcgt tggaatatac    420

gttgcacatt tatggcgatt ctgagtgtga gggcagactt ctgccaggct cagcacagca    480

ttttcgctga caagtgagct tggaggttct atgtgccata attaacattg ccttgaagac    540

tcctggacac cgagactggc ctcagaaata gttggctttt ttttttttta attgcaagca    600

tatttctttt aatgactcca gtaaaattaa gcatcaagta aacaagtgga aagtgaccta    660

cacttttaac ttgtctcact agtgcctaaa tgtagtaaag gctgcttaag ttttgtatgt    720

agttggattt tttggagtcc gaaggtatcc atctgcagaa attgaggccc aaattgaatt    780

tggattcaag tggattctaa atactttgct tatcttgaag agagaagctt cataaggaat    840

aaacaagttg aatagagaaa acactgattg ataataggca ttttagtggt ctttttaatg    900

ttttctgctg tgaaacattt caagatttat tgattttttt ttttcacttt ccccatcaca    960

ctcacacgca cgctcacact ttttatttgc cataatgaac cgtccagccc ctgtggagat   1020

ctcctatgag aacatgcgtt ttctgataac tcacaaccct accaatgcta ctctcaacaa   1080

gttcacagag gaacttaaga agtatggagt gacgactttg gttcgagttt gtgatgctac   1140

atatgataaa gctccagttg aaaaagaagg aatccacgtt ctagattggc catttgatga   1200

tggagctcca cccccctaatc agatagtaga tgattggtta aacctgttaa aaaccaaatt   1260

tcgtgaagag ccaggttgct gtgttgcagt gcattgtgtt gcaggattgg gaagggcacc   1320

tgtgctggtt gcacttgctt tgattgaatg tggaatgaag tacgaagatg cagttcagtt   1380

tataagacaa aaaagaaggg gagcgttcaa ttccaaacag ctgctttatt tggagaaata   1440

ccgacctaag atgcgattac gcttcagaga taccaatggg cattgctgtg ttcagtagaa   1500

ggaaatgtaa acgaaggctg acttgattgt gccatttaga gggaactctt ggtacctgga   1560

aatgtgaatc tggaatatta cctgtgtcat caaagtagtg atggattcag tactcctcaa   1620

ccactctcct aatgattgga acaaaagcaa acaaaaaaga aatctctcta taaaatgaat   1680

aaaatgttta agaaaagaga aagagaaaag gaattaattc agtgaaggat gattttgctc   1740

ctagttttgg agtttgaatt tctgccagga ttgaattatt ttgaaatctc ctgtcttttt   1800

aaactttttc aaaataggtc tctaaggaaa accagcagaa cattagcctg tgcaaaacca   1860

tctgtttggg gagcacactc ttccattatg cttggcacat agatctccct gtggtgggat   1920

tttttttttc cctttttttg tgggggaggg ttggtggtat atttttcccc tctttttttcc   1980
```

```
ttcctctcct acatctccct tttcccccga tccaagttgt agatggaata gaagcccttg   2040
ttgctgtaga tgtgcgtgca gtctggcagc cttaagccca cctgggcact tttagataaa   2100
aaaaaaaaaa aaacaaaaaa caacaccaaa aaaacagcag tgatatatat atatatatat   2160
atatatatat atatatatat atatatatat atatatatat atatatataa tataatatat   2220
atatatatat atatattttc caggtggttt ttagtcttta ctgatgaaag ggtgttcatg   2280
ttagtttctt caaaacccta tctaatacta ggcaaagtag ccaagagcct tttgttttgt   2340
ttttattttg ataaattagt ggagaaatgg cattttaaga ggagtctctt ctcaacttac   2400
ctgagagtcg aattcttctc ttccctaacc aatgaagcta agtggttatc ccagaaactt   2460
gtcttctaaa agggaggact ccaggccatc aataaagatg tccaggcagt gagcgtactt   2520
tttacaccct gtagaattgt gggctgtagc gttactctga ttttctgtct agtatcagag   2580
aatgctggta gcttaaaatt tttattttag gacttgtact ctgaattttc aggaaccgtc   2640
aaaggagcag cagcaaattc acatattttc gacttgagaa atgcttgtgg tatgtgtttt   2700
ccaaactgcc ccctatatgt aaagttcagt ttaaccactg attgccttgt tattactagg   2760
ttttttgaga ttaaaaaaaa aaaatccctg gtttaaaacc aacaatgatg cctagtgagt   2820
atgtgtccac aggccataac agggtagaag agagacatcg tgcaacccaa tgagtagtga   2880
agggactgtg ttgcttgtga agcggtgtag tagcattttt gcagattctt ggctgggttt   2940
agtgtactga tctagaaaag ctgtttttct gctcctttgt ggaaggcagt tatgatcagg   3000
ctgcatggac aaagcaggta gaggggcacc atcaggggct cttgcactat tttcacctct   3060
aaatattacg tactcagtag tgccctgctt ctagggctct gaatacgggc ttaaagtcat   3120
cttgtcctgc tggaatttgc tgtgcagagc cataagcctc ccattttgtt agcgtcagct   3180
aggccaatag gaacagaccg ggaccttgtc tcacactgat gatacctcac atgttgaccg   3240
gctatgtgaa ctgcctattt cctatgctgg agttttgatt tttaactaaa cgcaaatctg   3300
tagattctct cctctcccat cccagaaaac aaaacaaaat aatgcttttc gaaattgttt   3360
ctaggacttt aaaacataat ggtatatcca aaattcttta tttcagaatg caacaataga   3420
ttccattaat atagactcaa gatcaaaaca gcatacctgc taagctaaga tagatggtgt   3480
tgattccact gggttttgat caatacaata acaaaccttt ttcctttgac atactctgaa   3540
ttttgttgtt tgggggggagg gggtgtgtgt gtgtgtgtgt gtgtgtgtgt gtgtatgtgt   3600
gtgtgtgtgt gtgcacgcgc agtgtccatc agtatcagtg cctgcctgag ttaggaaaat   3660
tacattcctg gttctgtatt gaggagaagg atgtataaag caacatgaaa cattagccct   3720
ccttttattt taaagactaa tgttaattgt tcttaaaact ggattttttt tccttaaagc   3780
aatttttttc ttttcgattt aatgaagtat tgctagctga agccagtttg acatagagag   3840
atgtcagatt gatttgaaag gtgtgcagcc tgatttaaaa ccaaaccctg aacccttttta   3900
aagaacaata aaacatattt tacacgctca aaaaaaaaa                          3939
```

<210> SEQ ID NO 36
<211> LENGTH: 4451
<212> TYPE: DNA
<213> ORGANISM: Homo sapiens

<400> SEQUENCE: 36

```
gctccgcccc cgcgccgccg gccctagtct gcctgttttc gactcgcgct ccggctgctg     60
tcacttggct ctctggctgg agcttgagga cgcaaggagg gtttgtcact ggcagactcg    120
```

-continued

```
agactgtagg cactgccatg gcccctgtgc tcagtaagga ctcggcggac atcgagagta    180
tcctggcttt aaatcctcga acacaaactc atgcaactct gtgttccact tcggccaaga    240
aattagacaa gaaacattgg aaaagaaatc ctgataagaa ctgctttaat tgtgagaagc    300
tggagaataa ttttgatgac atcaagcaca cgactcttgg tgagcgagga gctctccgag    360
aagcaatgag atgcctgaaa tgtgcagatg ccccgtgtca gaagagctgt ccaactaatc    420
ttgatattaa atcattcatc acaagtattg caaacaagaa ctattatgga gctgctaaga    480
tgatattttc tgacaaccca cttggtctga cttgtggaat ggtatgtcca acctctgatc    540
tttgtgtagg tggatgcaat ttatatgcca ctgaagaggg acccattaat attggtggat    600
tgcagcaatt tgctactgag gtattcaaag caatgagtat cccacagatc agaaatcctt    660
cgctgcctcc cccagaaaaa atgtctgaag cctattctgc aaagattgct ctttttggtg    720
ctgggcctgc aagtataagt tgtgcttcct ttttggctcg attggggtac tctgacatca    780
ctatatttga aaaacaagaa tatgttggtg gtttaagtac ttctgaaatt cctcagttcc    840
ggctgccgta tgatgtagtg aattttgaga ttgagctaat gaaggacctt ggtgtaaaga    900
taatttgcgg taaaagcctt tcagtgaatg aaatgactct tagcactttg aaagaaaaag    960
gctacaaagc tgctttcatt ggaataggtt tgccagaacc caataaagat gccatcttcc   1020
aaggcctgac gcaggaccag ggttttata catccaaaga ctttttgcca cttgtagcca   1080
aaggcagtaa agcaggaatg tgcgcctgtc actctccatt gccatcgata cggggagtcg   1140
tgattgtact tggagctgga gacactgcct ttgactgtgc aacatctgct ctacgttgtg   1200
gagctcgccg tgtgttcatc gtcttcagaa aaggctttgt taatataaga gctgtccctg   1260
aggagatgga acttgctaag gaagaaaagt gtgaatttct gccattcctg tccccacgga   1320
aggttatagt aaaaggtggg agaattgttg ctatgcagtt tgttcggaca gagcaagatg   1380
aaactggaaa atggaatgaa gatgaagatc agatggtcca tctgaaagcc gatgtggtca   1440
tcagtgcctt tggttcagtt ctgagtgatc ctaaagtaaa agaagccttg agccctataa   1500
aatttaacag atggggtctc ccagaagtag atccagaaac tatgcaaact agtgaagcat   1560
gggtatttgc aggtggtgat gtcgttggtt tggctaacac tacagtggaa tcggtgaatg   1620
atggaaagca agcttcttgg tacattcaca aatacgtaca gtcacaatat ggagcttccg   1680
tttctgccaa gcctgaacta cccctctttt acactcctat tgatctggtg gacattagtg   1740
tagaaatggc cggattgaag tttataaatc cttttggtct tgctagcgca actccagcca   1800
ccagcacatc aatgattcga agagcttttg aagctggatg gggttttgcc ctcaccaaaa   1860
ctttctctct tgataaggac attgtgacaa atgtttcccc cagaatcatc cggggaacca   1920
cctctggccc catgtatggc cctggacaaa gctcctttct gaatattgag ctcatcagtg   1980
agaaaacggc tgcatattgg tgtcaaagtg tcactgaact aaaggctgac tttccagaca   2040
acattgtgat tgctagcatt atgtgcagtt acaataaaaa tgactggacg gaacttgcca   2100
agaagtctga ggattctgga gcagatgccc tggagttaaa tttatcatgt ccacatggca   2160
tgggagaaag aggaatgggc ctggcctgtg ggcaggatcc agagctggtg cggaacatct   2220
gccgctgggt taggcaagct gttcagattc cttttttgc caagctgacc ccaaatgtca   2280
ctgatattgt gagcatcgca agagctgcaa aggaaggtgg tgccaatggc gttacagcca   2340
ccaacactgt ctcaggtctg atgggattaa aatctgatgg cacaccttgg ccagcagtgg   2400
ggattgcaaa gcgaactaca tatggaggag tgtctgggac agcaatcaga cctattgctt   2460
tgagagctgt gacctccatt gctcgtgctc tgcctggatt tcccattttg gctactggtg   2520
```

gaattgactc tgctgaaagt ggtcttcagt ttctccatag tggtgcttcc gtcctccagg 2580
tatgcagtgc cattcagaat caggatttca ctgtgatcga agactactgc actggcctca 2640
aagccctgct ttatctgaaa agcattgaag aactacaaga ctgggatgga cagagtccag 2700
ctactgtgag tcaccagaaa gggaaaccag ttccacgtat agctgaactc atggacaaga 2760
aactgccaag ttttggacct tatctggaac agcgcaagaa aatcatagca gaaaacaaga 2820
ttagactgaa agaacaaaat gtagcttttt caccacttaa gagaaactgt tttatcccca 2880
aaaggcctat tcctaccatc aaggatgtaa taggaaaagc actgcagtac cttggaacat 2940
ttggtgaatt gagcaacgta gagcaagttg tggctatgat tgatgaagaa atgtgtatca 3000
actgtggtaa atgctacatg acctgtaatg attctggcta ccaggctata cagtttgatc 3060
cagaaaccca cctgcccacc ataaccgaca cttgtacagg ctgtactctg tgtctcagtg 3120
tttgccctat tgtcgactgc atcaaaatgg tttccaggac aacaccttat gaaccaaaga 3180
gaggcgtacc cttatctgtg aatccggtgt gttaaggtga tttgtgaaac agttgctgtg 3240
aactttcatg tcacctacat atgctgatct tttaaaatca tgatccttgt gttcagctct 3300
ttccaaatta aaacaaatat acattttcta aataaaaata tgtaatttca aaatacattt 3360
gtaagtgtaa aaaatgtctc atgtcaatga ccattcaatt agtggtcata aaatagaata 3420
attcttttct gaggatagta gttaaataac tgtgtggcag ttaattggat gttcactgcc 3480
agttgtctta tgtgaaaaat taactttttt gtggcaatta gtgtgacagt ttccaaattg 3540
ccctatgctg tgctccatat ttgatttcta attgtaagtg aaattaagca ttttgaaaca 3600
aagtactctt taacatacaa gaaaatgtat ccaaggaaac attttatcat taaaaattac 3660
ctttaatttt aatgctgttt ctaagaaaat gtagttagct ccataaagta caaatgaaga 3720
aagtcaaaaa attatttgct atggcaggat aagaaagcct aaaattgagt ttgtagaact 3780
ttattaagta aaatcccctt cgctgaaatt gcttattttt ggtgttggat agaggatagg 3840
gagaatattt actaactaaa taccattcac tactcatgcg tgagatgggt gtacaaactc 3900
atcctctttt aatggcattt ctctttaaac tatgttccta acaaaatgag atgataggat 3960
agatcctggt taccactctt ttgctgtgca catacgggct ctgactggtt ttaatagtca 4020
ccttcatgat tatagcaact aatgtttgaa caaagctcaa agtatgcaat gcttcattat 4080
tcaagaatga aaaatataat gttgataata tatattaagt gtgccaaatc agtttgacta 4140
ctctctgttt tagtgtttat gtttaaaaga aatatatttt ttgttattat tagataatat 4200
ttttgtattt ctctattttc ataatcagta aatagtgtca tataaactca tttatctcct 4260
cttcatggca tcttcaatat gaatctataa gtagtaaatc agaaagtaac aatctatggc 4320
ttatttctat gacaaattca agagctagaa aaataaaatg tttcattatg cacttttaga 4380
aatgcatatt tgccacaaaa cctgtattac tgaataatat caaataaaat atcataaagc 4440
attttaaaaa a 4451

<210> SEQ ID NO 37
<211> LENGTH: 2753
<212> TYPE: DNA
<213> ORGANISM: Homo sapiens

<400> SEQUENCE: 37
gagcgaccgt cggggccggc tggggccgga gctcggggct cggtgggcct acagcggctc 60
cggacggacc cccggggctg gggagtcggg gaggcctgcc ccggccccct gcccgcggcc 120
gccatggcgg agaattggaa gaactgcttc gaggaggagc tcatctgccc tatctgcctg 180
cacgttttcg tggagccagt gcagctgccg tgcaaacaca acttctgccg gggctgcatc 240
ggcgaggcgt gggccaagga cagcggcctc gtacgctgcc cagagtgcaa ccaggcctac 300
aaccagaagc cgggcctgga gaagaacctg aagctcacca acatcgtgga gaagttcaat 360
gccctgcacg tggagaagcc gccggcggcg ctgcactgcg tgttctgccg ccgcggcccc 420
ccgctgcccg cgcagaaggt ctgcctgcgc tgcgaggcgc cctgctgcca gtcccacgtg 480
cagacgcacc tgcagcagcc ctccaccgcc cgcgggcacc tcctggtgga ggcggacgac 540
gtgcgggcct ggagctgccc gcagcacaac gcctaccgcc tctaccactg cgaggccgag 600
caggtggccg tgtgccagta ctgctgctac tacagcggcg cgcatcaggg acactcggtg 660
tgcgacgtgg agatccgaag gaatgaaatc cggaagatgc tcatgaagca gcaggaccgg 720
ctggaggagc gagagcagga cattgaggac cagctgtaca aactcgagtc agacaagcgc 780
ctggtggagg agaaagtgaa ccaactgaag gaggaagttc ggctgcagta cgagaagctg 840
caccagctgc tggacgagga cctgcggcag acagtggagg tcctagacaa ggcccaggcc 900
aagttctgca gcgagaacgc agcgcaggcg ctgcacctcg gggagcgcat gcaggaggcc 960
aagaagctgc tgggctccct gcagctgctc tttgataaga cggaggatgt cagcttcatg 1020
aagaacacca agtctgtgaa aatcctgatg gacaggaccc agacctgcac gagcagcagc 1080
ctttccccca ctaagatcgg ccacctgaac tccaagctct tcctgaacga agtggccaag 1140
aaggagaagc agctgcggaa aatgctagaa ggccccttca gcacgccggt gcccttcctg 1200
cagagtgtcc ccctgtaccc ttgcggcgtg agcagctctg ggcggaaaa gcgcaagcac 1260
tcaacggcct tcccagaggc cagtttccta gagacgtcgt cgggccctgt gggcggccag 1320
tacggggcgg cgggcacagc cagcggtgag ggccagtctg ggcagcccct ggggccctgc 1380
agctccacgc agcacttggt ggccctgccg ggcggcgccc aaccagtgca ctcaagcccc 1440
gtgttccccc catcgcagta tcccaatggc tccgccgccc agcagcccat gctcccccag 1500
tatggcggcc gcaagattct cgtctgttct gtggacaact gttactgttc ttccgtggcc 1560
aaccatggcg gccaccagcc ctacccccgc tccggccact ttccctggac agtgccctcg 1620
caggagtact cacacccgct cccgcccaca ccctccgtcc cccagtccct tcccagcctg 1680
gcggtcagag actggcttga cgcctcccag cagcccggcc accaggattt ctacagggtg 1740
tatgggcagc cgtccaccaa acactacgtg acgagctaac gccacgcagg cggcggggcg 1800
ctggggaatc ttcctcccca gcccccgggc tcgggagtta tgcatccaga gacctgccct 1860
tctaccttcc tcgcctcccc tcttcctcat tccattgccc caggtctttt ccttttggat 1920
tttgttttgg ttttggcttt gtttttgatt ttttttatt atgaatctcc tggacgcaga 1980
ggtgacagtg ggagctggcc tgggccagga cggcaggtgg ccctggagat gggaaagtgt 2040
ctgtgtcgag gcgctgagct ctctctctgt ttctcctttt ttcctctact ccttcccctt 2100
cacacccccg tggctggaag gaacctcggc ttccctgaaa gcttgggggt cccacccttc 2160
ttaccccacc cgggaggaac gcccagggcc ccgggcttgt ttctcctctt gttttccttt 2220
tgggcagttt gatcactgat cgagtaagga atgaccttta gattgtgcga cttttgtttt 2280
tgttttttta aattttttta aaccaagaat gatttctcct gcttccttct cctcaccatc 2340
ttcccagacg gagttcaaag gccacttctc aagcagcttt tggcaccttc agcctcagag 2400
tggaatcttt taaagacagg acccctatgt ccaggaaagg ggaaaaggaa ctttgccaat 2460
gatagtgacc acagcaaaag caaataataa taatattaat aataataaag agaaataaaa 2520
taataaaata aaaaacaata gcacagccct tgttgaggtc agcagggagg aggggctgcc 2580
cggagttggg tccttgcctg gattttgaca cagcaacttc ctgtagtgag cactttgtat 2640
gaatcgtgga cttcctgttc tcaaggcgca ggtatttatt ctgtatctgt ctagagcaca 2700
caccaaaatc caaccttcta ataaacatga tggcgcagtc ccacaaaaaa aaa 2753

<210> SEQ ID NO 38
<211> LENGTH: 5346
<212> TYPE: DNA
<213> ORGANISM: Homo sapiens

<400> SEQUENCE: 38
ggggagcagg cgggggagcg ggcgggaagc agtgggagcg cgcgtgcgcg cggccgtgca 60
gcctgggcag tgggtcctgc ctgtgacgcg cggcggcggt cggtcctgcc tgtaacggcg 120
gcggcggctg ctgctccaga cacctgcggc ggcggcggcg accccgcggc gggcgcggag 180
atgtggcccc tggtagcggc gctgttgctg ggctcggcgt gctgcggatc agctcagcta 240
ctatttaata aaacaaaatc tgtagaattc acgttttgta atgacactgt cgtcattcca 300
tgctttgtta ctaatatgga ggcacaaaac actactgaag tatacgtaaa gtggaaattt 360
aaaggaagag atatttacac ctttgatgga gctctaaaca agtccactgt ccccactgac 420
tttagtagtg caaaaattga agtctcacaa ttactaaaag gagatgcctc tttgaagatg 480
gataagagtg atgctgtctc acacacagga aactacactt gtgaagtaac agaattaacc 540
agagaaggtg aaacgatcat cgagctaaaa tatcgtgttg tttcatggtt ttctccaaat 600
gaaaatattc ttattgttat tttcccaatt tttgctatac tcctgttctg ggacagtttt 660
ggtattaaaa cacttaaata tagatccggt ggtatggatg agaaaacaat tgctttactt 720
gttgctggac tagtgatcac tgtcattgtc attgttggag ccattctttt cgtcccaggt 780
gaatattcat taaagaatgc tactggcctt ggtttaattg tgacttctac agggatatta 840
atattacttc actactatgt gtttagtaca gcgattggat taacctcctt cgtcattgcc 900
atattggtta ttcaggtgat agcctatatc ctcgctgtgg ttggactgag tctctgtatt 960
gcggcgtgta taccaatgca tggccctctt ctgatttcag gtttgagtat cttagctcta 1020
gcacaattac ttggactagt ttatatgaaa tttgtggctt ccaatcagaa gactatacaa 1080
cctcctagga aagctgtaga ggaacccctt aatgcattca aagaatcaaa aggaatgatg 1140
aatgatgaat aactgaagtg aagtgatgga ctccgatttg gagagtagta agacgtgaaa 1200
ggaatacact tgtgtttaag caccatggcc ttgatgattc actgttgggg agaagaaaca 1260
agaaaagtaa ctggttgtca cctatgagac ccttacgtga ttgttagtta agtttttatt 1320
caaagcagct gtaatttagt taataaaata attatgatct atgttgtttg cccaattgag 1380
atccagtttt ttgttgttat ttttaatcaa ttaggggcaa tagtagaatg gacaatttcc 1440
aagaatgatg cctttcaggt cctagggcct ctggcctcta ggtaaccagt ttaaattggt 1500
tcagggtgat aactacttag cactgccctg gtgattaccc agagatatct atgaaaacca 1560
gtggcttcca tcaaaccttt gccaactcag gttcacagca gctttgggca gttatggcag 1620
tatggcatta gctgagaggt gtctgccact tctgggtcaa tggaataata aattaagtac 1680
aggcaggaat ttggttggga gcatcttgta tgatctccgt atgatgtgat attgatggag 1740
atagtggtcc tcattcttgg gggttgccat tcccacattc ccccttcaac aaacagtgta 1800
acaggtcctt cccagattta gggtactttt attgatggat atgttttcct tttattcaca 1860

-continued

```
taaccccttg aaaccctgtc ttgtcctcct gttacttgct tctgctgtac aagatgtagc   1920
accttttctc ctctttgaac atggtctagt gacacggtag caccagttgc aggaaggagc   1980
cagacttgtt ctcagagcac tgtgttcaca cttttcagca aaaatagcta tggttgtaac   2040
atatgtattc ccttcctctg atttgaaggc aaaaatctac agtgtttctt cacttctttt   2100
ctgatctggg gcatgaaaaa agcaagattg aaatttgaac tatgagtctc ctgcatggca   2160
acaaaatgtg tgtcaccatc aggccaacag gccagccctt gaatggggat ttattactgt   2220
tgtatctatg ttgcatgata aacattcatc accttcctcc tgtagtcctg cctcgtactc   2280
cccttcccct atgattgaaa agtaaacaaa acccacattt cctatcctgg ttagaagaaa   2340
attaatgttc tgacagttgt gatcgcctgg agtactttta gacttttagc attcgttttt   2400
tacctgtttg tggatgtgtg tttgtatgtg catacgtatg agataggcac atgcatcttc   2460
tgtatggaca aaggtggggt acctacagga gagcaaaggt taattttgtg cttttagtaa   2520
aaacatttaa atacaaagtt ctttattggg tggaattata tttgatgcaa atatttgatc   2580
acttaaaact tttaaaactt ctaggtaatt tgccacgctt tttgactgct caccaatacc   2640
ctgtaaaaat acgtaattct tcctgtttgt gtaataagat attcatattt gtagttgcat   2700
taataatagt tatttcttag tccatcagat gttcccgtgt gcctctttta tgccaaattg   2760
attgtcatat ttcatgttgg gaccaagtag tttgcccatg gcaaacctaa atttatgacc   2820
tgctgaggcc tctcagaaaa ctgagcatac tagcaagaca gctcttcttg aaaaaaaaaa   2880
tatgtataca caaatatata cgtatatcta tatatacgta tgtatataca cacatgtata   2940
ttcttccttg attgtgtagc tgtccaaaat aataacatat atagagggag ctgtattcct   3000
ttatacaaat ctgatggctc ctgcagcact ttttccttct gaaaatattt acattttgct   3060
aacctagttt gttactttaa aaatcagttt tgatgaaagg agggaaaagc agatggactt   3120
gaaaaagatc caagctccta ttagaaaagg tatgaaaatc tttatagtaa aatttttttat   3180
aaactaaagt tgtacctttt aatatgtagt aaactctcat ttatttgggg ttcgctcttg   3240
gatctcatcc atccattgtg ttctctttaa tgctgcctgc cttttgaggc attcactgcc   3300
ctagacaatg ccaccagaga tagtggggga aatgccagat gaaaccaact cttgctctca   3360
ctagttgtca gcttctctgg ataagtgacc acagaagcag gagtcctcct gcttgggcat   3420
cattgggcca gttccttctc tttaaatcag atttgtaatg gctcccaaat tccatcacat   3480
cacatttaaa ttgcagacag tgttttgcac atcatgtatc tgttttgtcc cataatatgc   3540
tttttactcc ctgatcccag tttctgctgt tgactcttcc attcagtttt atttattgtg   3600
tgttctcaca gtgacaccat ttgtcctttt ctgcaacaac ctttccagct acttttgcca   3660
aattctattt gtcttctcct tcaaaacatt ctcctttgca gttcctcttc atctgtgtag   3720
ctgctctttt gtctcttaac ttaccattcc tatagtactt tatgcatctc tgcttagttc   3780
tattagtttt ttggccttgc tcttctcctt gattttaaaa ttccttctat agctagagct   3840
tttctttctt tcattctctc ttcctgcagt gttttgcata catcagaagc taggtacata   3900
agttaaatga ttgagagttg gctgtattta gatttatcac tttttaatag ggtgagcttg   3960
agagttttct ttctttctgt tttttttttt tgtttttttt tttttttttt tttttttttt   4020
ttttgactaa tttcacatgc tctaaaaacc ttcaaaggtg attattttttc tcctggaaac   4080
tccaggtcca ttctgtttaa atccctaaga atgtcagaat taaaataaca gggctatccc   4140
gtaattggaa atatttcttt tttcaggatg ctatagtcaa tttagtaagt gaccaccaaa   4200
ttgttatttg cactaacaaa gctcaaaaca cgataagttt actcctccat ctcagtaata   4260
```

aaaattaagc tgtaatcaac cttctaggtt tctcttgtct taaaatgggt attcaaaaat 4320
ggggatctgt ggtgtatgta tggaaacaca tactccttaa tttacctgtt gttggaaact 4380
ggagaaatga ttgtcgggca accgtttatt ttttattgta ttttatttgg ttgagggatt 4440
tttttataaa cagttttact tgtgtcatat tttaaaatta ctaactgcca tcacctgctg 4500
gggtcctttg ttaggtcatt ttcagtgact aatagggata atccaggtaa ctttgaagag 4560
atgagcagtg agtgaccagg cagtttttct gcctttagct ttgacagttc ttaattaaga 4620
tcattgaaga ccagctttct cataaatttc tctttttgaa aaaaagaaag catttgtact 4680
aagctcctct gtaagacaac atcttaaatc ttaaaagtgt tgttatcatg actggtgaga 4740
gaagaaaaca ttttgttttt attaaatgga gcattattta caaaaagcca ttgttgagaa 4800
ttagatccca catcgtataa atatctatta accattctaa ataaagagaa ctccagtgtt 4860
gctatgtgca agatcctctc ttggagcttt tttgcatagc aattaaaggt gtgctatttg 4920
tcagtagcca ttttttttgca gtgatttgaa gaccaaagtt gttttacagc tgtgttaccg 4980
ttaaaggttt ttttttttat atgtattaaa tcaatttatc actgtttaaa gctttgaata 5040
tctgcaatct ttgccaaggt acttttttat ttaaaaaaaa acataacttt gtaaatatta 5100
ccctgtaata ttatatatac ttaataaaac attttaagct attttgttgg gctatttcta 5160
ttgctgctac agcagaccac aagcacattt ctgaaaaatt taatttatta atgtattttt 5220
aagttgctta tattctaggt aacaatgtaa agaatgattt aaaatattaa ttatgaattt 5280
tttgagtata atacccaata agcttttaat tagagcagag ttttaattaa aagttttaaa 5340
tcagtc 5346

<210> SEQ ID NO 39
<211> LENGTH: 1247
<212> TYPE: DNA
<213> ORGANISM: Homo sapiens

<400> SEQUENCE: 39
ggacagccgg gcaggcgggg ctgggcgcgg gcggcggcgg cccggaggag aacgggcgga 60
gggcgcgggc cgaccgggcg caccgaccat ggcctccaaa tgccccaagt gcgacaagac 120
cgtgtacttc gccgagaagg tgagctccct ggggaaggac tggcacaagt tctgcctcaa 180
gtgcgagcgc tgcagcaaga cgctgacgcc cgggggccac gccgagcatg acgggaagcc 240
gttctgccac aagccgtgct acgccaccct gttcggaccc aaaggcgtga acatcggggg 300
cgcgggctcc tacatctacg agaagcccct ggcggagggg ccgcaggtca ccggccccat 360
cgaggtcccc gcggcccgag cagaggagcg gaaggcgagc ggcccccga aggggcccag 420 cagagcctcc agtgtcacca ctttcaccgg ggagcccaac acgtgcccgc gctgcagcaa 480
gaaggtgtac ttcgctgaga aggtgacgtc tctgggcaag gattggcacc ggccctgcct 540
gcgctgcgag cgctgcggga agacactgac ccccggcggg cacgcggagc acgacggcca 600
gccctactgc cacaagccct gctatggaat cctcttcgga cccaagggag tgaacaccgg 660
tgcggtgggc agctacatct atgaccggga ccccgaaggc aaggtccagc cctaggctac 720
agcggctctc atgatgtggg ctcacctgcg ccccagaccc tgcaggggcc cccctgcttg 780
gctctgctgg gagagtgctc agccgcccag tcctgcctgc aagcccaggg cgagtattgg 840
aggaggggca gccacgggca gagcaccatg cccatccccg agtctctggt gtgtctgccc 900
cctctggcat cctctgggcg tcccatgatc ccttctgtgt ctgcgtgtcc gaatccccgt 960

-continued

```
gtgaccctgt cccagcattt tcccgccgac cctgcgtgtc cccgtggcgc tgtccgctct   1020

ccctctcctg ctgcccaccc acctgccagt gttatttatg ctcccttcgt gggtgatggc   1080

cacgccctca ccatgtccct ggcagagggc ttccctccgg gatcccctgc ctggtgccca   1140

cactgcctcg caagcgctcg ccaccctcac gtggctcacc tgctgttgag ccttgtgctg   1200

tcaataaacg gtttgaggat tgcaggattg tcaaaaaaaa aaaaaaa                 1247
```

<210> SEQ ID NO 40
<211> LENGTH: 2397
<212> TYPE: DNA
<213> ORGANISM: Homo sapiens

<400> SEQUENCE: 40

```
cacgcgcccc tcctccgcat ctgagcgggg gagcggcggc ccccagctga atgggcgcga     60

gagcggcgct gggggcgggt gggggcgcgg ggtaccgggc tggcggccgg ccggcgcccc    120

ctcattagta tgcggacgaa ggcggcgggc tgcgcggagc ggcgtcccct gcagccgcgg    180

accgaggcag cggcggcacc tgccggccga gcaatgccaa gtgagtacac ctatgtgaaa    240

ctgagaagtg attgctcgag gccttccctg caatggtaca cccgagctca aagcaagatg    300

agaaggccca gcttgttatt aaaagacatc ctcaaatgta cattgcttgt gtttggagtg    360

tggatccttt atatcctcaa gttaaattat actactgaag aatgtgacat gaaaaaaatg    420

cattatgtgg accctgacca tgtaaagaga gctcagaaat atgctcagca agtcttgcag    480

aaggaatgtc gtcccaagtt tgccaagaca tcaatggcgc tgttatttga gcacaggtat    540

agcgtggact tactcccttt tgtgcagaag gcccccaaag acagtgaagc tgagtccaag    600

tacgatcctc cttttgggtt ccggaagttc tccagtaaag tccagaccct cttggaactc    660

ttgccagagc acgacctccc tgaacacttg aaagccaaga cctgtcggcg ctgtgtggtt    720

attggaagcg gaggaatact gcacggatta gaactgggcc acaccctgaa ccagttcgat    780

gttgtgataa ggttaaacag tgcaccagtt gagggatatt cagaacatgt tggaaataaa    840

actactataa ggatgactta tccagagggc gcaccactgt ctgaccttga atattattcc    900

aatgacttat ttgttgctgt tttatttaag agtgttgatt tcaactggct tcaagcaatg    960

gtaaaaaagg aaaccctgcc attctgggta cgactcttct tttggaagca ggtggcagaa   1020

aaaatcccac tgcagccaaa acatttcagg attttgaatc cagttatcat caaagagact   1080

gcctttgaca tccttcagta ctcagagcct cagtcaaggt tctggggccg agataagaac   1140

gtccccacaa tcggtgtcat tgccgttgtc ttagccacac atctgtgcga tgaagtcagt   1200

ttggcgggtt ttggatatga cctcaatcaa cccagaacac ctttgcacta cttcgacagt   1260

caatgcatgg ctgctatgaa ctttcagacc atgcataatg tgacaacgga aaccaagttc   1320

ctcttaaagc tggtcaaaga gggagtggtg aaagatctca gtggaggcat tgatcgtgaa   1380

ttttgaacac agaaaacctc agttgaaaat gcaactctaa ctctgagagc tgtttttgac   1440

agccttcttg atgtatttct ccatcctgca gatactttga agtgcagctc atgtttttaa   1500

cttttaattt aaaaacacaa aaaaaatttt agctcttccc actttttttt tcctatttat   1560

ttgaggtcag tgtttgtttt tgcacaccat tttgtaaatg aaacttaaga attgaattgg   1620

aaagacttct caaagagaat tgtatgtaac gatgttgtat tgatttttaa gaaagtaatt   1680

taatttgtaa aacttctgct cgtttacact gcacattgaa tacaggtaac taattggaag   1740

gagaggggag gtcactcttt tgatggtggc cctgaacctc attctggttc cctgctgcgc   1800

tgcttggtgt gacccacgga ggatccactc ccaggatgac gtgctccgta gctctgctgc   1860
```

tgatactggg tctgcgatgc agcggcgtga ggcctgggct ggttggagaa ggtcacaacc 1920
cttctctgtt ggtctgcctt ctgctgaaag actcgagaac caaccaggga agctgtcctg 1980
gaggtccctg gtcggagagg gacatagaat ctgtgacctc tgacaactgt gaagccaccc 2040
tgggctacag aaaccacagt cttcccagca attattacaa ttcttgaatt ccttggggat 2100
tttttactgc cctttcaaag cacttaagtg ttagatctaa cgtgttccag tgtctgtctg 2160
aggtgactta aaaaatcaga acaaaacttc tattatccag agtcatggga gagtacaccc 2220
tttccaggaa taatgttttg ggaaacactg aaatgaaatc ttcccagtat tataaattgt 2280
gtatttaaaa aaaagaaact tttctgaatg cctacctggc ggtgtatacc aggcagtgtg 2340
ccagtttaaa aagatgaaaa agaataaaaa cttttgagga acaaaaaaaa aaaaaaa 2397

<210> SEQ ID NO 41
<211> LENGTH: 2697
<212> TYPE: DNA
<213> ORGANISM: Homo sapiens

<400> SEQUENCE: 41
acttgtccgt cacgtgcggc cgcccggcct ctcggccttg ccgcgcgcct ggcggggttg 60
ggggggcggg gaccaagatc tgctgcgcct gcgttgtggg cgttctcggg gagctgctgc 120
cgtagctgcc gccgccgcta ccaccgcgtt cgggtgtaga atttggaatc cctgcgccgc 180
gttaacaatg aagcagagtt cgaacgtgcc ggctttcctc agcaagctgt ggacgcttgt 240
ggaggaaacc cacactaacg agttcatcac ctggagccag aatggccaaa gttttctggt 300
cttggatgag caacgatttg caaaagaaat tcttcccaaa tatttcaagc acaataatat 360
ggcaagcttt gtgaggcaac tgaatatgta tggtttccgt aaagtagtac atatcgactc 420
tggaattgta aagcaagaaa gagatggtcc tgtagaattt cagcatcctt acttcaaaca 480
aggacaggat gacttgttgg agaacattaa aaggaaggtt tcatcttcaa aaccagaaga 540
aaataaaatt cgtcaggaag atttaacaaa aattataagt agtgctcaga aggttcagat 600
aaaacaggaa actattgagt ccaggctttc tgaattaaaa agtgagaatg agtccctttg 660
gaaggaggtg tcagaattac gagcaaagca tgcacaacag caacaagtta ttcgaaagat 720
tgtccagttt attgttacat tggttcaaaa taaccaactt gtgagtttaa aacgtaaaag 780
gcctctactt ctaaacacta atggagccca aaagaagaac ctgtttcagc acatagtcaa 840
agaaccaact gataatcatc atcataaagt tccacacagt aggactgaag gtttaaagcc 900
aagggagagg atttcagatg acatcattat ttatgatgtt actgatgata atgcagatga 960
agaaaatatc ccagttattc cagaaactaa tgaggatgtt atatctgatc cctccaactg 1020
tagccagtac cctgatattg tcatcgttga agatgacaat gaagatgagt atgcacctgt 1080
cattcagagt ggagagcaga atgaaccagc cagagaatcc ctaagttcag gcagtgatgg 1140
cagcagccct ctcatgtcta gtgctgtcca gctaaatggc tcatccagtc tgacctcaga 1200
agatccagtg accatgatgg attccatttt gaatgataac atcaatcttt tgggaaaggt 1260
tgagctgttg gattatcttg acagtattga ctgcagttta gaggacttcc aggccatgct 1320
atcaggaaga caatttagca tagacccaga tctcctggtt gatcttttca ctagttctgt 1380
gcagatgaat cccacagatt acatcaataa tacaaaatct gagaataaag gattagaaac 1440
taccaagaac aatgtagttc agccagtttc ggaagaggga agaaaatcta aatccaaacc 1500
agataagcag cttatccagt ataccgcctt tccacttctt gcattcctcg atgggaaccc 1560

```
tgcttcttct gttgaacagg cgagtacaac agcatcatca gaagttttgt cctctgtaga   1620

taaacccata gaagttgatg agcttctgga tagcagccta gacccagaac caacccaaag   1680

taagcttgtt cgcctggagc cattgactga agctgaagct agtgaagcta cactgtttta   1740

tttatgtgaa cttgctcctg cacctctgga tagtgatatg ccacttttag atagctaaat   1800

ccccaggaag tggactttac atgtatatat tcatcaaaat gatgaactat ttattttaaa   1860

gtatcatttg gtactttttt tgtaaattgc tttgttttgt ttaatcagat actgtggaat   1920

aaaagcacct tttgcttttc tcactaacca cacactcttg cagagctttc aggtgttact   1980

cagctgcata gttacgcaga tgtaatgcac attattggcg tatctttaag ttggattcaa   2040

atggccattt ttctccaatt ttggtaaatt ggatatcttt tttttacaaa tacgaccatt   2100

aacctcagtt aaatttttgt ttgttttcct gtttgatgct gtctatttgc attgagtgta   2160

agtcatttga actaatggta taactcctaa agctttctct gctccagtta tttttattaa   2220

atatttttca cttggcttat ttttaaaact gggaacataa agtgcctgta tcttgtaaaa   2280

cttcatttgt ttcttttggt tcagagaagt tcatttatgt tcaaagacgt ttattcatgt   2340

tcaacaggaa agacaaagtg tacgtgaatg ctcgctgtct gatagggttc cagctccata   2400

tatatagaaa gatcgggggt gggatgggat ggagtgagcc ccatccagtt agttggacta   2460

gttttaaata aaggttttcc ggtttgtgtt tttttgaacc atactgttta gtaaaataaa   2520

tacaatgaat gttgagtact agtgtctgtt atgtgtcttc tttagaggtg acactcacat   2580

gaaacaattt tttcttctca taggaagcag tagctttaaa ctgtctgtgg ttcattattc   2640

tcaatatgaa tcataccaag atatttgtgc ctcatctcga aaatatattg tatattg      2697
```

```
<210> SEQ ID NO 42
<211> LENGTH: 1562
<212> TYPE: DNA
<213> ORGANISM: Homo sapiens

<400> SEQUENCE: 42

gcgggcggca ttctggcgcg gagcggagcg gcggcgggcg cagctagcgg gtcggccgcg     60

gagcggaggt gcagctcggc ttcccccggc acccctcccc ctcgggcgcc agccccaccc    120

ctccgccggc cgggccgacc ccgccgtact atcccctgcg gcgcgagccc ggggcggctc    180

caagcgcccc ccagcagacc cccatcatgg gcagccagag ctccaaggct ccccggggcg    240

acgtgaccgc cgaggaggca gcaggcgctt cccccgcgaa ggccaacggc caggagaatg    300

gccacgtgaa aagcaatgga gacttatccc ccaagggtga aggggagtcg ccccctgtga    360

acggaacaga tgaggcagcc ggggccactg gcgatgccat cgagccagca ccccctagcc    420

agggtgctga ggccaagggg gaggtccccc ccaaggagac cccccaagaag aagaagaaat    480

tctctttcaa gaagcctttc aaattgagcg gcctgtcctt caagagaaat cggaaggagg    540

gtgggggtga ttcttctgcc tcctcaccca cagaggaaga gcaggagcag gggagatcg     600

gtgcctgcag cgacgagggc actgctcagg aagggaaggc cgcagccacc cctgagagcc    660

aggaacccca ggccaagggg gcagaggcta gtgcagcctc agaagaagag gcagggcccc    720

aggctacaga gccatccact ccctcggggc cggagagtgg ccctacacca gccagcgctg    780

agcagaatga gtagctaggt aggggcaggt gggtgatctc taagctgcaa aaactgtgct    840

gtccttgtga ggtcactgcc tggacctggt gccctggctg ccttcctgtg cccagaaagg    900

aaggggctat tgcctcctcc cagccacgtt ccctttcctc ctctccctcc tgtggattct    960

cccatcagcc atctggttct cctcttaagg ccagttgaag atggtccctt acagcttccc   1020
```

aagttaggtt agtgatgtga aatgctcctg tccctggccc tacctccttc cctgtcccca 1080
cccctgcata aggcagttgt tggttttctt ccccaattct tttccaagta ggttttgttt 1140
accctactcc ccaaatccct gagccagaag tggggtgctt atactcccaa accttgagtg 1200
tccagccttc ccctgttgtt tttagtctct tgtgctgtgc ctagtggcac ctgggctggg 1260
gaggacactg ccccgtctag gtttttataa atgtcttact caagttcaaa cctccagcct 1320
gtgaatcaac tgtgtctctt ttttgacttg gtaagcaagt attaggcttt ggggtggggg 1380
gaggtctgta atgtgaaaca acttcttgtc ttttttttctc ccactgttgt aaataacttt 1440
taatggccaa accccagatt tgtacttttt ttttttttct aactgctaaa accattctct 1500
tccacctggt tttactgtaa catttggaaa aggaataaat gtcgtccctt tagtggtgct 1560
tt 1562

<210> SEQ ID NO 43
<211> LENGTH: 2000
<212> TYPE: DNA
<213> ORGANISM: Homo sapiens

<400> SEQUENCE: 43
agtcgctgag ccctggcgcc tccttaaagc cgcagctccg ccccgaccgc cccgcccgcc 60
agtccgtcct cagaccctcc caaccgccgg gtccccgccg cctcggcgga gtgttgtaga 120
gcctcgagcc tgcgaggagc gcgccgcccg ccagctccct gcgtcccgtc ccgcgtcccc 180
gcgttcccgc gtcctgcgat ccgccgccat ggccagtgag gagctggcgt gcaagctgga 240
gcgccggctg cggcgcgagg aggccgagga gagtggcccc cagctggctc ccctcggcgc 300
cccagccccg gagcccaagc ccgagcccga gcctcccgcc cgtgcgccca cggccagcgc 360
cgacgcggag ctgagcgccc agctgagccg gcggctggac atcaacgagg gcgctgcgcg 420
gccccggcgc tgcagggtct tcaaccccta cacggagttc ccggagttca gccgccgcct 480
catcaaggac ctggagagca tgttcaaact gtatgacgct gggcgggatg gcttcatcga 540
cctgatggag ctgaagctga tgatggagaa gctgggggcc ccccagaccc acctgggcct 600
gaagagcatg atcaaggagg tggatgagga cttcgatggc aagctcagct tccgggagtt 660
cctgctcatt ttccacaagg ccgcggcagg ggagctgcag gaggacagtg ggctgatggc 720
gctggcaaag ctttctgaga tcgatgtggc cctggagggt gtcaaaggtg ccaagaactt 780
ctttgaagcc aaggtccaag ccttgtcatc ggccagtaag tttgaagcag agttgaaagc 840
tgagcaagat gagcggaagc gggaggagga ggagaggcgg ctccgccagg cagccttcca 900
gaaactcaag gccaacttca atacatagtc ctgctgacct tgccctctgc ccacagctgt 960
gcctcacaga tgccccgaga agagatgact aggcatcttc atcactgctg tcggtcccct 1020
ccctgagcca gcatctccat ccaccacccc gtgccagctc ccgtgccagc cttcattcct 1080
cccagtgtcc aagcccctcc aggagggtcc tggggtgggc cagatgcctg cccacctctg 1140
tctcctgcct ctgctcctct gcccttctta tagccagaac ttgtatcttc tcagcaacct 1200
tcactttgtc cttgtccctt taccattccc catcaaagag tagtctgcta tatcaatttg 1260
tgtagatatg tctgtctttt tgggtcctca gagaaaatgc ccattttctc ggagaattct 1320
ctgcactcct ctctgcttca cattcaactt ccctgttctc atctttggta ggattctgcc 1380
agttgctttt gcatcttctg ttcctgggta atggtgggtc ttaatggagg ctgggtggac 1440
cactgcccgt ccactcttca acaggaggaa cagcatgcca ccatagtaac acacattaga 1500
gaaaggacag aggtctgctc cttcctgcca cctttctcct ggccccttag cattccccca 1560
gtccctccct cttcaccttg ctccgtctat gtcttcccag ctcagccttt tccccactct 1620
taaatactgt actacttcac tgtaagaacg aaagaatagt taggatacca atgagtaaaa 1680
gggttcctgt tcactctgac tctgtgcaaa ttgtattaca gtagaccgct gacgttccca 1740
agtgacagat ccagggcctt tcaaacatcc ccaaagtcat ggccatactc accattagcc 1800
agtttctaac atctgtttca gggtatccag ctgtagatgt tcttatcccc catacttgtg 1860
agttcttggg gttgctcaca aatactaggg gtttttgttg tatttttaac aaatatatcc 1920
taatgtcata tttattctct tttgtaactg ctgtctttac aataaagaaa tcatctgcct 1980
ttctatctta aaaaaaaaaa 2000

<210> SEQ ID NO 44
<211> LENGTH: 2733
<212> TYPE: DNA
<213> ORGANISM: Homo sapiens

<400> SEQUENCE: 44
ggcagaggag cgagtgcagc ggccagcagc acatccccgc tccacagtcg ccgcagtcgc 60
cgcagccgcc gccgccgccc cgcgcgccca accgccgcgg ccccctgccc cgccggcctg 120
ccagtgagag agcggcgagg gggcgcccgg ccggactctg agcctagtcc tctcgcgctg 180
cggccgcccg cgcctcctcg gccgcctgtc gggcatgaaa accaaattct gcaccggggg 240
cgaggcggag ccctcgccgc tcgggctgct gctgagctgc ggtagcggca gcgcggcccc 300
ggcgcccggc gtggggcagc agcgcgacgc cgccagcgac ctcgagtcca agcagctggg 360
cggccaacag ccgccgctcg cgctgccccc tccgccgccg ctgccgctgc cgctgccgct 420
gccccagccc ccgccgccgc agccgcccgc agacgagcag ccggagcccc ggacgcggcg 480
cagggcctat ctgtggtgca aggagttcct gcccggcgcc tggcggggcc tccgcgagga 540
cgagttccac atcagtgtca tcagaggcgg ccttagcaac atgctgttcc agtgctccct 600
acctgacacc acagccaccc ttggtgatga gcctcggaaa gtgctcctgc ggctgtatgg 660
agcgattttg cagatgaggt cctgtaataa agagggatcc gaacaagctc agaaagaaaa 720
tgaatttcaa ggggctgagg ccatggttct ggagagcgtt atgtttgcca ttctcgcaga 780
gaggtcactt gggccaaaac tctatggcat ctttccccaa ggccgactgg agcagttcat 840
cccgagccgg cgattagata ctgaagaatt aagtttgcca gatatttctg cagaaatcgc 900
cgagaaaatg gctacatttc atggtatgaa aatgccattc aataaggaac caaaatggct 960
ttttggcaca atggaaaagt atctaaagga agtgctgaga attaaattta ctgaggaatc 1020
cagaattaaa aagctccaca aattgctcag ttacaatctg cccttggaac tggaaaacct 1080
gagatcattg cttgaatcta ctccatctcc agttgtattt tgtcataatg actgtcaaga 1140
aggtaatatc ttgttgctgg aaggccgaga gaattctgaa aaacagaaac tgatgctcat 1200
tgatttcgaa tacagcagtt acaattacag ggattcgac attggaaatc acttctgtga 1260
gtggatgtat gattatagct atgaaaaata ccccttttttc agagcaaaca tccggaagta 1320
tcccaccaag aaacaacagc tccattttat ttccagttac ttgcctgcat tccaaaatga 1380
ctttgaaaac ctcagtactg aagaaaaatc cattataaaa gaagaaatgt tgcttgaagt 1440
taataggttt gcccttgcat ctcatttcct ctggggactg tggtccattg tacaagccaa 1500
gatttcatct attgaatttg ggtacatgga ctacgcccaa gcaaggtttg atgcctattt 1560
ccaccagaag aggaagcttg ggtgtgactt gtggggagga ctccatccac ctcatcactg 1620
gactgcatgg ggaggcagca gagcggggtc ccctctgtgc ttcgactact gctcctgtgg 1680
caggaggctt tgggtggctc actactgaac acatgtgtat gatactaaag acggtattaa 1740
aatggagcga cgtttatttc atctcttgtt tacgatttca ctaggactca gaaacgagat 1800
cgggaagcag aaatatagtg caatagtgca acatctctga atccttttaa tctagagaag 1860
gcatttcata tttgggggct aaggtttcca gtcagatgag gcaaacagca agagtaagca 1920
gtgttacttg caggtacttt ggttaatgtt gatttaaatt ttcatgaatg tgctggtgaa 1980
cactgtgacc aggcttttgt agatggcgat gtgttataga cggtgctcac tcccaaggga 2040
cagcaagtga gcagagatgt actgcaaagt cgccagtcac tgctgcaagg tggcctctgc 2100
ctggggcctc cagaagctgc tcctttaccc tcttggtccc atggctgaag ctggagcagc 2160
ggattgctct ggagcagcca aggccgccag cgtgtggagc agagctctcc cctcctgctg 2220
ggcgtgtgtg acactgatga gtttcactgt actgcatgtg acttctcccc tgcccttcct 2280
cctgatggag tgtgcagaca gccatgcgtg gccacggggg cagtgtgagg acctccctgt 2340
ctcccggctc ccctcccagg ggagccagct gcttgaccta gctctttggg cctctcctgc 2400
cctctgctct gcctggagtg tcggatcctg tgagtaggct gggcctcccc tgggcagggt 2460
tctccaaggg cccggtttcc cggcccttac ctttcctgat gcccctgaca tcatcattct 2520
tgtgggagac agcagcctgt atgtggtgtg gggcgtggat cgagtgtagc tgtgaaatcc 2580
atatatatga aatgtcctgc gggatacagt cttagctgac tttttttac tctgaactct 2640 tatttgaatt gttttttgtg catatatttc tgctaccaca gagattgtac tatacaaata 2700
aaaaaataaa aacccaaaaa aaaaaaaaaa aaa 2733

<210> SEQ ID NO 45
<211> LENGTH: 2391
<212> TYPE: DNA
<213> ORGANISM: Homo sapiens

<400> SEQUENCE: 45
aagagaggaa ggcttaaaga gccagactgc gcagccagga ctggggtgat gggcgctgtc 60
ctgccaggcc aaagaatgaa gatgtagccc cgcccccaac ctagggagga ggaccagccc 120
ggttcctgtc ctgcccccgc aacctcgccc cgattccact ccgggaacct cggcgatgct 180
gagccaagac cacttctgaa tcagggatga cttgtctagt gaacctaggg tcagagccat 240
cagttggaaa ggctgggagg agcctggaga aagagggcga ccttccttgg gatctgtgcg 300
ctccctcctt gcctccccct ccagcctccc acttggtagc accttcctga tccccttatc 360
tctaaggcgc tcagggaaat gccccgctgc gggagccttc tgggaaatgc tgccctggcc 420
acccaggaac catgagccct gcagccccgg tcccgcctga ctccgctctg gaaagtcctt 480
ttgaagaaat ggccctggtg aggggcggct ggctgtggag acagagctcc atcctccgcc 540
gctggaagcg gaactggttt gccctgtggc tggacgggac cctgggatac taccacgatg 600
agacagcgca ggacgaggag gaccgtgtgc tcatccactt caatgtccgt gacataaaga 660
tcggcccaga gtgccatgat gtgcagcccc cagagggccg gagccgagat ggcctgctga 720
ctgtgaacct acgggaaggc ggccgcctgc acctctgtgc ggagaccaag gatgatgccc 780
tagcatggaa gacagcactg ctggaggcaa actccacccc ggccccagct ggagccaccg 840
tccctcccag gagccgccgg gtttgctcca aggtcaggtg tgtgacccgc tcgtggagcc 900
cctgtaaggt tgagaggcgg atctgggtgc gcgtctacag cccgtaccaa gactactacg 960
aggtggtgcc ccccaatgca cacgaggcca cgtatgtccg cagctactac ggaccgccct 1020
acgcaggccc tggcgtgacg cacgtgatag tgcgggagga tccctgctac agcgccggcg 1080
cccctctggc catgggcatg cttgcgggag ccgccactgg ggcggcgctg ggctcgctca 1140
tgtggtcgcc ctgctggttc tgagccctgg gactcggagc actgacccct gcgcttggat 1200
tgctagactc ctcttcctcc tggaccccat cctctaccat ccaagccctg tcccactttg 1260
gccctatcct ctccattagc tccttccggg tttggaccat tccccccact ccctaccctt 1320
aatccccaca tgggaagaag ctatcatcac aggtacaaac atcgcttgaa gtcttcacat 1380
ctaccactag acacccccaa aatctgttat agacatttat ggatacattt cctctaaaca 1440
caacagggca cagcaaatac gacttcattt ggcttcgagt tccccaggcg ctgtagacac 1500
aacatgaatc gggctctctg ctctctcctt agggagctcg agtcctggtg gggagaacag 1560
gagtaaacaa ggacttgaca aagctgaaga gttatcagtc ctttgacaag gacaggtggg 1620
gcagggagca agacaggtag gctggaagaa cagttattgg caagtatgca gagccgtgaa 1680
cgtcatggca tgtccaagga attaaatggg agttcatttg ggctggggtg gaggctggga 1740
tcagaccgtg gtgggccttc aagctaagga gcttcctagg tgaaagggga gatgtgagcc 1800
ttctctggag ggaagtttca tgattgcatc tataatgaat atattgcctg ttttgtgaat 1860
actgacacat gtccatacct aaaacactcc tgagttaagt cccatccttc ccacaaacag 1920
cttcctggct ggtacccatg ataacaattg agctgaacct ggggacccct ggttggggaa 1980
caggtgagtt ctatttgaga cttccagccc tagaaagctg cctccgtcca gaaatgcctc 2040
tcacaccagg agctcggccc tctctttgta gctgtgactg tcaccctctc aggctttgtc 2100
tcatccttca ttctgaataa gatggcagtg ttctcctctg ggcctgatc cacctctaca 2160 ccagcccagg aagccccatc tgtgcctgcc ctcaggtggt ccaccagtct ccccctttgg 2220
ttcccttcca gtctcttccc cctttctatc ccaatcacca atagaaatgc taacatccct 2280
gcctggtagc cagactagcc cactaaagct cccctgtaaa tgggggctcc attagttctg 2340
ctgccgagac taataaagat ttggttggct ctagcagtaa aaaaaaaaaa a 2391

<210> SEQ ID NO 46
<211> LENGTH: 5371
<212> TYPE: DNA
<213> ORGANISM: Homo sapiens

<400> SEQUENCE: 46
tcactcactg gggagcccgg cggtggcggc acctttcgag gtagacccgc tgagctgcta 60
gcccgccggc cagcgagtga gaggtcggac agactgtgga gccgacagac tgaaggacag 120
cggcaccgcc agacggccag aaagttccgc catgagctgg ggcacggagc tgtgggatca 180
gttcgacagc ttagacaagc atacacaatg ggaattgac ttcttggaaa gatatgccaa 240
atttgttaaa gagaggatag aaattgaaca gaactatgcg aaacaattga gaaatctggt 300
taagaagtac tgccccaaac gttcatccaa agatgaagag ccacggttta cctcgtgtgt 360 agccttttt aatatcctta atgagttaaa tgactatgca ggacagcgag aagttgtagc 420
agaagaaatg gcgcacagag tgtatggtga attaatgaga tatgctcatg atctgaaaac 480
tgaaagaaaa atgcatctgc aagaaggacg aaaagctcaa caatatcttg acatgtgctg 540
gaaacagatg gataatagta aaaagaagtt tgaaagagaa tgtagagagg cagaaaaggc 600
acaacagagt tatgaaagat tggataatga tactaatgca accaaggcag atgttgaaaa 660
ggccaaacag cagttgaatc tgcgtacgca tatggccgat gaaaataaaa atgaatatgc 720

```
tgcacaatta caaaacttta atggagaaca acataaacat ttttatgtag tgattcctca    780
gatttacaag caactacaag aaatggacga acgaaggact attaaactca gtgagtgtta    840
cagaggattt gctgactcag aacgcaaagt tattcccatc atttcaaaat gtttggaagg    900
aatgattctt gcagcaaaat cagttgatga aagaagagac tctcaaatgg tggtagactc    960
cttcaaatct ggttttgaac ctccaggaga ctttccattt gaagattaca gtcaacatat   1020
atatagaacc atttctgatg ggactatcag tgcatccaaa caggagagtg ggaagatgga   1080
tgccaaaacc acagtaggaa aggccaaggg caaattgtgg ctctttggaa agaagccaaa   1140
gggcccagca ctagaagatt tcagtcatct gccaccagaa cagagacgta aaaaactaca   1200
gcagcgcatt gatgaactta acagagaact acagaaagaa tcagaccaaa aagatgcact   1260
caacaaaatg aaagatgtat atgagaagaa tccacaaatg gggggatccag ggagtttgca   1320
gcctaaatta gcagagacca tgaataacat tgaccgccta cgaatggaaa tccataagaa   1380
tgaggcttgg ctctctgaag tcgaaggcaa aacaggtggg agaggagaca gaagacatag   1440
cagtgacata aatcatcttg taacacaggg acgagaaagt cctgagggaa gttacactga   1500
tgatgcaaac caggaagtcc gtgggccacc ccagcagcat ggtcaccaca atgagtttga   1560
tgatgaattt gaggatgatg atcccttgcc tgctattgga cactgcaaag ctatctaccc   1620
ttttgatgga cataatgaag gtactctagc aatgaaagaa ggtgaagttc tctacattat   1680
agaggaggac aaaggtgacg gatggacaag agctcggaga cagaacggtg aagaaggcta   1740
cgttcccacg tcatacatag atgtaactct agagaaaaac agtaaaggtg cagtaactta   1800
tatctaaact aaccaggcac ctttgtgcca tgtgtgacat aggaagagta acataaaatg   1860
aaaacacatt caacaggttg aaaaaaataa ggaaacttaa agggcatcca agattaattg   1920
ttcactatgt gagctgagtg taggcttgat cttgtgaata ttaccacaag aaacattttg   1980
tggcacttta ctgtttgagt aacgttggtg tgaagcttaa ttgatgcctt ttgctttatg   2040
tcccgcttaa gtctgtgtga aggatttgtg tttttctgcc ttacaaatag aatttgattt   2100
attgggcagg aattcatgga tagtaatgct ctctgccccc tttacttcag aaaacacagt   2160
gactttagtg aatttgaata gtgaaactgc tctgaaatgc tatggaaagc cgactcccca   2220
aagagtggtt tcttctagaa gtttgaattt gtagctacag tttccaagaa gaaaaatagt   2280
agttggataa tttagtaaaa taataacatc attttcattt tcttacctat tcttaacttt   2340
ggtttcctaa aggaagaaaa tgagcaggta gcacataatc tatttaagta gatttaaaga   2400
gagtttcaaa ataaatctcc tggtctagct cttaggtgaa taaaatagat tttgtttgag   2460
acctcaaaat attttgaggt tagctggtaa ttttcaataa tttacaagct tccttccaaa   2520
ctaatctcat actttgtat gtttcatctt gaaaatatct tttgggaaat accactttag   2580
tgattattta gcatttagca gttacacata ggaaaataca cagttacata gaaaaataca   2640
catttgaaga tagaggaaac cttgaatgga ggggaagtgt tgacaaattt taatttttaa   2700
aggagaaact ttttgactat ctgggttaga ggaagatatg tgtaccgcct ttagggcatt   2760
ttgttatttc cgctgaatca ttagttatta ggatagataa atttttccaa ttagtttcag   2820
caagcgttgt tggaaacact gtgcagtcaa ggattgtgca gtgctggttg tgtgaccaca   2880
ccctgagtca gtggtgtggg gaagtaaagt gtgaagaagc agtaagattg gtttttaatt   2940
ttgcccatgt tttaaatttt cctggtgttt tcggtagctg actataaaat gatagagaca   3000
tttgggacag gcactttaaa ctgaacaccc cttttggttt taccaaaggt cttcagtaat   3060
```

-continued

```
tgttcttttc tttttcctcc tggactgcag gttcctgaag agggtttctg aggaaatggg   3120
caagatgttg aaggaggtta catgcagctg cttttggggg agggtattag agttgtcagg   3180
ctcaaagaga gtgagagaag caagttgcat gagtgcatgc agacatgatt tttttttac    3240
taacttcatt agcatttcca tacattgttt ttaaaaatca taataccaac ccttaagttc   3300
ctagttcaca gttattccca caaaagaaaa agccaacaat agtgtaccat ttttctattt   3360
attttattgc tgtctaatca ataaagaatg cagagctgtc aaaaaatgtg tcttacatta   3420
gctgtcccaa caggattgtc ttccctccca gctctgtttt aattggcttt tagacccact   3480
atctgtcaga tccttgccat ctgtcagtgt ctgcctgcgc cacctccgtg cttgcttaac   3540
atcctgttgc atgtctagcg tgattgagct agatttttca ggcatgtctt tagattccct   3600
tgttcttgtc aaagccttgt tttgttttac atttgtagtg caaatcactt tgtcaaacat   3660
ctccagcact aatgtttcca tcttagtatt tgtgcacact gctataactt ccccactgca   3720
aacattccag ttttggcatt acgaagaagt agctgtgaac ctgaagtatt tatgataaga   3780
aaaagaaaac atctctgctg tagcctacag cccagttgaa agaactcttt gaaacgtgat   3840
acatcttcag cacctcagtc tgggaagaat ctagtcagca ctgaaatcct ggcataataa   3900
acacagaaga tattcaccac ctcaagacaa aggactattg tcaaaagtca gctgcttcca   3960
ttcaaatgct gccttaaact tgagtgccta aatctgttga ttgccaacac taccactaca   4020
gtatcccaca aagggcttta tgtgtcagct cagtgcgacc tgctttaact ctgcagcacc   4080
gctgcagctg ccgatgtagc ctcggtaggt ggctattaga gctctaccat atacagtggt   4140
gcatcttcaa atttatgcat caaactaaag acatgtccaa gtccatttta atttcctcag   4200
tggttttatg agaagtttta tgggcctccc ccaattgtct ttttattttg ggttatgacg   4260
atcatgtttg ataattacaa tgatagtctc tttccacgtg atgcttttgt ttgaacctga   4320
taaaatttag tgaaactttg taatgatcta tgtgcacttt tacttgtaaa atggaatttc   4380
tgtatgttta tacttgtaaa tatgattgtt gttagtgctc ctgttgctca tggtgtcctg   4440
cctcgcattt gtgattctgt taatgacatg tatcttaact aatttcttag tggtgttgta   4500
atagggagat ggggcaggtg gggggttatt tgtaccactg aatcttcatt aatttggttc   4560
tttactgttt tgaggggaga aagaacgtga aatggtttgt gtattattga attttaagca   4620
atattttaga agctgtgtga ctgctttaat aactttttcc cagtgttatt tgaatcatac   4680
tacccgttat actaaagctg aatgacaatt gtgtgaaagt tactgccttc ataagatcaa   4740
gtcaccactg ttacacagct gacatatagt gtattacctt tgcagctagt aaactataaa   4800
gtttagatat tgaatctcgt tacagggtta tttatataat gtgacattat tcagtactga   4860
cagactacat gaagtagttt taaaatctag tgctattttt attttaaagg ttagcaatga   4920
ggaggaaatg tgatctggct gtgtttgtct tctgtacaaa gcctgaagtg cttatggttt   4980
tttggctaac agccacagag ggcaaagttt aagactttct tgtaaggact aactgttctt   5040
ttcaagctac tgtttgtttt tctaaaagca ggatttgctt ccgtaggagg caagttcctt   5100
gatgtggaat agtgcaacct gtatatgggt tattataata ggaaagacat ttgtacttgc   5160
acagtttaaa tcattcttaa attttgaaca tgtgaattgt cccaaaaaat ctttaatttt   5220
ttggtaattt ttactctttt tgtgcacatg ttgatttctt aatggtaaat ccttcattta   5280
aagatagtgt tctctgttga gaatatttac atggaataaa acaatctttt catggcctgt   5340
taaaaaaaaa aaaaaaaaaa aaaaaaaaaa a                                  5371
```

<210> SEQ ID NO 47
<211> LENGTH: 2406
<212> TYPE: DNA
<213> ORGANISM: Homo sapiens

<400> SEQUENCE: 47
ctagtcccga ttatggttat tacagtttga tgaaatgtgg ctgagatcat tggcactgtg 60
gagattaaga aatgtgaggt cagagtgttg ggtaaattgt tcctgcgagt gttaaggttg 120
tcaggataat ggtgggaatg gggtgaagat gacaactcag caatgacaca agaagagagt 180
gacacagaaa gattcagtag ctgagaactt gagcgtagat atgttgtggg caggagggaa 240
atgatttgga tggaagtagc caagtaagtg agaaaggaaa gactttccaa caaaacttgg 300
cttagctcac tcagatccct gagctgcaaa cttcttctat acctttctta ccttttccag 360
tgctgctgac ttcaccccac ttgcagggca tttgtgcaga tggttgtttg ttgaggagga 420
atgtgcttaa tgttttagga accagttaca ttcaaggatg cctctgtggc cttcaccgag 480
gaggagtgag gtcacctgga ctctgctccc aggaagctgt gcggagctgt gatgctgggc 540
aactacagaa acttggtctt ggagacttga atgaaaattc tgtggagaat cttcagcaga 600
aaacacttca ggatctgtta catgagcttt cctcctggct agttttggaa ggcatggcca 660
gtacaattac tggaagtcag gattgtattg tgaatcatcg aggggaagtg gatggggagc 720
ctgaactaga tatttcccct tgtcaacagt ggggagaagc atcttctcct atttccagaa 780
acagggacag tgtgatgact cttcaaagtg gttgtttcga aaacattgaa agtgaaacat 840
atttgccttt gaaagtctca agccaaatag acacacaaga ctcttcagtg aagttctgta 900
agaatgagcc tcaggatcat caggaaagca gacgtctctt tgtaatggaa gaaagcactg 960
agagaaaagt gataaagggg gaaagttgtt cagagaacct tcaagttaaa ctggtgtctg 1020
atggacaaga actggcctcg ccattgttaa atggtgaggc aacttgccag aatggccagt 1080
taaaagaatc tttggatccc attgactgta actgcaaaga cattcatgga tggaaatcac 1140
aggtggtcag ttgtagtcag cagagagctc atacagagga gaaaccctgt gaccataata 1200
actgtgggaa aatacttaac accagcccag atggtcatcc atatgagaaa atccacactg 1260
cagagaaaca atacgaatgt agtcagtgtg gtaagaactt cagtcaaagc tcagagctac 1320
tacttcatca gagagaccac acagaagaaa aaccctacaa atgtgagcaa tgtgggaagg 1380
gcttcacaag gagctcgagt ctgcttatcc atcaggcagt ccacacagat gagaagcctt 1440
ataagtgtga caagtgtggg aagggcttca ccaggagctc aagtctgctc atccatcatg 1500
ccgtccatac aggcgaaaaa ccttataaat gtgacaagtg tgggaagggc tttagtcaga 1560
gctccaaact gcacatccac cagcgagtcc acactggaga gaagccctat gagtgtgagg 1620
agtgtggtat gagcttcagt cagcgctcaa acctgcacat ccaccagcga gtacacacag 1680
gagagaggcc ctacaagtgt ggtgagtgtg ggaagggctt cagtcagagc tcgaaccttc 1740
acattcaccg gtgcatccac acaggagaga agccttacca atgctatgag tgtgggaagg 1800
gtttcagcca gagctcggat cttcgcatcc atctcagagt ccacactgga gagaagccct 1860
atcactgtgg caagtgtggg aagggattta gccagagttc caaactcctc atccaccaga 1920
gagtacatac tggagagaag ccctatgagt gcagcaagtg tgggaagggc ttcagccaga 1980
gctccaacct tcacatccac cagcgggttc acaagaaaga tcctcgctaa ctgacattag 2040
cccattcagg tcttcacagc gctcatactg taaaaactgt taaatattta gtatcactct 2100
tactttatat tctacaaagg agagagatgt aagggttatt tagatatgtt ccctcactga 2160

```
aaaatcactc attcaaaata tttaagtatc aagcactttg ttatgctgta caatgaatgg   2220

attgttcttg tttctcagat gggtagagta aaagtgtctg tactttacaa ttcaactaca   2280

tgttctaccc agcattttaa cggcaagaac tttatattta ttctcaagca gggcatgttt   2340

ccctttgttc acattctctg agaaattgaa actctggttt ctcttcaaaa aaaaaaaaaa   2400

aaaaaa                                                              2406


<210> SEQ ID NO 48
<211> LENGTH: 6647
<212> TYPE: DNA
<213> ORGANISM: Homo sapiens

<400> SEQUENCE: 48

gggaatcttt ttcgggctcc cgggggcgga gggaagggag cgcgcgtgcg cgcgcccggc     60

cggccgtcgc cgcggtgacc gtcctcggag tccgtcggct cgcgccccgc ccccgtcgcc    120

ccctcccctg tcgcgcgctg gggctgtttc tcgctccttc cgagttaccg ccgccgtcgc    180

cgccgctcct cctctcccgg tcctgggttt ccttggcgct gcggccgccg ctccctctgc    240

gacctgtatg aggaggagga ggaggaggat gtgaagatgg cggagctgca gatgctgctg    300

gaagaggaaa tcccgggggg ccgccgggcc ctcttcgaca gctacacaaa tctggaacgg    360

gtggccgatt actgcgagaa caactacata cagtcagcag ataagcagag agccctagaa    420

gaaaccaaag cctacaccac ccaatcctta gcaagtgttg cctatctgat aaacaccttg    480

gccaacaatg tcctgcagat gctggatatc caggcatccc agctacgaag gatggaatct    540

tcaatcaatc atatttcaca aacagttgat attcataaag agaaagttgc aagaagagaa    600

attggtattt tgactaccaa taaaaacact tcaaggacac ataagattat tgctccagcc    660

aaccttgaac gaccagttcg ttatattaga aaacctattg actatacaat tctagatgat    720

attggacatg gagtaaagtg gttgcttaga tttaaggtga gtacccagaa catgaagatg    780

ggtgggctgc cgcgtacaac acctccaact cagaagcccc ctagtccccc tatgtcaggg    840

aaagggacac ttgggcggca ctccccctat cgcacactgg agccagtgcg tcctccagtg    900

gtaccaaatg attacgtacc tagcccaacc cgtaatatgg ctccctcgca gcagagccct    960

gtgaggacag cttctgtgaa tcaaagaaat cgaacttaca gcagcagtgg gagtagtgga   1020

gggagccacc caagtagtcg gagcagcagt cgagagaaca gtggaagtgg tagtgtgggg   1080

gttcctattg ctgttcctac tccatctcct cccagtgtct ttccagcccc tgctggctct   1140

gctggcactc ctcccccttcc tgctacttct gcatctgccc ctgctcctct tgttcctgct   1200

actgtccctt cctccactgc cccagacgct gctgctgggg gtgcccagac ccttgctgat   1260

ggcttcactt ctccaactcc ccctgttgtt tcttccactc cccctacagg tcatcctgta   1320

cagttctaca gcatgaatag gcctgcctct cgccatactc ccccaacaat agggggctcg   1380

ttgccctata gacgccctcc ttccattact tcacaaacaa gccttcagaa tcagatgaat   1440

ggaggacctt tttatagcca gaatccagtt tcagatacac cacctccacc gccacctgtg   1500

gaagaaccag tctttgatga gtctcccccca cctcctcctc ctccagaaga ttacgaagag   1560

gaggaagctg ctgtggttga gtatagtgat ccttatgctg aagaggaccc accgtgggct   1620

ccacgttctt acttggaaaa ggttgtggca atttatgact atacaaaaga caaggaagat   1680

gagctgtcct ttcaggaagg agccattatt tatgtcatca agaagaatga cgatggttgg   1740

tatgagggag ttatgaatgg agtgactggg ctttttcctg ggaattacgt tgagtctatc   1800

atgcattatt ctgagtaaag ctcagcaggg ctgtgcttgc ctcacaggaa tagtcaggtc   1860
```

-continued ttcccagatt atctgaaggc cctggggatt ccactccagt aaagtagaat gaaggataca 1920
aatgataaaa attacacttt ttttttggt ttattcccca gtattaaaaa caaagcaagc 1980
tgagtctgaa caaatggatc tttctgccat catttgtaca atgctgagct gtctggattg 2040
aaataaaatg accattttta tgtatgtcaa aggtataaca gcataactgt gtagccaaaa 2100
caaaatcaga ttaagactga ttcagaaaaa tctgggatct ttctcaggaa tactgtatac 2160
ccttgggatt tctcctcctg cagaatctgt ggcattggat gttcttcatt gcctgtgcta 2220
aggggttaac ctcatggccc agtgggtacc ctagcccctt cttttcttcc acttgtatga 2280
agaggaggga accaacattt aaataccaca cttaaccatt tttacaatta tttcagatgg 2340 ctttttttcct ctgtgacact gtaaattctg cattctctca gcacttgagt gcaccaaacg 2400
agtgaatgct gaactcactt gcatcccttc atgtttctgt ttgtggatta taaggatgat 2460
gaaatgtgaa agtctcccaa cactctgagg gtggtgaacg attgccaccc gtttgatttt 2520
aatgtgctgc tgcatgagac tgcattgttg ctaatggcca gtgtacccag atgtgaagtg 2580
tggtaggctg gttcatatgt ggaggtgggt gtgtgaagct agacacgaag gtccctaagg 2640
ttctgaagag acttgaactg tggaaatgct cttagcaggc atcccgaacc cctgcttcgg 2700
tgctgttttg aggagtagga tcttggagtt cagaccaact atgactatca tttccttcac 2760
tatctagaaa aacgctattc tactttggaa gagaatagta gttattttca agtctcctga 2820
cagtcactgg gagtacaagg tttgctaatg tgctctctgg acgttattaa tggccagtat 2880
tagttgctgc tgtattactg actcgcttag ctgtagaaag ggtaatactc tcctgatttt 2940
gtatgattgg actcttaagt agctgctgtt agtcagaatt aaaacccatc tcagactaag 3000
aatataatga ataagattaa taggccaaaa tatgtatcta atcacattga taaaaattaa 3060
tataactgac acaataaaac acatttcccc catctgtaca ataaatacag cttcaaattc 3120
agtggagtct gtagggcaga taactttaat catcactact gtagtcagta taagaaatgc 3180
tgaaaaaaat ccaggagggc ttgtctcttt gtgggtggtc actgtgatgt tgggccagct 3240
cctgttcagg tccagagctg ctaacgtggg ttctactcag tcccagtgac ttggccagaa 3300
tagagctttg ccaggtaact gccctgtgct aggtgaaagg ggaaaagcag tagctggata 3360
tatttcaaat gaggttttga acaagttcag aaagtggaac ttgattgaaa agtgaacaag 3420
tgtagtagtg tgtgagaaaa ttcagatggt gtcggatgca gaagttaata ttccacttaa 3480
tgttatctga gcattaaaaa tcatcagcat ttaactgaga ccccactata gagtttcctt 3540
atcaagactt tttggtttta aagttgtttt taatgcattg caagttacaa tagctatttt 3600
gcttttagat ttttcccagc actttgtatt tattagcttt cattaacttg cctccagtat 3660
acattccact tcgtgctttt cttaggtcat ttctacatcc cttattcctt gttttcctgc 3720
agtgtaatgg ccctgaatgt cctctgagcc ttcagctcca ttatggaccc aaactagact 3780
atacttggat aagttaagct cttcttcgtg tactggtcta taattagaaa aactgtttta 3840
aattagatgt tcccattatt tatttaaaca gctttttgct gagaaagctt agtggattaa 3900
tgaggcagag ggtgttttga aatccaataa atagttccca caggctgggt gtggtggctt 3960
atgcctgtaa tcccagcact ttcggaggcc gaggtgggtg gatcatgagg tcaataaatt 4020
gagaccatcc tggccaacat ggtgaaaccc catctctact aaaaacacaa aaattagctg 4080
ggcgtggtgg cgcacacctg tagtcccagc tacttgggag gctgaggcag gagaatcact 4140
ggaacctggg aggcagaggt tgcagtgagc cgagattgtg ccactgcact ccagcctggt 4200

-continued

```
gacagagcga gactccatca aaaaaaaaaa aaaaaagttc ccacagctca ccactacaga   4260
agcagggaag acaactatgc agaaaacaga gttagtggcg gtcagcagga atgcagctgg   4320
tcttttggac ccctacggga tgggggcagt gcagaagaca ctggtgaagt cctttatact   4380
gaagacctgt ggttgggagc aggggtagtc catgggtctg ctgatttttt ttccctattt   4440
agtactaatg tgtgtgtgat ctttgtttta caaacagtac cttttgggtt ttctgcatat   4500
tttataattt ttgtacagtt ttgaattcta tagattgtct tggaaggata ctgtgtgatg   4560
ggtcaggcac acagtaattg gagactttta atgtatgtaa tatttcatag attgcatgct   4620
attaatcatc tgtgagggta gtatttttttg ttttattgta agtttccctc tttttttata   4680
aattaaaaga tggttggtat taggaatttc aaatgaatgc agaaaatctt acatgctgtg   4740
tactattaat attataacag acgatccaag tccaaaatct gaccaataaa gcaaccattt   4800
tatcaagata gagggattct aatgggagag ggattcttc cctcctgaag tttgtgtgtc   4860
cagtcccctt aaaaaaaatg aatagttgtc ttttcttgtc atattaatac tcgaaagtcc   4920
atggtggtat taatgaaagt acactttatt gttgcctttg aacttacggc caaggcaata   4980
aatcagaaac aaaaatagtg ccaatgtgtc aaaatcgaca tctgagagat tcagcctccc   5040
atttggaata aatatgaatc ttctaagcta tcttgtttaa tattttccat catttagcta   5100
cttcctatct ccctcagagg cgcctgctgt tcccatttta gagttgacag tggcctgcta   5160
attttgctat gttcctaaaa gttactgggt gtgagacatt ttcatcccct ccttttcct   5220
actgctggtg tttattatcc agctagacaa tattttatgc atatttaccg tgatgtctgg   5280
accgtacctg tgctccttgg cagtttatgt tgaagataac taaagatttt tctctttggg   5340
aggcatcaaa atgatggtag tttgctttta tctttttatg ttcattttct tttagtaggt   5400
gacctttctg cattaagaac tgtttttatc ttttactacc ttttcttttc tcctttgtgg   5460
agacagcatg acatgtcctg aaggtcacct ttgcctttga aaaaggtttg atggaggaat   5520
tcacaggtga ctgacaagtc tttgaaaaga atgggatctg ctcacttctg gtctttttgg   5580
ccgggaactc ctgattggtg ttaaggtggt aatttccccc atataagatt tagaatcact   5640
gagtttgagc tagatgaaat ttttaaaatt tctggttgtc tcattagact gatgaggtga   5700
gttttcttct tcatatgaac agctagttaa taacagcaga gttctcactc agtgctcagt   5760
acttaatttt ccactgcacc acaactgtct taactaaatg tgctgtattt ttctttaaaa   5820
gttaagagtt ctatttggtg ttttcaggaa tatacgtgaa aagacatgcc atgttttggt   5880
aaataccatc agagttgtgt aaaggcgtgt actaagtgca atcttaattt gtggaaataa   5940
tcttcattta cccctcctaa aactacactc agtataaaca ctttcccata aggtgtgtgc   6000
agtaaaaatg ttatattact ccaacactgg caggagcaca gcacagcagc cttattggag   6060
agagccttat aaaagtgatt aaatggaggc attgagctca ttacctttaa gtttactttg   6120
tgctgacctt tgttcctgtt ttgagaatct catataatta ttaaaaaaaa aaaacaatta   6180
aaacgaaacg gcggggccta gctgtgtata aatgatcctt gctgaatatc ttaaggtttt   6240
ttgtaagaaa aaagaaaaac caacaaaaaa agcttatttt cacattaaaa tgaaacctct   6300
tttgcaactt aagaattcta tggaaaagca gtttttatca tattttgtgt ccatgcacca   6360
tttttcttaa aatggcttac aaaaaagaat gtaaacaatt tgtgatctgg ccagttgtac   6420
ttttagctcc cagagggaga gttggtggta ttatgagttg agtaaaaacc atccagggga   6480
acttgaggga gcagtctgtt gccagtaatg ttccttgtgt gccattaaac cacctccaga   6540
tgagtggagg aacatcactt tttaattttt taattgtatt tggaattgtt gccgtgtact   6600
```

aagaacttga cctaaataaa atcccacaaa gtatattcaa aaaaaaa 6647

<210> SEQ ID NO 49
<211> LENGTH: 1072
<212> TYPE: DNA
<213> ORGANISM: Homo sapiens

<400> SEQUENCE: 49
gcgcgctgga aggacactga gtcaccaacc accgccatgg gccggaagcc accgccctcg 60
cgtcaactgc aatctagagc gcggcgcatc ccgtgagccc gcggggaact acgactcccg 120
gcatgctccg cggccaccgg aattaaccct tcagggctgg gggccgcgct atgccccgcc 180
ccctccccag ccccagacac ggaccccgca ggccaactgg ctccctgccc ctgcccccgc 240
cccttgacat cccagactcc ctggctattt aaacagagat gggtgccccc atccgcacac 300
tgtcctttgg ccaccggaca tcatgcctcc caagaaggat gttcccgtga agaaaccagc 360
agggccctcc atctccaaac ctgctgctaa gccagcagca gcaggggctc ctccagccaa 420
gaccaaagct gagccagctg tcccccaggc ccctcagaaa acccaggagc ctccagtcga 480
tctctccaaa gtggtgatcg agtttaacaa ggaccagctg gaggagttca aggaggcctt 540
cgagctgttt gaccgagtgg gggatggcaa gatcctgtac agccagtgtg gggacgtgat 600
gagggccctg ggccagaacc ccaccaacgc cgaggtgctc aaggtcctgg ggaaccccaa 660
gagtgatgag ctgaagtcgc ggcgtgtgga ctttgagact ttcctgccca tgctccaggc 720
agtggccaag aaccgaggcc aaggcacata tgaggactac ttggaggggt ttcgtgtgtt 780
tgacaaggag gggaacggca aagtcatggg agcagagctc agacatgttc tcaccaccct 840
tggagagaag atgactgagg aggaggtgga gaccgttctg gcaggacacg aggacagcaa 900
cggctgcatc aactacgagg ccttcttgaa acacatccta agcgtctgag tgctgcagat 960
ccagtggggt ccggacactg ggccccgcag gcgaaagcac gttccagcca ccaggaggcc 1020
acctattgtt tcaaaataaa gactgggttc ctctcttggt ttcaaaaaaa aa 1072

<210> SEQ ID NO 50
<211> LENGTH: 4997
<212> TYPE: DNA
<213> ORGANISM: Homo sapiens

<400> SEQUENCE: 50
agactctcgg tctgtccgct gggggcgcgc gcggtgtgtg gcaggcggca gcggcgctgg 60
cggccgagtg cgcttgtcac gcgtggcggt gcgtggttgc taggggcgcc tgaggctgcc 120
gggtagccca gcaggccgag ggaggaagta gcgtggagcc ggtgccgagc cggggcgaag 180
ctggatcccc tagatagact gtcttcaagc tcactgatat tttcctctgc ttgatccatt 240
gtgctgttga gagcctctag taaatttttc agactgacag acttcaagga tgcagctgct 300
actaccggag gtgtgtggca ccttacctca gcaaggccat gagaccgtgt ggccatgatg 360
tgggcccctc atggcctcag caggaacaca gcactatagt attggcctcc gccagaaaaa 420
cagcttcaag cagagtggtc cctcaggcac agtacctgcc acgccacctg agaaaccctc 480
ggagggcaga gtctggcctc aggcccatca gcaagtgaag ccaatctgga agctggaaaa 540
gaagcaagtg gagacactgt cagcagggtt gggcccaggc ctcttgggcg tcccacccca 600
gccagcatat ttcttttgcc ccagcacttt atgtagctct gggaccacgg ctgtcattgc 660
aggccacagc agttcctgtt acctacactc tctcccggac ttgttcaaca gcaccctgct 720

-continued

```
ataccgccgc tccagctata ggcaaaaacc gtaccagcaa ctggagtctt tctgcttgcg    780
ttcgagcccg tcagaaaaaa gcccttttc tctccctcaa aagagcctcc ctgtcagtct    840
cactgccaac aaggccactt cttccatggt cttctccatg gcccagccca tggcctcctc    900
atccacagaa ccatacctct gcttggcagc ggctggggaa aacccttcag ggaagagcct    960
ggcctctgcc atctcaggga agatcccatc tccactctct tcctcctata agcccatgct   1020
gaataataat tccttcatgt ggccaaatag cacgccagtg cctttattgc agaccacaca   1080
gggcctgaag ccagtatcgc cacccaagat ccagcctgtc tcctggcatc attcaggggg   1140
tactggagac tgtgcaccgc agcctgttga ccataaggtg cccaaaagca ttggcactgt   1200
cccagctgat gccagtgccc atatcgcctt gtctaccgct agctcccacg acacatccac   1260
caccagtgtt gcctcttcct ggtataaccg gaataactta gccatgaggg cagagccact   1320
ttcctgtgct ctggatgaca gctctgattc ccaggatcca actaaggaga ttcggttcac   1380
tgaggccgtg aggaaattga ccgcaagagg ctttgagaag atgccgaggc aaggctgcca   1440
gcttgaacag tctagtttcc tgaaccccag cttccagtgg aatgtcctca acaggagcag   1500
gcggtggaaa cctcctgcgg taaatcagca gtttcctcag gaggatgctg gatcggtcag   1560
gcgggtcctc cctggtgcct cagatacctt ggggttggac aatacagtct tctgtaccaa   1620
gcgtatcagc attcacctcc ttgcctcaca tgccagtggg ctcaatcaca accctgcctg   1680
tgaatctgta attgactcct cagcatttgg agaaggcaaa gctccaggtc cccttttcc   1740
tcaaactctt ggcatagcca acgtggccac ccgcctctct tccatccagc tgggccagtc   1800
tgagaaggag agacctgagg aggccaggga gctggactca tctgataggg atattagttc   1860
agctactgac ctccagccag atcaggctga gactgaagat acagaagaag aactagtaga   1920
tggtttggaa gactgttgta gccgtgatga gaatgaagag gaggagggag actcagagtg   1980
ctcctcatta agtgctgtct cccccagcga atcggtggcc atgatctcta gaagctgtat   2040
ggaaattctg accaaacccc tttccaatca tgagaaagtt gtccgaccag ccctcatcta   2100
cagtctcttt cccaacgttc cccctaccat ctattttggc actcgggatg agagagtgga   2160
gaaacttccc tgggaacaga ggaagttgct ccgatggaag atgagcacag tgacccccaa   2220
cattgtcaag cagaccattg gacggtccca cttcaaaatc agcaaaagaa acgatgactg   2280
gctgggctgc tggggtcacc acatgaagtc tcctagtttc cgatccattc gagagcatca   2340
gaagctaaac catttcccag gctcattcca gattgggagg aaggaccggc tatggcggaa   2400
cctgtcacgt atgcagagcc gctttggcaa gaaggagttc agtttcttcc cccagtcctt   2460
tatcctgccc caggacgcca agctcctgcg caaagcgtgg gagagcagca gccgccaaaa   2520
gtggattgtg aagccaccag catcagctcg aggcattggc atccaggtta ttcacaagtg   2580
gagtcagctc cccaagcgaa ggcccctcct ggtacagagg tatctacaca aaccctacct   2640
catcagcggc agcaagtttg acctgcggat ctatgtttat gtcacttcct acgatcctct   2700
gcggatttac ctcttttcag atggactggt ccgctttgcc agttgcaagt attcgccttc   2760
catgaagagc cttggcaata agttcatgca cctgaccaac tacagtgtca ataaaaagaa   2820
tgccgagtac caggccaatg cagatgaaat ggcttgccag ggccacaaat gggcactgaa   2880
ggctttgtgg aactacctga gccagaaggg agtcaatagc gacgccatct gggagaagat   2940
aaaggatgtt gttgtcaaaa ctatcatctc gtcagagccc tatgtgacca gcctgctcaa   3000
gatgtatgtg cgacggccct atagctgcca tgaactcttt ggttttgaca tcatgctaga   3060
cgaaaacctc aagccctggg tcctggaagt caacatttcc ccaagcctcc actccagctc   3120
```

tccactggat atcagcatca aaggccagat gattcgtgac cttctgaatc tggcaggttt 3180
tgtcctgccc aatgcagagg atatcatttc cagccccagc agctgcagca gctccaccac 3240
cagcctgccc acctcccctg gggacaaatg tcgaatggct ccagagcatg tcactgcaca 3300
gaagatgaag aaagcctatt atctgaccca gaaaattcct gatcaggact tctatgcatc 3360
tgtgctggat gtcctgacac cagatgatgt tcggattctg gttgagatgg aagatgagtt 3420
ttctcgccgt ggtcagtttg aacgaatttt tccttctcat atctcctctc gctatctccg 3480 ctttttgag cagccacgat atttcaacat tctcaccacc caatgggaac agaaatacca 3540
tggcaacaag cttaaaggag tagatctgct ccggagttgg tgctacaaag ggttccacat 3600
gggagttgtc tctgattctg ctccagtgtg gtctctcccg acatcacttc tgactatctc 3660
aaaggatgac gtgatactca atgccttcag caaatcagag actagcaagc tgggaaaaca 3720
aagctcctgt gaggttagcc tactactctc tgaagacggg accacgccca aatccaagaa 3780
gactcaagct ggcctttccc cttatcccca gaaacccagt tcctcaaagg acagtgagga 3840
caccagcaaa gagcccagcc tttctaccca gacgttacct gtgatcaagt gctctgggca 3900
gacttcaaga ctttctgctt cctccacttt ccagtcaatc agtgactccc tcctggctgt 3960
gagcccataa ctggcctctc tccaaaagcc tctgcccagg agcatgggca tcagctacct 4020
cacgggaacc agcctgctgt tcagaccagt ctgacccct accccttca ccctgtccct 4080 cctcagagta tttttgaag tggttgcatt atagagatgg gtatttgtag ggccggaggg 4140
atggtagtga tggggagaag gtgaggaagg gtcaccctct gtcacctgtc tgcctggctg 4200
gcacctcata tctcagcaga gaagccagtg gtggccacgc agccttataa agcaggtttt 4260
ggtttctacc ttaagtgagc catgtgtggt ttgtctgggg gccctggtgt ggttgctgag 4320
ttgtagctca agaggagaaa acatacagaa catatttgga ccggaaatcc tttgttctga 4380
atttgagggg gtcttctgag gtccttactt ccttaggtct ttcctcaccc ctctcccacc 4440
gctgtcctga ggagaaaccc ttgaacttcc tcagtagaca ggcggagagg ccacaacatg 4500
ccgaacccat ttcctgtcat cctagtcttg ggtcttcacc gcctccttcc aaatacccac 4560
cctgccagca gccctaggtc ttcctgttct gaccccccat cactgctcgt tcagccttct 4620
agatgtctct ctcgtggaca tctgttcttt agctgttggc tttctctgag gtgtgagagg 4680
gtctatgaac tttgtgaatt tcccatggcc ccagtgaagg agcccagata atcccagtag 4740
ctgttacctg tctccatgta tcaaaggaca cagtccaggg ggagggtgga aggagatgtg 4800
gtttctctat agtgcaacaa acatggtttc tcaatgttct gctgtgcagc aagcagggtc 4860
tggcggcttg gtaggtgggt ttcaggagca gtcactattg taggatgggc ttccaatcaa 4920
acctcagact aaactcttgt actgaactga ttctacctcc ctcctctaga ctcagtaaac 4980
agtgactatt caataaa 4997

<210> SEQ ID NO 51
<211> LENGTH: 4246
<212> TYPE: DNA
<213> ORGANISM: Homo sapiens

<400> SEQUENCE: 51
attgaacagt ccagatatac tgatttccag cccatatttc ctgcttttaa gctcctttgg 60
tcttatttcc ctcttctttc tgaaaagtta taaaatgaat gaagggcaga atgtttcttg 120
cccaaccatg attcaggagg cagctcagcc acagaacagg caagtgtagc attgcctgga 180

-continued

```
ggaaaaggac ttgtagaggc aggtcccaga tggatccacc ccagactttt caaagaagac    240
acctccttca tcttgtgttc taaaaccttg caagttcagg aagaaaccat ctgcatccat    300
attgaaaacc tgacacaatg tatgcagcag gctcagtgtg agtgaactgg aggcttctct    360
acaacatgac ccaaaggagc attgcaggtc ctatttgcaa cctgaagttt gtgactctcc    420
tggttgcctt aagttcagaa ctcccattcc tgggagctgg agtacagctt caagacaatg    480
ggtataatgg attgctcatt gcaattaatc ctcaggtacc tgagaatcag aacctcatct    540
caaacattaa ggaaatgata actgaagctt cattttacct atttaatgct accaagagaa    600
gagtattttt cagaaatata aagattttaa tacctgccac atggaaagct aataataaca    660
gcaaaataaa acaagaatca tatgaaaagg caaatgtcat agtgactgac tggtatgggg    720
cacatggaga tgatccatac accctacaat acagagggtg tggaaaagag ggaaaataca    780
ttcatttcac acctaatttc ctactgaatg ataacttaac agctggctac ggatcacgag    840
gccgagtgtt tgtccatgaa tgggcccacc tccgttgggg tgtgttcgat gagtataaca    900
atgacaaacc tttctacata aatgggcaaa atcaaattaa agtgacaagg tgttcatctg    960
acatcacagg catttttgtg tgtgaaaaag gtccttgccc ccaagaaaac tgtattatta   1020
gtaagctttt taaagaagga tgcaccttta tctacaatag cacccaaaat gcaactgcat   1080
caataatgtt catgcaaagt ttatcttctg tggttgaatt ttgtaatgca agtacccaca   1140
accaagaagc accaaaccta cagaaccaga tgtgcagcct cagaagtgca tgggatgtaa   1200
tcacagactc tgctgacttt caccacagct ttcccatgaa tgggactgag cttccacctc   1260
ctcccacatt ctcgcttgta caggctggtg acaaagtggt ctgtttagtg ctggatgtgt   1320
ccagcaagat ggcagaggct gacagactcc ttcaactaca acaagccgca gaattttatt   1380
tgatgcagat tgttgaaatt cataccttcg tgggcattgc cagtttcgac agcaaaggag   1440
agatcagagc ccagctacac caaattaaca gcaatgatga tcgaaagttg ctggtttcat   1500
atctgcccac cactgtatca gctaaaacag acatcagcat ttgttcaggg cttaagaaag   1560
gatttgaggt ggttgaaaaa ctgaatggaa aagcttatgg ctctgtgatg atattagtga   1620
ccagcggaga tgataagctt cttggcaatt gcttacccac tgtgctcagc agtggttcaa   1680
caattcactc cattgccctg ggttcatctg cagccccaaa tctggaggaa ttatcacgtc   1740
ttacaggagg tttaaagttc tttgttccag atatatcaaa ctccaatagc atgattgatg   1800
ctttcagtag aatttcctct ggaactggag acattttcca gcaacatatt cagcttgaaa   1860
gtacaggtga aaatgtcaaa cctcaccatc aattgaaaaa cacagtgact gtggataata   1920
ctgtgggcaa cgacactatg tttctagtta cgtggcaggc cagtggtcct cctgagatta   1980
tattatttga tcctgatgga cgaaaatact acacaaataa ttttatcacc aatctaactt   2040
ttcggacagc tagtctttgg attccaggaa cagctaagcc tgggcactgg acttacaccc   2100
tgaacaatac ccatcattct ctgcaagccc tgaaagtgac agtgacctct cgcgcctcca   2160
actcagctgt gcccccagcc actgtggaag cctttgtgga aagagacagc ctccattttc   2220
ctcatcctgt gatgatttat gccaatgtga aacagggatt ttatcccatt cttaatgcca   2280
ctgtcactgc cacagttgag ccagagactg gagatcctgt tacgctgaga ctccttgatg   2340
atggagcagg tgctgatgtt ataaaaaatg atggaattta ctcgaggtat tttttctcct   2400
ttgctgcaaa tggtagatat agcttgaaag tgcatgtcaa tcactctccc agcataagca   2460
ccccagccca ctctattcca gggagtcatg ctatgtatgt accaggttac acagcaaacg   2520
gtaatattca gatgaatgct ccaaggaaat cagtaggcag aaatgaggag gagcgaaagt   2580
```

```
ggggctttag ccgagtcagc tcaggaggct ccttttcagt gctgggagtt ccagctggcc   2640
cccaccctga tgtgtttcca ccatgcaaaa ttattgacct ggaagctgta aaagtagaag   2700
aggaattgac cctatcttgg acagcacctg gagaagactt tgatcagggc caggctacaa   2760
gctatgaaat aagaatgagt aaaagtctac agaatatcca agatgacttt aacaatgcta   2820
ttttagtaaa tacatcaaag cgaaatcctc agcaagctgg catcagggag atatttacgt   2880
tctcacccca aatttccacg aatggacctg aacatcagcc aaatggagaa acacatgaaa   2940
gccacagaat ttatgttgca atacgagcaa tggataggaa ctccttacag tctgctgtat   3000
ctaacattgc ccaggcgcct ctgtttattc cccccaattc tgatcctgta cctgccagag   3060
attatcttat attgaaagga gttttaacag caatgggttt gataggaatc atttgcctta   3120
ttatagttgt gacacatcat actttaagca ggaaaaagag agcagacaag aaagagaatg   3180
gaacaaaatt attataaata aatatccaaa gtgtcttcct tcttagatat aagacccatg   3240
gccttcgact acaaaaacat actaacaaag tcaaattaac atcaaaactg tattaaaatg   3300
cattgagttt ttgtacaata cagataagat tttacatgg tagatcaaca aattcttttt   3360
gggggtagat tagaaaaccc ttacactttg gctatgaaca aataataaaa attattcttt   3420
aaagtaatgt ctttaaaggc aaagggaagg gtaaagtcgg accagtgtca aggaaagttt   3480
gttttattga ggtggaaaaa tagccccaag cagagaaaag gagggtaggt ctgcattata   3540
actgtctgtg tgaagcaatc atttagttac tttgattaat ttttcttttc tccttatctg   3600
tgcagaacag gttgcttgtt tacaactgaa gatcatgcta tattttatat atgaagcccc   3660
taatgcaaag ctctttacct cttgctattt tgttatatat attacagatg aaatctcact   3720
gctaatgctc agagatcttt tttcactgta agaggtaacc tttaacaata tgggtattac   3780
ctttgtctct tcataccggt tttatgacaa aggtctattg aatttatttg tttgtaagtt   3840
tctactccca tcaaagcagc tttctaagtt attgccttgg ttattatgga tgatagttat   3900
agcccttata atgccttaac taaggaagaa aagatgttat tctgagtttg ttttaataca   3960
tatatgaaca tatagtttta ttcaattaaa ccaaagaaga ggtcagcagg gagatactaa   4020
cctttggaaa tgattagctg gctctgtttt ttggttaaat aagagtcttt aatcctttct   4080
ccatcaagag ttacttacca agggcagggg aagggggata tagaggtcac aaggaaataa   4140
aaatcatctt tcatctttaa ttttactcct tcctcttatt tttttaaaag attatcgaac   4200
aataaaatca tttgcctttt taattaaaaa aaaaaaaaaa aaaaaa                  4246
```

<210> SEQ ID NO 52
<211> LENGTH: 2220
<212> TYPE: DNA
<213> ORGANISM: Homo sapiens

<400> SEQUENCE: 52

```
gaacttcttt cctggcacag gactcactgt gccccttccc gctgtgggta caaggtctgc     60
cccccacccc agctctccaa agcccaccgg cctccctgga ggccgaggtc gacggcccgt    120
cgcaccggga gggggggctc ccaggggtgc cccacgcacg gtcaaggtcc cgcgccaagc    180
ggggaccggg ctgggccgga agcgggcacg gtactcgcgg caaactagcg tgggcgagtc    240
ctgattgcag tcggacctgc cgccgcggca cttaacagtt tgcagagtgc ttcccgcccc    300
tgatctcatt ggagccttcg gacagcccag cccatggcca ccgatgcccc catttcacgc    360
ctgaggaagc ggaggctcag acgggccacc agcccctccg gaggctggcc cgggagcgcc    420
```

-continued

```
tggcagcgtc gggtctagga gccggctccc tcctgctccc tcctccgcgc cgcccggggt    480
gtgcccgccg tctgtgtgca ccactgctga gcccagctcc ggcgccctcg cctctgctgt    540
gggccccggg gacgcggggt caggccaccg cgttggccag gccgctgcag gtaggcacgg    600
cccccaccag gcgccatgga ctggaagaca ctccaggccc tactgagcgg tgtgaacaag    660
tactccacag cgttcgggcg catctggctg tccgtggtgt tcgtcttccg ggtgctggta    720
tacgtggtgg ctgcagagcg cgtgtggggg gatgagcaga aggactttga ctgcaacacc    780
aagcagcccg gctgcaccaa cgtctgctac gacaactact tccccatctc caacatccgc    840
ctctgggccc tgcagctcat cttcgtcaca tgcccctcgc tgctggtcat cctgcacgtg    900
gcctaccgtg aggagcggga gcgccggcac cgccagaaac acggggacca gtgcgccaag    960
ctgtacgaca acgcaggcaa gaagcacgga ggcctgtggt ggacctacct gttcagcctc   1020
atcttcaagc tcatcattga gttcctcttc ctctacctgc tgcacactct ctggcatggc   1080
ttcaatatgc cgcgcctggt gcagtgtgcc aacgtggccc cctgccccaa catcgtggac   1140
tgctacattg cccgacctac cgagaagaaa atcttcacct acttcatggt gggcgcctcc   1200
gccgtctgca tcgtactcac catctgtgag ctctgctacc tcatctgcca cagggtcctg   1260
cgaggcctgc acaaggacaa gcctcgaggg ggttgcagcc cctcgtcctc cgccagccga   1320
gcttccacct gccgctgcca ccacaagctg gtggaggctg gggaggtgga tccagaccca   1380
ggcaataaca agctgcaggc ttcagcaccc aacctgaccc ccatctgacc acagggcagg   1440
ggtggggcaa catgcgggct gccaatggga catgcagggc ggtgtggcag gtggagaggt   1500
cctacagggg ctgagtgacc ccactctgag ttcactaagt tatgcaactt tcgttttggc   1560
agatattttt tgacactggg aactgggctg tctagccggg tataggtaac ccacaggccc   1620
agtgccagcc ctcaaaggac atagactttg aaacaagcga attaactatc tacgctgcct   1680
gcaaggggcc acttagggca ctgctagcag ggcttcaacc aggaagggat caacccagga   1740
agggatgatc aggagaggct tccctgagga cataatgtgt aagagaggtg agaagtgctc   1800
ccaagcagac acaacagcag cacagaggtc tggaggccac acaaaaagtg atgctcgccc   1860
tgggctagcc tcagcagacc taaggcatct ctactccctc cagaggagcc gcccagattc   1920
ctgcagtgga gaggaggtct tccagcagca gcaggtctgg agggctgaga atgaacctga   1980
ctagaggttc tggagatacc cagaggtccc ccaggtcatc acttggctca gtggaagccc   2040
tctttcccca aatcctactc cctcagcctc aggcagtggt gctcccatct tcctccccac   2100
aactgtgctc aggctggtgc cagcctttca gaccctgctc ccagggactt gggtggatgc   2160
gctgatagaa catcctcaag acagtttcct tgaaatcaat aaatactgtg ttttataaaa   2220
```

<210> SEQ ID NO 53
<211> LENGTH: 1521
<212> TYPE: DNA
<213> ORGANISM: Homo sapiens

<400> SEQUENCE: 53

```
ttacattagc aagagagcaa gttgttccag tagtcgcctg gcaggagaat ttgaaagggt     60
gccccaaagg acaatctcta aaggggtaag ggagatacct accttgtctg gtaggggaga    120
tgtttcgttt tcatgcttta ccagaaaatc cacttccctg ccgaccttag tttcaaagct    180
tattcttaat tagagacaag aaacctgttt caacttgaag acaccgtatg aggtgaatgg    240
acagccagcc accacaatga aagaaatcaa accaggaata acctatgctg aacccacgcc    300
tcaatcgtcc ccaagtgttt cctgacacgc atctttgctt acagtgcatc acaactgaag    360
```

aatggggttc aacttgacgc ttgcaaaatt accaaataac gagctgcacg gccaagagag 420
tcacaattca ggcaacagga gcgacgggcc aggaaagaac accacccttc acaatgaatt 480
tgacacaatt gtcttgccgg tgctttatct cattatattt gtggcaagca tcttgctgaa 540
tggtttagca gtgtggatct tcttccacat taggaataaa accagcttca tattctatct 600
caaaaacata gtggttgcag acctcataat gacgctgaca tttccatttc gaatagtcca 660
tgatgcagga tttggacctt ggtacttcaa gtttattctc tgcagataca cttcagtttt 720
gttttatgca aacatgtata cttccatcgt gttccttggg ctgataagca ttgatcgcta 780
tctgaaggtg gtcaagccat ttggggactc tcggatgtac agcataacct tcacgaaggt 840
tttatctgtt tgtgtttggg tgatcatggc tgttttgtct ttgccaaaca tcatcctaac 900
aaatggtcag ccaacagagg acaatatcca tgactgctca aaacttaaaa gtcctttggg 960
ggtcaaatgg catacggcag tcacctatgt gaacagctgc ttgtttgtgg ccgtgctggt 1020
gattctgatc ggatgttaca tagccatatc caggtacatc cacaaatcca gcaggcaatt 1080
cataagtcag tcaagccgaa agcgaaaaca taaccagagc atcagggttg ttgtggctgt 1140 gtttttttacc tgctttctac catatcactt gtgcagaatt ccttttactt ttagtcactt 1200
agacaggctt ttagatgaat ctgcacaaaa aatcctatat tactgcaaag aaattacact 1260
tttcttgtct gcgtgtaatg tttgcctgga tccaataatt tactttttca tgtgtaggtc 1320
attttcaaga aggctgttca aaaaatcaaa tatcagaacc aggagtgaaa gcatcagatc 1380
actgcaaagt gtgagaagat cggaagttcg catatattat gattacactg atgtgtaggc 1440
cttttattgt ttgttggaat cgatatgtac aaagtgtaaa taaatgtttc ttttcattat 1500
ccttgcttga gcccatcaaa a 1521

<210> SEQ ID NO 54
<211> LENGTH: 1336
<212> TYPE: DNA
<213> ORGANISM: Homo sapiens

<400> SEQUENCE: 54
gagagacaca gagtccggca ttggtcccag gcagcagtta gcccgccgcc cgcctgtgtg 60
tccccagagc catggagaga gccagtctga tccagaaggc caagctggca gagcaggccg 120
aacgctatga ggacatggca gccttcatga aaggcgccgt ggagaagggc gaggagctct 180
cctgcgaaga gcgaaacctg ctctcagtag cctataagaa cgtggtgggc ggccagaggg 240
ctgcctggag ggtgctgtcc agtattgagc agaaaagcaa cgaggagggc tcggaggaga 300
aggggcccga ggtgcgtgag taccgggaga aggtggagac tgagctccag ggcgtgtgcg 360
acaccgtgct gggcctgctg gacagccacc tcatcaagga ggccggggac gccgagagcc 420
gggtcttcta cctgaagatg aagggtgact actaccgcta cctggccgag gtggccaccg 480
gtgacgacaa gaagcgcatc attgactcag cccggtcagc ctaccaggag gccatggaca 540
tcagcaagaa ggagatgccg cccaccaacc ccatccgcct gggcctggcc ctgaactttt 600
ccgtcttcca ctacgagatc gccaacagcc ccgaggaggc catctctctg gccaagacca 660
ctttcgacga ggccatggct gatctgcaca ccctcagcga ggactcctac aaagacagca 720
ccctcatcat gcagctgctg cgagacaacc tgacactgtg gacggccgac aacgccgggg 780
aagagggggg cgaggctccc caggagcccc agagctgagt gttgcccgcc accgccccgc 840
cctgccccct ccagtccccc accctgccga gaggactagt atggggtggg aggccccacc 900

-continued

```
cttctcccct aggcgctgtt cttgctccaa agggctccgt ggagagggac tggcagagct    960

gaggccacct ggggctgggg atcccactct tcttgcagct gttgagcgca cctaaccact   1020

ggtcatgccc ccacccctgc tctccgcacc cgcttcctcc cgaccccagg accaggctac   1080

ttctcccctc ctcttgcctc cctcctgccc ctgctgcctc tgatcgtagg aattgaggag   1140

tgtcccgcct tgtggctgag aactggacag tggcaggggc tggagatggg tgtgtgtgtg   1200

tgtgtgtgtg tgtgtgtgtg tgtgcgcgcg cgccagtgca agaccgagat tgagggaaag   1260

catgtctgct gggtgtgacc atgtttcctc tcaataaagt tcccctgtga cactcaaaaa   1320

aaaaaaaaaa aaaaaa                                                   1336
```

<210> SEQ ID NO 55
<211> LENGTH: 838
<212> TYPE: DNA
<213> ORGANISM: Homo sapiens

<400> SEQUENCE: 55

```
tgctgtttgt ggaaaataaa gcattctata ggcggagcta gtgaacgcct cttttaaaac     60

acgagtctcc acacttccct gttcactttg gttccagcat cctgtccagc aaagaagcaa    120

tcagccaaaa tgatacctgg aggcttatct gaggccaaac ccgccactcc agaaatccag    180

gagattgttg ataaggttaa accacagctt gaagaaaaaa caaatgagac ttacggaaaa    240

ttggaagctg tgcagtataa aactcaagtt gttgctggaa caaattacta cattaaggta    300

cgagcaggtg ataataaata tatgcacttg aaagtattca aaagtcttcc cggacaaaat    360

gaggacttgg tacttactgg ataccaggtt gacaaaaaca aggatgacga gctgacgggc    420

ttttagcagc atgtacccaa agtgttctga ttccttcaac tggctactga gtcatgatcc    480

ttgctgataa atataaccat caataaagaa gcattctttt ccaaagaaat tatttcttca    540

attatttctc atttattgta ttaagcagaa attacctttt ctttctcaaa atcagtgtta    600

ttgctttaga gtataaactc catataaatt gatggcaatt ggaaatctta taaaaactag    660

tcaagcctaa tgcaactggc taaaggatag taccaccctc acccccacca taggcaggct    720

ggatcgtgga ctatcaattc accagcctcc ttgttccctg tggctgctga taacccaaca    780

ttccatctct accctcatac ttcaaaatta aatcaagtat tttacaaaaa aaaaaaaa      838
```

<210> SEQ ID NO 56
<211> LENGTH: 5561
<212> TYPE: DNA
<213> ORGANISM: Homo sapiens

<400> SEQUENCE: 56

```
aaagcagcag agacgctgca gagggctttt cttagacatc aactgcagac ggctggcagg     60

atagaagcag cggctcactt ggactttttc accagggaaa tcagagacaa tgatggggct    120

cttccccaga actacagggg ctctggccat cttcgtggtg gtcatattgg ttcatggaga    180

attgcgaata gagactaaag gtcaatatga tgaagaagag atgactatgc aacaagctaa    240

aagaaggcaa aaacgtgaat gggtgaaatt tgccaaaccc tgcagagaag gagaagataa    300

ctcaaaaaga aacccaattg ccaagattac ttcagattac caagcaaccc agaaaatcac    360

ctaccgaatc tctggagtgg gaatcgatca gccgcctttt ggaatctttg ttgttgacaa    420

aaacactgga gatattaaca taacagctat agtcgaccgg gaggaaactc caagcttcct    480

gatcacatgt cgggctctaa atgcccaagg actagatgta gagaaaccac ttatactaac    540

ggttaaaatt ttggatatta atgataatcc tccagtattt tcacaacaaa ttttcatggg    600
```

```
tgaaattgaa gaaaatagtg cctcaaactc actggtgatg atactaaatg ccacagatgc    660
agatgaacca aaccacttga attctaaaat tgccttcaaa attgtctctc aggaaccagc    720
aggcacaccc atgttcctcc taagcagaaa cactggggaa gtccgtactt tgaccaattc    780
tcttgaccga gagcaagcta gcagctatcg tctggttgtg agtggtgcag acaaagatgg    840
agaaggacta tcaactcaat gtgaatgtaa tattaaagtg aaagatgtca acgataactt    900
cccaatgttt agagactctc agtattcagc acgtattgaa gaaaatattt taagttctga    960
attacttcga tttcaagtaa cagatttgga tgaagagtac acagataatt ggcttgcagt   1020
atatttcttt acctctggga atgaaggaaa ttggtttgaa atacaaactg atcctagaac   1080
taatgaaggc atcctgaaag tggtgaaggc tctagattat gaacaactac aaagcgtgaa   1140
acttagtatt gctgtcaaaa acaaagctga atttcaccaa tcagttatct ctcgataccg   1200
agttcagtca accccagtca caattcaggt aataaatgta agagaaggaa ttgcattccg   1260
tcctgcttcc aagacattta ctgtgcaaaa aggcataagt agcaaaaaat tggtggatta   1320
tatcctggga acatatcaag ccatcgatga ggacactaac aaagctgcct caaatgtcaa   1380
atatgtcatg ggacgtaacg atggtggata cctaatgatt gattcaaaaa ctgctgaaat   1440
caaatttgtc aaaaatatga accgagattc tactttcata gttaacaaaa caatcacagc   1500
tgaggttctg gccatagatg aatacacggg taaaacttct acaggcacgg tatatgttag   1560
agtacccgat ttcaatgaca attgtccaac agctgtcctc gaaaaagatg cagtttgcag   1620
ttcttcacct tccgtggttg tctccgctag aacactgaat aatagataca ctggccccta   1680
tacatttgca ctggaagatc aacctgtaaa gttgcctgcc gtatggagta tcacaaccct   1740
caatgctacc tcggccctcc tcagagccca ggaacagata cctcctggag tataccacat   1800
ctccctggta cttacagaca gtcagaacaa tcggtgtgag atgccacgca gcttgacact   1860
ggaagtctgt cagtgtgaca acaggggcat ctgtggaact tcttacccaa ccacaagccc   1920
tgggaccagg tatggcaggc cgcactcagg gaggctgggg cctgccgcca tcggcctgct   1980
gctccttggt ctcctgctgc tgctgttggc cccccttctg ctgttgacct gtgactgtgg   2040
ggcaggttct actgggggag tgacaggtgg ttttatccca gttcctgatg gctcagaagg   2100
aacaattcat cagtggggaa ttgaaggagc ccatcctgaa gacaaggaaa tcacaaatat   2160
ttgtgtgcct cctgtaacag ccaatggagc cgatttcatg gaaagttctg aagtttgtac   2220
aaatacgtat gccagaggca cagcggtgga aggcacttca ggaatggaaa tgaccactaa   2280
gcttggagca gccactgaat ctggaggtgc tgcaggcttt gcaacaggga cagtgtcagg   2340
agctgcttca ggattcggag cagccactgg agttggcatc tgttcctcag ggcagtctgg   2400
aaccatgaga acaaggcatt ccactggagg aaccaataag gactacgctg atggggcgat   2460
aagcatgaat tttctggact cctacttttc tcagaaagca tttgcctgtg cggaggaaga   2520
cgatggccag gaagcaaatg actgcttgtt gatctatgat aatgaaggcg cagatgccac   2580
tggttctcct gtgggctccg tgggttgttg cagttttatt gctgatgacc tggatgacag   2640
cttcttggac tcacttggac ccaaatttaa aaaacttgca gagataagcc ttggtgttga   2700
tggtgaaggc aaagaagttc agccaccctc taaagacagc ggttatggga ttgaatcctg   2760
tggccatccc atagaagtcc agcagacagg atttgttaag tgccagactt tgtcaggaag   2820
tcaaggagct tctgctttgt ccacctctgg gtctgtccag ccagctgttt ccatccctga   2880
ccctctgcag catggtaact atttagtaac ggagacttac tcggcttctg gttccctcgt   2940
```

-continued

```
gcaaccttcc actgcaggct ttgatccact tctcacacaa aatgtgatag tgacagaaag   3000
ggtgatctgt cccatttcca gtgttcctgg caacctagct ggcccaacgc agctacgagg   3060
gtcacatact atgctctgta cagaggatcc ttgctcccgt ctaatatgac cagaatgagc   3120
tggaatacca cactgaccaa atctggatct ttggactaaa gtattcaaaa tagcatagca   3180
aagctcactg tattgggcta ataatttggc acttattagc ttctctcata aactgatcac   3240
gattataaat taaatgtttg ggttcatacc ccaaaagcaa tatgttgtca ctcctaattc   3300
tcaagtacta ttcaaattgt agtaaatctt aaagtttttc aaaaccctaa aatcatattc   3360
gccaggaaat tttcctaaac attcttaagc ttctattttt cccctgccaa aggaaggtgt   3420
ttatcatttt aaaatgcaat gtgatttagt ggattaagca ggagcgctgg ttcttgtctc   3480
cattgccttt tcttatatca ttgataatga tgtaagaatc acaaggggcc gggcgcggtg   3540
gctcacgcct gtaatcccag cactttggga ggccgaggca ggtggatcat gaggtcagga   3600
gatcgagacc atcctggcta acaaggtgaa accccgtctc tactaaaaat acaaaaaatt   3660
agccgggcgc agtggcgggc gcctgtagtc ccagctactc gggaggctga ggcaggagaa   3720
tggcatgaac ccgggaagcg gagcttgcag tgagccgaga ttgcgccact gcagtccgca   3780
gtccggcctg ggcgacagag cgagactccg tctcaaaaaa aaaaaaaaaa aaagaatcac   3840
aaggtatttg ctaaagcatt ttgagctgct tggaaaaagg gaagtagttg cagtagagtt   3900
tcttccatct tcttggtgct gggaagccat atatgtgtct tttactcaag ctaaggggta   3960
taagcttatg tgttgaattt gctacatcta tatttcacat attctcacaa taagagaatt   4020
ttgaaataga aatatcatag aacatttaag aaagtttagt ataaataata ttttgtgtgt   4080
tttaatccct ttgaagggat ctatccaaag aaaatatttt acactgagct ccttcctaca   4140
cgtctcagta acagatcctg tgttagtctt tgaaaatagc tcattttttta aatgtcagtg   4200
agtagatgta gcatacatat gatgtataat gacgtgtatt atgttaacaa tgtctgcaga   4260
ttttgtagga atacaaaaca tggccttttt tataagcaaa acgggccaat gactagaata   4320
acacataggg caatctgtga atatgtatta taagcagcat tccagaaaag tagttggtga   4380
aataattttc aagtcaaaaa gggatatgga aagggaatta tgagtaacct ctattttttta   4440
agccttgctt ttaaattaaa cagctacagc catttaagcc ttgaggataa taaagcttga   4500
gagtaataat gttaggttag caaaggttta gatgtatcac ttcatgcatg ctaccatgat   4560
agtaatgcag ctcttcgagt catttctggt cattcaagat attcaccctt ttgcccatag   4620
aaagcaccct acctcacctg cttactgaca ttgtcttagc tgatcacaag atcattatca   4680
gcctccatta ttccttactg tatataaaat acagagtttt atattttcct ttcttcgttt   4740
ttcaccatat tcaaaaccta aatttgtttt tgcagatgga atgcaaagta atcaagtgtt   4800
tgtgctttca cctagaaggg tgtggtcctg aaggaaagag gtcccctaaa tatcccccac   4860
cctggtgctc ctccctctcc ctggtaccct gactaccagg aagtcaggtg ctagagcagc   4920
tggagaagtg caggcagcct gtgcttccac agatgggggt gctgctgcaa caaggctttc   4980
aatgtgccca tcttaggtgg gagaagctag atcctgtgca gcagcctggt aagtcctgag   5040
gaggttccat tgctcttcct gctgctgtcc tttgcttctc aacggtggct cgctctacag   5100
tctagagcac atgcagctaa cttgtgcctc tgcttatgca tgagggttaa attaacaacc   5160
ataaccttca tttgaagttc aaaggtgtat tcaggatcct caaagcattt taaccttgcc   5220
gcttaaaacc caatttaccg tgaaatggga attttgctgc attgttaaac tgtagtggaa   5280
accatgctat agtaataaag gttatataag agagaaattg aaattaaatg tgtttttaaa   5340
```

-continued tttcaaaaaa aaatcaatct ttaggatgac ttaaaaattg atttgccatg taaaatgtat 5400
ctgcattttt tacacaaaac ttgttttaag cataaaattt taaaactgta ctacttgatg 5460
tattatacat tttgaaccat atgtattaaa ccataaacag tataatgttg ttataataaa 5520
acaggcaata aatttataaa taaaagctga aaaaaaaaaa a 5561

<210> SEQ ID NO 57
<211> LENGTH: 2105
<212> TYPE: DNA
<213> ORGANISM: Homo sapiens

<400> SEQUENCE: 57
ggagcgcgcg ctctgggcgc cgggacgaca ctccagcccc gggggacccg ccgcccagct 60
cccgagggtg cggcagcctc tggccactca gccggggccg agagggagct gccgggcggg 120
caggcgccgc aggcacccgg cgggcagggc ggggcagggc aagacggccg cctccgcaag 180
tgccacccgg cccacccggt tctctccctt ctgcctggga cgtcagcgga cggggcgctc 240
gcgggccggg gctgtatggg gctcccgcgc gggtcgttct tctggctgct gctcctgctc 300
acggctgcct gctcggggct cctctttgcc ctgtacttct cggcggtgca gcggtacccg 360
gggccagcgg ccggagccag ggacaccaca tcatttgaag cattctttca atccaaggca 420
tcgaattctt ggacaggaaa gggccaggcc tgccgacacc tgcttcacct ggccattcag 480
cggcaccccc acttccgtgg cctgttcaat ctctccattc cagtgctgct gtggggggac 540
ctcttcaccc cagcgctctg ggaccgcctg agccaacaca aagccccgta tggctggcgg 600
gggctctctc accaagtcat cgcctccacc ctgagccttc tgaacggctc agagagtgcc 660
aagctgtttg ccccgcccag ggacacccct ccaaagtgta tccggtgtgc cgtggtgggc 720
aacggaggca ttctgaatgg gtcccgccag ggtcccaaca tcgatgccca tgactatgta 780
ttcagactca atggagctgt gatcaaaggc ttcgagcgcg atgtgggcac caagacttcc 840
ttctatggtt tcactgtgaa cacgatgaag aactccctcg tctcctactg gaatctgggc 900
ttcacctccg tgccacaagg acaggacctg cagtatatct tcatcccctc agacatccgc 960
gactatgtga tgctgagatc ggccattctg ggcgtgcctg tccctgaggg cctagataaa 1020
ggggacaggc cgcacgccta ttttggacca gaagcctctg ccagtaaatt caagctgcta 1080
catccggact tcatcagcta cctgacagaa aggttcttga aatcaaagtt gattaacaca 1140
cattttggag acctatatat gcctagtacc ggggctctca tgctgctgac agctttgcat 1200
acctgtgacc aggtcagtgc ctatggattc atcacaagca actactggaa attttccgac 1260
cactatttcg aacgaaaaat gaagccattg atattttatg caaaccacga tctgtccctg 1320
gaagctgccc tgtggaggga cctgcacaag gccggcatcc ttcagctgta ccagcgctga 1380
ccccaatgca ctgagccctt tgcttcttca agagttgcgg ccctgatcct ctcaagtggc 1440
caaaagcttt tttaactttt caatcttcac cttcccttgc caacagaggg cactggggtg 1500
aattcaagat tttcatcgag gtctgttcaa tataggacac cccagcttgt ccttggctca 1560
tccaagaact cttctgtatc taaaacaata catctcaatc ttggccaagg gaaaatggac 1620
tgctttgctg gattggcact gagcaacttt aggaaatgtc ggtggagtgt tcagcaagat 1680
cagacagcag tccaggtcaa aggcaaacac acacgctcca gcccaaatcc tcctggtggc 1740
acatcctacc ccagatgcta aagtgattca aggactccag gacacctctt aagagccttt 1800
ctaagaacat gataggctta cttctgctcc ataataaagt gggagaaaaa agccagaata 1860

-continued taacttaaga ctagataact gcgtacatga tggaccattt tttttttttt ggctgggtag 1920
agaaatcata taaaacgcag gctgtttagc atggagatga ctctcagaac actgggaggg 1980
tctggcactt gatgggggtt agttgcttgg cagcctgcct gccactgagg gaagtcccat 2040
tagagatgta tcaccacctt gtcaccaaca ggatgatgtc accaggtaat aaaccttcat 2100
cctca 2105

<210> SEQ ID NO 58
<211> LENGTH: 1376
<212> TYPE: DNA
<213> ORGANISM: Homo sapiens

<400> SEQUENCE: 58
agcacacccg gcaggctctg tcctggaaac aggcttcaac gggcttcccc gaaaaccttc 60
cccgcttctg gatatgaaat tcaagctgct tgctgagtcc tattgccggc tgctgggagc 120
caggagagcc ctgaggagta gtcactcagt agcagctgac gcgtgggtcc accatgaact 180
ggagtatctt tgagggactc ctgagtgggg tcaacaagta ctccacagcc tttgggcgca 240
tctggctgtc tctggtcttc atcttccgcg tgctggtgta cctggtgacg gccgagcgtg 300
tgtggagtga tgaccacaag gacttcgact gcaatactcg ccagcccggc tgctccaacg 360
tctgctttga tgagttcttc cctgtgtccc atgtgcgcct ctgggccctg cagcttatcc 420
tggtgacatg cccctcactg ctcgtggtca tgcacgtggc ctaccgggag gttcaggaga 480
agaggcaccg agaagcccat ggggagaaca gtgggcgcct ctacctgaac cccggcaaga 540
agcggggtgg gctctggtgg acatatgtct gcagcctagt gttcaaggcg agcgtggaca 600
tcgcctttct ctatgtgttc cactcattct accccaaata tatcctccct cctgtggtca 660
agtgccacgc agatccatgt cccaatatag tggactgctt catctccaag ccctcagaga 720
agaacatttt caccctcttc atggtggcca cagctgccat ctgcatcctg ctcaacctcg 780
tggagctcat ctacctggtg agcaagagat gccacgagtg cctggcagca aggaaagctc 840
aagccatgtg cacaggtcat cacccccacg gtaccacctc ttcctgcaaa caagacgacc 900
tcctttcggg tgacctcatc tttctgggct cagacagtca tcctcctctc ttaccagacc 960
gcccccgaga ccatgtgaag aaaaccatct tgtgaggggc tgcctggact ggtctggcag 1020
gttgggcctg gatggggagg ctctagcatc tctcataggt gcaacctgag agtgggggag 1080
ctaagccatg aggtaggggc aggcaagaga gaggattcag acgctctggg agccagttcc 1140
tagtcctcaa ctccagccac ctgccccagc tcgacggcac tgggccagtt cccccctctgc 1200 tctgcagctc ggtttccttt tctagaatgg aaatagtgag ggccaatgcc cagggttgga 1260
gggaggaggg cgttcataga agaacacaca tgcgggcacc ttcatcgtgt gtggcccact 1320
gtcagaactt aataaaagtc aactcatttg ctggtaaaaa aaaaaaaaaa aaaaaa 1376

<210> SEQ ID NO 59
<211> LENGTH: 3549
<212> TYPE: DNA
<213> ORGANISM: Homo sapiens

<400> SEQUENCE: 59
atcattccag tttggcaact tcacttgtag ggctgtttta atcaagctgc ccaaagtccc 60
ccaatcactc ctggaataca cagagagagg cagcagcttg ctcagcggac aaggatgctg 120
ggcgtgaggg accaaggcct gccctgcact cgggcctcct ccagccagtg ctgaccaggg 180
acttctgacc tgctggccag ccaggacctg tgtggggagg ccctcctgct gccttggggt 240

-continued

```
gacaatctca gctccaggct acagggagac cgggaggatc acagagccag catgttacag    300
gatcctgaca gtgatcaacc tctgaacagc ctcgatgtca aacccctgcg caaaccccgt    360
atccccatgg agaccttcag aaaggtgggg atccccatca tcatagcact actgagcctg    420
gcgagtatca tcattgtggt tgtcctcatc aaggtgattc tggataaata ctacttcctc    480
tgcgggcagc ctctccactt catcccgagg aagcagctgt gtgacggaga gctggactgt    540
cccttggggg aggacgagga gcactgtgtc aagagcttcc ccgaagggcc tgcagtggca    600
gtccgcctct ccaaggaccg atccacactg caggtgctgg actcggccac agggaactgg    660
ttctctgcct gtttcgacaa cttcacagaa gctctcgctg agacagcctg taggcagatg    720
ggctacagca gcaaacccac tttcagagct gtggagattg gcccagacca ggatctggat    780
gttgttgaaa tcacagaaaa cagccaggag cttcgcatgc ggaactcaag tgggccctgt    840
ctctcaggct ccctggtctc cctgcactgt cttgcctgtg ggaagagcct gaagaccccc    900
cgtgtggtgg gtggggagga ggcctctgtg gattcttggc cttggcaggt cagcatccag    960
tacgacaaac agcacgtctg tggagggagc atcctggacc cccactgggt cctcacggca   1020
gcccactgct tcaggaaaca taccgatgtg ttcaactgga aggtgcgggc aggctcagac   1080
aaactgggca gcttcccatc cctggctgtg gccaagatca tcatcattga attcaacccc   1140
atgtacccca aagacaatga catcgccctc atgaagctgc agttcccact cactttctca   1200
ggcacagtca ggcccatctg tctgcccttc tttgatgagg agctcactcc agccacccca   1260
ctctggatca ttggatgggg ctttacgaag cagaatggag ggaagatgtc tgacatactg   1320
ctgcaggcgt cagtccaggt cattgacagc acacggtgca atgcagacga tgcgtaccag   1380
ggggaagtca ccgagaagat gatgtgtgca ggcatcccgg aagggggtgt ggacacctgc   1440
cagggtgaca gtggtgggcc cctgatgtac caatctgacc agtggcatgt ggtgggcatc   1500
gttagttggg gctatggctg cgggggcccg agcaccccag gagtatacac caaggtctca   1560
gcctatctca actggatcta caatgtctgg aaggctgagc tgtaatgctg ctgccccttt   1620
gcagtgctgg gagccgcttc cttcctgccc tgcccacctg gggatccccc aaagtcagac   1680
acagagcaag agtccccttg ggtacacccc tctgcccaca gcctcagcat ttcttggagc   1740
agcaaagggc ctcaattcct ataagagacc ctcgcagccc agaggcgccc agaggaagtc   1800
agcagcccta gctcggccac acttggtgct cccagcatcc cagggagaga cacagcccac   1860
tgaacaaggt ctcaggggta ttgctaagcc aagaaggaac tttcccacac tactgaatgg   1920
aagcaggctg tcttgtaaaa gcccagatca ctgtgggctg gagaggagaa ggaaagggtc   1980
tgcgccagcc ctgtccgtct tcacccatcc ccaagcctac tagagcaaga aaccagttgt   2040
aatataaaat gcactgccct actgttggta tgactaccgt tacctactgt tgtcattgtt   2100
attacagcta tggccactat tattaaagag ctgtgtaaca tctctggcat aggctagctg   2160
gaatgcttga taagaactga gctgggatga ttgaactttc attctttggc ttggggagaa   2220
aagaagtcct ggggaagcaa ttgagtctca aagtagaggc aggggaaaaa agagttaggg   2280
agaccagatc tgctgagtgg cagcaagagt gagctgcaga ttacagaaac cagggtgagc   2340
aagtttgagt cccacacagg gccttctccc tttgcctctt tccctccctc cctgcctgtg   2400
ataatcagcc aggagccagg gataacctat gacttgggaa agagatgagt taggcagtca   2460
agggtgacat tcaatcaggg atccacaagt ggctggaaag aaatgctggt cctgtgtcct   2520
aactttttcc gcctggagag ccctcagtgt ggcttcttac atttaaaaaa caaaaaggat   2580
```

-continued

```
cagctgccag gtgtgaggca gtccccaagc tgagttgtga ggatgtaagc atgaataagt   2640

ccctgcactc aaaatggtca aagaattaaa ccccatggac ttttttggca tctgtatgaa   2700

agcttgggtt ttctgaggac tgtcttgcta tagttaagtc agatcctaga tgaaatatac   2760

ttgttcatac tgtactaggt tcttaggaaa caacagaatt cctcaaatgc caaaaacaaa   2820

gaaaatagaa acccagaaaa caaaacaaaa taaaacaaaa ccatcagaac tgtgagtgga   2880

aactaaggtg atgatctggg agcaatacac taaaatcttg ggtcgagacc tatatgaagg   2940

ctggcagtgg agctaaacct ggacacactg aagacaaggg agctgaacca gggctcctac   3000

atgaagcagg gataactgat ggcagtaaat gtggtctcaa attgcagatg gtctggagga   3060

aaatttccca aatttagagc ctcaggattc ccaaagatcc tccaaatatg agctcacaat   3120

caaagatcag agacgttgaa aaataaaaaa caccttaagt gggcagcata aaaaacagct   3180

aatttagaac cccaaaggct tcagatgtca gaatattaga gacttatgat aataagcaat   3240

atttgcagag tatttgtatg tgccagacac tattgtaagt gcttcatcat gtactgattc   3300

atttaatact cacagaaatc tgtgagatgg gtattattct tatcctcact ctatggatta   3360

aaaaaactaa ggcacaaagt ggttaagctc cttgcctgag attatagact gtaagttgaa   3420

cgtgagcact tggaatacag agttcatgct gtaaactacc acactatagg gcctccaata   3480

tgataattta taaaatattt gaataaaaaa tgaatactag ttccacattt taaaaaaaaa   3540

aaaaaaaaa                                                           3549


<210> SEQ ID NO 60
<211> LENGTH: 3309
<212> TYPE: DNA
<213> ORGANISM: Homo sapiens

<400> SEQUENCE: 60

ttcagcccct ctcccgggct gcgcctccgc actccgggcc cgggcagaag ggggtgcgcc     60

tcggccccac cacccaggga gcagccgagc tgaaaggccg ggaaccgcgg cttgcgggga    120

ccacagctcc cgaaagcgac gttcggccac cggaggagcg ggagccaagc aggcggagct    180

cggcgggaga ggtgcgggcc gaatccgagc cgagcggaga ggaatccggc agtagagagc    240

ggactccagc cggcggaccc tgcagccctc gcctgggaca gcggcgcgct gggcaggcgc    300

ccaagagagc atcgagcagc ggaacccgcg aagccggccc gcagccgcga cccgcgcagc    360

ctgccgctct cccgccgccg gtccgggcag catgaggcgc gcggcgctct ggctctggct    420

gtgcgcgctg gcgctgagcc tgcagccggc cctgccgcaa attgtggcta ctaatttgcc    480

ccctgaagat caagatggct ctggggatga ctctgacaac ttctccggct caggtgcagg    540

tgctttgcaa gatatcacct tgtcacagca gaccccctcc acttggaagg acacgcagct    600

cctgacggct attcccacgt ctccagaacc caccggcctg gaggctacag ctgcctccac    660

ctccaccctg ccggctggag aggggcccaa ggagggagag gctgtagtcc tgccagaagt    720

ggagcctggc ctcaccgccc gggagcagga ggccaccccc cgacccaggg agaccacaca    780

gctcccgacc actcatcagg cctcaacgac cacagccacc acggcccagg agcccgccac    840

ctcccacccc cacagggaca tgcagcctgg ccaccatgag acctcaaccc ctgcaggacc    900

cagccaagct gaccttcaca ctccccacac agaggatgga ggtccttctg ccaccgagag    960

ggctgctgag gatggagcct ccagtcagct cccagcagca gagggctctg gggagcagga   1020

cttcaccttt gaaacctcgg gggagaatac ggctgtagtg gccgtggagc ctgaccgccg   1080

gaaccagtcc ccagtggatc agggggccac gggggcctca cagggcctcc tggacaggaa   1140
```

-continued agaggtgctg ggaggggtca ttgccggagg cctcgtgggg ctcatctttg ctgtgtgcct 1200
ggtgggtttc atgctgtacc gcatgaagaa gaaggacgaa ggcagctact ccttggagga 1260
gccgaaacaa gccaacggcg gggcctacca gaagcccacc aaacaggagg aattctatgc 1320
ctgacgcggg agccatgcgc cccctccgcc ctgccactca ctaggccccc acttgcctct 1380
tccttgaaga actgcaggcc ctggcctccc ctgccaccag gccacctccc cagcattcca 1440
gcccctctgg tcgctcctgc ccacggagtc gtggggtgtg ctgggagctc cactctgctt 1500
ctctgacttc tgcctggaga cttagggcac caggggtttc tcgcatagga cctttccacc 1560
acagccagca cctggcatcg caccattctg actcggtttc tccaaactga agcagcctct 1620
ccccaggtcc agctctggag gggaggggga tccgactgct ttggacctaa atggcctcat 1680
gtggctggaa gatcctgcgg gtggggcttg gggctcacac acctgtagca cttactggta 1740
ggaccaagca tcttgggggg gtggccgctg agtggcaggg gacaggagtc cactttgttt 1800
cgtggggagg tctaatctag atatcgactt gtttttgcac atgtttcctc tagttctttg 1860
ttcatagccc agtagacctt gttacttctg aggtaagtta agtaagttga ttcggtatcc 1920
ccccatcttg cttccctaat ctatggtcgg gagacagcat cagggttaag aagacttttt 1980 ttttttttt ttaaactagg agaaccaaat ctggaagcca aaatgtaggc ttagtttgtg 2040
tgttgtctct tgagtttgtc gctcatgtgt gcaacagggt atggactatc tgtctggtgg 2100
ccccgtttct ggtggtctgt tggcaggctg gccagtccag gctgccgtgg ggccgccgcc 2160
tctttcaagc agtcgtgcct gtgtccatgc gctcagggcc atgctgaggc ctgggccgct 2220
gccacgttgg agaagcccgt gtgagaagtg aatgctggga ctcagccttc agacagagag 2280
gactgtaggg agggcggcag ggcctggag atcctcctgc agaccacgcc cgtcctgcct 2340
gtggcgccgt ctccaggggc tgcttcctcc tggaaattga cgaggggtgt cttgggcaga 2400
gctggctctg agcgcctcca tccaaggcca ggttctccgt tagctcctgt ggccccaccc 2460
tgggccctgg gctggaatca ggaatatttt ccaaagagtg atagtctttt gcttttggca 2520
aaactctact taatccaatg ggtttttccc tgtacagtag attttccaaa tgtaataaac 2580
tttaatataa agtagtcctg tgaatgccac tgccttcgct tcttgcctct gtgctgtgtg 2640
tgacgtgacc ggacttttct gcaaacacca acatgttggg aaacttggct cgaatctctg 2700
tgccttcgtc tttcccatgg ggagggattc tggttccagg gtccctctgt gtatttgctt 2760
ttttgttttg gctgaaattc tcctggaggt cggtaggttc agccaaggtt ttataaggct 2820
gatgtcaatt tctgtgttgc caagctccaa gccccatctt ctaaatggca aaggaaggtg 2880
gatggcccca gcacagcttg acctgaggct gtggtcacag cggaggtgtg gagccgaggc 2940
ctaccccgca gacaccttgg acatcctcct cccacccggc tgcagaggcc agaggccccc 3000
agcccagggc tcctgcactt acttgcttat ttgacaacgt ttcagcgact ccgttggcca 3060
ctccgagagg tgggccagtc tgtggatcag agatgcacca ccaagccaag ggaacctgtg 3120
tccggtattc gatactgcga ctttctgcct ggagtgtatg actgcacatg actcgggggt 3180
ggggaaaggg gtcggctgac catgctcatc tgctggtccg tgggacggtg cccaagccag 3240
aggctgggtt catttgtgta acgacaataa acggtacttg tcatttcggg caaaaaaaaa 3300
aaaaaaaaa 3309

<210> SEQ ID NO 61
<211> LENGTH: 3973
<212> TYPE: DNA

<213> ORGANISM: Homo sapiens

<400> SEQUENCE: 61
cggacggggc cgccccgatg ggacgccgcg ctccggcccc tgcgcgccgc tgagccgagc 60
gccccccgct gccgagaccc ccgccgccac cgccagccgc tgccccctcg cccccgcccg 120
ggccgggagc ctcgtccccg tcccccggaa agctggattt ccgaggctgg aggcgcctgg 180
ccggctgggt ggggaccacc atgggcaacg cggccggcag cgccgagcag cccgcgggcc 240
ccgccgcgcc gcccccaag cagcccgcgc ctcccaagca gccgatgccc gcggccggag 300
agctggagga gaggttcaac cgcgccctga actgcatgaa cttgccccca gacaaggtcc 360
agctgctgag ccagtatgac aacgagaaga agtgggagct catctgtgat caggagcggt 420
ttcaagtcaa gaatcccccc gcagcctaca tccagaagct gaagagctat gtggatactg 480
gtggggtcag ccgaaaggta gcagctgatt ggatgtccaa cctggggttt aagaggcgag 540
ttcaggagtc cacgcaggtg ctacgggagc tggagacctc cctgaggacc aaccacattg 600
ggtgggtgca ggagttcctc aatgaagaga accgtggcct ggatgtgctg ctcgagtacc 660
tggcctttgc ccagtgctct gtcacgtatg acatggagag cacagacaac ggggcttcca 720
actcagagaa aaacaagccc ctggagcagt ctgtggaaga cctcagcaag ggtccaccct 780
cctccgtgcc caaaagccgc cacctgacca tcaagctgac cccagcccac agcaggaagg 840
ccctgcggaa ttcccgcatc gtcagccaga aggacgacgt ccacgtctgt attatgtgcc 900
tacgcgccat catgaactac cagtctggct tcagccttgt catgaaccac ccagcctgtg 960
tcaatgagat tgctctgagc ctcaacaaca agaaccccag aaccaaggct ctggtgctgg 1020
agctgctggc ggccgtgtgc ttggtgcggg gaggacatga catcatcctt gcagcctttg 1080
acaacttcaa ggaggtgtgt ggggagcagc accgctttga aaagctgatg gaatatttcc 1140
ggaatgagga cagcaacatc gacttcatgg tggcctgcat gcagttcatc aacattgtgg 1200
tacattcggt ggagaacatg aacttccgtg tcttcctgca atatgagttc acccacttgg 1260
gcctggacct gtacttggag aggcttcggc tcaccgagag tgacaagctg caggtgcaga 1320
tccaggcgta cctggacaat atttttgatg tgggggcgct gctggaggac acagagacca 1380
agaacgctgt gctggagcac atggaggaac tgcaggagca agtggcgctg ctgacagagc 1440
ggcttcggga cgcggagaac gaatccatgg ccaagattgc agaactggaa aaacagctaa 1500
gccaggcgcg caaggagttg gagaccctgc gggagcgctt cagcgaatcg accgccatgg 1560
gcgcctccag gcgtccccca gagcctgaga aagcgcctcc cgctgccccg acgcggccct 1620
cggccctgga gctgaaggtg gaggagctgg aggagaaggg gttaatccgt attctgcggg 1680
ggccggggga tgctgtctcc atcgagatcc tccccgtcgc tgtggcaact ccgagcggcg 1740
gtgatgctcc gactccgggg gtgccgaccg gctcccccag cccagatctc gcacctgcag 1800
cagagccggc tcccggagca gcgccaccgc cgccgccccc actgcccggc ctcccctccc 1860
cgcaggaagc cccgccctct gcgcccccac aggccccgcc tctccctggc agcccggagc 1920
ccccgcctgc gccgccgctg cccggagacc tgccgccccc acccccgcca ccgccaccac 1980
ctccgggcac tgacgggccg gtgcctccgc cgccgccgcc gccgccgccg cctcccggag 2040
gtcctcctga tgccctagga agacgcgact cagaattggg cccaggagtg aaggccaaga 2100
agcccatcca gactaagttc cgaatgccac tcttgaactg ggtggcactg aaacccagcc 2160
agatcaccgg cactgtcttc acagagctca atgatgagaa ggtgctgcag gagctagaca 2220
tgagtgattt tgaggaacag ttcaagacca agtcccaagg ccccagcctg gacctcagcg 2280
ctctcaagag taaggcagcc cagaaggccc ccagcaaggc gacactcatt gaggccaacc 2340
gggccaagaa cttggccatc accctgcgga agggcaacct gggggccgag cgcatctgcc 2400
aagccattga ggcgtacgac ctgcaggctc tgggcctgga cttcctggag ctgctgatgc 2460
gcttcctgcc cacagagtat gagcgcagcc tcatcacccg ctttgagcgg gagcagcggc 2520
caatggagga gctgtcagag gaggaccgct tcatgctatg cttcagccgc atcccgcgcc 2580
tgccggagcg catgaccaca ctcaccttcc tgggcaactt cccggacaca gcccagctgc 2640
tcatgccgca actgaatgcc atcattgcag cctcaatgtc catcaagtcc tctgacaaac 2700
tccgccagat cctggagatt gtcctggcct ttggcaacta catgaacagt agcaagcgtg 2760
gggcagccta tggcttccgg ctccagagcc tggatgcgct gttggagatg aagtcgactg 2820
atcgcaagca gacgctgctg cactacctgg tgaaggtcat tgctgagaag tacccgcaac 2880
tcacaggctt ccacagcgac ctgcacttcc tggacaaggc gggctcagtg tccctggaca 2940
gtgtcctggc ggacgtgcgc tccctgcagc gaggcctaga gttgacacag agagagtttg 3000
tgcggcagga tgactgcatg gtgctcaagg agttcctgag ggccaactcg cccaccatgg 3060
acaagctgct ggcagacagc aagacggctc aggaggcctt tgagtctgtg gtggagtact 3120
tcggagagaa ccccaagacc acatccccag gcctgttctt ctccctcttt agccgcttca 3180
ttaaggccta caagaaagct gagcaggagg tggaacagtg gaaaaaagaa gccgctgccc 3240
aggaggcagg cgctgatacc ccgggcaaag gggagccccc agcacccaag tcaccgccaa 3300
aggcccggcg gccacagatg gacctcatct ctgagctgaa acggaggcag cagaaggagc 3360
cactcattta tgagagcgac cgtgatgggg ccattgaaga catcatcaca gtgatcaaga 3420
cggtgccctt cacggcccgc accggcaagc ggacatcccg gctcctctgt gaggccagcc 3480
tgggagaaga gatgcccctc tagcccctca gatctgcgga accagcccta catccgcgca 3540
gacacaggcc gccgcagtgc ccgtcggcgt cccccgggcc ccccactgca ggtcacctcc 3600
gacctctcgc tgtagccgct atttctgcag gtggattctg caggggtgtg gggccgtgga 3660
caggctgagg ctcaaggaag gtggtcctca gctcggctgg ccgggcagcc cctcctccgc 3720
tgtggcccgc ctcaaacggg ctggtgcatc ctcctcttgg ccacagaggg cagcatcgcc 3780
cgccccttcc cccaaatgct gcttgcagca cccaccctaa agccccctcc aaatagccat 3840
acttagcctc agcaggagcc tggcctgtaa cttataaagt gcacctcgcc cccgcaagcc 3900
ccagccccga ggaccgtcca tggaccttat ttttatatga gattaataaa gatgtttgca 3960
aaaaaaaaaa aaa 3973

<210> SEQ ID NO 62
<211> LENGTH: 6932
<212> TYPE: DNA
<213> ORGANISM: Homo sapiens

<400> SEQUENCE: 62
gcatttaaaa gacagcgtga gactcgcgcc ctccggcacg gaaaaggcca ggcgacaggt 60
gtcgcttgaa aagactgggc ttgtccttgc tggtgcatgc gtcgtcggcc tctgggcagc 120
aggtttacaa aggaggaaaa cgacttcttc tagatttttt tttcagtttc ttctataaat 180
caaaacatct caaaatggag acctaaaatc cttaaaggga cttagtctaa tctcgggagg 240
tagttttgtg catgggtaaa caaattaagt attaactggt gttttactat ccaaagaatg 300
ctaattttat aaacatgatc gagttatata aggtatacca taatgagttt gattttgaat 360

-continued

```
ttgatttgtg gaaataaagg aaaagtgatt ctagctgggg catattgtta aagcattttt    420
ttcagagttg gccaggcagt ctcctactgg cacattctcc cattatgtag aatagaaata    480
gtacctgtgt ttgggaaaga ttttaaaatg agtgacagtt atttggaaca aagagctaat    540
aatcaatcca ctgcaaatta aagaaacatg cagatgaaag ttttgacaca ttaaaatact    600
tctacagtga caaagaaaaa tcaagaacaa agctttttga tatgtgcaac aaatttagag    660
gaagtaaaaa gataaatgtg atgattggtc aagaaattat ccagttattt acaaggccac    720
tgatatttta aacgtccaaa agtttgttta aatgggctgt taccgctgag aatgatgagg    780
atgagaatga tggttgaagg ttacatttta ggaaatgaag aaacttagaa aattaatata    840
aagacagtga tgaatacaaa gaagattttt ataacaatgt gtaaaatttt tggccaggga    900
aaggaatatt gaagttagat acaattactt acctttgagg gaaataattg ttggtaatga    960
gatgtgatgt ttctcctgcc acctggaaac aaagcattga agtctgcagt tgaaaagccc   1020
aacgtctgtg agatccagga aaccatgctt gcaaaccact ggtaaaaaaa aaaaaaaaaa   1080
aaaaaaaaag ccacagtgac ttgcttattg gtcattgcta gtattatcga ctcagaacct   1140
ctttactaat ggctagtaaa tcataattga gaaattctga attttgacaa ggtctctgct   1200
gttgaaatgg taaatttatt atttttttg tcatgataaa ttctggttca aggtatgcta   1260
tccatgaaat aatttctgac caaaactaaa ttgatgcaat ttgattatcc atcttagcct   1320
acagatggca tctggtaact tttgactgtt ttaaaaaata aatccactat cagagtagat   1380
ttgatgttgg cttcagaaac atttagaaaa acaaaagttc aaaaatgttt tcaggaggtg   1440
ataagttgaa taactctaca atgttagttc tttgaggggg acaaaaaatt taaaatcttt   1500
gaaaggtctt attttacagc catatctaaa ttatcttaag aaaattttta acaaagggaa   1560
tgaaatatat atcatgattc tgtttttcca aaagtaacct gaatatagca atgaagttca   1620
gttttgttat tggtagtttg ggcagagtct ctttttgcag cacctgttgt ctaccataat   1680
tacagaggac atttccatgt tctagccaag tatactatta gaataaaaaa acttaacatt   1740
gagttgcttc aacagcatga aactgagtcc aaaagaccaa atgaacaaac acattaatct   1800
ctgattattt attttaaata gaatatttaa ttgtgtaaga tctaatagta tcattatact   1860
taagcaatca tattcctgat gatctatggg aaataactat tatttaatta atattgaaac   1920
caggttttaa gatgtgttag ccagtcctgt tactagtaaa tctctttatt tggagagaaa   1980
ttttagattg ttttgttctc cttattagaa ggattgtaga aagaaaaaaa tgactaattg   2040
gagaaaaatt ggggatatat catatttcac tgaattcaaa atgtcttcag ttgtaaatct   2100
taccattatt ttacgtacct ctaagaaata aaagtgcttc taattaaaat atgatgtcat   2160
taattatgaa atacttcttg ataacagaag ttttaaaata gccatcttag aatcagtgaa   2220
atatggtaat gtattatttt cctcctttga gttaggtctt gtgctttttt ttcctggcca   2280
ctaaatttca caatttccaa aaagcaaaat aaacatattc tgaatatttt tgctgtgaaa   2340
cacttgacag cagagctttc caccatgaaa agaagcttca tgagtcacac attacatctt   2400
tgggttgatt gaatgccact gaaacattct agtagcctgg agaagttgac ctacctgtgg   2460
agatgcctgc cattaaatgg catcctgatg gcttaataca catcactctt ctgtgaaggg   2520
ttttaatttt caacacagct tactctgtag catcatgttt acattgtatg tataaagatt   2580
atacaaaggt gcaattgtgt atttcttcct taaaatgtat cagtatagga tttagaatct   2640
ccatgttgaa actctaaatg catagaaata aaaataataa aaaatttttc attttggctt   2700
ttcagcctag tattaaaact gataaaagca aagccatgca caaaactacc tccctagaga   2760
```

aaggctagtc ccttttcttc cccattcatt tcattatgaa catagtagaa aacagcatat 2820
tcttatcaaa tttgatgaaa agcgccaaca cgtttgaact gaaatacgac ttgtcatgtg 2880
aactgtaccg aatgtctacg tattccactt ttcctgctgg ggttcctgtc tcagaaagga 2940
gtcttgctcg tgctggtttc tattacactg gtgtgaatga caaggtcaaa tgcttctgtt 3000
gtggcctgat gctggataac tggaaaagag gagacagtcc tactgaaaag cataaaaagt 3060
tgtatcctag ctgcagattc gttcagagtc taaattccgt taacaacttg gaagctacct 3120
ctcagcctac ttttccttct tcagtaacaa attccacaca ctcattactt ccgggtacag 3180
aaaacagtgg atatttccgt ggctcttatt caaactctcc atcaaatcct gtaaactcca 3240
gagcaaatca agatttttct gccttgatga gaagttccta ccactgtgca atgaataacg 3300
aaaatgccag attacttact tttcagacat ggccattgac ttttctgtcg ccaacagatc 3360
tggcaaaagc aggcttttac tacataggac ctggagacag agtggcttgc tttgcctgtg 3420
gtggaaaatt gagcaattgg gaaccgaagg ataatgctat gtcagaacac ctgagacatt 3480
ttcccaaatg cccatttata gaaaatcagc ttcaagacac ttcaagatac acagtttcta 3540
atctgagcat gcagacacat gcagcccgct ttaaaacatt ctttaactgg ccctctagtg 3600
ttctagttaa tcctgagcag cttgcaagtg cgggtttttta ttatgtgggt aacagtgatg 3660
atgtcaaatg cttttgctgt gatggtggac tcaggtgttg ggaatctgga gatgatccat 3720
gggttcaaca tgccaagtgg tttccaaggt gtgagtactt gataagaatt aaaggacagg 3780
agttcatccg tcaagttcaa gccagttacc ctcatctact tgaacagctg ctatccacat 3840
cagacagccc aggagatgaa aatgcagagt catcaattat ccattttgaa cctggagaag 3900
accattcaga agatgcaatc atgatgaata ctcctgtgat taatgctgcc gtggaaatgg 3960
gctttagtag aagcctggta aaacagacag ttcagagaaa aatcctagca actggagaga 4020
attatagact agtcaatgat cttgtgttag acttactcaa tgcagaagat gaaataaggg 4080
aagaggagag agaaagagca actgaggaaa aagaatcaaa tgatttatta ttaatccgga 4140
agaatagaat ggcacttttt caacatttga cttgtgtaat tccaatcctg gatagtctac 4200
taactgccgg aattattaat gaacaagaac atgatgttat taaacagaag acacagacgt 4260
ctttacaagc aagagaactg attgatacga ttttagtaaa aggaaatatt gcagccactg 4320
tattcagaaa ctctctgcaa gaagctgaag ctgtgttata tgagcattta tttgtgcaac 4380
aggacataaa atatattccc acagaagatg tttcagatct accagtggaa gaacaattgc 4440
ggagactaca agaagaaaga acatgtaaag tgtgtatgga caaagaagtg tccatagtgt 4500
ttattccttg tggtcatcta gtagtatgca aagattgtgc tccttcttta agaaagtgtc 4560
ctatttgtag gagtacaatc aagggtacag ttcgtacatt tctttcatga agaagaacca 4620
aaacatcgtc taaactttag aattaattta ttaaatgtat tataacttta acttttatcc 4680
taatttggtt tccttaaaat tttatttat ttacaactca aaaaacattg ttttgtgtaa 4740
catatttata tatgtatcta aaccatatga acatatattt tttagaaact aagagaatga 4800
taggcttttg ttcttatgaa cgaaaaagag gtagcactac aaacacaata ttcaatcaaa 4860
atttcagcat tattgaaatt gtaagtgaag taaaacttaa gatatttgag ttaaccttta 4920
agaattttaa atattttggc attgtactaa taccgggaac atgaagccag gtgtggtggt 4980
atgtgcctgt agtcccaggc tgaggcaaga gaattacttg agcccaggag tttgaatcca 5040
tcctgggcag catactgaga ccctgccttt aaaaacaaac agaacaaaaa caaaacacca 5100

-continued

```
gggacacatt tctctgtctt ttttgatcag tgtcctatac atcgaaggtg tgcatatatg   5160
ttgaatgaca ttttagggac atggtgtttt tataaagaat tctgtgagaa aaaatttaat   5220
aaagcaacaa aaattactct tattcttcat tgctttattt caatgacatt ggatagttta   5280
gtcactccca gactctttcc ataccttctt aaagcctctc aaatattgaa ctacagttta   5340
tactccttcc cataagatgc ttcttcattg acacttgtag aacacggggt caacacatca   5400
taaaatctat tatggaatgc ctgagacaag aatcaaacag tccctttagt aagtttgttt   5460
attcacttct ctattgattc attcaagaag tctcatgcca gccccaccta ttggaagaag   5520
gtctgagttt tattcttatc tctttggtat taattctgaa acttagaaag tacactggtt   5580
agcaatgctt gggaccaaca ggttgttctg gtaaataaat ctgtttcata ttgtcagtgc   5640
aacaaaatgt cccccctctgc attatgttat tggtactcaa cacgtccgag tcataactct   5700
gtcctttgct tcttatagag gtattaggtc ttcaagagca gaagtaagac tgtaataggg   5760
aatactcagg ggaaggcagg caaaggctag tcatctaaac cagttctaga tgtctgtata   5820
ggggcagatg gctctgtaag ggcagaaggg aaagacccct tcataagggt cacagctgac   5880
aatcctataa caaaagacag gttaacaaga gaaaaactta acaaatttat ttaatcacag   5940
atttacatca ccggggagcc ttcgtaatga agatccaaaa ttacagggga aactgtgcat   6000
ttttatgctt aggtttgata atgaatggac agccctgaag aatagtgatt ggaaaaaaag   6060
gatatgatct aatgggaata gacacaggtt ggggacccag caaggcctgt ctgttcagat   6120
tattcttggt ctctgtgcag cattccttcc tcctggatat agggcagggc ctgtatggga   6180
tggggatatt ataacctgct atcaagcaag gtaggtcaga gaatttattt atggccagct   6240
cttacatagt taggtgagga aagattagag tactatcttt aagatgtaag tctggcattg   6300
tggaaagatg gttccagttt ctatgaccta ccttggggaa gaggaattca agtttctgtg   6360
gcttgccttc agggagaatg aggctgagac aggagggcag gataacatca gagaaaaact   6420
ttgcttctga ggccttcact ttgggttttc tgagccccaa catctgctag tgttgtaaag   6480
agaacaatta gggaccaagt gaggggagga aagaatccat ctctgcattc tgatgctggg   6540
agacttattt ccttgaaatg caattgattt tgcctctgct aagaggctct gctggctacc   6600
catgtactag ccagtgtcct gcatgggtgc taggctgaat tatttgtaat tgtgcttagg   6660
tgatttgtaa ctcaggtata gggtatttaa atagtaggca ccctttttgc accatgtgtt   6720
ttttttttta tctagttctt gtatactaca gataatattt gaactttgtc atctcactgt   6780
aaaacttttg ttcatttctc attatggtaa taaatagcta ttataaccaa cccatttatt   6840
caaatatgtt atttccctaa gtgttatttt gacattttgt tttggaaaaa ataaatcacc   6900
atagataata aaaaaaaaaa aaaaaaaaaa aa                                  6932
```

<210> SEQ ID NO 63
<211> LENGTH: 1375
<212> TYPE: DNA
<213> ORGANISM: Homo sapiens

<400> SEQUENCE: 63

```
cgggctgtca tgctcgcaca tgtgccatta attgacaaga atgctgctca agttggctga     60
tcaagagata ggcagtgcaa aggaacagga tttgagacag cccagggttt cctcttcaag    120
taggtctaaa acattttttt ttctcattga cttccttcct gttctaactg ccagtactca    180
gaagtcagag ttgagagaca gaggcacccc ggacagagac gtgaagcact gaataaatag    240
atcagaatga ctgaaaaagc cccagagcca catgtggagg aggatgacga tgatgagctg    300
```

-continued

```
gacagcaagc tcaattataa gcctccacca cagaagtccc tgaaagagct gcaggaaatg    360
gacaaagatg atgagagtct aattaagtac aagaaaacgc tgctgggaga tggtcctgtg    420
gtgacagatc cgaaagcccc caatgtcgtt gtcacccggc tcaccctggt ttgtgagagt    480
gccccgggac caatcaccat ggaccttact ggagatctgg aagccctcaa aaaggaaacc    540
attgtgttaa aggaaggttc tgaatataga gtcaaaattc acttcaaagt gaacagggat    600
attgtgtcag gcctgaaata cgttcagcac acctacagga ctggggtgaa agtggataaa    660
gcaacattta tggttggcag ctatggacct cggcctgagg agtatgagtt cctcactcca    720
gttgaggagg ctcccaaggg catgctggcg cgaggcacgt accacaacaa gtccttcttc    780
accgacgatg acaagcaaga ccacctcagc tgggagtgga acctgtcgat taagaaggag    840
tggacagaat gaatgcatcc accccttcc ccaccccttgc cacctggaag aattctctca    900
ggcgtgttca gcaccctgtc cctcctccct gtccacagct gggtccctct tcaacactgc    960
cacatttcct tattgatgca tcttttccca ccctgtcact caacgtggtc cctagaacaa   1020
gaggcttaaa accgggcttt cacccaacct gctccctctg atcctccatc agggccagat   1080
cttccacgtc tccatctcag tacacaatca tttaatattt ccctgtctta cccctattca   1140
agcaactaga ggccagaaaa tggcaaatt atcactaaca ggtctttgac tcaggttcca    1200
gtagttcatt ctaatgccta gattcttttg tggttgttgc tggcccaatg agtccctagt   1260
cacatcccct gccagaggga gttcttcttt tgtgagagac actgtaaacg acacaagaga   1320
acaagaataa aacaataact gtgtgtgttc tggctgagaa aaaaaaaaaa aaaaa        1375
```

<210> SEQ ID NO 64
<211> LENGTH: 5425
<212> TYPE: DNA
<213> ORGANISM: Homo sapiens

<400> SEQUENCE: 64

```
cccgggccac cgcctccgcc cggctgcccg cccggactgt cgcggcccgc ggtggcgacg      60
gcggccgctg caaagtttcc ccggcggcgg cggcccgggg gcgcatcctc ccgcaactgt     120
caagcgctgg cggcggaaat gatgaggcgc tggccatttt ccgagcccgg gtttcctgcc     180
tgagccccgc tcgagcgagc cgcgagcgag gagccggcgg gcgggagagg acgcgcccag     240
ggcgggggcc cgcccgcccc ctcgggattt cgagggcccg ggggcgcgcg acgccatggg     300
ccggccgggc ccagagctcc tgtctctcag cccggccgca ccacctgggt ctccgccatg     360
aacgggcctg ccctgcagcc ctcctcgccc tcttccgcgc cctcagcctc cccggcggcg     420
gccccgcggg gctggagcga gttctgtgag ttgcacgccg tagcggcggc ccgggagctg     480
gcccgccagt actggctgtt cgcccgggag catccgcagc acgcgccgct gcgcgccgag     540
ctggtgtcgc tgcagttcac cgacctcttc cagcgctact tctgccgcga ggtgcgcgac     600
ggacgggcgc cgggccgcga ctaccgggac acaggccgtg ggccccccagc caaggccgag    660
gcgtccccgg agccaggccc cggccccgcc gcccctggcc tgcccaaggc ccgcagctct     720
gaggagctgg ccccgccgcg gccgcccggg ccctgctcct tccagcactt tcgccgcagc     780
ctccgccaca tcttccgccg ccgctcggcc ggggagctgc cagcggccca caccgctgcc     840
gcccccggga cccccggaga ggctgctgag acccccgccc ggcctggcct ggccaagaag     900
ttcctgccct ggagcctggc ccgggagccg ccacccgagg cgctgaagga ggcggtgctg     960
cgctacagcc tggccgacga ggcctccatg gacagcgggg cacgctggca gcgcgggagg    1020
```

ctggcgctgc gccgggcccc gggccccgat ggccccgacc gcgtgctgga gctcttcgac 1080
ccacccaaga gttcaaggcc caagctacaa gcagcttgct ccagcatcca ggaggtccgg 1140
tggtgcacac ggcttgagat gcctgacaac ctttacacct ttgtgctgaa ggtgaaggac 1200
cggacagaca tcatctttga ggtgggagac gagcagcagc tgaattcatg gatggctgag 1260
ctctcggagt gcacaggccg agggctggag agcacagaag cagagatgca tattccctca 1320
gccctagagc ctagcacgtc cagctcccca aggggcagca cagattccct taaccaaggt 1380
gcttctcctg gggggctgct ggacccggcc tgccagaaga cggaccattt cctgtcctgc 1440 taccctggt tccacggccc catctccaga gtgaaagcag ctcagctggt tcagctgcag 1500
ggccctgatg ctcatggagt gttcctggtg cggcagagcg agacgcggcg tggggaatac 1560
gtgctcactt tcaactttca ggggatagcc aagcacctgc gcctgtcgct gacagagcgg 1620
ggccagtgcc gtgtgcagca cctccacttt ccctcggtcg tggacatgct ccaccacttc 1680
cagcgctcgc ccatcccact cgagtgcggc gccgcctgtg atgtccggct ctccagctac 1740
gtggtagtcg tctcccaacc accaggttcc tgcaacacgg tcctcttccc tttctccctt 1800
cctcactggg attcagagtc ccttcctcac tggggttcag agttgggcct tccccacctt 1860
agttcttctg gctgtccccg ggggctcagc ccagagggtc tcccagggcg atcctcaccc 1920
cccgagcaga tcttccacct ggtgccttcg cccgaagaac tggccaacag cctgcagcac 1980
ctggagcatg agcctgtgaa tcgagcccgg gactcggact acgaaatgga ctcatcctcc 2040
cggagccacc tgcgggccat agacaatcag tacacacctc tctgaccagt gaggaattcc 2100
aggcctcaac agctgccctt gaggagcaca ggcagaagtg tgaacttgtg aatgtaattg 2160
atctttcctt ccttccagag aaagatttaa gggacactgt taactgctcg tgccagtttg 2220
gaagtgaccc ttctattagg cctgttgaag ggccctcctg taggtttcat ctatccacct 2280
ggctttctcc ttattgttta cagatgtagt tcttgttaga ggatgccgct agctcctgcc 2340
cggggtccct atgcccagtc cccgttactc ttagagaaag gagttggggt gagggccaga 2400
gctggcagtg gaaacttgtt ctctttttca ctgacactgt cacagcggat gacagacttt 2460
ctacggggag gagggggga tcatcaggaa gcccagaaca ctaacaagcg gttctcccat 2520
ctaccgtcag tccacatggc aggtctgctg tgtccacacc acagatgacc acatctaatc 2580
ctgcttctac tctcagcttt aggacaaaag ctctgtcaga ggcacaagct gaaggtcaaa 2640
aatgatttaa aacattttac ctcagactaa tttctttaaa ggattcaggt tcaaaactta 2700
accactgctt atttcagtgc actgtttcaa ctaacaccca tgctattttt gtagtcagaa 2760
acagctatgc aaaccctacc taatttacag tctgagccag catgctggct tgtctactgc 2820
atcctcggga cagtcacctg ccactgagtg gccactgtcc ttcctaaatg tcaagaagtg 2880
aagtatgtca ccctttcagg gaaattcagg caattactga aataggaggg tggcaagaac 2940
agttctatcc tggtgcctta cgaataaaaa actggattct ggtttacagc agctttacag 3000
tgatagttaa attaactggg gctaggggaa gagcaagcaa aaagggaaga aggactccta 3060
ggccctttct agtaaatcct tcagcaacaa ggctggcttg gtgccctcca agcatctaat 3120
ggcttattaa attatcccac aagtgggttt taggctcctt ttttgagcca aaatggaagc 3180
tgggaatctg gtgccataac taatgagaaa ctcctttaat agcccacaat cagtgttctg 3240
ttctagctgg ctactgcttc actggattga gaatctatct atctccttgc acacatgggc 3300
acacacaatc tccaccatcc agggaggtcc tgaagtcaaa tctctatcta tacaagtgat 3360
acaattcata gggggctggc tcctcccaga acctgtctgg aggctcagaa acgggggcag 3420

```
tgacagtgga gtcagctgct cttgggtgcc agcagagcca ttcagtacaa cccccaggct   3480
cacagcagtg gcttctagga aactgggagt ttagatcagc tttacagata catcgatcag   3540
aggctaaaat gaaacctcag cctaaaactc ataggactga ctgcctggga ggagggttag   3600
gtctgcttct tccacttata cttagtctct gtgctccaag aggtcaaatt tttgcttcta   3660
gaatttcctt ggggtctttc agagggtggg ggaacaaacc cctatgcact tttctttttt   3720
tttttttga gatggagttt ctcttgtcaa ccgggctgga gtgcagtggt gcaatcttgg   3780
ctcactgcaa cctccacctt cctggttcaa gcgattctgc ctcgacctct caagtagctg   3840
ggattacaag caccagccac catgcctggc taattttgta tttttagtag agacagggtt   3900
tcaccatgtt ggccaggctg gtctcgaatg tctgacctca ggtgatccac ccgccttggc   3960
ctcccaaagt gctgggatta caggcgcgag ccaccgcgcc cagcctacac cacttttagt   4020
accaacactc ttgggtgatt tcatggaccc taaagcagac ctgacactga tccagatttg   4080
cagtccattt ttaaggacac ctgtctttat ttcctcaaag tcaagcagct ttctctggaa   4140
aatgaatgct aattagtgtg aaccaaaaga gtaagtaaga gtctgaagtt tttttaaagg   4200
agaaagctta ttatggaaag tcactggtcc tcccctccgc acaggaaagg tacccagtag   4260
ataatgaacc aaattaagtt ccctccctcc agccagaagt taaacatctg ggatatgacg   4320
tcttcatgcc aggggcactc atttcttagc agcctctcta catacatctc tcaggtggtg   4380
ccaagaggca caccaggtag agcaaactta gcagctctga ctaacaggct gcaaagtgca   4440
agttcagatt ctgtggcaga gatttggaag gcacccacct ccagactgct tcccgtccaa   4500
gttaccagga cagctcaaaa acatgctgac agaaaactcc catggctcta ggaagaagtg   4560
acactaagcc aacacctttc tttatgtggg agcagaatca gctgatgaag gggtgggcag   4620
cagtgtgggg caggcacccc actggctgca gctagcccac cataggcaca gcacatccca   4680
ccactctcct tccagtcctg accaggcccc agccggcaac ttctaccgag agccatggct   4740
caacaccaaa ctggacagta gacatcatga tccctccagt tagctctaat tacagacccc   4800
accagtacag cttgacagct cccggcacca tcccttcctt catctgactt attgaacttt   4860
tacaaactaa cagtcaccag caccaaagaa ttaagtcaac taacctgcct tgaattttag   4920
accagcaatc catatggctt tatctggtat aaatcttctg cctttgatca tttctggacc   4980
gtaggaaaaa ggaatagcaa tcattaaaat cttgggccag agaacactat ttttacataa   5040
cagtttctta acctaaagtc aaggccttgg actcttccct gagggttgcc tgagattcct   5100
tcatgctttc tattcaggac taagtccctt actgcaaatg tgttagctct aacatctccc   5160
acaagctaga ggaacttgcg agtatattaa caaggacaca tctgacatcc tgtgtttggt   5220
tagaatatac agcacattgt gataacataa agtggattca tcttgtatca ttataggcag   5280
aaggtatttg gcaaattttt atgtattgtt ttatgtactg tacaagtaac ttattcttga   5340
ataatgcaaa ttttgctata atgtacaaat tgctatatgt gaattaaaaa gttttcagaa   5400
tcttgaaaaa aaaaaaaaaa aaaaa                                         5425
```

<210> SEQ ID NO 65
<211> LENGTH: 1697
<212> TYPE: DNA
<213> ORGANISM: Homo sapiens

<400> SEQUENCE: 65

```
atttccagtg ctagaggccc acagtttcag tctcatctgc ctccactcgg cctcagttcc     60
```

```
tcatcactgt tcctgtgctc acagtcatca attatagacc ccacaacatg cgccctgaag    120

acagaatgtt ccatatcaga gctgtgatct tgagagccct ctccttggct ttcctgctga    180

gtctccgagg agctggggcc atcaaggcgg accatgtgtc aacttatgcc gcgtttgtac    240

agacgcatag accaacaggg gagtttatgt ttgaatttga tgaagatgag atgttctatg    300

tggatctgga caagaaggag accgtctggc atctggagga gtttggccaa gccttttcct    360

ttgaggctca gggcgggctg gctaacattg ctatattgaa caacaacttg aataccttga    420

tccagcgttc caaccacact caggccacca acgatccccc tgaggtgacc gtgtttccca    480

aggagcctgt ggagctgggc cagcccaaca ccctcatctg ccacattgac aagttcttcc    540

caccagtgct caacgtcacg tggctgtgca acggggagct ggtcactgag ggtgtcgctg    600

agagcctctt cctgcccaga acagattaca gcttccacaa gttccattac ctgacctttg    660

tgccctcagc agaggacttc tatgactgca gggtggagca ctggggcttg gaccagccgc    720

tcctcaagca ctgggaggcc caagagccaa tccagatgcc tgagacaacg gagactgtgc    780

tctgtgccct gggcctggtg ctgggcctag tcggcatcat cgtgggcacc gtcctcatca    840

taaagtctct gcgttctggc catgaccccc gggcccaggg gaccctgtga aatactgtaa    900

aggtgacaaa atatctgaac agaagaggac ttaggagaga tctgaactcc agctgcccta    960

caaactccat ctcagctttt cttctcactt catgtgaaaa ctactccagt ggctgactga   1020

attgctgacc cttcaagctc tgtccttatc cattacctca aagcagtcat tccttagtaa   1080

agtttccaac aaatagaaat taatgacact ttggtagcac taatatggag attatccttt   1140

cattgagcct tttatcctct gttctccttt gaagaacccc tcactgtcac cttcccgaga   1200

ataccctaag accaataaat acttcagtat ttcagagcgg ggagactctg agtcattctt   1260

actggaagtc taggaccagg tcacatgtga atactatttc ttgaaggtgt ggtttcaacc   1320

tctgttgccg atgtggttac taaaggttct gatcccactt gaacggaaag gtctgaggat   1380

attgattcag tcctgggttt ttccctaact acaggatagg gtggggtaga gaaaggatat   1440

ttgggggaaa ttttacttgg atgaagattt tcttggatgt agtttgaaga ctgcagtgtt   1500

tgaagtctct gagggaagag atttggtctg tctggatcaa gatttcaggc agattaggat   1560

tccattcaca gcccctgagc ttccttccca aggctgtatt gtaattatag caatatttca   1620

tggaggattt ttctacatga taaactaaga gccaagaaat aaaattttta aaatgcccta   1680

aaaaaaaaaa aaaaaaa                                                  1697
```

<210> SEQ ID NO 66
<211> LENGTH: 1401
<212> TYPE: DNA
<213> ORGANISM: Homo sapiens

<400> SEQUENCE: 66

```
ggaggaggag cctctgccag actggagaga agcaggcctg agcctcccca aaggcagctc     60

ctggggactc ccaggaccac aggctgagac gagacgcagg gtggctggag gaagtgagag    120

gtgaactcag cctgggactg gctgggcgag actctccacc tgctccctgg gaccatcgcc    180

caccatggct gtggcccagc agctgcgggc cgagagtgac tttgaacagc ttccggatga    240

tgttgccatc tcggccaaca ttgctgacat cgaggagaag agaggcttca ccagccactt    300

tgttttcgtc atcgaggtga agacaaaagg aggatccaag tacctcatct accgccgcta    360

ccgccagttc catgctttgc agagcaagct ggaggagcgc ttcgggccag acagcaagag    420

cagtgccctg gcctgtaccc tgcccacact cccagccaaa gtctacgtgg gtgtgaaaca    480
```

```
ggagatcgcc gagatgcgga tacctgccct caacgcctac atgaagagcc tgctcagcct    540

gccggtctgg gtgctgatgg atgaggacgt ccggatcttc ttttaccagt cgccctatga    600

ctcagagcag gtgccccagg cactccgccg gctccgcccg cgcacccgga aagtcaagag    660

cgtgtcccca cagggcaaca gcgttgaccg catggcagct ccgagagcag aggctctatt    720

tgacttcact ggaaacagca aactggagct gaatttcaaa gctggagatg tgatcttcct    780

cctcagtcgg atcaacaaag actggctgga gggcactgtc cggggagcca cgggcatctt    840

ccctctctcc ttcgtgaaga tcctcaaaga cttccctgag gaggacgacc ccaccaactg    900

gctgcgttgc tactactacg aagacaccat cagcaccatc aaggacatcg cggtggagga    960

agatctcagc agcactcccc tattgaaaga cctgctggag ctcacaaggc gggagttcca   1020

gagagaggac atagctctga attaccggga cgctgagggg gatctggttc ggctgctgtc   1080

ggatgaggac gtagcgctca tggtgcggca ggctcgtggc ctcccctccc agaagcgcct   1140

cttcccctgg aagctgcaca tcacgcagaa ggacaactac agggtctaca acacgatgcc   1200

atgagctgac ggtgtccctg gagcagtgag gggacaccag caaaaacctt cagctctcag   1260

aggagattgg gaccaggaaa acctgggagg atgggcagac ttcctgtctt tgaggctaat   1320

ggacccgtgg ggcttgtaat ctgtctcttt ctactattta catctgattt aaataaacca   1380

ttccatctga aaggggcaaa a                                               1401
```

<210> SEQ ID NO 67
<211> LENGTH: 3372
<212> TYPE: DNA
<213> ORGANISM: Homo sapiens

<400> SEQUENCE: 67

```
taaaaccagg aagtgaagtc cccgagcacg ttagaaagcc tgacatggcc tgactcggga     60

cagctcagag cagggcagaa ctggggacac tctgggccgg ccttctgcct gcatggacgc    120

tctgaagcca ccctgtctct ggaggaacca cgagcgaggg aagaaggaca gggactcgtg    180

tggcaggaag aactcagagc cgggaagccc ccattcacta gaagcactga gagatgcggc    240

cccctcgcag ggtctgaatt tcctgctgct gttcacaaag atgcttttta tctttaactt    300

tttgttttcc ccacttccga ccccggcgtt gatctgcatc ctgacatttg gagctgccat    360

cttcttgtgg ctgatcacca gacctcaacc cgtcttacct cttcttgacc tgaacaatca    420

gtctgtggga attgagggag gagcacggaa gggggtttcc cagaagaaca atgacctaac    480

aagttgctgc ttctcagatg ccaagactat gtatgaggtt ttccaaagag gactcgctgt    540

gtctgacaat gggccctgct tgggatatag aaaaccaaac cagccctaca gatggctatc    600

ttacaaacag gtgtctgata gagcagagta cctgggttcc tgtctcttgc ataaaggtta    660

taaatcatca ccagaccagt ttgtcggcat ctttgctcag aataggccag agtggatcat    720

ctccgaattg gcttgttaca cgtactctat ggtagctgta cctctgtatg acaccttggg    780

accagaagcc atcgtacata ttgtcaacaa ggctgatatc gccatggtga tctgtgacac    840

accccaaaag gcattggtgc tgatagggaa tgtagagaaa ggcttcaccc cgagcctgaa    900

ggtgatcatc cttatggacc cctttgatga tgacctgaag caaagagggg agaagagtgg    960

aattgagatc ttatccctat atgatgctga gaacctaggc aaagagcact tcagaaaacc   1020

tgtgcctcct agcccagaag acctgagcgt catctgcttc accagtggga ccacaggtga   1080

ccccaaagga gccatgataa cccatcaaaa tattgtttca aatgctgctg cctttctcaa   1140
```

-continued

```
atgtgtggag catgcttatg agcccactcc tgatgatgtg gccatatcct acctccctct   1200
ggctcatatg tttgagagga ttgtacaggc tgttgtgtac agctgtggag ccagagttgg   1260
attcttccaa ggggatattc ggttgctggc tgacgacatg aagactttga agcccacatt   1320
gtttcccgcg gtgcctcgac tccttaacag gatctacgat aaggtacaaa atgaggccaa   1380
gacacccttg aagaagttct tgttgaagct ggctgtttcc agtaaattca aagagcttca   1440
aaagggtatc atcaggcatg atagtttctg ggacaagctc atctttgcaa agatccagga   1500
cagcctgggc ggaagggttc gtgtaattgt cactggagct gcccccatgt ccacttcagt   1560
catgacattc ttccgggcag caatgggatg tcaggtgtat gaagcttatg gtcaaacaga   1620
atgcacaggt ggctgtacat ttacattacc tggggactgg acatcaggtc acgttggggt   1680
gcccctggct tgcaattacg tgaagctgga agatgtggct gacatgaact actttacagt   1740
gaataatgaa ggagaggtct gcatcaaggg tacaaacgtg ttcaaaggat acctgaagga   1800
ccctgagaag acacaggaag ccctggacag tgatggctgg cttcacacag gagacattgg   1860
tcgctggctc ccgaatggaa ctctgaagat catcgaccgt aaaaagaaca ttttcaagct   1920
ggcccaagga gaatacattg caccagagaa gatagaaaat atctacaaca ggagtcaacc   1980
agtgttacaa atttttgtac acggggagag cttacggtca tccttagtag gagtggtggt   2040
tcctgacaca gatgtacttc cctcatttgc agccaagctt ggggtgaagg gctcctttga   2100
ggaactgtgc caaaaccaag ttgtaaggga agccatttta gaagacttgc agaaaattgg   2160
gaaagaaagt ggccttaaaa cttttgaaca ggtcaaagcc atttttcttc atccagagcc   2220
attttccatt gaaaatgggc tcttgacacc aacattgaaa gcaaagcgag gagagctttc   2280
caaatacttt cggacccaaa ttgacagcct gtatgagcac atccaggatt aggataaggt   2340
acttaagtac ctgccggccc actgtgcact gcttgtgaga aaatggatta aaaactattc   2400
ttacatttgt tttgcctttc ctcctatttt tttttaacct gttaaactct aaagccatag   2460
cttttgtttt atattgagac atataatgtg taaacttagt tcccaaataa atcaatcctg   2520
tctttcccat cttcgatgtt gctaatatta aggcttcagg gctactttta tcaacatgcc   2580
tgtcttcaag atcccagttt atgttctgtg tccttcctca tgatttccaa ccttaatact   2640
attagtaacc acaagttcaa gggtcaaagg gaccctctgt gccttcttct ttgttttgtg   2700
ataaacataa cttgccaaca gtctctatgc ttatttacat cttctactgt tcaaactaag   2760
agatttttaa attctgaaaa actgcttaca attcatgttt tctagccact ccacaaacca   2820
ctaaaatttt agttttagcc tatcactcat gtcaatcata tctatgagac aaatgtctcc   2880
gatgctcttc tgcgtaaatt aaattgtgta ctgaagggaa aagtttgatc ataccaaaca   2940
tttcctaaac tctctagtta gatatctgac ttgggagtat taaaaattgg gtctatgaca   3000
tattgtccaa aaggaatgct gttcttaaag cattatttac agtaggaact ggggagtaaa   3060
tctgttccct acagtttgct gctgagctgg aagctgtggg ggaaggagtt gacaggtggg   3120
cccagtgaac ttttccagta aatgaagcaa gcactgaata aaaacctcct gaactgggaa   3180
caaagatcta caggcaagca agatgcccac acaacaggct tattttctgt gaaggaacca   3240
actgatctcc cccacccttg gattagagtt cctgctctac cttacccaca gataacacat   3300
gttgtttcta cttgtaaatg taaagtcttt aaaataaact attacagata cttaaaaaaa   3360
aaaaaaaaaa aa                                                       3372
```

<210> SEQ ID NO 68
<211> LENGTH: 1855

<212> TYPE: DNA
<213> ORGANISM: Homo sapiens

<400> SEQUENCE: 68
ctctgaaggg agctactcag aagcgggagt ctccgagaga agaaaagcag gtggaaggag 60
aggaagcgga tgccgtgggg tttacagcag gaaaatccgt ggagacagca gatccgagaa 120
gcggcgatgt ttgcgtagaa ccctgtacgt gcttccttcg gcctgtcgct cttcccttct 180
ctctgaccag caccatgctt ctcctggtga caagccttct gctctgtgag ttaccacacc 240
cagcattcct cctgatccca gagaaatcgg atctgcgaac agtggcacca gcctctagtc 300
tcaatgtgag gtttgactcc aggacgatga atttaagctg ggactgccaa gaaaacacaa 360
ccttcagcaa gtgtttctta actgacaaga agaacagagt cgtggaaccc aggctcagta 420
acaacgaatg ttcgtgcaca tttcgtgaaa tttgtctgca tgaaggagtc acatttgagg 480
ttcacgtgaa tactagtcaa agaggatttc aacagaaact gctttatcca aattcaggaa 540
gggagggtac cgctgctcag aatttctcct gtttcatcta caatgcggat ttaatgaact 600
gtacctgggc gaggggtccg acggcccccc gtgacgtcca gtatttttg tacatacgaa 660 actcaaagag aaggagggag atccggtgtc cttattacat acaagactca ggaacccatg 720
tgggatgtca cctggataac ctgtcaggat taacgtctcg caattacttt ctggttaacg 780
gaaccagccg agaaattggc atccaattct ttgattcact tttggacaca aagaaaatag 840
aacgattcaa ccctcccagc aatgtcaccg tacgttgcaa cacgacgcac tgcctcgtac 900
ggtggaaaca gcccaggacc tatcagaagc tgtcgtacct ggactttcag taccagctgg 960
acgtccacag aaagaatacc cagcctggca cggaaaacct actgattaat gtttctggtg 1020
atttggaaaa tagatacaac tttccaagct ctgagcccag agcaaaacac agtgtgaaga 1080
tcagagctgc agacgtccgc atcttgaatt ggagctcctg gagtgaagcc attgaatttg 1140
gttctgacga cgggaacctc ggctctgtgt acatttatgt gctcctaatc gtgggaaccc 1200
ttgtctgtgg catcgtcctc ggcttcctct ttaaaaggtt ccttaggata cagcggctgt 1260
tcccgccagt tccacagatc aaagacaaac tgaatgataa ccatgaggtg gaagacgaga 1320
tcatctggga ggaattcacc ccagaggaag ggaaaggcta ccgcgaagag gtcttgaccg 1380
tgaaggaaat tacctgagac ccagagggtg taggaatggc atggacatct ccgcctccgc 1440
gacacggggg aactgttttc ttgatgatgc tgtgaacctt tatatcattt tctatgtttt 1500
tatttaaaaa catgacattt ggggccaggc gcggtggctc acgcctgtaa tcccagcact 1560
ttgggaggcc aaggcaggcg gatcacctga ggtcaggagt tcaagaccag cctgcccaac 1620
atggtgaaac cccatctgga ctaaaaatgc agaaatttac ccaggcacgg cggcggacgc 1680
ccatcatccc agctacttgg gaggctgagg caggagaatt gcttgaaccc gtgaggcgga 1740
ggttgtagtg agccaagatc gcaccattgc acaccaacct gcgtgacaga gcaagattgc 1800
atctcaaaac aaacaataat aataaataat aaaaacctga tatttggctg ggcaa 1855

<210> SEQ ID NO 69
<211> LENGTH: 2240
<212> TYPE: DNA
<213> ORGANISM: Homo sapiens

<400> SEQUENCE: 69
ggagggcagc cagcagcttc cccttctctg ccctgctcca ggcaccaggc tctttcccct 60
tcagtgtctc agaggagggg acggcagcac catggacccc cgcttgtcca ctgtccgcca 120

-continued

```
gacctgctgc tgcttcaatg tccgcatcgc aaccaccgcc ctggccatct accatgtgat    180
catgagcgtc ttgttgttca tcgagcactc agtagaggtg gcccatggca aggcgtcctg    240
caagctctcc cagatgggct acctcaggat cgctgacctg atctccagct tcctgctcat    300
caccatgctc ttcatcatca gcctgagcct actgatcggc gtagtcaaga accgggagaa    360
gtacctgctg cccttcctgt ccctgcaaat catggactat ctcctgtgcc tgctcaccct    420
gctgggctcc tacattgagc tgcccgccta cctcaagttg gcctcccgga gccgtgctag    480
ctcctccaag ttcccccctga tgacgctgca gctgctggac ttctgcctga gcatcctgac    540
cctctgcagc tcctacatgg aagtgcccac ctatctcaac ttcaagtcca tgaaccacat    600
gaattacctc cccagccagg aggatatgcc tcataaccag ttcatcaaga tgatgatcat    660
cttttccatc gccttcatca ctgtccttat cttcaaggtc tacatgttca agtgcgtgtg    720
gcggtgctac agattgatca agtgcatgaa ctcggtggag gagaagagaa actccaagat    780
gctccagaag gtggtcctgc cgtcctacga ggaagccctg tctttgccat cgaagacccc    840
agagggggggc ccagcaccac ccccatactc agaggtgtga ccctcgccag gccccagccc    900
cagtgctggg aggggtggag ctgcctcata atctgctttt ttgctttggt ggcccctgtg    960
gcctgggtgg gccctcccgc ccctccctgg caggacaatc tgcttgtgtc tccctcgctg   1020
gcctgctcct cctgcagggc ctgtgagctg ctcacaactg ggtcaacgct ttaggctgag   1080
tcactcctcg ggtctctcca taattcagcc caacaatgct tggtttattt caatcagctc   1140
tgacacttgt ttagacgatt ggccattcta aagttggtga gtttgtcaag caactatcga   1200
cttgatcagt tcagccaagc aactgacaaa tcaaaaaccc acttgtcagt tcagtaaaat   1260
aatttggtca aacaacagtc tattgcattg atttataaat agttgtcagt tcacatagca   1320
atttaatcaa gtaatcatta attagttacc ccctatatat aaatatatgt aatcaatttc   1380
ttcaaatagc ttgcttacat gataatcaat tagccaacca tgagtcattt agaatagtga   1440
taaatagaat acacagaata gtgatgaaat tcaatttaaa aaatcacgtt agcctccaaa   1500
ccatttaatt caaatgaacc catcaactgg atgccaactc tggcgaatgt aggacctctg   1560
agtggctgta taattgttaa ttcaaatgaa attcatttaa acagttgaca aactgtcatt   1620
caacaattag ctccaggaaa taacagttat ttcatcataa aacagtccct tcaaacacac   1680
aattgttctg ctgaagagtt gtcatcaaca atccaatgct cacctattca gttgctctgt   1740
ggtcagtgtg gctgcataac agtggattcc atgaaaggag tcattttagt gatgagctgc   1800
cagtccattc ccaggccagg ctgtcgctgg ccatccattc agtcgattca gtcataggcg   1860
aatctgttct gcccgaggct tgtggtcaag caaaaattca gccctgaaat caggcacatc   1920
tgttcgttgg actaaaccca caggttagtt cagtcaaagc aggcaacccc cttgtgggca   1980
ctgaccctgc cactggggtc atggcggttg tggcagctgg ggaggtttgg ccccaacagc   2040
cctcctgtgc ctgcttccct gtgtgtcggg gtcctccagg gagctgaccc agaggtggag   2100
gccacggagg cagggtctct ggggactgtc ggggggtaca gagggagaag gctctgcaag   2160
agctccctgg caataccccc ttgtgtaatt gctttgtgtg cgacagggag gaagtttcaa   2220
taaagcagca acaagcttct                                               2240
```

<210> SEQ ID NO 70
<211> LENGTH: 2135
<212> TYPE: DNA
<213> ORGANISM: Homo sapiens

<400> SEQUENCE: 70

-continued

```
aaagccgacc gagacggagc cgctgtcaac tctccaactc agctcagctg atcggttgcc     60
gccgccgccg ccgccagatt ctggaggcga agaacgcaaa gctgagaaca tggacgttaa    120
tatcgcccca ctccgcgcct gggacgattt cttcccgggt tccgatcgct ttgcccggcc    180
ggacttcagg gacatttcca aatggaacaa ccgcgtagtg agcaacctgc tctattacca    240
gaccaactac ctggtggtgg ctgccatgat gatttccatt gtggggtttc tgagtccctt    300
caacatgatc ctgggaggaa tcgtggtggt gctggtgttc acagggtttg tgtgggcagc    360
ccacaataaa gacgtccttc gccggatgaa gaagcgctac cccacgacgt tcgttatggt    420
ggtcatgttg gcgagctatt tccttatctc catgtttgga ggagtcatgg tctttgtgtt    480
tggcattact tttcctttgc tgttgatgtt tatccatgca tcgttgagac ttcggaacct    540
caagaacaaa ctggagaata aaatggaagg aataggtttg aagaggacac cgatgggcat    600
tgtcctggat gccctagaac agcaggaaga aggcatcaac agactcactg actatatcag    660
caaagtgaag gaataaacat aacttacctg agctagggtt gcagcagaaa ttgagttgca    720
gcttgccctt gtccagacct atgttctgct tgcgtttttg aaacaggagg tgcacgtacc    780
acccaattat ctatggcagc atgcatgtat aggccgaact attatcagct ctgatgtttc    840
agagagaaga cctcagaaac cgaaagaaaa ccaccaccct cctattgtgt ctgaagtttc    900
acgtgtgttt atgaaatcta atgggaaatg gatcacacga tttctttaag ggaattaaaa    960
aaaataaaag aattacggct tttacagcaa caatacgatt atcttatagg aaaaaaaaaa   1020
tcattgtaaa gtatcaagac aatacgagta aatgaaaagg ctgttaaagt agatgacatc   1080
atgtgttagc ctgttcctaa tcccctagaa ttgtaatgtg tgggatataa attagttttt   1140
attattctct taaaaatcaa agatgatctc tatcactttg ccacctgttt gatgtgcagt   1200
ggaaactggt taagccagtt gttcatactt cctttacaaa tataaagata gctgtttagg   1260
atattttgtt acatttttgt aaatttttga aatgctagta atgtgttttc accagcaagt   1320
atttgttgca aacttaatgt cattttcctt aagatggtta cagctatgta acctgtatta   1380
ttctggacgg acttattaaa atacaaacag acaaaaaata aaacaaaact tgagttctat   1440
ttaccttgca catttttgt tgttacagtg aaaaaaatgg tccaagaaaa tgtttgccat   1500
ttttgcattg tttcgttttt aactggaaca tttagaaaga aggaaatgaa tgtgcatttt   1560
attaattcct taggggcaca aggaggacaa taatagctga tcttttgaaa tttgaaaaac   1620
gtctttagat gaccaagcaa aaagacttta aaaaatggta atgaaaatgg aatgcagcta   1680
ctgcagctaa taaaaaattt tagatagcaa ttgttacaac catatgcctt tatagctaga   1740
cattagaatt atgatagcat gagtttatac attctattat ttttcctccc tttctcatgt   1800
ttttataaat aggtaataaa aaatgttttg cctgccaatt gaatgatttc gtagctgaag   1860
tagaaacatt taggtttctg tagcattaaa ttgtgaagac aactggagtg gtacttactg   1920
aagaaactct ctgtatgtcc tagaataaga agcaatgatg tgctgcttct gatttttctt   1980
gcattttaaa ttctcagcca acctacagcc atgatcttta gcacagtgat atcaccatga   2040
cttcacagac atggtctaga atctgtaccc ttacccacat atgaagaata aaattgatta   2100
aaggtttttt tggtgagact ttatttaaaa aaaaa                               2135
```

<210> SEQ ID NO 71
<211> LENGTH: 2120
<212> TYPE: DNA
<213> ORGANISM: Homo sapiens

<400> SEQUENCE: 71
aattaaacac ttggagatat tccttgagga atgaaatgct tggtgagcag gcatacagtg 60
agggaaacac tggatatggt gtttcagaga atgtcagtgg aagcaggggt tattaaatgc 120
aaagcagctg tgctttggga gcagaagcaa cccttctcca ttgaggaaat agaagttgcc 180
ccaccaaaga ctaaagaagt tcgcattaag attttggcca caggaatctg tcgcacagat 240
gaccatgtga taaaaggaac aatggtgtcc aagtttccag tgattgtggg acatgaggca 300
actgggattg tagagagcat tggagaagga gtgactacag tgaaaccagg tgacaaagtc 360
atccctctct ttctgccaca atgtagagaa tgcaatgctt gtcgcaaccc agatggcaac 420
ctttgcatta ggagcgatat tactggtcgt ggagtactgg ctgatggcac caccagattt 480
acatgcaagg gcaaaccagt ccaccacttc atgaacacca gtacatttac cgagtacaca 540
gtggtggatg aatcttctgt tgctaagatt gatgatgcag ctcctcctga gaaagtctgt 600
ttaattggct gtgggttttc cactggatat ggcgctgctg ttaaaactgg caaggtcaaa 660
cctggttcca cttgcgtcgt ctttggcctg ggaggagttg gcctgtcagt catcatgggc 720
tgtaagtcag ctggtgcatc taggatcatt gggattgacc tcaacaaaga caaatttgag 780
aaggccatgg ctgtaggtgc cactgagtgt atcagtccca aggactctac caaacccatc 840
agtgaggtgc tgtcagaaat gacaggcaac aacgtgggat acacctttga agttattggg 900
catcttgaaa ccatgattga tgccctggca tcctgccaca tgaactatgg gaccagcgtg 960
gttgtaggag ttcctccatc agccaagatg ctcacctatg acccgatgtt gctcttcact 1020
ggacgcacat ggaagggatg tgtctttgga ggtttgaaaa gcagagatga tgtcccaaaa 1080
ctagtgactg agttcctggc aaagaaattt gacctggacc agttgataac tcatgtttta 1140
ccatttaaaa aaatcagtga aggatttgag ctgctcaatt caggacaaag cattcgaacg 1200
gtcctgacgt tttgagatcc aaagtggcag gaggtctgtg ttgtcatggt gaactggagt 1260
ttctcttgtg agagttccct catctgaaat catgtatctg tctcacaaat acaagcataa 1320
gtagaagatt tgttgaagac atagaaccct tataaagaat tattaacctt tataaacatt 1380
taaagtcttg tgagcacctg ggaattagta taataacaat gttaatattt ttgatttaca 1440
ttttgtaagg ctataattgt atcttttaag aaaacataca cttggatttc tatgttgaaa 1500
tggagatttt taagagtttt aaccagctgc tgcagatata taactcaaaa cagatatagc 1560
gtataaagat atagtaaatg catctcctag agtaatattc acttaacaca ttgaaactat 1620
tattttttag atttgaatat aaatgtattt tttaaacact tgttatgagt taagttggat 1680
tacattttga aatcagttca ttccatgatg catattactg gattagatta agaaagacag 1740
aaaagattaa gggacgggca catttttcaa cgattaagaa tcatcattac ataacttggt 1800
gaaactgaaa aagtatatca tatgggtaca caaggctatt tgccagcata tattaatatt 1860
ttagaaaata ttccttttgt aatactgaat ataaacatag agctagaatc atattatcat 1920
acttatcata atgttcaatt tgatacagta gaattgcaag tccctaagtc cctattcact 1980
gtgcttagta gtgactccat ttaataaaaa gtgtttttag tttttaacaa ctacactgat 2040
gtatctatat atatctataa catgttaaaa attcttaaga aaattaaaaa ttatataaaa 2100
tgaaaaaaaa aaaaaaaaaa 2120

<210> SEQ ID NO 72
<211> LENGTH: 5872
<212> TYPE: DNA
<213> ORGANISM: Homo sapiens

<400> SEQUENCE: 72
gggaatgctt tgtgcagcgc gcttgcgcgg tgtggcggcc gatgccgcta taaaggcttg 60
ttttgctgca gggctcatgc tcgggagcgt ggttgagcgg ctggcgcggt tgtcctggag 120
caggggcgca ggaattctga tgtgaaacta acagtctgtg agccctggaa cctccactca 180
gagaagatga aggatatcga cataggaaaa gagtatatca tccccagtcc tgggtataga 240
agtgtgaggg agagaaccag cacttctggg acgcacagag accgtgaaga ttccaagttc 300
aggagaactc gaccgttgga atgccaagat gccttggaaa cagcagcccg agccgagggc 360
ctctctcttg atgcctccat gcattctcag ctcagaatcc tggatgagga gcatcccaag 420
ggaaagtacc atcatggctt gagtgctctg aagcccatcc ggactacttc caaacaccag 480
cacccagtgg acaatgctgg gctttttttcc tgtatgactt tttcgtggct ttcttctctg 540
gcccgtgtgg cccacaagaa gggggagctc tcaatggaag acgtgtggtc tctgtccaag 600
cacgagtctt ctgacgtgaa ctgcagaaga ctagagagac tgtggcaaga agagctgaat 660
gaagttgggc cagacgctgc ttccctgcga agggttgtgt ggatcttctg ccgcaccagg 720
ctcatcctgt ccatcgtgtg cctgatgatc acgcagctgg ctggcttcag tggaccagcc 780
ttcatggtga aacacctctt ggagtatacc caggcaacag agtctaacct gcagtacagc 840
ttgttgttag tgctgggcct cctcctgacg gaaatcgtgc ggtcttggtc gcttgcactg 900
acttgggcat tgaattaccg aaccggtgtc cgcttgcggg gggccatcct aaccatggca 960
tttaagaaga tccttaagtt aaagaacatt aaagagaaat ccctgggtga gctcatcaac 1020
atttgctcca acgatgggca gagaatgttt gaggcagcag ccgttggcag cctgctggct 1080
ggaggacccg ttgttgccat cttaggcatg atttataatg taattattct gggaccaaca 1140
ggcttcctgg gatcagctgt ttttatcctc ttttacccag caatgatgtt tgcatcacgg 1200
ctcacagcat atttcaggag aaaatgcgtg gccgccacgg atgaacgtgt ccagaagatg 1260
aatgaagttc ttacttacat taaatttatc aaaatgtatg cctgggtcaa agcatttttct 1320
cagagtgttc aaaaaatccg cgaggaggag cgtcggatat tggaaaaagc tgggtacttc 1380
cagagcatca ctgtgggtgt ggctcccatt gtggtggtga ttgccagcgt ggtgaccttc 1440
tctgttcata tgaccctggg cttcgatctg acagcagcac aggctttcac agtggtgaca 1500
gtcttcaatt ccatgacttt tgctttgaaa gtaacaccgt tttcagtaaa gtccctctca 1560
gaagcctcag tggctgttga cagatttaag agtttgtttc taatggaaga ggttcacatg 1620
ataaagaaca aaccagccag tcctcacatc aagatagaga tgaaaaatgc caccttggca 1680
tgggactcct cccactccag tatccagaac tcgcccaagc tgacccccaa aatgaaaaaa 1740
gacaagaggg cttccagggg caagaaagag aaggtgaggc agctgcagcg cactgagcat 1800
caggcggtgc tggcagagca gaaaggccac ctcctcctgg acagtgacga gcggcccagt 1860
cccgaagagg aagaaggcaa gcacatccac ctgggccacc tgcgcttaca gaggacactg 1920
cacagcatcg atctggagat ccaagagggt aaactggttg gaatctgtgg cagtgtggga 1980
agtggaaaaa cctctctcat ttcagccatt ttaggccaga tgacgcttct agagggcagc 2040
attgcaatca gtggaacctt cgcttatgtg gcccagcagg cctggatcct caatgctact 2100
ctgagagaca acatcctgtt tgggaaggaa tatgatgaag aaagatacaa ctctgtgctg 2160
aacagctgct gcctgaggcc tgacctggcc attcttccca gcagcgacct gacggagatt 2220
ggagagcgag gagccaacct gagcggtggg cagcgccaga ggatcagcct tgcccgggcc 2280

-continued

```
ttgtatagtg acaggagcat ctacatcctg gacgaccccc tcagtgcctt agatgcccat   2340
gtgggcaacc acatcttcaa tagtgctatc cggaaacatc tcaagtccaa gacagttctg   2400
tttgttaccc accagttaca gtacctggtt gactgtgatg aagtgatctt catgaaagag   2460
ggctgtatta cggaaagagg cacccatgag gaactgatga atttaaatgg tgactatgct   2520
accattttta ataacctgtt gctgggagag acaccgccag ttgagatcaa ttcaaaaaag   2580
gaaaccagtg gttcacagaa gaagtcacaa gacaagggtc ctaaaacagg atcagtaaag   2640
aaggaaaaag cagtaaagcc agaggaaggg cagcttgtgc agctggaaga gaaagggcag   2700
ggttcagtgc cctggtcagt atatggtgtc tacatccagg ctgctggggg ccccttggca   2760
ttcctggtta ttatggccct tttcatgctg aatgtaggca gcaccgcctt cagcacctgg   2820
tggttgagtt actggatcaa gcaaggaagc gggaacacca ctgtgactcg agggaacgag   2880
acctcggtga gtgacagcat gaaggacaat cctcatatgc agtactatgc cagcatctac   2940
gccctctcca tggcagtcat gctgatcctg aaagccattc gaggagttgt ctttgtcaag   3000
ggcacgctgc gagcttcctc ccggctgcat gacgagcttt tccgaaggat ccttcgaagc   3060
cctatgaagt tttttgacac gacccccaca gggaggattc tcaacaggtt ttccaaagac   3120
atggatgaag ttgacgtgcg gctgccgttc caggccgaga tgttcatcca gaacgttatc   3180
ctggtgttct tctgtgtggg aatgatcgca ggagtcttcc cgtggttcct tgtggcagtg   3240
gggcccottg tcatcctctt ttcagtcctg cacattgtct ccagggtcct gattcgggag   3300
ctgaagcgtc tggacaatat cacgcagtca cctttcctct cccacatcac gtccagcata   3360
cagggccttg ccaccatcca cgcctacaat aaagggcagg agtttctgca cagataccag   3420
gagctgctgg atgacaacca agctcctttt tttttgttta cgtgtgcgat gcggtggctg   3480
gctgtgcggc tggacctcat cagcatcgcc ctcatcacca ccacggggct gatgatcgtt   3540
cttatgcacg ggcagattcc cccagcctat gcgggtctcg ccatctctta tgctgtccag   3600
ttaacggggc tgttccagtt tacggtcaga ctggcatctg agacagaagc tcgattcacc   3660
tcggtggaga ggatcaatca ctacattaag actctgtcct tggaagcacc tgccagaatt   3720
aagaacaagg ctccctcccc tgactggccc caggagggag aggtgacctt tgagaacgca   3780
gagatgaggt accgagaaaa cctccctctc gtcctaaaga aagtatcctt cacgatcaaa   3840
cctaaagaga agattggcat tgtggggcgg acaggatcag ggaagtcctc gctggggatg   3900
gccctcttcc gtctggtgga gttatctgga ggctgcatca agattgatgg agtgagaatc   3960
agtgatattg gccttgccga cctccgaagc aaactctcta tcattcctca agagccggtg   4020
ctgttcagtg gcactgtcag atcaaatttg gaccccttca accagtacac tgaagaccag   4080
atttgggatg ccctggagag gacacacatg aaagaatgta ttgctcagct acctctgaaa   4140
cttgaatctg aagtgatgga gaatggggat aacttctcag tgggggaacg gcagctcttg   4200
tgcatagcta gagccctgct ccgccactgt aagattctga ttttagatga agccacagct   4260
gccatggaca cagagacaga cttattgatt caagagacca tccgagaagc atttgcagac   4320
tgtaccatgc tgaccattgc ccatcgcctg cacacggttc taggctccga taggattatg   4380
gtgctggccc agggacaggt ggtggagttt gacaccccat cggtccttct gtccaacgac   4440
agttcccgat tctatgccat gtttgctgct gcagagaaca aggtcgctgt caagggctga   4500
ctcctccctg ttgacgaagt ctcttttctt tagagcattg ccattccctg cctggggcgg   4560
gcccctcatc gcgtcctcct accgaaacct tgcctttctc gattttatct ttcgcacagc   4620
agttccggat tggcttgtgt gtttcacttt tagggagagt catattttga ttattgtatt   4680
```

```
tattccatat tcatgtaaac aaaatttagt ttttgttctt aattgcactc taaaaggttc   4740
agggaaccgt tattataatt gtatcagagg cctataatga agctttatac gtgtagctat   4800
atctatatat aattctgtac atagcctata tttacagtga aaatgtaagc tgtttatttt   4860
atattaaaat aagcactgtg ctaataacag tgcatattcc tttctatcat ttttgtacag   4920
tttgctgtac tagagatctg gttttgctat tagactgtag gaagagtagc atttcattct   4980
tctctagctg gtggtttcac ggtgccaggt tttctgggtg tccaaaggaa gacgtgtggc   5040
aatagtgggc cctccgacag ccccctctgc cgcctcccca cggccgctcc aggggtggct   5100
ggagacgggt gggcggctgg agaccatgca gagcgccgtg agttctcagg gctcctgcct   5160
tctgtcctgg tgtcacttac tgtttctgtc aggagagcag cggggcgaag cccaggcccc   5220
ttttcactcc ctccatcaag aatggggatc acagagacat tcctccgagc cggggagttt   5280
ctttcctgcc ttcttctttt tgctgttgtt tctaaacaag aatcagtcta tccacagaga   5340
gtcccactgc ctcaggttcc tatggctggc cactgcacag agctctccag ctccaagacc   5400
tgttggttcc aagccctgga gccaactgct gctttttgag gtggcacttt ttcatttgcc   5460
tattcccaca cctccacagt tcagtggcag ggctcaggat ttcgtgggtc tgttttcctt   5520
tctcaccgca gtcgtcgcac agtctctctc tctctctccc ctcaaagtct gcaactttaa   5580
gcagctcttg ctaatcagtg tctcacactg gcgtagaagt ttttgtactg taaagagacc   5640
tacctcaggt tgctggttgc tgtgtggttt ggtgtgttcc cgcaaacccc ctttgtgctg   5700
tggggctggt agctcaggtg ggcgtggtca ctgctgtcat caattgaatg gtcagcgttg   5760
catgtcgtga ccaactagac attctgtcgc cttagcatgt ttgctgaaca ccttgtggaa   5820
gcaaaaatct gaaaatgtga ataaaattat tttggatttt gtaaaaaaaa aa           5872
```

<210> SEQ ID NO 73
<211> LENGTH: 2520
<212> TYPE: DNA
<213> ORGANISM: Homo sapiens

<400> SEQUENCE: 73

```
ggatggttgt ctattaactt gttcaaaaaa gtatcaggag ttgtcaaggc agagaagaga     60
gtgtttgcaa aagggggaaa gtagtttgct gcctctttaa gactaggact gagagaaaga    120
agaggagaga gaaagaaagg gagagaagtt tgagccccag gcttaagcct ttccaaaaaa    180
taataataac aatcatcggc ggcggcagga tcggccagag gaggagggaa gcgctttttt    240
tgatcctgat tccagtttgc ctctctcttt ttttccccca aattattctt cgcctgattt    300
tcctcgcgga gccctgcgct cccgacaccc ccgcccgcct cccctcctcc tctccccccg    360
cccgcgggcc ccccaaagtc ccggccgggc cgagggtcgg cggccgccgg cgggccgggc    420
ccgcgcacag cgcccgcatg tacaacatga tggagacgga gctgaagccg ccgggcccgc    480
agcaaacttc ggggggcggc ggcggcaact ccaccgcggc ggcggccggc ggcaaccaga    540
aaaacagccc ggaccgcgtc aagcggccca tgaatgcctt catggtgtgg tcccgcgggc    600
agcggcgcaa gatggcccag gagaacccca agatgcacaa ctcggagatc agcaagcgcc    660
tgggcgccga gtggaaactt ttgtcggaga cggagaagcg gccgttcatc gacgaggcta    720
agcggctgcg agcgctgcac atgaaggagc acccggatta taaataccgg ccccggcgga    780
aaaccaagac gctcatgaag aaggataagt acacgctgcc cggcgggctg ctggcccccg    840
gcggcaatag catggcgagc ggggtcgggg tgggcgccgg cctgggcgcg ggcgtgaacc    900
```

agcgcatgga cagttacgcg cacatgaacg gctggagcaa cggcagctac agcatgatgc 960
aggaccagct gggctacccg cagcacccgg gcctcaatgc gcacggcgca gcgcagatgc 1020
agcccatgca ccgctacgac gtgagcgccc tgcagtacaa ctccatgacc agctcgcaga 1080
cctacatgaa cggctcgccc acctacagca tgtcctactc gcagcagggc acccctggca 1140
tggctcttgg ctccatgggt tcggtggtca agtccgaggc cagctccagc ccccctgtgg 1200
ttacctcttc ctcccactcc agggcgccct gccaggccgg ggacctccgg gacatgatca 1260
gcatgtatct ccccggcgcc gaggtgccgg aacccgccgc ccccagcaga cttcacatgt 1320
cccagcacta ccagagcggc ccggtgcccg gcacggccat taacggcaca ctgcccctct 1380
cacacatgtg agggccggac agcgaactgg aggggggaga aattttcaaa gaaaaacgag 1440
ggaaatggga ggggtgcaaa agaggagagt aagaaacagc atggagaaaa cccggtacgc 1500
tcaaaaagaa aaaggaaaaa aaaaaatccc atcacccaca gcaaatgaca gctgcaaaag 1560
agaacaccaa tcccatccac actcacgcaa aaaccgcgat gccgacaaga aaacttttat 1620
gagagagatc ctggacttct ttttggggga ctatttttgt acagagaaaa cctggggagg 1680
gtggggaggg cgggggaatg gaccttgtat agatctggag gaaagaaagc tacgaaaaac 1740
tttttaaaag ttctagtggt acggtaggag ctttgcagga agtttgcaaa agtctttacc 1800
aataatattt agagctagtc tccaagcgac gaaaaaaatg ttttaatatt tgcaagcaac 1860
ttttgtacag tatttatcga gataaacatg gcaatcaaaa tgtccattgt ttataagctg 1920
agaatttgcc aatatttttc aaggagaggc ttcttgctga attttgattc tgcagctgaa 1980
atttaggaca gttgcaaacg tgaaaagaag aaaattattc aaatttggac attttaattg 2040
tttaaaaatt gtacaaaagg aaaaaattag aataagtact ggcgaaccat ctctgtggtc 2100
ttgtttaaaa agggcaaaag ttttagactg tactaaattt tataacttac tgttaaaagc 2160
aaaaatggcc atgcaggttg acaccgttgg taatttataa tagcttttgt tcgatcccaa 2220
ctttccattt tgttcagata aaaaaaacca tgaaattact gtgtttgaaa tattttctta 2280
tggtttgtaa tatttctgta aatttattgt gatattttaa ggttttcccc cctttatttt 2340
ccgtagttgt attttaaaag attcggctct gtattatttg aatcagtctg ccgagaatcc 2400
atgtatatat ttgaactaat atcatcctta taacaggtac attttcaact taagttttta 2460
ctccattatg cacagtttga gataaataaa tttttgaaat atggacactg aaaaaaaaaa 2520

<210> SEQ ID NO 74
<211> LENGTH: 2032
<212> TYPE: DNA
<213> ORGANISM: Homo sapiens

<400> SEQUENCE: 74
ggactctggg acgctcagac gccgcgcggg gcggggattg gtctgtggtc ctctctcggc 60
tcctcgcggc tcgcggcggc cgacggttcc tgggacacct gcttgcttgg cccgtccggc 120
ggctcagggc ttctctgctg cgctcccggt tcgctggacg ggaagaaggg ctgggccgtc 180
ccgtcccgtc cccatcggaa ccccaagtcg cgccgctgac ccgtcgcagg gcgagatgag 240
cgcggacgca gcggccgggg cgcccctgcc ccggctctgc tgcctggaga agggtccgaa 300
cggctacggc ttccacctgc acggggagaa gggcaagttg ggccagtaca tccggctggt 360
ggagcccggc tcgccggccg agaaggcggg gctgctggcg ggggaccggc tggtggaggt 420
gaacggcgaa aacgtggaga aggagaccca ccagcaggtg gtgagccgca tccgcgccgc 480
actcaacgcc gtgcgcctgc tggtggtcga ccccgagacg gacgagcagc tgcagaagct 540

```
cggcgtccag gtccgagagg agctgctgcg cgcccaggaa gcgccggggc aggccgagcc    600
gccggccgcc gccgaggtgc agggggctgg caacgaaaat gagcctcgcg aggccgacaa    660
gagccacccg gagcagcgcg agcttcggcc tcggctctgt accatgaaga agggccccag    720
tggctatggc ttcaacctgc acagcgacaa gtccaagcca ggccagttca tccggtcagt    780
ggacccagac tccccggctg aggcttcagg gctccgggcc caggatcgca ttgtggaggt    840
gaacggggtc tgcatggagg ggaagcagca tggggacgtg gtgtccgcca tcagggctgg    900
cggggacgag accaagctgc tggtggtgga cagggaaact gacgagttct tcaagaaatg    960
cagagtgatc ccatctcagg agcacctgaa tggtcccctg cctgtgccct tcaccaatgg   1020
ggagatacag aaggagaaca gtcgtgaagc cctggcagag gcagccttgg agagccccag   1080
gccagccctg gtgagatccg cctccagtga caccagcgag gagctgaatt cccaagacag   1140
ccccccaaaa caggactcca cagcgccctc gtctacctcc tcctccgacc ccatcctaga   1200
cttcaacatc tccctggcca tggccaaaga gagggcccac cagaaacgca gcagcaaacg   1260
ggccccgcag atggactgga gcaagaaaaa cgaactcttc agcaacctct gagcgccctg   1320
ctgccaccca gtgactggca gggccgagcc agcattccac cccacctttt tccttctccc   1380
caattactcc cctgaatcaa tgtacaaatc agcacccaca tcccctttct tgacaaatga   1440
tttttctaga gaactatgtt cttccctgac tttagggaag gtgaatgtgt tcccgtcctc   1500
ccgcagtcag aaaggagact ctgcctccct cctcctcact gagtgcctca tcctaccggg   1560
tgtccctttg ccaccctgcc tgggacatcg ctggaacctg caccatgcca ggatcatggg   1620
accaggcgag agggcaccct cccttcctcc cccatgtgat aaatgggtcc agggctgatc   1680
aaagaactct gactgcagaa ctgccgctct cagtggacag ggcatctgtt accctgagac   1740
ctgtggcaga cacgtcttgt tttcatttga tttttgttaa gagtgcagta ttgcagagtc   1800
tagaggaatt tttgtttcct tgattaacat gattttcctg gttgttacat ccagggcatg   1860
gcagtggcct cagccttaaa cttttgttcc tactcccacc ctcagcgaac tgggcagcac   1920
ggggagggtt tggctacccc tgcccatccc tgagccaggt accaccattg taaggaaaca   1980
ctttcagaaa ttcagctggt tcctccaaac ccttcaaaaa aaaaaaaaaa aa           2032
```

```
<210> SEQ ID NO 75
<211> LENGTH: 3583
<212> TYPE: DNA
<213> ORGANISM: Homo sapiens

<400> SEQUENCE: 75
```

```
gcggccgccc tgcgcgcgaa gctcgtggcc cgagaggggt gcggtcgggc cgacggaggc     60
ggggccctgg ctgcctctct ccctgctcat aggctggccg ctcaggcctg gccggcctcg    120
gggcctcggg attcgcggcg gcgctgccaa tcaggcgatc gggccccgcc cccccggagt    180
tgggtgaaat agaggcgggc gtcaagtgtc agtagtcgcg gggcaggtac gtgcgctcgc    240
ggttctctcg cggaggtcgg cggtggcggg agcgggctcc ggagagcctg agagcacggt    300
ggggcggggc gggagaaagt ggccgcccgg aggacgttgg cgtttacgtg tggaagagcg    360
gaagagtttt gcttttcgtg cgcgccttcg aaaactgcct gccgctgtct gaggagtcca    420
cccgaaacct cccctcctcc gccggcagcc ccgcgctgag ctcgccgacc caagccagcg    480
tgggcgaggt gggaagtgcg cccgacccgc gcctggagct gcgcccccga gtgcccatgg    540
ctacaagggt gctgagcatg agcgcccgcc tgggacccgt gccccagccg ccggcgccgc    600
```

aggacgagcc ggtgttcgcg cagctcaagc cggtgctggg cgccgcgaat ccggcccgcg 660
acgcggcgct cttccccggc gaggagctga agcacgcgca ccaccgcccg caggcgcagc 720
ccgcgcccgc gcaggccccg cagccggccc agccgcccgc caccggcccg cggctgcctc 780
cagaggacct ggtccagaca agatgtgaaa tggagaagta tctgacacct cagcttcctc 840
cagttcctat aattccagag cataaaaagt atagacgaga cagtgcctca gtcgtagacc 900
agttcttcac tgacactgaa gggttacctt acagtatcaa catgaacgtc ttcctccctg 960
acatcactca cctgagaact ggcctctaca aatcccagag accgtgcgta acacacatca 1020
agacagaacc tgttgccatt ttcagccacc agagtgaaac gactgcccct cctccggccc 1080
cgacccaggc cctccctgag ttcaccagta tattcagctc acaccagacc gcagctccag 1140
aggtgaacaa tattttcatc aaacaagaac ttcctacacc agatcttcat ctttctgtcc 1200
ctacccagca gggccacctg taccagctac tgaatacacc ggatctagat atgcccagtt 1260
ctacaaatca gacagcagca atggacactc ttaatgtttc tatgtcagct gccatggcag 1320
gccttaacac acacacctct gctgttccgc agactgcagt gaaacaattc cagggcatgc 1380
ccccttgcac atacacaatg ccaagtcagt ttcttccaca acaggccact tactttcccc 1440
cgtcaccacc aagctcagag cctggaagtc cagatagaca agcagagatg ctccagaatt 1500
taaccccacc tccatcctat gctgctacaa ttgcttctaa actggcaatt cacaatccaa 1560
atttacccac caccctgcca gttaactcac aaaacatcca acctgtcaga tacaatagaa 1620
ggagtaaccc cgatttggag aaacgacgca tccactactg cgattaccct ggttgcacaa 1680
aagtttatac caagtcttct catttaaaag ctcacctgag gactcacact ggtgaaaagc 1740
catacaagtg tacctgggaa ggctgcgact ggaggttcgc gcgatcggat gagctgaccc 1800
gccactaccg gaagcacaca ggcgccaagc ccttccagtg cggggtgtgc aaccgcagct 1860
tctcgcgctc tgaccacctg gccctgcata tgaagaggca ccagaactga gcactgcccg 1920
tgtgacccgt tccaggtccc ctgggctccc tcaaatgaca gacctaacta ttcctgtgta 1980
aaaacaacaa aaacaaacaa aagcaagaaa accacaacta aaactggaaa tgtatatttt 2040
gtatatttga gaaaacaggg aatacattgt attaatacca aagtgtttgg tcattttaag 2100
aatctggaat gcttgctgta atgtatatgg ctttactcaa gcagatctca tctcatgaca 2160
ggcagccacg tctcaacatg ggtaaggggt gggggtggag ggagtgtgt gcagcgtttt 2220
tacctaggca ccatcattta atgtgacagt gttcagtaaa caaatcagtt ggcaggcacc 2280
agaagaagaa tggattgtat gtcaagattt tacttggcat tgagtagttt ttttcaatag 2340
taggtaattc cttagagata cagtatacct ggcaattcac aaatagccat tgaacaaatg 2400
tgtgggtttt taaaaattat atacatatat gagttgccta tatttgctat tcaaaatttt 2460
gtaaatatgc aaatcagctt tataggttta ttacaagttt tttaggattc ttttggggaa 2520
gagtcataat tcttttgaaa ataaccatga atacacttac agttaggatt tgtggtaagg 2580
tacctctcaa cattaccaaa atcatttctt tagagggaag gaataatcat tcaaatgaac 2640
tttaaaaaag caaatttcat gcactgatta aaataggatt attttaaata caaaaggcat 2700
tttatatgaa ttataaactg aagagcttaa agatagttac aaaatacaaa agttcaacct 2760
cttacaataa gctaaacgca atgtcatttt taaaaagaag gacttagggt gtcgttttca 2820
catatgacaa tgttgcattt atgatgcagt ttcaagtacc aaaacgttga attgatgatg 2880
cagttttcat atatcgagat gttcgctcgt gcagtactgt tggttaaatg acaatttatg 2940
tggattttgc atgtaataca cagtgagaca cagtaatttt atctaaatta cagtgcagtt 3000

```
tagttaatct attaatactg actcagtgtc tgcctttaaa tataaatgat atgttgaaaa   3060

cttaaggaag caaatgctac atatatgcaa tataaaatag taatgtgatg ctgatgctgt   3120

taaccaaagg gcagaataaa taagcaaaat gccaaaaggg gtcttaattg aaatgaaaat   3180

ttaattttgt ttttaaaata ttgtttatct ttatttattt tgtggtaata tagtaagttt   3240

ttttagaaga caattttcat aacttgataa attatagttt tgtttgttag aaaagttgct   3300

cttaaaagat gtaaatagat gacaaacgat gtaaataatt ttgtaagagg cttcaaaatg   3360

tttatacgtg gaaacacacc tacatgaaaa gcagaaatcg gttgctgttt tgcttctttt   3420

tccctcttat ttttgtattg tggtcatttc ctatgcaaat aatggagcaa acagctgtat   3480

agttgtagaa ttttttgaga gaatgagatg tttatatatt aacgacaatt tttttttgg    3540

aaaataaaaa gtgcctaaaa gatgtaaaaa aaaaaaaaaa aaa                    3583
```

<210> SEQ ID NO 76
<211> LENGTH: 1105
<212> TYPE: DNA
<213> ORGANISM: Homo sapiens

<400> SEQUENCE: 76

```
cttgttcaaa cagcacttac aggtggggac ctgtttttgc taagtcatcc tggggatgct     60

caaagctcca ttgttagatc ctttctgtcc tccttcctgg ctcctccttc ctccccaccc    120

ctctaatagg ctcataagtg ggctcaggcc tctctgcggg gctcactctg cgcttcacca    180

tggctttcat tgccaagtcc ttctatgacc tcagtgccat cagcctggat ggggagaagg    240

tagatttcaa tacgttccgg ggcagggccg tgctgattga gaatgtggct tcgctctgag    300

gcacaaccac ccgggacttc acccagctca acgagctgca atgccgcttt cccaggcgcc    360

tggtggtcct tggcttccct tgcaaccaat ttggacatca ggagaactgt cagaatgagg    420

agatcctgaa cagtctcaag tatgtccgtc ctgggggtgg ataccagccc accttcaccc    480

ttgtccaaaa atgtgaggtg aatgggcaga acgagcatcc tgtcttcgcc tacctgaagg    540

acaagctccc ctacccttat gatgacccat ttccctcat gaccgatccc aagctcatca     600

tttggagccc tgtgcgccgc tcagatgtgg cctggaactt tgagaagttc ctcatagggc    660

cggagggaga gcccttccga cgctacagcc gcaccttccc aaccatcaac attgagcctg    720

acatcaagcg cctccttaaa gttgccatat agatgtgaac tgctcaacac acagatctcc    780

tactccatcc agtcctgagg agccttagga tgcagcatgc cttcaggaga cactgctgga    840

cctcagcatt cccttgatat cagtcccctt cactgcagag ccttgccttt cccctctgcc    900

tgtttccttt tcctctccca accctctggt tggtgattca acttgggctc caagacttgg    960

gtaagctctg ggccttcaca gaatgatggc accttcctaa accctcatgg gtggtgtctg   1020

agaggcgtga agggcctgga gccactctgc tagaagagac caataaaggg caggtgtgga   1080

aacggccaaa aaaaaaaaaa aaaaa                                         1105
```

<210> SEQ ID NO 77
<211> LENGTH: 1576
<212> TYPE: DNA
<213> ORGANISM: Homo sapiens

<400> SEQUENCE: 77

```
agttaaaaac agatttccca caagaccgac cggagcgccg atcagagcac ctgcccgggc     60

cacacatttc ctcctggagc acagcaagtg ccgcctaaat tacccgagtg agcatctctt    120
```

-continued

```
cccggcacga gaggcaggga ggccaaaggg ccgccaagct ggcctgggag aggcgtaggg    180

cggagcgaga gtggagtgac attcccgagg gcggagcccc agggcctccg agacccgtag    240

actcccgcct cccgcctcct ctaggccgcc ggccgcgaag cgctgagtca cggtgaggct    300

actggaccca cactctctta acctgccctc cctgcactcg ctcccggcgg ctcttcgcgt    360

cacccccgcc gctaaggctc caggtgccgc taccgcagcg tgagtacctg gggctcctgc    420

aggggtccac tagccctcca tcctctacag ctcagcatca gaacactctc tttttagact    480

ccgatatggg gtcctccaag aaagttactc tctcagtgct cagccgggag cagtcggaag    540

gggttggagc gagggtccgg agaagcattg gcagacccga gttaaaaaat ctggatccgt    600

ttttactgtt tgatgaattt aaaggaggta gaccaggagg atttcctgat catccacatc    660

gaggttttga aacagtatcc tacctcctgg aagggggcag catggcccat gaagacttct    720

gtggacacac tggtaaaatg aacccaggag atttgcagtg gatgactgcg ggccggggca    780

ttctgcacgc tgagatgcct tgctcagagg agccagccca tggcctacaa ctgtgggtta    840

atttgaggag ctcagagaag atggtggagc ctcagtacca ggaactgaaa agtgaagaaa    900

tccctaaacc cagtaaggat ggtgtgacag ttgctgtcat ttctggagaa gccctgggaa    960

taaagtccaa ggtttacact cgcacaccaa ccttatattt ggacttcaaa ttggacccag   1020

gagccaaaca ttcccaacct atccctaaag ggtggacaag cttcatttac acgatatctg   1080

gagatgtgta tattgggccc gatgatgcac aacaaaaaat agaacctcat cacacagcag   1140

tgcttggaga aggtgacagt gtccaggtgg agaacaagga tcccaagaga agccactttg   1200

tcttaattgc tggggagcca ttaagagaac cagttatcca acatggtcca tttgtgatga   1260

acaccaatga agagatttct caagctattc ttgatttcag aaacgcaaaa aatgggtttg   1320

aaagggccaa aacctggaaa tcaaagattg ggaactagtg gaaagcggaa gagcaggtct   1380

tgatgtgtcc tagaattttg ccatttctga gattgagcca ttgaaggcat tccatttcta   1440

aagcttattt agccggtgct tctaaagaat tccacactaa cgtgataaca tggtttttgt   1500

aacaataaat gtaggatatt tcctggcaca tgcaaataaa cctaatcatt gtttctttaa   1560

aaaaaaaaaa aaaaaa                                                    1576
```

<210> SEQ ID NO 78
<211> LENGTH: 2298
<212> TYPE: DNA
<213> ORGANISM: Homo sapiens

<400> SEQUENCE: 78

```
cagcttggtt tgggccaggt ggactggaag gggcggaggt aaccagaagc ggctagtggc     60

ggctgcctgc gtccccaacc ccctccgcgc agcgctcgcg acacgcgtgc caggagtggg    120

agcgagcggc ggggccagct gcgttctgag cctgggcgca gctgccatct gctctgggaa    180

gcaccagggt gtccccgccg ccctcagctc gaagtcagcc accatggagg cgcaggcaca    240

aggtttgttg gagactgaac cgttgcaagg aacagacgaa gatgcagtag ccagtgctga    300

cttctctagc atgctctctg aggaggaaaa ggaagagtta aaagcagagt tagttcagct    360

agaagacgaa attacaacac tacgacaagt tttgtcagcg aaagaaaggc atctagttga    420

gataaaacaa aaactcggca tgaacctgat gaatgaatta aaacagaact tcagcaaaag    480

ctggcatgac atgcagacta ccactgccta caagaaaaca catgaaaccc tgagtcacgc    540

agggcaaaag gcaactgcag ctttcagcaa cgttggaacg gccatcagca agaagttcgg    600

agacatgagt tactccattc gccattccat aagtatgcct gctatgagga attctcctac    660
```

```
tttcaaatca tttgaggaga gggttgagac aactgtcaca agcctcaaga cgaaagtagg    720
cggtacgaac cctaatggag gcagttttga ggaggtcctc agctccacgg cccatgccag    780
tgcccagagc ttggcaggag gctcccggcg gaccaaggag gaggagctgc agtgctaagt    840
ccagccagcg tgcagctgca tccagaaacc ggccactacc cagcccatct ctgcctgtgc    900
ttatccagat aagaagacca aaatcccgct gggaaaaacc caggccttga cattgttatt    960
caaatggccc ctccagaaag tttaatgatt tccatttgta tttgtgttga tgatggacca   1020
cttgaccatc acatttcagt attcatagat gactgtcaca ttttaaaatg ttcccacttg   1080
agcaggtaca caactggtca taattcctgt ctgtgtaatt cgatgtatat ttttccaaac   1140
atgtagctat tgtttgcttt gatttttgct tggcctcctt tatgatgtgc atgtccttga   1200
aggctgaatg aacagtccct ttcagttcag cagatcaaca ggatggagct cttcatgact   1260
gtctccagca ataggatgat ttactataaa tttcatccaa ctacttgtga tctctctcac   1320
ctacatcaat tatgtatgtt aatttcagca attaaaagaa ttgattttaa tgactttgaa   1380
ttcttaattt ctttgtctta aaagttgcta gttatgattt tacagatgca attttaaatc   1440
aacttttagc caggtgcggc ggctcacacc tgtaatccca actattttgg atgccaaggt   1500
gagaggattg cttgaggcca ggagttaaag atcagcctgg gcaacacaga ccctgtctct   1560
acaaaaaaag aaaaaaatta gccagacata gtgttgcttg cctgtagtcc cagctactct   1620
agaggctgag gcaggaggat tgcatgagcc taggagttcg aaactgcagt gagctatgat   1680
tgcaccactg cactactcca gcctgggtga cagagtggga cactgtctcc aaaaatagta   1740
ataataagta gtcaactttt actgctaatt tggtgaacat gagagaggat atgaaaataa   1800
atattacctc agctatccta ggatgttaaa ataatctcca attttaaaat tctctccaat   1860
ctacatacag tagtagttag tcagataaag gatatccaaa aaagagatag ctagaaaatg   1920
ggagaagcag agttctgcaa ccccttttcag tttgtaaatt gttcacatgt atgaaaataa   1980
ctggtattta tcaatccact cagatttctg cactaacttt tatcttatat atcatatgta   2040
tctcttttct ttttctaaat gggaacatat atttgttatt aggtggcaga gatatagcct   2100
taagatatat ttgtaaaatg cacactgaat agacatccaa cctaaaaaaa atcactattt   2160
aaaaagccca tataatatat acatatttgt tagcatgcta attgttcatg ttttgtgttt   2220
attaaataga agtgatatat atgacatttt gaagtaaagc acatctgaaa aattctactc   2280
aaaaaaaaaa aaaaaaaa                                                 2298
```

<210> SEQ ID NO 79
<211> LENGTH: 3580
<212> TYPE: DNA
<213> ORGANISM: Homo sapiens

<400> SEQUENCE: 79

```
gccgggcccc gccgccgccc gcgcgccccc gggcccccga cacacatgag attcttcagg     60
ctcactttca agtgcttcgt ggactgcttc tgactgcgcc gcccgcgccc cgcaccccgc    120
cgcccgcccg ccgccccgtc ccccggcccg gccgcccccc ggcccccggc cggcccgcgc    180
cctcggggcc ctccccggtg ccgccggtgc cccccgcctg accgccgccc cccgtgaggc    240
gccgcgaccc cggcccggcc gtgcggcccg ccgaggccat ggcgaagaag agcgccgaga    300
acggcatcta tagcgtgtcc ggcgacgaga agaagggccc cctcatcgcg cccgggcccg    360
acggggcccc ggccaagggc gacggccccg tgggcctggg gacacccggc ggccgcctgg    420
```

-continued

```
ccgtgccgcc gcgcgagacc tggacgcgcc agatggactt catcatgtcg tgcgtgggct    480
tcgccgtggg cttgggcaac gtgtggcgct tcccctacct gtgctacaag aacggcggag    540
gtgtgttcct tattccctac gtcctgatcg ccctggttgg aggaatcccc attttcttct    600
tagagatctc gctgggccag ttcatgaagg ccggcagcat caatgtctgg aacatctgtc    660
ccctgttcaa aggcctgggc tacgcctcca tggtgatcgt cttctactgc aacacctact    720
acatcatggt gctggcctgg ggcttctatt acctggtcaa gtcctttacc accacgctgc    780
cctgggccac atgtggccac acctggaaca ctcccgactg cgtggagatc ttccgccatg    840
aagactgtgc caatgccagc ctggccaacc tcacctgtga ccagcttgct gaccgccggt    900
cccctgtcat cgagttctgg gagaacaaag tcttgaggct gtctggggga ctggaggtgc    960
caggggccct caactgggag gtgacccttt gtctgctggc ctgctgggtg ctggtctact   1020
tctgtgtctg gaagggggtc aaatccacgg gaaagatcgt gtacttcact gctacattcc   1080
cctacgtggt cctggtcgtg ctgctggtgc gtggagtgct gctgcctggc gccctggatg   1140
gcatcattta ctatctcaag cctgactggt caaagctggg gtcccctcag gtgtggatag   1200
atgcggggac ccagattttc ttttcttacg ccattggcct gggggccctc acagccctgg   1260
gcagctacaa ccgcttcaac aacaactgct acaaggacgc catcatcctg gctctcatca   1320
acagtgggac cagcttcttt gctggcttcg tggtcttctc catcctgggc ttcatggctg   1380
cagagcaggg cgtgcacatc tccaaggtgg cagagtcagg gccgggcctg gccttcatcg   1440
cctacccgcg ggctgtcacg ctgatgccag tggccccact ctgggctgcc ctgttcttct   1500
tcatgctgtt gctgcttggt ctcgacagcc agtttgtagg tgtggagggc ttcatcaccg   1560
gcctcctcga cctcctcccg gcctcctact acttccgttt ccaaagggag atctctgtgg   1620
ccctctgttg tgccctctgc tttgtcatcg atctctccat ggtgactgat ggcgggatgt   1680
acgtcttcca gctgtttgac tactactcgg ccagcggcac caccctgctc tggcaggcct   1740
tttgggagtg cgtggtggtg gcctgggtgt acggagctga ccgcttcatg gacgacattg   1800
cctgtatgat cgggtaccga ccttgcccct ggatgaaatg gtgctggtcc ttcttcaccc   1860
cgctggtctg catgggcatc ttcatcttca acgttgtgta ctacgagccg ctggtctaca   1920
acaacaccta cgtgtacccg tggtggggtg aggccatggg ctgggccttc gccctgtcct   1980
ccatgctgtg cgtgccgctg cacctcctgg gctgcctcct cagggccaag ggcaccatgg   2040
ctgagcgctg gcagcacctg acccagccca tctggggcct ccaccacttg gagtaccgag   2100
ctcaggacgc agatgtcagg ggcctgacca ccctgacccc agtgtccgag agcagcaagg   2160
tcgtcgtggt ggagagtgtc atgtgacaac tcagctcaca tcaccagctc acctctggta   2220
gccatagcag cccctgcttc agccccaccg cacccctcca gggggcctgc ctttccctga   2280
cacttttggg gtctgcctgg gggaggaggg gagaaagcac catgagtgct cactaaaaca   2340
actttttcca tttttaataa aacgccaaaa atatcacaac ccaccaaaaa tagatgcctc   2400
tccccctcca gccctagccg agctggtcct aggccccgcc tagtgcccca cccccaccca   2460
cagtgctgca ctcctcctgc ccctgccacg cccaccccct gcccacctct ccaggctctg   2520
ctctgcagca cacccgtggg tgacccctca ccccagaagc agcagtggca gcttgggaaa   2580
tgtgaggaag ggaaggaggg agagacggga gggaggagag agaggagaag ggaggcaggg   2640
gaggggcagc agaaccaagg caaatatttc agctgggcta tacccctctc cccatccctg   2700
ttatagaagc ttagagagcc agccagcaat ggaaccttct ggttcctgcg ccaatcgcca   2760
ccagtatcaa ttgtgtgagc ttgggtgcga gtgcacgcgt gcgtgagtac ggagagtata   2820
```

-continued

```
tatagatctc tatctcttag caaaggtgaa tgccagatgt aaatggcgcc tctgggcaaa   2880
ggaggcttgt attttgcaca ttttataaaa acttgagaga atgagatttc tgcttgtata   2940
tttctaaaaa gaggaaggag cccaaaccat cctctcctta ccactcccat ccctgtgagc   3000
cctaccttac ccctctgccc ctagccaagg agtgtgaatt tatagatcta actttcatag   3060
gcaaaacaaa agcttcgagc tgttgcgtgt gtgagtctgt tgtgtggatg tgcgtgtgtg   3120
gtccccagcc ccagactgga ttggaaaagt gcatggtggg ggcctcgggg ctgtccccac   3180
gctgtccctt tgccacaagt ctgtggggca agaggctgca atattccgtc ctgggtgtct   3240
gggctgctaa cctggcctgc tcaggcttcc caccctgtgc ggggcacacc cccaggaagg   3300
gaccctggac acggctccca cgtccaggct taaggtggat gcacttcccg cacctccagt   3360
cttctgtgta gcagctttaa cccacgtttg tctgtcacgt ccagtcccga gacggctgag   3420
tgaccccaag aaaggcttcc ccgacaccca gacagaggct gcagggctgg ggctgggtga   3480
gggtggcggg cctgcgggga cattctactg tgctaaaaag ccactgcaga catagcaata   3540
aaaacatgtc attttccaaa gcaggaaaaa aaaaaaaaaa                         3580
```

<210> SEQ ID NO 80
<211> LENGTH: 2632
<212> TYPE: DNA
<213> ORGANISM: Homo sapiens

<400> SEQUENCE: 80

```
agctgaggga cgcgtcagcc aggcaccccg gggtgtggcc agaggacttc ggcgacgctt     60
ccccgagagt agccccccctc ctcaacccag aaaagacaac cccgcggggc tgcagcgagc   120
caggcatgct cactggcgca ggcccggccc gcagcccgag caggaagcgc cggcgctagg   180
cggccccctg cgctgccagc tggagccggg cggagccagc gccccggcgc agggtggctc   240
tgccagtccc cgcgcgcctg ggcggccgca cacgtgtcca ggcgtcacgt ccgcgcgcgc   300
ccccggggct tgcgtcagcg gctgttccag aagcgggtgg gccagggctc tgcgcaccgc   360
tggggttcgg ggcccgggac gccgccggga ggagggcacc gcgcggggtc cgacgcggag   420
gcgtgctcgg aacgccgggg gctgcggagt gcatcagcgc ggtccagccc tccgcctgcc   480
gggcgccgag cgtctccgcc gcccggacct gggctgggcg ccgtggcgtt gcctcggagc   540
tcgctgcccg cggggcgcgc accgccttga cccgggcggc cccgcggcag gcaggcgccc   600
gcagttccat ggttggttcg gagcgcgatg agccgcccgt cctccaccgg ccccagcgct   660
aataaaccct gcagcaagca gccgccgccg cagccccagc acactccgtc cccggctgcg   720
cccccggccg ccgccaccat ctcggctgcg ggccccggct cgtccgcggt gcccgccgcg   780
gcggcggtga tctcgggccc cggcggcggc ggcggggccg gcccggtgtc cccgcagcac   840
cacgagctga cctcgctctt cgagtgtccg gtctgctttg actatgtcct gcctcctatt   900
ctgcagtgcc aggccgggca cctggtgtgt aaccaatgcc gccagaagtt gagctgctgc   960
ccgacgtgca ggggcgccct gacgcccagc atcaggaacc tggctatgga gaaggtggcc  1020
tcggcagtcc tgtttccctg taagtatgcc accacgggct gttccctgac cctgcaccat  1080
acggagaaac cagaacatga agacatatgt gaataccgtc cctactcctg cccatgtcct  1140
ggtgcttcct gcaagtggca ggggtccctg gaagctgtga tgtcccatct catgcacgcc  1200
cacaagagca ttaccaccct tcagggagaa gacatcgtct ttctagctac agacattaac  1260
ttgccagggg ctgtcgactg ggtgatgatg cagtcatgtt ttggccatca cttcatgctg  1320
```

-continued

```
gtgctggaga aacaagagaa gtacgaaggc caccagcagt tttttgccat cgtcctgctc   1380
attggcaccc gcaagcaagc cgagaacttt gcctacagac tggagttgaa tgggaaccgg   1440
cggagattga cctgggaggc cacgccccgt tcgattcatg acggtgtggc tgcggccatc   1500
atgaacagcg actgccttgt tttcgacaca gccatagcac atctttttgc agataatggg   1560
aaccttggaa tcaatgttac tatttctaca tgttgtccat gatgtgactt tcgtaaacct   1620
tcaaaattat ttgggcatag tgctctatgt ttaataaagg tttttataga tgttttattc   1680
catatgtctt cacaagtcag gacccacaat tacccgtgtt ttgtttgaac agcagtgtcc   1740
catctggctt cgacccaaca aagttcatta acctgggatg aatggggttg gcctgttggt   1800
gatttggatg ctgttctgtg atctaaaaca actcttattg aattgtattt actccctaaa   1860
caacacttga caggctgttg cacagggctt ctatagatca gtgtgttagg aatgggaggc   1920
cccttcctgc ctgccttccc atattggtcc cttgacattg acaaaagcac agtgactgtc   1980
agcagattcc tttacttttg tttgtgggag gtaggaattg ttttaatgca ttttaaacag   2040
tgtttctgaa attggatggc tggctaatag acactgaatc acccggagtg cttatcttaa   2100
aattgcagat ttagggagcc tgccaattta acagtctcat caggtgattc ttttcaacag   2160
taatgtttga gaattactgg gttaaattgt gggaaagggt ccagatttta aaggtgcttt   2220
aaggttgccc tctgccgata ctgtttgtct ttctactgtt tcatccccta acttcccccca   2280
accctcaaat taaaactaga actatagatc cacatgaacg cacgcctgag atttggccac   2340
tcacctatgt tttgggtgga ttgcctagga aagcaagtca tatggccatt gatagttctc   2400
atgtaattag ttttgctcac cactagtaca gatgacccgt ttacacgtgg cttccctcgg   2460
aagccctcct caacagtagc tggtgtgaaa gactaaatca gtagagttgg aaaagcttta   2520
taaccggtgt gtcatatgct tgctatttaa agctgtgtgt tggttttgtt tttctgccac   2580
attcactagt tttttaataa atattttcca aaaatggata aaaaaaaaaa aa           2632
```

METHODS FOR SUBTYPING OF LUNG SQUAMOUS CELL CARCINOMA

CROSS REFERENCE

This application is a national phase of International Application No. PCT/US2017/033107, filed May 17, 2017, which claims priority from U.S. Provisional Application No. 62/337,645 filed May 17, 2016, U.S. Provisional Application No. 62/379,402 filed Aug. 25, 2016, U.S. Provisional Application No. 62/396,587 filed Sep. 19, 2016, U.S. Provisional Application No. 62/420,836 filed Nov. 11, 2016, and U.S. Provisional Application No. 62/425,717 filed Nov. 23, 2016, each of which is incorporated by reference herein in its entirety for all purposes.

FIELD OF THE INVENTION

The present invention relates to methods for determining a squamous cell carcinoma subtype of a lung sample and for predicting the response to a treatment for a patient inflicted with specific types of lung cancer.

STATEMENT REGARDING SEQUENCE LISTING

The Sequence Listing associated with this application is provided in text format in lieu of a paper copy, and is hereby incorporated by reference into the specification. The name of the text file containing the Sequence Listing is GNCN_010_01WO_SeqList_ST25.txt. The text file is 319 KB, and was created on May 16, 2017, and is being submitted electronically via EFS-Web.

BACKGROUND OF THE INVENTION

Lung cancer is the leading cause of cancer deaths both in the United States and worldwide. Approximately 172,000 tumors of the lung were diagnosed in 2005 with an estimated 163,000 deaths, more than colon, breast, and prostate combined. At least 75% of patients present with locally advanced disease. Although there has been much effort to improve screening using technology such as high-resolution CT, these methods often produce false positive results and usually do not change outcome. Thus, even small tumors detected early present a significant threat to patients with postoperative 5-year survival rates for stage I lung cancer estimated between 47 to 63 percent. For patients with advanced disease the prognosis is worse with median survivals well under a year. In general, palliative therapy is effective but not sustainable and the average impact on overall survival is approximately 3 months.

At the population level the underlying cause of lung cancer is clearly tobacco use, with 90% of all lung cancers attributed directly to smoking. Smoking is so tightly correlated with lung cancer that it confounds definitive association with most other risk factors; although asbestos, radon, and a number of lung irritants are generally accepted as lung cancer risk factors. A genetic association is strongly suspected, however, the exact mechanism remains to be determined outside of a select group of rare Mendelian cancer syndromes. Despite many classification schemes and ongoing clinical trials, there has been overall disappointing progress in the field of clinical diagnostics and therapeutics.

Four distinct intrinsic lung squamous cell carcinoma subtypes exist that vary in their genomic profiles including gene expression, mutational spectrum, and copy number alterations. The four biologic lung squamous cell carcinoma subtypes, primitive, classical, secretory and basal, differ not only in their genomic features, but also demonstrate potentially important differences in clinical features.

Most lung cancers are classified as non-small cell lung carcinoma (NSCLC) (>85%), which is a diverse group with subtypes occurring throughout the respiratory tract. Adenocarcinoma (AD) and squamous cell carcinomas (SCC or SQ), the two main subtypes of NSCLC, are diagnosed at near equal frequency but are often found at different locations with SCC occurring more centrally. The 6th edition of the consensus classification of lung cancers developed by the World Health Organization (WHO) describes no fewer than 90 malignant morphologic classes and variants. There can often be heterogeneity, especially in larger tumors >1.5 cm, making morphological classification more difficult and leading to designations such as adeno-squamous carcinoma. Further, studies of histologic diagnosis reproducibility have shown limited intra-pathologist agreement and inter-pathologist agreement. Variability in morphology, limited tissue samples, and the need for assessment of a growing list of therapeutically targeted markers pose challenges to the current diagnostic standard. This is further highlighted by the idea that differentiation among various morphologic subtypes of lung cancer can be essential in guiding patient management and additional molecular testing can be used to identify specific therapeutic target markers.

Currently, gene expression based lung squamous cell carcinoma (SQ) subtyping has been primarily restricted to a research protocol involving the extraction of RNA from fresh frozen lung tumors, followed by application of a nearest centroid predictor using quantitative gene expression of over 200 genes, as described in Wilkerson et al. Clin Cancer Res 2010; 16(19): 4864-75, which is herein incorporated by reference in its entirety. Gene expression based SQ subtyping has been shown to classify squamous cell carcinoma tumors into 4 biologically distinct subtypes basal, classical, primitive and secretory. Further, these four subtypes can vary in their survival outcomes, patient populations, biological processes and in their immunogenic response features. Despite evidence of prognostic and predictive benefits from SQ subtyping, the requirement for gene expression of >200 genes in combination with complex bioinformatics analyses, has hindered the application of SQ subtyping in drug development and/or in the clinic.

Cancer immunosurveillance is the principle that the immune system can identify precancerous and cancerous cells and kill these cells before they become clinically relevant, which has been demonstrated in immunodeficient mouse models. Innate and adaptive immune responses can work together to either promote or inhibit cancer growth, and evasion of immune destruction is an emerging hallmark of cancer. Historically, methods of immune stimulation were not effective for lung cancer patients in the clinic. Deficiencies in tumor antigen expression and presentation on antigen presenting cells (APCs), infiltration of immunosuppressive cells and cytokines, and ineffective T-cell activation can lead to immunosuppression at the tumor site. Advances in the understanding of cancer and the immune system have led to effective therapies that activate antitumor responses, even in tumors that have highly developed methods of immune evasion, such as lung cancer. However the high immunosuppressive effects caused by lung tumors limit the beneficial effects of these advances due to a delicate balance between immunoactivation and immunosuppression in a patient. For example, in NSCLC, the role of immunosuppressive cells hampering immune activation is high, which is suggested to be related to the type of tumor, advanced stage of the disease, and the tumor load.

Therefore, developing a method to effectively distinguish intrinsic lung squamous cell carcinoma subtypes is critical for clinical diagnosis and disease management. Accordingly, new methods are needed to further define populations that might be likely to respond to immunotherapy. The present invention addresses these and other needs in the field for determining a prognosis or disease outcome for SQ patient populations based in part on the SQ subtype (basal, classical, primitive, secretory) of the patient. The methods of the invention provide a means for determining the cellular and molecular origins of lung cancer (e.g., subtyping SQ) and can provide for more accurate diagnosis and applicable treatments as compared to diagnostic methods known in the art.

SUMMARY OF THE INVENTION

In one aspect, provided herein is a method for determining a squamous cell carcinoma (SQ) subtype of a lung tissue sample obtained from a patient, the method comprising detecting an expression level of at least one classifier biomarker of Table 1, wherein the detection of the expression level of the classifier biomarker specifically identifies a basal, classical, secretory or primitive SQ subtype. In some cases, the method further comprises comparing the detected levels of expression of the at least one classifier biomarkers of Table 1 to the expression of the at least one classifier biomarkers of Table 1 in at least one sample training set(s), wherein the at least one sample training set comprises expression data of the at least one classifier biomarkers of Table 1 from a reference SQ basal sample, expression data of the at least one classifier biomarkers of Table 1 from a reference SQ classical sample, expression data of the at least one classifier biomarkers of Table 1 from a reference SQ secretory sample, expression data of the at least one classifier biomarkers of Table 1 from a reference SQ primitive sample or a combination thereof; and classifying the sample as basal, classical, secretory or primitive subtype based on the results of the comparing step. In some cases, the comparing step comprises applying a statistical algorithm which comprises determining a correlation between the expression data obtained from the sample and the expression data from the at least one training set(s); and classifying the sample as a basal, classical, secretory or primitive subtype based on the results of the statistical algorithm. In some cases, the expression level of the classifier biomarker is detected at the nucleic acid level. In some cases, the nucleic acid level is RNA or cDNA. In some cases, the detecting an expression level comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers specific for at least one classifier biomarker of Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the at least one classifier biomarker comprises a plurality of classifier biomarkers. In some cases, the plurality of classifier biomarkers comprises at least two classifier biomarkers, at least 10 classifier biomarkers, at least 20 classifier biomarkers, at least 30 classifier biomarkers, at least 40 classifier biomarkers, at least 50 classifier biomarkers, at least 60 classifier biomarkers, or at least 70 classifier biomarkers of Table 1. In some cases, the at least one classifier biomarker comprises all the classifier biomarkers of Table 1.

In another aspect, provided herein is a method for determining a squamous cell carcinoma (SQ) subtype of a lung tissue sample obtained from a patient comprising detecting an expression level of at least one nucleic acid molecule that encodes a classifier biomarker having a specific expression pattern in lung cancer cells, wherein the classifier biomarker is selected from the group consisting of the classifier genes set forth in Table 1, the method comprising: (a) isolating nucleic acid material from a lung tissue sample from a patient; (b) mixing the nucleic acid material with oligonucleotides that are substantially complementary to portions of nucleic acid molecule of the classifier biomarker; and (c) detecting expression of the classifier biomarker. In some cases, the method further comprises comparing the detected levels of expression of the at least one classifier biomarkers of Table 1 to the expression of the at least one classifier biomarkers of Table 1 in at least one sample training set(s), wherein the at least one sample training set comprises expression data of the at least one classifier biomarkers of Table 1 from a reference SQ basal sample, expression data of the at least one classifier biomarkers of Table 1 from a reference SQ classical sample, expression data of the at least one classifier biomarkers of Table 1 from a reference SQ secretory sample, expression data of the at least one classifier biomarkers of Table 1 from a reference SQ primitive sample or a combination thereof; and classifying the sample as basal, classical, secretory or primitive subtype based on the results of the comparing step. In some cases, the comparing step comprises applying a statistical algorithm which comprises determining a correlation between the expression data obtained from the sample and the expression data from the at least one training set(s); and classifying the sample as a basal, classical, secretory or primitive subtype based on the results of the statistical algorithm. In some cases, the detecting the expression level comprises performing qRT-PCR or any hybridization-based gene assays. In some cases, the expression level is detected by performing qRT-PCR. In some cases, the detection of the expression level comprises using at least one pair of oligonucleotide primers specific for at least one classifier biomarker of Table 1. In some cases, the method further comprises predicting the response to a therapy for treating a subtype of lung squamous cell carcinoma (SQ) based on the detected expression level of the classifier biomarker. In some cases, the therapy is chemotherapy, angiogenesis inhibitors and/or immunotherapy. In some cases, the subtype of lung SQ is primitive and the therapy is an immunotherapy. In some cases, the sample is a formalin-fixed, paraffin-embedded (FFPE) lung tissue sample, fresh or a frozen tissue sample, an exosome, wash fluids, cell pellets or a bodily fluid obtained from the patient. In some cases, the bodily fluid is blood or fractions thereof, urine, saliva, or sputum. In some cases, the at least one nucleic acid molecule that encodes a classifier biomarker comprises a plurality of nucleic acid molecules that encode a plurality of classifier biomarkers. In some cases, the plurality of classifier biomarkers comprises at least two classifier biomarkers, at least 10 classifier biomarkers, at least 20 classifier biomarkers, at least 30 classifier biomarkers, at least 40 classifier biomarkers, at least 50 classifier biomarkers, at least 60 classifier biomarkers, or at least 70 classifier biomarkers selected from Table 1. In some cases, the at least one nucleic acid molecule that encodes a classifier biomarker comprises a plurality of nucleic acid molecules that include all the classifier biomarkers of Table 1.

In yet another aspect, provided herein is a method of detecting a biomarker in a lung tissue sample obtained from a patient, the method comprising measuring the expression level of a plurality of biomarker nucleic acids selected from Table 1 using an amplification, hybridization and/or sequencing assay. In some cases, the lung tissue sample was previously diagnosed as being squamous cell carcinoma. In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, or at least 70 biomarker nucleic acids of Table 1. In some cases, the plurality of biomarker nucleic acids comprises, consists essentially of or consists of all the classifier biomarker nucleic acids of Table 1.

In a further aspect, provided herein is a method of detecting a biomarker in a lung tissue sample obtained from a patient, the method consisting essentially of measuring the expression level of a plurality of biomarker nucleic acids selected from Table 1 using an amplification, hybridization and/or sequencing assay. In some cases, the lung tissue sample was previously diagnosed as being squamous cell carcinoma. In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, or at least 70 biomarker nucleic acids of Table 1. In some cases, the plurality of biomarker nucleic acids comprises, consists essentially of or consists of all the classifier biomarker nucleic acids of Table 1.

In one aspect, provided herein is a method of detecting a biomarker in a lung tissue sample obtained from a patient, the method consisting of measuring the expression level of a plurality of biomarker nucleic acids selected from Table 1 using an amplification, hybridization and/or sequencing assay. In some cases, the lung tissue sample was previously diagnosed as being squamous cell carcinoma. In some cases, the previous diagnosis was by histological examination. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the detection of the expression level comprises using at least one pair of oligonucleotide primers per each of the plurality of biomarker nucleic acids selected from Table 1. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, or at least 70 biomarker nucleic acids of Table 1. In some cases, the plurality of biomarker nucleic acids comprises, consists essentially of or consists of all the classifier biomarker nucleic acids of Table 1.

In another aspect, provided herein is a method of determining whether a squamous cell carcinoma patient is likely to respond to immunotherapy, the method comprising, determining the squamous cell carcinoma subtype of a lung tissue sample from the patient, wherein the squamous cell carcinoma subtype is selected from the group consisting of primitive, classical, secretory and basal; and based on the subtype, assessing whether the patient is likely to respond to immunotherapy. In some cases, the immunotherapy comprises checkpoint inhibitor therapy. In some cases, the checkpoint inhibitor targets PD-1 or PD-L1. In some cases, the checkpoint inhibitor targets CTLA-4. In some cases, the checkpoint inhibitor is Pembrolizumab, Nivolumab or an antigen fragment binding fragment thereof. In some cases, the checkpoint inhibitor is Ipilimumab or an antigen binding fragment thereof. In some cases, the patient is initially determined to have squamous cell carcinoma via a histological analysis of a sample. In some cases, the patient's squamous cell carcinoma subtype is selected from primitive, classical, secretory or basal, and is determined via a histological analysis of a sample obtained from the patient. In some cases, the sample is a formalin-fixed, paraffin-embedded (FFPE) lung tissue sample, fresh or a frozen tissue sample, an exosome, or a bodily fluid obtained from the patient. In some cases, the bodily fluid is blood or fractions thereof, urine, saliva, or sputum. In some cases, the determining the squamous cell carcinoma subtype comprises determining expression levels of a plurality of classifier biomarkers. In some cases, the determining the expression levels of the plurality of classifier biomarkers is at a nucleic acid level by performing RNA sequencing, reverse transcriptase polymerase chain reaction (RT-PCR) or hybridization based analyses. In some cases, the plurality of classifier biomarkers for determining the squamous cell carcinoma subtype is selected from a publically available lung squamous cell carcinoma dataset. In some cases, the publically available lung squamous cell carcinoma dataset is TCGA Lung SQ RNAseq dataset. In some cases, the plurality of classifier biomarkers for determining the squamous cell carcinoma subtype is selected from Table 1. In some cases, the RT-PCR is quantitative real time reverse transcriptase polymerase chain reaction (qRT-PCR). In some cases, the RT-PCR is performed with primers specific to the plurality of classifier biomarkers of Table 1. In some cases, the method further comprises comparing the detected levels of expression of the plurality of classifier biomarkers of Table 1 to the expression of the plurality of classifier biomarkers of Table 1 in at least one sample training set(s), wherein the at least one sample training set comprises expression data of the plurality of classifier biomarkers of Table 1 from a reference squamous cell carcinoma basal sample, expression data of the plurality of classifier biomarkers of Table 1 from a reference squamous cell carcinoma classical sample, expression data of the plurality of classifier biomarkers of Table 1 from a reference squamous cell carcinoma primitive sample, expression data of the plurality of classifier biomarkers of Table 1 from a reference squamous cell carcinoma secretory sample or a combination thereof; and classifying the first sample as basal, classical, primitive or secretory based on the results of the comparing step. In some cases, the comparing step comprises applying a statistical algorithm which comprises determining a correlation between the expression data obtained from the sample and the expression data from the at least one training set(s); and classifying the sample as a basal, classical, primitive or secretory subtype based on the results of the statistical algorithm. In some cases, the plurality of the classifier biomarkers comprise each of the classifier biomarkers set forth in Table 1.

In yet another aspect, provided herein is a method for selecting a squamous cell carcinoma patient for immunotherapy, the method comprising, determining a squamous cell carcinoma subtype of a lung tissue sample from the patient, based on the subtype; and selecting the patient for immunotherapy. In some cases, the immunotherapy comprises checkpoint inhibitor therapy. In some cases, the checkpoint inhibitor targets PD-1 or PD-L1. In some cases, the checkpoint inhibitor targets CTLA-4. In some cases, the checkpoint inhibitor is Pembrolizumab, Nivolumab or an antigen fragment binding fragment thereof. In some cases, the checkpoint inhibitor is Ipilimumab or an antigen binding fragment thereof. In some cases, the patient is initially determined to have squamous cell carcinoma via a histological analysis of a sample. In some cases, the patient's squamous cell carcinoma subtype is selected from primitive, classical, secretory or basal, and is determined via a histological analysis of a sample obtained from the patient. In some cases, the sample is a formalin-fixed, paraffin-embedded (FFPE) lung tissue sample, fresh or a frozen tissue sample, an exosome, or a bodily fluid obtained from the patient. In some cases, the bodily fluid is blood or fractions thereof, urine, saliva, or sputum. In some cases, the determining the squamous cell carcinoma subtype comprises determining expression levels of a plurality of classifier biomarkers. In some cases, the determining the expression levels of the plurality of classifier biomarkers is at a nucleic acid level by performing RNA sequencing, reverse transcriptase polymerase chain reaction (RT-PCR) or hybridization based analyses. In some cases, the plurality of classifier biomarkers for determining the squamous cell carcinoma subtype is selected from a publically available lung squamous cell carcinoma dataset. In some cases, the publically available lung squamous cell carcinoma dataset is TCGA Lung SQ RNAseq dataset. In some cases, the plurality of classifier biomarkers for determining the squamous cell carcinoma subtype is selected from Table 1. In some cases, the RT-PCR is quantitative real time reverse transcriptase polymerase chain reaction (qRT-PCR). In some cases, the RT-PCR is performed with primers specific to the plurality of classifier biomarkers of Table 1. In some cases, the method further comprises comparing the detected levels of expression of the plurality of classifier biomarkers of Table 1 to the expression of the plurality of classifier biomarkers of Table 1 in at least one sample training set(s), wherein the at least one sample training set comprises expression data of the plurality of classifier biomarkers of Table 1 from a reference squamous cell carcinoma basal sample, expression data of the plurality of classifier biomarkers of Table 1 from a reference squamous cell carcinoma classical sample, expression data of the plurality of classifier biomarkers of Table 1 from a reference squamous cell carcinoma primitive sample, expression data of the plurality of classifier biomarkers of Table 1 from a reference squamous cell carcinoma secretory sample or a combination thereof; and classifying the first sample as basal, classical, primitive or secretory based on the results of the comparing step. In some cases, the comparing step comprises applying a statistical algorithm which comprises determining a correlation between the expression data obtained from the sample and the expression data from the at least one training set(s); and classifying the sample as a basal, classical, primitive or secretory subtype based on the results of the statistical algorithm. In some cases, the plurality of the classifier biomarkers comprise each of the classifier biomarkers set forth in Table 1.

In one aspect, provided herein is a method of treating lung cancer in a subject, the method comprising: measuring the expression level of at least one biomarker nucleic acid in a lung cancer sample obtained from the subject, wherein the at least one biomarker nucleic acid is selected from a set of biomarkers listed in Table 1, wherein the presence, absence and/or level of the at least one biomarker indicates a subtype of the lung cancer; and administering an immunotherapeutic agent based on the subtype of the lung cancer. In some cases, the lung cancer sample is a squamous cell carcinoma sample, and wherein the set of biomarkers is Table 1. In some cases, the at least one biomarker nucleic acid selected from the set of biomarkers comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, at least 70 biomarker nucleic acids or all of the biomarker nucleic acids of Table 1. In some cases, the lung tissue sample was previously diagnosed as being squamous cell carcinoma. In some cases, the previous diagnosis was by histological examination. In some cases, the method further comprises measuring the expression of at least one biomarker from an additional set of biomarkers. In some cases, the additional set of biomarkers comprise gene expression signatures of Innate Immune Cells (IIC), Adaptive Immune Cells (AIC), one or more individual immune biomarkers, one or more interferon (IFN) genes, one or more major histocompatibility complex, class II (MHCII) genes or a combination thereof. In some cases, the additional set of biomarkers comprises genes selected from Tables 4A, 4B, 5, 6, 7, or a combination thereof. In some cases, the gene expression signatures of AICs are selected from Table 4A. In some cases, the gene expression signature of IICs are selected from Table 4B. In some cases, the one or more individual immune biomarkers are selected from Table 5. In some cases, the one or more IFN genes are selected from Table 6. In some cases, the one or more MHCII genes are selected from Table 7. In some cases, the measuring the expression level is conducted using an amplification, hybridization and/or sequencing assay. In some cases, the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays, Northern blotting, or any other equivalent gene expression detection techniques. In some cases, the expression level is detected by performing qRT-PCR. In some cases, the sample is a formalin-fixed, paraffin-embedded (FFPE) lung tissue sample, fresh or a frozen tissue sample, an exosome, wash fluids, cell pellets, or a bodily fluid obtained from the patient. In some cases, the bodily fluid is blood or fractions thereof, urine, saliva, or sputum. In some cases, the subject's squamous cell carcinoma subtype is selected from primitive, classical, secretory or basal. In some cases, the lung cancer subtype is primitive and wherein the immunotherapeutic agent comprises a checkpoint inhibitor. In some cases, the checkpoint inhibitor targets PD-1 or PD-L1. In some cases, the checkpoint inhibitor targets CTLA-4. In some cases, the checkpoint inhibitor is Pembrolizumab, Nivolumab or an antigen fragment binding fragment thereof. In some cases, the checkpoint inhibitor is Ipilimumab or an antigen binding fragment thereof. In some cases, the at least one biomarker nucleic acid is a plurality of biomarker nucleic acids, wherein the plurality of biomarker nucleic acids comprises at least one biomarker nucleic acid listed in Table 1 in combination with one or more biomarker nucleic acids from a publically available lung squamous cell carcinoma dataset, wherein the presence, absence and/or level of the plurality of biomarker nucleic acids indicates a subtype of the lung cancer. In some cases, the at least one biomarker nucleic acid is a plurality of biomarker nucleic acids, wherein the plurality of biomarker nucleic acids comprises all of the biomarker nucleic acids listed in Table 1 in combination with one or more biomarker nucleic acids from a publically available lung squamous cell carcinoma dataset, wherein the presence, absence and/or level of the plurality of biomarker nucleic acids indicates a subtype of the lung cancer. In some cases, the publically available lung squamous cell carcinoma dataset is TCGA Lung SQ RNAseq dataset.

BRIEF DESCRIPTION OF THE FIGURES

FIG. 2 illustrates the lung SQ datasets used in the study described in Example 1.

FIG. 7A-7B is for SQ showing survival associations of immune cell signatures and markers by subtype in the TCGA cohort (FIG. 7A) or the TGCA, UNC and Raponi cohorts (FIG. 7B). Subtype specific immune marker hazard ratios and 95% confidence intervals were for 5 year overall survival in the TCGA cohort (n=501 SQ) for FIG. 7A.

FIG. 16 illustrates agreement of SQ subtype prediction by the 80 gene signature (CLANC80) provided herein with the 208-gene classifier to define the gold standard subtype for multiple validation datasets and the newly collected FFPE validation dataset. The agreement with Lee, Raponi (rap), FFPE, TGCA and UNC is 84%, 91%, 87%, 88%, and 89%, respectively.

DETAILED DESCRIPTION OF THE INVENTION

Overview

Figure 1:
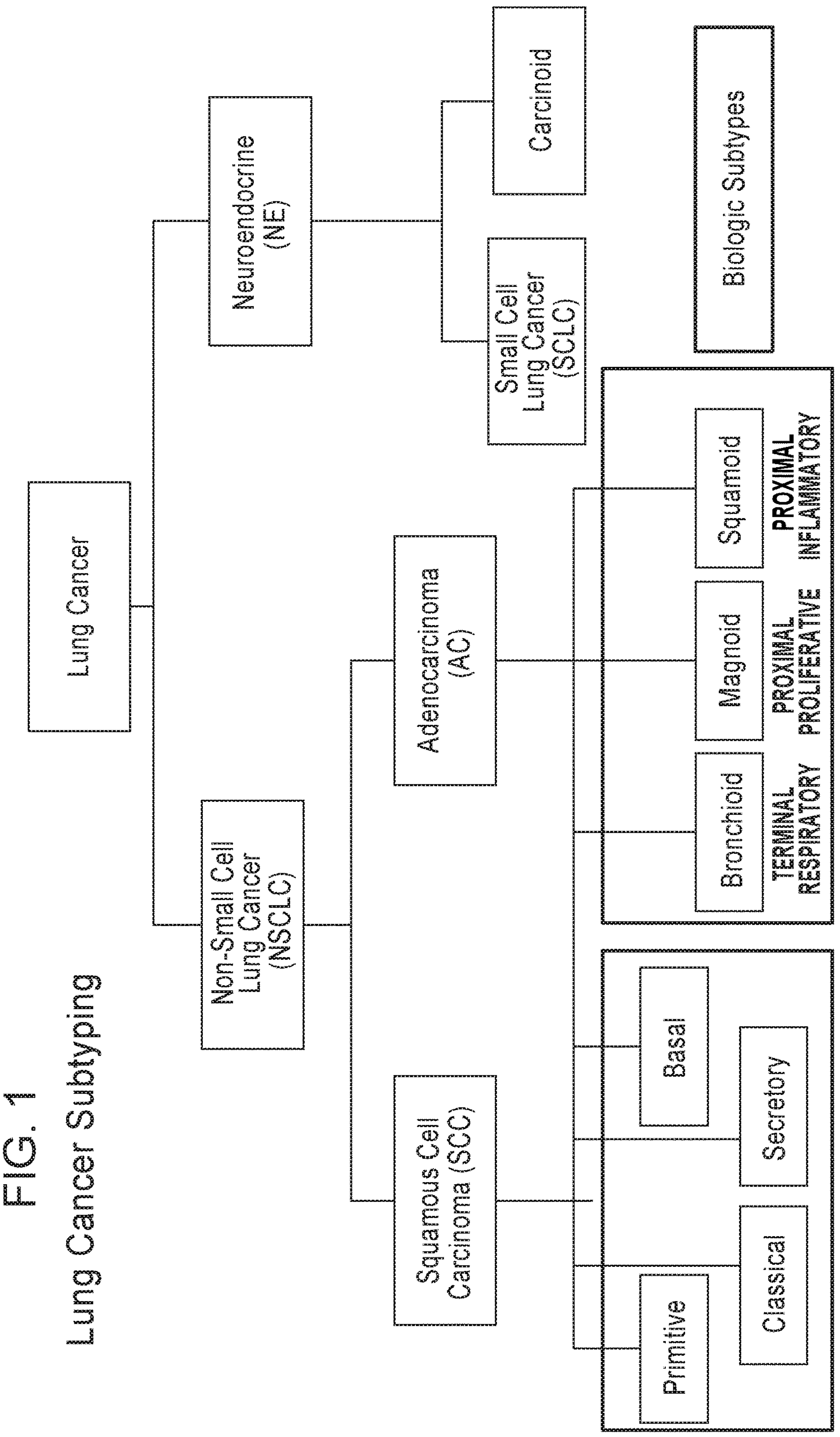
FIG. 1 illustrates lung cancer subtyping and the biologic subtypes of squamous cell carcinoma (SCC or SQ) and Adenocarcinoma (AC or AD).

The present invention provides kits, compositions and methods for identifying or diagnosing lung cancer. That is, the methods can be useful for molecularly defining subsets of lung cancer, specifically lung squamous cell carcinoma (SQ). The methods provide a classification of lung cancer that can be prognostic and predictive for therapeutic response. While a useful term for epidemiologic purposes, "lung cancer" may not refer to a specific disease, but rather can represent a heterogeneous collection of tumors of the lung, bronchus, and pleura. For practical purposes, lung cancer can generally be divided into two histological subtypes-small cell lung cancer (SCLC) and non-small cell lung cancer (NSCLC). These main tumor types can present at different frequencies, can have different anatomic locations, c an have different predilections for metastasis, may respond differently to therapy, and may likely be derived from different cell progenitors.

"Determining a squamous cell carcinoma subtype" can include, for example, diagnosing or detecting the presence and type of lung squamous cell carcinoma, monitoring the progression of the disease, and identifying or detecting cells or samples that are indicative of subtypes.

In one embodiment, lung cancer status is assessed through the evaluation of expression patterns, or profiles, of a plurality of classifier genes or biomarkers in one or more subject samples. For the purpose of discussion, the term "subject", or "subject sample", refers to an individual regardless of health and/or disease status. A subject can be a subject, a study participant, a patient, a control subject, a screening subject, or any other class of individual from whom a sample is obtained and assessed in the context of the invention. Accordingly, a subject can be diagnosed with lung squamous cell carcinoma (including subtypes, or grades thereof), can present with one or more symptoms of lung SQ cancer, or a predisposing factor, such as a family (genetic) or medical history (medical) factor, for lung cancer, can be undergoing treatment or therapy for lung cancer, or the like. Alternatively, a subject can be healthy with respect to any of the aforementioned factors or criteria. It will be appreciated that the term "healthy" as used herein, is relative to lung cancer status, as the term "healthy" cannot be defined to correspond to any absolute evaluation or status. Thus, an individual defined as healthy with reference to any specified disease or disease criterion, can in fact be diagnosed with any other one or more diseases, or exhibit any other one or more disease criterion, including one or more other cancers.

As used herein, an "expression profile" or a "biomarker profile" or "gene signature" comprises one or more values corresponding to a measurement of the relative abundance, level, presence, or absence of expression of a biomarker or a discriminative or classifier gene. An expression profile can be derived from a subject prior to or subsequent to a diagnosis of lung cancer, can be derived from a biological sample collected from a subject at one or more time points prior to or following treatment or therapy, can be derived from a biological sample collected from a subject at one or more time points during which there is no treatment or therapy (e.g., to monitor progression of disease or to assess development of disease in a subject diagnosed with or at risk for lung cancer), or can be collected from a healthy subject. The term subject can be used interchangeably with patient. The patient can be a human patient. The one or more biomarkers of the biomarker profiles provided herein are selected from one or more biomarkers of Table 1.

As used herein, the term "determining an expression level" or "determining an expression profile" or "detecting an expression level" or "detecting an expression profile" as used in reference to a biomarker or classifier means the application of a biomarker specific reagent such as a probe, primer or antibody and/or a method to a sample, for example a sample of the subject or patient and/or a control sample, for ascertaining or measuring quantitatively, semi-quantitatively or qualitatively the amount of a biomarker or biomarkers, for example the amount of biomarker polypeptide or mRNA (or cDNA derived therefrom). For example, a level of a biomarker can be determined by a number of methods including for example immunoassays including for example immunohistochemistry, ELISA, Western blot, immunoprecipitation and the like, where a biomarker detection agent such as an antibody for example, a labeled antibody, specifically binds the biomarker and permits for example relative or absolute ascertaining of the amount of polypeptide biomarker, hybridization and PCR protocols where a probe or primer or primer set are used to ascertain the amount of nucleic acid biomarker, including for example probe based and amplification based methods including for example microarray analysis, RT-PCR such as quantitative RT-PCR (qRT-PCR), serial analysis of gene expression (SAGE), Northern Blot, digital molecular barcoding technology, for example Nanostring Counter Analysis, and TaqMan quantitative PCR assays. Other methods of mRNA detection and quantification can be applied, such as mRNA in situ hybridization in formalin-fixed, paraffin-embedded (FFPE) tissue samples or cells. This technology is currently offered by the QuantiGene ViewRNA (Affymetrix), which uses probe sets for each mRNA that bind specifically to an amplification system to amplify the hybridization signals; these amplified signals can be visualized using a standard fluorescence microscope or imaging system. This system for example can detect and measure transcript levels in heterogeneous samples; for example, if a sample has normal and tumor cells present in the same tissue section. As mentioned, TaqMan probe-based gene expression analysis (PCR-based) can also be used for measuring gene expression levels in tissue samples, and this technology has been shown to be useful for measuring mRNA levels in FFPE samples. In brief, TaqMan probe-based assays utilize a probe that hybridizes specifically to the mRNA target. This probe contains a quencher dye and a reporter dye (fluorescent molecule) attached to each end, and fluorescence is emitted only when specific hybridization to the mRNA target occurs. During the amplification step, the exonuclease activity of the polymerase enzyme causes the quencher and the reporter dyes to be detached from the probe, and fluorescence emission can occur. This fluorescence emission is recorded and signals are measured by a detection system; these signal intensities are used to calculate the abundance of a given transcript (gene expression) in a sample.

In one embodiment, the "expression profile" or a "biomarker profile" or "gene signature" associated with the gene cassettes or classifier genes described herein (e.g., Tables 1 and 2) can be useful for distinguishing between normal and tumor samples. In another embodiment, the tumor samples are lung SQ samples. In another embodiment, SQ can be further classified as basal, classical, primitive or secretory based upon an expression profile determined using the methods provided herein. The characterization of basal, classical, primitive or secretory squamous cell carcinoma using gene expression has been described in Wilkerson M D, et al. Clin Cancer Res 2010; 16(19): 4864-75.

Expression profiles using the classifier or biomarker genes disclosed herein (e.g., Table 1) can provide valuable molecular tools for specifically identifying lung squamous cell carcinoma subtypes, and for evaluating therapeutic efficacy in treating lung squamous cell carcinoma. Accordingly, the invention provides methods for screening and classifying a subject for molecular SQ subtypes and methods for monitoring efficacy of certain therapeutic treatments for lung SQ.

In some instances, a single classifier gene provided herein is capable of identifying subtypes of lung squamous cell carcinoma with a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%.

In some instances, a single classifier gene as provided herein is capable of determining lung squamous cell carcinoma subtypes with a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%.

The present invention also encompasses a system capable of distinguishing various subtypes of lung squamous cell carcinoma not detectable using current methods. This system can b e capable of processing a large number of subjects and subject variables such as expression profiles and other diagnostic criteria. The methods described herein can also be used for "pharmacometabonomics," in analogy to pharmacogenomics, e.g., predictive of response to therapy. In this embodiment, subjects could be divided into "responders" and "nonresponders" using the expression profile as evidence of "response," and features of the expression profile could then be used to target future subjects who would likely respond to a particular therapeutic course.

The expression profile can be used in combination with other diagnostic methods including histochemical, immunohistochemical, cytologic, immunocytologic, and visual diagnostic methods including histologic or morphometric evaluation of lung tissue.

In various embodiments of the present invention, the expression profile derived from a subject is compared to a reference expression profile. A "reference expression profile" can be a profile derived from the subject prior to treatment or therapy; can be a profile produced from the subject sample at a particular time point (usually prior to or following treatment or therapy, but can also include a particular time point prior to or following diagnosis of lung cancer); or can be derived from a healthy individual or a pooled reference from healthy individuals. A reference expression profile can be generic for lung cancer, or can be specific to different subtypes of lung squamous cell carcinoma.

The reference expression profile can be compared to a test expression profile. A "test expression profile" can be derived from the same subject as the reference expression profile except at a subsequent time point (e.g., one or more days, weeks or months following collection of the reference expression profile) or can be derived from a different subject. In summary, any test expression profile of a subject can be compared to a previously collected profile from a subject that has a basal, classical, primitive or secretory subtype.

The classifier biomarkers of the invention can include nucleic acids (RNA, cDNA, and DNA) and proteins, and variants and fragments thereof. Such biomarkers can include DNA comprising the entire or partial sequence of the nucleic acid sequence encoding the biomarker, or the complement of such a sequence. The biomarkers described herein can include RNA comprising the entire or partial sequence of any of the nucleic acid sequences of interest, or their non-natural cDNA products, obtained synthetically in vitro in a reverse transcription reaction. The biomarker nucleic acids can also include any expression product or portion thereof of the nucleic acid sequences of interest. A biomarker protein can be a protein encoded by or corresponding to a DNA biomarker of the invention. A biomarker protein can comprise the entire or partial amino acid sequence of any of the biomarker proteins or polypeptides. The biomarker nucleic acid can be extracted from a cell or can be cell free or extracted from an extracellular vesicular entity such as an exosome.

A "classifier biomarker" or "biomarker" or "classifier gene" can be any gene or protein whose level of expression in a tissue or cell is altered compared to that of a normal or healthy cell or tissue. For example, a "classifier biomarker" or "biomarker" or "classifier gene" can be any gene or protein whose level of expression in a tissue or cell is altered in a specific lung squamous cell carcinoma subtype. The detection of the biomarkers of the invention can permit the determination of the specific subtype. The "classifier biomarker" or "biomarker" or "classifier gene" may be one that is up-regulated (e.g. expression is increased) or down-regulated (e.g. expression is decreased) relative to a reference or control as provided herein. The reference or control can be any reference or control as provided herein. In some embodiments, the expression values of genes that are up-regulated or down-regulated in a particular subtype of lung squamous cell carcinoma can be pooled into one gene cassette. The overall expression level in each gene cassette is referred to herein as the "'expression profile" and is used to classify a test sample according to the subtype of lung squamous cell carcinoma. However, it is understood that independent evaluation of expression for each of the genes disclosed herein can be used to classify tumor subtypes without the need to group up-regulated and down-regulated genes into one or more gene cassettes. In some cases, as shown in Table 2, a total of 80 biomarkers can be used for SQ subtype determination. For each SQ subtype, 10 of the 20 biomarkers can be negatively correlated genes while 10 can be positively correlated genes which can be selected as the gene signature of a specific SQ subtype.

The classifier biomarkers of the invention can include any gene or protein that is selectively expressed in lung SQ, as defined herein above. Sample biomarker genes are listed in Table 1 or 2, below. In Table 2, the first column of the table represents the biomarker list selected for distinguishing basal SQ. The second column of the table represents the biomarker list selected for classical SQ. The third column of the table represents the biomarker list selected for distinguishing primitive SQ. The fourth column of the table represents the biomarker list selected for distinguishing secretory SQ.

The relative gene expression levels as represented by the tsat as described herein of the classifier biomarkers for lung SQ subtyping are shown in Table 1. In one embodiment, the gene expression levels of the classifier biomarkers for lung SQ subtyping are shown in Table 1. In one embodiment, all 80 genes can be used to classify the subtypes of SQ. In one embodiment, the first 20 genes are the selected gene signature biomarkers for basal, with gene numbers 1-10 up-regulated and gene numbers 11-20 down-regulated compared to anon-basal sample. In another embodiment, gene numbers 21-40 are the selected gene signature biomarkers specific for classical, with gene numbers 21-30 up-regulated and gene numbers 31-40 down-regulated compared to anon-classical sample. In yet another embodiment, gene numbers 41-60 are the selected gene signature biomarkers specific for primitive, with gene numbers 41-50 up-regulated and gene numbers 51-60 down-regulated compared to anon-primitive sample. In yet another embodiment, gene numbers 61-80 are the selected gene signature biomarkers specific for secretory, with gene numbers 61-70 up-regulated and gene numbers 71-80 down-regulated compared to anon-primitive sample.

TABLE 1

Gene Centroids of the 80 Classifier Biomarkers for the Lung Squamous Cell Carcinoma (SQ) Subtypes

| Gene No. | Gene Symbol | Gene Name | basal | classical | primitive | secretory | GenBank Accession Number* | SEQ ID NO: |
|---|---|---|---|---|---|---|---|---|
| 1 | SERPINB4 | serpin family B member 4 | 15.1924 | −1.28178 | −10.0199 | −7.32845 | NM_002974.3 | 1 |
| 2 | CXCL1 | C—X—C motif chemokine ligand 1 | 14.47981 | −8.31954 | −8.37503 | 0.217875 | NM_001511.3 | 2 |
| 3 | S100A9 | S100 calcium binding protein A9 | 14.35103 | −5.8793 | −9.10206 | −1.88807 | NM_002965.3 | 3 |
| 4 | S100A8 | S100 calcium binding protein A8 | 14.00816 | −4.229 | −9.53669 | −3.08348 | NM_001319196.1 | 4 |

TABLE 1-continued

Gene Centroids of the 80 Classifier Biomarkers for the Lung Squamous Cell Carcinoma (SQ) Subtypes

| Gene No. | Gene Symbol | Gene Name | basal | classical | primitive | secretory | GenBank Accession Number* | SEQ ID NO: |
|---|---|---|---|---|---|---|---|---|
| 5 | SERPINB3 | serpin family B member 3 | 13.97538 | 1.502713 | −10.9279 | −8.54433 | NM_006919.2 | 5 |
| 6 | EPHA2 | EPHA2 | 12.36835 | −4.75069 | −8.27087 | −1.67711 | NM_004431.4 | 6 |
| 7 | S100A2 | S100 calcium binding protein A2 | 12.02474 | 2.060853 | −9.93545 | −7.83677 | NM_005978.3 | 7 |
| 8 | MMP10 | matrix metallopeptidase 10 | 11.70464 | −5.18263 | −3.79013 | −3.73457 | NM_002425.2 | 8 |
| 9 | IL4R | interleukin 4 receptor | 11.67838 | −11.2637 | −9.61741 | 7.418712 | NM_000418.3 | 9 |
| 10 | PDZK1IP1 | PDZK1-interacting protein 1 | 11.00384 | −9.67747 | −7.37829 | 4.707793 | NM_005764.3 | 10 |
| 11 | CDK5RAP2 | CDK5 regulatory subunit associated protein 2 | −13.3044 | 15.44094 | 0.582601 | −3.89079 | NM_018249.5 | 11 |
| 12 | FAM125B | family with sequence similarity 125, member B | −12.2853 | 4.665284 | 4.308726 | 4.558947 | BC028675.1 | 12 |
| 13 | CABC1 | chaperone activity of bc1 complex-like | −10.3757 | 4.343061 | 7.391224 | 0.672574 | AB073905.1 | 13 |
| 14 | ODC1 | ornithine decarboxylase 1 | −10.1908 | 15.84852 | 0.119301 | −7.30631 | NM_002539.2 | 14 |
| 15 | LPIN1 | lipin 1 | −10.134 | 3.748752 | 3.061368 | 4.230976 | NM_145693.2 | 15 |
| 16 | WASF1 | WAS protein family member 1 | −9.89134 | 18.55734 | 1.814068 | −11.9252 | NM_003931.2 | 16 |
| 17 | USP13 | ubiquitin specific peptidase 13 (isopeptidase T-3) | −9.17202 | 7.072314 | 7.133335 | −3.50892 | NM_003940.2 | 17 |
| 18 | NUP210 | nucleoporin 210 | −8.91997 | 5.496247 | 2.508106 | 1.366756 | NM_024923.3 | 18 |
| 19 | GLI2 | GLI Family Zinc Finger 2 | −8.58227 | 17.05556 | −5.643 | −6.1972 | NM_005270.4 | 19 |
| 20 | SPAG5 | sperm associated antigen 5 | −8.26995 | 8.478108 | 6.146636 | −5.34162 | NM_006461.3 | 20 |
| 21 | ME1 | malic enzyme 1 | −11.1058 | 21.38387 | −2.66141 | −10.605 | NM_002395.5 | 21 |
| 22 | TALDO1 | transaldolase 1 | −11.3472 | 21.05835 | −2.95802 | −9.76549 | NM_006755.1 | 22 |
| 23 | AKR1C3 | aldo-keto reductase family 1, member C3 | −6.34178 | 19.62236 | −6.31166 | −10.9917 | NM_003739.5 | 23 |
| 24 | TXN | thioredoxin | −7.28934 | 19.56185 | −6.64144 | −9.68306 | NM_003329.3 | 24 |
| 25 | ALDH3A1 | aldehyde dehydrogenase 3 family member A1 | −4.42445 | 19.16675 | −7.69158 | −11.4995 | NM_001135168.1 | 25 |
| 26 | CHST7 | carbohydrate sulfotransferase 7 | −6.70839 | 18.66004 | −5.80704 | −9.87835 | NM_019886.3 | 26 |
| 27 | ADAM 23 | ADAM metallopeptidase domain 23 | −7.14726 | 18.4093 | −5.05087 | −9.67848 | NM_003812.3 | 27 |

TABLE 1-continued

Gene Centroids of the 80 Classifier Biomarkers for the Lung Squamous Cell Carcinoma (SQ) Subtypes

| Gene No. | Gene Symbol | Gene Name | basal | classical | primitive | secretory | GenBank Accession Number* | SEQ ID NO: |
|---|---|---|---|---|---|---|---|---|
| 28 | TUFT1 | tuftelin 1 | −6.31534 | 18.07229 | −4.12497 | −10.8461 | NM_020127.2 | 28 |
| 29 | FOXE1 | forkhead box E1 | −2.047 | 17.53642 | −9.74136 | −10.6746 | NM_004473.3 | 29 |
| 30 | ALDH3A2 | aldehyde dehydrogenase 3 family member A2 | −7.7634 | 15.83759 | −4.12228 | −6.78263 | NM_001031806.1 | 30 |
| 31 | PHC2 | polyhomeotic homolog 2 | 5.947711 | −19.3491 | 3.975339 | 12.79184 | NM_198040.2 | 31 |
| 32 | SLC43A3 | solute carrier family 43 member 3 | 2.164732 | −15.4786 | 4.435501 | 12.06209 | NM_014096.3 | 32 |
| 33 | CAPZB | capping actin protein of muscle Z-line beta subunit | 9.697325 | −15.4337 | −0.08505 | 7.331941 | NM_004930.4 | 33 |
| 34 | FAM46A | family with sequence similarity 46 member A | 9.050488 | −14.8822 | 0.551123 | 6.928165 | NM_017633.2 | 34 |
| 35 | PTP4A2 | protein tyrosine phosphatase type IVA, member 2 | 5.400389 | −14.838 | 1.837093 | 9.801226 | NM_080391.3 | 35 |
| 36 | DPYD | dihydropyrimidine dehydrogenase | 8.78203 | −14.5434 | −5.09695 | 10.92233 | NM_000110.3 | 36 |
| 37 | TRIM8 | tripartite motif containing 8 | 3.847394 | −14.5393 | −1.94247 | 13.84298 | NM_030912.2 | 37 |
| 38 | CD47 | CD47 molecule | 8.84354 | −14.3091 | −2.8533 | 8.964713 | NM_001777.3 | 38 |
| 39 | CRIP2 | cysteine rich protein 2 | 4.809366 | −14.1729 | 1.781357 | 9.711258 | NM_001312.3 | 39 |
| 40 | ST3GAL5 | ST3 beta-galactoside alpha-2,3-sialyltransferase 5 | 2.667885 | −13.865 | −1.29718 | 13.85595 | NM_003896.3 | 40 |
| 41 | HSF2 | heat shock transcription factor 2 | −5.79001 | 1.050968 | 11.39169 | −3.33599 | NM_004506.3 | 41 |
| 42 | MARCKSL1 | MARCKS like 1 | 1.317716 | −10.696 | 9.825417 | 3.621776 | NM_023009.6 | 42 |
| 43 | EFHD1 | EF-hand domain family member D1 | −2.47675 | −11.1247 | 9.620027 | 8.265181 | NM_025202.3 | 43 |
| 44 | CHKA | choline kinase alpha | −2.84869 | −7.08145 | 9.530024 | 4.135237 | NM_001277.2 | 44 |
| 45 | PLEKHB1 | pleckstrin homology domain containing B1 | −5.94374 | −6.54778 | 9.307835 | 6.960047 | NM_021200.2 | 45 |
| 46 | FNBP1L | formin binding protein 1 like | 2.207537 | −13.5657 | 9.226556 | 6.372445 | NM_001024948.2 | 46 |
| 47 | ZNF239 | zinc finger protein 239 | −2.61452 | −7.55963 | 8.698057 | 5.033708 | NM_005674.2 | 47 |

TABLE 1-continued

Gene Centroids of the 80 Classifier Biomarkers for the Lung Squamous Cell Carcinoma (SQ) Subtypes

| Gene No. | Gene Symbol | Gene Name | basal | classical | primitive | secretory | GenBank Accession Number* | SEQ ID NO: |
|---|---|---|---|---|---|---|---|---|
| 48 | ABI2 | Abelson interactor 2 | −8.51982 | 0.375002 | 8.621929 | 2.322745 | NM_001282925.1 | 48 |
| 49 | MYL6B | Myosin light chain 6B | −1.67839 | −4.74647 | 8.614632 | 0.913087 | NM_001199629.1 | 49 |
| 50 | TTLL4 | Tubulin Tyrosine Ligase Like 4 | −4.42597 | −4.4529 | 8.316108 | 3.698664 | NM_014640.4 | 50 |
| 51 | CLCA2 | Chloride Channel Accessory 2 | 11.3747 | 9.8531 | −13.5607 | −13.3641 | NM_006536.5 | 51 |
| 52 | GJB3 | Gap Junction Protein Beta 3 | 9.738857 | 1.975392 | −12.8741 | −3.19459 | NM_024009.2 | 52 |
| 53 | GPR87 | G Protein-Coupled Receptor 87 | 8.675319 | 3.714366 | −12.5406 | −4.28629 | NM_023915.3 | 53 |
| 54 | SFN | Stratifin | 9.34036 | 7.030931 | −12.0548 | −9.10453 | NM_006142.3 | 54 |
| 55 | CSTA | Cystatin A | 8.521125 | 6.642274 | −11.6462 | −8.09435 | NM_005213.3 | 55 |
| 56 | DSG3 | Desmoglein 3 | 8.011909 | 9.629873 | −11.4831 | −11.0649 | NM_001944.2 | 56 |
| 57 | ST6GALNAC2 | ST6 N-Acetylgalactosaminide Alpha-2,6-Sialyltransferase 2 | 3.15872 | 10.40711 | −11.4486 | −6.84553 | NM_006456.2 | 57 |
| 58 | GJB5 | Gap Junction Protein 3 Beta 5 | 9.68863 | 5.741838 | −11.4122 | −8.47546 | NM_005268.3 | 58 |
| 59 | TMPRSS4 | Transmembrane Protease, Serine 4 | 7.421295 | 10.31518 | −10.907 | −11.6365 | NM_019894.3 | 59 |
| 60 | SDC1 | Syndecan 1 | 7.820035 | 8.717049 | −10.7889 | −10.3298 | NM_001006946.1 | 60 |
| 61 | FMNL1 | Formin Like 1 | −1.24826 | −12.3922 | −4.15625 | 18.39415 | NM_005892.3 | 61 |
| 62 | BIRC3 | Baculoviral IAP Repeat Containing 3 | 0.52973 | −12.5421 | −4.71506 | 17.09129 | NM_001165.4 | 62 |
| 63 | ARHGDIB | Rho GDP Dissociation inhibitor Beta | 1.579196 | −12.7865 | −4.70303 | 16.25141 | NM_001175.6 | 63 |
| 64 | SH2B3 | SH2B Adaptor Protein 3 | −3.48062 | −9.12196 | −3.04569 | 16.23607 | NM_005475.2 | 64 |
| 65 | HLA-DPA1 | Major Histocompatibility Complex, Class II, DP Alpha 1 | −2.12031 | −9.65989 | −3.99607 | 16.09867 | NM_033554.3 | 65 |
| 66 | NCF4 | Neutrophil Cytosolic Factor 4 | 1.545361 | −11.6937 | −6.10253 | 16.0617 | NM_000631.4 | 66 |
| 67 | ACSL5 | Acyl-CoA Synthetase Long-Chain Family Member 5 | 1.654978 | −14.5012 | −1.66186 | 15.91216 | NM_016234.3 | 67 |
| 68 | CSF2RA | Colony Stimulating Factor 2 Receptor Alpha Subunit | −1.37456 | −10.508 | −2.90331 | 15.48108 | NM_006140.4 | 68 |
| 69 | LAPTM5 | Lysosomal Protein Transmembrane 5 | −1.16591 | −9.77656 | −4.28777 | 15.43442 | NM_006762.2 | 69 |

TABLE 1-continued

Gene Centroids of the 80 Classifier Biomarkers for the Lung Squamous Cell Carcinoma (SQ) Subtypes

| Gene No. | Gene Symbol | Gene Name | basal | classical | primitive | secretory | GenBank Accession Number* | SEQ ID NO: |
|---|---|---|---|---|---|---|---|---|
| 70 | ARL6IP5 | ADP-ribosylation-like factor 6 interacting protein 5 | 3.195006 | −13.6479 | −4.55752 | 15.41665 | NM_006407.3 | 70 |
| 71 | ADH7 | Alcohol Dehydrogenase 7 (Class IV), Mu Or Sigma | 0.182052 | 20.14673 | −9.26939 | −16.3334 | NM_001166504.1 | 71 |
| 72 | ABCC5 | ATP Binding Cassette Subfamily C Member 5 | −1.26645 | 17.73313 | −4.3337 | −15.6431 | NM_005688.3 | 72 |
| 73 | SOX2 | SRY-Box 2 | −2.70147 | 15.71135 | 0.455164 | −15.3051 | NM_003106.3 | 73 |
| 74 | SLC9A3R1 | Solute Carrier Family 9, Subfamily A (NHE3, Cation Proton Antiporter 3), Member 3 Regulator 1 | 1.902295 | 17.71886 | −9.60834 | −15.1497 | NM_004252.4 | 74 |
| 75 | KLF5 | Kruppel-Like Factor 5 (intestinal) | 4.456364 | 13.41893 | −8.16611 | −14.0138 | NM_001730.4 | 75 |
| 76 | GPX2 | Glutathione Peroxidase 2 | −2.8397 | 17.49375 | −3.93026 | −14.0021 | NM_002083.3 | 76 |
| 77 | PIR | Pirin | −4.58676 | 16.97955 | −1.18296 | −13.5651 | NM_003662.3 | 77 |
| 78 | TPD52L1 | Tumor Protein D52-Like 1 | 1.334706 | 10.49961 | 0.210322 | −13.4769 | NM_003287.3 | 78 |
| 79 | SLC6A8 | Solute Carrier family 6 Member 8 | 3.006892 | 11.83057 | −4.32575 | −13.4647 | NM_005629.3 | 79 |
| 80 | SIAH2 | Siah E3 Ubiquitin Protein Ligase 2 | 1.897743 | 11.60785 | −2.92619 | −13.0552 | NM_005067.5 | 80 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 2

Classifier Biomarkers Selected for Basal, Classical, Primitive and Secretory SQ Subtypes

| Basal | Classical | Primitive | Secretory |
|---|---|---|---|
| SERPINB4 | ME1 | HSF2 | FMNL1 |
| CXCL1 | TALDO1 | MARCKSL1 | BIRC3 |
| S100A9 | AKR1C3 | EFHD1 | ARHGD1B |
| S100A8 | TXN | CHKA | SH2B3 |
| SERPINB3 | ALDH3A1 | PLEKHB1 | HLA-DPA1 |
| EPHA2 | CHST7 | FNBP1L | NCF4 |
| S100A2 | ADAM23 | ZNF239 | ACSL5 |
| MMP10 | TUFT1 | AB12 | CSF2RA |
| IL4R | FOXE1 | MYL6B | LAPTM5 |
| PDZK1LP1 | ALDH3A2 | TTLL4 | ARL61P5 |
| CDK5RAP2 | PHC2 | CLCA2 | ADH7 |
| FAM125B | SLC43A3 | GJB3 | ABCC5 |
| CABC1 | CAPZB | GPR87 | SOX2 |
| CDC1 | FAM46A | SFN | SLC9A3R1 |
| LPIN1 | PTP4A2 | CSTA | KLF5 |
| WASF1 | DPYD | DSG3 | GPX2 |
| USP13 | TRIM8 | ST6GALNAC2 | PIR |
| NUP210 | CD47 | GJB5 | TPD52L1 |
| GL12 | CRIP2 | TMPRSS4 | SLC6A8 |
| SPAG5 | ST3GAL5 | SDC1 | SIAH2 |

Diagnostic Uses

In one embodiment, the methods and compositions provided herein allow for the differentiation of the four subtypes of squamous cell carcinoma: (1) basal; (2) classical; (3) primitive; and (4) secretory, with fewer genes needed than the molecular SQ subtyping methods known in the art.

In general, the methods provided herein are used to classify a lung cancer sample as a particular lung cancer subtype (e.g. subtype of squamous cell carcinoma). In one embodiment, the method comprises detecting or determining an expression level of at least one of the classifier biomarkers of any publically available Lung AD expression dataset. In one embodiment, the method comprises measuring, detecting or determining an expression level of at least one of the classifier biomarkers of Table 1 in a lung cancer sample obtained from a patient or a subject.

The lung cancer sample for the detection or differentiation methods described herein can be a sample previously determined or diagnosed as a squamous cell carcinoma sample. The previous diagnosis can be based on a histological analysis. The histological analysis can be performed by one or more pathologists.

In one embodiment, the measuring or detecting step employed in the methods provided herein is at the nucleic acid level by performing RNA-seq, a reverse transcriptase polymerase chain reaction (RT-PCR) or a hybridization assay with oligonucleotides that are substantially complementary to portions of cDNA molecules of the at least one classifier biomarker (such as the classifier biomarkers of Table 1) under conditions suitable for RNA-seq, RT-PCR or hybridization and obtaining expression levels of the at least one classifier biomarkers based on the detecting step. The expression levels of the at least one of the classifier biomarkers are then compared to reference expression levels of the at least one of the classifier biomarker (such as the classifier biomarkers of Table 1) from at least one sample training set. The at least one sample training set can comprise, (i) expression levels of the at least one biomarker from a sample that overexpresses the at least one biomarker, (ii) expression levels from a reference basal, classical, primitive or secretory SQ subtype, or (iii) expression levels from an squamous cell carcinoma free lung sample, and classifying the lung tissue sample as a basal, classical, primitive or secretory subtype. The lung cancer sample can then be classified as a basal, classical, primitive or secretory subtype of squamous cell carcinoma based on the results of the comparing step. In one embodiment, the comparing step can comprise applying a statistical algorithm which comprises determining a correlation between the expression data obtained from the lung tissue or cancer sample and the expression data from the at least one training set(s); and classifying the lung tissue or cancer sample as a basal, classical, primitive or secretory subtype based on the results of the statistical algorithm.

In one embodiment, the methods provided herein comprise probing the levels of at least one of the classifier biomarkers provided herein, such as the classifier biomarkers of Table 1 at the nucleic acid level, in a lung cancer sample obtained from the patient. The lung cancer sample can be a sample previously determined or diagnosed as a squamous cell carcinoma sample. The previous diagnosis can be based on a histological analysis. The histological analysis can be performed by one or more pathologists. The probing step, in one embodiment, comprises mixing the sample with one or more oligonucleotides that are substantially complementary to portions of cDNA molecules of the at least one classifier biomarkers provided herein, such as the classifier biomarkers of Table 1 under conditions suitable for hybridization of the one or more oligonucleotides to their complements or substantial complements; detecting whether hybridization occurs between the one or more oligonucleotides to their complements or substantial complements; and obtaining hybridization values of the at least one classifier biomarkers based on the detecting step. The hybridization values of the at least one classifier biomarkers are then compared to reference hybridization value(s) from at least one sample training set. For example, the at least one sample training set comprises hybridization values from a reference basal, classical, primitive or secretory sample. The lung cancer sample is classified, for example, as basal, classical, primitive or secretory based on the results of the comparing step.

The lung tissue sample can be any sample isolated from a human subject or patient. For example, in one embodiment, the analysis is performed on lung biopsies that are embedded in paraffin wax. In one embodiment, the sample can be a fresh frozen lung tissue sample. In another embodiment, the sample can be a bodily fluid obtained from the patient. The bodily fluid can be blood or fractions thereof (i.e., serum, plasma), urine, saliva, sputum or cerebrospinal fluid (CSF). The sample can contain cellular as well as extracellular sources of nucleic acid for use in the methods provided herein. The extracellular sources can be cell-free DNA and/or exosomes. In one embodiment, the sample can be a cell pellet or a wash. This aspect of the invention provides a means to improve current diagnostics by accurately identifying the major histological types, even from small biopsies. The methods of the invention, including the RT-PCR methods, are sensitive, precise and have multi-analyte capability for use with paraffin embedded samples. See, for example, Cronin et al. (2004) *Am. J Pathol.* 164 (1):35-42, herein incorporated by reference.

Formalin fixation and tissue embedding in paraffin wax is a universal approach for tissue processing prior to light microscopic evaluation. A major advantage afforded by formalin-fixed paraffin-embedded (FFPE) specimens is the preservation of cellular and architectural morphologic detail in tissue sections. (Fox et al. (1985) J Histochem Cytochem 33:845-853). The standard buffered formalin fixative in which biopsy specimens are processed is typically an aqueous solution containing 37% formaldehyde and 10-15% methyl alcohol. Formaldehyde is a highly reactive dipolar compound that results in the formation of protein-nucleic acid and protein-protein crosslinks in vitro (Clark et al. (1986) J Histochem Cytochem 34:1509-1512; McGhee and von Hippel (1975) Biochemistry 14:1281-1296, each incorporated by reference herein).

In one embodiment, the sample used herein is obtained from an individual, and comprises formalin-fixed paraffin-embedded (FFPE) tissue. However, other tissue and sample types are amenable for use herein. In one embodiment, the other tissue and sample types can be fresh frozen tissue, wash fluids, or cell pellets, or the like. In one embodiment, the sample can be a bodily fluid obtained from the individual. The bodily fluid can be blood or fractions thereof (e.g., serum, plasma), urine, sputum, saliva or cerebrospinal fluid (CSF). A biomarker nucleic acid as provided herein can be extracted from a cell or can be cell free or extracted from an extracellular vesicular entity such as an exosome.

Methods are known in the art for the isolation of RNA from FFPE tissue. In one embodiment, total RNA can be isolated from FFPE tissues as described by Bibikova et al. (2004) American Journal of Pathology 165:1799-1807, herein incorporated by reference. Likewise, the High Pure RNA Paraffin Kit (Roche) can be used. Paraffin is removed by xylene extraction followed by ethanol wash. RNA can be isolated from sectioned tissue blocks using the MasterPure Purification kit (Epicenter, Madison, Wis.); a DNase I treatment step is included. RNA can be extracted from frozen samples using Trizol reagent according to the supplier's instructions (Invitrogen Life Technologies, Carlsbad, Calif.). Samples with measurable residual genomic DNA can be resubjected to DNase I treatment and assayed for DNA contamination. All purification, DNase treatment, and other steps can be performed according to the manufacturer's protocol. After total RNA isolation, samples can be stored at −80° C. until use.

General methods for mRNA extraction are well known in the art and are disclosed in standard textbooks of molecular biology, including Ausubel et al., ed., Current Protocols in Molecular Biology, John Wiley & Sons, New York 1987-1999. Methods for RNA extraction from paraffin embedded tissues are disclosed, for example, in Rupp and Locker (Lab Invest. 56:A67, 1987) and De Andres et al. (Biotechniques 18:42-44, 1995). In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Other commercially available RNA isolation kits include MasterPure™. Complete DNA and RNA Purification Kit (Epicentre, Madison, Wis.) and Paraffin Block RNA Isolation Kit (Ambion, Austin, Tex.). Total RNA from tissue samples can be isolated, for example, using RNA Stat-60 (Tel-Test, Friendswood, Tex.). RNA prepared from a tumor can be isolated, for example, by cesium chloride density gradient centrifugation. Additionally, large numbers of tissue samples can readily be processed using techniques well known to those of skill in the art, such as, for example, the single-step RNA isolation process of Chomczynski (U.S. Pat. No. 4,843,155, incorporated by reference in its entirety for all purposes).

In one embodiment, a sample comprises cells harvested from a lung tissue sample, for example, a squamous cell carcinoma sample. Cells can be harvested from a biological sample using standard techniques known in the art. For example, in one embodiment, cells are harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract nucleic acid, e.g, messenger RNA. All samples obtained from a subject, including those subjected to any sort of further processing, are considered to be obtained from the subject.

The sample, in one embodiment, is further processed before the detection of the biomarker levels of the combination of biomarkers set forth herein. For example, mRNA in a cell or tissue sample can be separated from other components of the sample. The sample can be concentrated and/or purified to isolate mRNA in its non-natural state, as the mRNA is not in its natural environment. For example, studies have indicated that the higher order structure of mRNA in vivo differs from the in vitro structure of the same sequence (see, e.g., Rouskin et al. (2014). Nature 505, pp. 701-705, incorporated herein in its entirety for all purposes).

mRNA from the sample in one embodiment, is hybridized to a synthetic DNA probe, which in some embodiments, includes a detection moiety (e.g., detectable label, capture sequence, barcode reporting sequence). Accordingly, in these embodiments, a non-natural mRNA-cDNA complex is ultimately made and used for detection of the biomarker. In another embodiment, mRNA from the sample is directly labeled with a detectable label, e.g., a fluorophore. In a further embodiment, the non-natural labeled-mRNA molecule is hybridized to a cDNA probe and the complex is detected.

In one embodiment, once the mRNA is obtained from a sample, it is converted to complementary DNA (cDNA) in a hybridization reaction or is used in a hybridization reaction together with one or more cDNA probes. cDNA does not exist in vivo and therefore is a non-natural molecule. Furthermore, cDNA-mRNA hybrids are synthetic and do not exist in vivo. Besides cDNA not existing in vivo, cDNA is necessarily different than mRNA, as it includes deoxyribonucleic acid and not ribonucleic acid. The cDNA is then amplified, for example, by the polymerase chain reaction (PCR) or other amplification method known to those of ordinary skill in the art. For example, other amplification methods that may be employed include the ligase chain reaction (LCR) (Wu and Wallace, Genomics, 4:560 (1989), Landegren et al., Science, 241:1077 (1988), incorporated by reference in its entirety for all purposes, transcription amplification (Kwoh et al., *Proc. Natl. Acad. Sci. USA,* 86:1173 (1989), incorporated by reference in its entirety for all purposes), self-sustained sequence replication (Guatelli et al., *Proc. Nat. Acad. Sci. USA,* 87:1874 (1990), incorporated by reference in its entirety for all purposes), incorporated by reference in its entirety for all purposes, and nucleic acid based sequence amplification (NASBA). Guidelines for selecting primers for PCR amplification are known to those of ordinary skill in the art. See, e.g., McPherson et al., PCR Basics: From Background to Bench, Springer-Verlag, 2000, incorporated by reference in its entirety for all purposes. The product of this amplification reaction, i.e., amplified cDNA is also necessarily a non-natural product. First, as mentioned above, cDNA is a non-natural molecule. Second, in the case of PCR, the amplification process serves to create hundreds of millions of cDNA copies for every individual cDNA molecule of starting material. The numbers of copies generated are far removed from the number of copies of mRNA that are present in vivo.

In one embodiment, cDNA is amplified with primers that introduce an additional DNA sequence (e.g., adapter, reporter, capture sequence or moiety, barcode) onto the fragments (e.g., with the use of adapter-specific primers), or mRNA or cDNA biomarker sequences are hybridized directly to a cDNA probe comprising the additional sequence (e.g., adapter, reporter, capture sequence or moiety, barcode). Amplification and/or hybridization of mRNA to a cDNA probe therefore serves to create non-natural double stranded molecules from the non-natural single stranded cDNA, or the mRNA, by introducing additional sequences and forming non-natural hybrids. Further, as known to those of ordinary skill in the art, amplification procedures have error rates associated with them. Therefore, amplification introduces further modifications into the cDNA molecules. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature, and (iv) the chemical addition of a detectable label to the cDNA molecules.

In some embodiments, the expression of a biomarker of interest is detected at the nucleic acid level via detection of non-natural cDNA molecules.

In some embodiments, the methods provided herein for lung cancer SQ subtyping includes detecting expression levels of a classifier biomarker set. In some embodiments, the detecting includes all of the classifier biomarkers of Table 1 at the nucleic acid level or protein level. In another embodiment, a single or a subset or a plurality of the classifier biomarkers of Table 1 are detected, for example, from about 10 to about 20. For example, in one embodiment, from about 5 to about 10, from about 10 to about 20, from about 20 to about 40, from about 40 to about 60, from about 60 to about 80 of the biomarkers in Table 1 are detected in a method to determine the lung cancer SQ subtype. In another embodiment, each of the biomarkers from Table 1 is detected in a method to determine the lung cancer subtype. In another embodiment, 20 of the biomarkers from Table 1 are selected as the gene signatures for a specific lung cancer SQ subtype.

The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like. In some cases, the primers useful for the amplification methods (e.g., RT-PCR or qRT-PCR) are any forward and reverse primers suitable for binding to a classifier gene provided herein, such as the classifier biomarkers listed in Table 1.

The biomarkers described herein include RNA comprising the entire or partial sequence of any of the nucleic acid sequences of interest, or their non-natural cDNA product, obtained synthetically in vitro in a reverse transcription reaction. The term "fragment" is intended to refer to a portion of the polynucleotide that generally comprise at least 10, 15, 20, 50, 75, 100, 150, 200, 250, 300, 350, 400, 450, 500, 550, 600, 650, 700, 800, 900, 1,000, 1,200, or 1,500 contiguous nucleotides, or up to the number of nucleotides present in a full-length biomarker polynucleotide disclosed herein. A fragment of a biomarker polynucleotide will generally encode at least 15, 25, 30, 50, 100, 150, 200, or 250 contiguous amino acids, or up to the total number of amino acids present in a full-length biomarker protein of the invention.

In some embodiments, overexpression, such as of an RNA transcript or its expression product, is determined by normalization to the level of reference RNA transcripts or their expression products, which can be all measured transcripts (or their products) in the sample or a particular reference set of RNA transcripts (or their non-natural cDNA products). Normalization is performed to correct for or normalize away both differences in the amount of RNA or cDNA assayed and variability in the quality of the RNA or cDNA used. Therefore, an assay typically measures and incorporates the expression of certain normalizing genes, including well known housekeeping genes, such as, for example, GAPDH and/or β-Actin. Alternatively, normalization can be based on the mean or median signal of all of the assayed biomarkers or a large subset thereof (global normalization approach).

Isolated mRNA can be used in hybridization or amplification assays that include, but are not limited to, Southern or Northern analyses, PCR analyses and probe arrays, NanoString Assays. One method for the detection of mRNA levels involves contacting the isolated mRNA or synthesized cDNA with a nucleic acid molecule (probe) that can hybridize to the mRNA encoded by the gene being detected. The nucleic acid probe can be, for example, a cDNA, or a portion thereof, such as an oligonucleotide of at least 7, 15, 30, 50, 100, 250, or 500 nucleotides in length and sufficient to specifically hybridize under stringent conditions to the non-natural cDNA or mRNA biomarker of the present invention.

As explained above, in one embodiment, once the mRNA is obtained from a sample, it is converted to complementary DNA (cDNA) in a hybridization reaction. Conversion of the mRNA to cDNA can be performed with oligonucleotides or primers comprising sequence that is complementary to a portion of a specific mRNA. Conversion of the mRNA to cDNA can be performed with oligonucleotides or primers comprising random sequence. Conversion of the mRNA to cDNA can be performed with oligonucleotides or primers comprising sequence that is complementary to the poly(A) tail of an mRNA. cDNA does not exist in vivo and therefore is a non-natural molecule. In a further embodiment, the cDNA is then amplified, for example, by the polymerase chain reaction (PCR) or other amplification method known to those of ordinary skill in the art. PCR can be performed with the forward and/or reverse primers comprising sequence complementary to at least a portion of a classifier gene provided herein, such as the classifier biomarkers in Table 1. The product of this amplification reaction, i.e., amplified cDNA is necessarily a non-natural product. As mentioned above, cDNA is a non-natural molecule. Second, in the case of PCR, the amplification process serves to create hundreds of millions of cDNA copies for every individual cDNA molecule of starting material. The number of copies generated is far removed from the number of copies of mRNA that are present in vivo.

In one embodiment, cDNA is amplified with primers that introduce an additional DNA sequence (adapter sequence) onto the fragments (with the use of adapter-specific primers). The adaptor sequence can be a tail, wherein the tail sequence is not complementary to the cDNA. For example, the forward and/or reverse primers comprising sequence complementary to at least a portion of a classifier gene provided herein, such as the classifier biomarkers from Table 1 can comprise tail sequence. Amplification therefore serves to create non-natural double stranded molecules from the non-natural single stranded cDNA, by introducing barcode, adapter and/or reporter sequences onto the already non-natural cDNA. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (ii) adapter sequences are added to the ends of cDNA molecules to make DNA sequences that do not exist in vivo, (iii) the error rate associated with amplification further creates DNA sequences that do not exist in vivo, (iv) the disparate structure of the cDNA molecules as compared to what exists in nature, and (v) the chemical addition of a detectable label to the cDNA molecules.

In one embodiment, the synthesized cDNA (for example, amplified cDNA) is immobilized on a solid surface via hybridization with a probe, e.g., via a microarray. In another embodiment, cDNA products are detected via real-time polymerase chain reaction (PCR) via the introduction of fluorescent probes that hybridize with the cDNA products. For example, in one embodiment, biomarker detection is assessed by quantitative fluorogenic RT-PCR (e.g., with TaqMan® probes). For PCR analysis, well known methods are available in the art for the determination of primer sequences for use in the analysis.

Biomarkers provided herein in one embodiment, are detected via a hybridization reaction that employs a capture probe and/or a reporter probe. For example, the hybridization probe is a probe derivatized to a solid surface such as a bead, glass or silicon substrate. In another embodiment, the capture probe is present in solution and mixed with the patient's sample, followed by attachment of the hybridization product to a surface, e.g., via a biotin-avidin interaction (e.g., where biotin is a part of the capture probe and avidin is on the surface). The hybridization assay, in one embodiment, employs both a capture probe and a reporter probe. The reporter probe can hybridize to either the capture probe or the biomarker nucleic acid. Reporter probes e.g., are then counted and detected to determine the level of biomarker(s) in the sample. The capture and/or reporter probe, in one embodiment contain a detectable label, and/or a group that allows functionalization to a surface.

For example, the nCounter gene analysis system (see, e.g., Geiss et al. (2008) Nat. Biotechnol. 26, pp. 317-325, incorporated by reference in its entirety for all purposes, is amenable for use with the methods provided herein.

Hybridization assays described in U.S. Pat. Nos. 7,473,767 and 8,492,094, the disclosures of which are incorporated by reference in their entireties for all purposes, are amenable for use with the methods provided herein, i.e., to detect the biomarkers and biomarker combinations described herein.

Biomarker levels may be monitored using a membrane blot (such as used in hybridization analysis such as Northern, Southern, dot, and the like), or microwells, sample tubes, gels, beads, or fibers (or any solid support comprising bound nucleic acids). See, for example, U.S. Pat. Nos. 5,770,722, 5,874,219, 5,744,305, 5,677,195 and 5,445,934, each incorporated by reference in their entireties.

In one embodiment, microarrays are used to detect biomarker levels. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316, each incorporated by reference in their entireties. High-density oligonucleotide arrays are particularly useful for determining the gene expression profile for a large number of RNAs in a sample.

Techniques for the synthesis of these arrays using mechanical synthesis methods are described in, for example, U.S. Pat. No. 5,384,261. Although a planar array surface is generally used, the array can be fabricated on a surface of virtually any shape or even a multiplicity of surfaces. Arrays can be nucleic acids (or peptides) on beads, gels, polymeric surfaces, fibers (such as fiber optics), glass, or any other appropriate substrate. See, for example, U.S. Pat. Nos. 5,770,358, 5,789,162, 5,708,153, 6,040,193 and 5,800,992, each incorporated by reference in their entireties. Arrays can be packaged in such a manner as to allow for diagnostics or other manipulation of an all-inclusive device. See, for example, U.S. Pat. Nos. 5,856,174 and 5,922,591, each incorporated by reference in their entireties.

Serial analysis of gene expression (SAGE) in one embodiment is employed in the methods described herein. SAGE is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, Velculescu et al. Science 270:484-87, 1995; Cell 88:243-51, 1997, incorporated by reference in its entirety.

An additional method of biomarker level analysis at the nucleic acid level is the use of a sequencing method, for example, RNAseq, next generation sequencing, and massively parallel signature sequencing (MPSS), as described by Brenner et al. (Nat. Biotech. 18:630-34, 2000, incorporated by reference in its entirety). This is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3.0\times10^6$ microbeads/$cm^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Another method of biomarker level expression analysis at the nucleic acid level is the use of an amplification method such as, for example, RT-PCR or quantitative RT-PCR (qRT-PCR). Methods for determining the level of biomarker mRNA in a sample may involve the process of nucleic acid amplification, e.g., by RT-PCR (the experimental embodiment set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. Numerous different PCR or qRT-PCR protocols are known in the art and can be directly applied or adapted for use using the presently described compositions for the detection and/or quantification of expression of discriminative genes in a sample. See, for example, Fan et al. (2004) Genome Res. 14:878-885, herein incorporated by reference. Generally, in PCR, a target polynucleotide sequence is amplified by reaction with at least one oligonucleotide primer or pair of oligonucleotide primers. The primer(s) hybridize to a complementary region of the target nucleic acid and a DNA polymerase extends the primer(s) to amplify the target sequence. Under conditions sufficient to provide polymerase-based nucleic acid amplification products, a nucleic acid fragment of one size dominates the reaction products (the target polynucleotide sequence which is the amplification product). The amplification cycle is repeated to increase the concentration of the single target polynucleotide sequence. The reaction can be performed in any thermocycler commonly used for PCR.

Quantitative RT-PCR (qRT-PCR) (also referred as real-time RT-PCR) is preferred under some circumstances because it provides not only a quantitative measurement, but also reduced time and contamination. As used herein, "quantitative PCR" (or "real time qRT-PCR") refers to the direct monitoring of the progress of a PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time. A DNA binding dye (e.g., SYBR green) or a labeled probe can be used to detect the extension product generated by PCR amplification. Any probe format utilizing a labeled probe comprising the sequences of the invention may be used.

Immunohistochemistry methods are also suitable for detecting the levels of the biomarkers of the present invention. Samples can be frozen for later preparation or immediately placed in a fixative solution. Tissue samples can be fixed by treatment with a reagent, such as formalin, gluteraldehyde, methanol, or the like and embedded in paraffin. Methods for preparing slides for immunohistochemical analysis from formalin-fixed, paraffin-embedded tissue samples are well known in the art.

In one embodiment, the levels of the biomarkers provided herein, such as the classifier biomarkers of Table 1 (or subsets thereof, for example 10 to 20, 20 to 30, 30 to 40, 40 to 50, 50 to 60, 60 to 70, or 70 to 80 biomarkers), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

In one embodiment, lung squamous cell carcinoma subtypes can be evaluated using levels of protein expression of one or more of the classifier genes provided herein, such as the classifier biomarkers listed in Table 1. The level of protein expression can be measured using an immunological detection method. Immunological detection methods which can be used herein include, but are not limited to, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and well known in the art (see, e.g., Ausubel e t a 1, eds, 1994, *Current Protocols in Molecular Biology*, Vol. I, John Wiley & Sons, Inc., New York, which is incorporated by reference herein in its entirety).

In one embodiment, antibodies specific for biomarker proteins are utilized to detect the expression of a biomarker protein in a body sample. The method comprises obtaining a body sample from a patient or a subject, contacting the body sample with at least one antibody directed to a biomarker that is selectively expressed in lung cancer cells, and detecting antibody binding to determine if the biomarker is expressed in the patient sample. A preferred aspect of the present invention provides an immunocytochemistry technique for diagnosing lung cancer subtypes. One of skill in the art will recognize that the immunocytochemistry method described herein below may be performed manually or in an automated fashion.

As provided throughout, the methods set forth herein provide a method for determining the lung cancer SQ subtype of a patient. Once the biomarker levels are determined, for example by measuring non-natural cDNA biomarker levels or non-natural mRNA-cDNA biomarker complexes, the biomarker levels are compared to reference values or a reference sample, for example with the use of statistical methods or direct comparison of detected levels, to make a determination of the lung cancer molecular SQ subtype. Based on the comparison, the patient's lung cancer sample is SQ classified, e.g., as basal, classical, primitive or secretory.

In one embodiment, expression level values of the at least one classifier biomarkers provided herein, such as the classifier biomarkers of Table 1 are compared to reference expression level value(s) from at least one sample training set, wherein the at least one sample training set comprises expression level values from a reference sample(s). In a further embodiment, the at least one sample training set comprises expression level values of the at least one classifier biomarkers provided herein, such as the classifier biomarkers of Table 1 from a basal, classical, primitive, secretory sample, or a combination thereof.

In a separate embodiment, hybridization values of the at least one classifier biomarkers provided herein, such as the classifier biomarkers of Table 1 are compared to reference hybridization value(s) from at least one sample training set, wherein the at least one sample training set comprises hybridization values from a reference sample(s). In a further embodiment, the at least one sample training set comprises hybridization values of the at least one classifier biomarkers provided herein, such as the classifier biomarkers of Table 1 from a proximal basal, classical, primitive, secretory sample, or a combination thereof. Methods for comparing detected levels of biomarkers to reference values and/or reference samples are provided herein. Based on this comparison, in one embodiment a correlation between the biomarker levels obtained from the subject's sample and the reference values is obtained. An assessment of the lung cancer SQ subtype is then made.

Various statistical methods can be used to aid in the comparison of the biomarker levels obtained from the patient and reference biomarker levels, for example, from at least one sample training set.

In one embodiment, a supervised pattern recognition method is employed. Examples of supervised pattern recognition methods can include, but are not limited to, the nearest centroid methods (Dabney (2005) Bioinformatics 21(22):4148-4154 and Tibshirani et al. (2002) Proc. Natl. Acad. Sci. USA 99(10):6576-6572); soft independent modeling of class analysis (SIMCA) (see, for example, Wold, 1976); partial least squares analysis (PLS)(see, for example, Wold, 1966; Joreskog, 1982; Frank, 1984; Bro, R., 1997); linear discriminant analysis (LDA) (see, for example, Nillson, 1965); K-nearest neighbour analysis (KNN) (sec, for example, Brown et al., 1996); artificial neural networks (ANN) (see, for example, Wasserman, 1989; Anker et al., 1992; Hare, 1994); probabilistic neural networks (PNNs) (see, for example, Parzen, 1962; Bishop, 1995; Speckt, 1990; Broomhead et al., 1988; Patterson, 1996); rule induction (RI) (see, for example, Quinlan, 1986); and, Bayesian methods (see, for example, Bretthorst, 1990a, 1990b, 1988). In one embodiment, the classifier for identifying tumor subtypes based on gene expression data is the centroid based method described in Mullins et al. (2007) Clin Chem. 53(7):1273-9, each of which is herein incorporated by reference in its entirety.

In other embodiments, an unsupervised training approach is employed, and therefore, no training set is used.

Referring to sample training sets for supervised learning approaches again, in some embodiments, a sample training set(s) can include expression data of a plurality or all of the classifier biomarkers (e.g., all the classifier biomarkers of Table 1) from an squamous cell carcinoma sample. The plurality of classifier biomarkers can comprise at least two classifier biomarkers, at least 10 classifier biomarkers, at least 20 classifier biomarkers, at least 30 classifier biomarkers, at least 40 classifier biomarkers, at least 50 classifier biomarkers, at least 60 classifier biomarkers, or at least 70 classifier biomarkers of Table 1. In some embodiments, the sample training set(s) are normalized to remove sample-to-sample variation.

In some embodiments, comparing can include applying a statistical algorithm, such as, for example, any suitable multivariate statistical analysis model, which can be parametric or non-parametric. In some embodiments, applying the statistical algorithm can include determining a correlation between the expression data obtained from the human lung tissue sample and the expression data from the squamous cell carcinoma training set(s). In some embodiments, cross-validation is performed, such as (for example), leave-one-out cross-validation (LOOCV). In some embodiments, integrative correlation is performed. In some embodiments, a Spearman correlation is performed. In some embodiments, a centroid based method is employed for the statistical algorithm as described in Mullins et al. (2007) Clin Chem. 53(7):1273-9, and based on gene expression data, which is herein incorporated by reference in its entirety.

Results of the gene expression performed on a sample from a subject (test sample) may be compared to a biological sample(s) or data derived from a biological sample(s) that is known or suspected to be normal ("reference sample" or "normal sample", e.g., non-squamous cell carcinoma sample). In some embodiments, a reference sample or reference gene expression data is obtained or derived from an individual known to have a particular molecular subtype of squamous cell carcinoma, i.e., basal, classical, secretory or primitive.

The reference sample may be assayed at the same time, or at a different time from the test sample. Alternatively, the biomarker level information from a reference sample may be stored in a database or other means for access at a later date.

The biomarker level results of an assay on the test sample may be compared to the results of the same assay on a reference sample. In some cases, the results of the assay on the reference sample are from a database, or a reference value(s). In some cases, the results of the assay on the reference sample are a known or generally accepted value or range of values by those skilled in the art. In some cases the comparison is qualitative. In other cases the comparison is quantitative. In some cases, qualitative or quantitative comparisons may involve but are not limited to one or more of the following: comparing fluorescence values, spot intensities, absorbance values, chemiluminescent signals, histograms, critical threshold values, statistical significance values, expression levels of the genes described herein, mRNA copy numbers.

In one embodiment, an odds ratio (OR) is calculated for each biomarker level panel measurement. Here, the OR is a measure of association between the measured biomarker values for the patient and an outcome, e.g., lung squamous cell carcinoma subtype. For example, see, *J. Can. Acad. Child Adolesc. Psychiatry* 2010; 19(3): 227-229, which is incorporated by reference in its entirety for all purposes.

In one embodiment, a specified statistical confidence level may be determined in order to provide a confidence level regarding the lung cancer subtype. For example, it may be determined that a confidence level of greater than 90% may be a useful predictor of the lung cancer subtype. In other embodiments, more or less stringent confidence levels may be chosen. For example, a confidence level of about or at least about 50%, 60%, 70%, 75%, 80%, 85%, 90%, 95%, 97.5%, 99%, 99.5%, or 99.9% may be chosen. The confidence level provided may in some cases be related to the quality of the sample, the quality of the data, the quality of the analysis, the specific methods used, and/or the number of gene expression values (i.e., the number of genes) analyzed. The specified confidence level for providing the likelihood of response may be chosen on the basis of the expected number of false positives or false negatives. Methods for choosing parameters for achieving a specified confidence level or for identifying markers with diagnostic power include but are not limited to Receiver Operating Characteristic (ROC) curve analysis, binormal ROC, principal component analysis, odds ratio analysis, partial least squares analysis, singular value decomposition, least absolute shrinkage and selection operator analysis, least angle regression, and the threshold gradient directed regularization method.

Determining the lung squamous cell carcinoma subtype in some cases can be improved through the application of algorithms designed to normalize and or improve the reliability of the gene expression data. In some embodiments of the present invention, the data analysis utilizes a computer or other device, machine or apparatus for application of the various algorithms described herein due to the large number of individual data points that are processed. A "machine learning algorithm" refers to a computational-based prediction methodology, also known to persons skilled in the art as a "classifier," employed for characterizing a gene expression profile or profiles, e.g., to determine the lung squamous cell carcinoma subtype. The biomarker levels, determined by, e.g., microarray-based hybridization assays, sequencing assays (e.g., RNAseq), NanoString assays, quantitative amplification assays, etc., are in one embodiment subjected to the algorithm in order to classify the profile. Supervised learning generally involves "training" a classifier to recognize the distinctions among subtypes such as basal positive, classical positive, secretory positive or primitive positive, and then "testing" the accuracy of the classifier on an independent test set. Therefore, for new, unknown samples the classifier can be used to predict, for example, the class (e.g., basal vs. classical vs. secretory vs. magnoid) in which the samples belong.

In some embodiments, a robust multi-array average (RMA) method may be used to normalize raw data. The RMA method begins by computing background-corrected intensities for each matched cell on a number of microarrays. In one embodiment, the background corrected values are restricted to positive values as described by Irizarry et al. (2003). Biostatistics April 4 (2): 249-64, incorporated by reference in its entirety for all purposes. After background correction, the base-2 logarithm of each background corrected matched-cell intensity is then obtained. The background corrected, log-transformed, matched intensity on each microarray is then normalized using the quantile normalization method in which for each input array and each probe value, the array percentile probe value is replaced with the average of all array percentile points, this method is more completely described by Bolstad et al. Bioinformatics 2003, incorporated by reference in its entirety. Following quantile normalization, the normalized data may then be fit to a linear model to obtain an intensity measure for each probe on each microarray. Tukey's median polish algorithm (Tukey, J. W., Exploratory Data Analysis. 1977, incorporated by reference in its entirety for all purposes) may then be used to determine the log-scale intensity level for the normalized probe set data.

Various other software programs may be implemented. In certain methods, feature selection and model estimation may be performed by logistic regression with lasso penalty using glmnet (Friedman et al. (2010). *Journal of statistical software* 33(1): 1-22, incorporated by reference in its entirety). Raw reads may be aligned using TopHat (Trapnell et al. (2009). *Bioinformatics* 25(9): 1105-11, incorporated by reference in its entirety). In methods, top features (N ranging from 10 to 200) are used to train a linear support vector machine (SVM) (Suykens J A K, Vandewalle J. Least Squares Support Vector Machine Classifiers. *Neural Processing Letters* 1999; 9(3): 293-300, incorporated by reference in its entirety) using the e1071 library (Meyer D. Support vector machines: the interface to libsvm in package e1071. 2014, incorporated by reference in its entirety). Confidence intervals, in one embodiment, are computed using the pROC package (Robin X, Turck N, Hainard A, et al. pROC: an open-source package for R and S+ to analyze and compare ROC curves. *BMC bioinformatics* 2011; 12: 77, incorporated by reference in its entirety).

In addition, data may be filtered to remove data that may be considered suspect. In one embodiment, data derived from microarray probes that have fewer than about 4, 5, 6, 7 or 8 guanosine+cytosine nucleotides may be considered to be unreliable due to their aberrant hybridization propensity or secondary structure issues. Similarly, data deriving from microarray probes that have more than about 12, 13, 14, 15, 16, 17, 18, 19, 20, 21, or 22 guanosine+cytosine nucleotides may in one embodiment be considered unreliable due to their aberrant hybridization propensity or secondary structure issues.

In some embodiments of the present invention, data from probe-sets may be excluded from analysis if they are not identified at a detectable level (above background).

In some embodiments of the present disclosure, probe-sets that exhibit no, or low variance may be excluded from further analysis. Low-variance probe-sets are excluded from the analysis via a Chi-Square test. In one embodiment, a probe-set is considered to be low-variance if its transformed variance is to the left of the 99 percent confidence interval of the Chi-Squared distribution with (N−1) degrees of freedom. (N−1)*Probe-set Variance/(Gene Probe-set Variance). Chi-Sq (N−1) where N is the number of input CEL files, (N−1) is the degrees of freedom for the Chi-Squared distribution, and the "probe-set variance for the gene" is the average of probe-set variances across the gene. In some embodiments of the present invention, probe-sets for a given mRNA or group of mRNAs may be excluded from further analysis if they contain less than a minimum number of probes that pass through the previously described filter steps for GC content, reliability, variance and the like. For example in some embodiments, probe-sets for a given gene or transcript cluster may be excluded from further analysis if they contain less than about 1, 2, 3, 4, 5, 6, 7, 8, 9, 10, 11, 12, 13, 14, 15, or less than about 20 probes.

Methods of biomarker level data analysis in one embodiment further include the use of a feature selection algorithm as provided herein. In some embodiments of the present invention, feature selection is provided by use of the LIMMA software package (Smyth, G. K. (2005). Limma: linear models for microarray data. In: Bioinformatics and Computational Biology Solutions using R and Bioconductor, R. Gentleman, V. Carey, S. Dudoit, R. Irizarry, W. Huber (eds.), Springer, New York, pages 397-420, incorporated by reference in its entirety for all purposes).

Methods of biomarker level data analysis, in one embodiment, include the use of a pre-classifier algorithm. For example, an algorithm may use a specific molecular fingerprint to pre-classify the samples according to their composition and then apply a correction/normalization factor. This data/information may then be fed in to a final classification algorithm which would incorporate that information to aid in the final diagnosis.

Methods of biomarker level data analysis, in one embodiment, further include the use of a classifier algorithm as provided herein. In one embodiment of the present invention, a diagonal linear discriminant analysis, k-nearest neighbor algorithm, support vector machine (SVM) algorithm, linear support vector machine, random forest algorithm, or a probabilistic model-based method or a combination thereof is provided for classification of microarray data. In some embodiments, identified markers that distinguish samples (e.g., of varying biomarker level profiles, and/or varying molecular subtypes of squamous cell carcinoma (e.g., basal, classical, secretory, primitive)) are selected based on statistical significance of the difference in biomarker levels between classes of interest. In some cases, the statistical significance is adjusted by applying a Benjamin Hochberg or another correction for false discovery rate (FDR).

In some cases, the classifier algorithm may be supplemented with a meta-analysis approach such as that described by Fishel and Kaufman et al. 2007 Bioinformatics 23(13): 1599-606, incorporated by reference in its entirety for all purposes. In some cases, the classifier algorithm may be supplemented with a meta-analysis approach such as a repeatability analysis.

Methods for deriving and applying posterior probabilities to the analysis of biomarker level data are known in the art and have been described for example in Smyth, G. K. 2004 *Stat. Appi. Genet. Mol. Biol.* 3: Article 3, incorporated by reference in its entirety for all purposes. In some cases, the posterior probabilities may be used in the methods of the present invention to rank the markers provided by the classifier algorithm.

A statistical evaluation of the results of the biomarker level profiling may provide a quantitative value or values indicative of one or more of the following: molecular subtype of squamous cell carcinoma (basal, classical, secretory, primitive); the likelihood of the success of a particular therapeutic intervention, e.g., angiogenesis inhibitor therapy, chemotherapy, or immunotherapy. In one embodiment, the data is presented directly to the physician in its most useful form to guide patient care, or is used to define patient populations in clinical trials or a patient population for a given medication. The results of the molecular profiling can be statistically evaluated using a number of methods known to the art including, but not limited to: the students T test, the two sided T test, Pearson rank sum analysis, hidden Markov model analysis, analysis of q-q plots, principal component analysis, one way ANOVA, two way ANOVA, LIMMA and the like.

In some cases, accuracy may be determined by tracking the subject over time to determine the accuracy of the original diagnosis. In other cases, accuracy may be established in a deterministic manner or using statistical methods. For example, receiver operator characteristic (ROC) analysis may be used to determine the optimal assay parameters to achieve a specific level of accuracy, specificity, positive predictive value, negative predictive value, and/or false discovery rate.

In some cases, the results of the biomarker level profiling assays, are entered into a database for access by representatives or agents of a molecular profiling business, the individual, a medical provider, or insurance provider. In some cases, assay results include sample classification, identification, or diagnosis by a representative, agent or consultant of the business, such as a medical professional. In other cases, a computer or algorithmic analysis of the data is provided automatically. In some cases the molecular profiling business may bill the individual, insurance provider, medical provider, researcher, or government entity for one or more of the following: molecular profiling assays performed, consulting services, data analysis, reporting of results, or database access.

In some embodiments of the present invention, the results of the biomarker level profiling assays are presented as a report on a computer screen or as a paper record. In some embodiments, the report may include, but is not limited to, such information as one or more of the following: the levels of biomarkers (e.g., as reported by copy number or fluorescence intensity, etc.) as compared to the reference sample or reference value(s); the likelihood the subject will respond to a particular therapy, based on the biomarker level values and the lung squamous cell carcinoma subtype and proposed therapies.

In one embodiment, the results of the gene expression profiling may be classified into one or more of the following: basal positive, classical positive, secretory positive, primitive positive, basal negative, classical negative, secretory negative, primitive negative; likely to respond to angiogenesis inhibitor, immunotherapy or chemotherapy; unlikely to respond to angiogenesis inhibitor, immunotherapy or chemotherapy; or a combination thereof.

In some embodiments of the present invention, results are classified using a trained algorithm. Trained algorithms of the present invention include algorithms that have been developed using a reference set of known gene expression values and/or normal samples, for example, samples from individuals diagnosed with a particular molecular subtype of squamous cell carcinoma. In some cases, a reference set of known gene expression values are obtained from individuals who have been diagnosed with a particular molecular subtype of squamous cell carcinoma, and are also known to respond (or not respond) to angiogenesis inhibitor therapy. In some cases, a reference set of known gene expression values are obtained from individuals who have been diagnosed with a particular molecular subtype of squamous cell carcinoma, and are also known to respond (or not respond) to immunotherapy. In some cases, a reference set of known gene expression values are obtained from individuals who have been diagnosed with a particular molecular subtype of squamous cell carcinoma, and are also known to respond (or not respond) to chemotherapy.

Algorithms suitable for categorization of samples include but are not limited to k-nearest neighbor algorithms, support vector machines, linear discriminant analysis, diagonal linear discriminant analysis, updown, naive Bayesian algorithms, neural network algorithms, hidden Markov model algorithms, genetic algorithms, or any combination thereof.

When a binary classifier is compared with actual true values (e.g., values from a biological sample), there are typically four possible outcomes. If the outcome from a prediction is p (where "p" is a positive classifier output, such as the presence of a deletion or duplication syndrome) and the actual value is also p, then it is called a true positive (TP); however if the actual value is n then it is said to be a false positive (FP). Conversely, a true negative has occurred when both the prediction outcome and the actual value are n (where "n" is a negative classifier output, such as no deletion or duplication syndrome), and false negative is when the prediction outcome is n while the actual value is p. In one embodiment, consider a test that seeks to determine whether a person is likely or unlikely to respond to angiogenesis inhibitor therapy. A false positive in this case occurs when the person tests positive, but actually does respond. A false negative, on the other hand, occurs when the person tests negative, suggesting they are unlikely to respond, when they actually are likely to respond. The same holds true for classifying a lung cancer subtype.

The positive predictive value (PPV), or precision rate, or post-test probability of disease, is the proportion of subjects with positive test results who are correctly diagnosed as likely or unlikely to respond, or diagnosed with the correct lung cancer subtype, or a combination thereof. It reflects the probability that a positive test reflects the underlying condition being tested for. Its value does however depend on the prevalence of the disease, which may vary. In one example the following characteristics are provided: FP (false positive); TN (true negative); TP (true positive); FN (false negative). False positive rate ($\alpha$)=FP/(FP+TN)-specificity; False negative rate ($\beta$)=FN/(TP+FN)-sensitivity; Power=sensitivity=1-$\beta$; Likelihood-ratio positive=sensitivity/(1-specificity); Likelihood-ratio negative=(1-sensitivity)/specificity. The negative predictive value (NPV) is the proportion of subjects with negative test results who are correctly diagnosed.

In some embodiments, the results of the biomarker level analysis of the subject methods provide a statistical confidence level that a given diagnosis is correct. In some embodiments, such statistical confidence level is at least about, or more than about 85%, 90%, 91%, 92%, 93%, 94%, 95%, 96%, 97%, 98%, 99% 99.5%, or more.

In some embodiments, the method further includes classifying the lung tissue sample as a particular lung cancer subtype based on the comparison of biomarker levels in the sample and reference biomarker levels, for example present in at least one training set. In some embodiments, the lung tissue sample is classified as a particular subtype if the results of the comparison meet one or more criterion such as, for example, a minimum percent agreement, a value of a statistic calculated based on the percentage agreement such as (for example) a kappa statistic, a minimum correlation (e.g., Pearson's correlation) and/or the like.

It is intended that the methods described herein can be performed by software (stored in memory and/or executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including Unix utilities, C, C++, Java™, Ruby, SQL, SAS®, the R programming language/software environment, Visual Basic™, and other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

Some embodiments described herein relate to devices with a non-transitory computer-readable medium (also can be referred to as a non-transitory processor-readable medium or memory) having instructions or computer code thereon for performing various computer-implemented operations and/or methods disclosed herein. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

In some embodiments, a single biomarker, or from about 10 to about 20, from about 20 to about 30, from about 20 to about 40, from about 40 to about 50, from about 40 to about 60, from about 60 to about 70, from about 60 to about 80, from about 20 to about 60, from about 20 to about 80, from about 40 to about 80 biomarkers (e.g., as disclosed in Table 1) is capable of classifying subtypes of lung squamous cell carcinoma with a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein (e.g., in Table 1) can be used to obtain a predictive success of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

In some embodiments, a single biomarker, or from about 10 to about 20, from about 20 to about 30, from about 20 to about 40, from about 40 to about 50, from about 40 to about 60, from about 60 to about 70, from about 60 to about 80, from about 20 to about 60, from about 20 to about 80, from about 40 to about 80 biomarkers (e.g., as disclosed in Table 1) is capable of classifying lung squamous cell carcinoma subtypes with a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between. In some embodiments, any combination of biomarkers disclosed herein can be used to obtain a sensitivity or specificity of at least about 70%, at least about 71%, at least about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, up to 100%, and all values in between.

Classifier Gene Selection

Figure 9:
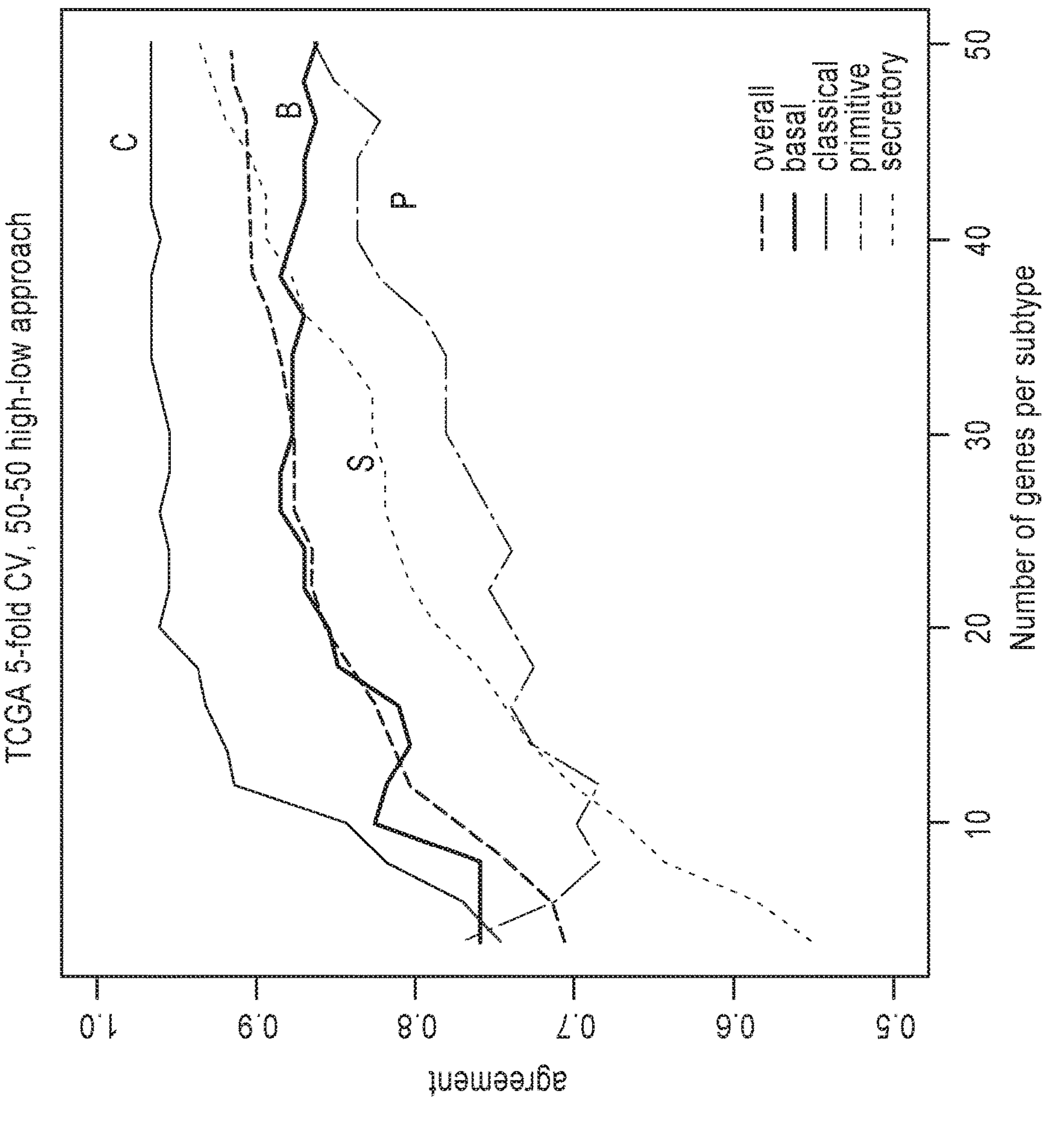
FIG. 9 illustrates a five-fold cross validation study performed on the Cancer Genome Atlas (TCGA) RNASeq lung SQ dataset in order to determine an optimal number of genes to include for subtyping SQ.

In one embodiment, the methods and compositions provided herein are useful for analyzing the expression of a set of biomarkers in a sample (e.g., lung tissue sample or a lung SQ sample) from a patient, whereby the set of biomarkers comprise a fewer number of biomarkers than methods known in the art for molecularly classifying lung SQ subtype. In some cases, the set of biomarkers is less than 250, 240, 230, 220, 210, 200, 150, 100, 95 or 90 biomarkers. In some cases, the set of biomarkers is the set of 80 biomarkers listed in Table 1. In some cases, the set of biomarkers is a sub-set of biomarkers listed Table 1. The biomarkers or classifier genes useful in the methods and compositions provided herein can be selected from one or more lung squamous cell carcinoma datasets from one or more databases. The databases can be public databases. In one embodiment, classifier genes (e.g., one or more genes listed in Table 1 and Table 2) useful in the methods and compositions provided herein for detecting or diagnosing lung squamous cell carcinoma subtypes were selected from a lung squamous cell carcinoma RNAseq dataset from The Cancer Genome Atlas (TCGA). In one embodiment, classifier genes useful for the methods and compositions provided herein such as those in Table 1 are selected by subjecting a large set of classifier genes to an in silico based process in order to determine the minimum number of genes whose expression profile can be used to determine an SQ subtype of sample obtained from a subject. In some cases, the large set of classifier genes can be a lung SQ RNAseq dataset such as, for example, from TCGA. In some cases, the large set of classifier genes can be the 208-gene classifier disclosed in Wilkerson et al. (Clin Cancer Res 2010; 16(19):4864-4875), whereby the 208-gene classifier can serve to define gold standard subtype. The in silico process for selecting a gene cassette as provided herein for determining lung SQ subtype of a sample from a patient can comprise, applying or using a Classifying arrays to Nearest Centroid (CLaNC) algorithm with modification on the standard 208 classifier genes to choose an equal number of negatively and positively correlated genes for each subtype. For determination of the optimal number of genes (e.g. 20 per subtype as shown in Table 1) to include in the signature, the process can further comprise performing a 5-fold cross validation using TCGA lung squamous cell carcinoma dataset as provided herein to produce cross-validation curves as shown in FIG. 9. To get the final list of gene classifiers, the method can further comprise applying the Classifying arrays to Nearest Centroid (CLaNC) to the entire TCGA data set minus 20% of samples with the lowest gold standard subtype prediction strength, and removing an equal number from each subtype.

In one embodiment, the method further comprises validating the gene classifiers. Validation can comprise testing the expression of the classifiers in several fresh frozen publicly available array and RNAseq datasets and calling the subtype based on said expression levels and subsequently comparing the expression with the gold standard subtype calls as defined by the previously published 208-gene signature disclosed in Wilkerson et al. (Clin Cancer Res 2010; 16(19):4864-4875). Final validation of the gene signature (e.g., Table 1) can then be performed in a newly collected RNAseq dataset of archived formalin-fixed paraffin-embedded (FFPE) squamous cell carcinoma samples to assure comparable performance in the FFPE samples. In one embodiment, the classifier biomarkers of Table 1 were selected based on the in silico CLaNC process described herein. The gene symbols and official gene names are listed in column 2 and column 3, respectively.

In one embodiment, the methods of the invention require the detection of at least 1, 2, 3, 4, 5, 6, 78, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 classifier biomarkers in a lung cancer cell sample (e.g., lung SQ cancer sample) obtained from a patient in order to identify a basal, classical, secretory or primitive lung squamous cell carcinoma subtype. The same applies for other classifier gene expression datasets as provided herein.

In another embodiment, the methods of the invention require the detection of a total of at least 1, at least 2, at least 5, at least 10, at least 20, at least 40, at least 60 or up to 80 classifier biomarkers out of the 80 gene biomarkers of Table 1 in a lung cancer cell sample (e.g., lung SQ cancer sample) obtained from a patient in order to identify a basal, classical, secretory or primitive lung squamous cell carcinoma subtype. The same applies for other classifier gene expression datasets as provided herein.

In one embodiment, at least 1, at least 2, at least 3, at least 4, at least 5, at least 6, at least 7, at least 8, at least 9 or up to 10 biomarkers of Table 1 are "up-regulated" in a specific subtype of lung squamous cell carcinoma. In another embodiment, at least 1, at least 2, at least 3, at least 4, at least 5, at least 6, at least 7, at least 8, at least 9 or up to 10 biomarkers of Table 1 are "down-regulated" in a specific subtype of lung squamous cell carcinoma. The same applies for other classifier gene expression datasets as provided herein.

In one embodiment, the expression level of an "up-regulated" biomarker as provided herein is increased by about 0.5-fold, about 1-fold, about 1.5-fold, about 2-fold, about 2.5-fold, about 3-fold, about 3.5-fold, about 4-fold, about 4.5-fold, about 5-fold, and any values in between. In another embodiment, the expression level of a "down-regulated" biomarker as provided herein is decreased by about 0.8-fold, about 1.4-fold, about 2-fold, about 2.6-fold, about 3.2-fold, about 3.6-fold, about 4-fold, and any values in between.

It is recognized that additional genes or proteins can be used in the practice of the invention. In general, genes useful in classifying the subtypes of lung squamous cell carcinoma, include those that are independently capable of distinguishing between normal versus tumor, or between different classes or grades of lung cancer. A gene is considered to be capable of reliably distinguishing between subtypes if the area under the receiver operator characteristic (ROC) curve is approximately 1.

Clinical/Therapeutic Uses

In one embodiment, a method is provided herein for determining a disease outcome or prognosis for a patient suffering from cancer. In some cases, the cancer is lung cancer. The disease outcome or prognosis can be measured by examining the overall survival for a period of time or intervals (e.g., 0 to 36 months or 0 to 60 months). In one embodiment, survival is analyzed as a function of subtype (e.g., for lung cancer, SQ (basal, classical, secretory or primitive)). Relapse-free and overall survival can be assessed using standard Kaplan-Meier plots as well as Cox proportional hazards modeling.

In one embodiment, upon determining a patient's lung cancer subtype, the patient is selected for suitable therapy, for example chemotherapy or drug therapy with an angiogenesis inhibitor or immunotherapy. In one embodiment, upon determining a patient's lung cancer subtype, the patient is administered a suitable therapeutic agent, for example chemotherapeutic agent(s) or an angiogenesis inhibitor or immunotherapeutic agent(s). In one embodiment, the therapy is immunotherapy, and the immunotherapeutic agent is a checkpoint inhibitor, monoclonal antibody, biological response modifier, therapeutic vaccine or cellular immunotherapy.

The methods of present invention are also useful for evaluating clinical response to therapy, as well as for endpoints in clinical trials for efficacy of new therapies. The extent to which sequential diagnostic expression profiles move towards normal can be used as one measure of the efficacy of the candidate therapy.

In one embodiment, the methods of the invention also find use in predicting response to different lines of therapies based on the subtype of lung squamous cell carcinoma (SQ). For example, chemotherapeutic response can be improved by more accurately assigning tumor subtypes. Likewise, treatment regimens can be formulated based on the tumor subtype. For example, clinical trials have shown convincing evidence that the VEGF inhibitor, bevacizumab, can be effective in the treatment of NSCLC. In one embodiment, the primitive SQ subtype can have enhanced response to immunotherapy. In another embodiment, all subtypes can have enhanced response to chemotherapies, angiogenesis inhibitor treatments, and immunotherapies.

In one embodiment, upon determining a patient's lung squamous cell carcinoma subtype, the patient is selected for suitable therapy, for example chemotherapy, immunotherapy or drug therapy with an angiogenesis inhibitor. In one embodiment, upon determining a patient's lung squamous cell carcinoma subtype using the methods provided herein, a suitable therapeutic agent, for example a chemotherapeutic agent(s), an immunotherapeutic agent or an angiogenesis inhibitor is administered to the patient.

Angiogenesis Inhibitors

In one embodiment, upon determining a patient's lung SQ subtype, the patient is selected for drug therapy with an angiogenesis inhibitor. Upon making a determination of whether a patient is likely to respond to angiogenesis inhibitor therapy, or selecting a patient for angiogenesis inhibitor therapy, in one embodiment, the patient is administered the angiogenesis inhibitor. The angiogenesis in inhibitor can be any of the angiogenesis inhibitors described herein In one embodiment, the therapy is angiogenesis inhibitor therapy, and the angiogenesis inhibitor is a vascular endothelial growth factor (VEGF) inhibitor, a VEGF receptor inhibitor, a platelet derived growth factor (PDGF) inhibitor or a PDGF receptor inhibitor.

Each biomarker panel can include one, two, three, four, five, six, seven, eight, nine, ten, 20, 40, 60, 80 or more biomarkers usable by a classifier (also referred to as a "classifier biomarker") to assess whether an squamous cell carcinoma patient is likely to respond to angiogenesis inhibitor therapy; to select an squamous cell carcinoma patient for angiogenesis inhibitor therapy; to determine a "hypoxia score" and/or to subtype an squamous cell carcinoma sample as basal, classical, secretory or primitive molecular subtype. As used herein, the term "classifier" can refer to any algorithm for statistical classification, and can be implemented in hardware, in software, or a combination thereof. The classifier can be capable of 2-level, 3-level, 4-level, or higher, classification, and can depend on the nature of the entity being classified. One or more classifiers can be employed to achieve the aspects disclosed herein.

In general, methods of determining whether a squamous cell carcinoma patient is likely to respond to angiogenesis inhibitor therapy, or methods of selecting a squamous cell carcinoma patient for angiogenesis inhibitor therapy are provided herein. In one embodiment, the method comprises assessing whether the patient's squamous cell carcinoma subtype is basal, classical, secretory or primitive using the methods described herein (e.g., assessing the expression of one or more classifier biomarkers of Table 1) and probing an squamous cell carcinoma sample from the patient for the levels of at least five biomarkers selected from the group consisting of RRAGD, FABP5, UCHL1, GAL, PLOD, DDIT4, VEGF, ADM, ANGPTL4, NDRG1, NP, SLC16A3, and C14ORF58 (see Table 3) at the nucleic acid level. In a further embodiment, the probing step comprises mixing the sample with five or more oligonucleotides that are substantially complementary to portions of nucleic acid molecules of the at least five biomarkers under conditions suitable for hybridization of the five or more oligonucleotides to their complements or substantial complements, detecting whether hybridization occurs between the five or more oligonucleotides to their complements or substantial complements; and obtaining hybridization values of the sample based on the detecting steps. The hybridization values of the sample are then compared to reference hybridization value(s) from at least one sample training set, wherein the at least one sample training set comprises (i) hybridization value(s) of the at least five biomarkers from a sample that overexpresses the at least five biomarkers, or overexpresses a subset of the at least five biomarkers, (ii) hybridization values of the at least five biomarkers from a reference basal, classical, secretory or primitive sample, or (iii) hybridization values of the at least five biomarkers from an squamous cell carcinoma free lung sample. A determination of whether the patient is likely to respond to angiogenesis inhibitor therapy, or a selection of the patient for angiogenesis inhibitor is then made based upon (i) the patient's squamous cell carcinoma subtype and (ii) the results of comparison.

TABLE 3

Biomarkers for hypoxia profile

| Name | Abbreviation | GenBank Accession No.* |
|---|---|---|
| RRAGD | Ras-related GTP binding D | BC003088 |
| FABP5 | fatty acid binding protein 5 | M94856 |
| UCHL1 | ubiquitin carboxyl-terminal esterase L1 | NM_004181 |
| GAL | Galanin | BC030241 |
| PLOD | procollagen-lysine, 2-oxoglutarate 5-dioxygenase lysine hydroxylase | M98252 |
| DDIT4 | DNA-damage-inducible transcript 4 | NM_019058 |
| VEGF | vascular endothelial growth factor | M32977 |
| ADM | Adrenomedullin | NM_001124 |
| ANGPTL4 | angiopoietin-like 4 | AF202636 |
| NDRG1 | N-myc downstream regulated gene 1 | NM_006096 |
| NP | nucleoside phosphorylase | NM 000270 |
| SLC16A3 | solute carrier family 16 monocarboxylic acid transporters, member 3 | NM_004207 |
| C14ORF58 | chromosome 14 open reading frame 58 | AK000378 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

The aforementioned set of thirteen biomarkers, or a subset thereof, is also referred to herein as a "hypoxia profile".

In one embodiment, the method provided herein includes determining the levels of at least five biomarkers, at least six biomarkers, at least seven biomarkers, at least eight biomarkers, at least nine biomarkers, or at least ten biomarkers, or five to thirteen, six to thirteen, seven to thirteen, eight to thirteen, nine to thirteen or ten to thirteen biomarkers selected from RRAGD, FABP5, UCHL1, GAL, PLOD, DDIT4, VEGF, ADM, ANGPTL4, NDRG1, NP, SLC16A3, and C14ORF58 in an squamous cell carcinoma sample obtained from a subject. Biomarker expression in some instances may be normalized against the expression levels of all RNA transcripts or their expression products in the sample, or against a reference set of RNA transcripts or their expression products. The reference set as explained throughout, may be an actual sample that is tested in parallel with the squamous cell carcinoma sample, or may be a reference set of values from a database or stored dataset. Levels of expression, in one embodiment, are reported in number of copies, relative fluorescence value or detected fluorescence value. The level of expression of the biomarkers of the hypoxia profile together with squamous cell carcinoma subtype as determined using the methods provided herein can be used in the methods described herein to determine whether a patient is likely to respond to angiogenesis inhibitor therapy.

In one embodiment, the levels of expression of the thirteen biomarkers (or subsets thereof, as described above, e.g., five or more, from about five to about 13), are normalized against the expression levels of all RNA transcripts or their non-natural cDNA expression products, or protein products in the sample, or of a reference set of RNA transcripts or a reference set of their non-natural cDNA expression products, or a reference set of their protein products in the sample.

In one embodiment, angiogenesis inhibitor treatments include, but are not limited to an integrin antagonist, a selectin antagonist, an adhesion molecule antagonist, an antagonist of intercellular adhesion molecule (ICAM)-1, ICAM-2, ICAM-3, platelet endothelial adhesion molecule (PCAM), vascular cell adhesion molecule (VCAM)), lymphocyte function-associated antigen 1 (LFA-1), a basic fibroblast growth factor antagonist, a vascular endothelial growth factor (VEGF) modulator, a platelet derived growth factor (PDGF) modulator (e.g., a PDGF antagonist).

In one embodiment of determining whether a subject is likely to respond to an integrin antagonist, the integrin antagonist is a small molecule integrin antagonist, for example, an antagonist described by Paolillo et al. (Mini Rev Med Chem, 2009, volume 12, pp. 1439-1446, incorporated by reference in its entirety), or a leukocyte adhesion-inducing cytokine or growth factor antagonist (e.g., tumor necrosis factor-α (TNF-α), interleukin-1β (IL-1β), monocyte chemotactic protein-1 (MCP-1) and a vascular endothelial growth factor (VEGF)), as described in U.S. Pat. No. 6,524,581, incorporated by reference in its entirety herein.

The methods provided herein are also useful for determining whether a subject is likely to respond to one or more of the following angiogenesis inhibitors: interferon gamma 10, interferon gamma 1β (Actimmune®) with pirfenidone, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with salvia and *Schisandra chinensis*, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI109, secretin, STX100, TGF-β Inhibitor, transforming growth factor, β-receptor 2 oligonucleotide, VA999260, XV615 or a combination thereof.

In another embodiment, a method is provided for determining whether a subject is likely to respond to one or more endogenous angiogenesis inhibitors. In a further embodiment, the endogenous angiogenesis inhibitor is endostatin, a 20 kDa C-terminal fragment derived from type XVIII collagen, angiostatin (a 38 kDa fragment of plasmin), a member of the thrombospondin (TSP) family of proteins. In a further embodiment, the angiogenesis inhibitor is a TSP-1, TSP-2, TSP-3, TSP-4 and TSP-5. Methods for determining the likelihood of response to one or more of the following angiogenesis inhibitors are also provided a soluble VEGF receptor, e.g., soluble VEGFR-1 and neuropilin 1 (NPR1), angiopoietin-1, angiopoietin-2, vasostatin, calreticulin, platelet factor-4, a tissue inhibitor of metalloproteinase (TIMP) (e.g., TIMP1, TIMP2, TIMP3, TIMP4), cartilage-derived angiogenesis inhibitor (e.g., peptide troponin I and chrondomodulin I), a disintegrin and metalloproteinase with thrombospondin motif 1, an interferon (IFN), (e.g., IFN-α, IFN-β, IFN-γ), a chemokine, e.g., a chemokine having the C—X—C motif (e.g., CXCL10, also known as interferon gamma-induced protein 10 or small inducible cytokine B10), an interleukin cytokine (e.g., IL-4, IL-12, IL-18), prothrombin, antithrombin III fragment, prolactin, the protein encoded by the TNFSF15 gene, osteopontin, maspin, canstatin, proliferin-related protein.

In one embodiment, a method for determining the likelihood of response to one or more of the following angiogenesis inhibitors is provided is angiopoietin-1, angiopoietin-2, angiostatin, endostatin, vasostatin, thrombospondin, calreticulin, platelet factor-4, TIMP, CDAI, interferon α, interferon β, vascular endothelial growth factor inhibitor (VEGI) meth-1, meth-2, prolactin, VEGI, SPARC, osteopontin, maspin, canstatin, proliferin-related protein (PRP), restin, TSP-1, TSP-2, interferon gamma 1β, ACUHTR028, αVβ5, aminobenzoate potassium, amyloid P, ANG1122, ANG1170, ANG3062, ANG3281, ANG3298, ANG4011, anti-CTGF RNAi, Aplidin, *Astragalus membranaceus* extract with salvia and schisandra chinensis, atherosclerotic plaque blocker, Azol, AZX100, BB3, connective tissue growth factor antibody, CT140, danazol, Esbriet, EXC001, EXC002, EXC003, EXC004, EXC005, F647, FG3019, Fibrocorin, Follistatin, FT011, a galectin-3 inhibitor, GKT137831, GMCT01, GMCT02, GRMD01, GRMD02, GRN510, Heberon Alfa R, interferon α-2β, ITMN520, JKB119, JKB121, JKB122, KRX168, LPA1 receptor antagonist, MGN4220, MIA2, microRNA 29a oligonucleotide, MMI0100, noscapine, PBI4050, PBI4419, PDGFR inhibitor, PF-06473871, PGN0052, Pirespa, Pirfenex, pirfenidone, plitidepsin, PRM151, Px102, PYN17, PYN22 with PYN17, Relivergen, rhPTX2 fusion protein, RXI09, secretin, STX100, TGF-β Inhibitor, transforming growth factor, β-receptor 2 oligonucleotide, VA999260, XV615 or a combination thereof.

In yet another embodiment, the angiogenesis inhibitor can include pazopanib (Votrient), sunitinib (Sutent), sorafenib (Nexavar), axitinib (Inlyta), ponatinib (Iclusig), vandetanib (Caprelsa), cabozantinib (Cometrig), ramucirumab (Cyramza), regorafenib (Stivarga), ziv-aflibercept (Zaltrap), motesanib, or a combination thereof. In another embodiment, the angiogenesis inhibitor is a VEGF inhibitor. In a further embodiment, the VEGF inhibitor is axitinib, cabozantinib, aflibercept, brivanib, tivozanib, ramucirunab or motesanib. In yet a further embodiment, the angiogenesis inhibitor is motesanib.

In one embodiment, the methods provided herein relate to determining a subject's likelihood of response to an antagonist of a member of the platelet derived growth factor (PDGF) family, for example, a drug that inhibits, reduces or modulates the signaling and/or activity of PDGF-receptors (PDGFR). For example, the PDGF antagonist, in one embodiment, is an anti-PDGF aptamer, an anti-PDGF antibody or fragment thereof, an anti-PDGFR antibody or fragment thereof, or a small molecule antagonist. In one embodiment, the PDGF antagonist is an antagonist of the PDGFR-α or PDGFR-β. In one embodiment, the PDGF antagonist is the anti-PDGF-β aptamer E10030, sunitinib, axitinib, sorefenib, imatinib, imatinib mesylate, nintedanib, pazopanib HCl, ponatinib, MK-2461, dovitinib, pazopanib, crenolanib, PP-121, telatinib, imatinib, KRN 633, CP 673451, TSU-68, Ki8751, amuvatinib, tivozanib, masitinib, motesanib diphosphate, dovitinib dilactic acid, linifanib (ABT-869).

Immunotherapy

In one embodiment, provided herein is a method for determining whether a squamous cell carcinoma (SQ) lung cancer patient is likely to respond to immunotherapy by determining the subtype of SQ of a sample obtained from the patient and, based on the SQ lung cancer subtype, assessing whether the patient is likely to respond to immunotherapy. In another embodiment, provided herein is a method of selecting a patient suffering from SQ for immunotherapy by determining an SQ subtype of a sample from the patient and, based on the SQ subtype, selecting the patient for immunotherapy. The determination of the SQ subtype of the sample obtained from the patient can be performed using any method for subtyping SQ known in the art. In one embodiment, the sample obtained from the patient has been previously diagnosed as being SQ, and the methods provided herein are used to determine the SQ subtype of the sample. The previous diagnosis can be based on a histological analysis. The histological analysis can be performed by one or more pathologists. In one embodiment, the SQ subtyping is performed via gene expression analysis of a set or panel of biomarkers or subsets thereof in order to generate an expression profile. The gene expression analysis can be performed on a lung cancer sample (e.g., lung cancer SQ sample) obtained from a patient in order to determine the presence, absence or level of expression of one or more biomarkers selected from a publically available lung cancer database described herein and/or Table 1 provided herein. The SQ subtype can be selected from the group consisting of primitive, classical, secretory and basal. The immunotherapy can be any immunotherapy provided herein. In one embodiment, the immunotherapy comprises administering one or more checkpoint inhibitors. The checkpoint inhibitors can be any checkpoint inhibitor provided herein such as, for example, a checkpoint inhibitor that targets PD-1, PD-LI or CTLA4.

As disclosed herein, the biomarkers panels, or subsets thereof, can be those disclosed in any publically available SQ gene expression dataset or datasets. In one embodiment, the lung cancer is SQ and the biomarker panel or subset thereof is, for example, TCGA lung SQ RNAseq gene expression dataset (n=501). In one embodiment, the lung cancer is SQ and the biomarker panel or subset thereof is, for example, the SQ gene expression dataset (n=75) disclosed in Lee et al. (Cancer Res 2008; 14(22): 7397-7404), the contents of which are herein incorporated by reference in its entirety. In one embodiment, the lung cancer is SQ and the biomarker panel or subset thereof is, for example, the SQ gene expression dataset (n=130) disclosed in Raponi et al. (Cancer Res 2006: 66(7): 466-472), the contents of which are herein incorporated by reference in its entirety. In one embodiment, the lung cancer is SQ and the biomarker panel or subset thereof is, for example, the SQ gene expression dataset (n=56) disclosed in Wilkerson et al. (Clin Cancer Res 2010; 16(19):4864-4875), the contents of which are herein incorporated by reference in its entirety. In one embodiment, the lung cancer is SQ and the biomarker panel or subset thereof is, for example, the SQ gene expression dataset disclosed in Table 1. In Table 2, the first column of the table represents the biomarker list for distinguishing basal. The second column of the table represents the biomarker list for classical. The third column of the table represents the biomarker list for distinguishing primitive. The last column of the table represents the biomarker list for distinguishing secretory. In some cases, as shown in Table 2, a total of 80 biomarkers can be used for SQ subtype determination. For each SQ subtype in Table 2, 10 of the 20 biomarkers can be negatively correlated genes, while 10 can be positively correlated genes which can be selected as the gene signature of a specific SQ subtype.

In some embodiments, the method for lung cancer subtyping (e.g., SQ subtyping) includes detecting expression levels of a classifier biomarker set. The classifier biomarker set can be a set of biomarkers from a publically available database such as, for example, TCGA lung SQ RNASeq gene expression dataset(s) or any other dataset provided herein. In some embodiments, the detecting includes all of the classifier biomarkers of Table 1 or any other dataset provided herein at the nucleic acid level or protein level. In another embodiment, a single classifier biomarker of Table 1 or a subset of the classifier biomarkers of Table 1 or any other dataset provided herein are detected, for example, from about five to about twenty. In another embodiment, a single classifier biomarker of Table 1 or a subset of the classifier biomarkers of Table 1 and/or any other dataset provided herein are detected, for example, from about 20 to about 80. In another embodiment, all of the classifier biomarkers of Table 1 or any other dataset provided herein are detected. In another embodiment, at least one or all of the classifier biomarkers of Table 1 in combination with one or more classifier biomarkers of any other SQ dataset provided herein are detected. The detecting can be performed by any suitable technique including, but not limited to, RNA-seq, a reverse transcriptase polymerase chain reaction (RT-PCR), a microarray hybridization assay, or another hybridization assay, e.g., a NanoString assay for example, with primers and/or probes specific to the classifier biomarkers, and/or the like. In some cases, the primers useful for the amplification methods (e.g., RT-PCR or qRT-PCR) are any forward and reverse primers suitable for binding to a classifier gene from a dataset provided herein alone or in combination.

In one embodiment, from about 1 to about 5, about 5 to about 10, from about 5 to about 15, from about 5 to about 20, from about 5 to about 25, from about 5 to about 30, from about 5 to about 35, from about 5 to about 40, from about 5 to about 45, from about 5 to about 50, from about 5 to about 55, from about 5 to about 60, from about 5 to about 65, from about 5 to about 70, from about 5 to about 75, or from about 5 to about 80 of the biomarkers in any of the SQ gene expression datasets provided herein, including, for example, Table 1 for an SQ lung sample are detected in a method to determine the lung cancer subtype as provided herein. In another embodiment, each of the biomarkers from any one of the SQ gene expression datasets provided herein, including, for example, Table 1 for an SQ lung sample are detected in a method to determine the lung cancer subtype as provided herein.

In one embodiment, the methods provided herein further comprise determining the presence, absence or level of immune activation in a SQ subtype. The presence or level of immune cell activation can be determined by creating an expression profile or detecting the expression of one or more biomarkers associated with innate immune cells and/or adaptive immune cells associated with each SQ subtype in a sample (e.g., lung cancer sample) obtained from a patient. In one embodiment, immune cell activation associated with a SQ subtype is determined by monitoring the immune cell signatures of Bindea et al (Immunity 2013; 39(4); 782-795), the contents of which are herein incorporated by reference in its entirety. In one embodiment, the method further comprises measuring single gene immune biomarkers, such as, for example, CTLA4, PDCD1 and CD274 (PD-LI), PDCDLG2 (PD-L2) and/or IFN gene signatures. The presence or a detectable level of immune activation (Innate and/or Adaptive) associated with a SQ subtype can indicate or predict that a patient with said SQ subtype may be amendable to immunotherapy. The immunotherapy can be treatment with a checkpoint inhibitor as provided herein. In one embodiment, the primitive subtype of SQ has immune expression. In one embodiment, a method is provided herein for detecting the expression of at least one classifier biomarker provided herein in a sample (e.g., lung cancer SQ sample) obtained from a patient further comprises administering an immunotherapeutic agent following detection of immune activation as provided herein in said sample.

In one embodiment, the method comprises determining a subtype of a lung cancer SQ sample and subsequently determining a level of immune cell activation of said subtype. In one embodiment, the subtype is determined by determining the expression levels of one or more classifier biomarkers using sequencing (e.g., RNASeq), amplification (e.g., qRT-PCR) or hybridization assays (e.g., microarray analysis) as described herein. The one or more biomarkers can be selected from a publically available database (e.g., TCGA lung SQ RNASeq gene expression datasets or any other publically available SQ gene expression datasets provided herein). In some embodiments, the biomarkers of Table 1 can be used to specifically determine the subtype of an SQ lung sample obtained from a patient. In one embodiment, the level of immune cell activation is determined by measuring gene expression signatures of immunomarkers. The immunomarkers can be measured in the same and/or different sample used to subtype the lung cancer sample as described herein. The immunomarkers that can be measured can comprise, consist of, or consistently essentially of innate immune cell (IIC) and/or adaptive immune cell (AIC) gene signatures, interferon (IFN) gene signatures, individual immunomarkers, major histocompatibility complex class II (MHC class II) genes or a combination thereof. The gene expression signatures for both IICs and AICs can be any known gene signatures for said cell types known in the art. For example, the immune gene signatures can be those from Bindea et al. (Immunity 2013; 39(4); 782-795). In one embodiment, the immunomarkers for use in the methods provided herein are selected from Table 4A and/or Table 4B. The individual immunomarkers can be CTLA4, PDCD1 and CD274 (PD-L1). In one embodiment, the individual immunomarkers for use in the methods provided herein are selected from Table 5. The immunomarkers can be one or more interferon (INF) genes. In one embodiment, the immunomarkers for use in the methods provided herein are selected from Table 6. The immunomarkers can be one or more MHCII genes. In one embodiment, the immunomarkers for use in the methods provided herein are selected from Table 7. In yet another embodiment, the immunomarkers for use in the methods provided herein are selected from Tables 4A, 4B, 5, 6, 7, or a combination thereof.

TABLE 4A

Adaptive immune cell (AIC) gene signature immunomarkers for use in the methods provided herein.

| | Cell Type | | | | | |
|---|---|---|---|---|---|---|
| | B cells | T cells | T helper cells | Tcm | Tem | Th1 cells |
| Human Gene (Gene Name; GenBank Accession No.*) | ABCB4 (ATP binding cassette subfamily B member 4; NM_000443) | BCL11B (B-cell lymphoma/leukaemia 11B; AJ404614.1) | ANP32B (acidic nuclear phosphoprotein 32 family member B; NM_006401.2) | AQP3 (aquaporine 3; NM_004925.4) | AKT3 (AKT serine/threonine kinase 3; NM_005465.4) | APBB2 (amyloid beta precursor protein binding family B member 2; NM_001166054.1) |
| | BACH2 (BTB domain and CNC homolog 2; NM_021813.3) | CD2 (CD2 molecule; NM_001328609.1) | ASF1A (anti-silencing function 1A histone chaperone; NM_014034.2) | ATF7IP (activating transcription factor 7 interacting protein; NM_181352.1) | C7orf54 (staphylococcal nuclease and tudor domain containing 1 (SND1); NG_051199.1) | APOD (apolipoprotein D; NM_001647.3) |
| | BCL11A (B-cell CLL/lymphoma 11A; NM_022893.3) | CD28 (CD28 molecule; NM_001243078.1) | ATF2 (activating transcription factor 2; NM_001256093.1) | ATM (ATM serine/threonine kinase; NM_000051.3) | CCR2 (C-C motif chemokine receptor 2; NM_001123396.1) | ATP9A (ATPase phospholipid transporting 9A; NM_006045.2) |
| | BLK (BLK proto-oncogene, Src family tyrosine kinase; NM_001715.2) | CD3D (CD3d molecule; NM_000732.4) | BATF (basic leucine zipper ATF-like transcription factor; NM_006399.3) | CASP8 (caspase 8; NM_001228.4) | DDX17 (DEAD-box helicase 17; NM_006386.4) | BST2 (bone marrow stromal cell antigen 2; NM_004335.3) |
| | BLNK (B-cell linker; NM_013314.3) | CD3E (CD3e molecule; NM_000733.3) | C13orf34 (aurora borealis; EU834129.1) | CDC14A (cell division cycle 14A; NM_003672.3) | EWSR1 (EWS RNA binding protein 1; NM_013986.3) | BTG3 (BTG anti-proliferation factor 3; NM_001130914.1) |
| | CCR9 (C-C motif chemokine receptor 9; NM_031200.2) | CD3G (CD3g molecule; NM_000073.2) | CD28 (CD28 molecule; NM_006139.3) | CEP68 (centrosomal protein 68; NM_015147.2) | FLI1 (Fli-1 proto-oncogene, ETS transcription factor; NM_002017.4) | CCL4 (C-C motif chemokine ligand 4; NM_002984.3) |
| | CD19 (CD19 molecule; NM_001178098.1) | CD6 (CD6 molecule; NM_006725.4) | DDX50 (DEAD-box helicase 50; NM_024045.1) | CG030 (BRCA2 region, mRNA sequence CG030; U50531.1) | GDPD5 (glycerophosphodiester phosphodiesterase domain containing 5; NM_030792.6) | CD38 (CD38 molecule; NM_001775.3) |
| | CD72 (CD72 molecule; NM_001782.2) | CD96 (CD96 molecule; NM_198196.2) | FAM111A (family with sequence similarity 111 member A; NM_022074.3) | CLUAP1 (clusterin associated protein 1; NM_015041.2) | LTK (leukocyte receptor tyrosine kinase; NM_002344.5) | CD70 (CD70 molecule; NM_001252.4) |
| | COCH (cochlin; NM_001135058.1) | GIMAP5 (GTPase, IMAP family member 5; NM_018384.4) | FRYL (FRY like transcription coactivator; NM_015030.1) | CREBZF (CREB/ATF bZIP transcription factor; NM_001039618.2) | MEFV (Mediterranean fever; NM_000243.2) | CMAH (cytidine monophospho-N-acetylneuraminic acid hydroxylase, pseudogene; NR_002174.2) |
| | CR2 (complement C3d receptor 2; | ITM2A (integral membrane protein | FUSIP1 (serine and arginine rich splicing | CYLD (CYLD lysine 63 deubiquitinase; | NFATC4 (nuclear factor of activated | CSF2 (colony stimulating factor 2; |

TABLE 4A-continued

Adaptive immune cell (AIC) gene signature immunomarkers for use in the methods provided herein.
Cell Type

| | | | | | |
|---|---|---|---|---|---|
| NM_001006658.2) | 2A; NM_004867.4) | factor 10; NM_006625.5) | NM_015247.2) | T-cells 4; NM_001136022.2) | NM_000758.3) |
| DTNB (dystrobrevin beta; NM_021907.4) | LCK (LCK proto-oncogene, Src family tyrosine kinase; NM_001042771.2) | GOLGA8A (golgin A8 family member A; NM_181077.3) | CYorf15B (taxilin gamma pseudogene, Y-linked; NR_045128.1) | PRKY (protein kinase, Y-linked, pseudogene; NR_028062.1) | CTLA4 (cytotoxic T-lymphocyte associated protein 4; NM_005214.4) |
| FAM30A (family with sequence similarity 30, member A; NR_026800.2) | NCALD (neurocalcin delta; NM_001040624.1) | ICOS (inducible T-cell costimulator; NM_012092.3) | DOCK9 (dedicator of cytokinesis 9; NM_015296.2) | TBC1D5 (TBC1 domain family member 5; NM_001134381.1) | DGKI (diacylglycerol kinase iota; NM_004717.3) |
| FCRL2 (Fc receptor like 2; NM_030764.3) | PRKCQ (protein kinase C theta; NM_006257.4) | ITM2A (integral membrane protein 2A; NM_004867.4) | FOXP1 (forkhead box P1; NM_032682.5) | TBCD (tubulin folding cofactor D; NM_005993.4) | DOK5 (docking protein 5; NM_018431.4) |
| GLDC (glycine decarboxylase; NM_000170.2) | SH2D1A (SH2 domain containing 1A; NM_002351.4) | LRBA (LPS responsive beige-like anchor protein; NM_001199282.2) | FYB (FYN binding protein; NM_001465.4) | TRA (T cell receptor alpha delta locus; NG_001332.3) | DPP4 (dipeptidyl peptidase 4; NM_001935.3) |
| GNG7 (G protein subunit gamma 7; NM_052847.2) | SKAP1 (src kinase associated phosphoprotein 1; NM_001075099.1) | NAP1L4 (nucleosome assembly protein 1 like 4; NM_005969.3) | HNRPH1 (heterogeneous nuclear ribonucleoprotein H1 (H); NM_001257293.1) | VIL2 (ezrin; NM_003379.4) | DUSP5 (dual specificity phosphatase 5; NM_004419.3) |
| HLA-DOB (major histocompatibility complex, class II, DO beta; NM_002120.3) | TRA (T cell receptor alpha delta locus; NG_001332.3) | NUP107 (nucleoporin 107; NM_020401.3) | INPP4B (inositol polyphosphate-4-phosphatase type II B; NM_003866.3) | | EGFL6 (EGF like domain multiple 6; NM_015507.3) |
| HLA-DQA1 (major histocompatibility complex, class II, DQ alpha 1; NM_002122.3) | TRAC (nuclear receptor corepressor 2; NM_006312.5) | PHF10 (PHD finger protein 10; NM_018288.3) | KLF12 (Kruppel like factor 12; NM_007249.4) | | GGT1 (gamma-glutamyltransferase 1; NM_013421.2) |
| IGHA1 (immunoglobulin heavy locus; NG_001019.6) | TRAT1 (T cell receptor associated transmembrane adaptor 1; NM_016388.3) | PPP2R5C (protein phosphatase 2 regulatory subunit B', gamma; NM_001161725.1) | LOC202134 (family with sequence similarity 153 member B; NM_001265615.1) | | HBEGF (heparin binding EGF like growth factor; NM_001945.2) |
| IGHG1 (immunoglobulin heavy locus; NG_001019.6) | TRBC1 (T cell receptor beta locus; NG_001333.2) | RPA1 (replication protein A1; NM_002945.3) | MAP3K1 (mitogen-activated protein kinase kinase kinase 1, E3 ubiquitin protein ligase; NM_005921.1) | | IFNG (interferon gamma; NM_000619.2) |
| IGHM (immunoglobulin heavy locus; NG_001019.6) | | SEC24C (SEC24 homolog C, COPII coat complex component; NM_004922.3) | MLL (lysine (K)-specific methyltransferase 2A; NM_005933.3) | | IL12RB2 (interleukin 12 receptor subunit beta 2; NM_001319233.1) |

TABLE 4A-continued

| Adaptive immune cell (AIC) gene signature immunomarkers for use in the methods provided herein. Cell Type | | | |
|---|---|---|---|
| IGKC (immunoglobulin kappa locus, proximal V-cluster and J-C cluster; NG_000834.1) | SLC25A12 (solute carrier family 25 member 12; NM_003705.4) | NEFL (neurofilament, light polypeptide; NM_006158.4) | IL22 (interleukin 22; NM_020525.4) |
| IGL (immunoglobulin lambda locus; NG_000002.1) | TRA (T cell receptor alpha delta locus; NG_001332.3) | NFATC3 (nuclear factor of activated T-cells 3; NM_173165.2) | LRP8 (LDL receptor related protein 8; NM_017522.4) |
| KIAA0125 (family with sequence similarity 30, member A; NR_026800.2) | UBE2L3 (ubiquitin conjugating enzyme E2 L3; NM_003347.3) | PCM1 (pericentriolar material 1; NM_001315507.1) | LRRN3 (leucine rich repeat neuronal 3; NM_018334.4) |
| MEF2C (myocyte enhancer factor 2C; NM_001308002.1) | YME1L1 (YME1 like 1 ATPase; NM_001253866.1) | PCNX (pecanex homolog 1; NM_014982.2) | LTA (lymphotoxin alpha; NM_000595.3) |
| MICAL3 (microtubule associated monooxygenase, calponin and LIM domain containing 3; NM_001136004.3) | | PDXDC2 (pyridoxal dependent decarboxylase domain containing 2, pseudogene; NR_003610.1) | SGCB (sarcoglycan, beta (43 kDa dystrophin-associated glycoprotein); NM_000232.4) |
| MS4A1 (membrane spanning 4-domains A1; NM_021950.3) | | PHC3 (polyhomeotic homolog 3; NM_001308116.1) | SYNGR3 (synaptogyrin 3; NM_004209.5) |
| OSBPL10 (oxysterol binding protein like 10; NM_017784.4) | | POLR2J2 (RNA polymerase II subunit J2; NM_032959.5) | ZBTB32 (zinc finger and BTB domain containing 32; NM_014383.2) |
| PNOC (prepronociceptin; NM_001284244.1) | | PSPC1 (paraspeckle component 1; NM_001042414.2) | |
| QRSL1 (glutaminyl-tRNA synthase (glutamine-hydrolyzing)-like 1; NM_018292.4) | | REPS1 (RALBP1 associated Eps domain containing 1; NM_001128617.2) | |
| SCN3A (sodium voltage-gated channel alpha subunit 3; NM_001081677.1) | | RP11-74E24.2 (zinc finger CCCH-type domain-containing-like; NM_001271675.1) | |
| SLC15A2 (solute carrier family 15 member 2; XM_017007074.1) | | RPP38 (ribonuclease P/MRP subunit p38; NM_001265601.1) | |

TABLE 4A-continued

Adaptive immune cell (AIC) gene signature immunomarkers for use in the methods provided herein.
Cell Type

| | | |
|---|---|---|
| | SPIB (Spi-B transcription factor; NM_001244000.1) | SLC7A6 (solute carrier family 7 member 6; NM_003983.5) |
| | TCL1A (T-cell leukemia/lymphoma 1A; NM_001098725.1) | SNRPN (small nuclear ribonucleoprotein polypeptide N; NM_022807.3) |
| | TNFRSF17 (TNF receptor superfamily member 17; NM_001192.2) | ST3GAL1 (ST3 beta-galactoside alpha-2,3-sialyltransferase 1; NM_173344.2) |
| | | STX16 (syntaxin 16; NM_001204868.1) |
| | | TIMM8A (translocase of inner mitochondrial membrane 8 homolog A; NM_001145951.1) |
| | | TRAF3IP3 (TRAF3 interacting protein 3; NM_001320144.1) |
| | | TXK (TXK tyrosine kinase; NM_003328.2) |
| | | USP9Y (ubiquitin specific peptidase 9, Y-linked; NG_008311.1) |

| | Th2 cells | TFH | Th17 cells | TReg | CD8 T cells | Tgd | Cytotoxic cells |
|---|---|---|---|---|---|---|---|
| Human Gene (Gene Name; GenBank Accession No.*) | ADCY1 (adenylate cyclase 1; NM_001281768.1) | B3GAT1 (beta-1,3-glucuronyltransferase 1; NM_018644.3) | IL17A (interleukin 17A; NM_002190.2) | FOXP3 (forkhead box P3; NM_014009.3) | ABT1 (activator of basal transcription 1; NM_013375.3) | C1orf61 (chromosome 1 open reading frame 61; NM_006365.2) | APBA2 (amyloid beta precursor protein binding family A member 2; NM_005503.3) |
| | AHI1 (Abelson helper integration site 1; NM_001134831.1) | BLR1 (c-x-c chemokine receptor type 5; EF444957.1) | IL17RA (interleukin 17 receptor A; NM_014339.6) | | AES (amino-terminal enhancer of split; NM_198969.1) | CD160 (CD160 molecule; NM_007053.3) | APOL3 (apolipoprotein L3; NM_014349.2) |
| | AI582773 (tn17d08.x1 NCI_CGAP_Brn25 *Homo sapiens* cDNA clone; AI582773.1) | C18orf1 (low density lipoprotein receptor class A domain containing 4; NM_181481.4) | RORC (RAR related orphan receptor C; NM_001001523.1) | | APBA2 (amyloid beta precursor protein binding family A member 2; NM_001130414.1) | FEZ1 (Fasciculation And Elongation Protein Zeta 1; AF123659.1) | CTSW (cathepsin W; NM_001335.3) |

TABLE 4A-continued

Adaptive immune cell (AIC) gene signature immunomarkers for use in the methods provided herein.
Cell Type

| | | | | | | |
|---|---|---|---|---|---|---|
| ANK1 (ankyrin 1; NM_020476.2) | CDK5R1 (cyclin dependent kinase 5 regulatory subunit 1; NM_003885.2) | | | ARHGAP8 (Rho GTPase activating protein 8; NM_001198726.1) | TARP (TCR gamma alternate reading frame protein; NM_001003806.1) | DUSP2 (dual specificity phosphatase 2; NM_004418.3) |
| BIRC5 (baculoviral IAP repeat containing 5; NM_001012271.1) | CHGB (chromogranin B; NM_001819.2) | | | C12orf47 (MAPKAPK5 antisense RNA 1; NR_015404.1) | TRD (T cell receptor alpha delta locus; NG_001332.3) | GNLY (granulysin; NM_012483.3) |
| CDC25C (cell division cycle 25C; NM_001318098.1) | CHI3L2 (chitinase 3 like 2; NM_001025199.1) | | | C19orf6 (transmembrane protein 259; NM_001033026.1) | TRGV9 (T cell receptor gamma V region 9; X69385.1) | GZMA (granzyme A; NM_006144.3) |
| CDC7 (cell division cycle 7; NM_001134420.1) | CXCL13 (C-X-C motif chemokine ligand 13; NM_006419.2) | | | C4orf15 (HAUS augmin like complex subunit 3; NM_001303143.1) | | GZMH (granzyme H; NM_001270781.1) |
| CENPF (centromere protein F; NM_016343.3) | HEY1 (hes related family bHLH transcription factor with YRPW motif 1; NM_001282851.1) | | | CAMLG (calcium modulating ligand; NM_001745.3) | | KLRB1 (killer cell lectin like receptor B1; NM_002258.2) |
| CXCR6 (killer cell lectin like receptor B1; NM_002258.2) | HIST1H4K (histone cluster 1 H4 family member k; NM_003541.2) | | | CD8A (CD8a molecule; NM_001768.6) | | KLRD1 (killer cell lectin like receptor D1; NM_001114396.1) |
| DHFR (dihydrofolate reductase; NM_001290354.1) | ICA1 (islet cell autoantigen 1; NM_001136020.2) | | | CD8B (CD8b molecule; NM_001178100.1) | | KLRF1 (killer cell lectin like receptor F1; NM_001291822.1) |
| EVI5 (ecotropic viral integration site 5; NM_001308248.1) | KCNK5 (potassium two pore domain channel subfamily K member 5; NM_003740.3) | | | CDKN2AIP (CDKN2A interacting protein; NM_001317343.1) | | KLRK1 (killer cell lectin like receptor K1; NM_007360.3) |
| GATA3 (GATA binding protein 3; NM_001002295.1) | KIAA1324 (KIAA1324; NM_001284353.1) | | | DNAJB1 (DnaJ heat shock protein family (Hsp40) member B1; NM_001313964.1) | | NKG7 (natural killer cell granule protein 7; NM_005601.3) |
| GSTA4 (glutathione S-transferase alpha 4; NM_001512.3) | MAF (MAF bZIP transcription factor; NM_001031804.2) | | | FLT3LG (fms related tyrosine kinase 3 ligand; NM_001278638.1) | | RORA (RAR related orphan receptor A; NM_134262.2) |
| HELLS (helicase, lymphoid-specific; | MAGEH1 (MAGE family member H1; | | | GADD45A (growth arrest and DNA | | RUNX3 (runt related |

TABLE 4A-continued

Adaptive immune cell (AIC) gene signature immunomarkers for use in the methods provided herein.
Cell Type

| | | | |
|---|---|---|---|
| NM_001289074.1) | NM_014061.4) | damage inducible alpha; NM_001199742.1) | transcription factor 3; NM_004350.2) |
| IL26 (interleukin 26; NM_018402.1) | MKL2 (MKL1/myocardin like 2; NM_014048.4) | GZMM (granzyme M; NM_001258351.1) | SIGIRR (single Ig and TIR domain containing; NM_001135054.1) |
| LAIR2 (leukocyte associated immunoglobulin like receptor 2; NM_021270.4) | MYO6 (myosin VI; NM_001300899.1) | KLF9 (Kruppel like factor 9; NM_001206.2) | WHDC1L1 (WAS protein homolog associated with actin, golgi membranes and microtubules pseudogene 3; NR_003521.1) |
| LIMA1 (LIM domain and actin binding 1; NM_001243775.1) | MYO7A (myosin VIIA; NM_001127179.2) | LEPROTL1 (leptin receptor overlapping transcript-like 1; NM_001128208.1) | ZBTB16 (zinc finger and BTB domain containing 16; NM_001018011.1) |
| MB (myoglobin; NM_203377.1) | PASK (PAS domain containing serine/threonine kinase; NM_001252119.1) | LIME1 (Lck interacting transmembrane adaptor 1; NM_017806.3) | |
| MICAL2 (microtubule associated monooxygenase, calponin and LIM domain containing 2; NM_001282663.1) | PDCD1 (programmed cell death 1; NM_005018.2) | MYST3 (MYST histone acetyltransferase (monocytic leukemia) 3; NM_006766.4) | |
| NEIL3 (nei like DNA glycosylase 3; NM_018248.2) | POMT1 (protein O-mannosyltransferase 1; NM_001136114.1) | PF4 (platelet factor 4; NM_002619.3) | |
| PHEX (phosphate regulating endopeptidase homolog, X-linked; NM_000444.5) | PTPN13 (protein tyrosine phosphatase, non-receptor type 13; NM_080685.2) | PPP1R2 (protein phosphatase 1 regulatory inhibitor subunit 2; NM_001291504.1) | |
| PMCH (pro-melanin concentrating hormone; NM_002674.3) | PVALB (parvalbumin; NM_001315532.1) | PRF1 (perforin 1; NM_005041.4) | |
| PTGIS (12 synthase; NM_000961.3) | SH3TC1 (SH3 domain and tetratricopeptide repeats 1; NM_018986.4) | PRR5 (proline rich 5; NM_181333.3) | |

TABLE 4A-continued

Adaptive immune cell (AIC) gene signature immunomarkers for use in the methods provided herein.
Cell Type

| | | |
|---|---|---|
| SLC39A14 (solute carrier family 39 member 14; NM_001135153.1) | SIRPG (signal regulatory protein gamma; NM_018556.3) | RBM3 (RNA binding motif (RNP1, RRM) protein 3; NM_006743.4) |
| SMAD2 (SMAD family member 2; NM_001135937.2) | SLC7A10 (solute carrier family 7 member 10; NM_019849.2) | SF1 (splicing factor 1; NM_004630.3) |
| SNRPD1 (small nuclear ribonucleoprotein D1 polypeptide; NM_001291916.1) | SMAD1 (SMAD family member 1; NM_001003688.1) | SFRS7 (serine and arginine rich splicing factor 7; NM_001031684.2) |
| WDHD1 (WD repeat and HMG-box DNA binding protein 1; NM_001008396.2) | ST8SIA1 (ST8 alpha-N-acetyl-neuraminide alpha-2,8-sialyltransferase 1; NM_001304450.1) | SLC16A7 (solute carrier family 16 member 7; NM_001270622.1) |
| | STK39 (serine/threonine kinase 39; NM_013233.2) | TBCC (tubulin folding cofactor C; NM_003192.2) |
| | THADA (THADA, armadillo repeat containing; | THUMPD1 (THUMP domain containing 1; NM_017736.4) |

TABLE 4A-continued

Adaptive immune cell (AIC) gene signature immunomarkers for use in the methods provided herein.

Cell Type

| | |
|---|---|
| NM_001271644.1) | |
| TOX (thymocyte selection associated high mobility group box; NM_014729.2) | TMC6 (transmembrane channel like 6; NM_001321185.1) |
| TSHR (thyroid stimulating hormone receptor; NM_000369.2) | TSC22D3 (TSC22 domain family member 3; NM_001318470.1) |
| ZNF764 (zinc finger protein 764; NM_001172679.1) | VAMP2 (vesicle associated membrane protein 2; NM_014232.2) |
| | ZEB1 (zinc finger E-box binding homeobox 1; NM_001128128.2) |
| | ZFP36L2 (ZFP36 ring finger protein like 2; NM_006887.4) |
| | ZNF22 (zinc finger protein 22; NM_006963.4) |
| | ZNF609 (zinc finger protein 609; NM_015042.1) |
| | ZNF91 (zinc finger protein 91; NM_001300951.1) |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 4B

Innate immune cell (IIC) gene signature immunomarkers for use in the methods provided herein.

| | Cell Type | | | | |
|---|---|---|---|---|---|
| | NK cells | NK CD56dim cells | NK CD56bright cells | DC | iDC |
| Human Gene (Gene Name; GenBank Accession No.*) | ADARB1 (adenosine deaminase, RNA specific B1; NM_001112) | EDG8 (sphingosine-1-phosphate receptor 5; NM_001166215.1) | BG255923 (lysophosphatidylcholine acyltransferase 4; NM_153613.2) | CCL13 (C-C motif chemokine ligand 13; NM_005408.2) | ABCG2 (ATP-binding cassette, sub-family G (WHITE), member 2 (Junior blood group); NM_001257386.1) |
| | AF107846 (neuroendocrine-specific Golgi protein p55; AF107846.1) | FLI20699 (cDNA FLI20699 fis, clone KAIA2372; AK000706.1) | DUSP4 (dual specificity phosphatase 4; NM_057158.3) | CCL17 (C-C motif chemokine ligand 17; NM_002987.2) | BLVRB (biliverdin reductase B; NM_000713.2) |
| | AL080130 (cDNA DKFZp434E033 (from clone DKFZp434E033); AL080130.1) | GTF3C1 (general transcription factor IIIC subunit 1; NM_001286242.1) | FOXJ1 (forkhead box J1; NM_001454.3) | CCL22 (C-C motif chemokine ligand 22; NM_002990.4) | CARD9 (caspase recruitment domain family member 9; NM_052814.3) |
| | ALDH1B1 (aldehyde dehydrogenase 1 family member B1; NM_000692.4) | GZMB (granzyme B; NM_004131.4) | MADD (MAP kinase activating death domain; NM_001135944.1) | CD209 (CD209 molecule; NM_001144899.1) | CD1A (CD1a molecule; NM_001763.2) |
| | ARL6IP2 (atlastin GTPase 2; NM_001330461.1) | IL21R (interleukin 21 receptor; NM_181079.4) | MPPED1 (metallophosphoesterase domain containing 1, mRNA; NM_001044370.1) | HSD11B1 (hydroxysteroid 11-beta dehydrogenase 1; NM_001206741.1) | CD1B (CD1b molecule; NM_001764.2) |
| | BCL2 (apoptosis regulator (BCL2); NM_000633.2) | KIR2DL3 (killer cell immunoglobulin like receptor, two Ig domains and long cytoplasmic tail 3; NM_015868.2) | MUC3B (mucin 3B cell surface associated; JQ511939.1) | NPR1 (natriuretic peptide receptor 1; NM_000906.3) | CD1C (CD1c molecule; NM_001765.2) |
| | CDC5L (cell division cycle 5 like; NM_001253.3) | KIR2DS1 (killer cell immunoglobulin like receptor, two Ig domains and short cytoplasmic tail 1; NM_014512.1) | NIBP (NIK and IKKbetta-binding protein; AY630619.1) | PPFIBP2 (PPFIA binding protein 2; XR_930917.2) | CD1E (CD1e molecule; NM_001185115.1) |
| | FGF18 (fibroblast growth factor 18; NM_003862.2) | KIR2DS2 (killer cell immunoglobulin like receptor, two Ig domains and short cytoplasmic tail 2; NM_001291700.1) | PLA2G6 (phospholipase A2 group VI; NM_001004426.1) | | CH25H (cholesterol 25-hydroxylase; NM_003956.3) |
| | FUT5 (fucosyltransferase 5; NM_002034.2) | KIR2DS5 (killer cell immunoglobulin like receptor, two Ig domains and short cytoplasmic tail 5; NM_014513.2) | RRAD (Ras related glycolysis inhibitor and calcium channel regulator; NM_001128850.1) | | CLEC10A (C-type lectin domain family 10 member A; NM_001330070.1) |

TABLE 4B-continued

| Innate immune cell (IIC) gene signature immunomarkers for use in the methods provided herein. Cell Type | | | | |
|---|---|---|---|---|
| | FZR1 (fizzy/cell division cycle 20 related 1; XM_005259573.4) | KIR3DL1 (killer cell immunoglobulin like receptor, three Ig domains and long cytoplasmic tail 1; NM_013289.2) | SEPT6 (septin 6; NM_145802.3) | CSF1R (colony stimulating factor 1 receptor; NM_001288705.1) |
| | GAGE2 (G antigen 2; NM_001127212.1) | KIR3DL2 (killer cell immunoglobulin like receptor, three Ig domains and long cytoplasmic tail 2; NM_006737.3) | XCL1 (X-C motif chemokine ligand 1; NM_002995.2) | CTNS (cystinosin, lysosomal cystine transporter; NM_001031681.2) |
| | IGFBP5 (insulin like growth factor binding protein 5; NM_000599.3) | KIR3DL3 (killer cell immunoglobulin like receptor, three Ig domains and long cytoplasmic tail 3; NM_153443.4) | | F13A1 (factor XIII a subunit; AH002691.2) |
| | LDB3 (LIM domain binding 3; NM_001171611.1) | KIR3DS1 (killer cell immunoglobulin like receptor, three Ig domains and short cytoplasmic tail 1; NM_001083539.2) | | FABP4 (fatty acid binding protein 4; NM_001442.2) |
| | LOC643313 (similar to hypothetical protein LOC284701; XM_933043.1) | SPON2 (spondin 2; NM_001199021.1) | | FZD2 (frizzled class receptor 2; NM_001466.3) |
| | LOC730096 (hypothetical protein LOC730096; NC_000022.9) | TMEPAI (prostate transmembrane protein, androgen induced 1; NM_199169.2) | | GSTT1 (glutathione S-transferase theta 1; NM_001293814.1) |
| | MAPRE3 (microtubule associated protein RP/EB family member 3; NM_001303050.1) | | | GUCA1A (guanylate cyclase activator 1A; NM_001319062.1) |
| | MCM3AP (minichromosome maintenance complex component 3 associated protein; NM_003906.4) | | | HS3ST2 (heparan sulfate (glucosamine) 3-O-sulfotransferase 2; NM_006043.1) |
| | MRC2 (mannose receptor C type 2; NM_006039.4) | | | LMAN2L (lectin, mannose binding 2 like; NM_001322355.1) |
| | NCR1 (natural cytotoxicity triggering receptor 1; NM_001242357.2) | | | MMP12 (matrix metallopeptidase 12; NM_002426.5) |
| | NM_014114 (PRO0097 protein; NM_014114.1) | | | MS4A6A (membrane spanning 4-domains A6A; NM_001330275.1) |
| | NM_014274 (transient receptor potential cation | | | NM_021941 (chromosome 21 open |

TABLE 4B-continued

Innate immune cell (IIC) gene signature immunomarkers for use in the methods provided herein.

| | Cell Type | | | | | |
|---|---|---|---|---|---|---|
| | channel, subfamily V, member 6; NM_014274.3)<br>NM_017616 (KN motif and ankyrin repeat domains 2; NM_015493.6)<br>PDLIM4 (PDZ and LIM domain 4; NM_003687.3)<br>PRX (periaxin; NM_020956.2)<br>PSMD4 (proteasome 26S subunit, non-ATPase 4; NM_001330692.1)<br>RP5-886K2.1 (neuronal thread protein AD7c-NTP; AF010144.1)<br>SLC30A5 (solute carrier family 30 member 5; NM_001251969.1)<br>SMEK1 (protein phosphatase 4 regulatory subunit 3A; NM_001284280.1)<br>SPN (sialophorin; NM_003123.4)<br>TBXA2R (thromboxane A2 receptor; NM_001060.5)<br>TCTN2 (tectonic family member 2; NM_001143850.2)<br>TINAGL1 (tubulointerstitial nephritis antigen like 1; NM_001204415.1)<br>XCL1 (X-C motif chemokine ligand 1; NM_002995.2)<br>XCL2 (X-C motif chemokine ligand 2; NM_003175.3)<br>ZNF205 (zinc finger protein 205; NM_001278158.1)<br>ZNF528 (zinc finger protein 528; NM_032423.2)<br>ZNF747 (zinc finger protein 747; NM_023931.3) | | | | | reading frame 97; NM_021941.1)<br>NUDT9 (nudix hydrolase 9; NM_001248011.1)<br>PPARG (peroxisome proliferator activated receptor gamma; NM_005037.5)<br>PREP (prolyl endopeptidase; NM_002726.4)<br>RAP1GAP (RAP1 GTPase activating protein; NM_001330383.1)<br>SLC26A6 (solute carrier family 26 member 6; NM_001281733.1)<br>SLC7A8 (solute carrier family 7 member 8; NR_049767.1)<br>SYT17 (synaptotagmin 17; NM_001330509.1)<br>TACSTD2 (tumor-associated calcium signal transducer 2; NM_002353.2)<br>TM7SF4 (dendrocyte expressed seven transmembrane protein; NM_001257317.1)<br>VASH1 (vasohibin 1; NM_014909.4) |
| | aDC | pDC | Eosinophils | Macrophages | Mast cells | Neutrophils |
| Human Gene (Gene Name; | CCL1 | IL3RA (interleukin 3 | ABHD2 (abhydrolase | APOE (apolipoprotein | ABCC4 (ATP binding | ALPL (alkaline |

TABLE 4B-continued

Innate immune cell (IIC) gene signature immunomarkers for use in the methods provided herein.
Cell Type

| | | | | | | |
|---|---|---|---|---|---|---|
| GenBank Accession No.*) | (Chemokine (C-C motif) ligand 1: NM_002981) | receptor subunit alpha; NM_001267713.1) | domain containing 2; NM_007011.7) | E; NM_001302691.1) | cassette subfamily C member 4; NM_001301829.1) | phosphatase, liver/bone/kidney; NM_001127501.3) |
| | EBI3 (Epstein-Barr virus induced 3; NM_005755.2) | | ACACB (acetyl-CoA carboxylase beta; NM_001093.3) | ATG7 (autophagy related 7; NM_001144912.1) | ADCYAP1 (adenylate cyclase activating polypeptide 1; NM_001117.4) | BST1 (bone marrow stromal cell antigen 1; NM_004334.2) |
| | INDO (indoleamine-pyrrole 2,3 dioxygenase; AY221100.1) | | C9orf156 (tRNA methyltransferase O; NM_001330725.1) | BCAT1 (branched chain amino acid transaminase 1; NM_001178094.1) | CALB2 (calbindin 2; NM_001740.4) | CD93 (CD93 molecule; NM_012072.3) |
| | LAMP3 (lysosomal associated membrane protein 3; NM_014398.3) | | CAT (catalase; NM_001752.3) | CCL7 (C-C motif chemokine ligand 7; NM_006273.3) | CEACAM8 (carcinoembryonic antigen related cell adhesion molecule 8; NM_001816.3) | CEACAM3 (carcinoembryonic antigen related cell adhesion molecule 3; NM_001277163.2) |
| | OAS3 (2'-5'-oligoadenylate synthetase 3; NM_006187.3) | | CCR3 (C-C motif chemokine receptor 3; NM_178329.2) | CD163 (CD163 molecule; NM_203416.3) | CMA1 (chymase 1, mast cell; NM_001308083.1) | CREB5 (cAMP responsive element binding protein 5; NM_001011666.2) |
| | | | CLC (Charcot-Leyden crystal galectin; NM_001828.5) | CD68 (CD68 molecule; NM_001040059.1) | CPA3 (carboxypeptidase A3; NM_001870.3) | CRISPLD2 (cysteine rich secretory protein LCCL domain containing 2; NM_031476.3) |
| | | | CYSLTR2 (cysteinyl leukotriene receptor 2; NM_001308471.1) | CD84 (CD84 molecule; NM_001184881.1) | CTSG (cathepsin G; NM_001911.2) | CSF3R (colony stimulating factor 3 receptor; NM_172313.2) |
| | | | EMR1 (EGF-like module containing mucin-like hormone receptor-like 1; DQ217942.1) | CHI3L1 (chitinase 3 like 1; NM_001276.2) | ELA2 (neutrophil elastase; EU617980.1) | CYP4F3 (cytochrome P450 family 4 subfamily F member 3; NM_001199209.1) |
| | | | EPN2 (epsin 2; NM_001102664.1) | CHIT1 (chitinase 1; NM_001270509.1) | GATA2 (GATA binding protein 2; NM_001145661.1) | DYSF (dysferlin; NM_001130455.1) |
| | | | GALC (galactosylceramidase; NM_000153.3) | CLEC5A (C-type lectin domain family 5 member A; | HDC (histidine decarboxylase; NM_002112.3) | FCAR (Fc fragment of IgA receptor; NM_133278.3) |

TABLE 4B-continued

Innate immune cell (IIC) gene signature immunomarkers for use in the methods provided herein.
Cell Type

| | | | |
|---|---|---|---|
| | NM_001301167.1) | | |
| GPR44 (orphan G protein-coupled receptor; AF118265.1) | COL8A2 (collagen type VIII alpha 2 chain; NM_001294347.1) | HPGD (hydroxyprostaglandin dehydrogenase 15-(NAD); NM_001256307.1) | FCGR3B (Fc fragment of IgG receptor IIIb; NM_001271035.1) |
| HES1 (hes family bHLH transcription factor 1; NM_005524.3) | COLEC12 (collectin subfamily member 12; NM_130386.2) | KIT (KIT proto-oncogene receptor tyrosine kinase; NM_000222.2) | FLI11151 (hypothetical protein FLI11151; BC006289.2) |
| HIST1H1C (histone cluster 1 H1 family member c; NM_005319.3) | CTSK (cathepsin K; NM_000396.3) | LOC339524 (long intergenic non-protein coding RNA 1140; NR_026985.1) | FPR1 (formyl peptide receptor 1; NM_001193306.1) |
| HRH4 (histamine receptor H4; NM_001143828.1) | CXCL5 (C-X-C motif chemokine ligand 5; NM_002994.4) | LOH11CR2A (BCSC-1 isoform; AY366508.1) | FPRL1 (formyl peptide receptor-like receptor; M84562.1) |
| IGSF2 (immunoglobulin superfamily, member 2; BC130327.1) | CYBB (cytochrome b-245 beta chain; NM_000397.3) | MAOB (monoamine oxidase B; NM_000898.4) | G0S2 (G0/G1 switch 2; NM_015714.3) |
| IL5RA (interleukin 5 receptor subunit alpha; NM_001243099.1) | DNASE2B (deoxyribonuclease 2 beta; NM_058248.1) | MLPH (melanophilin; NM_001042467.2) | HIST1H2BC (histone cluster 1 H2B family member c; NM_003526.2) |
| KBTBD11 (kelch repeat and BTB domain containing 11; NM_014867.2) | EMP1 (epithelial membrane protein 1; NM_001423.2) | MPO (myeloperoxidase; NM_000250.1) | HPSE (heparanase; NM_001098540.2) |
| KCNH2 (potassium voltage-gated channel, subfamily H (eag-related), member 2; NM_000238.3) | FDX1 (ferredoxin 1; NM_004109.4) | MS4A2 (membrane spanning 4-domains A2; NM_001256916.1) | IL8RA (interleukin 8 receptor alpha; L19591.1) |
| LRP5L (LDL receptor related protein 5 like; NM_001135772.1) | FN1 (fibronectin 1; NM_001306131.1) | NM_003293 (tryptase alpha/beta 1; NM_003294.3) | IL8RB (interleukin-8 receptor type B; U11878.1) |
| MYO15B (myosin XVB; NM_001309242.1) | GM2A(GM2 ganglioside activator; NM_000405.4) | NR0B1 (nuclear receptor subfamily 0 group B member 1; NM_000475.4) | KCNJ15 (potassium voltage-gated channel subfamily J member 15; NM_001276438.1) |
| RCOR3 (REST corepressor 3; NM_001136224.2) | GPC4 (glypican 4; NM_001448.2) | PGDS (hematopoietic prostaglandin D synthase; NM_014485.2) | KIAA0329 (tectonin beta-propeller repeat containing 2; NM_014844.4) |
| RNASE2 (ribonuclease A family member 2; NM_002934.2) | KAL1 (anosmin 1; NM_000216.3) | PPM1H (protein phosphatase, Mg2+/Mn2+ dependent 1H; NM_020700.1) | LILRB2 (leukocyte immunoglobulin like receptor B2; NR_103521.2) |

TABLE 4B-continued

| Innate immune cell (IIC) gene signature immunomarkers for use in the methods provided herein. Cell Type | | | | |
|---|---|---|---|---|
| | RNU2 (U2 snRNA; U57614.1) | MARCO (macrophage receptor with collagenous structure; NM_006770.3) | PRG2 (proteoglycan 2, pro eosinophil major basic protein; NM_001302927.1) | MGAM (maltase-glucoamylase; NM_004668.2) |
| | RRP12 (ribosomal RNA processing 12 homolog; NM_001284337.1) | ME1 (malic enzyme 1; NM_002395.5) | PTGS1 (prostaglandin-endoperoxide synthase 1; NM_000962.3) | MME (membrane metalloendopeptidase; NM_007289.2) |
| | SIAH1 (siah E3 ubiquitin protein ligase 1; NM_003031.3) | MS4A4A (membrane spanning 4-domains A4A; NM_001243266.1) | SCG2 (secretogranin II; NM_003469.4) | PDE4B (phosphodiesterase 4B; NM_001297440.1) |
| | SMPD3 (sphingomyelin phosphodiesterase 3; NM_018667.3) | MSR1 (macrophage scavenger receptor 1; NM_138716.2) | SIGLEC6 (sialic acid binding Ig like lectin 6; NM_198845.5) | S100A12 (S100 calcium binding protein A12; NM_005621.1) |
| | SYNJ1 (synaptojanin 1; NM_001160302.1) | PCOLCE2 (procollagen C-endopeptidase enhancer 2; NM_013363.3) | SLC18A2 (solute carrier family 18 member A2; NM_003054.4) | SIGLEC5 (sialic acid binding Ig like lectin 5; NM_003830.3) |
| | TGIF1 (TGFB induced factor homeobox 1; NM_174886.2) | PTGDS (prostaglandin D2 synthase; NM_000954.5) | SLC24A3 (solute carrier family 24 member 3; NM_020689.3) | SLC22A4 (solute carrier family 22 member 4; NM_003059.2) |
| | THBS1 (thrombospondin 1; NM_003246.3) | RAI14 (retinoic acid induced 14; NM_001145525.1) | TAL1 (T-cell acute lymphocytic leukemia 1; X51990.1) | SLC25A37 (solute carrier family 25 member 37; NM_001317812.1) |
| | THBS4 (thrombospondin 4; NM_001306213.1) | SCARB2 (scavenger receptor class B member 2; NM_001204255.1) | TPSAB1 (tryptase alpha/beta 1; NM_003294.3) | TNFRSF10C (TNF receptor superfamily member 10c; NM_003841.3) |
| | TIPARP (TCDD inducible poly(ADP-ribose) polymerase; NM_001184718.1) | SCG5 (secretogranin V; NM_001144757.2) | TPSB2 (tryptase beta 2; NM_024164.5) | VNN3 (vanin 3; NM_001291703.1) |
| | TKTL1 (transketolase like 1; NM_001145934.1) | SGMS1 (sphingomyelin synthase 1; NM_147156.3) | | |
| | | SULT1C2 (sulfotransferase family 1C member 2; NM_176825.2) | | |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 5

Individual Immunomarkers for use in the methods provided herein.

| Gene Name | Abbreviation | GenBank Accession No.* |
|---|---|---|
| Programmed Death Ligand 1 | PDL1 | NM_014143 |
| programmed death ligand 2 | PDL2 | AY254343 |
| programmed cell death 1 | PDCD1 | NM_005018 |
| cytotoxic T-lymphocyte associated protein 4 | CTLA4 | NM_005214 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 6

Interferon (IFN) Genes for use in the methods provided herein.

| Gene Name | Abbreviation | GenBank Accession No.* |
|---|---|---|
| Chemokine (C-X-C Motif) Ligand 10 | CXCL10 | NM_001565 |
| C-X-C motif chemokine ligand 9 | CXCL9 | NM_002416 |
| interferon alpha inducible protein 27 | IFI27 | NM_001130080 |
| interferon induced protein with tetratricopeptide repeats 1 | IFIT1 | NM_001548 |
| interferon induced protein with tetratricopeptide repeats 2 | IFIT2 | NM_001547 |
| interferon induced protein with tetratricopeptide repeats 3 | IFIT3 | NM_001549 |
| MX dynamin like GTPase 1 | MX1 | NM_001144925 |
| MX dynamin like GTPase 2 | MX2 | XM_005260983 |
| 2'-5'-oligoadenylate synthetase 1 | OAS1 | NM_016816 |
| 2'-5'-oligoadenylate synthetase 2 | OAS2 | NM_016817 |
| signal transducer and activator of transcription 1 | STAT1 | NM_007315 |
| signal transducer and activator of transcription 2 | STAT2 | NM_005419 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

TABLE 7

MHC class II genes for use in the methods provided herein.

| Name | Abbreviation | GenBank Accession No.* |
|---|---|---|
| CD74 | *Homo sapiens* CD74 molecule (CD74) | NM_001025159 |
| CIITA | class II major histocompatibility complex transactivator | NM_001286402 |
| CTSH | cathepsin H | NM_004390 |
| HLA-DMA | *Homo sapiens* major histocompatibility complex, class II, DM alpha | NM_006120 |
| HLA-DPA1 | *Homo sapiens* major histocompatibility complex, class II, DP alpha 1 | NM_033554 |
| HLA-DPB1 | Human MHC class II lymphocyte antigen (HLA-DP) beta chain | M83664 |
| HLA-DQA1 | *Homo sapiens* major histocompatibility complex, class II, DQ alpha 1 | NM_002122 |
| HLA-DRB1 | *Homo sapiens* major histocompatibility complex, class II, DR beta 1 | NM_002124 |
| HLA-DRB5 | *Homo sapiens* major histocompatibility complex, class II, DR beta 5 | NM_002125 |

TABLE 7-continued

MHC class II genes for use in the methods provided herein.

| Name | Abbreviation | GenBank Accession No.* |
|---|---|---|
| HLA-DRB6 | *Homo sapiens* major histocompatibility complex, class II, DR beta 6 | NR_001298 |
| NCOA1 | *Homo sapiens* nuclear receptor coactivator 1 | NM_003743 |

*Each GenBank Accession Number is a representative or exemplary GenBank Accession Number for the listed gene and is herein incorporated by reference in its entirety for all purposes. Further, each listed representative or exemplary accession number should not be construed to limit the claims to the specific accession number.

In one embodiment, upon determining a patient's SQ lung cancer subtype using any of the methods and classifier biomarkers panels or subsets thereof as provided herein alone or in combination with determining expression of one or more immune cell markers as provided herein, the patient is selected for treatment with or administered an immunotherapeutic agent. The immunotherapeutic agent can be a checkpoint inhibitor, monoclonal antibody, biological response modifiers, therapeutic vaccine or cellular immunotherapy.

In another embodiment, the immunotherapeutic agent is a checkpoint inhibitor. In some cases, a method for determining the likelihood of response to one or more checkpoint inhibitors is provided. In one embodiment, the checkpoint inhibitor is a PD-1/PD-LI checkpoint inhibitor. The PD-1/PD-LI checkpoint inhibitor can be nivolumab, pembrolizumab, atezolizumab, durvalumab, lambrolizumab, or avelumab. In one embodiment, the checkpoint inhibitor is a CTLA-4 checkpoint inhibitor. The CTLA-4 checkpoint inhibitor can be ipilimumab or tremelimumab. In one embodiment, the checkpoint inhibitor is a combination of checkpoint inhibitors such as, for example, a combination of one or more PD-1/PD-LI checkpoint inhibitors used in combination with one or more CTLA-4 checkpoint inhibitors.

In one embodiment, the immunotherapeutic agent is a monoclonal antibody. In some cases, a method for determining the likelihood of response to one or more monoclonal antibodies is provided. The monoclonal antibody can be directed against tumor cells or directed against tumor products. The monoclonal antibody can be panitumumab, matuzumab, necitumunab, trastuzumab, amatuximab, bevacizumab, ramucirumab, bavituximab, patritumab, rilotumumab, cetuximab, immu-132, or demcizumab.

In yet another embodiment, the immunotherapeutic agent is a therapeutic vaccine. In some cases, a method for determining the likelihood of response to one or more therapeutic vaccines is provided. The therapeutic vaccine can be a peptide or tumor cell vaccine. The vaccine can target MAGE-3 antigens, NY-ESO-1 antigens, p53 antigens, survivin antigens, or MUC1 antigens. The therapeutic cancer vaccine can be GVAX (GM-CSF gene-transfected tumor cell vaccine), belagenpumatucel-L (allogeneic tumor cell vaccine made with four irradiated NSCLC cell lines modified with TGF-beta2 antisense plasmid), MAGE-A3 vaccine (composed of MAGE-A3 protein and adjuvant AS15), (1)-BLP-25 anti-MUC-1 (targets MUC-1 expressed on tumor cells), CimaVax EGF (vaccine composed of human recombinant Epidermal Growth Factor (EGF) conjugated to a carrier protein), WT1 peptide vaccine (composed of four Wilms' tumor suppressor gene analogue peptides), CRS-207 (live-attenuated *Listeria monocytogenes* vector encoding human mesothelin), Bec2/BCG (induces anti-GD3 antibodies), GV1001 (targets the human telomerase reverse transcriptase), tergenpumatucel-L (consists of human lung cancer cells genetically modified to include a mouse gene to which the immune system responds strongly), TG4010 (targets the MUC antigen), racotumomab (anti-idiotypic antibody which mimics the NGcGM3 ganglioside that is expressed on multiple human cancers), tecemotide (liposomal BLP25; liposome-based vaccine made from tandem repeat region of MUC1) or DRibbles (a vaccine made from nine cancer antigens plus TLR adjuvants).

In one embodiment, the immunotherapeutic agent is a biological response modifier. In some cases, a method for determining the likelihood of response to one or more biological response modifiers is provided. The biological response modifier can trigger inflammation such as, for example, PF-3512676 (CpG 7909)(a toll-like receptor 9 agonist), CpG-ODN 2006 (downregulates Tregs), *Bacillus* Calmette-Guerin (BCG), *mycobacterium* vaccae (SRL172) (nonspecific immune stimulants now often tested as adjuvants). The biological response modifier can be cytokine therapy such as, for example, IL-2+ tumor necrosis factor alpha (TNF-alpha) or interferon alpha (induces T-cell proliferation), interferon gamma (induces tumor cell apoptosis), or Mda-7 (IL-24)(Mda-7/IL-24 induces tumor cell apoptosis and inhibits tumor angiogenesis). The biological response modifier can be a colony-stimulating factor such as, for example granulocyte colony-stimulating factor. The biological response modifier can be a multi-modal effector such as, for example, multi-target VEGFR: thalidomide and analogues such as lenalidomide and pomalidomide, cyclophosphamide, cyclosporine, denileukin diftitox, talactoferrin, trabecetedin or all-trans-retinmoic acid.

In one embodiment, the immunotherapy is cellular immunotherapy. In some cases, a method for determining the likelihood of response to one or more cellular therapeutic agents. The cellular immunotherapeutic agent can be dendritic cells (DCs) (ex vivo generated DC-vaccines loaded with tumor antigens), T-cells (ex vivo generated lymphokine-activated killer cells; cytokine-induce killer cells; activated T-cells; gamma delta T-cells), or natural killer cells.

In some cases, specific subtypes of SQ have different levels of immune activation (e.g., innate immunity and/or adaptive immunity) such that subtypes with elevated or detectable immune activation (e.g., innate immunity and/or adaptive immunity) are selected for treatment with one or more immunotherapeutic agents described herein. In one embodiment, the classical subtype of SQ has low immune activation as compared to other SQ subtypes or lung cancer subtypes. In some cases, specific subtypes of SQ have high or elevated levels of immune activation. In some cases, the secretory subtype of SQ has elevated levels of immune activation (e.g., innate immunity and/or adaptive immunity) as compared to other SQ subtypes or lung cancer subtypes. In one embodiment, SQ subtypes with low levels of or no immune activation (e.g., innate immunity and/or adaptive immunity) are not selected for treatment with one or more immunotherapeutic agents described herein.

Detection Methods

In one embodiment, the methods and compositions provided herein allow for the detection of at least one nucleic acid in a lung cancer sample (e.g. squamous cell carcinoma lung cancer sample) obtained from a subject. The at least one nucleic acid can be a classifier biomarker provided herein. In one embodiment, the at least one nucleic acid detected using the methods and compositions provided herein are selected from Table 1. In one embodiment, the methods of detecting the nucleic acid(s) (e.g., classifier biomarkers) in the lung cancer sample obtained from the subject comprises, consists essentially of, or consists of measuring the expression level of at least one or a plurality of biomarkers using any of the methods provided herein. The biomarkers can be selected from Table 1. In some cases, the plurality of biomarker nucleic acids comprises, consists essentially of or consists of at least two biomarker nucleic acids, at least 10 biomarker nucleic acids, at least 20 biomarker nucleic acids, at least 30 biomarker nucleic acids, at least 40 biomarker nucleic acids, at least 50 biomarker nucleic acids, at least 60 biomarker nucleic acids, at least 70 biomarker nucleic acids or all 80 biomarkers nucleic acids of Table 1. The detection can be at the nucleic acid level. The detection can be by using any amplification, hybridization and/or sequencing assay disclosed herein.

In another embodiment, the methods and compositions provided herein allow for the detection of at least one nucleic acid or a plurality of nucleic acids in a lung cancer sample (e.g. squamous cell carcinoma lung cancer sample) obtained from a subject such that the at least one nucleic acid is or the plurality of nucleic acids are selected from the biomarkers listed in Table 1 and the detection of at least one biomarker from a set of biomarkers whose presence, absence and/or level of expression is indicative of immune activation. The set of biomarkers for indicating immune activation can be gene expression signatures of and/or Adaptive Immune Cells (AIC) (e.g., Table 4A) and/or Innate Immune Cells (IIC)(e.g., Table 4B), individual immune biomarkers (e.g., Table 5), interferon genes (e.g., Table 6), major histocompatibility complex, class II (MHC II) genes (e.g., Table 7) or a combination thereof. The gene expression signatures of both IIC and AIC can be any gene signatures known in the art such as, for example, the gene signature listed in Bindea et al. (Immunity 2013; 39(4); 782-795). The detection can be at the nucleic acid level. The detection can be by using any amplification, hybridization and/or sequencing assay disclosed herein.

Kits

Kits for practicing the methods of the invention can be further provided. By "kit" is intended any manufacture (e.g., a package or a container) comprising at least one reagent, e.g., an antibody, a nucleic acid probe or primer, etc., for specifically detecting the expression of a biomarker of the invention. The kit may be promoted, distributed, or sold as a unit for performing the methods of the present invention. Additionally, the kits may contain a package insert describing the kit and methods for its use.

In one embodiment, kits for practicing the methods of the invention are provided. Such kits are compatible with both manual and automated immunocytochemistry techniques (e.g., cell staining). These kits comprise at least one antibody directed to a biomarker of interest, chemicals for the detection of antibody binding to the biomarker, a counterstain, and, optionally, a bluing agent to facilitate identification of positive staining cells. Any chemicals that detect antigen-antibody binding may be used in the practice of the invention. The kits may comprise at least 2, at least 3, at least 4, at least 5, at least 6, at least 7, at least 8, at least 9, at least 10, or more antibodies for use in the methods of the invention.

EXAMPLES

The present invention is further illustrated by reference to the following Examples. However, it should be noted that these Examples, like the embodiments described above, is illustrative and is not to be construed as restricting the scope of the invention in any way.

Example 1—Immune Cell Activation Differences Among Lung Squamous Cell Carcinoma Intrinsic Subtypes and Variable Correlation with CD274 (PD-L1) Expression Introduction Gene expression based subtyping in Lung Squamous Cell Carcinoma (SQ) classifies SQ tumors into distinct subtypes with variable biologic and clinical features. Gene expression based subtyping has consistently identified 4 subtypes with Lung SQ, Primitive, Classical, Basal and Secretory (1, 2) (see FIG. 1). SQ subtypes demonstrate key differences in genomic alterations, tumor drivers, prognosis, and likely response to various therapies (1-2).

Methods

Using previously published Bindea et al. (3) immune cell gene signatures (24 in total) and SQ subtyping gene expression signatures (1-2), several publically available lung SQ datasets (1-2 and 4-5) (see FIG. 2) were examined for immune cell features in relation to SQ subtypes. This investigation of immune differences by subtype used the 24 immune cell gene signatures from Bindea et al [3] that each had a varying number of genes and were classified as adaptive or innate immunity cell signatures (see Table 4A-4B). Adaptive Immune Cell (AIC) signatures (Table 4A) included Tcells, Central Memory T cells (Tcm), Effector Memory T cells (Tem), T helper cell (Th), Type 1 T helper cells (Th1), Type 2 T helper cells (Th2), T follicular helper cells (Tfh), T helper 17 cells (Th17), T Regulatory Cells (Treg), Gamma Delta T cells (Tgd), CD8 Tcells, Cytotoxic T cells, B cells, and Innate Immune Cell (IIC) signatures (Table 4B) included Natural Killer (NK), NK CD56dim cells, NK CD56bright cells, Dendritic cells (DC), Immature Dendritic Cells (iDC), Dendritic Cells (pDC), Activated Dendritic Cells (aDC), Mast cells, Eosinophils, Macrophages, and Neutrophils. In addition to the gene expression signatures of both Innate Immune Cells (IIC) and Adaptive Immune Cells (AIC), a 13 gene IFN signature (IFN; Table 6), a 13-gene MHC class II signature score (Forero [6]; Table 7) as well as single gene immune biomarkers in Table 5 (CTLA4, PDCD1, CD274 (PD-L1), and PDCDLG2 (PD-L2)) were examined in the 4 SQ subtypes (Primitive, Classical, Secretory, Basal).

For SQ, 4 published gene expression data sets of lung squamous cell carcinoma samples having a total of 762 patients were used, including TCGA [2], Lee et al [4], Raponi et al [5], and Wilkerson et al [1]. For TCGA, upper quantile normalized RSEM data was downloaded from Firehose and log 2 transformed. Normalized Affy array data was downloaded from GEO for Lee et al [4] (GSE8894) and Raponi et al [5] (GSE4573), and normalized Agilent array data was downloaded from GEO for Wilkerson et al [1] (GSE17710).

To determine the squamous cell carcinoma subtype (basal, classical, primitive, secretory), the published 208-gene nearest centroid classifier as described previously in Wilkerson et al [1] was used. After median centering of genes in the signature, each sample was assigned the subtype corresponding to the centroid with which it was maximally correlated. (Pearson)

Figure 3:
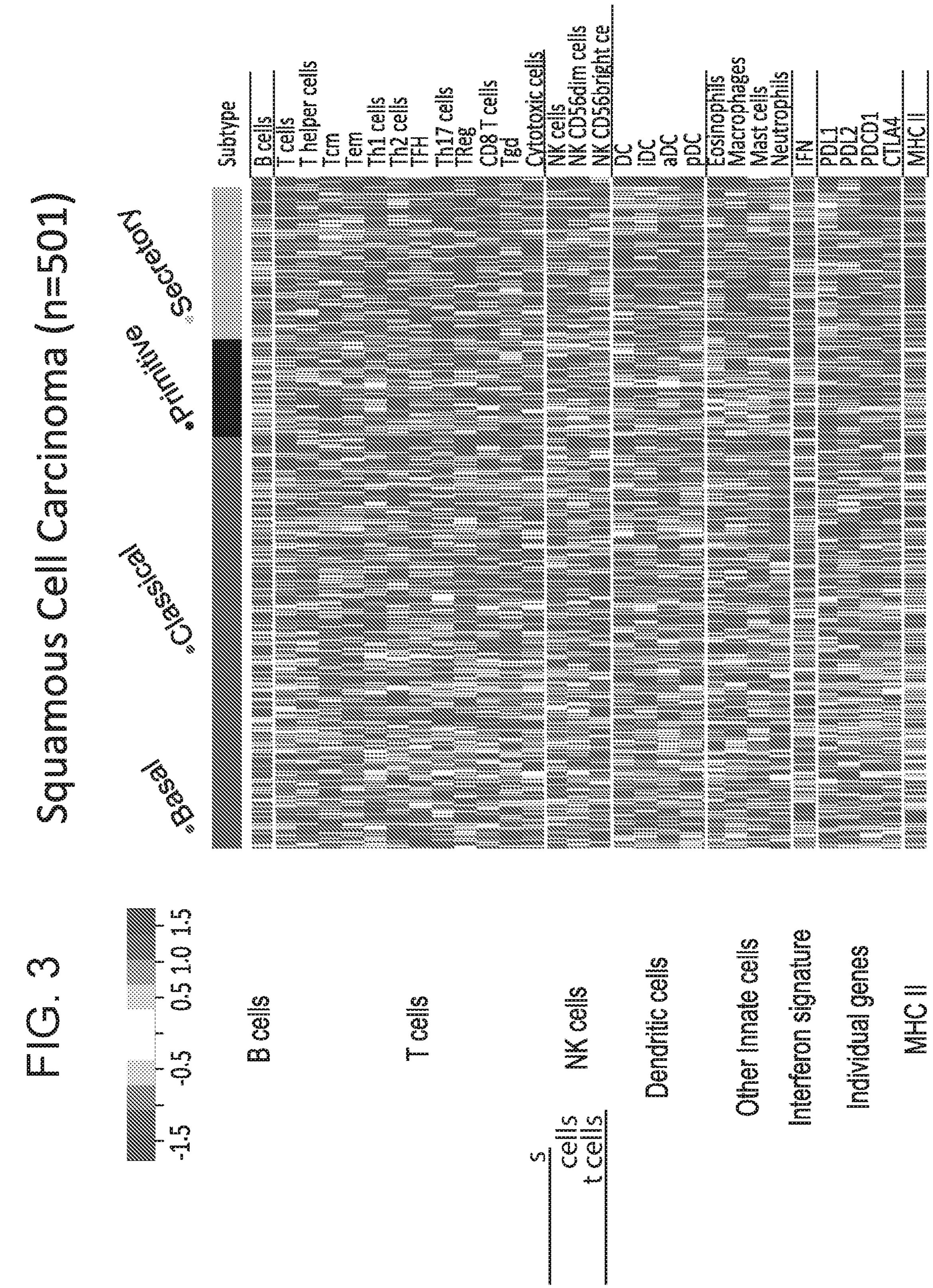
FIG. 3 illustrates a heatmap of immune cell signatures expression (i.e., Bindea et al reference from Example 1), other immune markers and individual immune markers in the Cancer Genome Atlas (TCGA) Lung SQ dataset.
Figure 4:
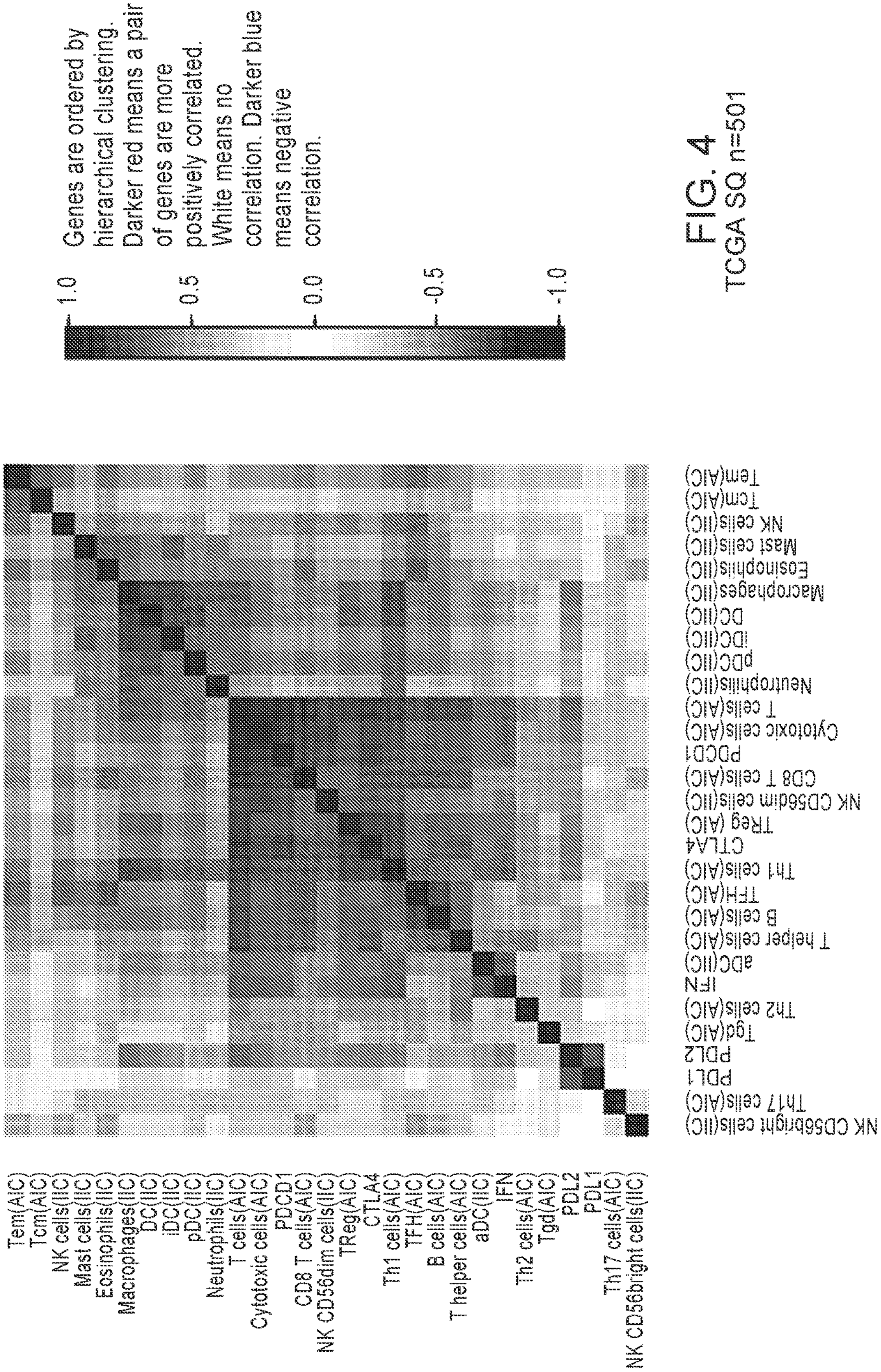
FIG. 4 illustrates correlation matrices of immune cell signatures in the TCGA SQ dataset where signatures were arranged by hierarchical clustering. White means no correlation.

Using the TCGA data for squamous cell carcinoma, the correlations were assessed among the 30 markers by plotting matrices of pairwise Spearman rank correlation coefficients where markers were ordered by hierarchical clustering (see FIG. 4). To investigate overall immunity marker trends by subtype, the expression heatmaps were plotted where samples were arranged by subtype and markers were grouped according to ordering in Bindea et al [3] (see FIG. 3). To evaluate the reproducibility of immunity marker differences among the subtypes, normalized T cell signatures were plotted by subtype for each data set (see FIG. 5).

Immune cell signature associations with tumor subtype and with CD274 expression were evaluated using linear regression. More specifically, to assess the prediction strength of subtype as a predictor of immune markers relative to that of PD-L1, a linear regression model of each signature with subtype the sole predictor, and again with PD-L1 the sole predictor, was fitted in the TCGA dataset. PD-L1 expression was treated as a low/medium/high categorical variable with equal proportions in each group. Scatter plots of adjusted R-squared when subtype was the predictor against adjusted R-squared when PD-L1 was the predictor were inspected for overall trends (see FIG. 6).

Using non-silent mutation burden per Mb data, available in the supplementary information from TCGA squamous cell carcinoma (Lawrence 2013), mutation burden-Tcell expression associations was investigated using the Kruskal Wallis test and the Spearman correlation coefficients, respectively. For TCGA squamous cell carcinoma, NFE2L2-subtype association was evaluated using the Kruskal Wallis test. To test whether NFE2L2 in SQ showed evidence of association after adjusting for subtype, a linear model for Tcell expression was fit with NFE2L2 expression in SQ as sole predictors and again following adjustment for subtype.

Subtype and immune signature associations with a 13-gene MHC class II signature [Forero [6]; Table 7, calculated as an average of all genes in the list (Table 7), were investigated using the Kruskal-Wallis test. For immune signature-MHC class II associations, Spearman correlation coefficients were calculated.

Hierarchical clustering of immune signatures and pairwise signature correlations were also analyzed. Survival signature associations of Stages I-III samples were evaluated with stratified cox proportional hazard models allowing for different baseline hazards in each dataset. More specifically, immune marker-survival associations in the TCGA data sets were tested, overall and separately within each subtype, using Cox proportional hazards models. Immune markers were centered and scaled to have mean 0 and variance 1, and stage IV patients were excluded. Evaluations within a specific subtype adjusted for stage, and overall evaluations adjusted for both stage and subtype. Forest plots showing hazard ratios and confidence intervals for each signature were made (see FIGS. 7A and 7B). All statistical analyses were conducted using R 3.2.0 software (http://www.R-project.org).

Results

Heatmap analysis and unsupervised hierarchical clustering of immune cell gene signatures provided separation of intrinsic subtypes of SQ (see FIGS. 3 and 4). Examination of Immune cell gene signatures (both AIC and IIC) as well as individual immune gene markers revealed clear differences among the SQ subtypes (see FIG. 3).

Figure 21:
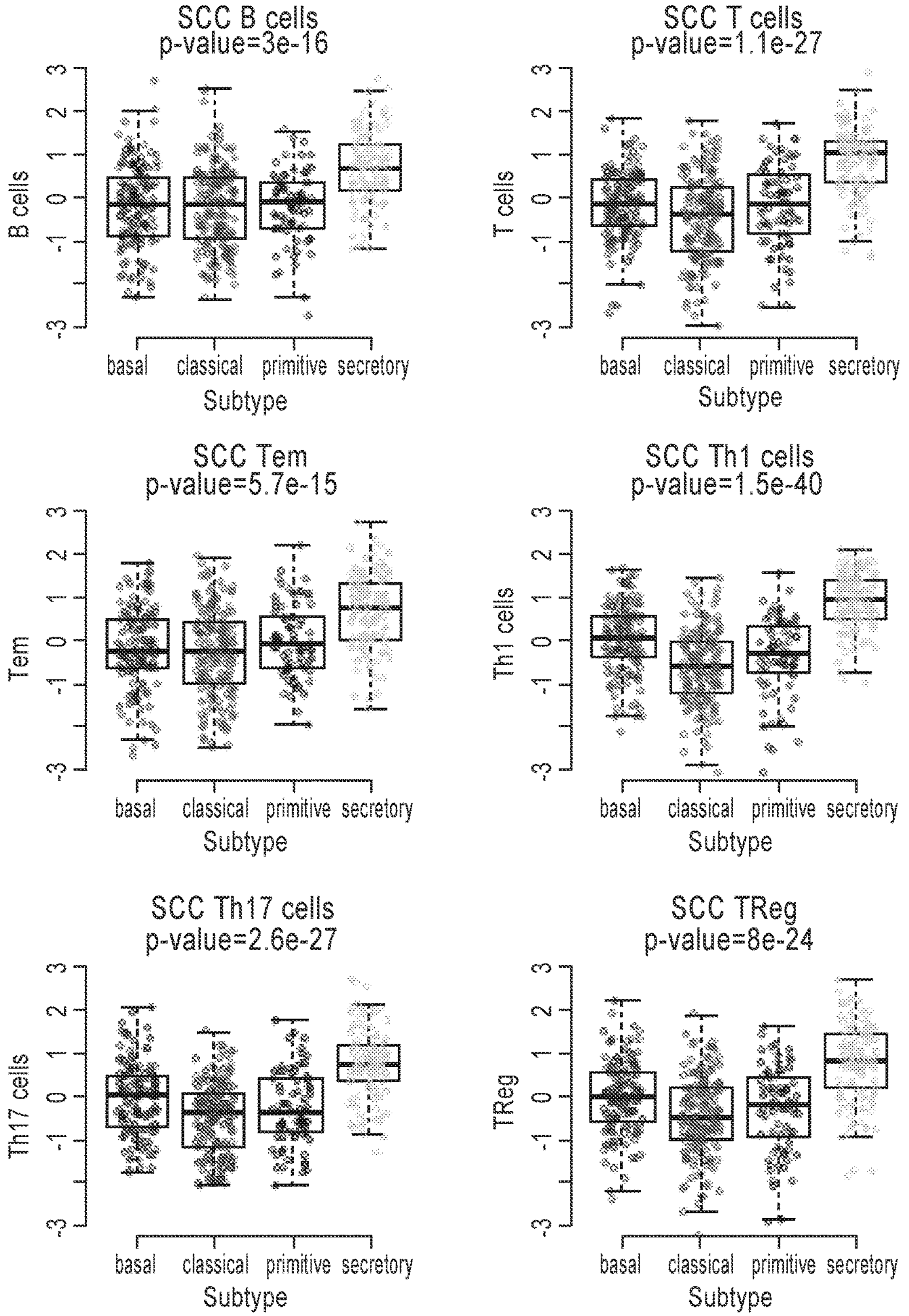
FIG. 21 illustrates box plots of all the immune cells and immunomarkers (i.e., IFN genes, MHCII genes and individual immunomarkers PDL1, PDL2, PDCD1 and CTLA4) by SQ subtype. SCC=squamous cell carcinoma.
Figure 21:
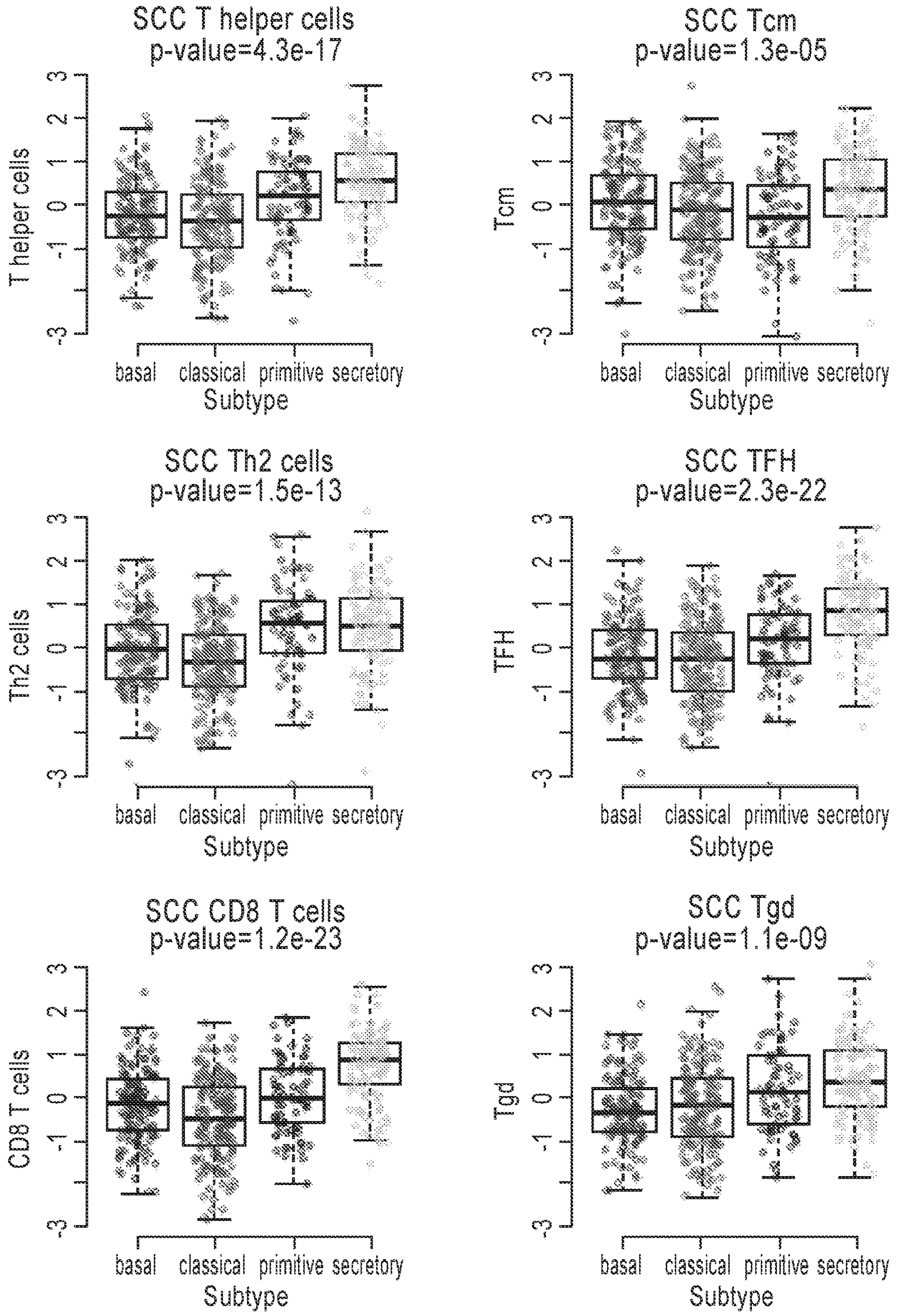
Figure 21:
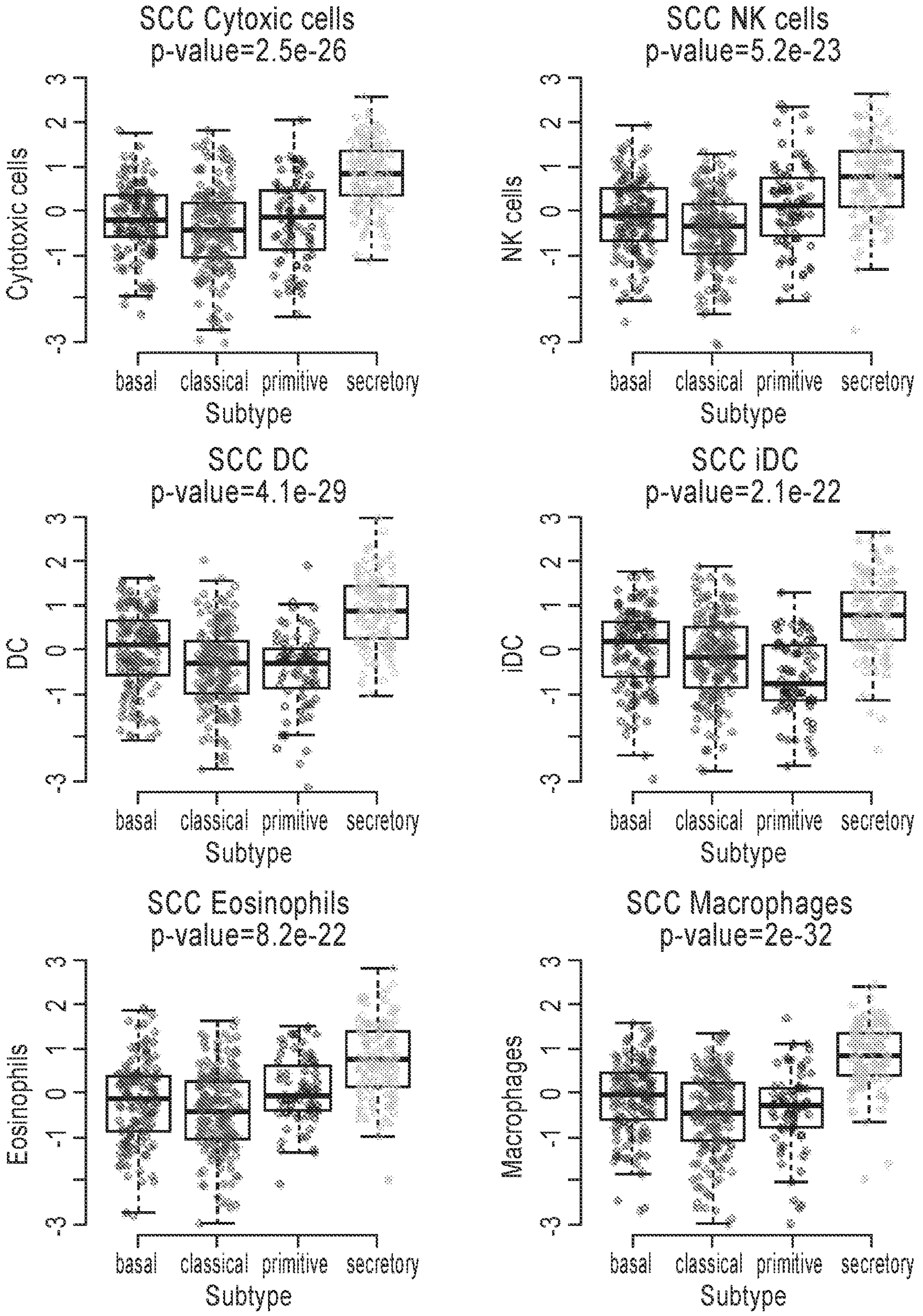
Figure 21:
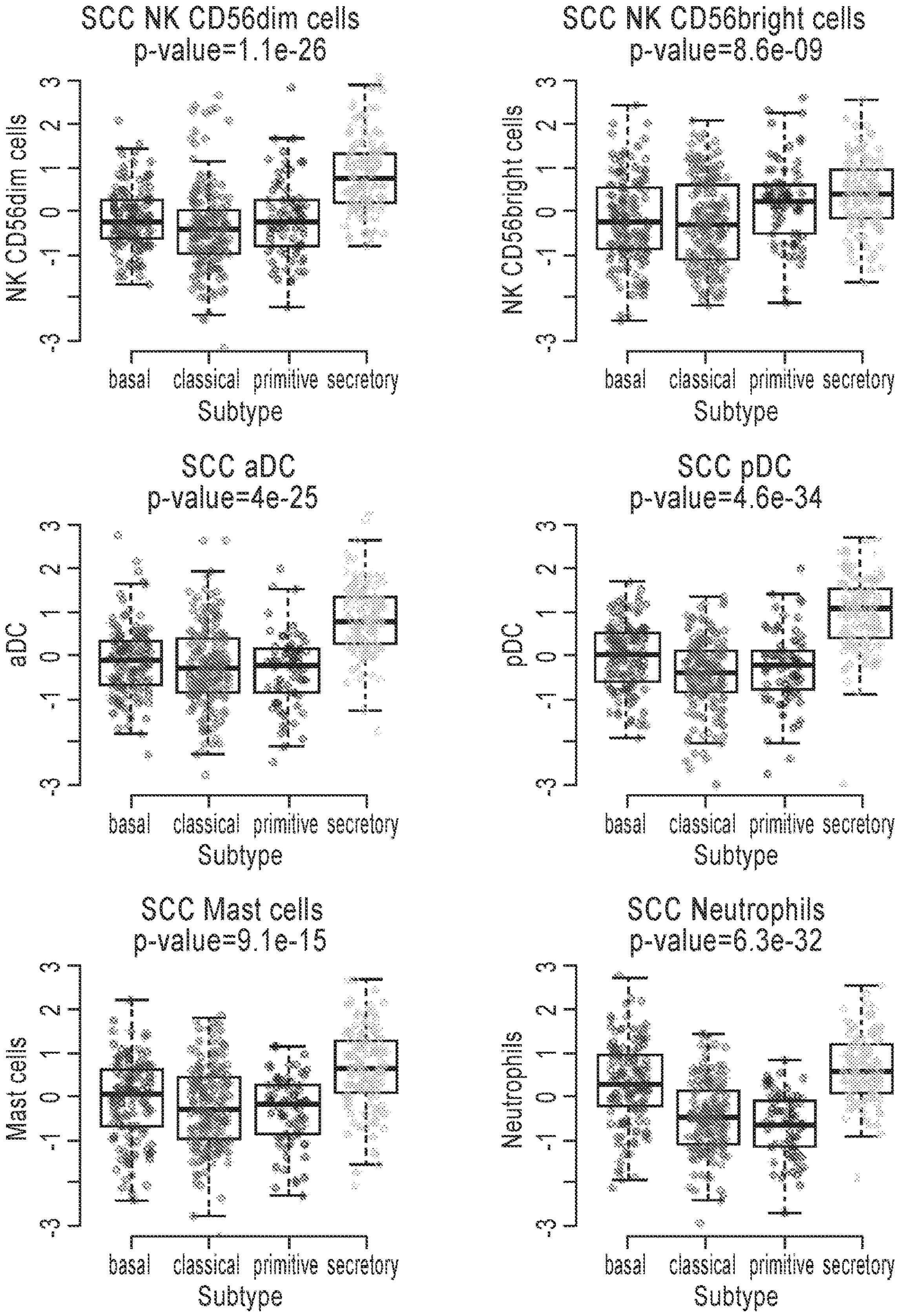
Figure 21:
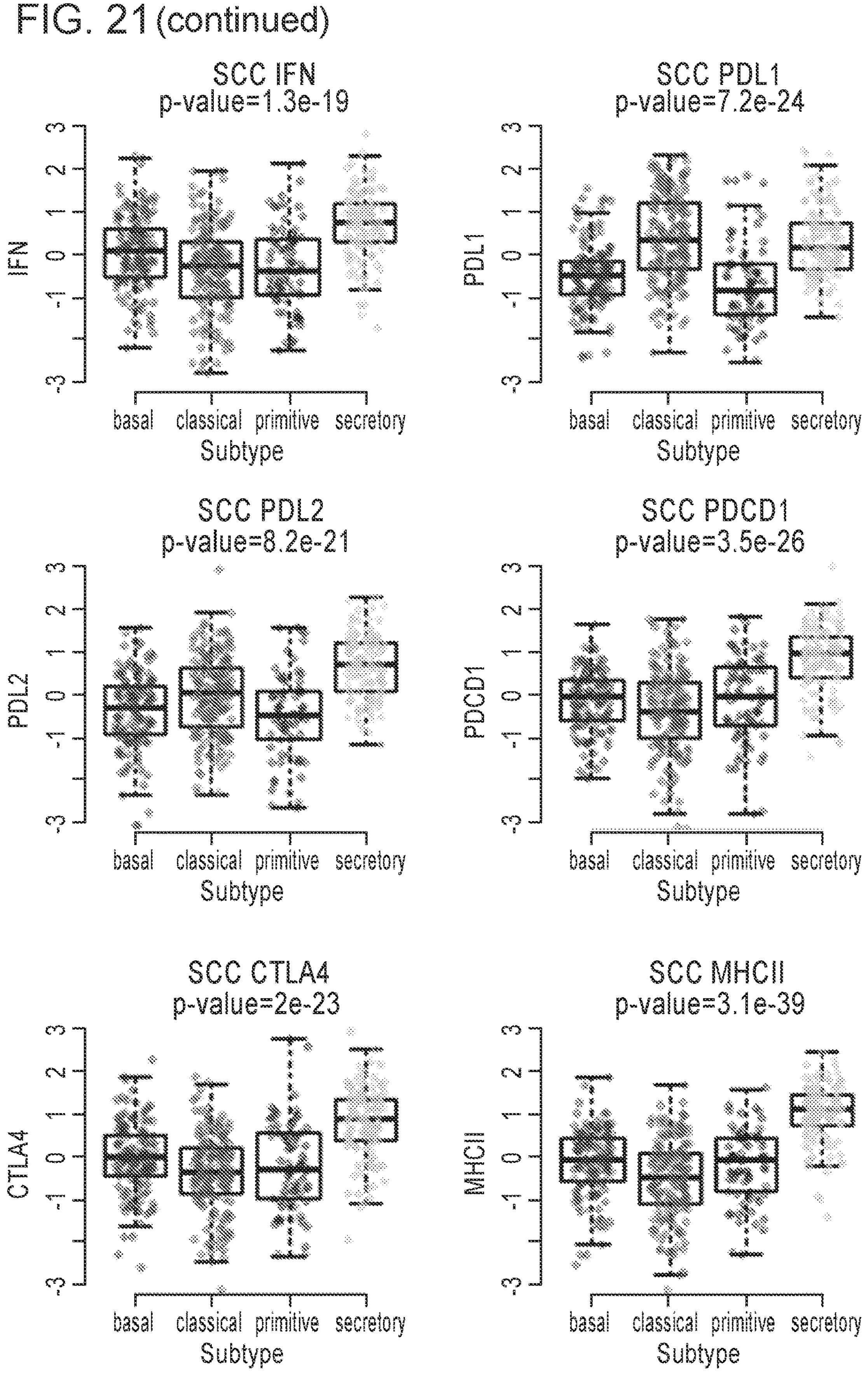

Among the SQ subtypes, the secretory subtype showed consistently higher immune cell expression of both innate and adaptive immune cells with one exception, the Th2 signature, where both primitive and secretory had comparable expression (FIG. 21). The classical subtype demonstrated the lowest immune cell expression of all the SQ subtypes. Unlike the case for AD subtypes, CD274 (PD-L1) expression did not correlate with other immune cell expression in SQ subtypes. This is especially obvious in the classical subtype where CD274 (PD-L1) expression was high despite relatively low expression of other immune cells (see FIG. 3 and FIG. 21). Overall, immune activation was most prominent in the secretory subtype of SQ demonstrating activation of both innate as well as adaptive immune cells. In contrast, the classical subtype of SQ demonstrated lower immune activation.

Using hierarchical clustering, correlation matrices revealed clustering of adaptive immune cells and innate immune cells (see FIG. 4). In SQ, adaptive immune features such as T cells, cytotoxic cells, CD8 cells, Th1 cells, PDCD1, CTLA4, and Tregs had high pairwise correlations and similarly for innate immune cells, including iDC, DC, macrophages, neutrophils, mast cells, and eosinophils are correlated (FIG. 4). Further, in SQ, NK CD56dim cells (cytolytic activity) were more strongly correlated with adaptive immune cells than with innate immune cells (see FIG. 4). In addition, TFH and B cells were more highly correlated with adaptive immune features in SQ (see FIG. 4).

Figure 6:
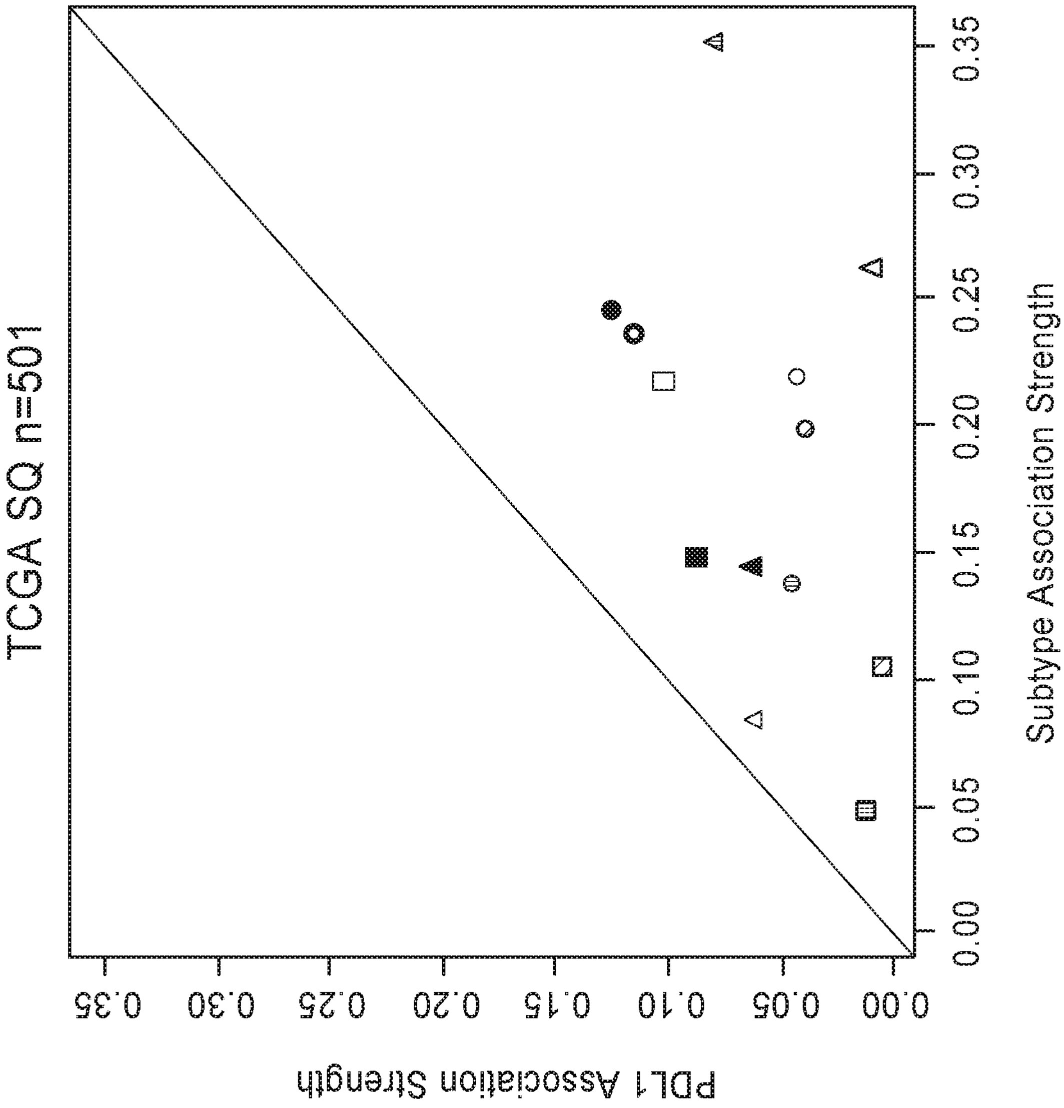
FIG. 6 illustrates association (adjusted R-squared) between CD274 (PD-L1) expression and adaptive immune cell (AIC) signatures in Squamous cell carcinoma (SCC or SQ) evaluation of the TCGA dataset. Association was consistently greater for subtypes than for PD-L1. In SQ, association was consistently greater for subtypes than for PD-LI as described in Example 1. Tcm=central memory T cells, Tem=Effector Memory T cells, Th1=Type 1 T helper cells, Th2=Type 2 T helper cells, TFH=T follicular helper cells, Th17=T helper 17 cells, Treg=Tregulatory cells, Tgd=Gamma Delta Tcells.

Strength of association of CD274 (PD-L1) expression with adaptive immune cell signatures, as compared to SQ subtype was conducted. As shown in FIG. 6, in SQ tumors, subtype was a better predictor of immune cell expression than CD274 (PD-L1) expression for all adaptive immune cells examined (median F-test p-value and adjusted R-squared were 2.16e-24 and 0.20 for subtype versus 1.86e-09 and 0.07 for CD274).

Figure 5:
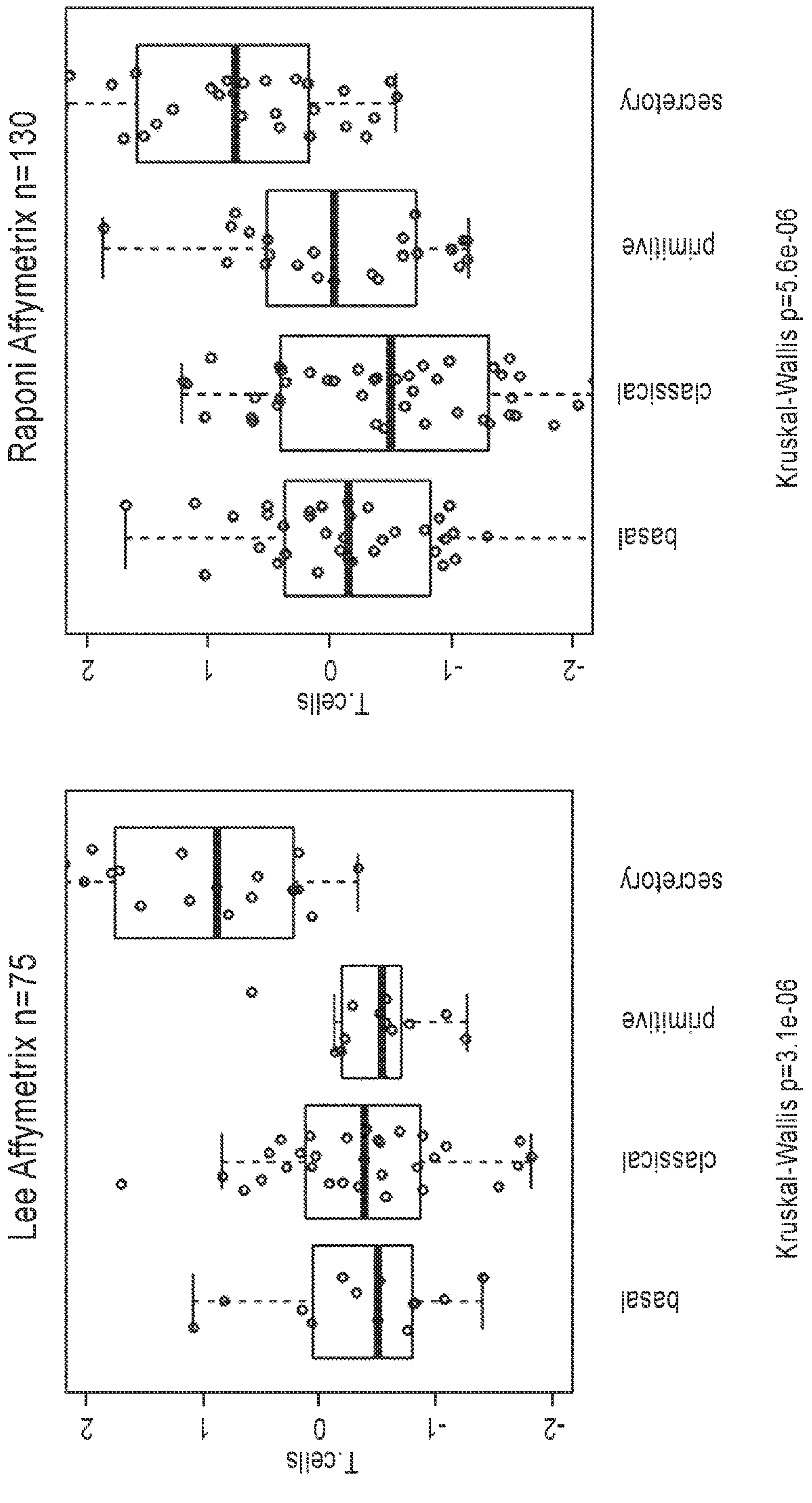
FIG. 5 illustrates reproducibility of T cell signature gene expression subtype patterns across multiple SQ datasets as described in Example 1. RNAseq (Illumina, San Diego, Calif.) and microarrays from both Affymetrix (Santa Clara, Calif.) and Agilent (Santa Clara, Calif.).

Immune cell signatures were primarily evaluated in the TCGA datasets, however SQ subtype immune differences, as measured by the immune cell signatures, were found to be very reproducible across multiple datasets (see FIG. 5). T cell immune cell signature expression subtype differences in SQ subtypes were remarkably reproducible across a variety of gene expression datasets derived from both frozen and FFPE samples and involving a variety of gene expression platforms including RNAseq (Illumina, San Diego, Calif.) and microarrays from both Affymetrix (Santa Clara, Calif.) and Agilent (Santa Clara, Calif.). Overall, immune cell signature gene expression patterns were consistent across multiple SQ (see FIG. 5) datasets.

Figure 22:
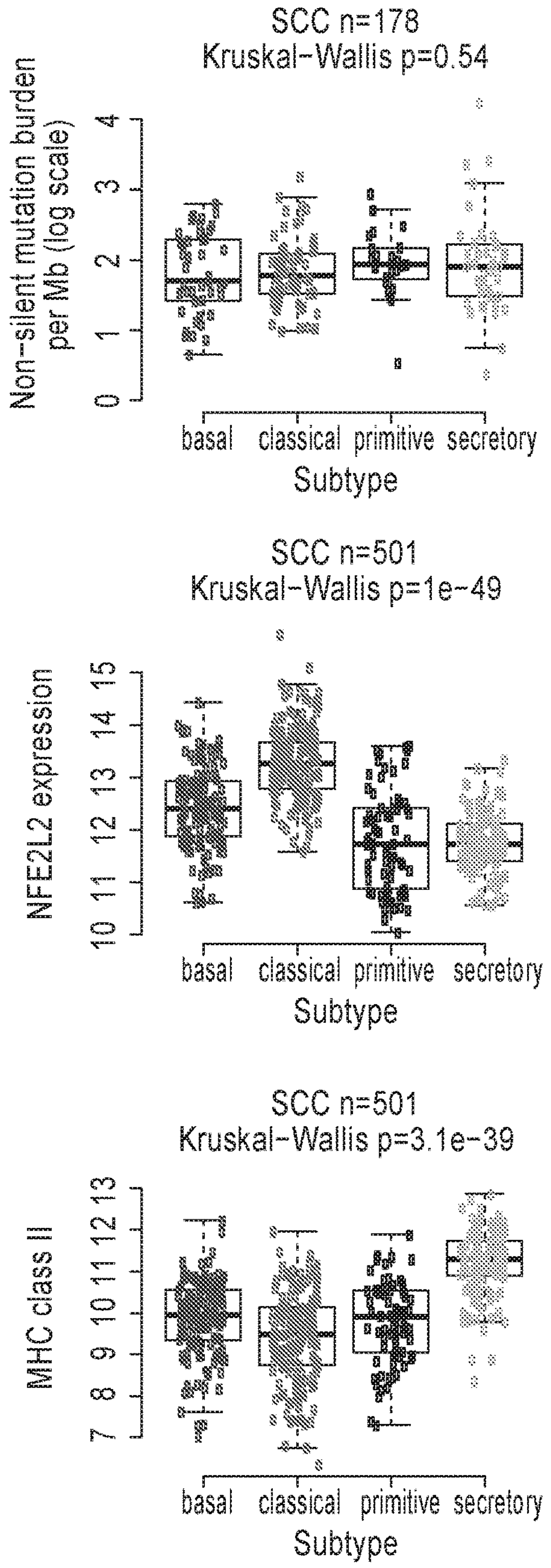
FIG. 22 illustrates Squamous cell carcinoma (SQ) subtype non-silent mutation burden, NFE2L2 expression in SQ, and MHC class II signature, with Kruskal-Wallis association test p-values. MHC II=Major Histocompatibility Class II gene signature.

In SQ, non-silent mutation burden was not significantly different across subtypes (see FIG. 22). Mutation burden was not strongly correlated with Tcell immune cell expression in SQ datasets (Spearman correlation=−0.08 in SQ).

Several other genomic features such as KEAP/NFE2L2 alterations in SQ (Hast [7]) have been suggested as possible contributors to reduced immune response in NSCLC. KEAP/NFE2L2 alterations, impacting the oxidative stress pathway, were enriched in the SQ classical subtype (FIG. 22). Alterations in the cyclooxygenase 2 (COX2) pathway as measured by increased NFE2L2 expression in SQ were associated with lower immune cell expression, however after adjustment for subtype using linear regression, NFE2L2 were significant predictors (NFE2L2 expression in SQ p=1.2E-07 to p=0.47 following adjustment for subtype).

The association of immune cell expression in SQ lung cancer with MHC class II genes was investigated using a published 13 gene MHC class II signature (Forero [6]). MHC class II gene expression was strongly correlated with several immune cells in SQ including Tcell expression (Spearman correlation=0.86 in SQ). Bcell expression (Spearman correlation=0.69 in SQ) and DC expression (Spearman correlation=0.76 in SQ). MHC class II gene expression was significantly higher in tumor adjacent normal lung tissue as compared with tumor and was differentially expressed across tumor subtypes (FIG. 22) In a linear model of the MHC class II signature as a predictor of Tcell immune cell expression, MHC class II remained significant following adjustment for SQ subtype (p<1E-50 for MHC II).

Figure 7A:
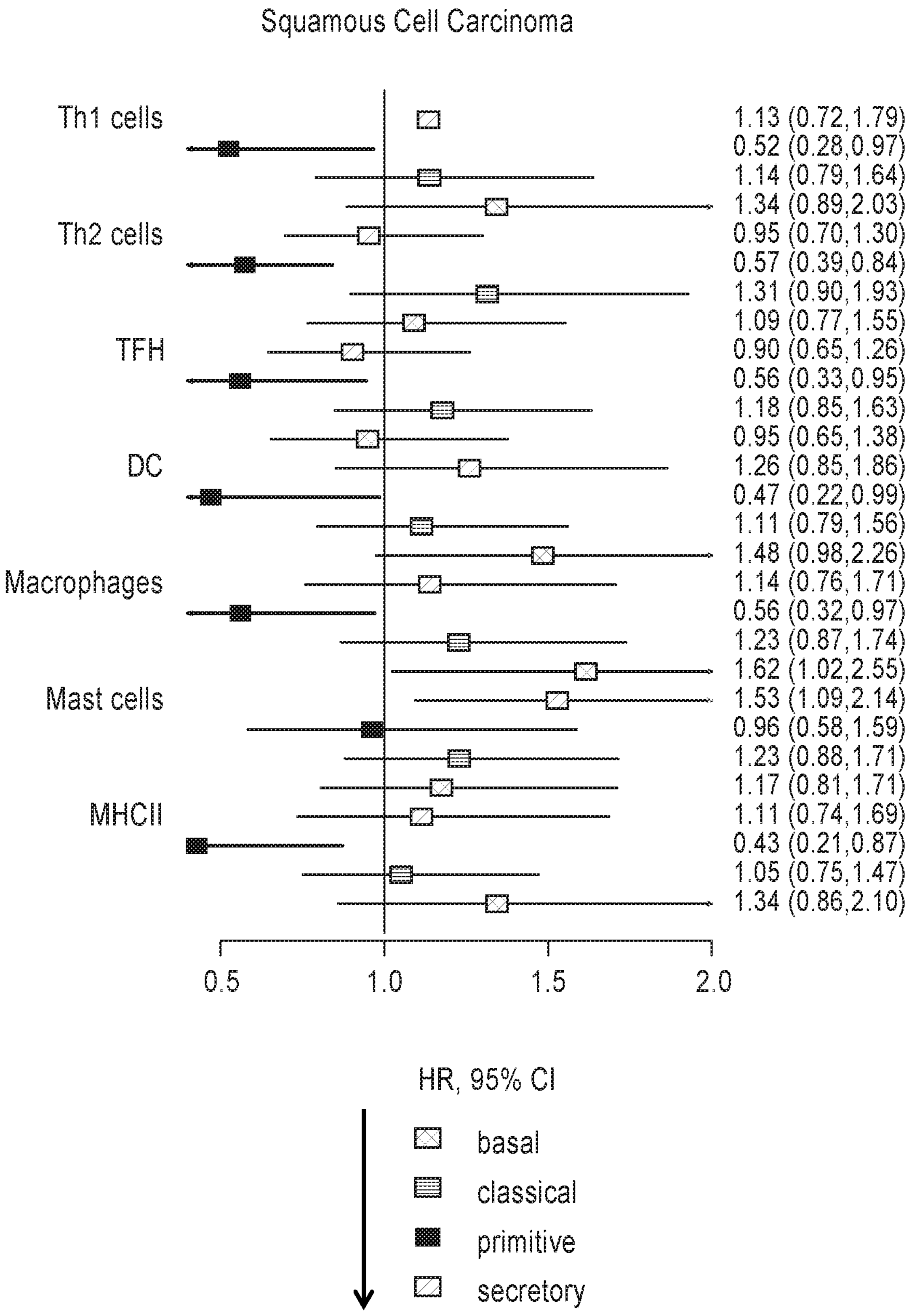
FIGS. 7A-7B illustrate signature-survival associations overall and by subtype as described in Example 1. Hazard Ratios (HR) and confidence intervals calculated from stratified cox models correspond to a unit increase in the normalized immune marker and were adjusted for pathological stage. Subtype specific HR's were adjusted for stage (overall adjusted by stage and subtype) and only immune features with significant associations (nominal $p<0.05$) for at least one subtype are shown. SQ=Squamous Cell Carcinoma, MHC II=Major Histocompatibility Class II gene signature, Th1=Type 1 T helper cells, Th2=Type 2 T helper cells, TFH=T follicular helper cells, Th17=T helper 17 cells, Treg=Tregulatory cells, DC=Dendritic cells, iDC=Immature Dendritic Cells.
Figure 7B:
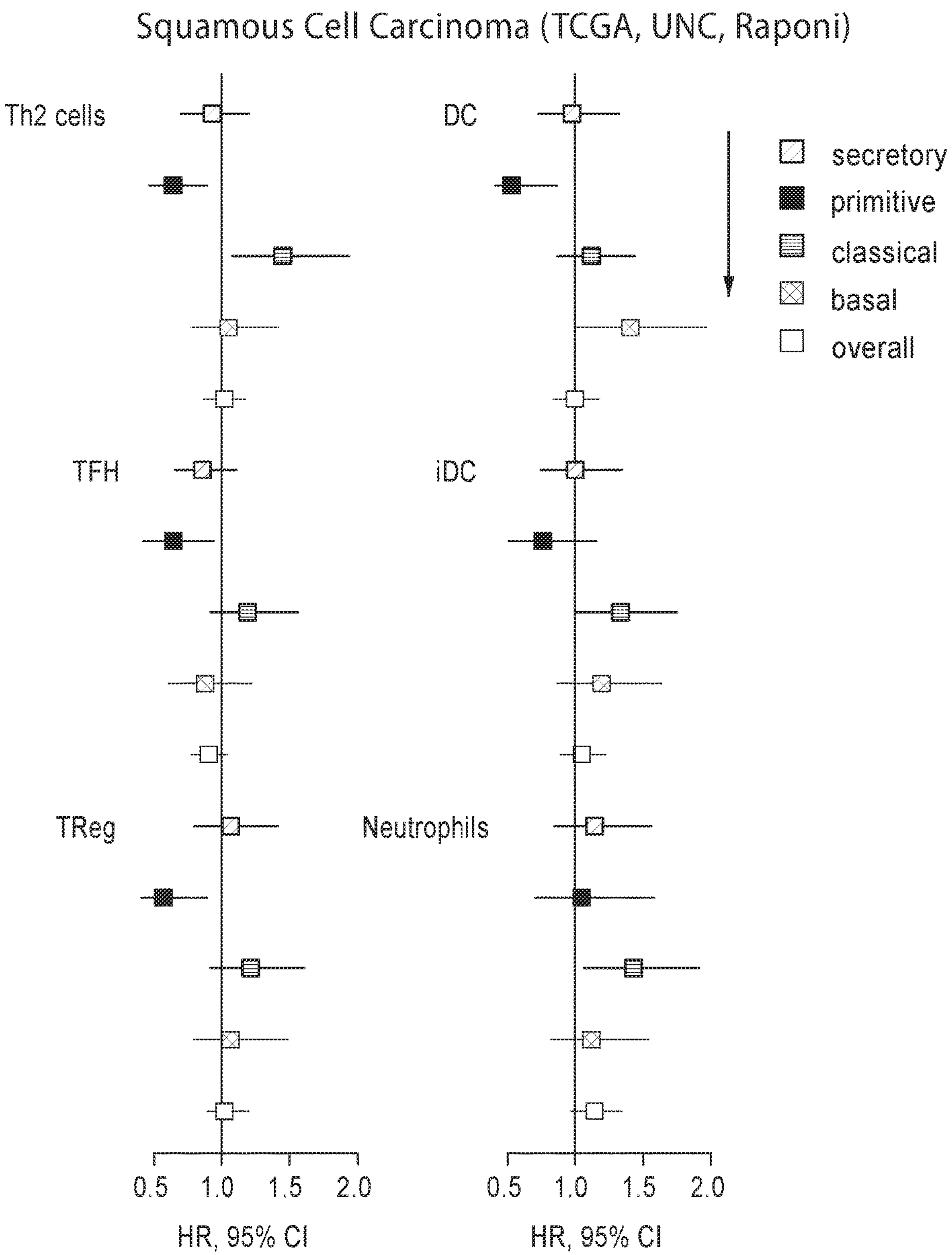

Using cox proportional hazard models, subtype specific hazard ratios (HRs) for one unit of increased expression were calculated. Subtype specific HRs were adjusted for pathologic stage and confidence intervals (CI) were calculated. Hazard ratios and confidence intervals for markers that were significant (nominal p-value<0.05) for at least one subtype are shown in FIGS. 7A-7B. The HR and CI for cell signatures or genes showing significant survival associations for one or more of the subtypes are shown in FIGS. 7A-7B. Among the SQ subtypes, a unit increase in expression of Th1, Th2, TFH, DC, macrophages, mast cells, and MHC class II was significantly associated with improved survival in the primitive subtype (FIGS. 7A-7B). Curiously, the secretory subtype did not show significant association with survival possibly due to the uniformly high expression of immune cells in the secretory subtype preventing demonstration of an incremental survival benefit per unit increase. In SQ, only the primitive subtype demonstrated significant immune cell expression associations with improved survival (p<0.01) (see FIG. 7A-7B).

Conclusion

Lung SQ gene expression subtypes vary in their immune landscape. Intrinsic biologic subtypes of SQ reveal key differences in immune cell activation, which were not always correlated with CD274 expression and demonstrated variable association with survival. SQ Classical subtype showed minimal immune infiltration (depressed immune cell expression) suggesting reduced response to immunoRX, while the secretory subtype showed elevated immune expression among the SQ tumor subtypes. In SQ, subtype appeared to be a better predictor of immune infiltration than CD274 (PD-LI). CD274 expression was not associated with AIC expression nor with improved survival in SQ. The SQ primitive subtype showed immune feature expression associated with improved survival. Further, non-silent mutation burden was not correlated with immune cell expression across subtypes; however, MHC class II gene expression was highly correlated. Increased immune and MHC II gene expression was associated with improved survival in the primitive subtype of SQ.

Incorporation by Reference

The following references are incorporated by reference in their entireties for all purposes.

1.) Wilkerson M D, et al. Clin Cancer Res 2010; 16(19): 4864-75. PMID 20643781

2.) TCGA Lung SQCC. Nature 2012; 489(7417): 519-525. PMID 22960745

3.) Bindea et al., Immunity 2013; 39(4): 782-95. PMID 24138885

4.) Lee E S, et al. Cancer Res 2008; 14(22): 7397-7404. PMID 19010856

5.) Raponi M, et al. Cancer Res 2006; 66(7): 466-72. PMID 16885343

6.) Forero A, Li Y, Dongquan C, et al. Expression of the MHC class II pathway in triple negative breast cancer tumor cells is associated with a good prognosis and infiltrating lymphocytes. Cancer Immunol Res 2016; 4(5): 390-399.

7.) Hast B E, Cloer E W, Goldfarb D, et al. Cancer-derived mutations in KEAP1 impair NRF2 degradation but not ubiquitination. Cancer Res 2014; 74(3): 808-817.

Example 2 Development and Validation of the Lune Squamous Cell Carcinoma Subtyping Signature Objective Lung squamous cell carcinoma (SQ) subtyping has been primarily restricted to a research protocol involving the extraction of RNA from Fresh Frozen lung tumors, followed by application of a nearest centroid predictor using quantitative gene expression of over 200 genes. Despite evidence of prognostic and predictive benefits from squamous cell carcinoma subtyping, the need for Fresh Frozen tissue, the requirement for gene expression of >200 genes in combination with complex bioinformatic analyses, has hindered the application of SQ subtyping in drug development and/or the clinic. The goal of this study was to develop a robust and efficient gene signature (with fewer genes needed) for differentiating the four subtypes of squamous cell carcinoma (i.e., basal, classical, secretory or primitive subtypes). The new efficient gene signature may serve to reliably subtype SQ from fresh frozen or FFPE tumor samples, making it amenable for diagnostic applications and/or drug development using any of the available quantitative RNA platforms (qRT-PCR, RNAseq, Affymetrix or Agilent Arrays). Development of the 80 gene signature for differentiating the subtypes of squamous cell carcinoma was performed as described in the methods herein.

Methods

Figure 8:
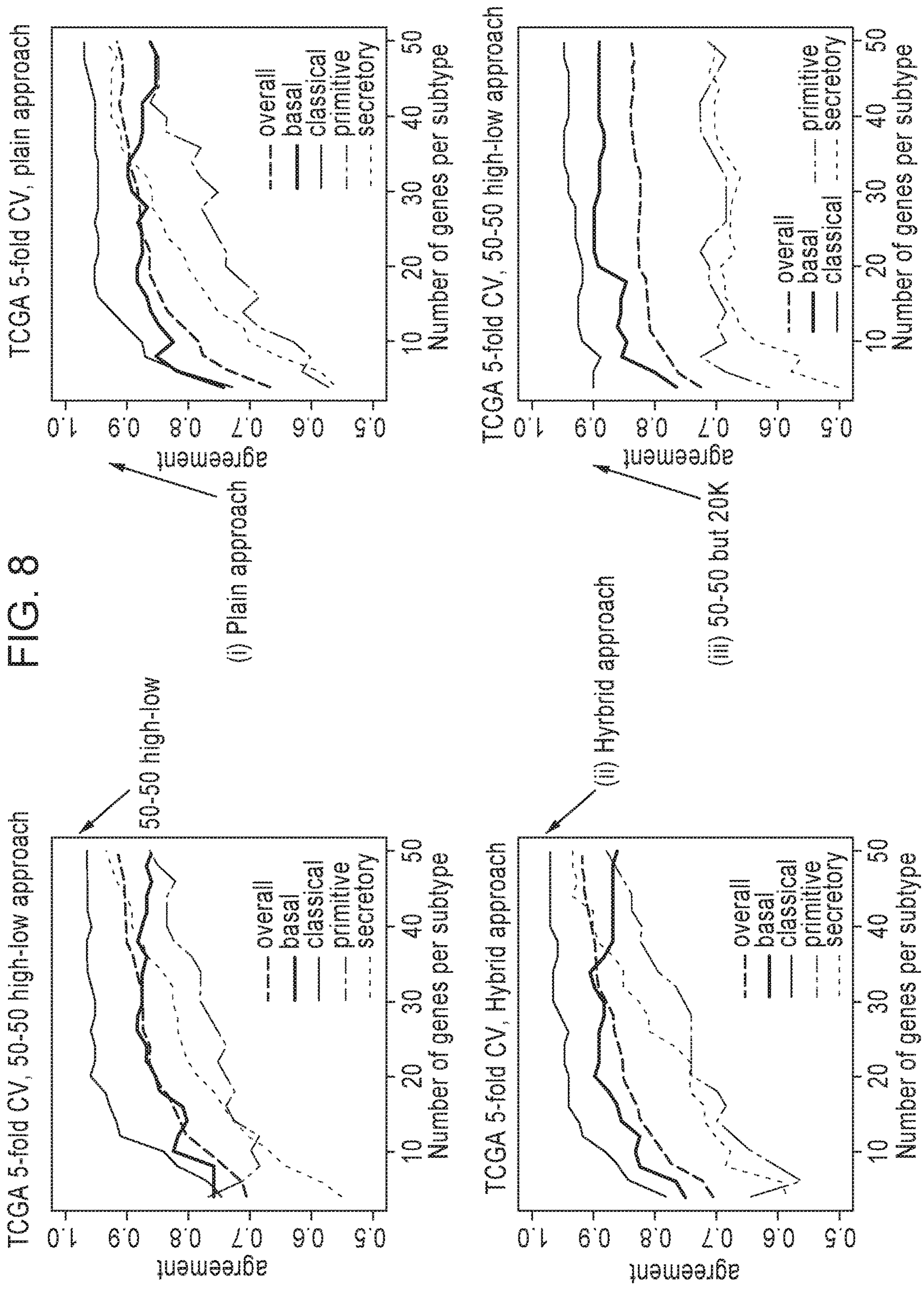
FIG. 8 illustrates a comparison of approaches (i.e., 50-50 high/low approach on TCGA RNASeq lung SQ dataset; plain approach; hybrid approach; 50-50 high/low approach on transcriptome (50-50 high/low 20K approach)) for selecting genes for inclusion in a gene set for subtyping lung SQ as described in Example 2. A five-fold cross validation study was performed on performed on the Cancer Genome Atlas (TCGA) on a RNASeq lung squamous cell carcinoma (SQ) dataset except for the 50-50 high/low 20K approach

Employing a Classifying arrays to Nearest Centroid (CLaNC) [1] algorithm, a number of approaches were tested to determine an optimal number of genes to include in a SQ subtyping gene signature. In one approach (plain approach in FIG. 8), the CLaNC was applied to the TCGA lung SQ RNAseq gene expression dataset (n=501) without modification. In a second approach (50-50 high low in FIGS. 8 and 9), the CLaNC was used on the TCGA lung SQ RNAseq gene expression dataset (n=501) with modification to select an equal number of negatively and positively correlated genes for each SQ subtype. In a third approach (50-50 but 20 k in FIG. 8), the CLaNC was used on the transcriptome dataset (n=20,000) with modification to select an equal number of negatively and positively correlated genes for each SQ subtype. In a final approach (hybrid approach in FIG. 8), the CLaNC was used on the TCGA lung SQ RNAseq gene expression dataset (n=501) with modification to select an equal number of negatively and positively correlated genes for the basal and secretory SQ subtypes, a number of negatively correlated gene for the primitive SQ subtype and a number of positively correlated genes for the classical SQ subtype. Examination of the optimal number of genes to include in the SQ signature was chosen based on evaluation of 5-fold cross validation curves for each approach described above (see FIG. 8). Ultimately, the 50-50 high low approach was selected as the approach for determining an optimal number of genes to include in the SQ subtyping gene signature. This approach showed that examination of the expression patterns of 20 genes per subtype or 80 total genes could be used to accurately subtype a SQ sample.

Figure 10:
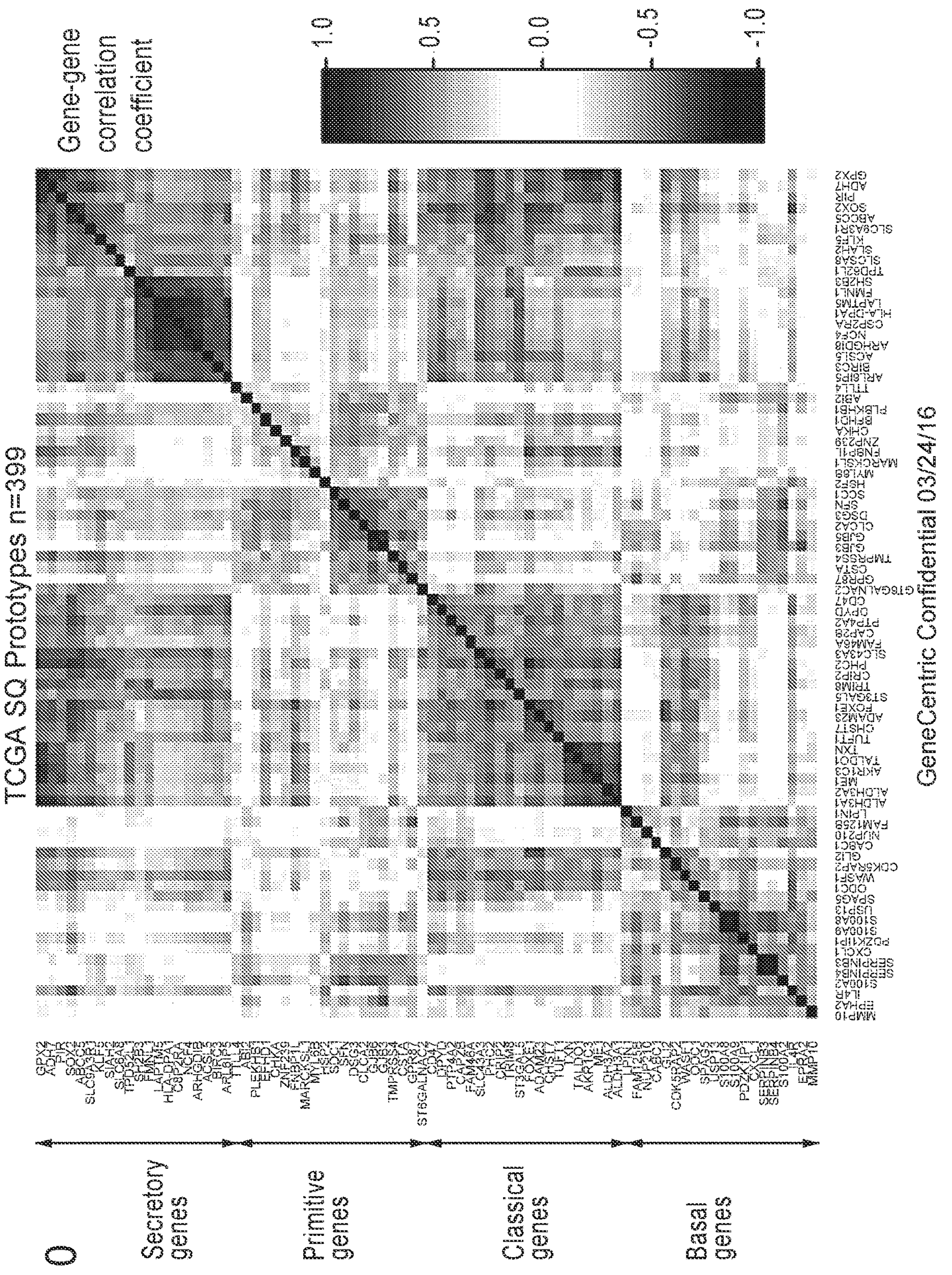
FIG. 10 illustrates gene-gene correlation coefficients and squamous cell carcinoma subtypes.
Figure 11:
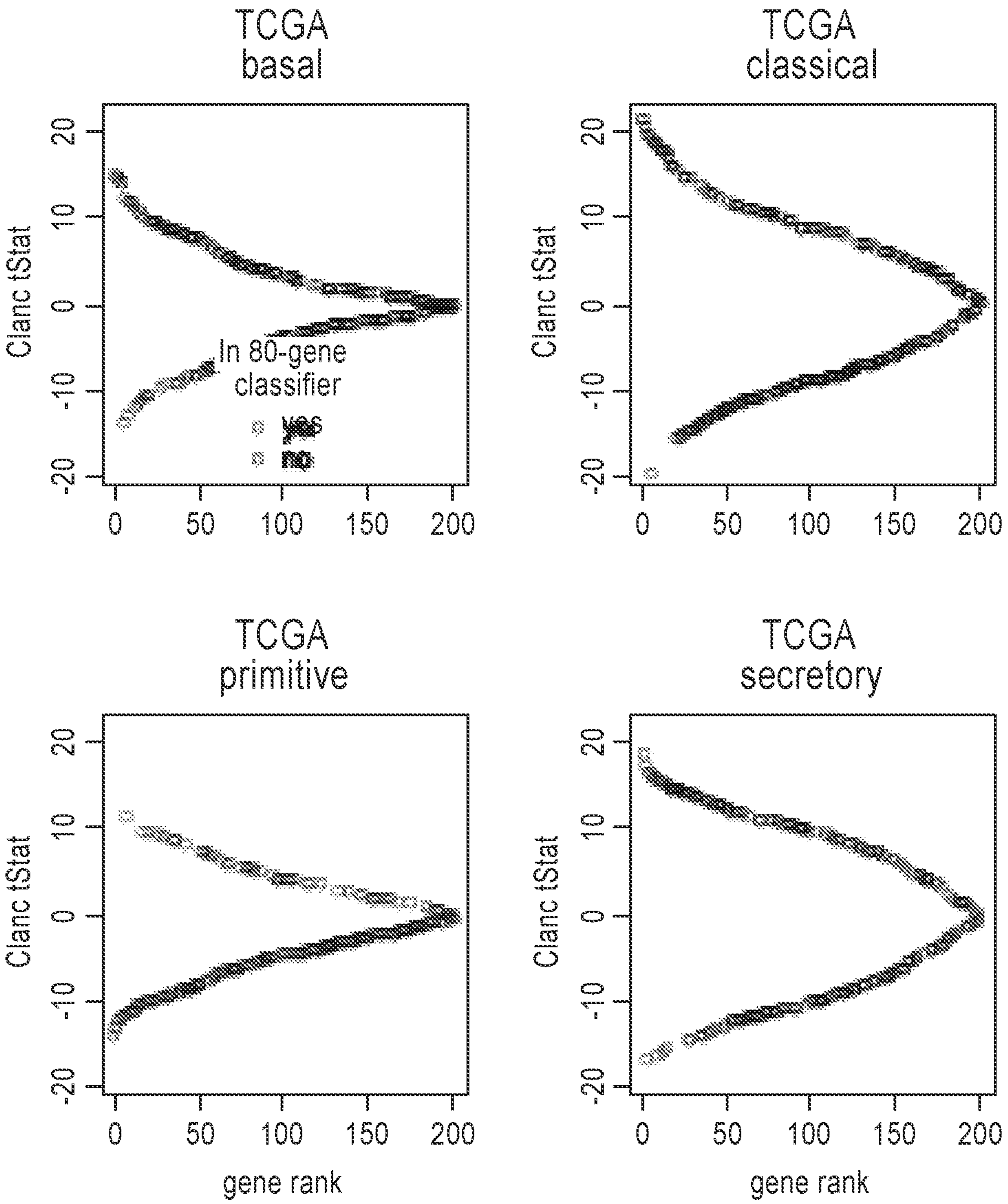
FIG. 11 illustrates the gene rank (X-axis) and t-statistic (Y-axis) of genes from the 208 gene gold standard SQ classifier that were selected by application of a Classifying arrays to Nearest Centroid (CLaNC) algorithm with modification to the lung RNASeq SQ dataset (n=506) from the Cancer Genome Atlas (TCGA) for inclusion in the SQ gene classifier set from Table 1.
Figure 12:
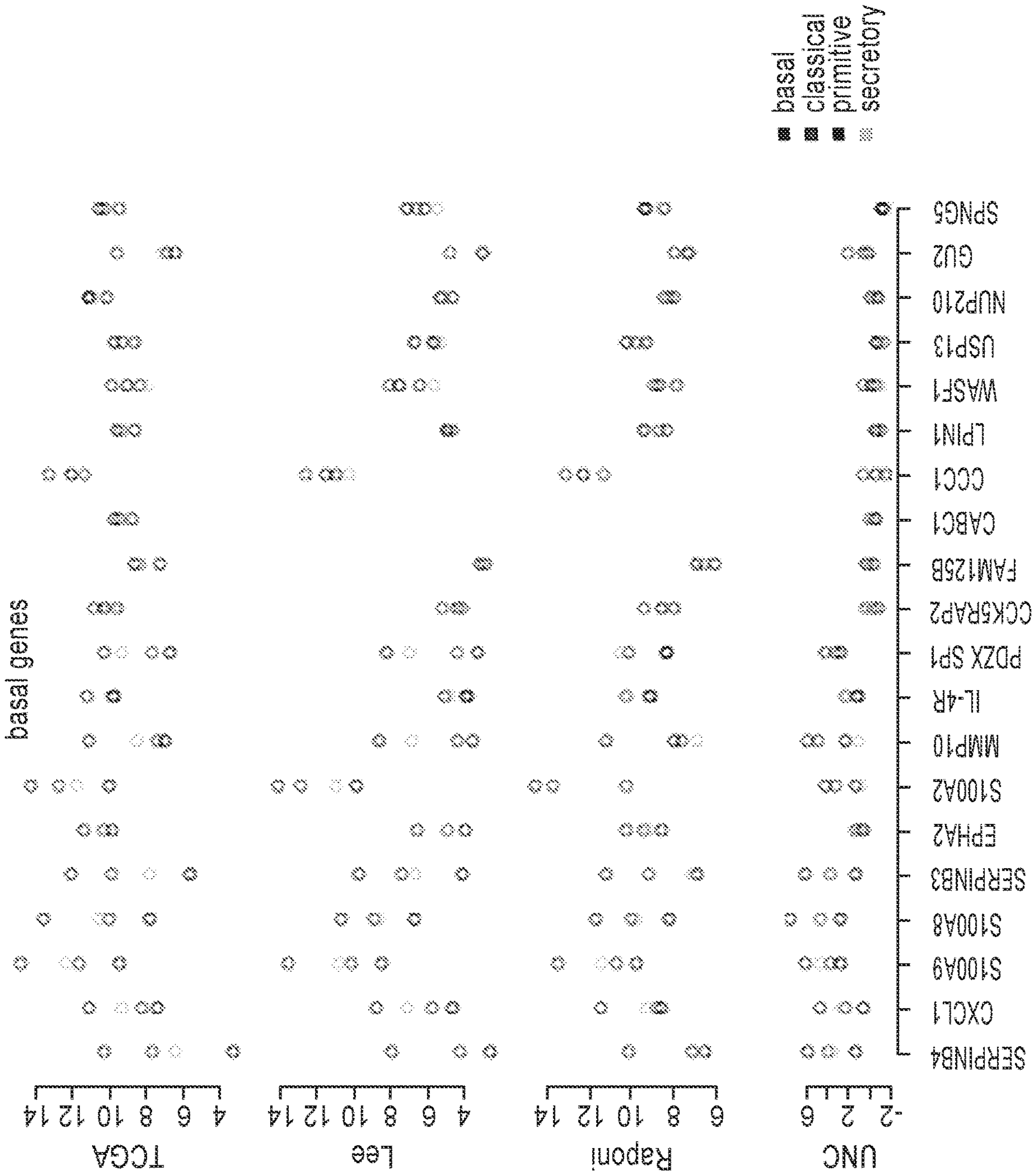
FIG. 12 illustrates the median gene expression of a subset of 20 genes from the 80 gene classifier selected for differentiating basal samples.
Figure 13:
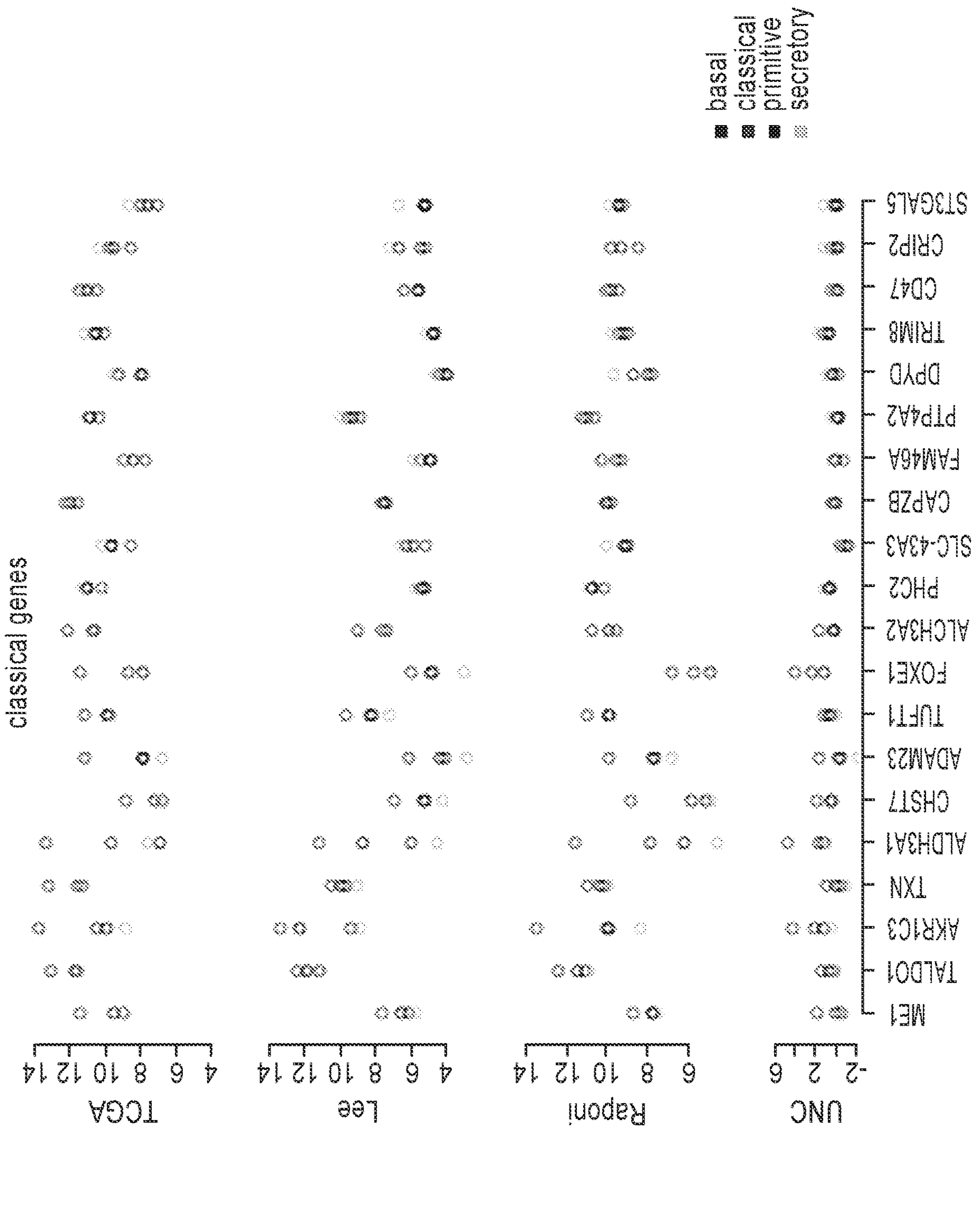
FIG. 13 illustrates the median gene expression of a subset of 20 genes from the 80 gene classifier selected for differentiating classical samples.
Figure 14:
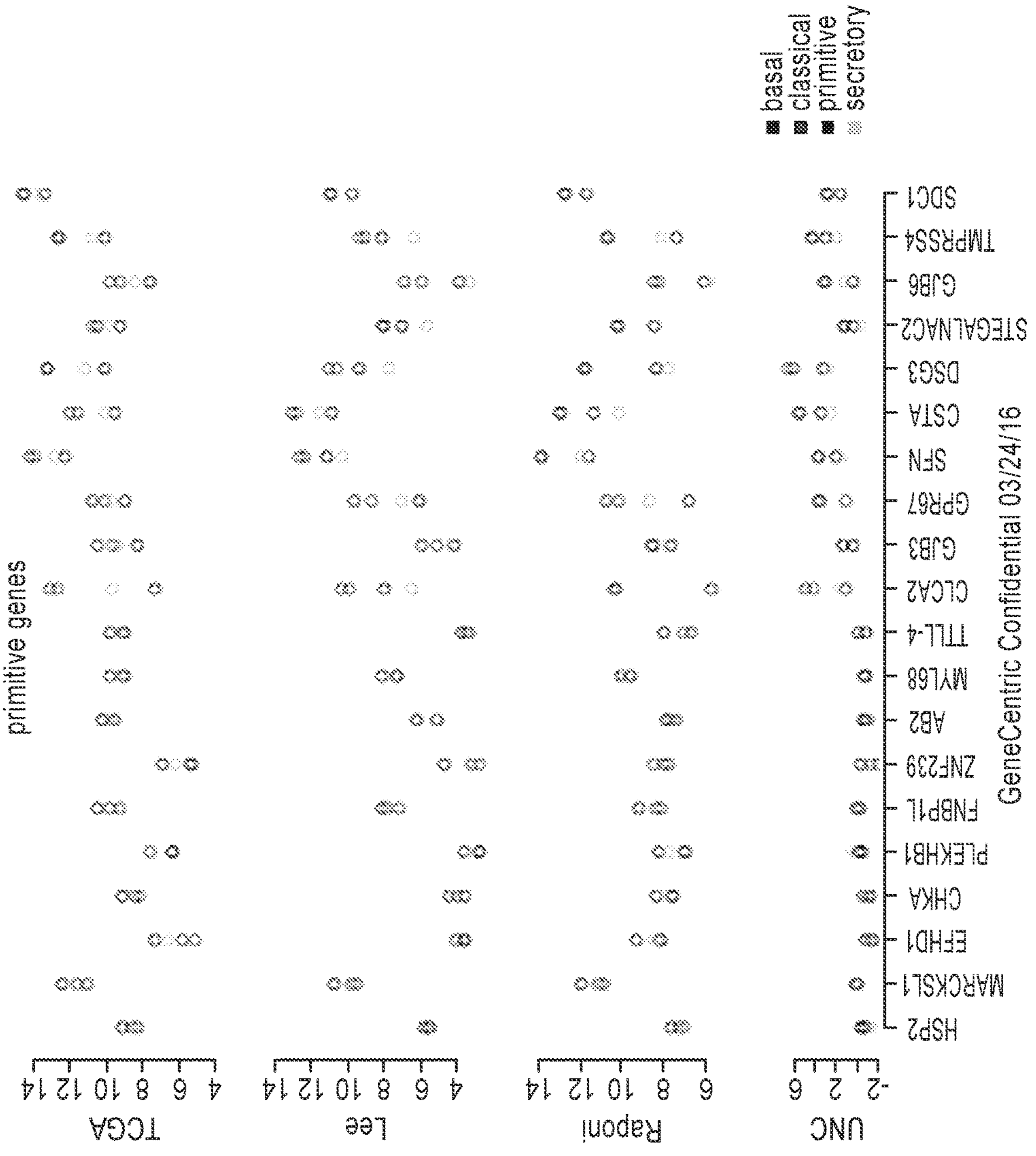
FIG. 14 illustrates the median gene expression of a subset of 20 genes from the 80 gene classifier selected for differentiating primitive samples.
Figure 15:
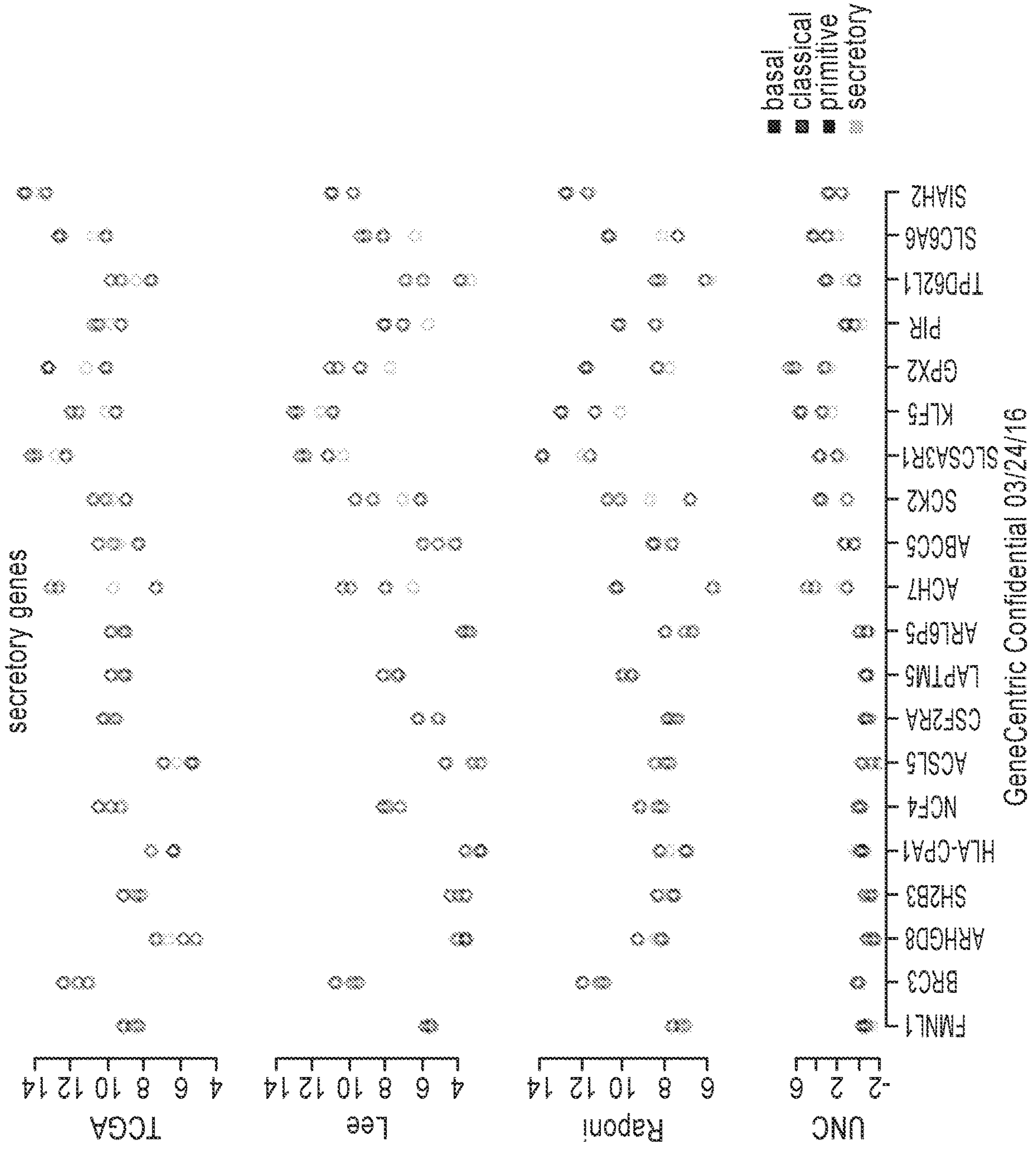
FIG. 15 illustrates the median gene expression of a subset of 20 genes from the 80 gene classifier selected for differentiating secretory samples.

Using the TCGA lung SQ RNAseq gene expression dataset (n=501) for training and the 208-gene classifier to define gold standard subtype, an 80-gene signature was developed that maintains low misclassification rates when applied to several independent test sets. Starting with the standard 208 classifier genes, the Classifying arrays to Nearest Centroid (CLaNC) [1] algorithm was used with modification to select an equal number of negatively and positively correlated genes for each subtype as described above. The optimal number of genes (20 per subtype) to include in the signature was chosen based on 5-fold cross validation curves performed using the TCGA lung SQ dataset (see FIGS. 8 and 9). Selection of prototype samples (FIG. 10) for training of the predictor entailed applying the CLaNC to the entire TCGA data set minus 20% of samples with the lowest gold standard subtype prediction strength, removing an equal number from each subtype. The gene rank of genes from the 80-gene signature in the gold standard 208 gene classifier [2] can be seen in FIG. 11.

The 80-gene signature was then tested in several Fresh Frozen publicly available array and RNAseq datasets [2, 3, 4, 5] and results were compared with the gold standard subtype calls as defined by the previously published 208-gene signature [2]. Final validation of the 80-gene signature (Table 1) was then performed in a newly collected RNAseq dataset of archived FFPE squamous cell carcinoma samples to assure comparable performance in FFPE samples.

In order to validate the consistent performance of the selected 80 gene signature, the newly collected FFPE samples were lung squamous cell carcinoma (SQ) residual archived samples (primarily surgical samples) that had been collected under an IRB approved protocol at the University of North Carolina in Chapel Hill, N.C. The samples were reviewed by a pathologist for tumor cells and three 10 μm tissue sections were macrodissected prior to extraction to enrich for tumor cells. RNA was quantitated and 100 ng was input per sample. Sequencing libraries were constructed using Illumina RNA-Access kits that enrich for the transcriptome. Sequencing libraries were under quality control by using a BA analyzer and quantified using qPCR. Sequence data was generated on an Illumina HiSeq platform (50 bp PE, 20-30 million reads) and was under quality control by using fastQC. Sequence results were aligned against hg19 reference sequence using STAR aligner and the transcriptome was built using Cufflinks [6]. Cuffcompare was used to annotate the transcriptome and counts of various expressed genes were calculated. RSEM expression count estimates were upper quartile normalized and log 2 transformed following the approach used in the Cancer Genome Atlas lung squamous cell carcinoma analysis [3, 7].

Results

The 80 gene signature gene list developed in this study is shown in Table 2, while the T statistics for the 80 gene signature gene list for each SQ subtype can be found in Table 1. The median gene expression of the 20 genes selected for each SQ subtype (basal, classical, primitive, or secretory) is shown in FIGS. 12, 13, 14 and 15, respectively. Agreement of subtype calls using the 80 gene signature with the published 208 gene signature subtype call in several different test datasets is shown in FIG. 16. The newly developed 80 gene signature demonstrated agreement in a range of 0.84-0.91 in the other 4 test datasets (FIG. 16) and the new collected FFPE samples (FIG. 16). Below is a summary of the test datasets, the types of the RNA platforms, and the numbers of the squamous cell carcinoma samples used.

| Reference | RNA Platform | Squamous Cell Carcinoma Samples |
|---|---|---|
| TCGA Squamous Cell Carcinoma | RNAseq | 501 |
| Lee | Affymetrix Arrays | 75 |
| Raponi | Affymetrix Arrays | 130 |

-continued

| Reference | RNA Platform | Squamous Cell Carcinoma Samples |
|---|---|---|
| UNC | RNAseq | 56 |
| Newly collected GeneCentric FFPE samples | RNAseq | 46 |

Conclusion

Development and validation of an efficient 80 gene signature for SQ subtyping was described. The resulting 80 gene signature maintains low misclassification rates when applied to several independent test sets. Thus, the new signature reliably subtypes SQ from fresh frozen or FFPE tumor samples and can perform reliably using gene expression data generated from a variety of platforms including RNAseq and Arrays.

Incorporation by Reference

The following references are incorporated by reference in their entireties for all purposes.

1.) Dabney A R. ClaNC: Point-and-click software for classifying microarrays to nearest centroids. Bioinformatics. 2006; 22: 122-123. doi:10.1093/bioinformatics/bti756
2.) Wilkerson M D, et al. Clin Cancer Res 2010; 16(19): 4864-75. PMID 20643781
3.) TCGA Lung SQCC. Nature 2012; 489(7417): 519-525. PMID 22960745
4.) Lee E S, et al. Cancer Res 2008; 14(22): 7397-7404. PMID 19010856
5.) Raponi M, et al. Cancer Res 2006; 66(7): 466-72. PMID 16885343
6.) Trapnell C, Williams B A, Pertea G, Mortazavi A, Kwan G, van Baren M J, et al. Transcript assembly and quantification by RNA-Seq reveals unannotated transcripts and isoform switching during cell differentiation. Nature biotechnology 2010; 28(5):511-5.
7.) Li B, and Dewey C N. RSEM: accurate transcript quantification from RNA-Seq data with or without a reference genome. BMC Bioinformatics 2011, 12:323 doi:10.1186/1471-2105-12-323

Example 3: Immune Cell Activation Differences Among Lung Squamous Cell Carcinoma Intrinsic Subtypes as Determined Using Lung Squamous Cell Carcinoma Subtyping 80 Gene Signature from Example 2

Methods

Using previously published Bindea et al. (1) immune cell gene signatures (24 in total) and the Lung SQ subtyping gene signature described in Example 2 for subtyping SQ, several publically available lung SQ datasets (2-5; see FIG. 2), were examined for immune cell features in relation to SQ subtypes. Gene expression signatures of both Innate Immune Cells (IIC) and Adaptive Immune Cells (AIC), a 13 gene IFN signature (IFN), as well as single gene immune biomarkers (CTLA4, PDCD1, and CD274 (PD-L1), PDCDLG2 (PD-L2)) were examined in the 4 SQ subtypes (basal, classical, primitive and secretory). Immune cell signature associations with tumor subtype and with CD274 expression were evaluated using linear regression. Hierarchical clustering of immune signatures and pairwise signature correlations were also analyzed. Survival signature associations of Stages I-III samples were evaluated with stratified cox proportional hazard models allowing for different baseline hazards in each dataset.

Results

Figure 17:
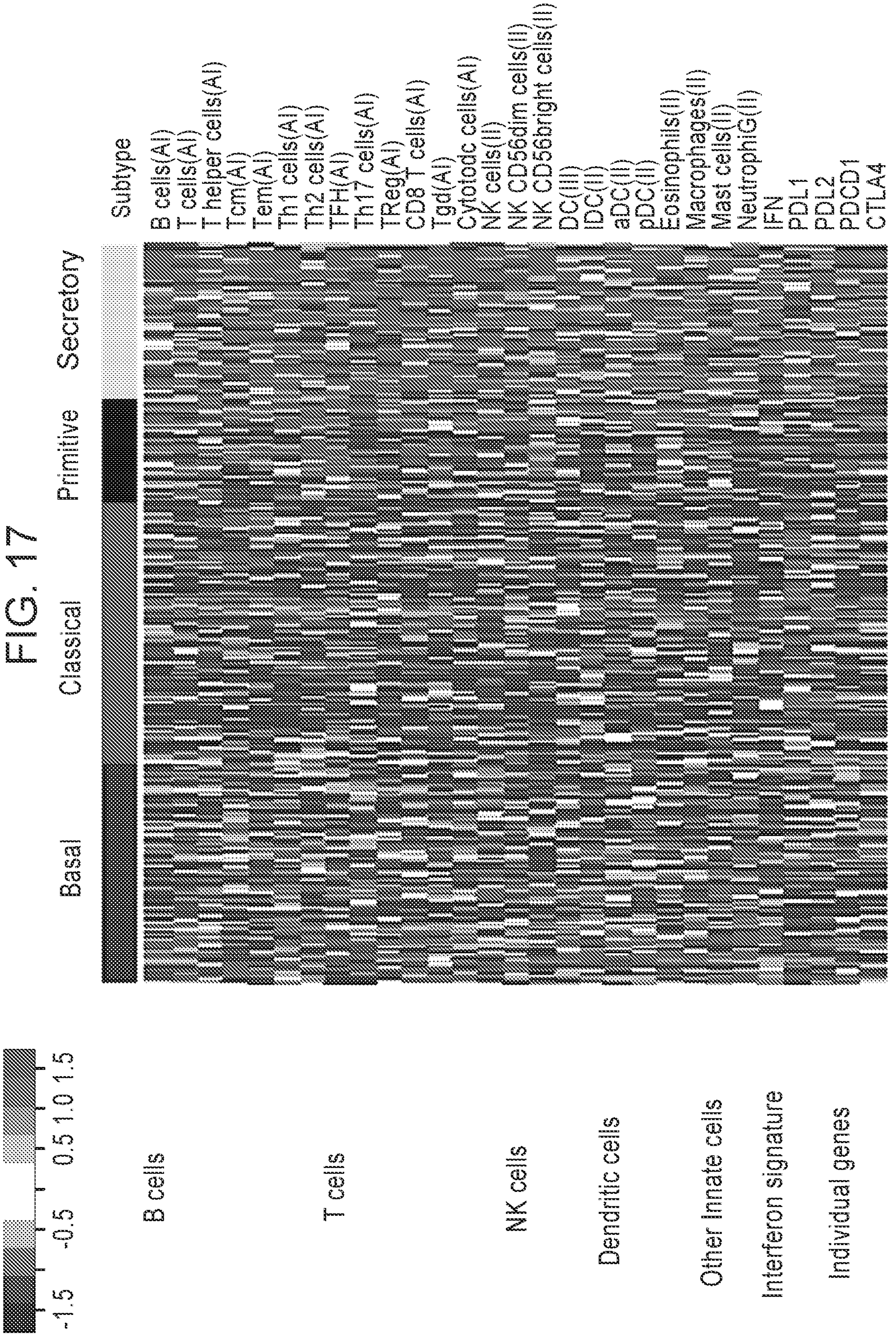
FIG. 17 illustrates a heatmap of immune cell signatures (i.e., Bindea et al reference from Example 3), other immune markers and individual immune markers in the Cancer Genome Atlas (TCGA) Lung SQ dataset.
Figure 18:
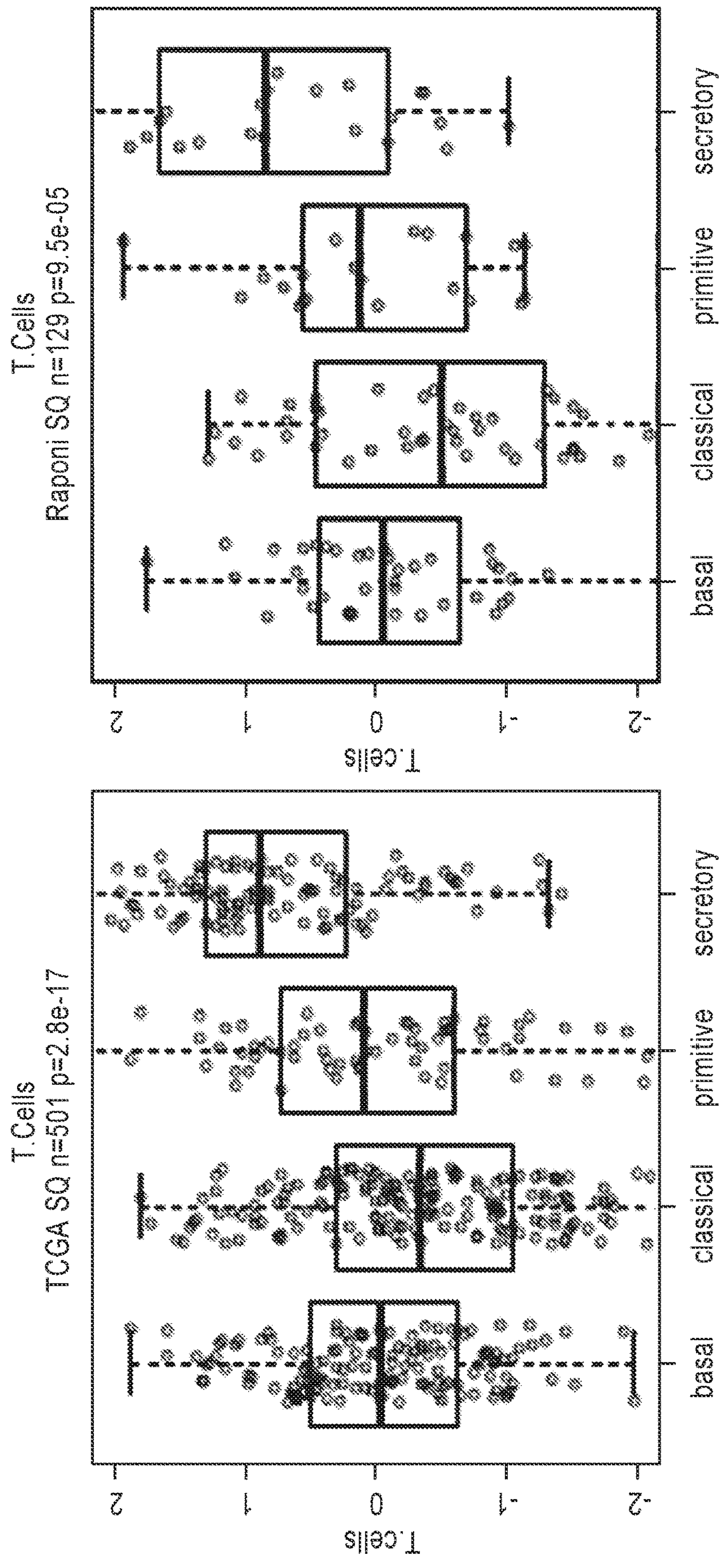
FIG. 18 illustrates reproducibility of T cell signature gene expression subtype patterns across multiple SQ datasets as described in Example 3.
Figure 18:
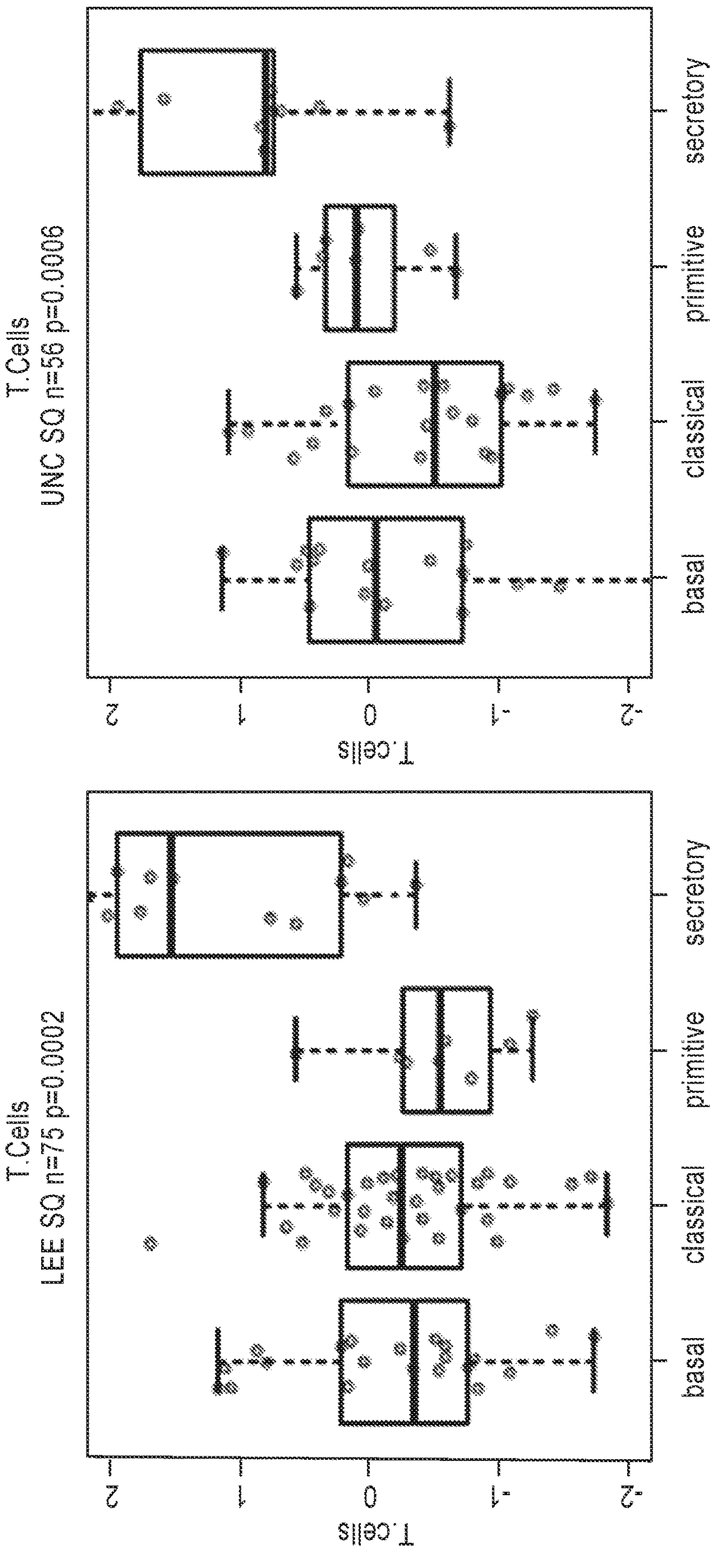
Figure 18:
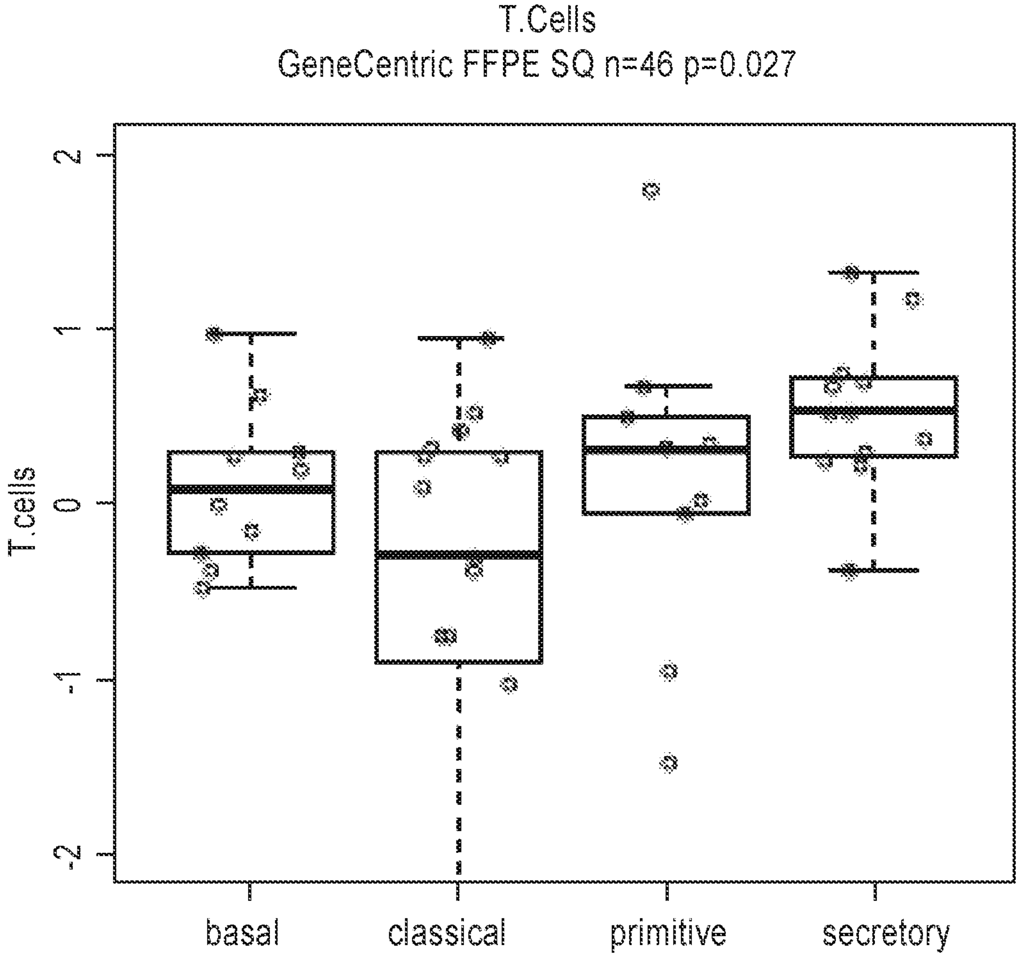
Figure 19:
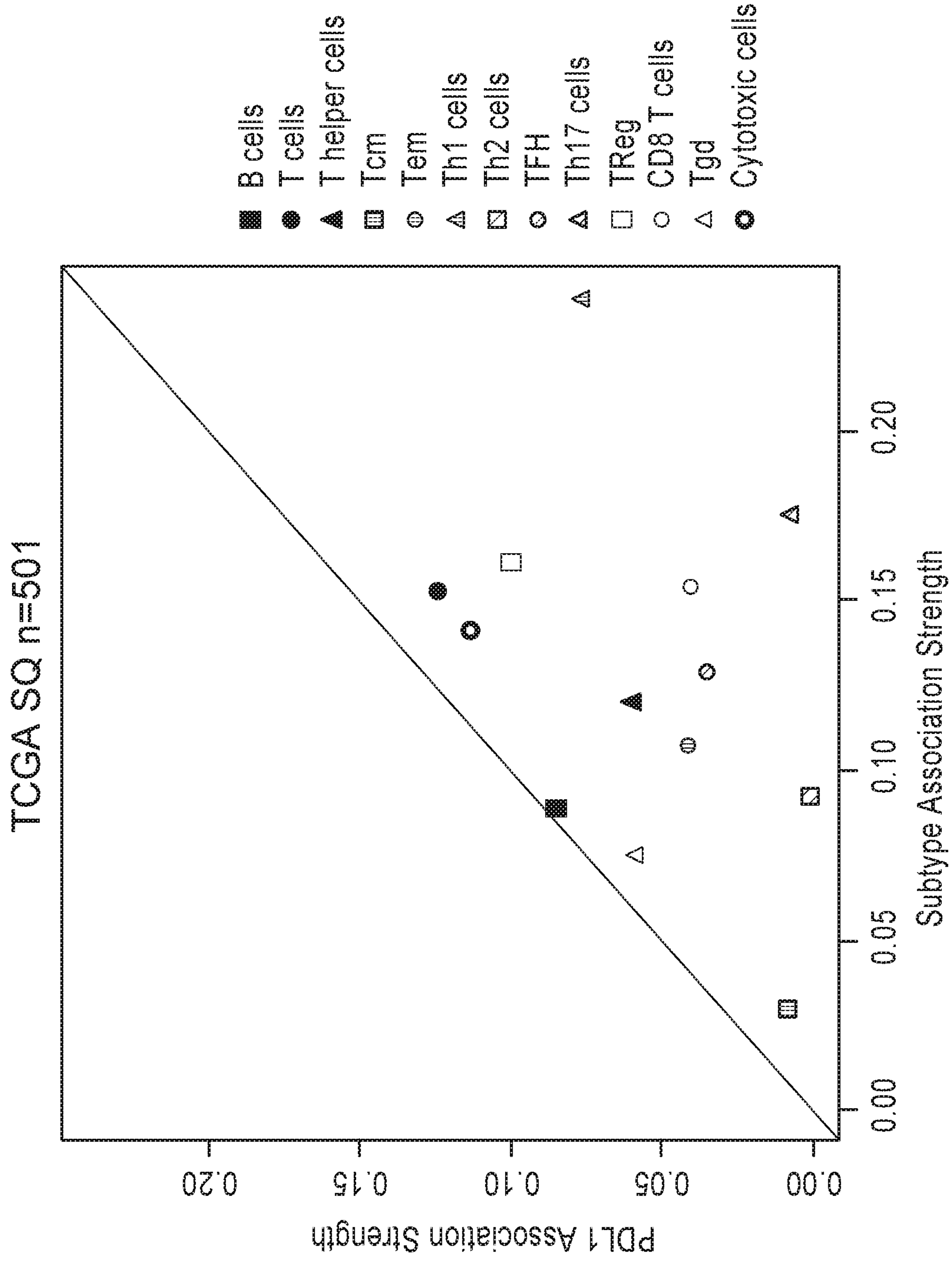
FIG. 19 illustrates an association (adjusted R-squared) between CD274 (PD-L1) expression and adaptive immune cell (AIC) signatures versus subtype and AIC signatures as described in Example 3. Tcm=central memory T cells, Tem=Effector Memory T cells, Th1=Type 1 T helper cells, Th2=Type 2 T helper cells, TFH=T follicular helper cells, Th17=T helper 17 cells, Treg=Tregulatory cells, Tgd=Gamma Delta Tcells.

Using the TCGA SQ dataset and the 80 gene SQ subtyping signature of Example 2, heatmap analysis and unsupervised hierarchical clustering of immune cell gene signatures provided separation of intrinsic subtypes of SQ in a similar fashion as to what was observed in Example 1 (see FIG. 3 and FIG. 17). Further, immune cell signature gene expression patterns were consistent across multiple SQ (see FIG. 18) datasets similar to that observed in Example 1 (see FIG. 5). As in Example 1, strength of association of CD274 (PD-L1) expression with adaptive immune cell signatures, as compared to SQ subtype was conducted. As shown in FIG. 19 (like in FIG. 6), in SQ tumors, subtype was a better predictor of immune cell expression than CD274 (PD-L1) expression for all adaptive immune cells examined.

Figure 20:
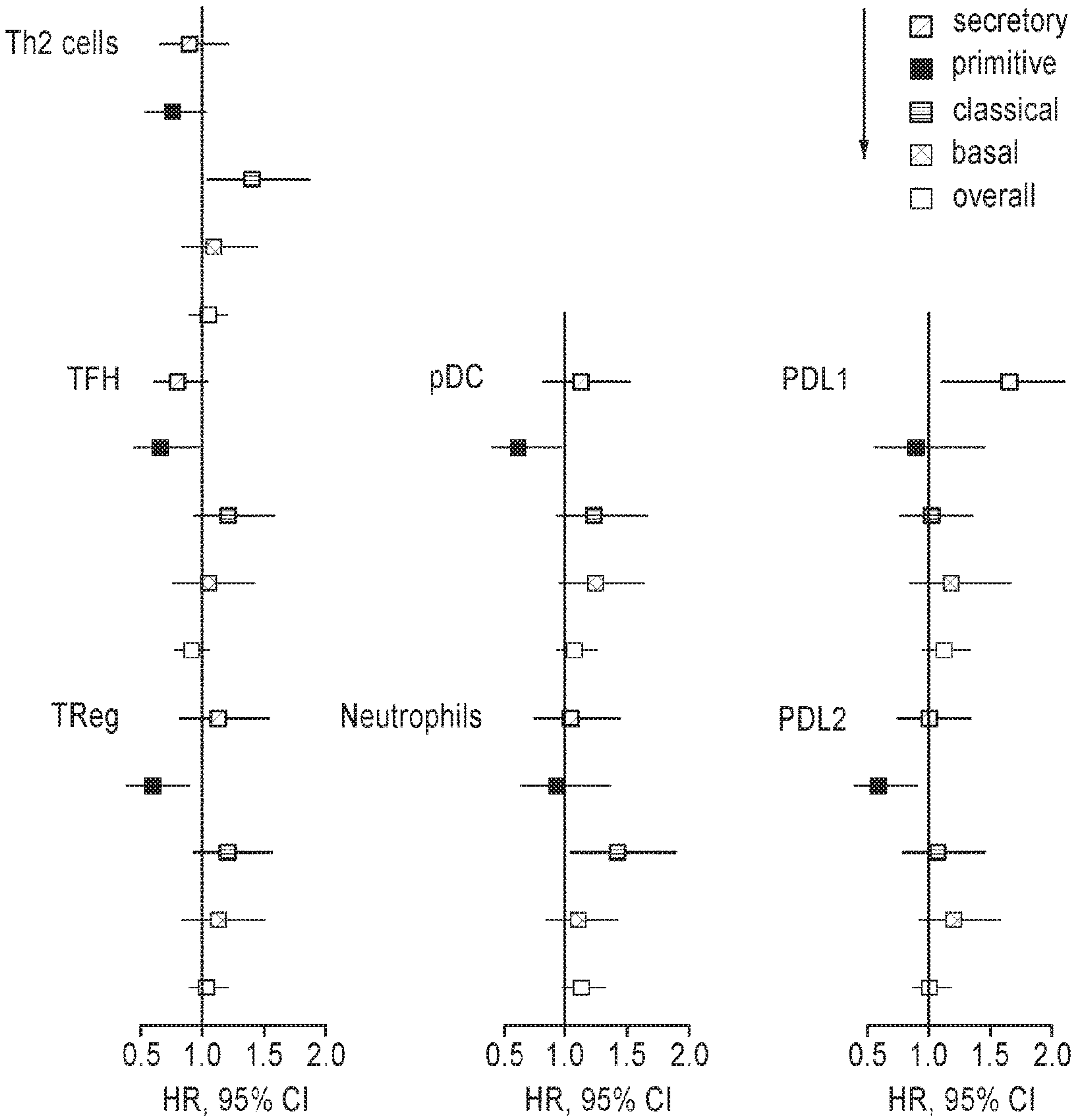
FIG. 20 illustrates for SQ signature-survival associations overall and by subtype as described in Example 3. Hazard Ratios (HR) and confidence intervals calculated from stratified cox models. Subtype specific HR's were adjusted for stage (overall adjusted by stage and subtype) and only immune features with significant associations ($p<0.05$) are shown.

Using cox proportional hazard models, subtype specific hazard ratios for one unit of increased expression were calculated as described in Example 1. Subtype specific HR's were adjusted for pathologic stage and confidence intervals were calculated. The HR and CI for cell signatures or genes showing significant survival associations for one or more of the subtypes are shown in FIG. 20. Among the SQ subtypes, a unit increase in expression of Th1, Th2, TFH, DC, macrophages, and mast cells was significantly associated with improved survival in the primitive subtype much like in Example 1 (see FIGS. 7A-7B and 20). Curiously, the secretory subtype did not show significant association with survival possibly due to the uniformly high expression of immune cells in the secretory subtype preventing demonstration of an incremental survival benefit per unit increase. Overall, in SQ, only the primitive subtype demonstrated significant immune cell expression associations with improved survival (see FIGS. 7A-7B and 20).

Conclusion

The 80 gene signature for SQ subtyping described in Example 2 showed similar results to the SQ subtyping gene signature(s) used in Example 1 in terms of showing how Lung SQ subtypes vary in their immune landscape. In agreement with the SQ subtyping gene signatures of Example 1, the SQ subtyping gene signature used in this example shows that Lung SQ gene expression subtypes vary in their immune landscape. Intrinsic biologic subtypes of SQ reveal key differences in immune cell activation, which were not always correlated with CD274 expression and demonstrated variable association with survival. SQ Classical subtype showed minimal immune infiltration suggesting reduced response to immunoRX. In SQ, subtype appeared to be a better predictor of immune infiltration than CD274 (PD-LI). CD274 expression was not associated with AIC expression nor with improved survival in SQ. The SQ primitive subtype showed immune feature expression associated with improved survival.

Incorporation by Reference

The following references are incorporated by reference in their entireties for all purposes.

1.) Bindea et al., Immunity 2013; 39(4): 782-95. PMID 24138885
2.) Wilkerson M D, et al. Clin Cancer Res 2010; 16(19): 4864-75. PMID 20643781
3.) TCGA Lung SQCC. Nature 2012; 489(7417): 519-525. PMID 22960745
4.) Lee E S, et al. Cancer Res 2008; 14(22): 7397-7404. PMID 19010856
5.) Raponi M, et al. Cancer Res 2006; 66(7): 466-72. PMID 16885343

Example 4—Expression Subtypes of Squamous Cell Carcinoma Reveal a Varied Immune Landscape and Unique Somatic Genetic Features Suggesting Differential Response to Multiple Drug Targets Introduction: Gene expression based subtyping in Lung Squamous Cell Carcinoma (SQ) classifies SQ tumors into distinct subtypes with variable outcomes and potential response to therapy. Gene expression based subtyping has consistently identified 4 subtypes with Lung SQ, Primitive, Classical, Basal and Secretory (1, 2) (see FIG. 1). SQ subtypes demonstrate key differences in genomic alterations, tumor drivers, prognosis, and likely response to various therapies (1-2).

Methods: As a follow up to the experiments conducted in Example 1, differential drug target gene expression was evaluated in the lung SQ subtypes from Example 1 that were determined using the TCGA lung cancer gene expression datasets (SQ n=501)[2] shown in FIG. 2. Previously published SQ subtypes (Primitive, Classical, Secretory, or Basal) were defined in Example 1 using gene expression patterns. In this example, the variable expression of genes from a clinical oncology solid tumor mutation panel (322 genes, see Table 8), 3 was examined in relation to SQ subtypes from Example 1 as a supplement to the examination of the immune cell gene signatures (Bindea et al. 24 immune cell types),[4] expression of single immune gene biomarkers (CTLA4, PDCD1 (PD-1), and CD274 (PD-L1)), proliferation (11 gene signature; see Table 9),[5] and non-silent mutation burden done in Example 1. Differential gene expression was assessed using the Kruskal-Wallis (KW) test with Bonferroni correction, while linear regression and Spearman correlations were used to evaluate association of non-silent mutation burden, tumor subtype, and CD274 (PD-L1) expression with immune cell expression.

Figure 23:
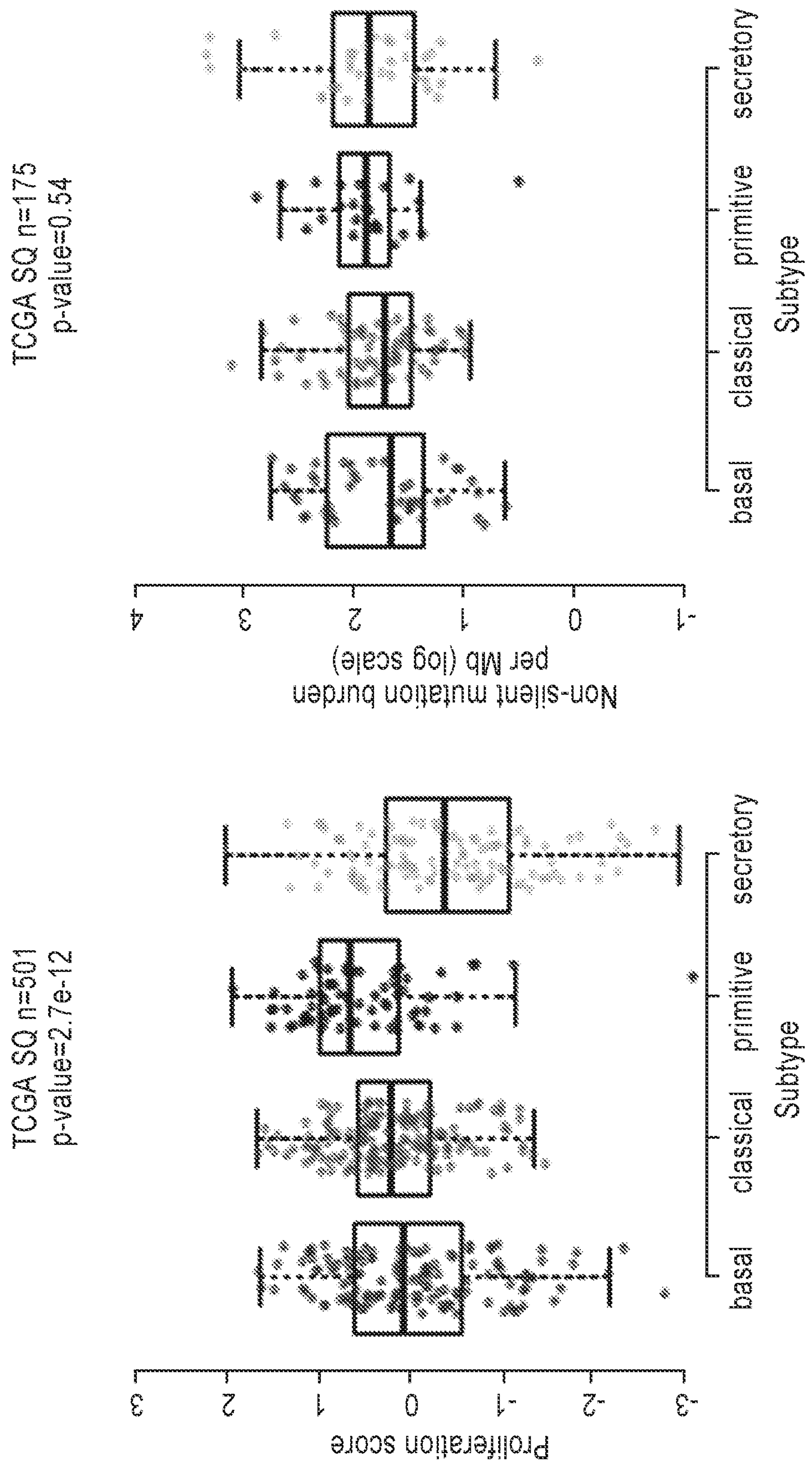
FIG. 23 illustrates significant Squamous cell carcinoma (SQ) subtype differences in proliferation, non-silent mutation burden, and key drug targets: CD274 (PD-L1), PDCD1 (PD-1), and CTLA4. SQ subtyping was determined as described in Example 4.
Figure 23:
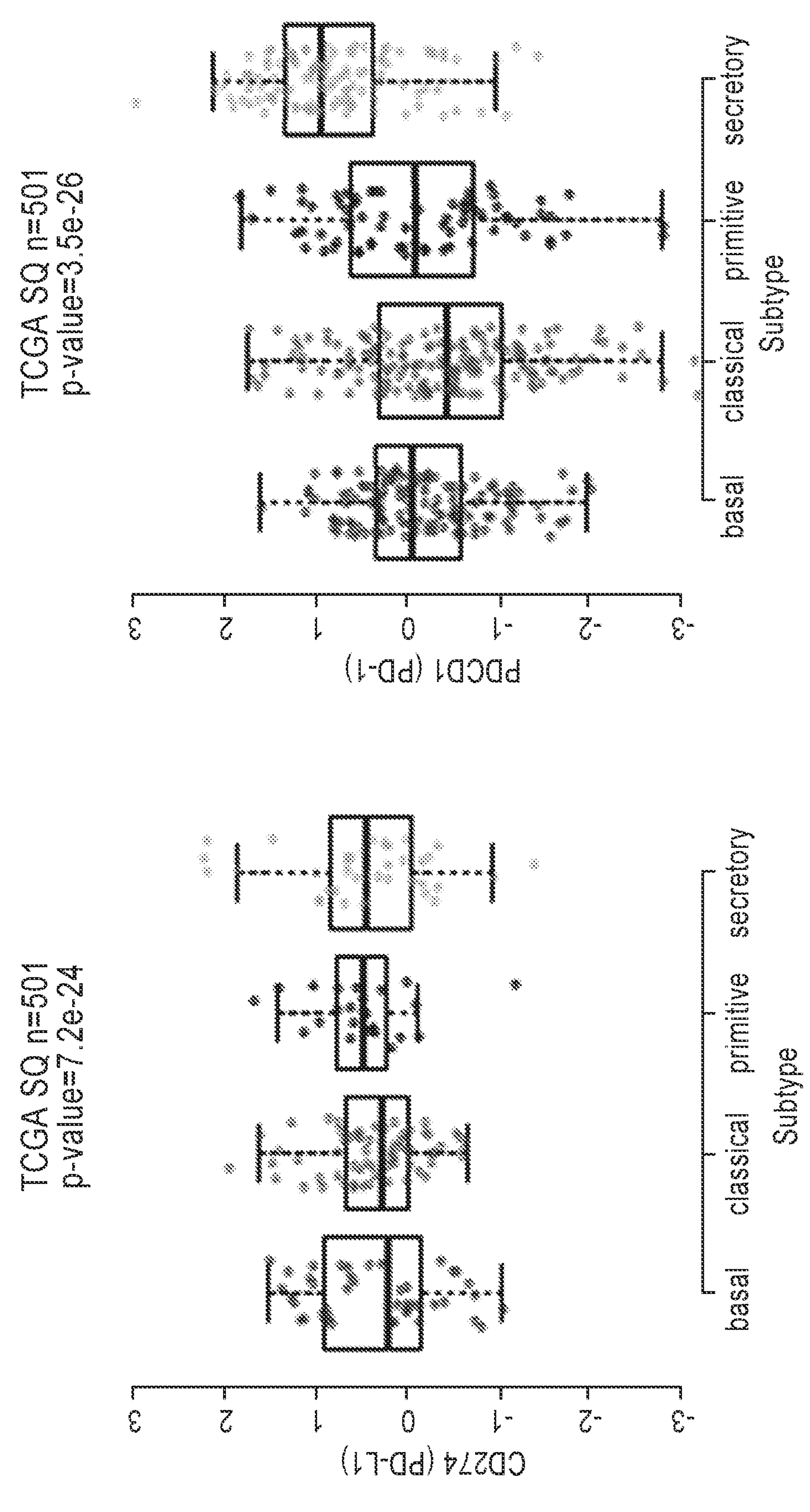
Figure 23:
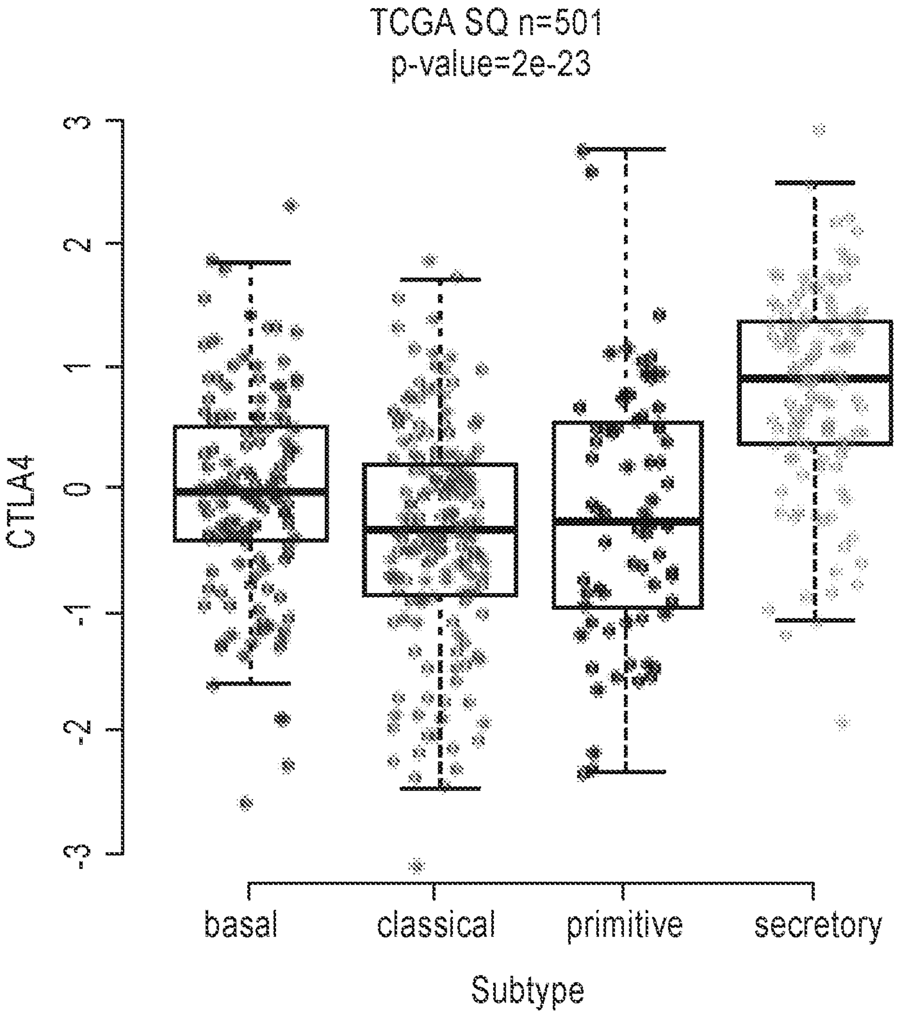
Figure 24:
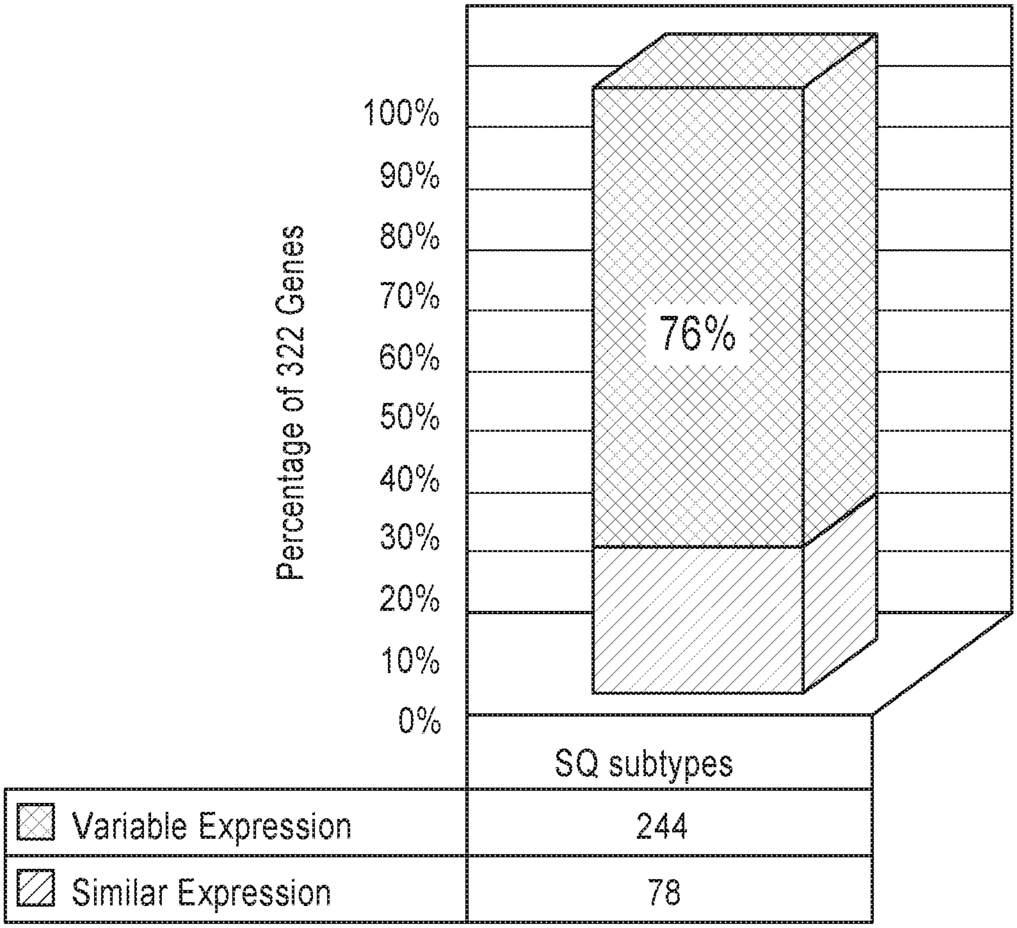
FIG. 24 illustrates significant drug target gene expression differences of SQ subtypes for the majority of genes in a clinical solid tumor mutation panel (322 genes disclosed in Table 8). In SQ subtypes, 76% showed differential expression (KW Bonferroni threshold $p<0.000155$). SQ subtyping was determined as described in Example 4.

Results: As shown in FIG. 24, variable expression of 208/322 tumor panel genes 244/322 (76%) in SQ subtypes were observed (KW Bonferroni threshold $p<0.000155$). Most drug target genes, including but not limited to SOX2, TGFBR2, SMO, CSF1R, PIK3CA, and HGF in SQ, exhibited strong differential expression across the subtypes ($p<1E-28$). Further, the top 25 genes from the 322 genes of the clinical oncology solid tumor mutation panel showing differential gene expression across the SQ subtypes can be seen in Table 10. Immune cell expression was also highly variable across subtypes (see FIG. 3). The SQCC secretory subtype demonstrated the greatest immune cell expression while the Classical subtype of SQ demonstrated low expression of immune cells (see FIG. 3). In SQ tumors, subtype was a better predictor of adaptive immune cell expression than CD274 (PD-L1) (median F-test p-value and adjusted R-squared were 2.16e-24 and 0.20 for subtype versus 1.86e-09 and 0.07 for CD274) (see FIG. 6). Non-silent mutation burden was not strongly correlated with immune cell expression (Spearman correlation=−0.08 in SQ) Overall, as shown in FIG. 23, there were significant SQ subtype differences in proliferation, non-silent mutation burden, and key drug targets CD274 (PD-L1), PDCD1 (PD-1), and CTLA4. SQ subtypes demonstrated significant differences in many drug target tumor panel genes and in immune cell expression but did not demonstrate differences in mutation burden.

Conclusion: Molecular subtypes of lung SQ vary in expression of the majority of key drug target genes included in a clinical solid tumor sequencing panel. Molecular subtypes of lung SQ revealed differential expression of host immune response and immune targets. Evaluation of subtypes as potential biomarkers for drug sensitivity should be investigated alone, and in combination with immune cell features and key mutation targets.

Incorporation by Reference

The following references are incorporated by reference in their entireties for all purposes.

1.) Wilkerson M D, et al. Clin Cancer Res 2010; 16(19): 4864-75. PMID 20643781
2.) TCGA Lung SQCC. Nature 2012; 489(7417): 519-525. PMID 22960745
3.) Foundation Medicine Solid Tumor Mutation Panel accessed October 2014.
4.) Bindea et al., Immunity 2013; 39(4): 782-95. PMID 24138885
5.) Neilson T O, et al. Clin Cancer Res 2010; 16(21): 522-5232. PMID 20837693.

Example 5: Expression Subtypes of Lung Squamous Cell Carcinoma Reveal a Varied Immune Landscape and Unique Somatic Genetic Features Suggesting Differential Response to Multiple Drug Targets Introduction: Just like in Example 4, the purpose of this Example was to assess the differential expression of clinically important genes across previously defined gene expression subtypes of Squamous Cell Carcinoma (SQ). In contrast to Example 4 where the SQ gene expression based subtyping was performed using the TCGA lung cancer gene expression datasets (SQ n=501)[2] as described in Example 1, gene expression based SQ subtyping in this Example was performed using the 80 gene sets described in Examples 2. Further, the clinically important genes were 322 genes (see Table 8) that constituted a clinical solid tumor mutation sequencing panel used in the management of oncology patients to identify genomic alterations impacting therapeutic management and/or to determine eligibility for targeted drug clinical trials. Just like in Example 4, differences in tumor proliferation were also assessed across the SQ subtypes using an 11 gene proliferation signature (see Table 9).

Methods: Using the TCGA lung cancer gene expression datasets (Squamous Cell Carcinoma (SQ) n=501),[1] differential drug target gene expression was evaluated in lung SQ subtypes. Subtype was defined in in SQ using the Clanc80 SQ subtyper (see Example 2 and described herein) as previously described (nearest centroid prediction).[3] SQ subtypes Primitive, Classical, Secretory, Basal were examined. Variable expression of genes from a clinical oncology solid tumor mutation panel (322 genes),[4] was examined in relation to SQ subtypes. Differential gene expression was assessed using the Kruskal-Wallis (KW) test with Bonferroni correction. Further, a proliferation score was calculated as the average expression (log 2 (RSEM+1)) of available genes in the 11-gene PAM50 proliferation signature[5]. Subtype-proliferation association was tested using the Kruskal-Wallis test.

Figure 25:
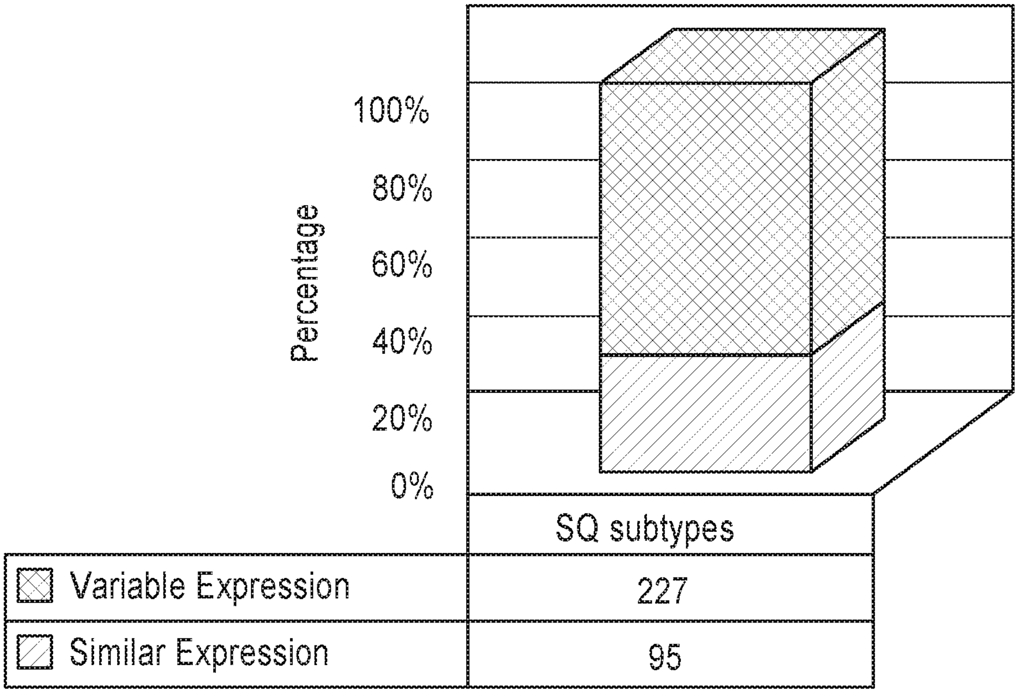
FIG. 25 illustrates significant drug target gene expression differences of SQ subtypes for the majority of genes in a clinical solid tumor mutation panel (322 genes disclosed in Table 8). In SQ subtypes, 70% showed differential expression (KW Bonferroni threshold $p<0.000155$). SQ subtyping was determined as described in Example 5.
Figure 26:
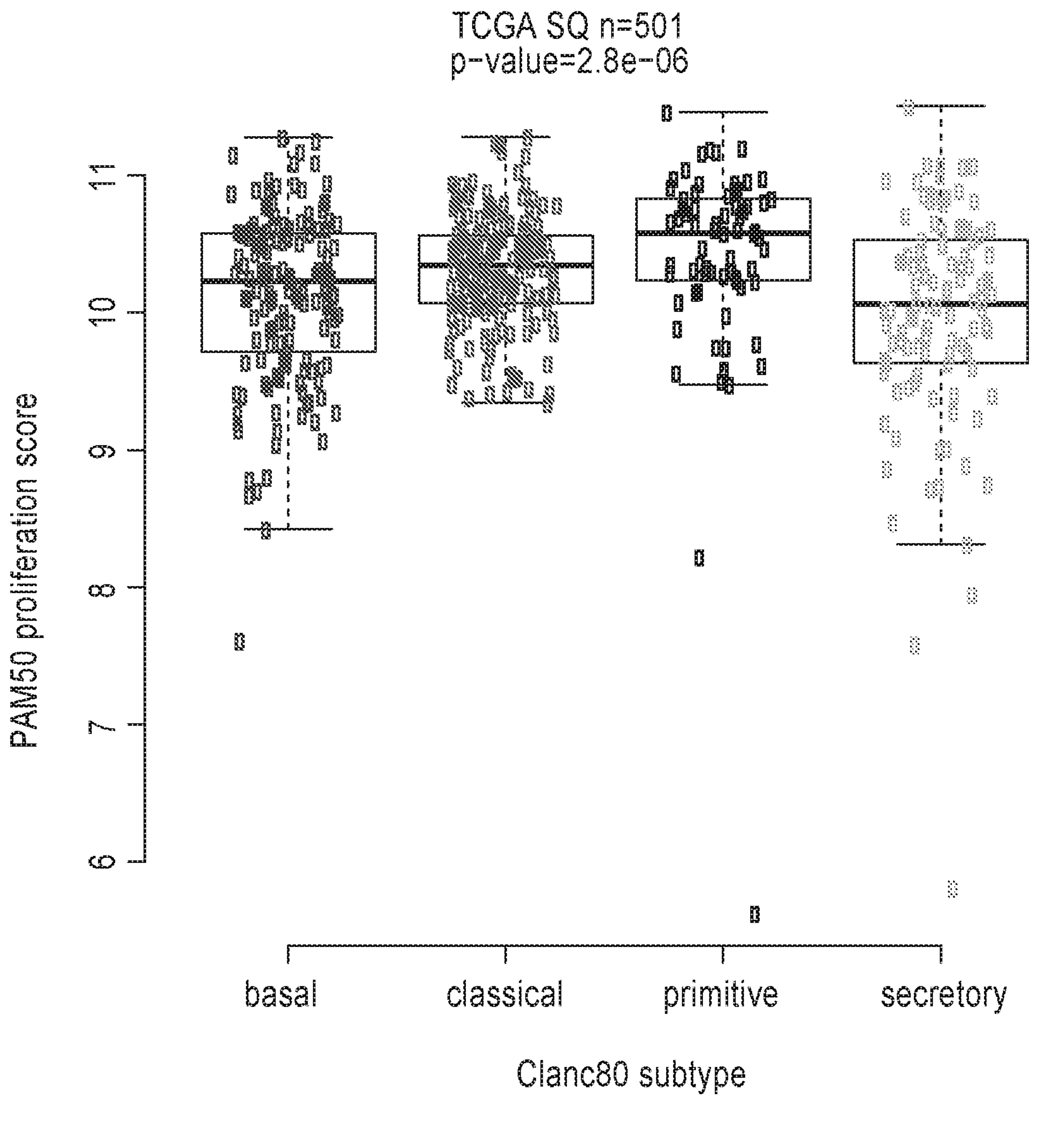
FIG. 26 illustrates significant Squamous cell carcinoma (SQ) subtype differences in proliferation. SQ subtyping was determined as described in Example 5.

Results: Similar to FIG. 32, FIG. 25 showed variable expression of 227/322 (70%) across the SQ subtypes were observed (KW Bonferroni threshold $p<0.000155$). Further, just like in FIG. 23 in Example 4, there were significant SQ subtype differences in proliferation (see. FIG. 26). Moreover, the top 25 genes from the 322 genes of the clinical oncology solid tumor mutation panel showing differential gene expression across the SQ subtypes seen in Table 11 are very similar to those found in Table 10.

Conclusion: Just like in Example 4, molecular subtypes of lung SQ vary in expression of the majority of key drug target genes included in a clinical solid tumor sequencing panel. Molecular subtypes of lung SQ revealed differential expression of host immune response and immune targets.

Incorporation by Reference

The following references are incorporated by reference in their entireties for all purposes.

1.) TCGA Lung SQCC. Nature 2012; 489(7417): 519-525. PMID 22960745

2.) Wilkerson M D, et al. Clin Cancer Res 2010; 16(19): 4864-75. PMID 20643781

3.) Foundation Medicine Solid Tumor Mutation Panel accessed Oct. 6, 2014.

4.) Neilson T O, Parker J S, Leung S, et al. Clin Cancer Res 2010; 16(21): 5222-5232. PMID 20837693

TABLE 8

| 322 genes of a clinical solid tumor mutation sequencing panel[3] | | | | | | | | |
|---|---|---|---|---|---|---|---|---|
| ABL1 | C11orf30 (EMSY) | DDR2 | FGFR4 | IL7R | MET | PIK3CA | SDHD | TSHR |
| ABL2 | CARD11 | DICER1 | FH | INHBA | MITF | PIK3CB | SETD2 | U2AF1 |
| ACVR1B | CBFB | DNMT3A | FLCN | INPP4B | MLH1 | PIK3CG | SF3B1 | VEGFA |
| AKTI | CBL | DOT1L | FLT1 | IRF2 | MPL | PIK3R1 | SLIT2 | VHL |
| AKT2 | CCND1 | EGFR | FLT3 | IRF4 | MRE11A | PIK3R2 | SMAD2 | WISP3 |
| AKT3 | CCND2 | EP300 | FLT4 | IRS2 | MSH2 | PLCG2 | SMAD3 | WT1 |
| ALK | CCND3 | EPHA3 | FOXL2 | JAK1 | MSH6 | PMS2 | SMAD4 | XPO1 |
| AMER1 (FAM123B) | CCNE1 | EPHA5 | FOXP1 | JAK2 | MTOR | POLD1 | SMARCA4 | ZBTB2 |
| APC | CD274 | EPHA7 | FRS2 | JAK3 | MUTYH | POLE | SMARCB1 | ZNF217 |
| AR | CD79A | EPHB1 | FUBP1 | JUN | MYC | PPP2R1A | SMO | ZNF703 |
| ARAF | CD79B | ERBB2 | GABRA6 | KAT6A (MYST3) | MYCL (MYCL1) | PRDM1 | SNCAIP | ETV4 |
| ARFRP1 | CDC73 | ERBB3 | GATA1 | KDM5A | MYCN | PREX2 | SOCS1 | ETV5 |
| ARID1A | CDH1 | ERBB4 | GATA2 | KDM5C | MYD88 | PRKAR1A | SOX10 | ETV6 |
| ARID1B | CDK12 | ERG | GATA3 | KDM6A | NF1 | PRKCI | SOX2 | ETV1 |
| ARID2 | CDK4 | ERRFI1 | GATA4 | KDR | NF2 | PRKDC | SOX9 | NFKBIA |
| ASXL1 | CDK6 | ESR1 | GATA6 | KEAP1 | NFE2L2 | PRSS8 | SPEN | |
| ATM | CDK8 | EZH2 | GID4 (C17orf39) | KEL | NFKBIA | PTCH1 | SPOP | |
| ATR | CDKN1A | FAM46C | GLI1 | KIT | NKX2-1 | PTEN | SPTA1 | |
| ATRX | CDKN1B | FANCA | GNA11 | KLHL6 | NOTCH1 | PTPN11 | SRC | |
| AURKA | CDKN2A | FANCC | GNA13 | KMT2A (MLL) | NOTCH2 | QKI | STAG2 | |
| AURKB | CDKN2B | FANCD2 | GNAQ | KMT2C (MLL3) | NOTCH3 | RAC1 | STAT3 | |
| AχIN1 | CDKN2C | FANCE | GNAS | KMT2D (MLL2) | NPM1 | RAD50 | STAT4 | |
| AXL | CEBPA | FANCF | GPR124 | KRAS | NRAS | RAD51 | STK11 | |
| BAP1 | CHD2 | FANCG | GRIN2A | LMO1 | NSD1 | RAFI | SUFU | |
| BARD1 | CHD4 | FANCL | GRM3 | LRP1B | NTRK1 | RANBP2 | SYK | |
| BCL2 | CHEK1 | FAS | GSK3B | LYN | NTRK2 | RARA | TAF1 | |
| BCL2L1 | CHEK2 | FAT1 | H3F3A | LZTR1 | NTRK3 | RB1 | TBX3 | |
| BCL2L2 | CIC | FBXW7 | HGF | MAGI2 | NUP93 | RBM10 | TERC | |
| BCOR | CREBBP | FGF10 | HNF1A | MAP2K1 | PAK3 | RET | TERT (promoter only) | |
| BCORL1 | CRKL | FGF14 | HRAS | MAP2K2 | PALB2 | RICTOR | TET2 | |
| BLM | CRLF2 | FGF19 | HSD3B1 | MAP2K4 | PARK2 | RNF43 | TGFBR2 | |
| BRAF | CSF1R | FGF23 | HSP90AA1 | MAP3K1 | PAX5 | ROS1 | TNFAIP3 | |
| BRCA1 | CTCF | FGF3 | IDH1 | MCL1 | PBRM1 | RPTOR | TNFRSF14 | |
| BRCA2 | CTNNA1 | FGF4 | IDH2 | MDM2 | PDCD1LG2 | RUNX1 | TOP1 | |
| BRD4 | CTNNB1 | FGF6 | IGF1R | MDM4 | PDGFRA | RUNX1T1 | TOP2A | |
| BRIP1 | CUL3 | FGFR1 | IGF2 | MED12 | PDGFRB | SDHA | TP53 | |
| BTG1 | CYLD | FGFR2 | IKBKE | MEF2B | PDK1 | SDHB | TSC1 | |
| BTK | DAXX | FGFR3 | IKZF1 | MEN1 | PIK3C2B | SDHC | TSC2 | |

TABLE 9

| 11 gene proliferation gene signature | | | |
|---|---|---|---|
| BIRC5 | CDCA1 (NUF2) | MKI67 | TYMS |
| CCNB1 | CEP55 | PTTG1 | UBE2C |
| CDC20 | KNTC2 (NDC80) | RRM2 | |

TABLE 10

Top 25 differentiated genes of the 322 tumor panel[3] for the SQ expression subtypes as determined in Example 4.

| SQ Genes | KW p value |
|---|---|
| NTRK2 | 2.41E−55 |
| SOX2 | 1.64E−54 |
| NFE2L2 | 1.05E−49 |
| TGFBR2 | 4.97E−40 |
| SMO | 7.91E−40 |
| KEAP1 | 1.14E−38 |
| GATA3 | 1.02E−37 |
| JAK1 | 7.23E−37 |
| JAK3 | 1.34E−36 |
| CSF1R | 3.16E−36 |
| FOXP1 | 4.18E−35 |
| AXL | 3.32E−34 |
| PTCH1 | 2.00E−33 |
| STAT4 | 2.61E−32 |
| TNFRSF14 | 6.17E−32 |
| ESR1 | 4.46E−31 |
| BTK | 5.65E−31 |
| FLT4 | 1.13E−30 |
| IKZF1 | 9.11E−30 |
| PIK3CA | 4.49E−29 |
| HGF | 6.64E−29 |
| LRP1B | 1.63E−28 |
| FANCC | 2.57E−28 |
| PIK3CG | 9.86E−28 |
| GATA6 | 5.03E−27 |

TABLE 11

Top 25 differentiated genes of the 322 tumor panel[3] for the SQ expression subtypes as determined in Example 5.

| SQ Genes | KW p value |
|---|---|
| NTRK2 | 7.84E−59 |
| SOX2 | 4.41E−58 |
| NFE2L2 | 1.26E−48 |
| KEAP1 | 1.83E−41 |
| SMO | 2.52E−41 |
| GATA3 | 6.38E−35 |
| FOXP1 | 2.88E−34 |
| JAK1 | 3.30E−34 |
| PTCH1 | 3.79E−34 |
| PIK3CA | 7.26E−33 |
| LRP1B | 9.39E−32 |
| JAK3 | 2.75E−31 |
| ESR1 | 1.40E−29 |
| GNA13 | 2.31E−29 |
| ETV4 | 6.10E−29 |
| FANCC | 1.44E−28 |
| PRKCI | 2.06E−28 |
| ERRFI1 | 1.75E−26 |
| AXL | 3.74E−26 |
| TNFRSF14 | 6.69E−26 |
| TGFBR2 | 8.42E−26 |
| EZH2 | 3.56E−25 |
| FLT4 | 1.70E−24 |
| CSF1R | 2.28E−24 |
| FGFR2 | 1.76E−23 |

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of assaying a lung sample obtained from a human patient, the method comprising measuring in a lung sample obtained from a human patient a nucleic acid expression level of each biomarker from a plurality of biomarkers consisting of only serpin family B member 4 (SERPINB4), C—X—C motif chemokine ligand 1 (CXCL1), S100 calcium binding protein A9 (S100A9), S100 calcium binding protein A8 (S100A8), serpin family B member 3 (SERPINB3), EPH receptor A2 (EPHA2), S100 calcium binding protein A2 (S100A2), matrix metallopeptidase 10 (MMP10), interleukin 4 receptor (IL4R), PDZK1-interacting protein 1 (PDZK1IP1), CDK5 regulatory subunit associated protein 2 (CDK5RAP2), family with sequence similarity 125, member B (FAM125B), chaperone activity of bc1 complex-like (CABC1), ornithine decarboxylase 1 (ODC1), lipin 1 (LPIN1), WAS protein family member 1 (WASF1), ubiquitin specific peptidase 13 (isopeptidase T-3) (USP13), nucleoporin 210 (NUP210), GLI Family Zinc Finger 2 (GLI2), sperm associated antigen 5 (SPAG5), malic enzyme 1 (ME1), transaldolase 1 (TALDO1), aldo-keto reductase family 1, member C3 (AKR1C3), thioredoxin (TXN), aldehyde dehydrogenase 3 family member A1 (ALDH3A1), carbohydrate sulfotransferase 7 (CHST7), ADAM metallopeptidase domain 23 (ADAM23), tuftelin 1 (TUFT1), forkhead box E1 (FOXE1), aldehyde dehydrogenase 3 family member A2 (ALDH3A2), polyhomeotic homolog 2 (PHC2), solute carrier family 43 member 3 (SLC43A3), capping actin protein of muscle Z-line beta subunit (CAPZB), family with sequence similarity 46 member A (FAM46A), protein tyrosine phosphatase type IVA, member 2 (PTP4A2), dihydropyrimidine dehydrogenase (DPYD), tripartite motif containing 8 (TRIM8), CD47 molecule (CD47), cysteine rich protein 2 (CRIP2), ST3 beta-galactoside alpha-2,3-sialyltransferase 5 (ST3GAL5), heat shock transcription factor 2 (HSF2), MARCKS like 1 (MARCKSL1), EF-hand domain family member D1 (EFHD1), choline kinase alpha (CHKA), pleckstrin homology domain containing B1 (PLEKHB1), formin binding protein 1 like (FNBP1L), zinc finger protein 239 (ZNF239), Abelson interactor 2 (ABI2), Myosin light chain 6B (MYL6B), Tubulin Tyrosine Ligase Like 4 (TTLL4), Chloride Channel Accessory 2 (CLCA2), Gap Junction Protein Beta 3 (GJB3), G Protein-Coupled Receptor 87 (GPR87), Stratifin (SFN), Cystatin A (CSTA), Desmoglein 3 (DSG3), ST6 N-Acetylgalactosaminide Alpha-2, 6-Sialyltransferase 2 (ST6GALNAC2), Gap Junction Protein Beta 5 (GJB5), Transmembrane Protease, Serine 4 (TMPRSS4), Syndecan 1 (SDC1), Formin Like 1 (FMNL1), Baculoviral IAP Repeat Containing 3 (BIRC3), Rho GDP Dissociation Inhibitor Beta (ARHGDIB), SH2B Adaptor Protein 3 (SH2B3), Major Histocompatibility Complex, Class I, DP Alpha 1 (HLA-DPA1), Neutrophil Cytosolic Factor 4 (NCF4), Acyl-CoA Synthetase Long-Chain Family Member 5 (ACSL5), Colony Stimulating Factor 2 Receptor Alpha Subunit (CSF2RA), Lysosomal Protein Transmembrane 5 (LAPTM5), ADP-ribosylation-like factor 6 interacting protein 5 (ARL6IP5), Alcohol Dehydrogenase 7 (Class IV), Mu Or Sigma (ADH7), ATP Binding Cassette Subfamily C Member 5 (ABCC5), SRY-Box 2 (SOX2), Solute Carrier Family 9, Subfamily A (NHE3, Cation Proton Antiporter 3), Member 3 Regulator 1 (SLC9A3R1), Kruppel-Like Factor 5 (Intestinal) (KLF5), Glutathione Peroxidase 2 (GPX2), Pirin (PIR), Tumor Protein D52-Like 1 (TPD52L1), Solute Carrier Family 6 Member 8 (SLC6A8), and Siah E3 Ubiquitin Protein Ligase 2 (SIAH2).

2. The method of claim 1, wherein the lung sample was previously diagnosed as being squamous cell carcinoma.

3. The method of claim 1, wherein the measuring is performed by an amplification, hybridization and/or sequencing assay, wherein the amplification, hybridization and/or sequencing assay comprises quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays or Northern blotting.

4. The method of claim 1, wherein the lung sample is a formalin-fixed, paraffin-embedded (FFPE) lung tissue sample, fresh or a frozen tissue sample, an exosome, wash fluids, cell pellets, or a bodily fluid obtained from the patient.

5. A method of treating lung cancer in a subject, the method comprising:

(a) determining the subtype a lung sample obtained from the subject, wherein the lung sample is a squamous cell carcinoma lung cancer sample, wherein the determining the subtype comprises:

(i) measuring a nucleic acid expression level of each biomarker of a plurality of the biomarkers consisting of only SERPINB4, CXCL1, S100A9, S100A8, SERPINB3, EPHA2, S100A2, MMP10, IL4R, PDZK1IP1, CDK5RAP2, FAM125B, CABC1, ODC1, LPIN1, WASF1, USP13, NUP210, GLI2, SPAG5, ME1, TALDO1, AKR1C3, TXN, ALDH3A1, CHST7, ADAM23, TUFT1, FOXE1, ALDH3A2, PHC2, SLC43A3, CAPZB, FAM46A, PTP4A2, DPYD, TRIM8, CD47, CRIP2, ST3GAL5, HSF2, MARCKSL1, EFHD1, CHKA, PLEKHB1, FNBP1L, ZNF239, ABI2, MYL6B, TTLL4, CLCA2, GJB3, GPR87, SFN, CSTA, DSG3, ST6GALNAC2, GJB5, TMPRSS4, SDC1, FMNL1, BIRC3, ARHGDIB, SH2B3, HLA-DPA1, NCF4, ACSL5, CSF2RA, LAPTM5, ARL6IP5, ADH7, ABCC5, SOX2, SLC9A3R1, KLF5, GPX2, PIR, TPD52L1, SLC6A8, and SIAH2;

(ii) comparing the measured nucleic acid expression levels of each biomarker of the plurality of the biomarkers of (a)(i) in at least one sample training set(s), wherein the at least one sample training set is a reference lung squamous cell carcinoma primitive sample, a reference lung squamous cell carcinoma classical sample, a reference lung squamous cell carcinoma secretory sample, a reference lung squamous cell carcinoma basal sample or a combination thereof, and (iii) classifying the subtype of lung squamous cell carcinoma as primitive, classical, secretory or basal based on the results of the comparing step; and (b) administering a therapeutic agent based on the subtype of the lung squamous cell carcinoma, wherein a primitive subtype is administered an immunotherapeutic agent, while a classical, secretory or basal subtype is administered a chemotherapeutic agent or an angiogenesis inhibitor.

6. The method of claim 5, wherein the lung sample was previously diagnosed as being a squamous cell carcinoma lung cancer sample.

7. The method of claim 5, wherein the measuring the expression level is conducted using an amplification, hybridization and/or sequencing assay, wherein the amplification, hybridization and/or sequencing assay comprises performing quantitative real time reverse transcriptase polymerase chain reaction (qRT-PCR), RNAseq, microarrays, gene chips, nCounter Gene Expression Assay, Serial Analysis of Gene Expression (SAGE), Rapid Analysis of Gene Expression (RAGE), nuclease protection assays or Northern blotting.

8. The method of claim 5, wherein the lung sample is a formalin-fixed, paraffin-embedded (FFPE) lung tissue sample, fresh or a frozen tissue sample, an exosome, wash fluids, cell pellets, or a bodily fluid obtained from the patient.

9. The method of claim 5, wherein the immunotherapeutic agent is a checkpoint inhibitor.

10. The method of claim 1, further comprising measuring a nucleic acid expression level of each biomarker from the plurality of biomarkers consisting of only SERPINB4, CXCL1, S100A9, S100A8, SERPINB3, EPHA2, S100A2, MMP10, IL4R, PDZK1IP1, CDK5RAP2, FAM125B, CABC1, ODC1, LPIN1, WASF1, USP13, NUP210, GLI2, SPAG5, ME1, TALDO1, AKR1C3, TXN, ALDH3A1, CHST7, ADAM23, TUFT1, FOXE1, ALDH3A2, PHC2, SLC43A3, CAPZB, FAM46A, PTP4A2, DPYD, TRIM8, CD47, CRIP2, ST3GAL5, HSF2, MARCKSL1, EFHD1, CHKA, PLEKHB1, FNBP1L, ZNF239, ABI2, MYL6B, TTLL4, CLCA2, GJB3, GPR87, SFN, CSTA, DSG3, ST6GALNAC2, GJB5, TMPRSS4, SDC1, FMNL1, BIRC3, ARHGDIB, SH2B3, HLA-DPA1, NCF4, ACSL5, CSF2RA, LAPTM5, ARL6IP5, ADH7, ABCC5, SOX2, SLC9A3R1, KLF5, GPX2, PIR, TPD52L1, SLC6A8, and SIAH2 in a normal lung sample, a primitive sample, a classical sample, a secretory sample or a basal sample.

11. The method of claim 5, wherein the comparing step comprises applying a statistical algorithm which comprises determining a correlation between the nucleic acid expression levels of each biomarker from the plurality of biomarkers obtained from the lung sample and the nucleic acid expression levels of each biomarker from the plurality of biomarkers from the at least one training set(s); and classifying the subtype of lung squamous cell carcinoma as a primitive, classical, secretory or basal subtype based on the results of the statistical algorithm.

12. The method of claim 9, wherein the checkpoint inhibitor targets PD-1, PD-LI or CTLA-4.

13. The method of claim 9, wherein the checkpoint inhibitor is a PD-1/PD-LI checkpoint inhibitor selected from the group consisting of nivolumab, pembrolizumab, atezolizumab, durvalumab, lambrolizumab, and avelumab.

14. The method of claim 9, wherein the checkpoint inhibitor is a CTLA-4 checkpoint inhibitor selected from ipilimumab and tremelimumab.

* * * * *